(12) United States Patent
Koppitz et al.

(10) Patent No.: US 11,319,324 B2
(45) Date of Patent: May 3, 2022

(54) PYRAZOLO-PYRROLO-PYRIMIDINE-DIONE DERIVATIVES AS P2X3 INHIBITORS

(71) Applicants: Bayer Aktiengesellschaft, Leverkusen (DE); Bayer Pharma Aktiengesellschaft, Berlin (DE)

(72) Inventors: Marcus Koppitz, Berlin (DE); Holger Siebeneicher, Berlin (DE); Nico Bräuer, Falkensee (DE); Elisabeth Pook, Wuppertal (DE); Andrea Rotgeri, Berlin (DE); Roland Neuhaus, Berlin (DE); Oliver Martin Fischer, Berlin (DE); Jens Nagel, Daxweiler (DE); Adam James Davenport, Abingdon (GB); James Lindsay Carr, Abingdon (GB); Robert James Townsend, Abingdon (GB); Nina Connelly Ursinyova, Abingdon (GB); Shelley Anne Parrott, Abingdon (GB)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/759,262

(22) PCT Filed: Oct. 18, 2018

(86) PCT No.: PCT/EP2018/078567
§ 371 (c)(1),
(2) Date: Apr. 24, 2020

(87) PCT Pub. No.: WO2019/081343
PCT Pub. Date: May 2, 2019

(65) Prior Publication Data
US 2021/0317128 A1 Oct. 14, 2021

(30) Foreign Application Priority Data
Oct. 27, 2017 (EP) ..................... 17198769

(51) Int. Cl.
*C07D 487/14* (2006.01)
(52) U.S. Cl.
CPC ................. *C07D 487/14* (2013.01)
(58) Field of Classification Search
CPC .................................................. C07D 487/14
USPC ................................................... 514/210.16
See application file for complete search history.

(56) References Cited

FOREIGN PATENT DOCUMENTS

| WO | WO9001031 A1 | 2/1990 |
| WO | WO0134127 A1 | 5/2001 |
| WO | WO2007150025 A2 | 2/2008 |
| WO | WO2008136756 A1 | 11/2008 |
| WO | WO2012112363 A1 | 8/2012 |
| WO | WO2013185124 A1 | 12/2013 |

OTHER PUBLICATIONS

"Isotopic Compositions of the Elements 1997," Pure & Appl. Chem.; 1998; 70(1):217-235.
Abdulqawi et al (2015) "P2X3 receptor antagonist (AF-219) in refractory chronic cough: A randomised, double-blind, placebo-controlled phase 2 study" Lancet 385: 1198-1205.
Berge et al. (1977). "Pharmaceutical Salts," J. Pharm. Sci. 66(1):1-19.
Bovolenta, S. et al. (2007). "Development of a Ca2+-Activated Photoprotein, Photina, and its Application to High-Throughput Screening," Society for Biomolecular Sciences, 12(5):694-704.
Burnstock (1993). "Physiological and pathological roles of purines: An update" Drug Dev. Res. 28: 195-206.
Burnstock (2013). "Introduction and perspective, historical note" Front. Cell. Neurosci. 7(227): 1-13.
Burnstock (2013). "Purinergic mechanisms and pain—An update" Eur. J. Pharmacol. 716:24-40.
Burnstock (2014). "Purinergic signalling in the gastrointestinal tract and related organs in health and disease" Purinergic Signal. 10:3-50.
Burnstock et al (2011). "Purinergic signalling: From normal behaviour to pathological brain function" Prog. Neurobiol. 95:229-274.
Chizh et al (2000). "P2X receptors and nociception" Pharmacol. Rev. 53(4): 553-568.

(Continued)

*Primary Examiner* — Taofiq A Solola
(74) *Attorney, Agent, or Firm* — Morrison & Foerster LLP

(57) ABSTRACT

The present invention covers substituted. Pyrazolo-pyrrolo-pyrimidine-dione (PPPD) compounds of general formula (I): in which $R^1$, $R^2$ and $R^3$ are as defined herein, methods of preparing said compounds, pharmaceutical compositions and combinations comprising said compounds and the use of said compounds for manufacturing pharmaceutical compositions for the treatment or prophylaxis of diseases, in particular of neurogenic diseases, as a sole agent or in combination with other active ingredients.

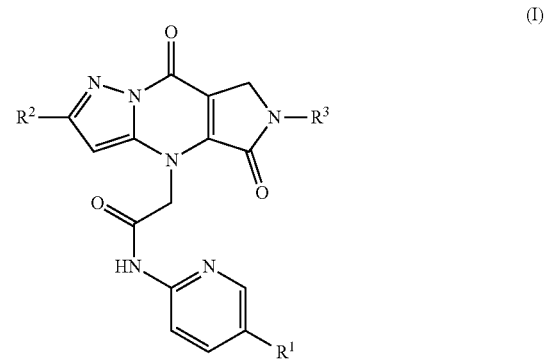

11 Claims, No Drawings

(56) References Cited

OTHER PUBLICATIONS

Cockayne et al (2000). "Urinary bladder hyporeflexia and reduced pain-related behaviour in P2X3-deficient mice" Nature 407: 1011-1015.
Coumar, M.S. et al. (2008). "Aurora kinase A inhibitors: Identification, SAR exploration and molecular modeling of 6,7-dihydro-4H-pyrazolo-[1,5-a]pyrrolo[3,4-d]pyrimidine-5,8-dione scaffold," Bioorganic & Medicinal Chemistry Letters, 18:1623-1627.
Cross et al. (1976). "International Union of Pure And Applied Chemistry: Organic Chemistry Division Commission on Nomenclature of Organic Chemistry" Pure & Appl. Chem. 45:11-30.
El Tayar, N. et al. (1984) "The lipophilicity of deuterium atoms. A comparison of shake-flask and HPLC methods," Int J Pharm; 19(3), 271-281.
Fabbretti, E. (2013). "ATP P2X3 receptors and neuronal sensitization," Frontiers in Cellular Neuroscience, 7(236):1-6.
Finger et al (2005). "ATP signaling is crucial for communication from taste buds to gustatory nerves" Science 310: 1495-1499.
Ford (2012). "In pursuit of P2X3 antagonists: novel therapeutics for chronic pain and afferent sensitization" Purinergic Signal. 8 (suppl 1):S3-S26.
Ford (2012). "P2X3 antagonists: Novel therapeutics for afferent sensitization and chronic pain" Pain Manag. 2(3):267-277.
Ford (2014). "P2X3 antagonism with AF-219: Clinical potential and findings" abstract at Purines 2014, International Conference on Nucleotides, Nucleosides and Nucleobases, published in Purinergic Siqnal. 10:657-854 at 662-663.
Ford et al (2013). "Inhibition of ATP-gated P2X3 channels by AF-219: An effective anti-tussive mechanism in chronic cough" abstract 7026 at European Respiratory Society Annual Congress, one page.
Ford, A.P. (2014). "P2X3 Antagonism for Sensitization-driven Signs and Symptoms of Common Diseases: POC Results in Distressing Respiratory, Somatosensory and Visceral Conditions," The 8th Annual Pain & Migraine Therapeutics Summit, Nov. 5 & 6, 2014, Agenda 1-12.
Ford, A.P. et al. (2013). "The therapeutic promise of ATP antagonism at P2X3 receptors in respiratory and urological disorders," Frontiers in Cellular Neuroscience, 7(267): 1-10.
Garcia-Guzman et al (1997). "Molecular characterization and pharmacological properties of the human P2X3 purinoceptor" Mol. Brain Res. 47:59-66.
Jiang (2012). "P2X receptor-mediated ATP purinergic signaling in health and disease" Cell Health Cytoskeleton 4:83-101.
Joseph et al (2013). "Role of endothelial cells in antihyperalgesia induced by a triptan and β-blocker" Neurosci. 232:83-89.
Kinnamon et al (2013). "A taste for ATP: Neurotransmission in taste buds" Front. Cell. Neurosci. 7:264, 1-7.
Macintyre, E.H. et al. (1972). "The Ultrastructure of Human and Murine Astrocytes and of Human Fibroblasts in Culture," Acta Path. Microbiol. Scand. Section A. 80:267-283.
Maltais, F. et al. (2009). "In Vitro and In Vivo Isotope Effects with Hepatitis C Protease Inhibitors: Enhanced Plasma Exposure of Deuterated Telaprevir versus Telaprevir in Rats," J. Med. Chem.; 52(24):7993-8001.
Milligan, G. et al. (1996). "G16 as a universal G protein adapter: implications for agonist screening strategies," Current Awareness, 17:235-237.
Mutlib, A.E. et al. (2000). "The Species-Dependent Metabolism of Efavirenz Produces a Nephrotoxic Glutathione Conjugate in Rats," Toxicology and Applied Pharmacology, 169:102-113.
Perrin, C. et al. (2005) "Stereochemistry of β-Deuterium Isotope Effects on Amine Basicity," J Am Chem Soc; 127:9641-9647.
Perrin, C. et al. (2007). "Secondary Deuterium Isotope Effects on the Acidity of Carboxylic Acids and Phenols," J. Am. Chem. Soc.; 129(14):4490-4497.
Prado et al (2013). "Neuronal P2X3 receptor activation is essential to the hyperalgesia induced by prostaglandins and sympathomimetic amines released during inflammation" Neuropharm. 67:252-258.
Saul et al (2013). "Heteromeric assembly of P2X subunits" Front. Cell. Neurosci. 7:250, 1-20.
Schneider, F. et al. (2006). Enhanced Plasma Concentration by Selective Deuteration of Rofecoxib in Rats, Arzneim.-Forsch./Drug Res.; 56(4):295-300.
Sharma, A. et al. (2013). "Nevirapine Bioactivation and Covalent Binding in the Skin," Chem. Res. Toxicol.; 26:410-421.
Souslova et al (2000). "Warm-coding deficits and aberrant inflammatory pain in mice lacking P2X3 receptors" Nature 407:1015-1017.
Strand, V. et al. (2014). "An Exploratory 4-Week Study of a P2X3 Antagonist AF-219 in the Treatment of Patients with Osteoarthritis (OA) of the Knee," ACR/ARHP Annual Meeting, Abstract No. 2240, 1-2.
Tjio, J.H. et al. (1958). "Genetics of Somatic Mammalian Cells," The Journal of Experimental Medicine, 108:259-271.
Vandenbeuch et al (2015). "Postsynaptic P2X3-containing receptors in gustatory nerve fibres mediate responses to all taste qualities in mice" J. Physiol. 593:1113-1125.
Wenthur, C. et al. (2013). "Discovery of (R)-(2-Fluoro-4-((-4-methoxyphenyl)ethynyl)phenyl) (3-Hydroxypiperidin-1-yl) methanone (ML337), An mGlu3 Selective and CNS Penetrant Negative Allosteric Modulator (NAM)," J. Med. Chem.; 56:5208-5212.
North (2003). "P2X3 receptors and peripheral pain mechanisms" J. Physiol. 554:301-308.

PYRAZOLO-PYRROLO-PYRIMIDINE-DIONE DERIVATIVES AS P2X3 INHIBITORS

CROSS REFERENCE TO RELATED APPLICATIONS

This application is a national stage application under 35 U.S.C. § 371 of International Application No. PCT/EP2018/078567, filed internationally on Oct. 18, 2018, which claims the benefit of European Application No. 17198769.6, filed Oct. 27, 2017.

The present invention covers substituted Pyrazolo-pyrrolo-pyrimidine-dione derivatives (PPPD compounds) of general formula (I) as described and defined herein, methods of preparing said compounds, pharmaceutical compositions and combinations comprising said compounds, and the use of said compounds for manufacturing pharmaceutical compositions for the treatment or prophylaxis of diseases, in particular of neurogenic disorders, as a sole agent or in combination with other active ingredients.

BACKGROUND

P2X purinoceptor 3 is a protein that in humans is encoded by the P2RX3 gene (Garcia-Guzman M, Stuhmer W, Soto F (September 1997). "Molecular characterization and pharmacological properties of the human P2X3 purinoceptor". Brain Res Mol Brain Res 47 (1-2): 59-66). The product of this gene belongs to the family of purinoceptors for ATP. This receptor functions as a ligand-gated ion channel and transduces ATP-evoked nociceptor activation.

P2X purinoreceptors are a family of ligand-gated ion channels that are activated by ATP. To date, seven members of this family have been cloned, comprising P2X1-7 [Burnstock 2013, front Cell Neurosci 7:227]. These channels can exist as homomers and heteromers [Saul 2013, front Cell Neurosci 7:250]. Purines, such as ATP, have been recognized as important neurotransmitters and by acting via their respective receptors they have been implicated in various physiological and pathophysiological roles [Burnstock 1993, Drug Dev Res 28:196-206; Burnstock 2011, Prog Neurobiol 95:229-274; Jiang 2012, Cell Health Cytoskeleton 4:83-101].

Among the P2X family members, in particular the P2X3 receptor has been recognized as an important mediator of nociception [Burnstock 2013, Eur J Pharmacol 716:24-40; North 2003, J Phyiol 554:301-308; Chizh 2000, Pharmacol Rev 53:553-568]. It is mainly expressed in dorsal root ganglia in a subset of nociceptive sensory neurons. During inflammation the expression of the P2X3 receptor is increased, and activation of P2X3 receptor has been described to sensitize peripheral nerves [Fabretti 2013, front Cell Neurosci 7:236].

The prominent role of the P2X3 receptor in nociception has been described in various animal models, including mouse and rat models for acute, chronic and inflammatory pain. P2X3 receptor knock-out mice show a reduced pain response [Cockayne 2000, Nature 407:1011-1015; Souslova 2000, Nature 407:1015-1017]. P2X3 receptor antagonists have been shown to act anti-nociceptive in different models of pain and inflammatory pain [Ford 2012, Purin Signal 8 (Suppl 1):53-526]. The P2X3 receptor has also been shown to integrate different nociceptive stimuli. Hyperalgesia induced by PGE2, ET-1 and dopamine have all been shown to be mediated via release of ATP and activation of the P2X3 receptor [Prado 2013, Neuropharm 67:252-258; Joseph 2013, Neurosci 232C: 83-89].

Besides its prominent role in nociception and in pain-related diseases involving both chronic and acute pain, the P2X3 receptor has been shown to be involved in genitourinary, gastrointestinal and respiratory conditions and disorders, including overactive bladder and chronic cough [Ford 2013, front Cell Neurosci 7:267; Burnstock 2014, Purin Signal 10(1):3-50]. ATP-release occurs in these 2 examples from epithelial cells, which in turn activates the P2X3 receptor and induces contraction of bladder and lung muscles respectively leading to premature voiding or cough.

P2X3 subunits do not only form homotrimers but also heterotrimers with P2X2 subunits. P2X3 subunits and P2X2 subunits are also expressed on nerve fibres innervating the tongue, therein taste buds [Kinnamon 2013, front Cell Neurosci 7:264]. In a phyiosological setting, receptors containing P2X3 and/or P2X2 subunits are involved in the transmission of taste from the tongue (bitter, sweet, salty, umami and sour). Recent data show that while blocking the P2X3 homomeric receptor alone is important to achieve anti-nociceptive efficacy, non-selective blockade of both the P2X3 homomeric receptor and the P2X2/3 heteromeric receptor leads to changes in taste perception which might limit the therapeutic use of non-selective P2X3 and P2X2/3 receptor antagonists [Ford 2014, purines 2014, abstract book p15]. Therefore, compounds that differentiate between P2X3 and P2X2/3 receptors are highly desirable.

Compounds blocking both the exclusively P2X3 subunit containing ion channel (P2X3 homomer) as well as the ion channel composed of P2X2 and P2X3 subunit (P2X2/3 heterotrimer) are called P2X3 and P2X2/3 nonselective receptor antagonists [Ford, Pain Manag 2012]. Clinical Phil trials demonstrated that AF-219, a P2X3 antagonist, leads to taste disturbances in treated subjects by affecting taste sensation via the tongue [e.g. Abdulqawi et al, Lancet 2015; Strand et al, 2015 ACR/ARMP Annual Meeting, Abstract 2240]. This side effect has been attributed to the blockade of P2X2/3 channels, i.e. the heterotrimer [A. Ford, London 2015 Pain Therapeutics Conference, congress report]. Both P2X2 and P2X3 subunits are expressed on sensory nerve fibers innervating the tongue. Knock-out animals deficient for P2X2 and P2X3 subunits show reduced taste sensation and even taste loss [Finger et al, Science 2005], whereas P2X3 subunit single knock-outs exhibit a mild or no change in phenotype with respect to taste. Moreover, 2 distinct populations of neurons have been described in the geniculate ganglion expressing either P2X2 and P2X3 subunits or P2X3 subunit alone. In an in vivo setting assessing taste preference towards an artificial sweetener via a lickometer, only at very high free plasma levels (>100 μM) effects on taste were observed, indicating that rather the P2X2 and P2X3 subunits expressing population plays a major role in taste sensation than the P2X3 subunit expressing population [Vandenbeuch et al, J Physiol. 2015]. Hence, as a modified taste perception has profound effects on the quality of life of patients, P2X3-homomeric receptor-selective antagonists are deemed to be superior towards non-selective receptor antagonists and are considered to represent a solution towards the problem of insufficient patient compliance during chronic treatment as indicated by increased drop-out rates during Phil trials [Strand et al, 2015 ACR/ARMP Annual Meeting, Abstract 2240 and A. Ford, London 2015 Pain Therapeutics Conference, congress report].

Pyrazolo-pyrrolo-pyrimidine-dione derivatives have been disclosed in prior art for the treatment or prophylaxis of different diseases:

In WO1990/01031 novel pyrazolo-pyrrolo-pyrimidine-diones have been found to be very useful to treat warmblooded animal patients suffering from the symptoms of atherosclerosis and cholesterol build up to relieve the same and for favourably altering the high density lipoprotein (HDL) to low density lipoprotein (LDL) ration in blood samples of such patients.

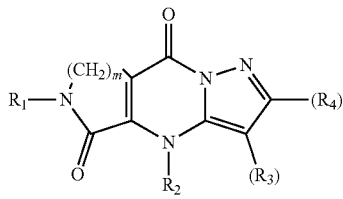

WO2007/150025 discloses novel purinone derivatives which are agonists of the HM7 4a receptor. Those compounds are useful in the treatment of a variety of diseases, such as cardiovascular diseases.

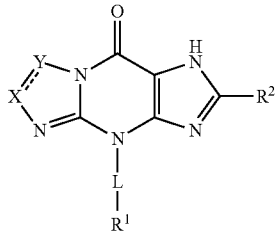

WO2001/034127 discloses phenyl acetamides that inhibit acyl-coenzyme A:cholesterol acyltransferase are known as ACAT inhibitors.

WO2013/185124 discloses broad-spectrum antimicrobial compounds of the following formula

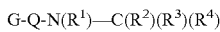

which generically encompasses Pyrazolo-pyrrolo-pyrimidine-dione (PPPD). However, pyridinyl derivatives are not covered by this formula.

So, the state of the art described above does not describe the specific pyrazolo-pyrrolo-pyrimidine-dione (PPPD) compounds of general formula (I) of the present invention as defined herein or an isomer, enantiomer, diastereomer, racemate, hydrate, solvate, or a salt thereof, or a mixture of same, as described and defined herein, and as hereinafter referred to as "compounds of the present invention", or their pharmacological activity.

Therefore, the underlying problem of the present invention therefore lies in the provision of novel PPPD compounds which are useful for treatment of diseases associated with the P2X3 receptor.

DESCRIPTION OF THE INVENTION

In accordance with a first aspect, the present invention covers compounds of general formula (I):

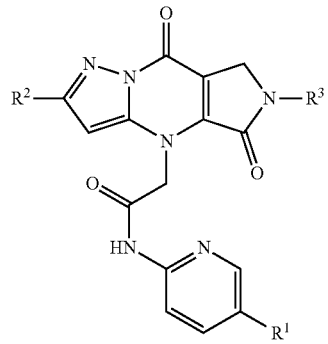

in which $R^1$ represents H, $C_1$-$C_6$-alkyl, $C_3$-$C_5$-cycloalkyl, —($C_1$-$C_3$-alkyl)-($C_3$-$C_5$-cycloalkyl) or halogen, wherein said $C_1$-$C_6$-alkyl, $C_3$-$C_5$-cycloalkyl and —($C_1$-$C_3$-alkyl)-($C_3$-$C_5$-cycloalkyl) are optionally substituted with one or more fluorine atoms;

$R^2$ represents

H,
OH,
halogen,
—CN,
—$CO_2$H,
—C(O)$R^5$,
—C(O)O$R^5$,
—C(O)$NH_2$,
—C(O)N($R^4$)($R^5$),
$NH_2$,
—N($R^4$)($R^5$),
—N($R^4$)C(O)$R^5$,
—N($R^4$)—C(O)O$R^5$,
—N($R^4$)C(O)N($R^4$)($R^5$),
—N($R^4$)$SO_2R^5$,
—$SO_2R^8$,
—$SO_2$N($R^8$)($R^9$),
$C_1$-$C_6$-alkyl, optionally substituted with 1 to 3 substituents $R^{2a}$ which are the same or different,
$C_2$-$C_6$-alkenyl, optionally substituted with 1 to 3 substituents $R^{2a}$ which are the same or different,
$C_2$-$C_6$-alkynyl, optionally substituted with 1 to 3 substituents $R^{2a}$ which are the same or different,
$C_3$-$C_7$-cycloalkyl, optionally substituted with one or more substituents $R^{2b}$ which are the same or different,
—$C_1$-$C_6$-alkyl, optionally substituted with 1 to 3 substituents $R^{2a}$ which are the same or different,
—O$C_3$-$C_7$-cycloalkyl, optionally substituted with one or more substituents $R^{2b}$ which are the same or different,
4- to 6-membered heterocycloalkyl, wherein said 4- to 6-membered heterocycloalkyl contains 1 or 2 heteroatoms or heteroatom-containing groups independently selected from N, NH, N($R^{2c}$), O, S, SO and $SO_2$, and wherein said 4- to 6-membered heterocycloalkyl is optionally substituted at one or more carbon atoms with 1 to 4 substituents $R^{2d}$ which are the same or different, and wherein optionally in said 4- to 6-membered heterocycloalkyl one —$CH_2$— group adjacent to a nitrogen atom, if present, is replaced by a —C(═O)— group,
5- to 6-membered heterocycloalkenyl, wherein said 5- to 6-membered heterocycloalkenyl contains 1 or 2 heteroatoms or heteroatom-containing groups independently selected from N, NH, N($R^{2c}$), O, S, SO and $SO_2$, and wherein said 5- to 6-membered heterocycloalkenyl is optionally substituted at one or more carbon atoms with 1 to 4 substituents $R^{2d}$ which are the same or different, and wherein optionally in said 5- to 6-membered heterocycloalkenyl one —$CH_2$— group adjacent to a nitrogen atom, if present, is replaced by a —C(=O)— group, 6- to 9-membered heterobicycloalkyl, wherein said 6- to 9-membered heterobicycloalkyl contains 1 or 2 heteroatoms or heteroatom-containing groups independently selected from N, NH, N($R^{2c}$), O, S, SO and $SO_2$, and wherein said 6- to 9-membered heterobicycloalkyl is optionally substituted at one or more carbon atoms with 1 to 4 substituents $R^{2d}$ which are the same or different, and wherein optionally in said 6- to 9-membered heterobicycloalkyl one —$CH_2$— group adjacent to a nitrogen atom, if present, is replaced by a —C(=O)— group, phenyl, optionally substituted with 1 to 3 substituents $R^{2d}$ which are the same or different, or 5- or 6-membered heteroaryl, wherein said 5-membered heteroaryl contains 1, 2 or 3 heteroatoms or heteroatom-containing groups independently selected from the group consisting of S, N, NH, N($R^{2c}$) and O, and wherein said 6-membered heteroaryl contains 1 or 2 N, and wherein said 5- or 6-membered heteroaryl is optionally substituted at one or more carbon atoms with 1 to 3 substituents $R^{2d}$ which are the same or different;

$R^{2a}$ represents $C_3$-$C_5$-cycloalkyl, optionally substituted with 1 to 3 substituents $R^{10}$ which are the same or different,

F,

Cl,

OH,

O($R^6$),

CN,

—C(O)$NH_2$,

—C(O)N($R^4$)($R^5$),

N($R^4$)($R^5$),

—N($R^4$)C(O)$R^5$, 4- to 6-membered heterocycloalkyl containing 1 or 2 heteroatoms or heteroatom-containing groups independently selected from N, NH, N($R^7$), O, S, SO and $SO_2$, and wherein said 4- to 6-membered heterocycloalkyl is optionally substituted at one or more carbon atoms with 1 to 4 substituents $R^{10}$ which are the same or different, and wherein optionally in said 4- to 6-membered heterocycloalkyl one —$CH_2$— group adjacent to a nitrogen atom, if present, is replaced by a —C(=O)— group, 5- to 6-membered heterocycloalkenyl containing 1 or 2 heteroatoms or heteroatom-containing groups independently selected from N, NH, N($R^7$), O, S, SO and $SO_2$, and wherein said 5- to 6-membered heterocycloalkenyl is optionally substituted at one or more carbon atoms with 1 to 4 substituents $R^{10}$ which are the same or different, and wherein optionally in said 5- to 6-membered heterocycloalkenyl one —$CH_2$— group adjacent to a nitrogen atom, if present, is replaced by a —C(=O)— group, 6- to 9-membered heterobicycloalkyl containing 1 or 2 heteroatoms or heteroatom-containing groups independently selected from N, NH, N($R^7$), O, S, SO and $SO_2$, and wherein said 6- to 9-membered heterobicycloalkyl is optionally substituted at one or more carbon atoms with 1 to 4 substituents $R^{10}$ which are the same or different, and wherein optionally in said 6- to 9-membered heterobicycloalkyl one —$CH_2$— group adjacent to a nitrogen atom, if present, is replaced by a —C(=O)— group, or 5- or 6-membered heteroaryl wherein said 5-membered heteroaryl contains 1, 2 or 3 heteroatoms or heteroatom-containing groups independently selected from S, N, NH, N($R^7$) and O, and wherein said 6-membered heteroaryl contains 1 or 2 N, and wherein said 5- or 6-membered heteroaryl is optionally substituted at one or more carbon atoms with 1 to 3 substituents $R^{10}$ which are the same or different;

$R^{2b}$ represents $C_1$-$C_4$-alkyl, Cl, F, OH, —C(O)N($R^4$)($R^5$), N($R^4$)($R^5$), —N($R^4$)C(O)$R^5$ or 4- to 6-membered heterocycloalkyl containing 1 or 2 heteroatoms or heteroatom-containing groups independently selected from NH, N, N($R^7$), O and $SO_2$, and wherein said $C_1$-$C_4$-alkyl and 4- to 6-membered heterocycloalkyl are optionally substituted at one or more carbon atoms with 1 to 4 substituents $R^{10}$ which are the same or different;

$R^{2c}$ represents $C_1$-$C_4$-alkyl, $C_3$-$C_5$-cycloalkyl, —($C_1$-$C_3$-alkyl)-($C_3$-$C_5$-cycloalkyl), —C(O)$R^5$, —C(O)O$R^5$, —$SO_2R^8$, or 4- to 6-membered heterocycloalkyl containing 1 or 2 heteroatoms or heteroatom-containing groups independently selected from N, NH, N($R^7$), O and $SO_2$; and wherein said $C_1$-$C_4$-alkyl, $C_3$-$C_5$-cycloalkyl, ($C_1$-$C_3$-alkyl)-($C_3$-$C_5$-cycloalkyl) and 4- to 6-membered heterocycloalkyl are optionally substituted at one or more carbon atoms with 1 to 4 substituents $R^{10}$ which are the same or different;

$R^{2d}$ represents F, Cl, OH, CN, —C(O)N($R^4$)($R^5$), N($R^4$)($R^5$), —N($R^4$)C(O)$R^5$, $C_1$-$C_4$-alkyl, $C_3$-$C_5$-cycloalkyl, —O$C_1$-$C_4$-alkyl, —O$C_3$-$C_5$-cycloalkyl or 4- to 6-membered heterocycloalkyl containing 1 or 2 heteroatoms or heteroatom-containing groups selected from N, NH, N($R^7$), O and $SO_2$; and wherein said $C_1$-$C_4$-alkyl, $C_3$-$C_5$-cycloalkyl, —O$C_1$-$C_4$-alkyl, —O$C_3$-$C_5$-cycloalkyl and 4- to 6-membered heterocycloalkyl are optionally substituted at one or more carbon atoms with 1 to 4 substituents $R^{10}$ which are the same or different;

$R^3$ represents $C_1$-$C_6$-alkyl, optionally substituted with 1 to 3 substituents $R^{3a}$ which are the same or different, $C_3$-$C_7$-cycloalkyl, optionally substituted with one or more substituents $R^{3b}$ which are the same or different, 4- to 6-membered heterocycloalkyl, wherein said 4- to 6-membered heterocycloalkyl is linked through a carbon atom and contains 1 or 2 heteroatoms or heteroatom-containing groups independently selected from N, NH, N($R^{3c}$), O, S, SO and $SO_2$, and wherein said 4- to 6-membered heterocycloalkyl is optionally substituted at one or more carbon atoms with 1 to 4 substituents $R^{3d}$ which are the same or different, 6- to 9-membered heterobicycloalkyl, wherein said 6- to 9-membered heterobicycloalkyl is linked through a carbon atom and contains 1 or 2 heteroatoms or heteroatom-containing groups independently selected from N, NH, N($R^{3c}$), O, S, SO and $SO_2$, and wherein said 6- to 9-membered heterobicycloalkyl is optionally substituted at one or more carbon atoms with 1 to 4 substituents $R^{3d}$ which are the same or different, phenyl, optionally substituted with 1 to 3 substituents $R^{3d}$ which are the same or different, or 5- or 6-membered heteroaryl, wherein said 5-membered heteroaryl is linked through a carbon atom and contains 1, 2 or 3 heteroatoms or heteroatom-containing groups independently selected from the group consisting of S, N, NH, N($R^{3c}$) and O, and wherein said 6-membered heteroaryl is linked through a carbon atom and contains 1 or 2 N, and wherein said 5- or 6-membered heteroaryl is optionally substituted at one or more carbon atoms with 1 to 3 substituents $R^{3d}$ which are the same or different;

$R^{3a}$ represents
  $C_3$-$C_5$-cycloalkyl, optionally substituted at one or more carbon atoms with 1 to 3 substituents $R^{10}$ which are the same or different,
  F,
  Cl,
  OH,
  O($R^6$),
  —CN,
  —C(O)$NH_2$,
  —C(O)N($R^4$)($R^5$),
  —N($R^4$)($R^5$),
  —$NH_2$,
  —N($R^4$)C(O)$R^5$,
  —N($R^4$)—C(O)O$R^5$,
  4- to 6-membered heterocycloalkyl containing 1 or 2 heteroatoms or heteroatom-containing groups independently selected from N, NH, N($R^7$), O, S, SO and $SO_2$, and wherein said 4- to 6-membered heterocycloalkyl is optionally substituted at one or more carbon atoms with 1 to 4 substituents $R^{10}$ which are the same or different, and wherein optionally in said 4- to 6-membered heterocycloalkyl one —$CH_2$— group adjacent to a nitrogen atom, if present, is replaced by a —C(=O)— group,
  5- to 6-membered heterocycloalkenyl containing 1 or 2 heteroatoms or heteroatom-containing groups independently selected from N, NH, N($R^7$), O, S, SO and $SO_2$, and wherein said 5- to 6-membered heterocycloalkenyl is optionally substituted at one or more carbon atoms with 1 to 4 substituents $R^{10}$ which are the same or different, and wherein optionally in said 5- to 6-membered heterocycloalkenyl one —$CH_2$— group adjacent to a nitrogen atom, if present, is replaced by a —C(=O)— group,
  6- to 9-membered heterobicycloalkyl containing 1 or 2 heteroatoms or heteroatom-containing groups independently selected from N, NH, N($R^7$), O and $SO_2$, and wherein said 6- to 9-membered heterobicycloalkyl is optionally substituted at one or more carbon atoms with 1 to 4 substituents $R^{10}$ which are the same or different, and wherein optionally in said 6- to 9-membered heterobicycloalkyl one —$CH_2$— group adjacent to a nitrogen atom, if present, is replaced by a —C(=O)— group,
  phenyl, optionally substituted with 1 to 3 substituents $R^{10}$ which are the same or different, or
  5- or 6-membered heteroaryl, wherein said 5-membered heteroaryl contains 1, 2 or 3 heteroatoms or heteroatom-containing groups independently selected from S, N, NH, N($R^7$) and O, and wherein said 6-membered heteroaryl contains 1 or 2 N, and wherein said 5- or 6-membered heteroaryl is optionally substituted at one or more carbon atoms with 1 to 3 substituents $R^{10}$ which are the same or different;

$R^{3b}$ represents $C_1$-$C_4$-alkyl, Cl, F, OH, —C(O)N($R^4$)($R^5$), —N($R^4$)C(O)($R^5$), —N($R^4$)($R^5$) or 4- to 6-membered heterocycloalkyl containing 1 or 2 heteroatoms or heteroatom-containing groups independently selected from NH, N, N($R^7$), O and $SO_2$, and wherein said $C_1$-$C_4$-alkyl and 4- to 6-membered heterocycloalkyl are optionally substituted with one or more substituents $R^{10}$ which are the same or different;

$R^{3c}$ represents $C_1$-$C_4$-alkyl, $C_3$-$C_5$-cycloalkyl, —C(O)$R^5$, —C(O)O$R^5$, —$SO_2R^3$, —C(O)N($R^4$)($R^5$), or 4- to 6-membered heterocycloalkyl containing 1 or 2 heteroatoms or heteroatom-containing groups independently selected from N, NH, N($R^7$), O and $SO_2$; and
  wherein said $C_1$-$C_4$-alkyl, $C_3$-$C_5$-cycloalkyl and 4- to 6-membered heterocycloalkyl are optionally substituted with one or more substituents $R^{10}$ which are the same or different;

$R^{4d}$ represents $C_1$-$C_4$-alkyl, $C_3$-$C_5$-cycloalkyl, F, Cl, OH, O($R^6$), CN, —C(O)N($R^4$)($R^5$), —N($R^4$)($R^5$), —N($R^4$)C(O)$R^5$, or 4- to 6-membered heterocycloalkyl containing 1 or 2 heteroatoms or heteroatom-containing groups independently selected from N, NH, N($R^7$), O and $SO_2$; and
  wherein said $C_1$-$C_4$-alkyl, $C_3$-$C_5$-cycloalkyl and 4- to 6-membered heterocycloalkyl are optionally substituted at one or more carbon atoms with 1 to 4 substituents $R^{10}$ which are the same or different;

$R^4$ represents H, $C_1$-$C_4$-alkyl or —($C_1$-$C_3$-alkyl)$_n$-($C_3$-$C_5$-cycloalkyl), wherein said $C_1$-$C_4$-alkyl and —($C_1$-$C_3$-alkyl)$_n$($C_3$-$C_5$-cycloalkyl) are optionally substituted with OH or 1 to 5 fluorine atoms;

$R^5$ represents
  $C_1$-$C_6$-alkyl, optionally substituted with 1 to 3 substituents $R^{5a}$ which are the same or different,
  $C_3$-$C_6$-cycloalkyl, optionally substituted with 1 to 3 substituents $R^{5b}$ which are the same or different,
  —($C_1$-$C_3$-alkyl)$_n$-(4- to 6-membered heterocycloalkyl), wherein said 4- to 6-membered heterocycloalkyl contains 1 or 2 heteroatoms or heteroatom-containing groups independently selected from NH, N, N($R^{5c}$), O, S, SO and $SO_2$, and wherein optionally in said 4- to 6-membered heterocycloalkyl one —$CH_2$— group adjacent to a nitrogen atom, if present, is replaced by a —C(=O)— group, and wherein said —($C_1$-$C_3$-alkyl)$_n$-(4- to 6-membered heterocycloalkyl) is optionally substituted at one or more carbon atoms with 1 to 4 substituents $R^{5d}$ which are the same or different;
  5- to 6-membered heterocycloalkenyl, wherein said 5- to 6-membered heterocycloalkenyl contains 1 or 2 heteroatoms or heteroatom-containing groups independently selected from N, NH, N($R^{5c}$), O, S, SO and $SO_2$, and wherein said 5- to 6-membered heterocycloalkenyl is optionally substituted at one or more carbon atoms with 1 to 4 substituents $R^{5d}$ which are the same or different, and wherein optionally in said 5- to 6-membered heterocycloalkenyl one —$CH_2$— group adjacent to a nitrogen atom, if present, is replaced by a —C(=O)— group;
  —($C_1$-$C_3$-alkyl)$_n$-(6- to 9-membered heterobicycloalkyl), wherein said 6- to 9-membered heterobicycloalkyl contains 1 or 2 heteroatoms or heteroatom-containing groups independently selected from NH, N, N($R^{5c}$), O, S, SO and $SO_2$, and wherein optionally in said 6- to 9-membered heterobicycloalkyl one —$CH_2$— group adjacent to a nitrogen atom, if present, is replaced by a —C(=O)— group, and wherein said —($C_1$-$C_3$-alkyl)$_n$-(6- to 9-membered heterobicycloalkyl) is optionally substituted at one or more carbon atoms with 1 to 4 substituents $R^{5d}$ which are the same or different;
  —($C_1$-$C_3$-alkyl)$_n$-phenyl, optionally substituted with 1 to 3 substituents $R^{5d}$ which are the same or different, or —($C_1$-$C_3$-alkyl)$_n$-(5- or 6-membered heteroaryl), wherein said 5-membered heteroaryl contains 1, 2 or 3 heteroatoms or heteroatom-containing groups independently selected from the group consisting of S, N, NH, N($R^{5c}$), and O, and wherein said 6-membered heteroaryl contains 1 or 2 N, and wherein said —($C_1$-$C_3$-alkyl)$_n$-(5- or 6-membered heteroaryl) is optionally substituted at one or more carbon atoms with 1 to 3 substituents $R^{5d}$ which are the same or different;

or $R^4$ and $R^5$ may be conjoined to form together with the nitrogen to which $R^4$ and $R^5$ are attached a 4- to 6-membered heterocycloalkyl, optionally containing 1 additional heteroatom or heteroatom-containing group independently selected from NH, N($R^{14}$), O and $SO_2$, and wherein optionally in said 4- to 6-membered heterocycloalkyl one —$CH_2$— group adjacent to a nitrogen atom, if present, is replaced by a —C(=O)— group, and wherein said 4- to 6-membered heterocycloalkyl is optionally substituted at one or more carbon atoms with 1 to 4 substituents $R^{13}$ which are the same or different, or 6- to 9-membered heterobicycloalkyl, optionally containing 1 additional heteroatom or heteroatom-containing group independently selected from NH, N($R^{14}$), O and $SO_2$, and wherein said 6- to 9-membered heterobicycloalkyl is optionally substituted at one or more carbon atoms with 1 to 4 substituents $R^{13}$ which are the same or different;

$R^{5a}$ represents OH, F, Cl, $C_3$-$C_5$-cycloalkyl, $OC_1$-$C_4$-alkyl, —C(O)N($R^{11}$)($R^{12}$), N($R^{11}$)($R^{12}$), or —N($R^{11}$)C(O)$R^{12}$, wherein said $C_3$-$C_5$-cycloalkyl and $OC_1$-$C_4$-alkyl are optionally substituted with OH, 1 to 5 fluorine atoms or phenyl, optionally substituted with 1 to 3 substituents $R^{5d}$ which are the same or different;

$R^{5b}$ represents OH, F, Cl, $C_1$-$C_4$-alkyl, $OC_1$-$C_4$-alkyl, —C(O)N($R^{11}$)($R^{12}$), N($R^{11}$)($R^{12}$), or —N($R^{11}$)C(O)$R^{12}$, wherein said $C_1$-$C_4$-alkyl and $OC_1$-$C_4$-alkyl are optionally substituted with OH or 1 to 5 fluorine atoms;

$R^6$ represents $C_1$-$C_4$-alkyl, —($C_1$-$C_3$-alkyl)$_n$-($C_3$-$C_5$-cycloalkyl), or —C(O)($R^{11}$)($R^{12}$), wherein said $C_1$-$C_4$-alkyl and —($C_1$-$C_3$-alkyl)$_n$-($C_3$-$C_5$-cycloalkyl) are optionally substituted with OH or 1 to 5 fluorine atoms;

$R^{5d}$ represents OH, F, Cl, $C_1$-$C_4$-alkyl, $OC_1$-$C_4$-alkyl, $C_3$-$C_5$-cycloalkyl, —C(O)N($R^{11}$)($R^{12}$), N($R^{11}$)($R^{12}$), or —N($R^{11}$)C(O)$R^{12}$, wherein said $C_1$-$C_4$-alkyl, $OC_1$-$C_4$-alkyl and $C_3$-$C_5$-cycloalkyl are optionally substituted with OH or 1 to 5 fluorine atoms;

$R^6$ represents $C_1$-$C_6$-alkyl, —($C_1$-$C_3$-alkyl)$_n$-($C_3$-$C_5$-cycloalkyl), —($C_1$-$C_3$-alkyl)$_n$-phenyl or —($C_1$-$C_3$-alkyl)$_n$-(6-membered heteroaryl) which are optionally substituted at one or more carbon atoms with one or more substituents independently selected from F, Cl, OH and —$OC_1$-$C_4$-alkyl;

$R^7$ represents
—C(O)$R^{12}$,
—C(O)O$R^{12}$,
$C_1$-$C_6$-alkyl, or
—($C_1$-$C_3$-alkyl)$_n$-($C_3$-$C_5$-cycloalkyl); and
wherein said $C_1$-$C_6$-alkyl and —($C_1$-$C_3$-alkyl)$_n$-($C_3$-$C_5$-cycloalkyl) are optionally substituted with one or more substituents independently selected from F, OH and $OC_1$-$C_4$-alkyl;

$R^9$ represents
$C_1$-$C_6$-alkyl,
—($C_1$-$C_3$-alkyl)$_n$-($C_3$-$C_6$-cycloalkyl), 4- to 6-membered heterocycloalkyl, wherein said 4- to 6-membered heterocycloalkyl contains 1 or 2 heteroatoms or heteroatom-containing groups selected from NH, N, N($R^{14}$) or O, —($C_1$-$C_3$-alkyl)$_n$-phenyl, or —($C_1$-$C_3$-alkyl)$_n$-(5- or 6-membered heteroaryl) wherein said 5-membered heteroaryl is linked through a carbon atom and contains 1, 2 or 3 heteroatoms or heteroatom-containing groups independently selected from the group consisting of S, N, NH, N($R^{14}$) and O, and wherein said 6-membered heteroaryl is linked through a carbon atom and contains 1 or 2 N; and wherein said $C_1$-$C_6$-alkyl, —($C_1$-$C_3$-alkyl)$_n$-($C_3$-$C_5$-cycloalkyl), 4- to 6-membered heterocycloalkyl, —($C_1$-$C_3$-alkyl)$_n$-phenyl and —($C_1$-$C_3$-alkyl)$_n$-(5- or 6-membered heteroaryl) are optionally substituted on one or more carbon atoms with 1 to 4 substituents $R^{13}$ which are the same or different;

$R^9$ represents H, $C_1$-$C_4$-alkyl or —($C_1$-$C_3$-alkyl)$_n$-($C_3$-$C_5$-cycloalkyl), wherein said $C_1$-$C_4$-alkyl and —($C_1$-$C_3$-alkyl)$_n$($C_3$-$C_5$-cycloalkyl) are optionally substituted with 1 to 5 fluorine atoms;

or $R^8$ and $R^9$ may be conjoined to form together with the nitrogen to which $R^8$ and $R^9$ are attached a 4- to 6-membered heterocycloalkyl, wherein said 4- to 6-membered heterocycloalkyl optionally contains 1 additional heteroatom or heteroatom-containing groups selected from NH, N($R^{14}$) or O, and wherein said 4- to 6-membered heterocycloalkyl is optionally substituted at one or more carbon atoms with 1 to 4 substituents $R^{13}$ which are the same or different;

$R^{10}$ represents F, Cl, $C_1$-$C_4$-alkyl, $OC_1$-$C_4$-alkyl, —C(O)N($R^{11}$)($R^{12}$), —N($R^{11}$)($R^{12}$), or —N($R^{11}$)C(O)$R^{12}$, wherein said $C_1$-$C_4$-alkyl and $OC_1$-$C_4$-alkyl are optionally substituted with 1 to 5 fluorine atoms;

$R^{11}$ represents H, $C_1$-$C_4$-alkyl or —($C_1$-$C_3$-alkyl)$_n$-($C_3$-$C_5$-cycloalkyl), wherein said $C_1$-$C_4$-alkyl and —($C_1$-$C_3$-alkyl)$_n$($C_3$-$C_5$-cycloalkyl) are optionally substituted with 1 to 5 fluorine;

$R^{12}$ represents $C_1$-$C_4$-alkyl, —($C_1$-$C_3$-alkyl)$_n$-($C_3$-$C_5$-cycloalkyl) or 4- to 6-membered heterocycloalkyl wherein said 4- to 6-membered heterocycloalkyl contains 1 or 2 heteroatoms or heteroatom-containing groups selected from NH, N, N($R^9$) and O, wherein said $C_1$-$C_4$-alkyl and —($C_1$-$C_3$-alkyl)$_n$($C_3$-$C_5$-cycloalkyl) are optionally substituted with 1 to 5 fluorine;

or $R^{11}$ and $R^{12}$ may be conjoined to form together with the nitrogen to which $R^{11}$ and $R^{12}$ are attached a 4- to 6-membered heterocycloalkyl, wherein said 4- to 6-membered heterocycloalkyl optionally contains 1 additional heteroatom or heteroatom-containing groups selected from NH, N($R^{14}$) or O, and wherein said 4- to 6-membered heterocycloalkyl is optionally substituted at one or more carbon atoms with 1 to 4 substituents $R^{13}$ which are the same or different;

$R^{13}$ represents F, Cl, $C_1$-$C_4$-alkyl, $C_3$-$C_5$-cycloalkyl or $OC_1$-$C_4$-alkyl, wherein said $C_1$-$C_4$-alkyl, $C_3$-$C_5$-cycloalkyl and $OC_1$-$C_4$-alkyl are optionally substituted with OH or 1 to 5 fluorine atoms;

$R^{14}$ represents $C_1$-$C_4$-alkyl, —($C_1$-$C_3$-alkyl)$_n$-($C_3$-$C_5$-cycloalkyl) or —C(O)($R^{11}$)($R^{12}$), wherein said $C_1$-$C_4$-alkyl and —($C_1$-$C_3$-alkyl)$_n$($C_3$-$C_5$-cycloalkyl) are optionally substituted with OH or 1 to 5 fluorine atoms;

n represents 0 or 1;

and stereoisomers, N-oxides, hydrates, solvates, and salts thereof, and mixtures of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen or oxygen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)-group. A hyphen at the beginning or at the end of such a composite substituent indicates the point of attachment of said composite substituent to the rest of the molecule. Unless otherwise indicated, should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

The terms as mentioned in the present text have the following meanings:

The term "halogen" or "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methyl butyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl, isobutyl, or tert-butyl group, more particularly 1, 2 or 3 carbon atoms ("$C_1$-$C_3$-alkyl"), e.g. a methyl, ethyl, n-propyl or isopropyl group.

The term "$C_2$-$C_6$-alkenyl" means a linear or branched, monovalent hydrocarbon group, which contains one or two double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then it is possible for said double bonds to be isolated from, or conjugated with, each other. Said alkenyl group is, for example, an ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropyl prop-2-enyl, 1-isopropyl prop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl, buta-1,3-dienyl, penta-1,4-dienyl or hexa-1,5-dienyl group. Particularly, said group is vinyl or allyl.

The term "$C_2$-$C_6$-alkynyl" means a linear or branched, monovalent hydrocarbon group which contains one triple bond, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl (or "propargyl"), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methyl-pent-4-ynyl, 2-methylpent-3-ynyl, 1-methylpent-3-ynyl, 4-methylpent-2-ynyl, 1-methyl-pent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropyl prop-2-ynyl, 2,2-dimethylbut-3-ynyl, 1,1-dimethylbut-3-ynyl, 1,1-dimethylbut-2-ynyl or 3,3-dimethylbut-1-ynyl group. Particularly, said alkynyl group is ethynyl, prop-1-ynyl or prop-2-ynyl.

The term "$C_3$-$C_7$-cycloalkyl" means a saturated, monovalent, mono- or bicyclic hydrocarbon ring which contains 3, 4, 5, 6 or 7 carbon atoms ("$C_3$-$C_7$-cycloalkyl"). Said $C_3$-$C_7$-cycloalkyl group is for example, a monocyclic hydrocarbon ring, e.g. a cyclopropyl, cyclobutyl, cyclopentyl, cyclohexyl or cycloheptyl group. The term "$C_3$-$C_6$-cycloalkyl" means a saturated, monovalent, mono- or bicyclic hydrocarbon ring which contains 3, 4, 5, or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl, or cyclohexyl group. The term "$C_3$-$C_5$-cycloalkyl" means a saturated, monovalent, mono- or bicyclic hydrocarbon ring which contains 3, 4, or 5 carbon atoms ("$C_3$-$C_5$-cycloalkyl"). Said $C_3$-$C_5$-cycloalkyl group is for example, a monocyclic hydrocarbon ring, e.g. a cyclopropyl, cyclobutyl, or cyclopentyl group. The term "4- to 6-membered heterocycloalkyl" means a monocyclic, saturated heterocycle with 4, 5 or 6 ring atoms in total, which contains one or two identical or different ring heteroatoms or heteroatom-containing groups from the series N, NH, N(R$^x$), O, S, SO and SO$_2$ with R$^x$ being R$^{2c}$, R$^{3c}$, R$^{5c}$, R$^7$, and R$^{14}$, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example.

Particularly, "4- to 6-membered heterocycloalkyl" means a 4- to 6-membered heterocycloalkyl as defined supra containing one ring nitrogen atom and optionally one further ring heteroatom or heteroatom-containing groups from the series: N, NH, N(R$^x$), O, S, SO and SO$_2$ with R$^x$ being R$^{2c}$, R$^{3c}$, R$^{5c}$, R$^7$, and R$^{14}$. More particularly, "5- or 6-membered heterocycloalkyl" means a monocyclic, saturated heterocycle with 5 or 6 ring atoms in total, containing one ring nitrogen atom and optionally one further ring heteroatom or heteroatom-containing groups from the series: N, NH, N(R$^x$), O, S, SO and SO$_2$ with x being R$^{2c}$, R$^{3c}$, R$^{5c}$, R$^7$, and R$^{14}$.

The term "5- to 6-membered heterocycloalkenyl" means a monocyclic, unsaturated, non-aromatic heterocycle with 5 or 6 ring atoms in total, which contains one or two double bonds and one or two identical or different ring heteroatoms or heteroatom-containing groups from the series: N, NH, N(R$^x$), O, S, SO and SO$_2$ with R$^x$ being R$^{2c}$, R$^{3c}$, R$^{5c}$, R$^7$, and R$^{14}$; it being possible for said heterocycloalkenyl group to be attached to the rest of the molecule via any one of the carbon atoms or, if present, a nitrogen atom.

Said heterocycloalkenyl group is, for example, 4H-pyranyl, 2H-pyranyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl or 4H-[1,4]thiazinyl.

The term "6- to 9-membered heterobicycloalkyl" is to be understood as meaning a saturated, monovalent bicyclic hydrocarbon radical in which the two rings share one or two common ring atoms, and wherein said bicyclic hydrocarbon radical contains 5, 6, 7 or 8 carbon atoms and one or two heteroatoms or heteroatom-containing groups independently selected from NH, N, N(R$^x$), O, S, SO and SO$_2$ with x being R$^{2c}$, R$^{3c}$, R$^{5c}$, R$^7$, and R$^{14}$, provided that the total number of ring atoms is not greater than 9. It is possible for said 6- to 9-membered heterobicycloalkyl to be attached to the rest of the molecule via any one of the carbon atoms or, if present, a nitrogen atom. Said 6- to 9-membered heterobicycloalkyl is, for example, azabicyclo[3.3.0]octyl, azabicyclo[4.3.0]nonyl, diazabicyclo[4.3.0]nonyl, oxazabicyclo-[4.3.0]nonyl or thiazabicyclo[4.3.0]nonyl.

Heterospirocycloalkyl, fused and bridged heterocycloalkyl as defined below, are also included within the scope of this definition.

The term "heterospirocycloalkyl" means a bicyclic, saturated heterocycle with 6, 7, 8 or 9 ring atoms in total, in which the two rings share one common ring carbon atom, which "heterospirocycloalkyl" contains one or two identical or different ring heteroatoms or heteroatom-containing groups from the series: NH, N, N(R$^x$), O, S, SO and SO$_2$ with R$^x$ being R$^{2c}$, R$^{3c}$, R$^{5c}$, R$^7$, and R$^{14}$; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, azaspiro[4,5]decyl, oxazaspiro [5.5]undecyl, diazaspiro[3.3]heptyl, thiazaspiro[3.3]heptyl, thiazaspiro[4.3]octyl, or one of the further homologous scaffolds such as spiro[3.4]-, spiro[4.4]-, spiro[2.4]-, spiro[2.5]-, spiro[2.6]-, spiro[3.5]-, spiro[3.6]- and spiro[4.5]-.

The term "fused heterocycloalkyl" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl group is, for example, azabicyclo[3.3.0]octyl, azabicyclo[4.3.0]nonyl, diazabicyclo[4.3.0]nonyl, oxazabicyclo[4.3.0]nonyl, thiazabicyclo[4.3.0]-nonyl or azabicyclo[4.4.0]decyl.

The term "bridged heterocycloalkyl" means a bicyclic, saturated heterocycle with 7, 8 or 9 ring atoms in total, in which the two rings share two common ring atoms which are not adjacent, which "bridged heterocycloalkyl" contains one or two identical or different ring heteroatoms from the series: N, O, S; it being possible for said bridged heterocycloalkyl group to be attached to the rest of the molecule via any one of the carbon atoms, except the spiro carbon atom, or, if present, a nitrogen atom.

Said bridged heterocycloalkyl group is, for example, azabicyclo[2.2.1]heptyl, oxazabicyclo[2.2.1]heptyl, thiazabicyclo[2.2.1]heptyl, diazabicyclo[2.2.1]heptyl, azabicyclo-[2.2.2]octyl, diazabicyclo[2.2.2]octyl, oxazabicyclo[2.2.2]octyl, thiazabicyclo[2.2.2]octyl, azabicyclo[3.2.1]octyl, diazabicyclo[3.2.1]octyl, oxazabicyclo[3.2.1]octyl, thiazabicyclo[3.2.1]octyl, azabicyclo[3.3.1]nonyl, diazabicyclo[3.3.1]nonyl, oxazabicyclo[3.3.1]nonyl, thiazabicyclo[3.3.1]-nonyl, azabicyclo[4.2.1]nonyl, diazabicyclo[4.2.1]nonyl, oxazabicyclo[4.2.1]nonyl or thiazabicyclo[4.2.1]nonyl.

The term "heteroaryl" means a monovalent, monocyclic aromatic ring having 5 or 6 ring atoms (a "5- or 6-membered heteroaryl" group), which contains one, two or three further ring heteroatoms or heteroatom-containing groups from the series: S, N, NH, N(RX) and O with RX being R$^{2c}$, R$^{3c}$, R$^{5c}$, R$^7$ and R$^{14}$, and which is bound via a ring carbon atom or optionally via a ring nitrogen atom (if allowed by valency).

Said heteroaryl group can be a 5-membered heteroaryl group, which contains 1, 2 or 3 heteroatoms or heteroatom-containing groups independently selected from the group consisting of S, N, NH, N(R$^x$), and O with x being R$^{2c}$, R$^{3c}$, R$^{5c}$, R$^7$ and R$^{14}$, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, which contains 1 or 2 N, such as, for example, pyridinyl, pyridazinyl, pyrimidinyl or pyrazinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group is a pyridinyl group.

The term "$C_1$-$C_6$", as used in the present text, e.g. in the context of the definition of "$C_1$-$C_6$-alkyl" means an alkyl group having a finite number of carbon atoms of 1 to 6, i.e. 1, 2, 3, 4, 5 or 6 carbon atoms.

Further, as used herein, the term "$C_3$-$C_7$", as used in the present text, e.g. in the context of the definition of "$C_3$-$C_7$-cycloalkyl", means a cycloalkyl group having a finite number of carbon atoms of 3 to 7, i.e. 3, 4, 5, 6 or 7 carbon atoms.

When a range of values is given, said range encompasses each value and sub-range within said range.

For example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_5$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_6$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)-sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$O, $^{14}$C, $^{15}$N, $^{17}$O, $^{18}$O, $^{32}$P, $^{33}$S, $^{33}$S, $^{34}$S, $^{35}$S, $^{36}$S, $^{18}$F, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with a further embodiment of the first aspect, the present invention covers compounds of general formula (I), wherein
$R^1$ represents H, methyl, ethyl, 1-cyclopropylmethyl, F, Cl or Br, wherein said methyl, ethyl and 1-cyclopropylmethyl are optionally substituted with one or more fluorine atoms.

Also preferred are compounds of general formula (I), wherein
$R^1$ represents H, methyl, F, Cl or Br, wherein said methyl is optionally substituted with one or more fluorine atoms.

Also preferred are compounds of general formula (I), wherein
$R^1$ represents H, methyl, F or Cl, wherein said methyl is optionally substituted with one or more fluorine atoms.

Also preferred are compounds of general formula (I), wherein
$R^1$ represents methyl, F or Cl, wherein said methyl is optionally substituted with one or more fluorine atoms.

Also preferred are compounds of general formula (I), wherein
R1 represents F, Cl or methyl.

Also preferred are compounds of general formula (I), wherein
$R^1$ represents F or $C_1$.

Also preferred are compounds of general formula (I), wherein
$R^1$ represents F.

Also preferred are compounds of general formula (I), wherein
$R^1$ represents $C_1$.

In accordance with a further embodiment of the first aspect, the present invention covers compounds of general formula (I), wherein
$R^2$ represents
—H,
Halogen,
—CN,
—C(O)N($R^4$)($R^5$),
—N($R^4$)($R^5$),
—N($R^4$)C(O)$R^5$,
$C_1$-$C_5$-alkyl, optionally substituted with 1 to 3 substituents $R^{2a}$ which are the same or different, $C_3$-$C_7$-cycloalkyl, optionally substituted with one or more substituents $R^{2b}$ which are the same or different, —$OC_1$-$C_6$-alkyl, optionally substituted with 1 to 3 substituents $R^{2a}$ which are the same or different, —$OC_3$-$C_7$-cycloalkyl, optionally substituted with one or more substituents $R^{2b}$ which are the same or different, 4- to 6-membered heterocycloalkyl, wherein said 4- to 6-membered heterocycloalkyl contains 1 or 2 heteroatoms or heteroatom-containing groups independently selected from N, NH, N($R^{2c}$), O, S, SO and $SO_2$, and wherein said 4- to 6-membered heterocycloalkyl is optionally substituted at one or more carbon atoms with 1 to 4 substituents $R^{2d}$ which are the same or different, and wherein optionally in said 4- to 6-membered heterocycloalkyl one —$CH_2$— group adjacent to a nitrogen atom, if present, is replaced by a —C(=O)— group, 6- to 9-membered heterobicycloalkyl, wherein said 6- to 9-membered heterobicycloalkyl contains 1 or 2 heteroatoms or heteroatom-containing groups independently selected from N, NH, N($R^{2c}$), O, S, SO and $SO_2$, and wherein said 6- to 9-membered heterobicycloalkyl is optionally substituted at one or more carbon atoms with 1 to 4 substituents $R^{2d}$ which are the same or different, and wherein optionally in said 6- to 9-membered heterobicycloalkyl one —$CH_2$— group adjacent to a nitrogen atom, if present, is replaced by a —C(=O)— group, phenyl, optionally substituted with 1 to 3 substituents $R^{2d}$ which are the same or different, or 5- or 6-membered heteroaryl, wherein said 5-membered heteroaryl contains 1, 2 or 3 heteroatoms or heteroatom-containing groups independently selected from the group consisting of S, N, NH, N($R^{2c}$) and O, and wherein said 6-membered heteroaryl contains 1 or 2 N, and wherein said 5- or 6-membered heteroaryl is optionally substituted at one or more carbon atoms with 1 to 3 substituents $R^{2d}$ which are the same or different.

In accordance with a further embodiment of the first aspect, the present invention covers compounds of general formula (I), wherein
$R^2$ represents
halogen,
—CN,
—$CO_2H$,
—C(O)O$R^5$,
—C(O)$NH_2$,
—C(O)N($R^4$)($R^5$),
$NH_2$,
—N($R^4$)($R^5$),
—N($R^4$)C(O)$R^5$,
—N($R^4$)—C(O)O$R^5$,
$C_1$-$C_6$-alkyl, optionally substituted with 1 to 3 substituents $R^{2a}$ which are the same or different,
$C_3$-$C_7$-cycloalkyl, optionally substituted with one or more substituents $R^{2b}$ which are the same or different,
4- to 6-membered heterocycloalkyl, wherein said 4- to 6-membered heterocycloalkyl contains 1 or 2 heteroatoms or heteroatom-containing groups independently selected from N, NH, N($R^{2c}$), O, S, SO and $SO_2$, and wherein said 4- to 6-membered heterocycloalkyl is optionally substituted at one or more carbon atoms with 1 to 4 substituents $R^{2d}$ which are the same or different, and wherein optionally in said 4- to 6-membered heterocycloalkyl one —$CH_2$— group adjacent to a nitrogen atom, if present, is replaced by a —C(=O)— group, phenyl, optionally substituted with 1 to 3 substituents $R^{2d}$ which are the same or different, or 6-membered heteroaryl, wherein said 6-membered heteroaryl contains 1 or 2 N, and wherein said 6-membered heteroaryl is optionally substituted at one or more carbon atoms with 1 to 3 substituents $R^{2d}$ which are the same or different.

In accordance with another embodiment of the first aspect, the present invention covers compounds of general formula (I), wherein
$R^2$ represents
—H,
halogen, in particular F, Cl or Br.

Also preferred are compounds of general formula (I), wherein
$R^2$ represents Cl or Br, in particular $C_1$.

Also preferred are compounds of general formula (I), wherein
$R^2$ represents Cl or Br, in particular Br.

In accordance with another embodiment of the first aspect, the present invention covers compounds of general formula (I), wherein
$R^2$ represents
—CN,
—C(O)N($R^4$)($R^5$),
—N($R^4$)($R^5$),
—N($R^4$)C(O)$R^5$.

In accordance with another embodiment of the first aspect, the present invention covers compounds of general formula (I), wherein
$R^2$ represents
—CN,
—C(O)N($R^4$)($R^5$).

In accordance with another embodiment of the first aspect, the present invention covers compounds of general formula (I), wherein
$R^2$ represents
—N($R^4$)($R^5$),
—N($R^4$)C(O)$R^5$.

In accordance with another embodiment of the first aspect, the present invention covers compounds of general formula (I), wherein
$R^2$ represents —N($R^4$)($R^5$).

In accordance with another embodiment of the first aspect, the present invention covers compounds of general formula (I), wherein
$R^2$ represents
$C_1$-$C_6$-alkyl, optionally substituted with 1 to 3 substituents $R^{2a}$ which are the same or different,
$C_3$-$C_7$-cycloalkyl, optionally substituted with one or more substituents $R^{2b}$ which are the same or different.

In accordance with another embodiment of the first aspect, the present invention covers compounds of general formula (I), wherein
$R^2$ represents
$C_1$-$C_6$-alkyl, optionally substituted with 1 to 3 substituents $R^{2a}$ which are the same or different.

In accordance with another embodiment of the first aspect, the present invention covers compounds of general formula (I), wherein
$R^2$ represents
4- to 6-membered heterocycloalkyl, wherein said 4- to 6-membered heterocycloalkyl contains 1 or 2 heteroatoms or heteroatom-containing groups independently selected from N, NH, N($R^{2c}$), O, S, SO and $SO_2$, and wherein said 4- to 6-membered heterocycloalkyl is optionally substituted at one or more carbon atoms with 1 to 4 substituents $R^{2d}$ which are the same or different, and wherein optionally in said 4- to 6-membered heterocycloalkyl one —CH$_2$— group adjacent to a nitrogen atom, if present, is replaced by a —C(=O)— group.

In accordance with another embodiment of the first aspect, the present invention covers compounds of general formula (I), wherein
$R^{2a}$ represents
C$_3$-C$_5$-cycloalkyl, optionally substituted with 1 to 3 substituents $R^{10}$ which are the same or different,
F,
Cl,
OH,
O(R$^6$),
—N(R$^4$)(R$^5$),
4- to 6-membered heterocycloalkyl containing 1 or 2 heteroatoms or heteroatom-containing groups independently selected from N, NH, N(R$^7$), O, S, SO and SO$_2$, and wherein said 4- to 6-membered heterocycloalkyl is optionally substituted at one or more carbon atoms with 1 to 4 substituents $R^{10}$ which are the same or different.

In accordance with another embodiment of the first aspect, the present invention covers compounds of general formula (I), wherein
$R^{2b}$ represents C$_1$-C$_4$-alkyl, Cl, F or OH, wherein said C$_1$-C$_4$-alkyl is optionally substituted at one or more carbon atoms with 1 to 3 substituents $R^{10}$ which are the same or different.

In accordance with another embodiment of the first aspect, the present invention covers compounds of general formula (I), wherein
$R^{2c}$ represents C$_1$-C$_4$-alkyl C$_3$-C$_5$-cycloalkyl, —C(O)R$^5$, —C(O)OR$^5$ or —SO$_2$R$^8$, wherein said C$_1$-C$_4$-alkyl and C$_3$-C$_5$-cycloalkyl are optionally substituted at one or more carbon atoms with 1 to 3 substituents $R^{10}$ which are the same or different.

In accordance with another embodiment of the first aspect, the present invention covers compounds of general formula (I), wherein
$R^{2d}$ represents C$_1$-C$_4$-alkyl, optionally substituted at one or more carbon atoms with 1 to 3 substituents $R^{10}$ which are the same or different.

Preferred are compounds of general formula (I), wherein
$R^2$ represents H, F, Cl, Br, CN, methyl, ethyl, propyl, propan-2-yl, 2-methylpropyl, cyclopropyl, tert-butyl, butan-2-yl, cyclobutyl, 2,2-dimethylpropyl, 3-methylbutan-2-yl, cyclopentyl, cyclohexyl, 1-cyclopropylmethyl, 1-cyclopropylethyl, 1-cyclobutylmethyl, 1-(1-methylcyclopropyl)methyl, difluoromethyl, trifluoromethyl, methoxymethyl, hydroxymethyl, 1-hydroxyethyl, 2-hydroxypropan-2-yl, phenyl, pyridin-4-yl, pyridin-3-yl, pyridin-2-yl, 2-methylpyridin-4-yl, 3-methylpyridin-4-yl, 6-methylpyridin-3-yl, 2-methylpyridin-3-yl, 6-methylpyridin-2-yl, 5-methylpyridin-2-yl, 3-methylpyridin-2-yl, 2,5-dimethylpyridin-4-yl, 4,6-dimethylpyridin-3-yl, 3,5-dimethylpyridin-2-yl, 3,6-dimethylpyridin-2-yl, oxetan-3-yl, oxan-4-yl, (oxan-4-yl)methyl, oxolan-2-yl, oxolan-3-yl, (oxolan-2-yl)methyl, (oxolan-3-yl)methyl, pyrrolidin-3-yl, 1-methylpyrrolidin-3-yl, 1-cyclobutylpyrrolidin-3-yl, piperidin-4-yl, 1-methylpiperidin-4-yl, 1-cyclobutylpiperidin-4-yl, 1-acetylpiperidin-4-yl, 1-(2,2-difluoroacetyl)piperidin-4-yl, 1-methanesulfonylpyrrolidin-3-yl, N-ethylcarboxamide, N-(2,2-difluoroethyl)carboxamide, N-cyclopropylcarboxamide, N-(cyclopropylmethyl)-carboxamide, N-(cyclopentylmethyl)-carboxamide, N,N-dimethylcarboxamide, N-methyl-N-ethylcarboxamide, N-cyclopropyl-N-methylcarboxamide, N-(cyclopropylmethyl)-N-methylcarboxamide, azetidine-1-carbonyl, piperidine-1-carbonyl, morpholine-4-carbonyl, 4-methylpiperazine-1-carbonyl, (2-fluorophenyl)carboxamide, (2-fluorophenyl)-N-methylcarboxamide, methylamino, ethylamino, (propan-2-yl)amino, cyclopropylamino, cyclobutylamino, cyclopentylamino, (2,2-difluoroethyl)amino, dimethylamino, ethyl(methyl)amino, cyclopropyl(methyl)amino, (cyclopropylmethyl)(methyl)amino, cyclopropyl(ethyl)amino, (cyclopropylmethyl)(ethyl)amino, cyclobutyl(methyl)amino, cyclobutyl(ethyl)amino, cyclopentyl(methyl)amino, N-acetamide, 2,2-difluoro-N-acetamide, N-oxane-4-carboxamide, 2-methoxy-N-acetamide, 2-(dimethylamino)-N-acetamide and N-1H-1,2,3-triazole-5-carboxamide.

In accordance with another embodiment of the first aspect, the present invention covers compounds of general formula (I), wherein
$R^3$ represents
C$_1$-C$_6$-alkyl, optionally substituted with 1 to 3 substituents $R^{1a}$ which are the same or different,
C$_3$-C$_7$-cycloalkyl, optionally substituted with one or more substituents $R^{3b}$ which are the same or different,
4- to 6-membered heterocycloalkyl, wherein said 4- to 6-membered heterocycloalkyl is linked through a carbon atom and contains 1 or 2 heteroatoms or heteroatom-containing groups independently selected from N, NH, N(R$^{3c}$), O, S, SO and SO$_2$, and wherein said 4- to 6-membered heterocycloalkyl is optionally substituted at one or more carbon atoms with 1 to 4 substituents $R^{3d}$ which are the same or different.

In accordance with another embodiment of the first aspect, the present invention covers compounds of general formula (I), wherein
$R^{1a}$ represents
C$_3$-C$_5$-cycloalkyl, optionally substituted at one or more carbon atoms with 1 to 3 substituents $R^{10}$ which are the same or different,
F,
Cl,
OH,
O(R$^6$),
—C(O)NH$_2$,
—C(O)N(R$^4$)(R$^5$),
—N(R$^4$)(R$^6$),
—NH$_2$,
—N(R$^4$)C(O)R$^5$,
—N(R$^4$)—C(O)OR$^6$,
4- to 6-membered heterocycloalkyl containing 1 or 2 heteroatoms or heteroatom-containing groups independently selected from N, NH, N(R$^7$), O, S, SO and SO$_2$, and wherein said 4- to 6-membered heterocycloalkyl is optionally substituted at one or more carbon atoms with 1 to 4 substituents $R^{10}$ which are the same or different.

In accordance with another embodiment of the first aspect, the present invention covers compounds of general formula (I), wherein
$R^{3b}$ represents C$_1$-C$_4$-alkyl, Cl or F.

In accordance with another embodiment of the first aspect, the present invention covers compounds of general formula (I), wherein
$R^{3c}$ represents C$_1$-C$_4$-alkyl, C$_3$-C$_5$-cycloalkyl, —C(O)R$^5$, —C(O)OR$^5$, —SO$_2$R$^3$, —C(O)N(R$^4$)(R$^5$) or 4- to 6-membered heterocycloalkyl containing 1 or 2 heteroatoms or heteroatom-containing groups independently selected from N, NH, N(R$^7$), O and SO$_2$; and wherein said $C_1$-$C_4$-alkyl, $C_3$-$C_5$-cycloalkyl and 4- to 6-membered heterocycloalkyl are optionally substituted with one or more substituents $R^{10}$ which are the same or different.

In accordance with another embodiment of the first aspect, the present invention covers compounds of general formula (I), wherein $R^{ad}$ represents $C_1$-$C_4$-alkyl, F or $C_1$.

Preferred are compounds of general formula (I), wherein $R^3$ represents ethyl, propyl, propan-2-yl, 2-methylpropyl, cyclopropyl, tert-butyl, butan-2-yl, cyclobutyl, 2,2-dimethylpropyl, 3-methylbutan-2-yl, cyclopentyl, cyclohexyl, 1-cyclopropylmethyl, 1-cyclopropylethyl, 1-cyclobutylmethyl, 1-(1-methylcyclopropyl)methyl, 2-hydroxyethyl, 2-methoxyethyl, 1-methoxypropan-2-yl, (2S)-1-methoxypropan-2-yl, (2R)-1-methoxypropan-2-yl, 1-methoxybutan-2-yl, 1-hydroxybutan-2-yl, 1,3-dimethoxypropan-2-yl, 1-hydroxypropan-2-yl, (2S)-hydroxypropan-2-yl, (2R)-hydroxypropan-2-yl, 2-(morpholin-4-yl)ethyl, 1-(morpholin-4-yl)propan-2-yl, (2S)-1-(morpholin-4-yl)propan-2-yl, (2R)-1-(morpholin-4-yl)propan-2-yl, 4-(propan-2-yl)morpholin-2-yl]methyl, (4-cyclopropylmorpholin-2-yl)methyl, (4-cyclobutylmorpholin-2-yl)methyl, 4-(3,3,3-trifluoropropyl)morpholin-2-yl]methyl, oxetan-3-yl, oxolan-3-yl, (oxolan-2-yl)methyl, (oxolan-3-yl)methyl, oxan-4-yl, (oxan-4-yl)methyl, pyrrolidin-3-yl, 1-(2,2-difluoroacetyl)pyrrolidin-3-yl, (pyrrolidin-3-yl)methyl, 1-(2,2-difluoroacetyl)pyrrolidin-3-yl]methyl and 2,2,2-trifluoroethyl, In accordance with another embodiment of the first aspect, the present invention covers compounds of general formula (I), wherein $R^4$ represents H or $C_1$-$C_4$-alkyl, optionally substituted with OH or 1 to 5 fluorine atoms.

In accordance with another embodiment of the first aspect, the present invention covers compounds of general formula (I), wherein $R^4$ represents $C_1$-$C_4$-alkyl, optionally substituted with OH or 1 to 5 fluorine atoms.

Also preferred are compounds of general formula (I), wherein $R^4$ represents H.

In accordance with another embodiment of the first aspect, the present invention covers compounds of general formula (I), wherein $R^5$ represents $C_1$-$C_6$-alkyl, optionally substituted with 1 to 3 substituents $R^{5a}$ which are the same or different, $C_3$-$C_6$-cycloalkyl, optionally substituted with 1 to 3 substituents $R^{5b}$ which are the same or different, —$(C_1$-$C_3$-alkyl$)_n$-(4- to 6-membered heterocycloalkyl), wherein said 4- to 6-membered heterocycloalkyl contains 1 or 2 heteroatoms or heteroatom-containing groups independently selected from NH, N, N($R^{5c}$), O, S, SO and $SO_2$, and wherein optionally in said 4- to 6-membered heterocycloalkyl one —$CH_2$— group adjacent to a nitrogen atom, if present, is replaced by a —C(=O)— group, and wherein said —$(C_1$-$C_3$-alkyl$)_n$-(4- to 6-membered heterocycloalkyl) is optionally substituted at one or more carbon atoms with 1 to 4 substituents $R^{5d}$ which are the same or different;

—$(C_1$-$C_3$-alkyl$)_n$-phenyl, optionally substituted with 1 to 3 substituents $R^{5d}$ which are the same or different, or —$(C_1$-$C_3$-alkyl$)_n$-(5- or 6-membered heteroaryl), wherein said 5-membered heteroaryl contains 1, 2 or 3 heteroatoms or heteroatom-containing groups independently selected from the group consisting of S, N, NH, N($R^{5c}$), and O, and wherein said 6-membered heteroaryl contains 1 or 2 N, and wherein said —$(C_1$-$C_3$-alkyl$)_n$-(5- or 6-membered heteroaryl) is optionally substituted at one or more carbon atoms with 1 to 3 substituents $R^{5d}$ which are the same or different.

In accordance with another embodiment of the first aspect, the present invention covers compounds of general formula (I), wherein $R^{5a}$ represents OH, F, Cl, $C_3$-$C_5$-cycloalkyl, $OC_1$-$C_4$-alkyl, wherein said $C_3$-$C_5$-cycloalkyl and $OC_1$-$C_4$-alkyl are optionally substituted with OH, 1 to 5 fluorine atoms or phenyl, optionally substituted with 1 to 3 substituents $R^{5d}$ which are the same or different.

In accordance with another embodiment of the first aspect, the present invention covers compounds of general formula (I), wherein $R^{5b}$ represents OH, F, Cl, $C_1$-$C_4$-alkyl or $OC_1$-$C_4$-alkyl.

In accordance with another embodiment of the first aspect, the present invention covers compounds of general formula (I), wherein $R^{5c}$ represents $C_1$-$C_4$-alkyl.

In accordance with another embodiment of the first aspect, the present invention covers compounds of general formula (I), wherein $R^{5d}$ represents OH, F, Cl, $C_1$-$C_4$-alkyl or $OC_1$-$C_4$-alkyl.

In accordance with another embodiment of the first aspect, the present invention covers compounds of general formula (I), wherein $R^4$ and $R^5$ may be conjoined to form together with the nitrogen to which $R^4$ and $R^5$ are attached a 4- to 6-membered heterocycloalkyl, optionally containing 1 additional heteroatom or heteroatom-containing group independently selected from NH, N($R^{14}$), O and $SO_2$, and wherein optionally in said 4- to 6-membered heterocycloalkyl one —$CH_2$— group adjacent to a nitrogen atom, if present, is replaced by a —C(=O)— group, and wherein said 4- to 6-membered heterocycloalkyl is optionally substituted at one or more carbon atoms with 1 to 4 substituents $R^{13}$ which are the same or different.

In accordance with another embodiment of the first aspect, the present invention covers compounds of general formula (I), wherein $R^6$ represents $C_1$-$C_6$-alkyl, —$(C_1$-$C_3$-alkyl$)_n$-($C_3$-$C_5$-cycloalkyl) or —$(C_1$-$C_3$-alkyl$)_n$-phenyl which are optionally substituted at one or more carbon atoms with one or more substituents independently selected from F, Cl, OH and —$OC_1$-$C_4$-alkyl.

In accordance with another embodiment of the first aspect, the present invention covers compounds of general formula (I), wherein $R^7$ represents
—C(O)$R^{12}$,
—C(O)O$R^{12}$,
$C_1$-$C_6$-alkyl, or
—$(C_1$-$C_3$-alkyl$)_n$-($C_3$-$C_5$-cycloalkyl); and
wherein said $C_1$-$C_6$-alkyl and —$(C_1$-$C_3$-alkyl$)_n$-($C_3$-$C_5$-cycloalkyl) are optionally substituted with one or more F atoms.

In accordance with another embodiment of the first aspect, the present invention covers compounds of general formula (I), wherein $R^3$ represents $C_1$-$C_6$-alkyl, optionally substituted on one or more carbon atoms with 1 to 3 substituents $R^{13}$ which are the same or different;

$R^9$ represents H or $C_1$-$C_4$-alkyl.

In accordance with another embodiment of the first aspect, the present invention covers compounds of general formula (I), wherein $R^{10}$ represents F, Cl, $C_1$-$C_4$-alkyl or $OC_1$-$C_4$-alkyl, wherein said $C_1$-$C_4$-alkyl and $OC_1$-$C_4$-alkyl are optionally substituted with 1 to 5 fluorine atoms.

In accordance with another embodiment of the first aspect, the present invention covers compounds of general formula (I), wherein $R^{11}$ represents H or $C_1$-$C_4$-alkyl, and
$R^{12}$ represents $C_1$-$C_4$-alkyl.

In accordance with another embodiment of the first aspect, the present invention covers compounds of general formula (I), wherein $R^{11}$ and $R^{12}$ may be conjoined to form together with the nitrogen to which $R^{11}$ and $R^{12}$ are attached a 4- to 6-membered heterocycloalkyl, wherein said 4- to 6-membered heterocycloalkyl optionally contains 1 additional heteroatom or heteroatom-containing groups selected from NH, $N(R^{14})$ or O.

In accordance with another embodiment of the first aspect, the present invention covers compounds of general formula (I), wherein $R^{13}$ represents F, Cl or $C_1$-$C_4$-alkyl.

In accordance with another embodiment of the first aspect, the present invention covers compounds of general formula (I), wherein $R^{14}$ represents $C_1$-$C_4$-alkyl.

In accordance with another embodiment of the first aspect, the present invention covers compounds of general formula (I), wherein n represents 0.

In a particular further embodiment of the first aspect, the present invention covers combinations of two or more of the above mentioned embodiments.

In accordance with a further embodiment of the first aspect, the present invention covers compounds of general formula (I), supra, in which:

$R^1$ represents H, $C_1$-$C_3$-alkyl or halogen, wherein said $C_1$-$C_3$-alkyl is optionally substituted with one or more fluorine atoms;

$R^2$ represents
—H,
halogen,
—CN,
—$CO_2H$,
—$C(O)OR^5$,
—$C(O)NH_2$,
—$C(O)N(R^4)(R^5)$,
$NH_2$,
—$N(R^4)(R^5)$,
—$N(R^4)C(O)R^5$,
—$N(R^4)$—$C(O)OR^5$,
$C_1$-$C_6$-alkyl, optionally substituted with 1 to 3 substituents $R^{2a}$ which are the same or different,
$C_3$-$C_7$-cycloalkyl, optionally substituted with one or more substituents $R^{2b}$ which are the same or different,
—$OC_1$-$C_6$-alkyl, optionally substituted with 1 to 3 substituents $R^{2a}$ which are the same or different,
—$OC_3$-$C_7$-cycloalkyl, optionally substituted with one or more substituents $R^{2b}$ which are the same or different,
4- to 6-membered heterocycloalkyl, wherein said 4- to 6-membered heterocycloalkyl contains 1 or 2 heteroatoms or heteroatom-containing groups independently selected from N, NH, $N(R^{2c})$, O, S, SO and $SO_2$, and wherein said 4- to 6-membered heterocycloalkyl is optionally substituted at one or more carbon atoms with 1 to 4 substituents $R^{2d}$ which are the same or different, 5- to 6-membered heterocycloalkenyl, wherein said 5- to 6-membered heterocycloalkenyl contains 1 or 2 heteroatoms or heteroatom-containing groups independently selected from N, NH, $N(R^{2c})$, O, S, SO and $SO_2$, and wherein said 5- to 6-membered heterocycloalkenyl is optionally substituted at one or more carbon atoms with 1 to 4 substituents $R^{2d}$ which are the same or different, 6- to 9-membered heterobicycloalkyl, wherein said 6- to 9-membered heterobicycloalkyl contains 1 or 2 heteroatoms or heteroatom-containing groups independently selected from N, NH, $N(R^{2c})$, O, S, SO and $SO_2$, and wherein said 6- to 9-membered heterobicycloalkyl is optionally substituted at one or more carbon atoms with 1 to 4 substituents $R^{2d}$ which are the same or different, phenyl, optionally substituted with 1 to 3 substituents $R^{2d}$ which are the same or different, or 5- or 6-membered heteroaryl, wherein said 5-membered heteroaryl contains 1, 2 or 3 heteroatoms or heteroatom-containing groups independently selected from the group consisting of S, N, NH, $N(R^{2c})$ and O, and wherein said 6-membered heteroaryl contains 1 or 2 N, and wherein said 5- or 6-membered heteroaryl is optionally substituted at one or more carbon atoms with 1 to 3 substituents $R^{2d}$ which are the same or different;

$R^{2a}$ represents
$C_3$-$C_5$-cycloalkyl, optionally substituted with 1 to 3 substituents $R^{10}$ which are the same or different,
F,
Cl,
OH,
$O(R^6)$,
—$N(R^4)(R^5)$,
4- to 6-membered heterocycloalkyl containing 1 or 2 heteroatoms or heteroatom-containing groups independently selected from N, NH, $N(R^7)$, O, S, SO and $SO_2$, and wherein said 4- to 6-membered heterocycloalkyl is optionally substituted at one or more carbon atoms with 1 to 4 substituents $R^{10}$ which are the same or different, $R^{2b}$ represents $C_1$-$C_4$-alkyl, Cl, F or OH, wherein said $C_1$-$C_4$-alkyl is optionally substituted at one or more carbon atoms with 1 to 3 substituents $R^{10}$ which are the same or different;

$R^{2c}$ represents $C_1$-$C_4$-alkyl, $C_3$-$C_5$-cycloalkyl, —$C(O)R^5$, —$C(O)OR^5$ or —$SO_2R^8$, wherein said $C_1$-$C_4$-alkyl and $C_3$-$C_5$-cycloalkyl are optionally substituted at one or more carbon atoms with 1 to 3 substituents $R^{10}$ which are the same or different;

$R^{2d}$ represents $C_1$-$C_4$-alkyl, optionally substituted at one or more carbon atoms with 1 to 3 substituents $R^{10}$ which are the same or different;

$R^3$ represents
$C_1$-$C_6$-alkyl, optionally substituted with 1 to 3 substituents $R^{3a}$ which are the same or different,
$C_3$-$C_6$-cycloalkyl, optionally substituted with one or more substituents $R^{3b}$ which are the same or different,
4- to 6-membered heterocycloalkyl, wherein said 4- to 6-membered heterocycloalkyl is linked through a carbon atom and contains 1 or 2 heteroatoms or heteroatom-containing groups independently selected from N, NH, $N(R^{3c})$, O, S, SO and $SO_2$, and wherein said 4- to 6-membered heterocycloalkyl is optionally substituted at one or more carbon atoms with 1 to 4 substituents $R^{3d}$ which are the same or different, $R^{3a}$ represents
- $C_3$-$C_5$-cycloalkyl, optionally substituted at one or more carbon atoms with 1 to 3 substituents $R^{10}$ which are the same or different,
- F,
- —Cl,
- OH,
- O($R^6$),
- —C(O)NH$_2$,
- —C(O)N($R^4$)($R^5$),
- —N($R^4$)($R^5$),
- NH$_2$,
- —N($R^4$)C(O)$R^5$,
- —N($R^4$)—C(O)O$R^5$,
- 4- to 6-membered heterocycloalkyl containing 1 or 2 heteroatoms or heteroatom-containing groups independently selected from N, NH, N($R^7$), O, S, SO and SO$_2$, and wherein said 4- to 6-membered heterocycloalkyl is optionally substituted at one or more carbon atoms with 1 to 4 substituents $R^{10}$ which are the same or different, $R^{3b}$ represents $C_1$-$C_3$-alkyl, Cl or F;

$R^{3c}$ represents $C_1$-$C_4$-alkyl, $C_3$-$C_5$-cycloalkyl, —C(O)$R^5$, —C(O)O$R^5$, —SO$_2R^3$ or —C(O)N($R^4$)($R^5$); and wherein said $C_1$-$C_4$-alkyl and $C_3$-$C_5$-cycloalkyl are optionally substituted with one or more substituents $R^{10}$ which are the same or different;

$R^{3d}$ represents $C_1$-$C_4$-alkyl;

$R^4$ represents H or $C_1$-$C_4$-alkyl;

$R^5$ represents
- $C_1$-$C_6$-alkyl, optionally substituted with 1 to 3 substituents $R^{5a}$ which are the same or different,
- $C_3$-$C_6$-cycloalkyl, optionally substituted with 1 to 3 substituents $R^{5b}$ which are the same or different,
- —($C_1$-$C_3$-alkyl)$_n$-phenyl, optionally substituted with 1 to 3 substituents $R^{5d}$ which are the same or different, or
- —($C_1$-$C_3$-alkyl)$_n$-(5- or 6-membered heteroaryl), wherein said 5-membered heteroaryl contains 1, 2 or 3 heteroatoms or heteroatom-containing groups independently selected from the group consisting of S, N, NH, N($R^{5c}$), and O, and wherein said 6-membered heteroaryl contains 1 or 2 N, and wherein said —($C_1$-$C_3$-alkyl)$_n$-(5- or 6-membered heteroaryl) is optionally substituted at one or more carbon atoms with 1 to 3 substituents $R^{5d}$ which are the same or different;

or $R^4$ and $R^5$ may be conjoined to form together with the nitrogen to which $R^4$ and $R^5$ are attached a
- 4- to 6-membered heterocycloalkyl, optionally containing 1 additional heteroatom or heteroatom-containing group independently selected from NH, N($R^{14}$) and O, and wherein said 4- to 6-membered heterocycloalkyl is optionally substituted at one or more carbon atoms with 1 to 4 substituents $R^{13}$ which are the same or different;

$R^{5a}$ represents OH, F, Cl, $C_3$-$C_5$-cycloalkyl, O$C_1$-$C_4$-alkyl, wherein said $C_3$-$C_5$-cycloalkyl and O$C_1$-$C_4$-alkyl are optionally substituted with OH, 1 to 5 fluorine atoms or phenyl, optionally substituted with 1 to 3 substituents $R^{5d}$ which are the same or different;

$R^{5b}$ represents OH, F, Cl, $C_1$-$C_4$-alkyl or O$C_1$-$C_4$-alkyl;

$R^{5c}$ represents $C_1$-$C_4$-alkyl;

$R^{5d}$ represents OH, F, Cl, $C_1$-$C_4$-alkyl or O$C_1$-$C_4$-alkyl;

$R^6$ represents $C_1$-$C_6$-alkyl, —($C_1$-$C_3$-alkyl)$_n$-($C_3$-$C_5$-cycloalkyl) or —($C_1$-$C_3$-alkyl)$_n$-phenyl;

$R^7$ represents
- —C(O)$R^{12}$,
- —C(O)O$R^{12}$,
- $C_1$-$C_6$-alkyl, or
- —($C_1$-$C_3$-alkyl)$_n$-($C_3$-$C_5$-cycloalkyl); and wherein said $C_1$-$C_6$-alkyl and —($C_1$-$C_3$-alkyl)$_n$-($C_3$-$C_5$-cycloalkyl) are optionally substituted with one or more fluorine atoms;

$R^8$ represents $C_1$-$C_3$-alkyl, optionally substituted at one or more carbon atoms with 1 to 3 substituents $R^{13}$ which are the same or different;

$R^9$ represents H or $C_1$-$C_3$-alkyl;

or $R^8$ and $R^9$ may be conjoined to form together with the nitrogen to which $R^8$ and $R^9$ are attached a 4- to 6-membered heterocycloalkyl, wherein said 4- to 6-membered heterocycloalkyl optionally contains 1 additional heteroatom or heteroatom-containing groups selected from NH, N($R^{14}$) or O;

$R^{10}$ represents F, Cl, $C_1$-$C_3$-alkyl or O$C_1$-$C_3$-alkyl;

$R^{11}$ represents H or $C_1$-$C_3$-alkyl;

$R^{12}$ represents $C_1$-$C_4$-alkyl;

or $R^{11}$ and $R^{12}$ may be conjoined to form together with the nitrogen to which $R^{11}$ and $R^{12}$ are attached a 4- to 6-membered heterocycloalkyl, wherein said 4- to 6-membered heterocycloalkyl optionally contains 1 additional heteroatom or heteroatom-containing groups selected from NH, N($R^{14}$) or O;

$R^{13}$ represents F, Cl or $C_1$-$C_3$-alkyl;

$R^{14}$ represents $C_1$-$C_3$-alkyl;

n represents 0;

and stereoisomers, N-oxides, hydrates, solvates, and salts thereof, and mixtures of same.

In accordance with a further embodiment of the first aspect, the present invention covers compounds of general formula (I), supra, in which:

$R^1$ represents H, F, C$_1$, Br or methyl;

$R^2$ represents
- —H,
- Br,
- —CN,
- —CO$_2$H,
- —C(O)O$R^5$,
- —C(O)N($R^4$)($R^5$),
- NH$_2$,
- —N($R^4$)($R^5$),
- —N($R^4$)C(O)$R^5$,
- —N($R^4$)—C(O)O$R^5$,
- $C_1$-$C_4$-alkyl, optionally substituted with 1 to 3 substituents $R^{2a}$ which are the same or different,
- $C_3$-$C_6$-cycloalkyl,
- 5- to 6-membered heterocycloalkyl, wherein said 5- to 6-membered heterocycloalkyl contains 1 heteroatom or heteroatom-containing group independently selected from NH, N($R^{2c}$) or O,
- 5- to 6-membered heterocycloalkenyl, wherein said 5- to 6-membered heterocycloalkenyl contains 1 heteroatom-containing group N($R^{2c}$),
- phenyl, optionally substituted with 1 to 3 substituents $R^{2d}$ which are the same or different, or
- 6-membered heteroaryl, containing 1 N and optionally substituted with 1 substituent $R^{2d}$;

$R^{2a}$ represents
- —F,
- OH,
- O($R^6$),
- N($R^4$)($R^5$),
- 6-membered heterocycloalkyl containing 1 O atom;

$R^{2c}$ represents methyl, cyclobutyl, —C(O)$R^5$, —C(O)O$R^5$ or —SO$_2R^8$;

$R^{2d}$ represents methyl;

R³ represents
  C₁-C₅-alkyl, optionally substituted with 1 substituent $R^{3a}$,
  C₄-C₅-cycloalkyl,
  4- to 6-membered heterocycloalkyl, wherein said 4- to 6-membered heterocycloalkyl is linked through a carbon atom and contains 1 heteroatom or heteroatom-containing group selected from NH, $N(R^{3c})$ or O,
$R^{1a}$ represents
  cyclopropyl,
  OH,
  $O(R^6)$,
  —C(O)N(R⁴)(R⁵),
  —N(R⁴)(R⁵),
  NH₂,
  —N(R⁴)—C(O)OR⁵,
  5- to 6-membered heterocycloalkyl containing 1 or 2 heteroatoms or heteroatom-containing groups independently selected from N, NH, N(R⁷) or O,
$R^{3c}$ represents methyl, cyclobutyl, —C(O)R⁵, —C(O)OR⁵, —SO₂R⁸, —C(O)N(R⁴)(R⁵);
R⁴ represents H or methyl;
R⁵ represents
  C₁-C₆-alkyl, optionally substituted with 1 to 2 substituents $R^{5a}$ which are the same or different,
  C₃-C₅-cycloalkyl,
  phenyl, optionally substituted with 1 substituent $R^{5d}$, or
  5-membered heteroaryl containing 1, 2 or 3 heteroatoms or heteroatom-containing groups independently selected from N or NH;
or
R⁴ and R⁵ may be conjoined to form together with the nitrogen to which R⁴ and R⁵ are attached a
  4- to 6-membered heterocycloalkyl, optionally containing 1 additional heteroatom or heteroatom-containing group independently selected from N(R¹⁴) or O;
$R^{5a}$ represents OH, F, cyclopropyl or methoxy, wherein said methoxy is optionally substituted with phenyl;
$R^{5d}$ represents F;
R⁶ represents methyl or CH₂-phenyl;
R⁷ represents
  —C(O)R¹²,
  —C(O)OR¹²,
  C₁-C₃-alkyl, optionally substituted with one to three F, or
  C₃-C₄-cycloalkyl;
R⁸ represents
  C₁-C₃-alkyl, optionally substituted at one carbon atom with 1 to 3 substituents R¹³;
R¹² represents C₁-C₄-alkyl;
R¹³ represents F;
R¹⁴ represents methyl;
n represents 0;
and stereoisomers, N-oxides, hydrates, solvates, and salts thereof, and mixtures of same.

The present invention covers any sub-combination within any embodiment or aspect of the present invention of compounds of general formula (I), supra.

The present invention covers methods of preparing compounds of the present invention of general formula (I), said methods comprising the steps as described in the Experimental Section herein.

The compounds according to the invention of general formula (I) can be prepared according to the following schemes 1 to 14. The schemes and procedures described below illustrate synthetic routes to the compounds of general formula (I) of the invention and are not intended to be limiting. It is clear to the person skilled in the art that the order of transformations as exemplified in schemes 1 to 14 can be modified in various ways. The order of transformations exemplified in these schemes is therefore not intended to be limiting. In addition, interconversion of any of the substituents, R¹, R² or R³ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art. Specific examples are described in the subsequent paragraphs.

The starting materials are either commercially available or can be prepared according to procedures available from the public domain, as understandable to the person skilled in the art. Specific examples are described in the Experimental Section.

Twelve routes for the preparation of compounds of general formula (I) are described in schemes 1 to 14.

Synthesis of Compounds of General Formula (I) of the Present Invention

Compounds of general formula (I) with the meaning of R¹, R² or R³ as defined in general formula (I), can be synthesised according to a general procedure depicted in Scheme 1 starting from synthons of the formula (II), by methods known to those skilled in the art.

One-pot conjugate addition of a primary amine of general formula (II), or salts thereof, with an alkyl acrylate (for example ethyl acrylate) of general formula (III) in protic solvent (such as ethanol) at temperatures between 0° C. and 50° C., followed by amidation with dialkyl oxalate (for example dimethyl oxalate, where ALK=methyl; or diethyl oxalate, where ALK=ethyl) of general formula (IV) in base (such as sodium ethoxide) at temperatures typically between rt and 100° C. and then Dieckmann cyclisation under aqueous acidic conditions (typically hydrochloric acid) at temperatures between rt and 100° C. to give cyclic β-ketoesters of general formula (V).

Cyclocondensation of a compound of general formula (V) with a 5-amino-1H-pyrazole of general formula (VI) in glacial acetic acid at temperatures between rt and 140° C. (typically at 120° C.) gives compounds of general formula (VII). Chemoselective N-alkylation of a compound of general formula (VII) with an alkyl haloacetate (such as ethyl bromoacetate or tert-butyl bromoacetate) of general formula (VIII) in the presence of base (such as potassium carbonate) and aprotic solvent (such as acetonitrile or DMF) at temperatures between rt and 120° C. (typically 100° C.) gives an ester compound of general formula (IX).

Ester group saponification of a compound of general formula (IX), where ALK=Me or Et, in a suitable solvent or solvent mixture (for example methanol, ethanol or tetrahydrofuran) with addition of an aqueous solution of an alkali metal hydroxide (for example lithium hydroxide or sodium hydroxide) at temperatures between 10° C. and 80° C. gives the corresponding carboxylic acid of general formula (X) after acidic reaction work up (for example with aqueous hydrochloric acid). Ester group saponification of a compound of general formula (IX), where ALK=tBu, under acidic conditions, for example in dichloromethane and trifluoroacetic acid at temperatures between 0° C. and 30° C. also affords the corresponding carboxylic acid of general formula (X) after concentration of the reaction mixture.

A carboxylic acid of formula (X) may react with a primary amine of general formula (XI) by methods known to those skilled in the art to give compounds of the general formula (I). The reaction takes place in that for example, a carboxylic acid of formula (X) is activated with reagents such as dicyclohexylcarbodiimide (DCC), 1-(3-dimethylaminopropyl)-3-ethylcarbodiimide (EDCI), N-hydroxybenzotriazole (HOBT), N-[(dimethylamino)-(3H-[1,2,3]triazolo[4,5-b]pyridin-3-yloxy)methyliden]-N-methylmethanaminium hexafluorophosphate (HATU) or propylphosphonic anhydride (T3P). For example, the reaction with HATU takes place in an inert solvent (such as N,N-dimethylformamide, dichloromethane, THF or dimethyl sulfoxide) in the presence of the appropriate 2-amino pyridine of general formula (XI) and a tertiary amine (such as triethylamine or diisopropylethylamine) at temperatures between −30° C. and +80° C.

It is also possible to convert a carboxylic acid of general formula (X) into the corresponding carboxylic acid chloride with an inorganic acid chloride (such as phosphorus pentachloride, phosphorus trichloride or thionyl chloride) or organic acid chloride (such as oxalyl chloride) and then into the target compounds of general formula (I), in pyridine or an inert solvent (such as N,N-dimethylformamide), in the presence of the appropriate 2-amino pyridine of general formula (XI) and a tertiary amine (for example trimethylamine or diisopropylethylamine) at temperatures between −30° C. and +80° C.

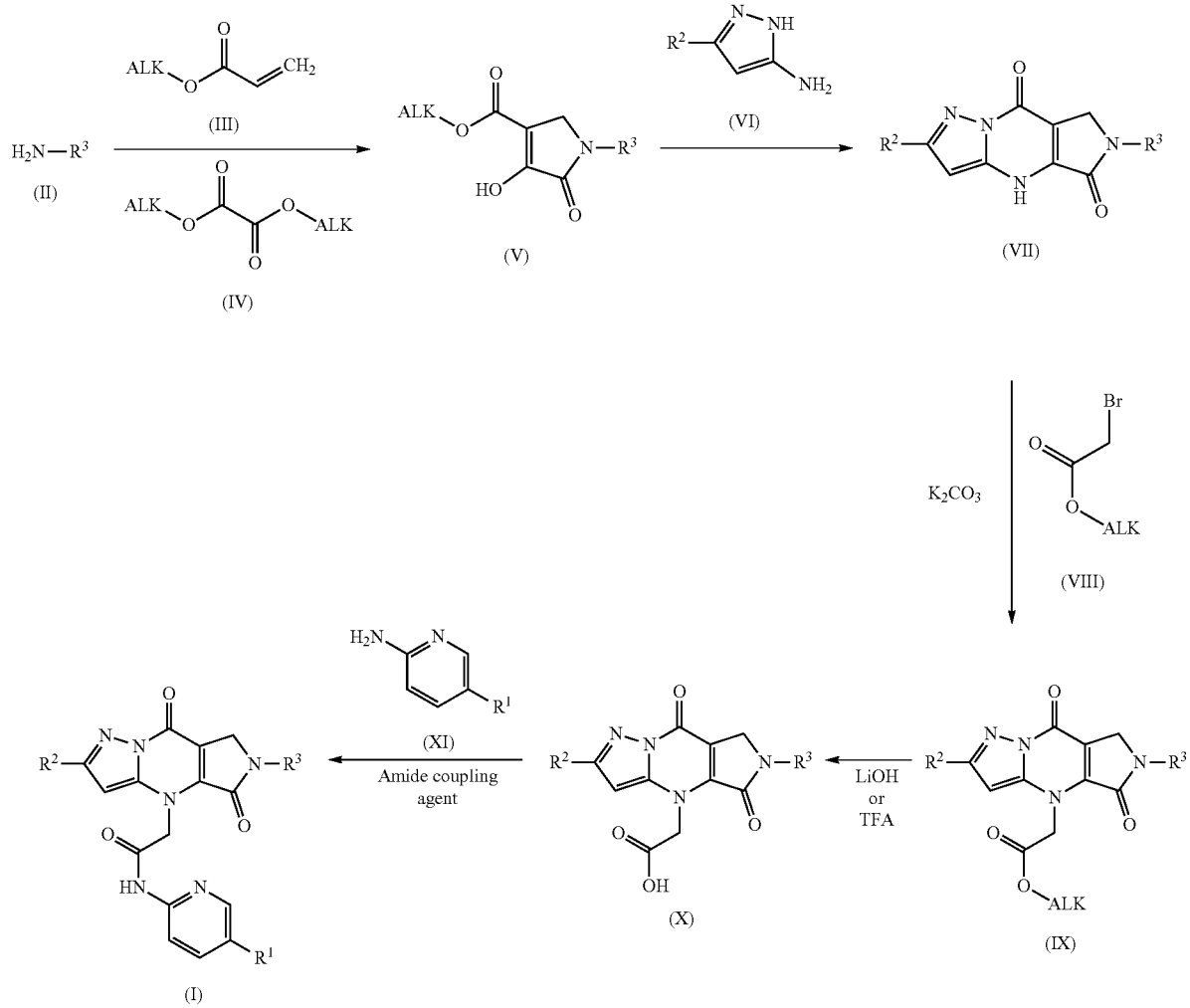

Scheme 1

Alternatively, cyclic β-ketoesters of general formula (V) may be prepared stepwise by preparing and isolating the amino-substituted beta-alaninester (IIIb) and subsequently reacting it with dialkyl oxalate of general formula (IV) in a base (such as sodium ethoxide) at temperatures between rt and 100° C. optionally followed by a Dieckmann cyclisation under aqueous acidic conditions (typically hydrochloric acid) at temperatures between rt and 100° C. as depicted in Scheme 1a.

Amino-substituted beta-alaninester (IIIb) may be prepared either by Michael addition of a primary amine of general formula (II), or salts thereof, with an alkyl acrylate of general formula (III) at temperatures between 0° C. and 50° C. or by reductive amination of a beta-alanine ester or salts thereof of general formula (IIIa) with an appropriate aldehyde of general formula (IIa) in presence of a reducing agent, like for example sodium cyanoborohydride in protic solvent mixtures such as dichloromethane/methanol/acetic acid at temperatures ranging from rt to 50° C., wherein $R^3$ is $CH_2-R^{3'}$.

Scheme 1a

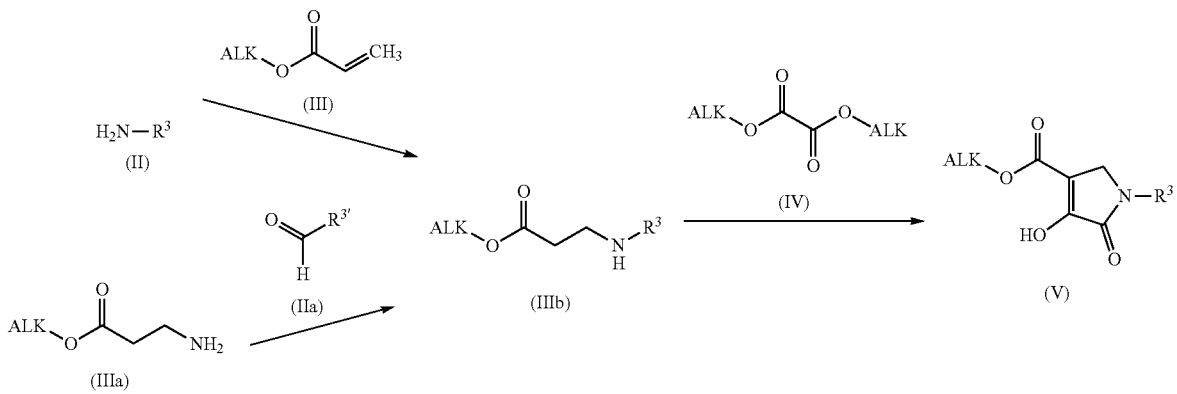

In an alternative approach outlined in Scheme 2, compounds of the general formula (XIII) can be obtained by reacting the appropriate 2-amino pyridine of general formula (XI) with α-halo-haloacetates of the general formula (XII) in an appropriate solvent (such as dichloromethane) in the presence of an organic base (for example trimethylamine or diisopropylethylamine) at temperatures between 5° C. and 30° C. Chemoselective N-alkylation of a compound of general formula (VII) with a haloacetamide of general formula (XIII) in the presence of a base (such as potassium carbonate) and an aprotic solvent (such as acetonitrile or DMF) at temperatures between rt and 120° C. (typically 100° C.) gives the compounds of general formula (I).

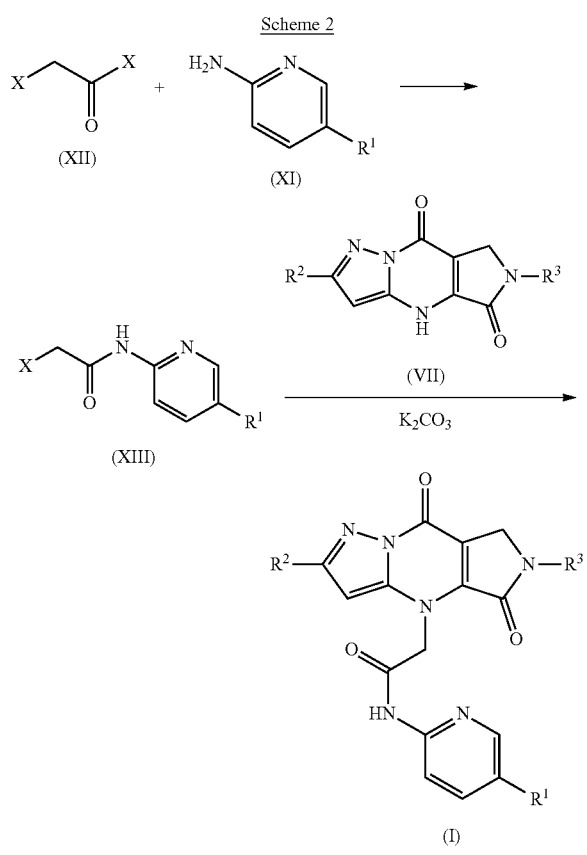

The starting materials of the general formula (II) are either commercially available or can be synthesized via methods known to those skilled in the art from the corresponding alcohol. For example, activation of the corresponding alcohol with p-toluenesulfonyl chloride in the presence of a base (such as triethylamine) in a suitable solvent (for example dichloromethane) followed by displacement with sodium azide in a suitable solvent (for example N,N-dimethylformamide) affords the equivalent azide, which can then undergo reduction with hydrogen in the presence of a palladium catalyst in solvents like ethanol, ethyl acetate or mixtures thereof to afford the desired amine of general formula (II). In an alternative approach, the phthalimide protected amine can be introduced by Mitsunobu reaction of the corresponding alcohol with phthalimide in the presence of a base (such as trimethylamine) and an azodicarboxylate (for example diethyl azodicarboxylate) in a suitable solvent (for example tetrahydrofuran) at temperatures between 0° C. and rt. Cleavage of the phthalamide protecting group with hydrazine monohydrate in ethanol at temperatures between 60° C. and 90° C. then affords the desired amine of general formula (II).

The 5-amino-1H-pyrazole starting materials of general formula (VI) are either commercially available, or can be accessed by methods known to those skilled in the art as depicted in Scheme 3. 5-Amino-1H-pyrazoles of general formula (VI) can be obtained from the synthons of the formula (XIV). Addition of acetonitrile reactant to alkyl esters of general formula (XIV) in aprotic solvents (for example tetrahydrofuran or acetonitrile) in the presence of base (such as sodium hydride or potassium tert-butoxide) at temperatures between 0° C. and 80° C. affords compounds of general formula (XV). Cyclisation of a compound of general formula (XV) with hydrazine monohydrate in ethanol at temperatures between 60° C. and 90° C. gives the desired 5-amino-1H-pyrazole of general formula (VI).

Alternatively, 5-nitro-1H-pyrazoles of the general formula (XVI) can be reduced with hydrogen gas in the presence of a palladium catalyst in solvents like ethanol, ethyl acetate or mixtures thereof to afford the desired 5-amine-1H-pyrazoles of general formula (VI).

Scheme 3

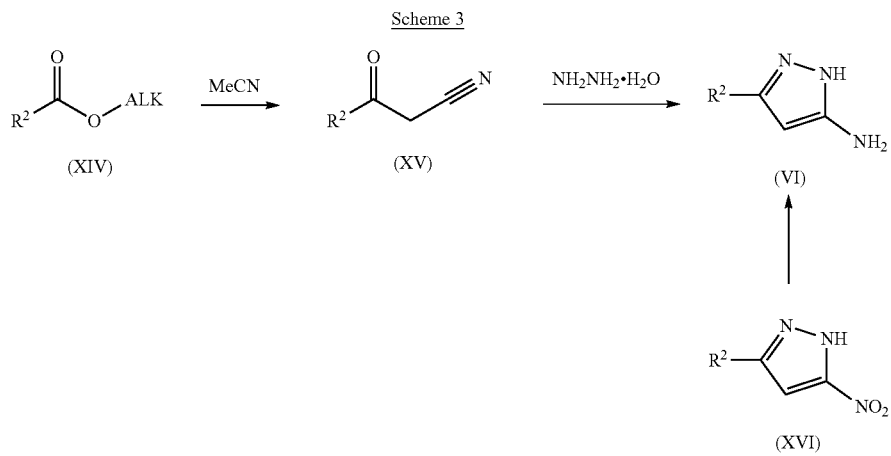

Compounds of general formula (VII), with the meaning of R² and R³ as defined in general formula (I), can be synthesised from compounds of general formula (XVII) where R²=bromide, according to a general procedure depicted in Scheme 4, by methods known to those skilled in the art. Stille reaction of compounds of the general formula (XVII) where R²=bromide with tributyl(1-ethoxyvinyl)stannane in a suitable solvent (for example toluene), a base (such as potassium or cesium carbonate) and a catalyst (for example tetrakis(triphenylphosphine)palladium(0)) at temperatures between 40° C. and 110° C. affords a ketone of the general formula (XVIII). Subsequent treatment with an Grignard reagent (for example methyl magnesium bromide) in a suitable solvent (such as tetrahydrofuran) at temperatures between 0° C. and rt affords intermediates of the general formula (VII), where R² is a tertiary alcohol.

In Scheme 4, general formula (VII) represents intermediates where R² is a tertiary alcohol group.

Compounds of general formula (I) with the meaning of R¹-R³ as defined in general formula (I), can be synthesised according to a general procedure depicted in Scheme 5 starting from compounds of general formula (XIX) where R²=bromide, by methods known to those skilled in the art. The compounds of the general formula (XX) can be obtained from bromides of general formula (XIX) by reaction with phenyl formate in a suitable solvent (for example acetonitrile or N,N-dimethylformamide), a base (such as trimethylamine or diisopropylethylamine) and a catalyst-ligand mixture (for example palladium(II) acetate/tri-tert-butylphosphonium tetrafluoroborate) by thermal heating or microwave irradiation at temperatures between 40° C. and 110° C. Phenyl esters of the general formula (XX) can be converted to the corresponding amide of general formula (I) (where R²=—C(O)N(R⁴)(R⁵)) by reaction with amines of the general formula (XXI) in a suitable aprotic solvent (such as acetonitrile or N,N-dimethylformamide) at temperatures between 0° C. and 80° C.

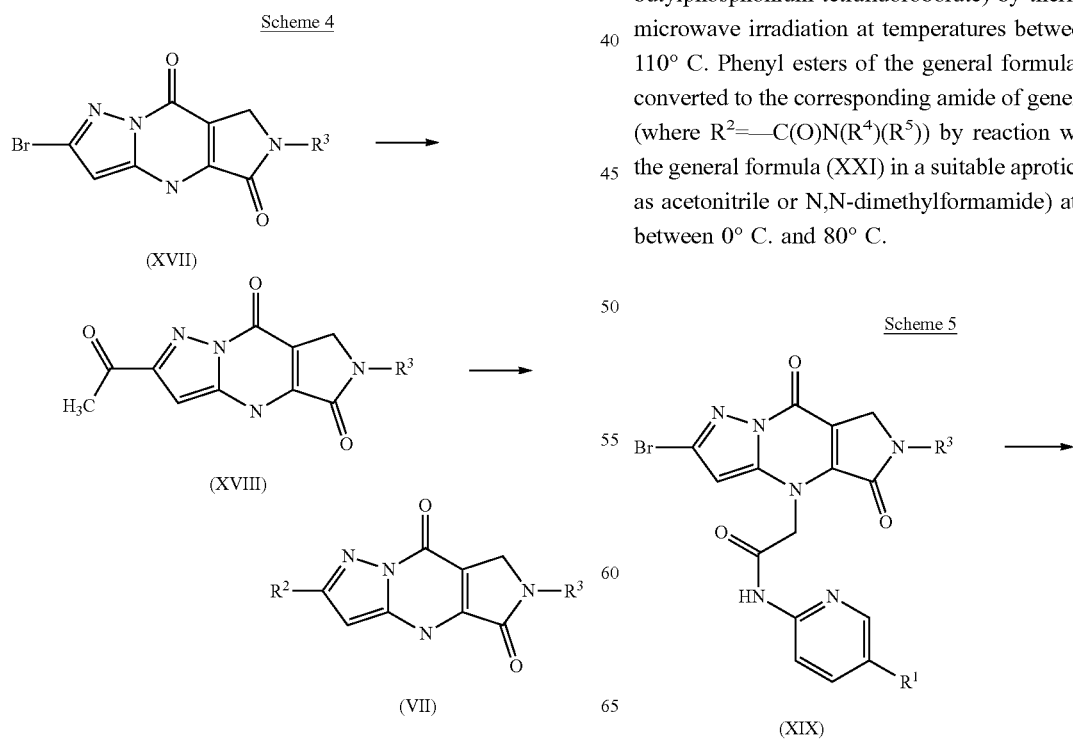

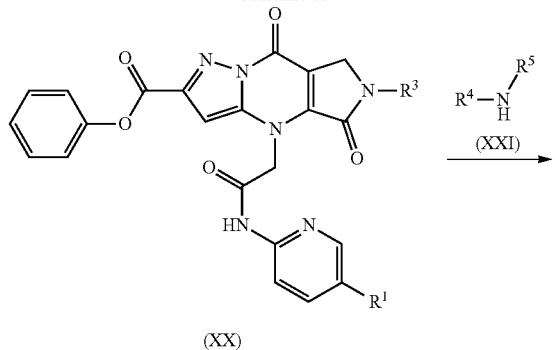 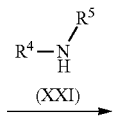 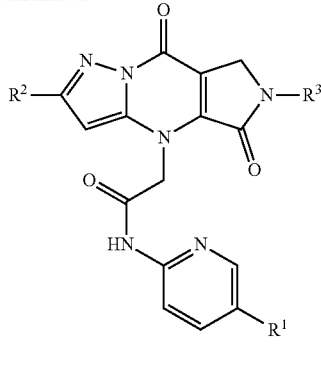

In Scheme 5, general formula (XXI) represents H—N(R⁴)(R⁵) and in general formula (I) R² represents —C(O)N(R⁴)(R⁵).

In addition, as depicted in Scheme 6 phenyl esters of the general formula (XX) can be reacted with an appropriate reducing agent (for example sodium borohydride) in an aprotic solvent or solvent mixture (such as tetrahydrofuran or N,N-dimethylformamide) at temperatures between 0° C. and 60° C. to give alcohol compounds of general formula (I), where R²=—CH₂OH.

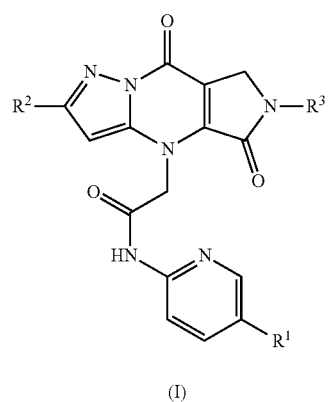

In Scheme 6 general formula (I) R² represents —CH₂OH.

Compounds of general formula (XIX) wherein R²=bromide, can also be reacted to form new compounds of general formula (I) by methods known to those skilled in the art, as illustrated in Scheme 7. Compounds of general formula (XIX) wherein R²=bromide are reacted with boronic acids of the general formula (XXII), wherein R²=optionally substituted phenyl or 5- to 6-membered heteroaryl, in a suitable solvent (for example 1,4-dioxane or N,N-dimethylformamide), a base (such as potassium or cesium carbonate) and a catalyst (for example [1,1'-bis(diphenylphosphino)ferrocene]dichloropalladium(II) or tetrakis(triphenylphosphine)-palladium(0)) by thermal heating or microwave irradiation at temperatures between 40° C. and 110° C. Alternatively, the respective pinacol ester of the boronic acid can be used in the reaction.

Scheme 6

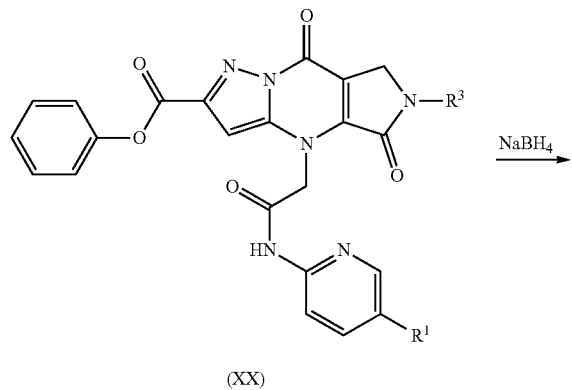

Scheme 7

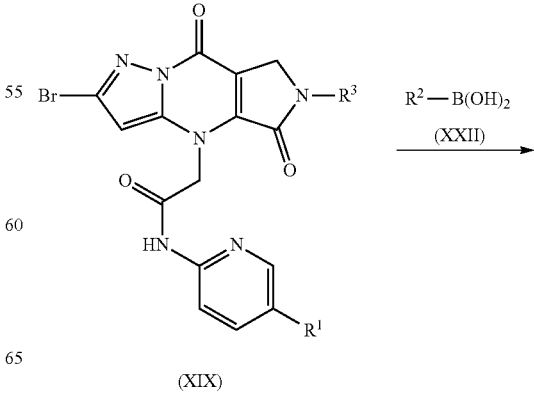

-continued

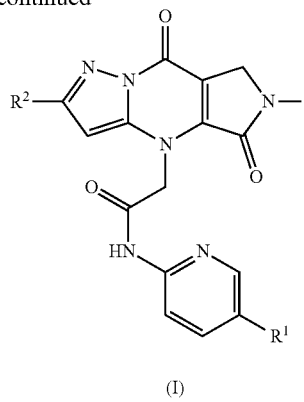

(I)

In Scheme 7 general formula (I) R² represents an optionally substituted phenyl or optionally substituted 5- to 6-membered heteroaryl.

Compounds of the general formula (I), where R²=CN, can be obtained from a bromide of general formula (XIX) by reaction with zinc cyanide in a suitable solvent (such as N,N-dimethylacetamide) with a catalyst (for example tris(dibenzylideneacetone)dipalladium(0)) and ligand (such as 1,1'-bis(diphenylphosphino)ferrocene) at temperatures between 80° C. and 140° C. as shown in Scheme 8.

Scheme 8

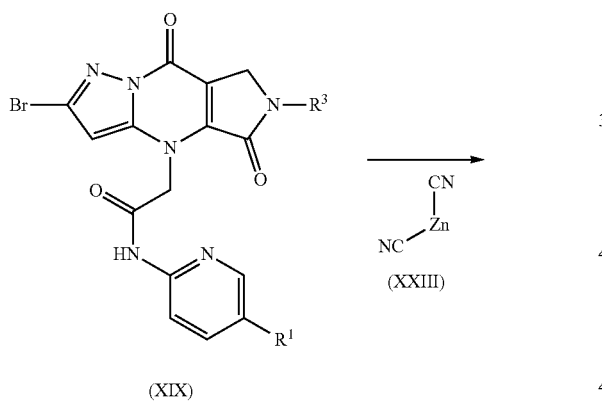

In Scheme 8 general formula (I) R² represents CN.

The compounds of the general formula (I), wherein R²=—N(R⁴)(R⁵), can be obtained from bromides of general formula (XIX) by reaction under Buchwald-Hartwig conditions as shown in Scheme 9. For example, a bromide of general formula (XIX) can be reacted with an amine of general formula (XXI), wherein R²=—N(R⁴)(R⁵), in a suitable solvent (such as 1,4-dioxane or toluene), a base (for example lithium bis(trimethylsilyl)amide or sodium tert-butoxide) a catalyst (for example bis(dibenzylideneacetone)palladium(0) or [(2-di-cyclohexylphosphino-3,6-dimethoxy-2',4',6'-triisopropyl-1,1'-biphenyl)-2-(2'-amino-1,1'-biphenyl)]palladium(II) methanesulfonate) and a ligand (such as 2-(di-tert-butylphosphino)-2',4',6'-triisopropyl-3,6-dimethoxy-1,1'-biphenyl or 1,1'-bis(di-tert-butylphosphino)ferrocene) at temperatures between 40° C. and 110° C.

Scheme 9

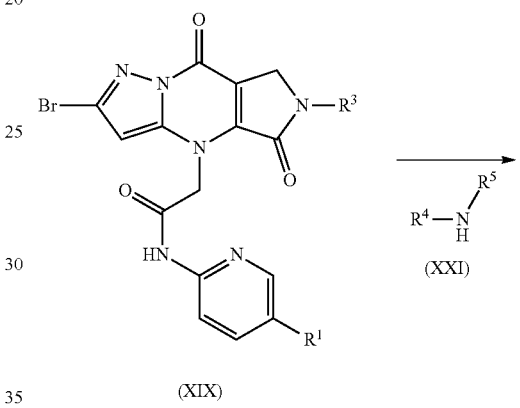

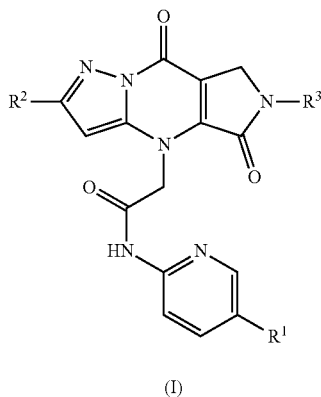

(I)

In Scheme 9 general formula (XXI) represents H—N(R⁴)(R⁵) and in general formula (I) R² is —N(R⁴)(R⁵).

In Scheme 10 bromides of general formula (XIX) can be reacted with heterocycloalkenyl or heterobicycloalkenyl boronic acids or boronic esters [for illustration, a dioxaborolane of general formula (XXIV) is shown], under the conditions outlined for Scheme 7, to afford compounds of general formula (I) wherein $R^{15}$ and $R^{16}$ together form an optionally substituted 5- to 6-membered heterocycloalkenyl or 6- to 9-membered heterobicycloalkenyl moiety. Furthermore, compounds of general formula (I) wherein $R^{15}$ and $R^{16}$ together form a 5- to 6-membered heterocycloalkenyl or a 6- to 9-membered heterobicycloalkenyl moiety can be reduced in a suitable solvent (such as ethanol or ethyl acetate, or mixtures thereof) with a catalyst (such as palladium on carbon) under an atmosphere of hydrogen gas at rt to new compounds of general formula (I), wherein $R^{15}$ and $R^{16}$ together form a optionally substituted 5- to 6-membered heterocycloalkyl or a 6- to 9-membered heterobicycloalkyl moiety.

Scheme 10

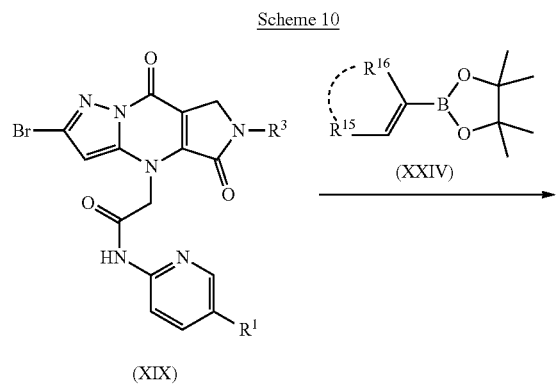

(XIX)

(I)

$R^{15}$ and $R^{16}$ together form a 5- to 6-membered heterocycloalkenyl or 6- to 9-membered heterobicycloalkenyl moiety

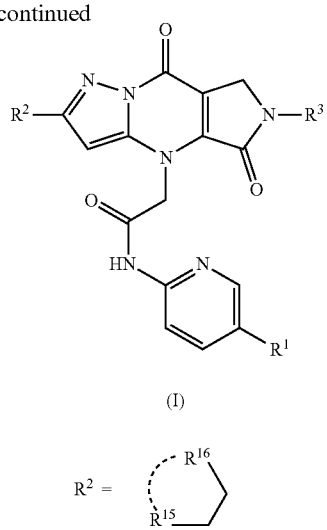

(I)

$R^{15}$ and $R^{16}$ together form a 5- to 6-membered heterocycloalkenyl or 6- to 9-membered heterobicycloalkenyl moiety In Scheme 10 general formula (I) $R^2$ represents an optionally substituted 5- to 6-membered heterocycloalkenyl, optionally substituted 4- to 6-membered heterocycloalkyl or an optionally substituted 6- to 9-membered heterobicycloalkyl.

Compounds of the general formula (I) where $R^2$=C(O)N($R^4$)($R^5$) can also be synthesised according to the route outlined in Scheme 11. Cyclocondensation of a compound of general formula (V), where $ALK^1$=$C_1$-$C_6$-alkyl (for example methyl or ethyl), with a 5-amino-1H-pyrazole of general formula (XXVII), where $ALK^2$=$C_1$-$C_6$-alkyl, in glacial acetic acid at temperatures between rt and 140° C. (typically at 120° C.) gives compounds of general formula (XXVIII). Ester group saponification of a compound of general formula (XXVIII) in a suitable solvent or solvent mixture (for example methanol, ethanol or tetrahydrofuran) with addition of an aqueous solution of an alkali metal hydroxide (for example lithium hydroxide or sodium hydroxide) at temperatures between 10° C. and 80° C., gives the corresponding carboxylic acid of general formula (XXIX) after acidic reaction work up (for example with aqueous hydrochloric acid). Regioselective N-alkylation of a compound of general formula (XXIX) with an alkyl haloacetate of general formula (XII) in the presence of base (such as potassium carbonate) and aprotic solvent (such as acetonitrile or DMF) at temperatures between rt and 120° C. (typically 100° C.) gives the carboxylic acid intermediates of general formula (XXX). A carboxylic acid of formula (XXX) may react with a primary or secondary amine of general formula (XXI) by methods previously described to give compounds of the general formula (I).

By extension, the order of the reaction sequence can be modified such that carboxylic acid compounds of general formula (XXIX) may be reacted first with a primary or secondary amine of general formula (XXI) under amide forming conditions, then secondly with an alkyl haloacetate of general formula (XII) in the presence of base to give compounds of the general formula (I).

Scheme 11

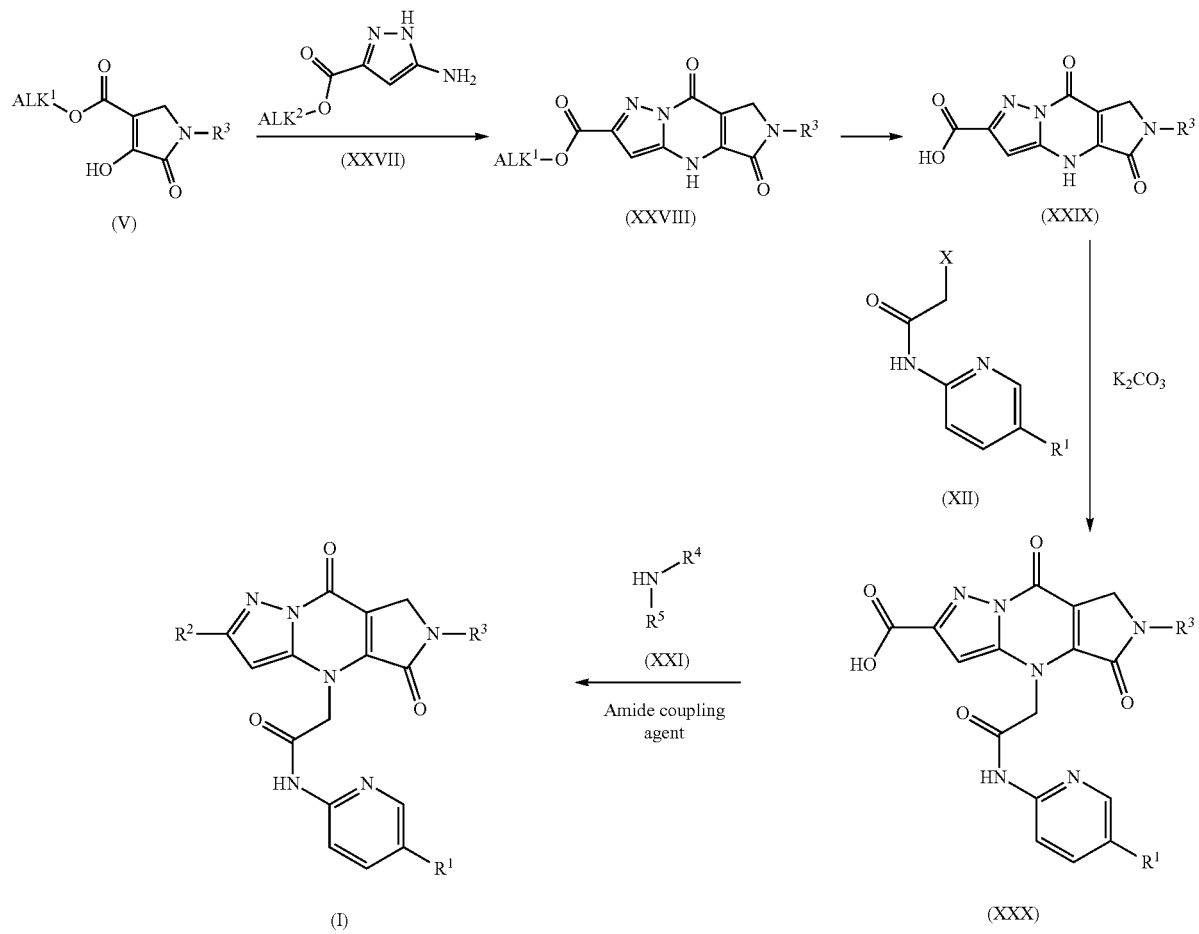

In Scheme 11 general formula (I), $R^2$ represents —C(O)N($R^4$)($R^5$) and $ALK^{1,2}$ represents $C_1$-$C_6$-alkyl.

Scheme 12 shows an alternative strategy to synthesise compounds of the general formula (I) where $R^2$=C(O)N($R^4$)($R^5$). N-alkylation of a compound of general formula (XXVIII) with tert-butyl bromoacetate in the presence of base (such as potassium carbonate) and aprotic solvent (such as acetonitrile or DMF) at temperatures between rt and 120° C. (typically 100° C.) gives an ester compound of general formula (XXXI). Ester group saponification of a compound of general formula (XXXI) under acidic conditions, for example in dichloromethane and trifluoroacetic acid at temperatures between 0° C. and 30° C., affords the corresponding carboxylic acid of general formula (XXXII) after concentration of the reaction mixture. A carboxylic acid of general formula (XXXII) may react with a 2-aminopyridine of general formula (XI) by methods previously outlined to give the compounds of the general formula (XXXIII). Reaction with primary or secondary amines of the general formula (XXI) in a suitable solvent (for example 1,2-dichloroethane or toluene) in the presence of trimethylaluminium by thermal heating or microwave irradiation at temperatures between 50° C. and 120° C. affords the corresponding compound of general formula (I), wherein $R^2$=—C(O)N($R^4$)($R^5$) and $ALK^3$=$C_1$-$C_6$-alkyl.

Scheme 12

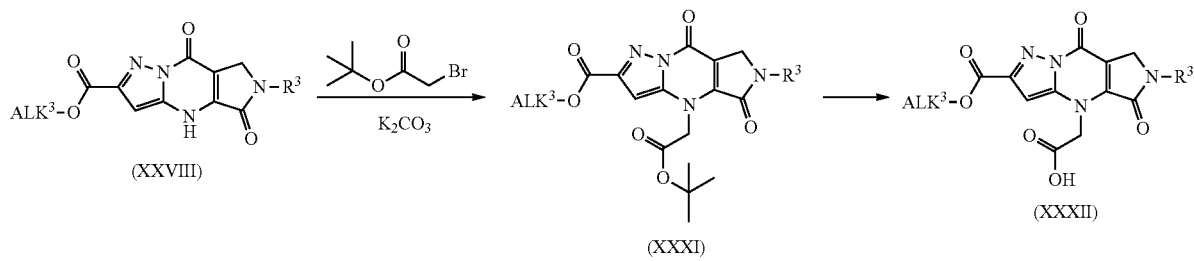

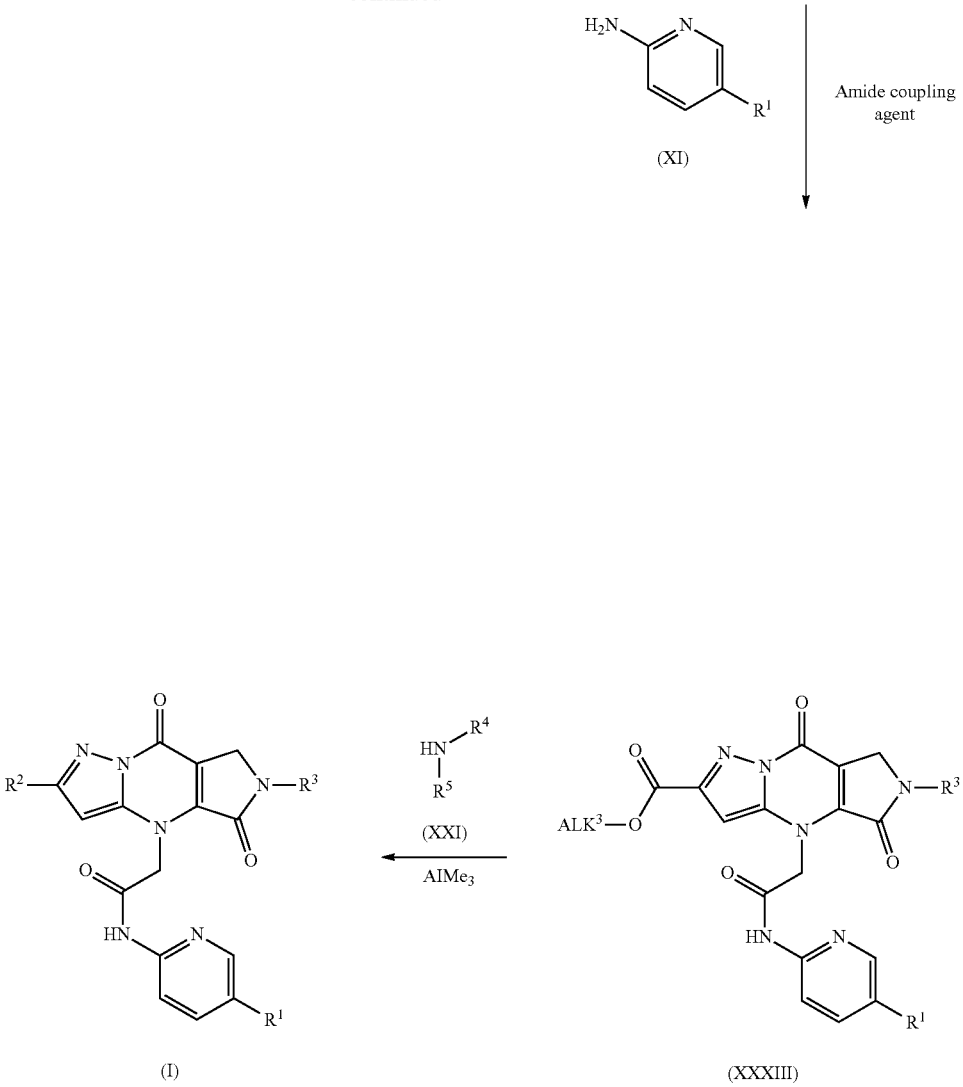

In Scheme 12 general formula (I), R² represents —C(O)N(R⁴)(R⁵) and ALK³ represents C₁-C₆-alkyl.

Compounds of general formula (I) can be further reacted to form new compounds of general formula (I) by those skilled in the art, as illustrated in Scheme 13. Alcohols of general formula (XXXIV) can be activated by conversion into a suitable leaving group (LG), for example a halide (such as chloro, bromo or iodo) or methanesulfonyloxy, p-toluenesulfonyloxy or trifluoromethanesulfonyloxy, by those skilled in the art. For example, by addition of thionyl chloride, CBr₄/PPh₃, I₂/PPh₃, methanesulfonyl chloride, p-toluenesulfonyl chloride or trifluoromethanesulfonic anhydride in a suitable solvent (for example dichloromethane) and in the presence of a base (such as N,N-diisopropylamine, triethylamine or imidazole) at temperatures between 0° C. and 100° C. to give compounds of the general formula (XXXV). Displacement of the leaving group (LG) of compounds of general formula (XXXV) with amines of general formula (XXI) in a suitable solvent (for example dichloromethane, acetonitrile or N,N-dimethylformamide) in the presence of a base (such as potassium carbonate, cesium carbonate, N,N-diisopropylamine or triethylamine) at temperatures between 0° C. and 120° C. gives compounds of general formula (I), wherein R² is —CH₂N(R⁴)(R⁵).

Scheme 13

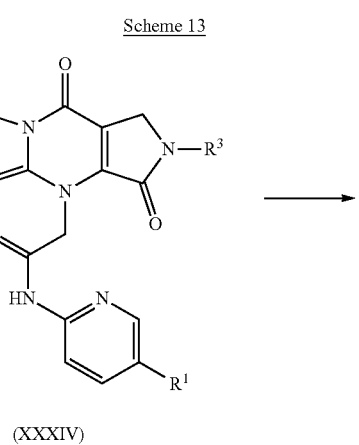

(XXXIV)

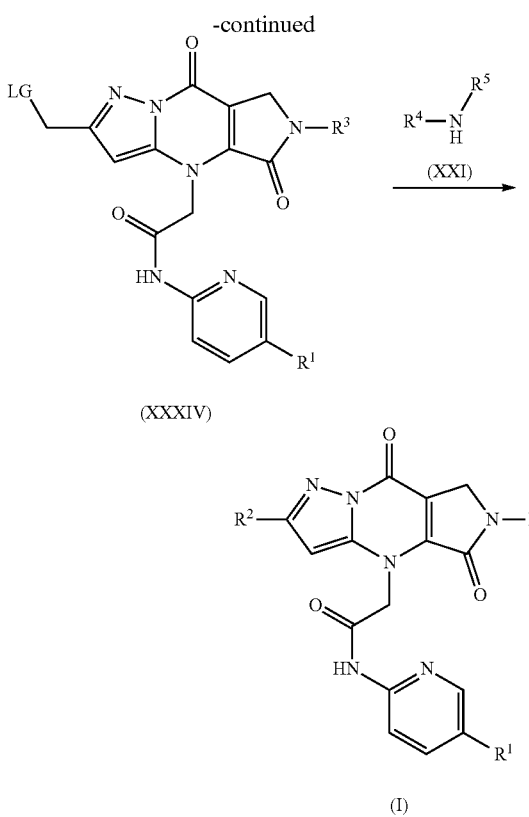

In Scheme 13 general formula (I), $R^2$ represents —$CH_2N(R^4)(R^5)$.

Compounds of general formula (I) can be further reacted to form new compounds of general formula (I) by those skilled in the art, as illustrated in Scheme 14. Compounds of general formula (XXXVI), equivalent to compounds of general formula (I) wherein $R^3$ is a benzyloxy-alkyl group (for example —$CH_2CH_2OCH_2Ph$), can be benzyl-deprotected using a palladium catalyst (such as palladium on carbon) in a suitable solvent (such as acetic acid) in the presence of a hydrogen gas at rt to give a compound of general formula (XXXVII), equivalent to compounds of general formula (I) wherein $R^3$ is —$CH_2CH_2OH$. Compounds of the general formula (I) wherein $R^3$ is —$CH_2CH_2N(R^4)(R^5)$, can be synthesised by activation of the corresponding alcohol of a compound of general formula (XXXVII) (for example with trifluoromethanesulfonic anhydride) in the presence of a base (for example pyridine) in a suitable aprotic solvent (such as dichloromethane, tetrahydrofuran or N,N-dimethylformamide) at temperatures between −78° C. and 0° C. to give a compound of general formula (XXXVIII). Displacement of the trifluoromethanesulfonate group with an amine of general formula (XXXIX) in a suitable solvent (for example dichloromethane, tetrahydrofuran or N,N-dimethylformamide) at temperatures between −10° C. and 60° C. gives compounds of general formula (I), wherein $R^3$ is —$CH_2CH_2N(R^4)(R^5)$.

Scheme 14

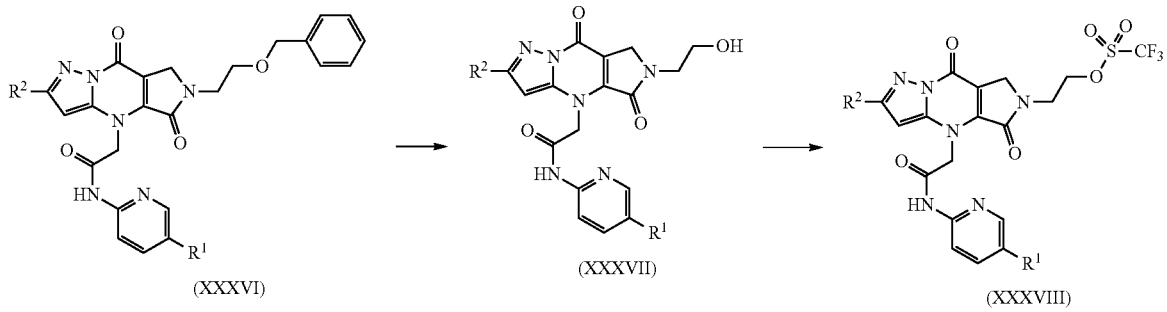

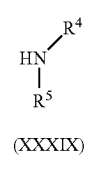

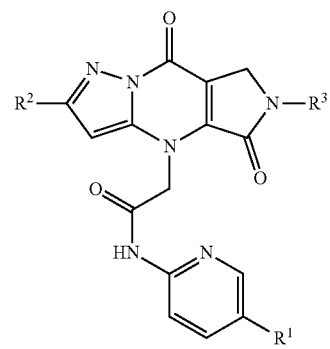

(I)

In Scheme 14 general formula (I), $R^3$ represents —$CH_2CH_2N(R^4)(R^5)$. General formula (XXXVI) is equivalent to general formula (I) where $R^3$ represents —$CH_2CH_2OCH_2Ph$. General formula (XXXVII) is equivalent to general formula (I) where $R^3$ represents —$CH_2CH_2OH$.

Compounds of general formula (I), where $R^2$ or $R^3$ contains a tert-butyl carbonate protected amine, can be reacted to form new compounds of general formula (I), where $R^2$ or $R^3$ contains a primary or secondary amine, or salts thereof, by treatment in a suitable solvent (such as dichloromethane or 1,4-dioxane) in the presence of acid (for example hydrochloric acid or trifluoroacetic acid). Additionally, compounds of general formula (I), where $R^2$ or $R^3$ contain a primary or secondary amine, or salts thereof, can be further transformed into new compounds by methods known to those skilled in the art by reaction of the amine moiety with carboxylic acids, acid chlorides, sulfonyl chlorides, alkyl halides, aldehydes or ketones to form compounds of general formula (I) with the meaning of $R^1$, $R^2$ and $R^3$ as defined in general formula (I).

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action and pharmacokinetic profile if supported by data, both of which could not have been predicted. Compounds of the present invention have surprisingly been found to effectively and selectively inhibit P2X3 and it is possible therefore that said compounds be used for the treatment or prophylaxis of diseases, preferably neurogenic disorders in humans and animals.

Compounds of general formula (I) of the present invention may therefore be used for the treatment or prophylaxis of following diseases:
  genitourinary, gastrointestinal, respiratory and pain-related diseases, conditions and disorders;
  gynecological diseases including dysmenorrhea (primary and secondary dysmenorrhea), dyspareunia, endometriosis, and adenomyosis; endometriosis-associated pain; endometriosis-associated symptoms, wherein said symptoms are in particular dysmenorrhea, dyspareunia, dysuria, or dyschezia; endometriosis-associated proliferation; pelvic hypersensitivity; uterine fibroid-associated pain and discomfort;
  urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular Interstitial cystitis; idiopathic bladder hypersensitivity [Ford 2014, purines 2014, abstract book p15];
  pain syndromes (including acute, chronic, inflammatory and neuropathic pain), preferably inflammatory pain, low back pain surgical pain, visceral pain, dental pain, periodontitis, premenstrual pain, endometriosis-associated pain, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, postherpetic neuralgia, chronic lower back pain, neck pain phantom limb pain, pelvic pain syndrome, chronic pelvic pain, neuroma pain, complex regional pain syndrome, pain associated with gastrointestinal distension, chronic arthritic pain and related neuralgias, and pain associated with cancer, Morphine-resistant pain, pain associated with chemotherapy, HIV and HIV treatment-induced neuropathy; and pain associated with diseases or disorders selected from the group consisting of hyperalgesia, allodynia, functional bowel disorders (such as irritable bowel syndrome) and arthritis (such as osteoarthritis, rheumatoid arthritis and ankylosing spondylitis);
Epilepsy, partial and generalized seizures;
Respiratory disorders including chronic obstructive pulmonary disorder (COPD) [Ford 2013, European Respiratory Society Annual Congress 2013], asthma [Ford 2014, 8th Pain & Migraine Therapeutics Summit], bronchospasm, pulmonary fibrosis, acute cough, chronic cough including chronic idiopathic and chronic refractory cough;

Gastrointestinal disorders including irritable bowel syndrome (IBS), inflammatory bowel disease (IBD), biliary colic and other biliary disorders, renal colic, diarrhea-dominant IBS, gastroesophageal reflux, gastrointestinal distension, Crohn's disease and the like;

neurodegenerative disorders such as Alzheimer's disease, Multiple Sclerosis, Parkinson's disease, Brain ischemia and traumatic brain injury;

myocardial infarction, lipid disorders;

pain-associated diseases or disorders selected from the group consisting of hyperalgesia, allodynia, functional bowel disorders (such as irritable bowel syndrome), gout, arthritis (such as osteoarthritis [Ford 2014, $8^{th}$ Pain & Migraine Therapeutics Summit], rheumatoid arthritis and ankylosing spondylitis), burning mouth syndrome, burns, migraine or cluster headaches, nerve injury, traumatic nerve injury, post-traumatic injuries (including fractures and sport injuries), neuritis, neuralgias, poisoning, ischemic injury, interstitial cystitis, cancer, trigeminal neuralgia, small fiber neuropathy, diabetic neuropathy, chronic arthritis and related neuralgias, HIV and HIV treatment-induced neuropathy, pruritus; impaired wound healing and disease of the skeleton like degeneration of the joints.

The present invention also provides methods of treating of following diseases and disorders:

genitourinary, gastrointestinal, respiratory and pain-related diseases, conditions and disorders;

gynecological diseases including dysmenorrhea (primary and secondary dysmenorrhea), dyspareunia, endometriosis, and adenomyosis; endometriosis-associated pain; endometriosis-associated symptoms, wherein said symptoms are in particular dysmenorrhea, dyspareunia, dysuria, or dyschezia; endometriosis-associated proliferation; pelvic hypersensitivity; uterine fibroid-associated pain and discomfort;

urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular Interstitial cystitis; idiopathic bladder hypersensitivity [Ford 2014, purines 2014, abstract book p15];

pain syndromes (including acute, chronic, inflammatory and neuropathic pain), preferably inflammatory pain, low back pain surgical pain, visceral pain, dental pain, periodontitis, premenstrual pain, endometriosis-associated pain, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, postherpetic neuralgia, chronic lower back pain, neck pain phantom limb pain, pelvic pain syndrome, chronic pelvic pain, neuroma pain, complex regional pain syndrome, pain associated with gastrointestinal distension, chronic arthritic pain and related neuralgias, and pain associated with cancer, Morphine-resistant pain, pain associated with chemotherapy, HIV and HIV treatment-induced neuropathy; and pain associated with diseases or disorders selected from the group consisting of hyperalgesia, allodynia, functional bowel disorders (such as irritable bowel syndrome) and arthritis (such as osteoarthritis, rheumatoid arthritis and ankylosing spondylitis);

Epilepsy, partial and generalized seizures;

Respiratory disorders including chronic obstructive pulmonary disorder (COPD) [Ford 2013, European Respiratory Society Annual Congress 2013], asthma [Ford 2014, 8th Pain & Migraine Therapeutics Summit], bronchospasm, pulmonary fibrosis, acute cough, chronic cough including chronic idiopathic and chronic refractory cough;

Gastrointestinal disorders including irritable bowel syndrome (IBS), inflammatory bowel disease (IBD), biliary colic and other biliary disorders, renal colic, diarrhea-dominant IBS, gastroesophageal reflux, gastrointestinal distension, Crohn's disease and the like;

neurodegenerative disorders such as Alzheimer's disease, Multiple Sclerosis, Parkinson's disease, Brain ischemia and traumatic brain injury;

myocardial infarction, lipid disorders;

pain-associated diseases or disorders selected from the group consisting of hyperalgesia, allodynia, functional bowel disorders (such as irritable bowel syndrome), gout, arthritis (such as osteoarthritis [Ford 2014, $8^{th}$ Pain & Migraine Therapeutics Summit], rheumatoid arthritis and ankylosing spondylitis), burning mouth syndrome, burns, migraine or cluster headaches, nerve injury, traumatic nerve injury, post-traumatic injuries (including fractures and sport injuries), neuritis, neuralgias, poisoning, ischemic injury, interstitial cystitis, cancer, trigeminal neuralgia, small fiber neuropathy, diabetic neuropathy, chronic arthritis and related neuralgias, HIV and HIV treatment-induced neuropathy, pruritus; impaired wound healing and disease of the skeleton like degeneration of the joints.

These diseases and disorders have been well characterized in humans, but also exist with a similar etiology in other mammals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as gynecological disease.

The compounds of the present invention can be used in particular in therapy and prevention, i.e. prophylaxis, of disease, specifically for genitourinary, gastrointestinal, respiratory and pain-related diseases, conditions and disorders;

gynecological diseases including dysmenorrhea (primary and secondary dysmenorrhea), dyspareunia, endometriosis, and adenomyosis; endometriosis-associated pain; endometriosis-associated symptoms, wherein said symptoms are in particular dysmenorrhea, dyspareunia, dysuria, or dyschezia; endometriosis-associated proliferation; pelvic hypersensitivity; uterine fibroid-associated pain and discomfort;

urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular Interstitial cystitis; idiopathic bladder hypersensitivity [Ford 2014, purines 2014, abstract book p15];

pain syndromes (including acute, chronic, inflammatory and neuropathic pain), preferably inflammatory pain, low back pain surgical pain, visceral pain, dental pain, periodontitis, premenstrual pain, endometriosis-associated pain, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, postherpetic neuralgia, chronic lower back pain, neck pain phantom limb pain, pelvic pain syndrome, chronic pelvic pain, neuroma pain, complex regional pain syndrome, pain associated with gastrointestinal distension, chronic arthritic pain and related neuralgias, and pain associated with cancer, Morphine-resistant pain, pain associated with chemotherapy, HIV and HIV treatment-induced neuropathy; and pain associated with diseases or disorders selected from the group consisting of hyperalgesia, allodynia, functional bowel disorders (such as irritable bowel syndrome) and arthritis (such as osteoarthritis, rheumatoid arthritis and ankylosing spondylitis);

Epilepsy, partial and generalized seizures;

Respiratory disorders including chronic obstructive pulmonary disorder (COPD) [Ford 2013, European Respiratory Society Annual Congress 2013], asthma [Ford 2014, 8th Pain & Migraine Therapeutics Summit], bronchospasm, pulmonary fibrosis, acute cough, chronic cough including chronic idiopathic and chronic refractory cough;

Gastrointestinal disorders including irritable bowel syndrome (IBS), inflammatory bowel disease (IBD), biliary colic and other biliary disorders, renal colic, diarrhea-dominant IBS, gastroesophageal reflux, gastrointestinal distension, Crohn's disease and the like;

neurodegenerative disorders such as Alzheimer's disease, Multiple Sclerosis, Parkinson's disease, Brain ischemia and traumatic brain injury;

myocardial infarction, lipid disorders;

pain-associated diseases or disorders selected from the group consisting of hyperalgesia, allodynia, functional bowel disorders (such as irritable bowel syndrome), gout, arthritis (such as osteoarthritis [Ford 2014, $8^{th}$ Pain & Migraine Therapeutics Summit], rheumatoid arthritis and ankylosing spondylitis), burning mouth syndrome, burns, migraine or cluster headaches, nerve injury, traumatic nerve injury, post-traumatic injuries (including fractures and sport injuries), neuritis, neuralgias, poisoning, ischemic injury, interstitial cystitis, cancer, trigeminal neuralgia, small fiber neuropathy, diabetic neuropathy, chronic arthritis and related neuralgias, HIV and HIV treatment-induced neuropathy, pruritus; impaired wound healing and disease of the skeleton like degeneration of the joints.

In accordance with a further aspect, the present invention covers compounds of general formula (I), as described supra, or stereoisomers, N-oxides, hydrates, solvates, and salts thereof, particularly pharmaceutically acceptable salts thereof, or mixtures of same, for use in the treatment or prophylaxis of diseases, in particular neurogenic disorders.

The pharmaceutical activity of the compounds according to the invention can be explained by their activity as P2X3 antagonists.

In accordance with a further aspect, the present invention covers the use of compounds of general formula (I), as described supra, or stereoisomers, N-oxides, hydrates, solvates, and salts thereof, particularly pharmaceutically acceptable salts thereof, or mixtures of same, for the treatment or prophylaxis of following diseases:

genitourinary, gastrointestinal, respiratory and pain-related diseases, conditions and disorders;

gynecological diseases including dysmenorrhea (primary and secondary dysmenorrhea), dyspareunia, endometriosis, and adenomyosis; endometriosis-associated pain; endometriosis-associated symptoms, wherein said symptoms are in particular dysmenorrhea, dyspareunia, dysuria, or dyschezia; endometriosis-associated proliferation; pelvic hypersensitivity; uterine fibroid-associated pain and discomfort;

urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular Interstitial cystitis; idiopathic bladder hypersensitivity [Ford 2014, purines 2014, abstract book p15];

pain syndromes (including acute, chronic, inflammatory and neuropathic pain), preferably inflammatory pain, low back pain surgical pain, visceral pain, dental pain, periodontitis, premenstrual pain, endometriosis-associated pain, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, postherpetic neuralgia, chronic lower back pain, neck pain phantom limb pain, pelvic pain syndrome, chronic pelvic pain, neuroma pain, complex regional pain syndrome, pain associated with gastrointestinal distension, chronic arthritic pain and related neuralgias, and pain associated with cancer, Morphine-resistant pain, pain associated with chemotherapy, HIV and HIV treatment-induced neuropathy; and pain associated with diseases or disorders selected from the group consisting of hyperalgesia, allodynia, functional bowel disorders (such as irritable bowel syndrome) and arthritis (such as osteoarthritis, rheumatoid arthritis and ankylosing spondylitis);

Epilepsy, partial and generalized seizures;

Respiratory disorders including chronic obstructive pulmonary disorder (COPD), asthma, bronchospasm, pulmonary fibrosis, acute cough, chronic cough including chronic idiopathic and chronic refractory cough;

Gastrointestinal disorders including irritable bowel syndrome (IBS), inflammatory bowel disease (IBD), biliary colic and other biliary disorders, renal colic, diarrhea-dominant IBS, gastroesophageal reflux, gastrointestinal distension, Crohn's disease and the like;

neurodegenerative disorders such as Alzheimer's disease, Multiple Sclerosis, Parkinson's disease, Brain ischemia and traumatic brain injury;

myocardial infarction, lipid disorders;

pain-associated diseases or disorders selected from the group consisting of hyperalgesia, allodynia, functional bowel disorders (such as irritable bowel syndrome), gout, arthritis (such as osteoarthritis, rheumatoid arthritis and ankylosing spondylitis), burning mouth syndrome, burns, migraine or cluster headaches, nerve injury, traumatic nerve injury, post-traumatic injuries (including fractures and sport injuries), neuritis, neuralgias, poisoning, ischemic injury, interstitial cystitis, cancer, trigeminal neuralgia, small fiber neuropathy, diabetic neuropathy, chronic arthritis and related neuralgias, HIV and HIV treatment-induced neuropathy, pruritus; impaired wound healing and disease of the skeleton like degeneration of the joints.

In accordance with a further aspect, the present invention covers the use of a compound of general formula (I), described supra, or a stereoisomer, an N-oxide, a hydrate, a solvate, or a salt thereof, particularly a pharmaceutically acceptable salt thereof, or a mixture of same, for the prophylaxis or treatment of diseases, in particular neurogenic disorders, particularly gynecological disorders, urinary tract disease states, respiratory disorders and pain-associated diseases or disorders.

In accordance with a further aspect, the present invention covers the use of compounds of general formula (I), as described supra, or stereoisomers, N-oxides, hydrates, solvates, and salts thereof, particularly pharmaceutically acceptable salts thereof, or mixtures of same, in a method of treatment or prophylaxis of diseases, in particular neurogenic disorders, particularly gynecological, urinary tract disease states, respiratory disorders and pain-associated diseases or disorders.

In accordance with a further aspect, the present invention covers use of a compound of general formula (I), as described supra, or stereoisomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular neurogenic disorders, particularly gynecological, urinary tract disease states, respiratory disorders and pain-associated diseases or disorders.

In accordance with a further aspect, the present invention covers a method of treatment or prophylaxis of diseases, in particular neurogenic disorders, particularly gynecological, urinary tract disease states, respiratory disorders and pain-associated diseases or disorders, using an effective amount of a compound of general formula (I), as described supra, or stereoisomers, N-oxides, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®)), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®)); alginates, gelatine), disintegrants (for example modified starch, carboxymethylcellulose-sodium, sodium starch glycolate (such as, for example, Explotab®)), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®)), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragir), polyvinylpyrrolidones (such as, for example, Kollidon®)), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prophylaxis of the following dieases:

genitourinary, gastrointestinal, respiratory and pain-related diseases, conditions and disorders;

gynecological diseases including dysmenorrhea (primary and secondary dysmenorrhea), dyspareunia, endometriosis, and adenomyosis; endometriosis-associated pain; endometriosis-associated symptoms, wherein said symptoms are in particular dysmenorrhea, dyspareunia, dysuria, or dyschezia; endometriosis-associated proliferation; pelvic hypersensitivity; uterine fibroid-associated pain and discomfort;

urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular Interstitial cystitis; idiopathic bladder hypersensitivity [Ford 2014, purines 2014, abstract book p15];

pain syndromes (including acute, chronic, inflammatory and neuropathic pain), preferably inflammatory pain, low back pain surgical pain, visceral pain, dental pain, periodontitis, premenstrual pain, endometriosis-associated pain, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, postherpetic neuralgia, chronic lower back pain, neck pain phantom limb pain, pelvic pain syndrome, chronic pelvic pain, neuroma pain, complex regional pain syndrome, pain associated with gastrointestinal distension, chronic arthritic pain and related neuralgias, and pain associated with cancer, Morphine-resistant pain, pain associated with chemotherapy, HIV and HIV treatment-induced neuropathy; and pain associated with diseases or disorders selected from the group consisting of hyperalgesia, allodynia, functional bowel disorders (such as irritable bowel syndrome) and arthritis (such as osteoarthritis, rheumatoid arthritis and ankylosing spondylitis);

Epilepsy, partial and generalized seizures;

Respiratory disorders including chronic obstructive pulmonary disorder (COPD) [Ford 2013, European Respiratory Society Annual Congress 2013], asthma [Ford 2014, 8th Pain & Migraine Therapeutics Summit], bronchospasm, pulmonary fibrosis, acute cough, chronic cough including chronic idiopathic and chronic refractory cough;

Gastrointestinal disorders including irritable bowel syndrome (IBS), inflammatory bowel disease (IBD), biliary colic and other biliary disorders, renal colic, diarrhea-dominant IBS, gastroesophageal reflux, gastrointestinal distension, Crohn's disease and the like;

neurodegenerative disorders such as Alzheimer's disease, Multiple Sclerosis, Parkinson's disease, Brain ischemia and traumatic brain injury;

myocardial infarction, lipid disorders;

pain-associated diseases or disorders selected from the group consisting of hyperalgesia, allodynia, functional bowel disorders (such as irritable bowel syndrome), gout, arthritis (such as osteoarthritis [Ford 2014, $8^{th}$ Pain & Migraine Therapeutics Summit], rheumatoid arthritis and ankylosing spondylitis), burning mouth syndrome, burns, migraine or cluster headaches, nerve injury, traumatic nerve injury, post-traumatic injuries (including fractures and sport injuries), neuritis, neuralgias, poisoning, ischemic injury, interstitial cystitis, cancer, trigeminal neuralgia, small fiber neuropathy, diabetic neuropathy, chronic arthritis and related neuralgias, HIV and HIV treatment-induced neuropathy, pruritus; impaired wound healing and disease of the skeleton like degeneration of the joints.

Particularly, the present invention covers a pharmaceutical combination, which comprises:
one or more first active ingredients, in particular compounds of general formula (I) as defined supra, and
one or more further active ingredients for treatment or prophylaxis of the following diseases:
genitourinary, gastrointestinal, respiratory and pain-related diseases, conditions and disorders;
gynecological diseases including dysmenorrhea (primary and secondary dysmenorrhea), dyspareunia, endometriosis, and adenomyosis; endometriosis-associated pain; endometriosis-associated symptoms, wherein said symptoms are in particular dysmenorrhea, dyspareunia, dysuria, or dyschezia; endometriosis-associated proliferation; pelvic hypersensitivity; uterine fibroid-associated pain and discomfort;
urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular Interstitial cystitis; idiopathic bladder hypersensitivity [Ford 2014, purines 2014, abstract book p15];
pain syndromes (including acute, chronic, inflammatory and neuropathic pain), preferably inflammatory pain, low back pain surgical pain, visceral pain, dental pain, periodontitis, premenstrual pain, endometriosis-associated pain, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, posttherpetic neuralgia, chronic lower back pain, neck pain phantom limb pain, pelvic pain syndrome, chronic pelvic pain, neuroma pain, complex regional pain syndrome, pain associated with gastrointestinal distension, chronic arthritic pain and related neuralgias, and pain associated with cancer, Morphine-resistant pain, pain associated with chemotherapy, HIV and HIV treatment-induced neuropathy; and pain associated with diseases or disorders selected from the group consisting of hyperalgesia, allodynia, functional bowel disorders (such as irritable bowel syndrome) and arthritis (such as osteoarthritis, rheumatoid arthritis and ankylosing spondylitis);

Epilepsy, partial and generalized seizures;

Respiratory disorders including chronic obstructive pulmonary disorder (COPD) [Ford 2013, European Respiratory Society Annual Congress 2013], asthma [Ford 2014, 8th Pain & Migraine Therapeutics Summit], bronchospasm, pulmonary fibrosis, acute cough, chronic cough including chronic idiopathic and chronic refractory cough;

Gastrointestinal disorders including irritable bowel syndrome (IBS), inflammatory bowel disease (IBD), biliary colic and other biliary disorders, renal colic, diarrhea-dominant IBS, gastroesophageal reflux, gastrointestinal distension, Crohn's disease and the like;

neurodegenerative disorders such as Alzheimer's disease, Multiple Sclerosis, Parkinson's disease, Brain ischemia and traumatic brain injury;

myocardial infarction, lipid disorders;

pain-associated diseases or disorders selected from the group consisting of hyperalgesia, allodynia, functional bowel disorders (such as irritable bowel syndrome), gout, arthritis (such as osteoarthritis [Ford 2014, $8^{th}$ Pain & Migraine Therapeutics Summit], rheumatoid arthritis and ankylosing spondylitis), burning mouth syndrome, burns, migraine or cluster headaches, nerve injury, traumatic nerve injury, post-traumatic injuries (including fractures and sport injuries), neuritis, neuralgias, poisoning, ischemic injury, interstitial cystitis, cancer, trigeminal neuralgia, small fiber neuropathy, diabetic neuropathy, chronic arthritis and related neuralgias, HIV and HIV treatment-induced neuropathy, pruritus; impaired wound healing and disease of the skeleton like degeneration of the joints.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known indication agents.

The compounds of the present invention can be administered as the sole pharmaceutical agent or in combination with one or more other pharmaceutical agents where the combination causes no unacceptable adverse effects. The present invention relates also to such combinations.

For example, the compounds of the present invention can be combined with known hormonal therapeutic agents.

In particular, the compounds of the present invention can be administered in combination or as comedication with Selective Progesterone Receptor Modulators (SPRMs) or hormonal contraceptives. SPRMs and hormonal contraceptives can be administered via oral, subcutan, transdermal, intrauterine or intravaginal route, for example as Combined Oral Contraceptives (COCs), or Progestin-Only-Pills (POPs) or hormone-containing devices like implants, patches or intravaginal rings.

COCs include but are not limited to birth control pills or a birth control method that includes a combination of an estrogen (estradiol) and a progestogen (progestin). The estrogenic part is in most of the COCs ethinyl estradiol. Some COCs contain estradiol or estradiol valerate.

Said COCs contain the progestins norethynodrel, norethindrone, norethindrone acetate, ethynodiol acetate, norgestrel, levonorgestrel, norgestimate, desogestrel, gestodene, drospirenone, dienogest, or nomegestrol acetate.

Birth control pills include for example but are not limited to Yasmin, Yaz, both containing ethinyl estradiol and drospirenone; Microgynon or Miranova containing levonorgestrel and ethinyl estradiol; Marvelon containing ethinyl estradiol and desogestrel; Valette containing ethinyl estradiol and dienogest; Belara and Enriqa containing ethinyl estradiol and chlormadinonacetate; Qlaira containing estradiol valerate and dienogest as active ingredients; and Zoely containing estradiol and normegestrol.

POPs are contraceptive pills that contain only synthetic progestogens (progestins) and do not contain estrogen. They are colloquially known as mini pills.

POPs include but are not limited to Cerazette containing desogestrel; Microlut containing levonorgestrel and Micronor containing norethindrone.

Other Progeston-Only forms are intrauterine devices (IUDs), for example Mirena containing levonorgestrel or injectables, for example Depo-Provera containing medroxyprogesterone acetate, or implants, for example Implanon containing etonogestrel.

Other hormone-containing devices with contraceptive effect which are suitable for a combination with the compounds of the present invention are vaginal rings like Nuvaring containing ethinyl estradiol and etonogestrel or transdermal systems like a contraceptive patch, for example Ortho-Evra or Apleek (Lisvy) containing ethinyl estradiol and gestodene.

A preferred embodiment of the present invention is the administration of a compound of general formula (I) in combination with a COC or a POP or other Progestin-Only forms as well as vaginal rings or contraceptive patches as mentioned above.

The compounds of the present invention can be combined with therapeutic agents or active ingredients, that are already approved or that are still under development for the treatment and/or prophylaxis of diseases which are related to or mediated by P2X3 receptor.

For the treatment and/or prophylaxis of urinary tract diseases, the compounds of the present invention can be administered in combination or as comedication with any substance that can be applied as therapeutic agent in the following indications:

Urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular interstitial cystitis; idiopathic bladder hypersensitivity.

For the treatment and/or prophylaxis of overactive bladder and symptoms related to overactive bladder, the compounds of the present invention can be administered in combination or as comedication, independently or in addition to behavioral therapy like diet, lifestyle or bladder training, with anticholinergics like oxybutynin, tolterodine, propiverine, solifenacin, darifenacin, trospium, fesoterdine; ß-3 agonists like mirabegron; neurotoxins like onabutolinumtoxin A; or antidepressants like imipramine, duloxetine.

For the treatment and/or prophylaxis of interstitial cystitis, the compounds of the present invention can be administered in combination or as comedication, independently or in addition to behavioral therapy like diet, lifestyle or bladder training, with pentosans like elmiron; NSAIDS (Non-Steroidal Antiinflammatory Drugs), either unselective NSAIDS like ibuprofen, diclofenac, aspirin, naproxen, ketoprofen, indomethacin; as well as Cox-2 selective NSAIDS like Parecoxib, Etoricoxib, Celecoxib; antidepressants like amitriptyline, imipramine; or antihistamines like loratadine.

For the treatment and/or prophylaxis of gynaecological diseases, the compounds of the present invention can be administered in combination or as comedication with any substance that can be applied as therapeutic agent in the following indications:

dysmenorrhea, including primary and secondary dysmenorrhea; dyspareunia; endometriosis; endometriosis-associated pain; endometriosis-associated symptoms, wherein said symptoms are in particular dysmenorrhea, dyspareunia, dysuria, or dyschezia.

For the treatment and/or prophylaxis of dysmenorrhea, including primary and secondary dysmenorrhea; dyspareunia; endometriosis and endometriosis-associated pain, the compounds of the present invention can be administered in combination or as comedication with pain medications, in particular NSAIDS like ibuprofen, diclofenac, aspirin, naproxen, ketoprofen, indomethacin; as well as Cox-2 selective NSAIDS like Parecoxib, Etoricoxib, Celecoxib; or in combination with ovulation inhibiting treatment, in particular COCs as mentioned above or contraceptive patches like Ortho-Evra or Apleek (Lisvy); or with progestogenes like dienogest (Visanne); or with GnRH analogous, in particular GnRH agonists and antagonists, for example leuprorelin, nafarelin, goserelin, cetrorelix, abarelix, ganirelix, degarelix; or with androgens: danazol.

For the treatment and/or prophylaxis of diseases which are associated with pain, or pain syndromes, the compounds of the present invention can be administered in combination or as comedication with any substance that can be applied as therapeutic agent in the following indications:

pain-associated diseases or disorders like hyperalgesia, allodynia, functional bowel disorders (such as irritable bowel syndrome) and arthritis (such as osteoarthritis, rheumatoid arthritis and ankylosing spondylitis), burning mouth syndrome, burns, migraine or cluster headache, nerve injury, traumatic nerve injury, post-traumatic injuries (including fractures and sport injuries), neuritis, neuralgia, poisoning, ischemic injury, interstitial cystitis, trigeminal neuralgia, small fiber neuropathy, diabetic neuropathy, chronic arthritis and related neuralgias, HIV and HIV treatment-induced neuropathy.

The compounds of the present invention can be combined with other pharmacological agents and compounds that are intended to treat inflammatory diseases, inflammatory pain or general pain conditions.

In addition to well-known medicaments which are already approved and on the market, the compounds of the present invention can be administered in combination with inhibitors of PTGES (prostaglandin E synthase), with inhibitors of IRAK4 (interleukin-1 receptor-associated kinase 4) and with antagonists of the prostanoid EP4 receptor (prostaglandin E2 receptor 4).

In particular, the compounds of the present invention can be administered in combination with pharmacological endometriosis agents, intended to treat inflammatory diseases, inflammatory pain or general pain conditions and/or interfering with endometriotic proliferation and endometriosis associated symptoms, namely with inhibitors of Aldo-ketoreductase1C3 (AKR1C3) and with functional blocking antibodies of the prolactin receptor.

For the treatment and/or prophylaxis of chronic cough and symptoms related to chronic cough, the compounds of the present invention can be administered in combination or as comedication with cough suppressants like dextromethorphan, benzonatate, codeine or hydrocodone; with inhalative agents to treat eosinophilic bronchitis, COPD or asthma like budesonide, beclomethasone, fluticasone, theophylline, ipatropiumbromid, montelukast or salbutamol; with drugs like proton pump inhibitors which are used to treat acid reflux, for example omeprazole, esomeprazole, lansoprazole, ranitidine, famotidine, cimetidine; and promotility agents such as metoclopramide; with nasal or topical glucocorticoids like fluticasone or mometasone or triamcinolone; or with oral antihistamines like loratadine, fexofenadine or cetirizine.

The compounds of the present invention can be combined with other pharmacological agents and compounds that are intended for the treatment, prevention or management of cancer.

In particular, the compounds of the present invention can be administered in combination with 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate,amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Furthermore, the compounds of the present invention can be combined with active ingredients, which are well known for the treatment of cancer-related pain and chronic pain. Such combinations include, but are not limited to NSAIDS (either unselective NSAIDS like ibuprofen, diclofenac, aspirin, naproxen, ketoprofen and indomethacin; and Cox-2 selective NSAIDS like Parecoxib, Etoricoxib and Celecoxib), step II opiods like codeine phosphate, dextropropoxyphene, dihydro-codeine, Tramadol), step III opiods like morphine, fentanyl, buprenorphine, oxymorphone, oxycodone and hydromorphone; and other medications used for the treatment of cancer pain like steroids as Dexamethasone and methylprednisolone; bisphosphonates like Etidronate, Clodronate, Alendronate, Risedronate, and Zoledronate; tricyclic antidepressants like Amitriptyline, Clomipramine, Desipramine, Imipramine and Doxepin; class I antiarrythmics like mexiletine and lidocaine; anticonvulsants like carbamazepine, Gabapentin, oxcarbazepine, phenytoin, pregabalin, topiramate, alprazolam, diazepam, flurazepam, pentobarbital and phenobarbital.

Experimental Section

Chemical names were generated using the ACD/Name software from ACD/Labs. In some cases generally accepted names of commercially available reagents were used in place of ACD/Name generated names.

The following table lists the abbreviations used in this paragraph and in the Examples section as far as they are not explained within the text body. Other abbreviations have their meanings customary per se to the skilled person.

| Abbreviation | Meaning |
| --- | --- |
| BrettPhos-G3 | [(2-Di-cyclohexylphosphino-3,6-dimethoxy-2',4',6'-triisopropyl-1,1'-biphenyl)-2-(2'-amino-1,1'-biphenyl)]palladium(II) methanesulfonate |
| $Cs_2CO_3$ | Cesium carbonate |
| DPPF | 1,1'-bis(diphenylphosphino)ferrocen |
| h | hour(s) |
| HATU | N-[(Dimethylamino)(3H-[1,2,3]triazolo[4,5-b]pyridin-3-yloxy)methylene]-N-methylmethanaminium hexafluorophosphate |
| HBr | Hydrogen bromide |
| HCl | Hydrochloric acid |
| HPLC | high performance liquid chromatography |
| $K_2CO_3$ | Potassium carbonate |
| KOtBu | Potassium 2-methylpropan-2-olate |
| KI | Potassium iodide |
| l | Liter |
| LC-MS | liquid chromatography - mass spectrometry |
| LC-MS | liquid chromatography - mass spectrometry |
| LiCl | Lithium chloride |
| LiHMDS | Lithium bis(trimethylsilyl)amide |
| LiOH | Lithium hydroxide |
| M | Molar |
| $MgSO_4$ | Magnesium sulfate |
| min | Minute(s) |
| µl | Microliter |
| ml | Millliliter |
| N | Normal |
| $NaBH_4$ | Sodium tetrahydroborate |
| $NaBH(OAc)_3$ | Sodium triacetoxyborohydride |
| $Na_2CO_3$ | Sodium carbonate |
| nd | Not determined |
| NaH | Sodium hydride |
| $NaHCO_3$ | Sodium bicarbonate |
| NaCl | Sodium chloride |
| NaI | Sodium iodide |
| NaOH | Sodium hydroxide |
| $Na_2SO_4$ | Sodium sulfate |
| $NH_3$ | Ammonia |
| $NH_4Cl$ | Ammonium chloride |
| $NH_4HCO_3$ | Ammonium hydrogencarbonate |
| NMR | nuclear magnetic resonance spectroscopy |
| $PdCl_2(PPh_3)_2$ | Bis(triphenylphosphine)palladium(II) dichloride |
| $Pd(dppf)Cl_2$ | [1,1'-Bis(diphenylphosphino)ferrocene]dichloropalladium(II) |
| $Pd(PPh_3)_4$ | Tetrakis(triphenylphosphine)palladium(0) |
| $Pd_2(dba)_3$ | Tris(dibenzylideneacetone)dipalladium(0) |
| $Pd(OAc)_2$ | Palladium (II) acetate |
| $PPh_3$ | Triphenylphosphine |
| $t-Bu_3Ph•HBF_4$ | Tri-tert-butylphosphonium tetrafluoroborate |
| ppm | parts per million |
| rt | Room temperature |
| $R_t$ | Retention time |
| sat. | Saturated |
| $T_3P$ | Propylphosphonic anhydride |
| tBu-BrettPhos | 2-(Di-tert-butylphosphino)-2',4',6'-triisopropyl-3,6-dimethoxy-1,1'-biphenyl |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Furthermore, the intermediates and examples according to the invention may be present as rotational isomers, in particular in NMR studies. In cases where the presence of rotamers are clearly visible by NMR, it is stated in the experimental section. Purity figures are generally based on corresponding peak integrations in the LC/MS chromatogram, but may additionally also have been determined with the aid of the $^1$H NMR spectrum.

In solvent-containing or contaminated batches, the formal yield may be ">100%"; in these cases the yield is not corrected for solvent or purity.

The multiplicities of proton signals in $^1$H NMR spectra reported in the paragraphs which follow represent the signal form observed in each case and do not take account of any higher-order signal phenomena. In general, the stated chemical shift refers to the centre of the signal in question. In the case of broad multiplets, an interval is given. Signals obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet or broad doublet) or are not listed.

The $^1$H NMR data of selected synthesis intermediates and working examples are stated in the form of $^1$H NMR peak lists. For each signal peak, first the δ[ppm]=value in ppm and then the signal intensity in round brackets are listed. The δ[ppm]=value/signal intensity number pairs for different signal peaks are listed with separation from one another by commas. The peak list for an example therefore takes the following form: δ[ppm]=$_1$ (intensity$_1$), δ[ppm]=2 (intensity$_2$), . . . , δ[ppm]=$_i$(intensity$_i$), . . . , δ[ppm]=$_n$ (intensity$_n$).

The intensity of sharp signals correlates with the height of the signals in a printed example of an NMR spectrum in cm and shows the true ratios of the signal intensities in comparison with other signals. In the case of broad signals, several peaks or the middle of the signal and the relative intensity thereof may be shown in comparison to the most intense signal in the spectrum. The lists of the $^1$H NMR peaks are similar to the conventional $^1$H NMR printouts and thus usually contain all peaks listed in a conventional NMR interpretation. In addition, like conventional $^1$H NMR printouts, they may show solvent signals, signals of stereoisomers of the target compounds which are likewise provided by the invention, and/or peaks of impurities. The peaks of stereoisomers of the target compounds and/or peaks of impurities usually have a lower intensity on average than the peaks of the target compounds (for example with a purity of >90%). Such stereoisomers and/or impurities may be typical of the particular preparation process. Their peaks can thus help in identifying reproduction of our preparation process with reference to "by-product fingerprints". An expert calculating the peaks of the target compounds by known methods (MestreC, ACD simulation, or using empirically evaluated expected values) can, if required, isolate the peaks of the target compounds, optionally using additional intensity filters. This isolation would be similar to the peak picking in question in conventional $^1$H NMR interpretation. A detailed description of the presentation of NMR data in the form of peak lists can be found in the publication "Citation of NMR Peaklist Data within Patent Applications" (cf. Research Disclosure Database Number 605005, 2014, 1 Aug. 2014 or http://www.researchdisclosure.com/searching-disclosures). In the peak picking routine described in Research Disclosure Database Number 605005, the parameter "MinimumHeight" can be set between 1% and 4%. Depending on the type of chemical structure and/or depending on the concentration of the compound to be analysed, it may be advisable to set the parameters "MinimumHeight" to values of <1%.

Analytical LC-MS Methods:

Method A: Instrument Agilent G1312A with Waters PDA detector and ZQ mass spectrometer or Shimadzu LC-MS-LC 20-AB-LC-MS 2010 MS detector; Column: Supelco Ascentis Express 2.1×30 mm, 2.7 μm; eluent A: water+0.1 vol % formic acid, eluent B: acetonitrile+0.1 vol % formic acid; gradient: 0-1.5 min 5-100% B, 1.5-1.6 min 100% B; flow 1.0 ml/min; temperature: 40° C.; PDA scan: 210-420 nm.

Method B: Instrument Agilent G1312A with Waters PDA detector and Qtof-micro mass spectrometer or Agilent G1312A with Waters PDA detector and ZQ mass spectrometer or Shimadzu LC-MS-LC 20-AB-LC-MS 2010 MS detector; Column: Waters Atlantis dC18 2.1×50 mm, 3 μm; eluent A: water+0.1 vol % formic acid, eluent B: acetonitrile+0.1 vol % formic acid; gradient: 0-2.5 min 5-100% B, 2.5-2.7 min 100% B; flow 1.0 ml/min; temperature: 40° C.; PDA scan: 210-420 nm.

Method C: Instrument Agilent G1312A with Waters PDA detector and ZQ mass spectrometer; Column: Phenomenex Gemini-NX C18 2.0×50 mm, 3 μm; eluent A: 2 mM ammonium hydrogencarbonate (buffered to pH 10), eluent B: acetonitrile; gradient: 0-1.8 min 1-100% B, 1.8-2.1 min 100% B; flow 1.0 ml/min; temperature: 40° C.; PDA scan: 210-420 nm.

Method D: Instrument Agilent G1312A with Waters PDA detector and Qtof-micro mass spectrometer or Shimadzu LC-MS-LC 20-AB-LC-MS 2010 MS detector; Column: Waters Atlantis dC18 2.1×100 mm, 3 µm; eluent A: water+0.1 vol % formic acid, eluent B: acetonitrile +0.1 vol % formic acid; gradient: 0-5.0 min 5-100% B, 5.0-5.4 min 100% B; flow 0.6 ml/min; temperature: 40° C.; PDA scan: 210-420 nm.

Method E: Instrument Agilent G1312A with Waters PDA detector and ZQ mass spectrometer; Column: Phenomenex Gemini-NX C18 2.0×100 mm, 3 µm; eluent A: 2 mM ammonium hydrogencarbonate (buffered to pH 10), eluent B: acetonitrile; gradient: 0-5.5 min 5-100% B, 5.5-5.9 min 100% B; flow 0.5 ml/min; temperature: 40° C.; PDA scan: 210-420 nm.

Method F: Instrument Waters Acquity UPLC-MS SingleQuad; Column: Phenomenex Kinetix-XB C18 2.1×100 mm, 1.7 µm; eluent A: water+0.1 vol % formic acid, eluent B: acetonitrile+0.1 vol % formic acid; gradient: 0-5.3 min 5-100% B, 5.3-5.8 min 100% B; flow 0.6 ml/min; temperature: 40° C.; PDA scan: 210-420 nm.

Method G: Instrument: Waters Acquity UPLC-MS SingleQuad; Column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method H: Instrument: Waters Acquity UPLC-MS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Method I: Instrument: Waters Acquity UPLC-MS SingleQuad; Column: Acquity UPLC BEH C18 1.7 µm 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method J: Instrument: Waters Acquity UPLC-MS SingleQuad; Column: Acquity UPLC BEH C18 1.7 µm 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Method K: Instrument: SHIMADZU LC-MS-UFLC 20-AD-LC-MS 2020 MS detector; Column: Ascentis Express C18 2.7 µm, 50×3.0 mm; eluent A: water+0.05 vol % trifluoroacetic acid, eluent B: acetonitrile+0.05 vol % trifluoroacetic acid; gradient: assigned for each compound; flow 1.5 ml/min; temperature: 40° C.; PDA scan: 190-400 nm.

Method L: Instrument: SHIMADZU LC-MS-UFLC 20-AD-LC-MS 2020 MS detector; Column: Ascentis Express C18 2.7 µm, 50×3.0 mm; eluent A: water+0.05 vol % ammonium hydrogencarbonate, eluent B: acetonitrile; gradient: assigned for each compound; flow 1.5 ml/min; temperature: 40° C.; PDA scan: 190-400 nm.

Method M: Instrument: SHIMADZU LC-MS-UFLC 20-AD-LC-MS 2020 MS detector; Column: CORTECS C18 2.7 µm, 50×2.1 mm; eluent A: water+0.05 vol % trifluoroacetic acid (99%), eluent B: acetonitrile+0.05 vol % trifluoroacetic acid; gradient: assigned for each compound; flow 1.5 ml/min; temperature: 40° C.; PDA scan: 190-400 nm.

Method N: Instrument: SHIMADZU LC-MS-UFLC 20-AD-LC-MS 2020 MS detector; Column: Kinetex EVO C18 2.6 µm, 50×3.0 mm; eluent A: water+0.05 vol % ammonium hydrogencarbonate, eluent B: acetonitrile; gradient: assigned for each compound; flow 1.5 ml/min; temperature: 40° C.; PDA scan: 190-400 nm.

Method O: Instrument: SHIMADZU LC-MS-UFLC 20-AD-LC-MS 2020 MS detector; Column: Kinetex XB-C18 2.6 µm, 50×3.0 mm; eluent A: water+0.05 vol % trifluoroacetic acid (99%), eluent B: acetonitrile+0.05 vol % trifluoroacetic acid; gradient: assigned for each compound; flow 1.5 ml/min; temperature: 45° C.; PDA scan: 190-400 nm.

Method P: Instrument: Waters Acquity with PDA detector and ZQ mass spectrometer; column: Acquity BEH C18 1.7 µm 2.1×50 mm; solvent A: Water+0.1% formic Acid; Solvent B: acetonitrile; gradient: 99% A to 1% A (1.6 min) to 1% A (0.4 min); flow: 0.8 ml/min; temperature: 60° C.; Injection Volume: 1.0 µl (0.1 mg-1 mg/ml sample concentration); Detection: PDA Scan Region 210-400 nm—plus fixed wavelength 254 nm; MS ESI (+),Scan region 170-800 m/z.

Method Q: Instrument: SHIMADZU LCMS-UFLC 20-AD-LCMS 2020 MS detector; Column: Cortecs-C18 2.7 µm, 50×2.1 mm; eluent A: water+0.09 vol % formic acid, eluent B: acetonitrile+0.1 vol % formic acid; gradient: assigned for each compound; flow 1.5 ml/min; temperature: 40° C.; PDA scan: 190-400 nm.

Method R: Instrument: SHIMADZU LCMS-UFLC 20-AD-LCMS 2020 MS detector; Column: Shim-pack XR-ODS, 2.2 µm, 3.0×50 mm; eluent A: water+0.05 vol % trifluoroacetic acid, eluent B: acetonitrile+0.05 vol % trifluoroacetic acid; gradient: assigned for each compound; flow 1.5 ml/min; temperature: 40° C.; PDA scan: 190-400 nm.

Method S: Instrument: SHIMADZU LCMS-UFLC 20-AD-LCMS 2020 MS detector; Column: Atlantis T3 2.7 µm, 100×4.6 mm; eluent A: water+0.05 vol % trifluoroacetic acid (99%), eluent B: acetonitrile+0.05 vol % trifluoroacetic acid; gradient: assigned for each compound; flow 1.5 ml/min; temperature: 35° C.; PDA scan: 190-400 nm.

Method T: Instrument: SHIMADZU LCMS-UFLC 20-AD-LCMS 2020 MS detector; Column: Kinetex EVO C18 2.6 µm, 50×3.0 mm; eluent A: water+0.03 vol % ammonium hydroxide, eluent B: acetonitrile; gradient: assigned for each compound; flow 1.5 ml/min; temperature: 40° C.; PDA scan: 190-400 nm.

Purification Methods:

Biotage Isolera™ chromatography system (http://www.biotage.com/product-area/flash-purification) using pre-packed silica and pre-packed modified silica cartridges.

Preparative HPLC, Method A: Instrument: pump: Gilson 331 & 332; auto injector: Gilsom GX281; UV detector: Gilson 159; collector: Gilson GX281 or pump: Gilson 333 & 334; auto injector: Gilsom GX281; UV detector: Gilson 155; collector: Gilson GX281; Column: Waters Xbridge C18 30×100 mm, 10 µm; eluent A: water+0.2 vol % ammonium hydroxide, eluent B: acetonitrile+0.2 vol % ammonium hydroxide; gradient: 0-2.5 min 5% B, 2.5-16.05 min 5-95% B, 16.05-18.2 min 95% B; flow 40 ml/min; injection volume 1500 µl; temperature: 25° C.; UV scan: 215 nm.

Preparative HPLC, Method B: Instrument pump: Gilson 331 & 332; auto injector: Gilsom GX281; UV detector: Gilson 159; collector: Gilson GX281; Column: Waters Sunfire C18 30×100 mm, 10 µm; eluent A: water+0.1 vol % formic acid, eluent B: acetonitrile+0.1 vol % formic acid; gradient: 0-2.0 min 5% B, 2.0-2.5 min 5-10% B, 2.5-14.5 min 10-100% B, 14.5-15.5 min 100% B; flow 40 ml/min; injection volume 1500 µl; temperature: 25° C.; UV scan: 215 nm.

Preparative HPLC, Method C: Instrument: Waters Autopurification MS SingleQuad; Column: Waters XBrigde C18 5 μm 100×30 mm; eluent A: water+0.1 vol % formic acid (99%), eluent B: acetonitrile; gradient: 0-5.5 min 5-100% B; flow 70 ml/min; temperature: 25° C.; DAD scan: 210-400 nm.

Preparative HPLC, Method D: Instrument: Waters Autopurification MS SingleQuad; Column: Waters XBrigde C18 5 μm 100×30 mm; eluent A: water+0.2 vol % aqueous ammonia (32%), eluent B: acetonitrile; gradient: 0-5.5 min 5-100% B; flow 70 ml/min; temperature: 25° C.; DAD scan: 210-400 nm.

Preparative HPLC, Method E: Instrument: pump: Labomatic HD-5000 or HD-3000, head HDK 280, lowpressure gradient module ND-B1000; manual injection valve: Rheodyne 3725i038; detector: Knauer Azura UVD 2.15; collector: Labomatic Labocol Vario-4000; column: Chromatorex RP C-18 10 μm, 125×30 mm; eluent A: water+0.1 vol % formic acid (99%), eluent B: acetonitrile;

gradient A: 0-15 min 1-25% B; flow: 60 mL/min;

gradient B: 0-15 min 10-50% B; flow: 60 mL/min;

gradient C: 0-15 min 15-55% B; flow: 60 mL/min;

gradient D: 0-15 min 30-70% B; flow: 60 mL/min;

gradient E: 0-15 min 40-80% B; flow: 60 mL/min;

gradient F: 0-15 min 65-100% B; flow: 60 mL/min;

temperature: 25° C.; solution: max. 250 mg/2 ml dimethyl sulfoxide; injection: 1×2 ml; Detection: UV 254 nm; Software: SCPA PrepCon5.

Preparative HPLC, Method F: Instrument: pump: Labomatic HD-5000 or HD-3000, head HDK 280, lowpressure gradient module ND-B1000; manual injection valve: Rheodyne 3725i038; detector: Knauer Azura UVD 2.15; collector: Labomatic Labocol Vario-4000; column: Chromatorex RP C-18 10 μm, 125×30 mm; eluent A: water+0.2 vol-% ammonia (32%), eluent B: acetonitrile;

gradient A: 0-15 min 1-25% B; flow: 60 mL/min;

gradient B: 0-15 min 10-50% B; flow: 60 mL/min;

gradient C: 0-15 min 15-55% B; flow: 60 mL/min;

gradient D: 0-15 min 30-70% B; flow: 60 mL/min;

gradient E: 0-15 min 40-80% B; flow: 60 mL/min;

gradient F: 0-15 min 65-100% B; flow: 60 mL/min;

temperature: 25° C.; solution: max. 250 mg/2 ml dimethyl sulfoxide; injection: 1×2 ml; Detection: UV 254 nm; Software: SCPA PrepCon5.

Preparative HPLC, Method G: Instrument: Sepiatec: Prep SFC100; Column: Chiralpak IB 5μ 250×30 mm; eluent A: carbon dioxide, eluent B: methanol; gradient: isocratic 25% B; flow 100 ml/min; temperature: 40° C.; UV: 220 nm; back pressure: 150 bar.

Experimental Section—Intermediates

Reaction times are either specified explicitly in the protocols of the experimental section, or reactions were run until completion. Chemical reactions were monitored and their completion was judged using methods well known to the person skilled in the art, such as thin layer chromatography, e.g. on plates coated with silica gel, or by LC-MS methods.

Intermediate 01-01 tert-butyl(2R)-2-({[(4-methylphenyl)sulfonyl]oxy}methyl)morpholine-4-carboxylate

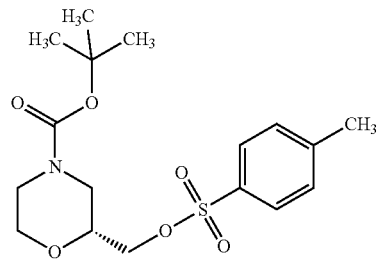 [SMILES: Cc1ccc(S(=O)(=O)OC[C@H]2CN(C(=O)OC(C)(C)C)CCO2)cc1]

To a mixture of tert-butyl(2R)-2-(hydroxymethyl)morpholine-4-carboxylate (7.5 g, 34.5 mmol) (CAS-No.: 135065-71-3), triethylamine (7.2 ml, 51.8 mmol) and trimethylamine hydrochloride (330 mg, 3.5 mmol) in dichloromethane (90 ml) was added 4-toluenesulfonyl chloride (9.9 g, 51.8 mmol) at 0° C. The reaction mixture was allowed to reach rt and was stirred at this temperature for 21 h. After this time, the reaction mixture was treated with N,N-dimethylethane-1,2-diamine (2.3 ml, 20.7 mmol) and was then washed successively with 1M aqueous hydrogen chloride solution, water and brine, dried (MgSO$_4$), filtered and concentrated under reduced pressure to afford 14.5 g (90% yield) of the title compound as a pale brown solid.

$^1$H NMR (500 MHz, DMSO-d6) δ[ppm]: 7.82-7.77 (m, 2H), 7.52-7.47 (m, 2H), 4.08 (dd, 1H), 4.01 (dd, 1H), 3.79-3.62 (m, 3H), 3.56-3.49 (m, 1H), 3.35-3.31 (m, 1H), 2.92-2.69 (m, 1H), 2.67-2.53 (m, 1H), 2.43 (s, 3H), 1.39 (s, 9H).

LC-MS (Analytical Method A) R$_t$=1.23 min, MS (ESI-pos): m/z=272 [M-Boc+H]$^+$.

Intermediate 01-02 tert-butyl(2R)-2-(azidomethyl)morpholine-4-carboxylate

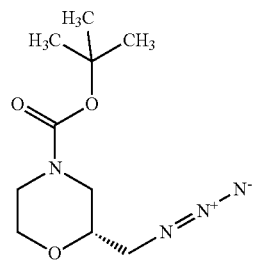 [SMILES: CC(C)(C)OC(=O)N1CCO[C@@H](CN=[NH+][NH-])C1]

To a solution of tert-butyl(2R)-2-({[(4-methylphenyl)sulfonyl]oxy}methyl)morpholine-4-carboxylate (14.5 g, 31.2 mmol) (intermediate 01-01) in N,N-dimethylformamide (78 ml) was added sodium azide (10.1 g, 156.0 mmol). The mixture was stirred at 45° C. for 21 h. After this time, the reaction mixture was allowed to cool to room temperature and partitioned between diethyl ether and saturated aqueous NaHCO$_3$ solution. The organic phase was separated and the aqueous phase was extracted with diethyl ether. The combined organic phases were washed twice with water, dried (MgSO$_4$), filtered and concentrated under reduced pressure to afford 8.5 g (94% yield, 84% purity) of the title compound as a yellow oil.

$^1$H NMR (500 MHz, Chloroform-d) δ [ppm]: 4.00-3.78 (m, 3H), 3.65-3.53 (m, 2H), 3.38-3.29 (m, 2H), 3.05-2.88 (m, 1H), 2.82-2.64 (m, 1H), 1.49 (s, 9H).

Intermediate 01-03 tert-butyl(2S)-2-(aminomethyl)morpholine-4-carboxylate

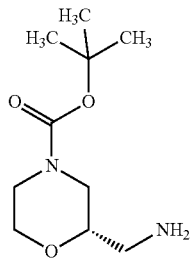

To a de-gassed solution of tert-butyl(2R)-2-(azidomethyl)morpholine-4-carboxylate (84% purity, 8.4 g, 29.3 mmol) (intermediate 01-02) in ethyl acetate (75 ml) was added Pd/C (10%, 1.9 g, 1.8 mmol). The mixture was stirred at room temperature under an atmosphere of hydrogen for a total of 22 h. After this time, the hydrogen atmosphere was removed and the catalyst was removed by filtration (Celite®) and washed with ethyl acetate (20 ml). The filtrate was concentrated in vacuo and purified by Biotage Isolera™ chromatography (silica gel, eluting with dichloromethane-DMAW90, 1:0 to 0:1). The product containing fractions were combined and concentrated in vacuo. The water and acetic acid were removed by dissolving the residue in ethyl acetate and washing with saturated aqueous NaHCO$_3$ solution. The aqueous phase was back-extracted twice with dichloromethane:isopropanol (8:2), with the combined organic phases dried (MgSO$_4$), filtered and concentrated under reduced pressure to afford 3.2 g (45%) of the title compound as a yellow oil.

$^1$H NMR (500 MHz, Chloroform-d) δ [ppm]: 4.00-3.74 (m, 3H), 3.60-3.52 (m, 1H), 3.44-3.36 (m, 1H), 2.95 (s, 1H), 2.85-2.74 (m, 2H), 2.67 (s, 1H), 1.49 (s, 9H).

LC-MS (Analytical Method A) R$_t$=0.60 min, MS (ESI-pos): m/z=217 [M+H]$^+$.

Intermediate 01-04 tert-butyl(2S)-2-({[(4-methylphenyl)sulfonyl]oxy}methyl)morpholine-4-carboxylate

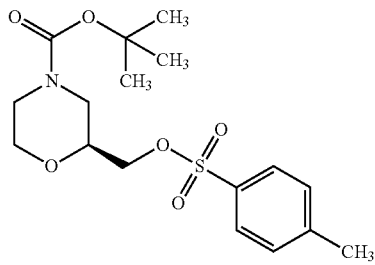 [SMILES: Cc1ccc(S(=O)(=O)OC[C@@H]2CN(C(=O)OC(C)(C)C)CCO2)cc1]

To a mixture of tert-butyl(2S)-2-(hydroxymethyl)morpholine-4-carboxylate (10.0 g, 46.0 mmol) (CAS-No.: 135065-76-8), triethylamine (9.6 ml, 69 mmol) and trimethylamine hydrochloride (440 mg, 4.6 mmol) in dichloromethane (120 ml) was added 4-methylbenzenesulfonyl chloride (13.2 g, 69.0 mmol). The reaction was stirred at rt for 2 h. After this time, the reaction mixture was treated with N,N-dimethylethane-1,2-diamine (3.0 ml, 27.6 mmol). The reaction mixture was washed with 1 M aqueous hydrogen chloride solution followed by water, dried (Na$_2$SO$_4$), filtered and concentrated under reduced pressure to afford 18.3 g (99% yield) of the title compound as a yellow oil.

$^1$H NMR (250 MHz, Chloroform-d) δ [ppm]: 1.45 (s, 9H), 2.45 (s, 3H), 2.56-2.75 (m, 1H), 2.77-2.97 (m, 1H), 3.46 (td, 1H), 3.52-3.67 (m, 1H), 3.72-3.92 (m, 3H), 3.93-4.10 (m, 2H), 7.35 (d, 2H), 7.80 (d, 2H).

LC-MS (Analytical Method A) R$_t$=1.23 min, MS (ESI-pos): m/z=272 [M-Boc+H]$^+$.

Intermediate 01-05 tert-butyl(2S)-2-(azidomethyl)morpholine-4-carboxylate

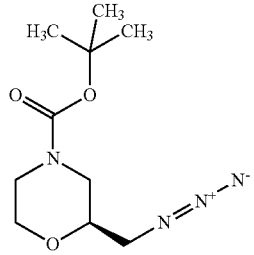 [SMILES: CC(C)(C)OC(=O)N1CCO[C@H](CN=[NH+][NH-])C1]

To a solution of tert-butyl(2S)-2-({[(4-methylphenyl)sulfonyl]oxy}methyl)morpholine-4-carboxylate (17.4 g, 37.5 mmol) (intermediate 01-04) in N,N-dimethylformamide (100 ml) was added sodium azide (12.2 g, 187.4 mmol). The mixture was stirred at 45° C. for 21 h. The temperature was increased to 60° C., and the reaction stirred for a further 18 h. The reaction mixture was cooled to rt and diluted with diethyl ether, and saturated aqueous NaHCO$_3$ solution was added. The organic phase was separated and the aqueous phase was extracted with diethyl ether. The combined organic phases were washed twice with water, dried (MgSO$_4$), filtered and concentrated under reduced pressure to afford the title compound (10.2 g, 90%) as a white powder.

$^1$H NMR (250 MHz, Chloroform-d) δ [ppm]: 4.01-3.73 (m, 3H), 3.65-3.44 (m, 2H), 3.34-3.26 (m, 2H), 3.06-2.85 (m, 1H), 2.79-2.62 (m, 1H), 1.47 (s, 9H).

LC-MS (Analytical Method A) R$_t$=1.11 min.

Intermediate 01-06 tert-butyl(2R)-2-(aminomethyl)morpholine-4-carboxylate

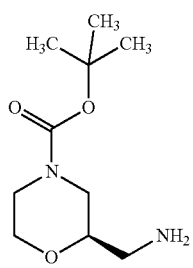

To a de-gassed solution of tert-butyl(2S)-2-(azidomethyl)morpholine-4-carboxylate (11.8 g, 48.7 mmol) (intermediate 01-05) in ethanol (75 ml) was added Pd/C (10%, 1.18 g, 1.1 mmol). The mixture was stirred at rt under an atmosphere of hydrogen for a total of 22 h. TLC (50% EtOAc in heptane, visualised with ninhydrin) showed incomplete conversion, so the mixture was filtered through glass fibre filter paper, re-treated with Pd/C (10%, 1.18 g, 1.1 mmol) and stirred under hydrogen for a further 3 h. The reaction mixture was filtered through glass fibre filter paper and concentrated under reduce pressure. The crude material was purified by Biotage Isolera™ chromatography (silica gel, eluting with dichloromethane-2 M ammonia in methanol, 1:0 to 22:3) to afford 9.0 g (90% yield) of the title compound as a brown gum.

$^1$H NMR (250 MHz, Chloroform-d) δ [ppm]: 1.45 (s, 9H), 2.54-2.70 (m, 1H), 2.69-2.79 (m, 2H), 2.82-3.01 (m, 1H), 3.34 (tdd, 1H), 3.44-3.58 (m, 1H), 3.74-3.94 (m, 3H).

Intermediate 01-07 methyl 5-nitro-1-{[2-(trimethylsilyl)ethoxy]methyl}-1H-pyrazole-3-carboxylate

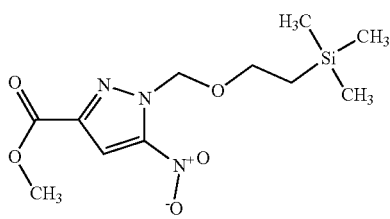

To a solution of methyl 5-nitro-1H-pyrazole-3-carboxylate (8.0 g, 46.8 mmol) (CAS-No.: 181585-93-3) in tetrahydrofuran (200 ml) was added sodium hydride (60% in mineral oil, 2.85 g, 70.1 mmol) at 0° C. and the resulting mixture was stirred at this temperature for 30 min. 2-(Trimethylsilyl)ethoxymethyl chloride (11.7 g, 70.1 mmol) was added to the above slurry at 0° C. and the resulting solution was stirred at room temperature for 2 h under nitrogen atmosphere. Upon completion of the reaction, water was slowly added at 0° C. and the resulting mixture was extracted with ethyl acetate. The combined organic layer was dried (Na$_2$SO$_4$), filtered and concentrated under reduced pressure. The residue was purified by column chromatography (silica gel, eluting with petroleum ether-ethyl acetate, 2:1) to afford 5.60 g (40% yield) of the product as colourless oil.

LC-MS (Analytical Method K, 0-1.2 min 5-100% B, 1.2-1.5 min 100% B): R$_t$=1.14 min; MS (ESIpos): m/z=272 [M+H—NO]$^+$.

Intermediate 01-08

5-nitro-1-{[2-(trimethylsilyl)ethoxy]methyl}-1H-pyrazole-3-carboxylic acid

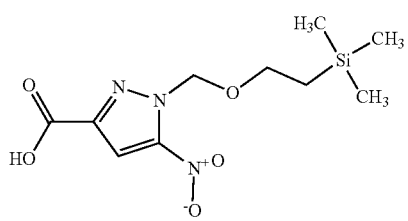

To a solution of methyl 5-nitro-1-((2-(trimethylsilyl)ethoxy)methyl)-1H-pyrazole-3-carboxylate, (8.0 g, 26.5 mmol) (intermediate 01-07) in tetrahydrofuran (70 ml) was added a solution of lithium hydroxide (2 M, 66 ml), and the resulting mixture was stirred at room temperature for 16 hours. Upon completion of the reaction, the solvent was removed in vacuo and the residue was re-dissolved with water. The pH value of the resulting solution was adjusted to 2-3 with diluted hydrochloric acid (4 M) and the precipitated solid was collected by filtration. The filter cake was dried in air to give 6.0 g (71% yield, 90% purity) of the title compound as a yellow solid.

LC-MS (Analytical Method M, 0-1.2 min 5-100% B, 1.2-1.7 min 100% B): R$_t$=1.12 min; MS (ESIneg): m/z=286 [M–H]$^+$.

Intermediate 01-09

(5-nitro-1-{[2-(trimethylsilyl)ethoxy]methyl}-1H-pyrazol-3-yl)methanol

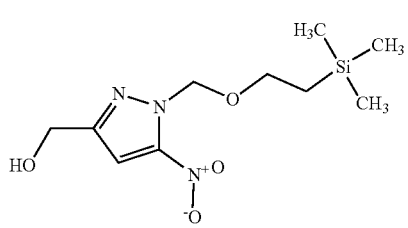

5-Nitro-1-((2-(trimethylsilyl)ethoxy)methyl)-1H-pyrazole-3-carboxylic acid (2 g, 7.0 mmol) (intermediate 01-08) was dissolved in borane in tetrahydrofuran (1 M, 100 ml) and the resulting mixture was stirred at rt for 16 h. Upon completion of the reaction, methanol (200 mL) was added at 0° C. and the solvent was removed in vacuo. The residue was diluted with water and the resulting mixture was extracted with ethyl acetate. The combined organic layer was dried (Na$_2$SO$_4$), filtered and the solvent was removed in vacuo. The residue was purified by silica gel column chromatography (petroleum ether: ethyl acetate=2:1) to give 1.0 g (52% yield) of the title compound as colorless oil.

LC-MS (Analytical Method K, 0-1.2 min 5-95% B, 1.2-1.7 min 95% B): R$_1$=1.11 min; MS (ESIpos): m/z=296 [M+Na]$^+$.

Intermediate 01-10

3-(methoxymethyl)-5-nitro-1-{[2-(trimethylsilyl)ethoxy]methyl}-1H-pyrazole

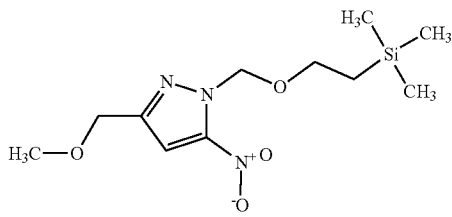

To a solution of (5-nitro-1-((2-(trimethylsilyl)ethoxy)methyl)-1H-pyrazol-3-yl)methanol (1.0 g, 3.7 mmol) (intermediate 01-9) in N,N-dimethylformamide (15 ml) was added sodium hydride (60% in mineral oil) (219 mg, 5.5 mmol) at 0° C. and the resulting mixture was stirred at 0° C. for 30 min. Iodomethane (1.0 g, 7.3 mmol) was added at 0° C. and the resulting solution was stirred at room temperature for 2 h under nitrogen atmosphere. Upon completion of the reaction, water was slowly added at 0° C. and the resulting mixture was extracted with ethyl acetate. The combined organic layer was dried (Na$_2$SO$_4$), filtered and concentrated in vacuo. The residue was purified by column chromatography (silica gel, eluting with petroleum ether-ethyl acetate, 1:5) to afford 900 mg (85% yield) of the title compound as a yellow oil.

LC-MS (Analytical Method K, 0-1.2 min 5-95% B, 1.2-1.7 min 95% B): R$_1$=1.28 min; MS (ESIpos): m/z=310 [M+Na]$^+$.

Intermediate 01-11

3-(methoxymethyl)-5-nitro-1H-pyrazole

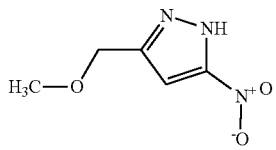

To a solution of 3-(methoxymethyl)-5-nitro-1-((2-(trimethylsilyl)ethoxy)methyl)-1H-pyrazole (900 mg, 3.1 mmol) (intermediate 01-10) in dichloromethane (16 ml) was added trifluoroacetic acid (4 ml) and the resulting mixture was stirred at room temperature for 3 h. Upon completion of the reaction, water was added and the resulting mixture was extracted with dichloromethane. The combined organic layer was dried (Na$_2$SO$_4$), filtered and concentrated under reduced pressure. The residue was purified by column chromatography (silica gel, eluting with petroleum ether-ethyl acetate, 1:5) to afford 400 mg (82% yield) of the title compound as yellow oil.

LC-MS (Analytical Method K, 0-1.2 min 5-95% B, 1.2-1.7 min 95% B): R$_1$=0.63 min; MS (ESIpos): m/z=158 [M+H]$^+$.

Intermediate 01-12

3-(methoxymethyl)-1H-pyrazol-5-amine

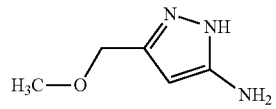

To a solution of 3-(methoxymethyl)-5-nitro-1H-pyrazole (400 mg, 2.5 mmol) (intermediate 01-13) in methanol (5 ml) was added palladium/carbon (10%, 100 mg) and the resulting mixture was stirred at rt for 3 h under hydrogen atmosphere (about 2 atm). Upon completion of the reaction, the catalyst was removed by filtration and the filtrate was concentrated in vacuo to give 300 mg (93% yield) of the title compound as yellow oil.

LC-MS (Analytical Method K, 0-1.2 min 5-100% B, 1.2-1.7 min 100% B): R$_1$=0.49 min; MS (ESIpos): m/z=128 [M+H]$^+$.

Intermediate 01-13

(5-nitro-1H-pyrazol-3-yl)methanol

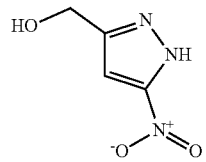

5-Nitro-1H-pyrazole-3-carboxylic acid (1.0 g, 6.36 mmol) (CAS-No.: 198348-89-9) was added into borane in tetrahydrofuran (1M, 25 ml) at 0° C. and the resulting mixture was stirred at rt for 18 h. Upon completion of the reaction, methanol was slowly added at 0° C. and the resulting solution was stirred at reflux for 2 h. After being cooled to rt, the solvent was removed in vacuo and the residues were purified by column chromatography (silica gel, eluting with dichloromethane-methanol, 10:1) to afford 625 mg (69% yield) of the title compound as a white solid.

LC-MS (Analytical Method L, 0-1.25 min 10-95% B, 1.25-1.75 min 95% B): R$_t$=0.49 min; MS (ESIneg): m/z=142 [M−H]$^−$.

Intermediate 01-14

(5-amino-1H-pyrazol-3-yl)methanol

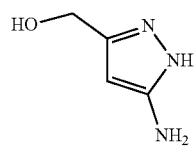

To a solution of (5-nitro-1H-pyrazol-3-yl)methanol (625 mg, 4.4 mmol) (intermediate 01-13) in methanol (5 ml) was added palladium/carbon (10%, 50 mg) and the resulting mixture was stirred at rt for 3 h under hydrogen atmosphere (about 2 atm). Upon completion of the reaction, the catalyst was removed by filtration and the filtrate was concentrated in vacuo to afford 505 mg (quant. yield) of the title compound as a yellow oil.

LC-MS (Analytical Method L, 0-1.25 min 10-95% B, 1.25-1.75 min 95% B): $R_t$=0.25 min; MS (ESIpos): m/z=114 [M+H]$^+$.

Intermediate 01-15 tert-butyl(3R)-3-[(1,3-dioxo-1,3-dihydro-2H-isoindol-2-yl)methyl]morpholine-4-carboxylate

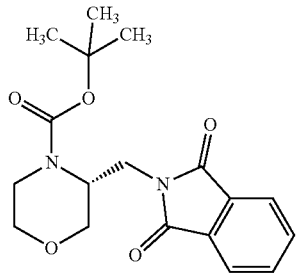 [SMILES: CC(C)(C)OC(=O)N1CCOC[C@H]1CN1C(=O)c2ccccc2C1=O]

To a solution of tert-butyl(3R)-3-(hydroxymethyl)morpholine-4-carboxylate (5.0 g, 23.0 mmol) (CAS-No.: 215917-99-0), triphenyl phosphine (12.1 g, 46.0 mmol), phthalimide (6.8 g, 46.0 mmol) in tetrahydrofuran (164 ml) at 0° C. was added diethyl azodicarboxylate (7.25 ml, 46.0 mmol) dropwise. After the completion of addition, the reaction mixture was allowed to reach rt, and was stirred for a total of 16 h. After this time, the reaction mixture was concentrated in vacuo, dissolved in dichloromethane and adsorbed onto silica gel. This material was loaded onto a large sinter containing ~3 cm depth of silica gel. The material was eluted with ethyl acetate/heptane (1:4, ~15 CV) and the filtrate concentrated in vacuo. The residual material was suspended in heptane/dichloromethane (95:5), warmed and the insoluble material removed by suction filtration. The filter cake was re-suspended in heptane/dichloromethane (95:5), warmed and re-filtered. The combined filtrates were concentrated in vacuo to afford 7.8 g (91% yield, 90% purity) of the title compound as an off-white solid.

$^1$H NMR (500 MHz, Chloroform-d) δ [ppm]: 1.10 (s, 9H), 3.41-3.53 (m, 2H), 3.59-3.71 (m, 2H), 3.83-4.01 (m, 3H), 4.30-4.40 (m, 1H), 4.39-4.51 (m, 1H), 7.61-7.78 (m, 2H), 7.80-7.94 (m, 2H).

LC-MS (Analytical method A): $R_t$=1.10 mins, MS (ESIPos): m/z=246 [M+H-Boc]$^+$.

Intermediate 01-16 tert-butyl(3R)-3-(aminomethyl)morpholine-4-carboxylate

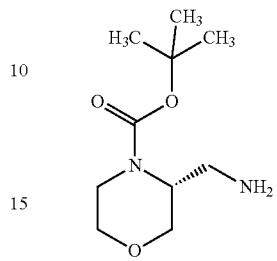

To a suspension of tert-butyl(3R)-3-[(1,3-dioxo-1,3-dihydro-2H-isoindol-2-yl)methyl]morpholine-4-carboxylate (90% purity, 7.8 g, 21.0 mmol) (intermediate 01-15) in ethanol (150 ml) was added hydrazine (4.1 ml) with the resulting mixture heated to 90° C. for 2 h. After this time, the reaction mixture was allowed to cool to rt and the solid was removed by vacuum filtration. The solid was washed with further aliquots of ethanol, with the filtrate concentrated in vacuo to afford a colourless solid. This material was triturated with dichloromethane, with the solid removed by vacuum filtration and the filtrate concentrated in vacuo to afford 5.2 g (97% yield, 85% purity) of the title compound as a golden oil.

$^1$H NMR (250 MHz, Chloroform-d) δ [ppm]: 1.49 (s, 9H), 2.87-3.04 (m, 2H), 3.04-3.19 (m, 1H), 3.46 (td, 1H), 3.56 (dd, 1H), 3.70-3.98 (m, 4H).

Intermediate 01-17

3-cyclohexyl-3-oxopropanenitrile

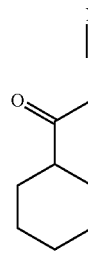

A suspension of sodium hydride (60% dispersion in mineral oil; 422 mg, 10.5 mmol) in tetrahydrofuran (5.0 ml) was heated under reflux for 10 min. The suspension was allowed to cool to ambient temperature before a prepared solution of methyl cyclohexanecarboxylate (500 μl, 3.5 mmol) (CAS-No.: 4630-82-4) and acetonitrile (560 μl, 11 mmol) in THF (5.0 ml) was added dropwise over a period of 5 min. The reaction mixture was heated under reflux for 5 h and cooled to rt. To the stirred solution 2-propanol was added and stirred at room temperature for 30 min. The solvent was evaporated and the residue was dissolved in water. The aqueous layer was washed with hexane, acidified with conc. hydrogen chloride solution and extracted with ethyl acetate. The organic layer was washed with brine,

Intermediate 01-18

3-oxo-3-(tetrahydro-2H-pyran-4-yl)propanenitrile

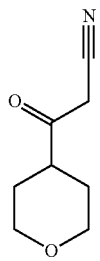

A suspension of sodium hydride (832 mg, 60%, 20.8 mmol) in dry tetrahydrofuran (15 ml, 180 mmol) was heated under reflux for 10 min. The suspension was allowed to cool to rt before a prepared solution methyl tetrahydro-2H-pyran-4-carboxylate (930 µl, 6.9 mmol) (CAS-No.: 110238-91-0) and acetonitrile (1.1 ml, 21 mmol) in dry tetrahydrofuran (15 ml, 180 mmol) was added dropwise over a period of 5 min. The reaction mixture was heated under reflux for 16 h and cooled to rt. To the stirred solution 2-propanol was added and stirred at rt for 30 min. The solvent was evaporated and the residue was dissolved with water. The aqueous layer was washed with hexane, acidified with concentrated HCl solution and extracted with ethyl acetate. The organics were washed with brine, dried over a water repellant filter and evaporated under reduced pressure to afford 1.11 g crude product.

$^1$H NMR (400 MHz, Chloroform-d) δ [ppm]: 1.65-1.92 (m, 4H), 2.58 (tt)+2.81 (tt, 1H), 3.41-3.49 (m, 2H), 3.52 (s, 1H), 3.93-4.06 (m, 2H)

LC-MS (Analytical Method G): $R_t$=0.52 min; MS (ESI-pos): m/z=154 [M+H]$^+$.

Intermediate 01-19

3-oxo-4-(tetrahydro-2H-pyran-4-yl)butanenitrile

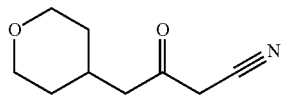 [SMILES: N#CCC(=O)CC1CCOCC1]

A suspension of sodium hydride (60% w/w in mineral oil; 348 mg, 8.7 mmol) in tetrahydrofuran (2.5 mL) was heated under reflux for 10 mins. The suspension was allowed to cool to rt before a prepared solution of ethyl tetrahydropyran-4-ylacetate (500 mg, 2.9 mmol) (CAS-No.: 103260-44-2) and acetonitrile (0.46 mL, 8.7 mmol) in tetrahydrofuran (2.5 mL) was added dropwise over a period of 5 min. The reaction mixture was heated to reflux for 5 h before being allowed to cool to rt. To the stirred solution 2-propanol (1 mL) was added and stirred at rt for 30 min. The mixture was diluted with water (15 mL). The solution was washed with heptane, acidified with concentrated aqueous HCl solution and extracted with ethyl acetate (2×20 ml). The combined organics were dried (MgSO$_4$), filtered and concentrated under reduced pressure. The crude material was purified by Biotage Isolera™ chromatography (silica gel, eluting with heptanes-ethyl acetate, 4:1 to 0:1) to afford of the title compound (448 mg, 81%) as a colourless oil.

$^1$H NMR (250 MHz, Chloroform-d) δ [ppm]: 1.35 (td, 2H), 1.58-1.68 (m, 2H), 2.05-2.24 (m, 1H), 2.57 (d, 2H), 3.34-3.50 (m, 4H), 3.94 (dd, 2H).

Intermediate 01-20

3-(5-methylpyridin-2-yl)-3-oxopropanenitrile

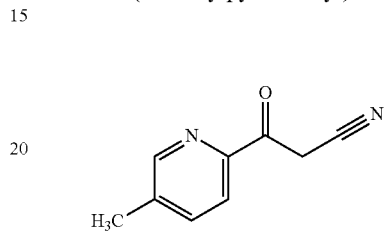

To toluene (100 ml) was added carefully sodium hydride (60% dispersion in mineral oil) (1.98 g, 60% purity, 49.6 mmol). The suspension was cooled to with an ice-bath to 4° C. To the cold suspension was added a prepared solution of methyl 5-methylpyridine-2-carboxylate (5.00 g, 33.1 mmol) and dry acetonitrile (2.6 ml, 50 mmol) in 50 ml toluene dropwise over a period of 15 minutes. The ice-bath was removed and the reaction mixture was stirred at room temperature for 1 h then heated at 65° C. for 4 h. at which time the mixture became so thick it was impossible to stir. Additional dry toluene (20 mL) was added to the thick suspension and stirring at 65° C. was continued for further 12 h. The reaction mixture was allowed to cool to room temperature then it was quenched with 2-propanol (15 mL). The suspension was stirred vigorously for 20 minutes at room temperature then acidified with 2 M aqueous hydrochloric acid to pH 3. The phases were separated and the aqueous layer was extracted twice with ethyl acetate. The combined organic phases were washed with brine, dried with a water-repellant filter and evaporated to dryness. The crude product was put to the high vacuum for 2 h to afford 4.78 g (90% yield) of the title compound.

LC-MS (Method G): $R_t$=0.80 min; MS (ESIpos): m/z=161 [M+H]$^+$ $^1$H NMR (400 MHz, DMSO-d6) δ[ppm]: 2.41 (s, 3H), 4.70 (s, 2H), 7.81-7.99 (m, 2H), 8.58 (br s, 1H).

Intermediate 01-21

3-oxo-3-(pyridin-4-yl)propanenitrile

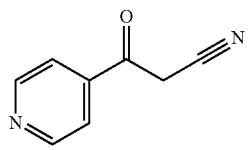 [SMILES: N#CCC(=O)c1ccncc1]

A solution of methyl isonicotinate (25.0 g, 182 mmol) and acetonitrile (11.2 g, 273 mmol) in toluene (200 mL) was slowly added to a mixture of sodium hydride (10.9 g, 273 mmol, 60% in mineral oil) in toluene (100 mL) at 0° C. The resulting mixture was then heated to 65° C. and stirred for overnight under nitrogen atmosphere. After cooling to room temperature, the solvent was removed in vacuo and water was added. Concentrated HCl was added to adjust the pH value to 8. The resulting solution was extracted with ethyl acetate and the combined organic layer was dried over anhydrous sodium sulfate and concentrated in vacuo to give 15.0 g (54%) of the product as orange oil.

LC-MS (Analytical Method N, 0-2.00 min 5-95% B): $R_t$=0.46 min; MS (ESIpos): m/z=147 [M+H]$^+$.

Intermediate 01-22

3-oxo-4-(pyridin-2-yl)butanenitrile

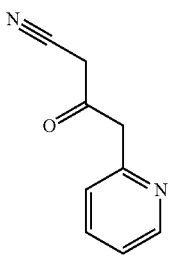 [SMILES: N#CCC(=O)Cc1ccccn1]

A solution of ethyl 2-(pyridin-2-yl)acetate (20.0 g, 121 mmol) and acetonitrile (6.0 g, 145 mmol) in toluene (150 mL) was slowly added to a mixture of sodium hydride (7.3 g, 182 mmol, 60% in mineral oil) in toluene (100 mL) at 0° C. The resulting mixture was heated to 65° C. and stirred for overnight under nitrogen atmosphere. After cooling to room temperature, the solvent was removed in vacuo and water was added. Concentrated HCl was added to adjust the pH value to 5 and the solvent was removed in vacuo to give 11.0 g (crude) of the product as brown oil.

LC-MS (Analytical Method N, 0-2.00 min 5-95% B): $R_t$=0.59 min; MS (ESIpos): m/z=161 [M+H]$^+$.

Intermediate 01-24

3-cyclohexyl-1H-pyrazol-5-amine

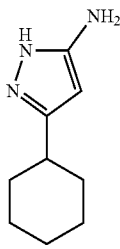

To a solution of 3-cyclohexyl-3-oxopropanenitrile (100 mg, 661 µmol) (intermediate 01-17) in anhydrous ethanol (1.0 ml, 17 mmol) and acetic acid (50 µl, 870 µmol) was added hydrazine hydrate (1:1) (250 µl, 65% purity, 3.3 mmol). The mixture was heated to reflux for 4 h. The reaction mixture was allowed to cool to rt. After this time saturated aqueous NaHCO$_3$ solution was added and extracted with ethyl acetate. The combined organic layers were washed with brine, dried with a water repellant filter and concentrated to afford 104 mg (95% yield) of the title compound.

$^1$H NMR (400 MHz, Chloroform-d) δ [ppm]: 1.20-1.48 (m, 6H), 1.63-1.90 (m, 4H), 1.90-2.02 (m, 3H), 2.48-2.59 (m, 1H), 5.43 (s, 1H).

LC-MS (Analytical Method G): $R_t$=0.68 min; MS (ESIpos): m/z=166 [M+H]$^+$.

Intermediate 01-25

3-(tetrahydro-2H-pyran-4-yl)-1H-pyrazol-5-amine

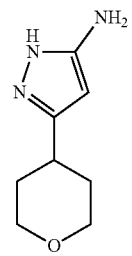

To a stirred solution of 3-oxo-3-(tetrahydro-2H-pyran-4-yl)propanenitrile (250 mg, 1.63 mmol) (intermediate 01-18) in dry ethanol (2.5 ml, 43 mmol) and glacial acetic acid (130 µl, 2.2 mmol) was added hydrazine hydrate (1:1) (610 µl, 65%, 8.2 mmol). The reaction mixture was heated for 2 h at reflux. The mixture was allowed to cool to rt before NaHCO$_3$ solution was added. The aqueous solution was extracted three times with ethyl acetate. The combined organic phases were washes with brine, dried over a water repellant filter and concentrated under reduced pressure to get 177 mg (63% yield) of the desired product.

$^1$H NMR (400 MHz, Chloroform-d) δ [ppm]: 1.69-1.87 (m, 4H), 2.80 (tt, 1H), 3.49 (td, 2H), 3.99-4.06 (m, 2H), 5.46 (s, 1H).

LC-MS (Analytical Method H): $R_t$=0.50 min; MS (ESIpos): m/z=168 [M+H]$^+$.

Intermediate 01-26

3-(tetrahydro-2H-pyran-4-ylmethyl)-1H-pyrazol-5-amine

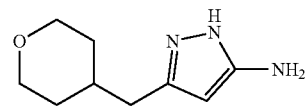

To a solution of 3-oxo-4-(tetrahydro-2H-pyran-4-yl)butanenitrile (448 mg, 2.36 mmol) (intermediate 01-19) in ethanol (4 mL) was added hydrazine hydrate (0.57 mL, 11.7 mmol), and the reaction was heated at reflux for 2 h. After this time, the solvent was removed, azeotroping with methanol, under reduced pressure to afford the title compound (405.9 mg 85%) as a yellow gum that was utilized directly without further purification.

$^1$H NMR (250 MHz, Chloroform-d) δ [ppm]: 1.26-1.42 (m, 2H), 1.53-1.67 (m, 2H), 1.66-1.85 (m, 1H), 2.47 (d, 2H), 3.34 (td, 2H), 3.66-4.27 (m, 5H), 5.45 (s, 1H).

Intermediate 01-27

3-(5-methylpyridin-2-yl)-1H-pyrazol-5-amine

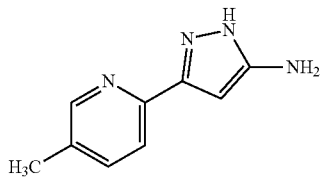

To a solution of 3-(5-methylpyridin-2-yl)-3-oxopropanenitrile (4.87 g, 30.4 mmol) (intermediate 01-20) in ethanol (50 ml) was acetic acid (5.0 ml) followed by hydrazine hydrate (7.4 ml, 150 mmol). The reaction mixture was heated to reflux for 2 h. The reaction was allowed to cool to room temperature then quenched with 30 mL saturated aqueous sodium hydrogencarbonate solution. The phases were separated and the aqueous phase was extracted with ethyl acetate. The combined organic layers were washed with brine, dried with a water-repellant filter and concentrated. While concentrating a thick solid was formed. The solid was slurried in 100 mL hexane and the collected by vacuum filtration to afford 4.71 g (89% yield) of the title compound.

LC-MS (Method H): $R_t$=0.63 min; MS (ESIpos): m/z=175 [M+H]$^+$ $^1$H NMR (400 MHz, DMSO-d6) δ[ppm]: 2.29 (s, 3H), 4.78 (br s, 2H), 5.88 (s, 1H), 7.58-7.62 (m, 1H), 7.62-7.68 (m, 1H), 8.34-8.39 (m, 1H)

Intermediate 01-28

3-(pyridin-4-yl)-1H-pyrazol-5-amine

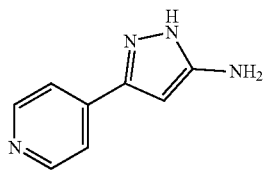

To a solution of 3-oxo-3-(pyridin-4-yl)propanenitrile (14.8 g, 98.7 mmol) (intermediate 01-21), in ethanol (250 mL) was added hydrazine hydrate (14.8 g, 296 mmol). The resulting mixture was stirred at 90° C. for 3 h. After cooling to room temperature, the solvent was removed in vacuo and the residue was purified with silica gel column chromatography (dichloromethane:methanol=15:1) to give 11.0 g (65%) of the product as a light yellow solid.

LC-MS (Analytical Method N, 0-2.00 min 5-95% B): $R_t$=0.77 min; MS (ESIpos): m/z=161 [M+H]$^+$.

Intermediate 01-29

3-[(pyridin-2-yl)methyl]-1H-pyrazol-5-amine

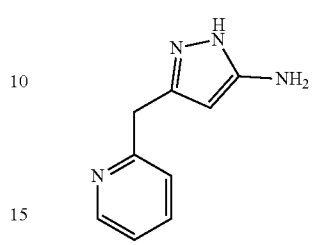

To a solution of 3-oxo-4-(pyridin-2-yl)butanenitrile (11.0 g, 34.3 mmol) (intermediate 01-22) in ethanol (120 mL) was added hydrazine hydrate (5.2 g, 103 mmol). The resulting mixture was stirred at 90° C. for 3 h. After cooling to room temperature, the solvent was removed in vacuo and the residue was purified with silica gel column chromatography (dichloromethane:methanol=15:1) to give 4.5 g (61%) of the product as a light yellow solid.

LC-MS (Analytical Method N, 0-2.00 min 5-95% B): $R_t$=0.72 min; MS (ESIpos): m/z=175 [M+H]$^+$.

Intermediate 01-31 tert-butyl 5-amino-3-(pyridin-4-yl)-1H-pyrazole-1-carboxylate

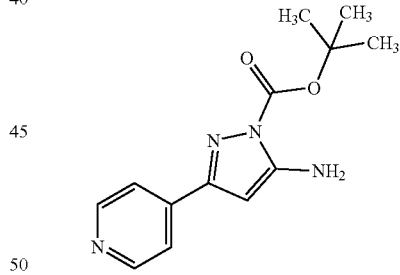

To a solution of 3-(pyridin-4-yl)-1H-pyrazol-5-amine (10.0 g, 58.0 mmol) (intermediate 01-28) in dichloromethane (200 mL) were added N,N-diisopropylethylamine (22.6 g, 174 mmol), di-tert-butyl dicarbonate (19.0 g, 87.1 mmol) and 4-dimethylaminopyridine (710 mg, 5.8 mmol). The resulting mixture was stirred at room temperature for 2 h. Upon the completion of the reaction, the solvent was removed in vacuo and the residue was purified with silica gel column chromatography (petroleum ether: ethyl acetate=1:1) to give 5.8 g (37%) of the product as a white solid.

$^1$H-NMR (400 MHz, DMSO-d6) δ[ppm]: 1.61 (s, 9H), 5.90 (s, 1H), 6.54 (s, 2H), 7.72 (d, 2H), 8.62 (d, 2H).

LC-MS (Analytical Method N, 0-3.00 min 5-95% B): $R_t$=1.39 min; MS (ESIpos): m/z=261 [M+H]$^+$.

Intermediate 01-32 tert-butyl 5-amino-3-[(pyridin-2-yl)methyl]-1H-pyrazole-1-carboxylate

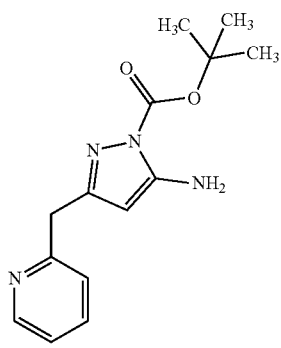 [SMILES: CC(C)(C)OC(=O)n1nc(Cc2ccccn2)cc1N]

To a solution of 3-(pyridin-2-ylmethyl)-1H-pyrazol-5-amine (5.7 g, 23.9 mmol) (intermediate 01-29) in dichloromethane (200 mL) were added N,N-diisopropylethylamine (9.3 g, 71.6 mmol), di-tert-butyl dicarbonate (7.8 g, 35.8 mmol) and 4-dimethylaminopyridine (292 mg, 2.4 mmol). The resulting mixture was stirred at room temperature for 2 h. Upon the completion of the reaction, the solvent was removed in vacuo and the residue was purified with silica gel column chromatography (dichloromethane:methanol=15:1) to give 2.7 g (34%) of the product as light yellow oil.

$^1$H-NMR (400 MHz, DMSO-d6) δ[ppm]: 1.55 (s, 9H), 3.85 (s, 2H), 5.11 (s, 1H), 6.23 (s, 2H), 7.22 (t, 1H), 7.28 (d, 1H), 7.69 (t, 1H), 8.47 (d, 1H).

LC-MS (Analytical Method N, 0-3.00 min 5-95% B): Rt=1.33 min; MS (ESIpos): m/z=275 [M+H]+.

Intermediate 01-34 ethyl N-[(4-fluorophenyl)methyl]-beta-alaninate

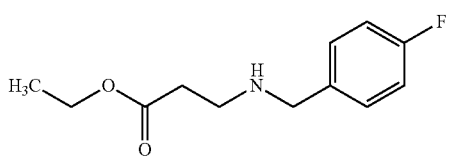

To a solution of ethyl beta-alaninate hydrogen chloride (1/1) (200 mg, 1.30 mmol) and 4-fluorobenzaldehyde (170 µl, 1.6 mmol) in dichloromethane (8.0 ml, 120 mmol) and methanol (2.0 ml, 49 mmol) was added sodium cyanoborohydride (164 mg, 2.60 mmol) and glacial acetic acid (89 µl, 1.6 mmol). The mixture was stirred for 16 h at room temperature. Approximately 20 mL saturated aqueous sodium hydrogencarbonate solution were added and vigorously stirred for 10 min at room temperature. The phases were separated and the aqueous layer was extracted twice with dichloromethane. The combined organic phases were dried with a water repellant filter and concentrated. The residue was dissolved with ethyl acetate, adsorbed on isolute and purified over Biotage Isolera Four (Biotage SNAP Cartridge KP-Sil 25 g; 0-60% ethyl acetate in hexane) to afford 138 mg (47% yield) of the title compound.

LC-MS (Method H): R$_t$=1.05 min; MS (ESIpos): m/z=226 [M+H]$^+$ $^1$H NMR (400 MHz, Chloroform-d) δ [ppm]: 1.25 (t, 3H), 1.73 (br s, 1H), 2.52 (t, 2H), 2.88 (t, 2H), 3.77 (s, 2H), 4.14 (q, 2H), 7.00 (t, 2H), 7.23-7.32 (m, 2H).

Intermediate 01-35

2,5-dimethyl-4-(4,4,5,5-tetramethyl-1,3,2-dioxaborolan-2-yl)pyridine

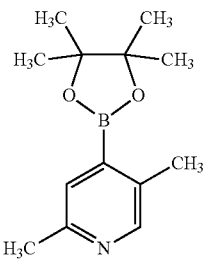

A mixture of 2,5-lutidine (2.5 g, 23.3 mmol), bis(pinacolato)diboron (5.9 g, 23.3 mmol) and 4,4'-di-tert-butyl-2,2'-bipyridine (25 mg, 0.093 mmol) in octane (25 ml) was degassed with a stream of N$_2$ for 10 mins. Bis(1,5-cyclooctadiene)diiridium(I) dichloride (31.3 mg, 0.047 mmol) was added, and the reaction mixture was stirred at reflux overnight. The reaction mixture was cooled, diluted with dichloromethane (300 ml) and transferred to a beaker equipped with a magnetic stirrer. Ice-cold water (200 ml) was added carefully with stirring, and the mixture stirred vigorously for 15 mins before being filtered through celite. The organic layer was separated and the aqueous layer was extracted with dichloromethane (2×100 ml). The combined organics were dried (MgSO$_4$), filtered and concentrated under reduced pressure to afford 4.65 g (51% yield, 60% purity) of the title compound as a brown viscous oil.

$^1$H NMR (250 MHz, Chloroform-d) δ [ppm]: 1.35 (s, 12H), 2.43 (s, 3H), 2.50 (s, 3H), 7.42 (s, 1H), 8.31 (s, 1H).

Intermediate 01-36 tert-butyl [1-(benzyloxy)-2-methylpropan-2-yl]carbamate

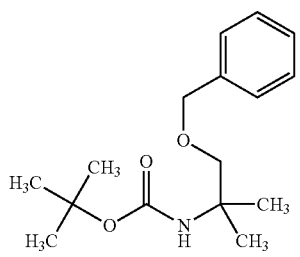

To a solution of tert-butyl 1-hydroxy-2-methylpropan-2-ylcarbamate (5.0 g, 26.4 mmol) in N,N-dimethylformamide (100 mL) were added potassium hydroxide (2.8 g, 50.2 mmol) and (bromomethyl)benzene (8.6 g, 50.2 mmol). The resulting mixture was stirred at room temperature overnight. Upon completion of the reaction, water was added and the resulting solution was extracted with ethyl acetate. The combined organic layer was washed with brine, dried over anhydrous sodium sulfate and concentrated in vacuo to give 5.0 g (67%) of the product as yellow oil.

LC-MS (Analytical Method Q, 0-2.00 min 5-100% B): $R_t$=1.20 min; MS (ESIpos): m/z=280 [M+H]$^+$.

Intermediate 01-37 tert-butyl [(±)-1-(benzyloxy)propan-2-yl]carbamate

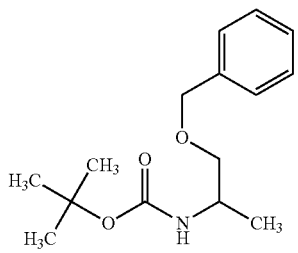

To a solution of tert-butyl 1-hydroxypropan-2-ylcarbamate (4.0 g, 22.8 mmol) in N,N-dimethylformamide (100 mL) were added potassium hydroxide (2.3 g, 41.1 mmol) and (bromomethyl)benzene (7.0 g, 41.1 mmol). The resulting mixture was stirred at room temperature overnight. Upon completion of the reaction, water was added and the resulting solution was extracted with ethyl acetate. The combined organic layer was washed with brine, dried over anhydrous sodium sulfate and concentrated in vacuo to give 5.0 g (58%) of the product as yellow oil.

LC-MS (Analytical Method R, 0-2.00 min 5-100% B): Rt=0.85 min; MS (ESIpos): m/z=266 [M+H]+.

Intermediate 01-38

1-(benzyloxy)-2-methylpropan-2-amine

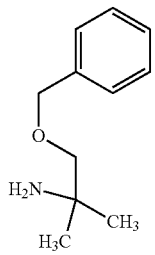

To a solution of tert-butyl 1-(benzyloxy)-2-methylpropan-2-ylcarbamate (5.0 g, 17.9 mmol) (intermediate 01-36) in dichloromethane (100 mL) was added trifluoroacetic acid (20 mL) and the resulting mixture was stirred at room temperature for 3 h. Upon completion of the reaction, the solvent was removed in vacuo and the residue was purified by C18 reversed phase chromatography [Mobile Phase A: Water (0.05% TFA), Mobile Phase B: Acetonitrile; Gradient: 5% B to 50% B in 30 min] to give 3.0 g (93%) of the product as a solid.

$^1$H-NMR (400 MHz, DMSO) δ [ppm]: 1.24 (s, 6H), 3.40 (s, 2H), 4.58 (s, 2H), 7.30-7.35 (m, 1H), 7.36-7.40 (m, 4H), 7.93 (br, 2H).

LC-MS (Analytical Method Q, 0-1.80 min 5-100% B): $R_t$=0.50 min; MS (ESIpos): m/z=180 [M+H]$^+$.

Intermediate 01-39

1-(benzyloxy)propan-2-amine

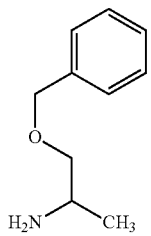

To a solution of tert-butyl 1-(benzyloxy)propan-2-ylcarbamate (5.0 g, 18.8 mmol) (intermediate 01-37) in dichloromethane (100 mL) was added trifluoroacetic acid (20 mL). The resulting mixture was stirred at room temperature for 5 h. Upon completion of the reaction, the solvent was removed in vacuo and the residue was purified by C18 reversed phase column chromatography [Mobile Phase A: Water (0.05% FA), Mobile Phase B: Acetonitrile; Gradient: 5% B to 50% B in 30 min] to give 3.0 g (96%) of the product as light yellow oil.

LC-MS (Analytical Method R, 0-2.00 min 5-100% B): $R_t$=0.79 min; MS (ESIpos): m/z=166 [M+H]$^+$.

Intermediate 01-40 ethyl N-[1-(benzyloxy)-2-methylpropan-2-yl]-beta-alaninate

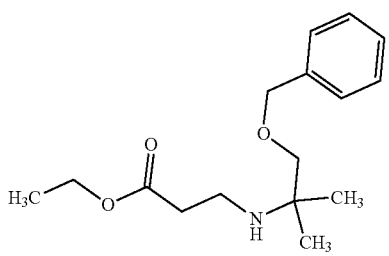

To a solution of 1-(benzyloxy)-2-methylpropan-2-amine (2.5 g, 13.9 mmol) (intermediate 01-38) in ethanol (150 mL) was added ethyl acrylate (27.9 g, 279 mmol). The resulting mixture was stirred at 80° C. overnight. After cooling to room temperature, the solvent was removed in vacuo. The residue was purified by C18 reversed phase chromatography [Mobile Phase A: Water (0.1% TFA), Mobile Phase B: Acetonitrile; Gradient: 2% B to 50% B in 30 min] to give 700 mg (18%) of the product as light yellow oil.

$^1$H-NMR (400 MHz, CD3OD) δ [ppm]: 1.28-1.34 (m, 9H), 2.73 (t, 2H), 3.20-3.26 (m, 2H), 3.51 (s, 2H), 4.19-4.25 (m, 2H), 4.64 (s, 2H), 7.32-7.44 (m, 5H), 8.43 (s, 1H).

LC-MS (Analytical Method K, 0-1.80 min 5-95% B): $R_t$=0.78 min; MS (ESIpos): m/z=280 [M+H]$^+$.

93

Intermediate 01-41 ethyl N-[(±)-1-(benzyloxy)propan-2-yl]beta-alaninate

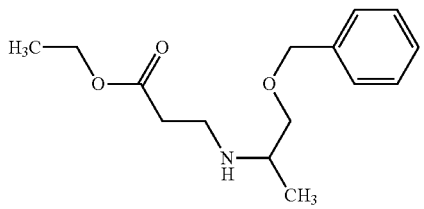

To a solution of 1-(benzyloxy)propan-2-amine (3.0 g, 18.2 mmol) (intermediate 01-39) in ethanol (200 mL) was added ethyl acrylate (36.4 g, 363 mmol). The resulting mixture was stirred at 80° C. overnight. After cooled to room temperature, the solvent was removed in vacuum. The residue was purified by C18 reversed phase column chromatography [Mobile Phase A: Water (0.1% FA), Mobile Phase B: Acetonitrile; Gradient: 10% B to 50% B in 30 min] to give 710 mg (14%) of the product as light yellow oil.

LC-MS (Analytical Method K, 0-3.00 min 5-95% B): $R_t$=0.95 min; MS (ESIpos): m/z=266 [M+H]$^+$.

Intermediate 01-42 tert-butyl 3-amino-5-ethyl-1H-pyrazole-1-carboxylate

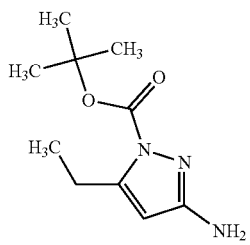

To a solution of 5-ethyl-1H-pyrazol-3-amine (16.7 g, 150 mmol) in THF (350 mL) was added triethylamine (21 ml, 150 mmol), DMAP (1.84 g, 15.0 mmol) and di-tert-butyl dicarbonate (32.8 g, 150 mmol). The resulting mixture was stirred at 0° C. for 2h and overnight at room temperature. The solution was diluted with water (100 mL) and extracted with ethyl acetate (3×100 mL) to yield after evaporation in vacuo 32.5 g of the crude product. Purification by Biotage Isolera™ chromatography (silica gel, hexane-ethyl acetate) yielded after evaporation and trituration with hexane, 5.61 g (18%) of the title compound as the minor isomer.

LC-MS (Method G): $R_t$=0.92 min; MS (ESIpos): m/z=212 [M+H]$^+$ $^1$H-NMR (400 MHz, DMSO-d6) δ[ppm]: 1.114 (1.41), 1.133 (3.08), 1.151 (1.46), 1.504 (16.00), 2.750 (0.93), 2.753 (0.91), 2.769 (0.90), 2.771 (0.89), 5.300 (1.36), 5.589 (1.44).

94

Intermediate 01-43

4-(4,4,5,5-tetramethyl-1,3,2-dioxaborolan-2-yl)-3,6-dihydro-2H-thiopyran 1,1-dioxide

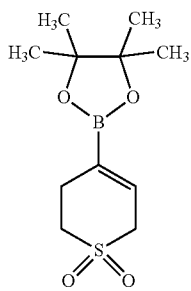

To a solution of 2-(3,6-dihydro-2H-thiopyran-4-yl)-4,4,5,5-tetramethyl-1,3,2-dioxaborolane (500 mg, 2.21 mmol) in acetone (15 mL) was added oxone (5.9 g, 35.4 mmol) dropwise at room temperature. The resulting mixture was stirred at 40° C. for 15 hours. After cooled to room temperature, the solvent was removed in vacuo. The residue was diluted with water and extracted with dichloromethane. The combined organic layer was washed with brine, dried over anhydrous sodium sulfate and concentrated in vacuo. The residue was purified by silica gel column chromatography (petroleum ether: ethyl acetate=1:1) to give 155 mg (27%) of the product as a white solid.

$^1$H-NMR (400 MHz, CD3OD): δ [ppm]=1.26 (s, 12H), 2.78-2.82 (m, 2H), 3.12 (t, 2H), 3.74-3.75 (m, 2H), 6.38-6.40 (m, 1H).

LC-MS (Analytical Method Q, 0-3.00 min 5-95% B): $R_t$=1.04 min; MS (ESIpos): m/z=259 [M+H]$^+$.

Intermediate 02-01 ethyl 4-hydroxy-5-oxo-1-(propan-2-yl)-2,5-dihydro-1H-pyrrole-3-carboxylate

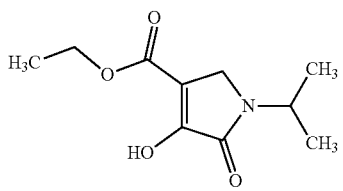

A mixture of isopropylamine (8.2 ml, 99.9 mmol) (CAS-No.: 75-31-0) and ethyl acrylate (10.8 ml, 99.9 mmol) in ethanol (115 ml) was stirred under a nitrogen atmosphere at rt for 23 h. Diethyl oxalate (13.6 ml, 99.9 mmol) and sodium ethoxide (21% in ethanol, 37 ml, 99.9 mmol) were then added successively and the reaction was heated at reflux for 3 h, after which time a yellow precipitate had formed. The reaction mixture was allowed to cool to rt, and the precipitate was collected by vacuum filtration. The solids were then taken up in boiling water, and acidified at 70° C. to pH 3 with 2M aqueous HCl solution. The resulting solution was allowed to cool to rt, and was extracted with ethyl acetate (3×50 ml). The organic phase was dried (MgSO$_4$), filtered and concentrated under reduced pressure to afford 13.5 g (92% yield) of the title compound as a pale yellow solid.
¹H NMR (250 MHz, Chloroform-d) δ [ppm]1.10 (d, 6H), 1.20 (t, 3H), 3.66 (s, 2H), 4.09 (q, 2H), 4.24-4.43 (m, 1H).
LC-MS (Analytical Method A) $R_t$=0.90 min, MS (ESIpos): m/z=214 [M+H]⁺.

Intermediate 02-02 ethyl 4-hydroxy-1-[(2S)-3-methylbutan-2-yl]-5-oxo-2,5-dihydro-1H-pyrrole-3-carboxylate

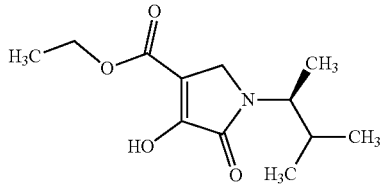 [SMILES: CCOC(=O)C1=C(O)C(=O)N([C@@H](C)C(C)C)C1]

2(S)-3-Methylbutan-2-amine (6.2 ml, 53.1 mmol) (CAS-No.: 22526-46-1) and ethyl acrylate (5.7 ml, 53.1 mmol) in ethanol (61 ml) were stirred for 60 h at rt under a nitrogen atmosphere. Dimethyl oxalate (6.3 g, 53.0 mmol) and sodium ethoxide (21% in ethanol, 19.8 ml, 53.1 mmol) were then added successively and the reaction was heated at 90° C. for 1 h. The reaction mixture was allowed to cool to rt and concentrated under reduced pressure. The residue was taken up in boiling water (~40 ml), and acidified at ca. 70° C. to pH 3 with concentrated HCl solution. The solution was allowed to cool to rt, and extracted with ethyl acetate (3×50 ml). The organic phase was dried (MgSO₄), filtered and concentrated under reduced pressure to afford 8.1 g (36% yield) of the title compound as a yellow crystalline solid.

LC-MS (Analytical Method A) $R_t$=1.00 min, MS (ESIpos): m/z=242 [M+H]⁺.

In analogy to the procedure described for Intermediates 02-01 and 02-02, the following intermediates were prepared using the appropriate amine, ethyl acrylate and diethyl oxalate or dimethyl oxalate.

| Int. | Structure<br>IUPAC-Name<br>¹H NMR | Synth. from<br>Yield<br>LC-MS |
|---|---|---|
| 02-03 | ethyl 1-(cyclopropylmethyl)-4-hydroxy-5-oxo-2,5-dihydro-1H-pyrrole-3-carboxylate<br>¹H NMR (500 MHz, Chloroform-d) δ [ppm] 4.44-4.16 (m, 2H), 3.54-3.24 (m, 2H), 1.34 (t, 7.1 Hz, 3H), 1.12-0.93 (m, 1H), 0.66-0.46 (m, 2H), 0.38-0.21 (m, 2H). O—H signal not observed | CAS-No.: 2516-47-4<br>81%<br>LC-MS (Analytical Method A)<br>$R_t$ = 0.88 min, MS (ESIpos):<br>m/z = 226 [M + H]⁺. |
| 02-04 | ethyl 1-[(2R)-butan-2-yl]-4-hydroxy-5-oxo-2,5-dihydro-1H-pyrrole-3-carboxylate | CAS-No.: 13250-12-9<br>47%<br>LC-MS (Analytical Method A)<br>$R_t$ = 0.97 min, MS (ESIpos):<br>m/z = 228 [M + H]⁺. |
| 02-05 | ethyl 1-cyclobutyl-4-hydroxy-5-oxo-2,5-dihydro-1H-pyrrole-3-carboxylate | CAS-No.: 2516-34-9<br>78%<br>LC-MS (Analytical Method A)<br>$R_t$ = 0.95 min, MS (ESIpos):<br>m/z = 225 [M + H]⁺. |

-continued

| Int. | Structure<br>IUPAC-Name<br>¹H NMR | Synth. from<br>Yield<br>LC-MS |
|---|---|---|
| 02-06 | ethyl 1-cyclopentyl-4-hydroxy-5-oxo-2,5-dihydro-1H-pyrrole-3-carboxylate | CAS-No.: 1003-03-8<br>67%<br>LC-MS (Analytical Method A)<br>$R_t$ = 0.99 min, MS (ESIpos):<br>m/z = 240 [M + H]⁺. |
| 02-07 | ethyl 4-hydroxy-5-oxo-1-(tetrahydro-2H-pyran-4-yl)-2,5-dihydro-1H-pyrrole-3-carboxylate<br>¹H NMR (250 MHz, DMSO-d6) δ [ppm] 9.34 (s, 1H), 4.22-4.11 (m, 2H), 3.98 (s, 2H), 3.91 (dd, 2H), 3.40-3.20 (m, 2H), 3.15 (t, 1H), 2.80 (t, 1H), 2.04-1.87 (m, 1H), 1.78-1.57 (m, 2H), 1.24-1.12 (m, 3H). | CAS-No.: 38041-19-9<br>59%<br>LC-MS (Analytical Method A)<br>$R_t$ = 0.81 min MS (ESIpos):<br>m/z = 256 [M + H]⁺. |
| 02-08 | ethyl 1-[2-(benzyloxy)ethyl]-4-hydroxy-5-oxo-2,5-dihydro-1H-pyrrole-3-carboxylate | CAS-No.: 38336-04-8<br>79%<br>LC-MS (Analytical Method A)<br>$R_t$ = 1.04 min, MS (ESIpos):<br>m/z = 306 [M + H]⁺. |
| 02-09 | ethyl 4-hydroxy-1-[(±)-1-methoxypropan-2-yl]-5-oxo-2,5-dihydro-1H-pyrrole-3-carboxylate<br>¹H NMR (250 MHz, Chloroform-d) δ [ppm]:<br>6.31 (s, 1H), 4.60-4.45<br>(m, 1H), 4.34 (q, 2H), 4.20-3.98 (m, 2H), 3.58-3.43 (m, 2H), 3.35 (s, 3H), 1.38 (q, 3H), 1.28 (d, 3H). | CAS-No.: 37143-54-7<br>58%<br>LC-MS (Analytical Method A)<br>$R_t$ = 0.87 min, MS (ESIpos):<br>m/z = 244 [M + H]⁺. |
| 02-10 | ethyl 4-hydroxy-5-oxo-1-[2-oxo-2-(pyrrolidin-1-yl)ethyl]-2,5-dihydro-1H-pyrrole-3-carboxylate<br>¹H NMR (250 MHz, Chloroform-d) δ [ppm]: 4.34 (q, 2H), 4.29-4.11 (m, 4H), 3.75-3.30 (m, 4H), 2.25-1.64 (m, 4H), 1.35 (t, 3H). | CAS-No.: 35855-14-2<br>65%<br>LC-MS (Analytical Method A)<br>$R_t$ = 0.81 min, MS (ESIpos):<br>m/z = 283 [M + H]⁺. |

-continued

| Int. | Structure<br>IUPAC-Name<br>¹H NMR | Synth. from<br>Yield<br>LC-MS |
|---|---|---|
| 02-11 | ethyl 4-hydroxy-1-(oxetan-3-yl)-5-oxo-2,5-dihydro-1H-pyrrole-3-carboxylate<br>¹H NMR (500 MHz, Chloroform-d) δ [ppm]: 5.49 (p, 1H), 4.96 (t, 2H), 4.80 (t, 2H), 4.39 (q, 2H), 4.32 (s, 2H), 1.40 (t, 3H). | CAS-No.: 21635-88-1<br>18%<br>LC-MS (Analytical Method A)<br>$R_t$ = 0.69 min, MS (ESIpos):<br>m/z = 228 [M + H]⁺. |
| 02-12 | ethyl 4-hydroxy-1-(2-methoxyethyl)-5-oxo-2,5-dihydro-1H-pyrrole-3-carboxylate | CAS-No.: 109-85-3<br>65%<br>LC-MS (Analytical Method A)<br>$R_t$ = 0.8 min, MS (ESIpos):<br>m/z = 230 [M + H]⁺. |
| 02-13 | ethyl 1-[(1S)-1-cyclopropylethyl]-4-hydroxy-5-oxo-2,5-dihydro-1H-pyrrole-3-carboxylate | CAS-No.: 195604-39-8<br>75%<br>LC-MS (Analytical Method A)<br>$R_t$ = 0.98 min, MS (ESIpos):<br>m/z = 240 [M + H]⁺. |
| 02-14 | ethyl 4-hydroxy-1-(2-hydroxy-2-methylpropyl)-5-oxo-2,5-dihydro-1H-pyrrole-3-carboxylate<br>¹H NMR (250 MHz, Chloroform-d) δ [ppm]: 6.00 (br s, 2H), 4.49-4.01 (m, 4H), 3.64-3.29 (m, 2H), 1.61-0.79 (m, 9H). | CAS-No.: 2854-16-2<br>54%<br>LC-MS (Analytical Method A)<br>$R_t$ = 0.77 min, MS (ESIpos):<br>m/z = 244 [M + H]⁺. |
| 02-15 | ethyl 4-hydroxy-1-[(2R)-1-methoxypropan-2-yl]-5-oxo-2,5-dihydro-1H-pyrrole-3-carboxylate | CAS-No.: 626220-76-6<br>63%<br>LC-MS (Analytical Method A)<br>$R_t$ = 0.87 min, MS (ESIpos):<br>m/z = 244 [M + H]⁺. |

-continued

| Int. | Structure<br>IUPAC-Name<br>¹H NMR | Synth. from<br>Yield<br>LC-MS |
|---|---|---|
| 02-16 | ethyl 1-[(2S)-butan-2-yl]-4-hydroxy-5-oxo-2,5-dihydro-1H-pyrrole-3-carboxylate<br>¹H NMR (250 MHz, DMSO-d6) δ [ppm]: 4.32 (m, 3H), 4.00-3.85 (m, 2H), 1.60 (m, 2H), 1.38 (t, 3H), 1.25 (d, 3H), 0.90 (t, 3H). | CAS-No.: 513-49-5<br>89%<br>LC-MS (Analytical Method A)<br>R$_t$ = 0.94 min, MS (ESIpos):<br>m/z = 228 [M + H]$^+$. |
| 02-17 | ethyl 4-hydroxy-1-[(2S)-2-hydroxypropyl]-5-oxo-2,5-dihydro-1H-pyrrole-3-carboxylate | CAS-No.: 2799-16-8<br>55%<br>LC-MS (Analytical Method A)<br>R$_t$ = 0.83 min, MS (ESIpos):<br>m/z = 230 [M + H]$^+$. |
| 02-18 | ethyl 1-[(1R)-1-oyolopropylethyl]-4-hydroxy-5-oxo-2,5-dihydro-1H-pyrrole-3-carboxylate<br>¹H NMR (500 MHz, Chloroform-d) δ [ppm]: 8.76 (br s, 1H), 4.36 (q, 2H), 4.16 (d, 1H), 4.05 (d, 1H), 3.63 (m, 1H), 1.38 (t, 3H), 1.32 (d, 3H), 1.02-0.94 (m, 1H), 0.69-0.61 (m, 1H), 0.51-0.44 (m, 1H), 0.40-0.31 (m, 2H). | CAS-No.: 6240-96-6<br>78%<br>LC-MS (Analytical Method A)<br>R$_t$ = 0.99 min, MS (ESIpos):<br>m/z = 240 [M + H]$^+$. |
| 02-19 | ethyl 4-hydroxy-5-oxo-1-[(±)-tetrahydrofuran-3-yl]-2,5-dihydro-1H-pyrrole-3-carboxylate<br>¹H NMR (400 MHz, CD3OD): δ [ppm]: 1.35 (t, 3H), 2.08-2.11 (m, 1H), 2.30-2.40 (m, 1H), 3.77-3.90 (m, 2H), 4.05-4.10 (m, 3H), 4.29 (q, 2H), 4.80-4.85 (m, 1H). | CAS-No.: 45379-55-3<br>76%<br>LC-MS (Analytical Method L, 0-1.2 min 10-95% B, 1.2-1.7 min 95% B): R$_t$ = 0.33 min; MS (ESIpos): m/z = 242 [M + H]$^+$ |

|  |  |
|---|---|
| Structure<br>IUPAC-Name<br>Int. ¹H NMR | Synth. from<br>Yield<br>LC-MS |

02-20

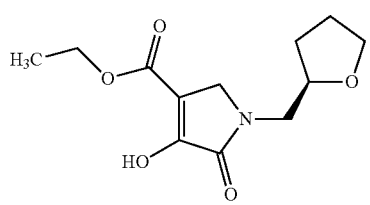

ethyl 4-hydroxy-5-oxo-1-[(2R)-tetrahydrofuran-2-ylmethyl]-2,5-dihydro-1H-pyrrole-3-carboxylate ¹H NMR (300 MHz, CD3OD): δ [ppm]: 1.31 (t, 3H), 1.58-1.65 (m, 1H), 1.92 (q, 2H), 1.97-2.05 (m, 1H), 3.42-3.49 (m, 1H), 3.60-3.66 (m, 1H), 3.70-3.77 (m, 1H), 3.83-3.90 (m, 1H), 4.06-4.10 (m, 2H), 4.12-4.16 (m, 1H), 4.23-4.81 (m, 2H).

CAS-No.: 7202-43-9
85%
LC-MS (Analytical Method K, 0-2.0 min 5-100% B, 2.0-2.8 min 100% B): R$_t$ = 0.92 min; MS (ESIpos): m/z = 256 [M + H]$^+$ 02-21

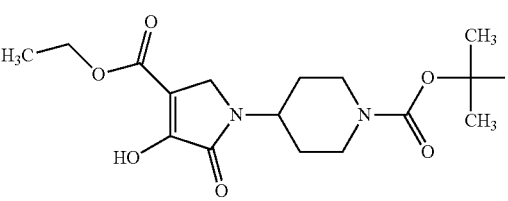

tert-butyl 4-[4-(ethoxycarbonyl)-3-hydroxy-2-oxo-2,5-dihydro-1H-pyrrol-1-yl]piperidine-1-carboxylate ¹H NMR (400 MHz, CD3OD): δ [ppm]: 1.33 (t, 3H), 1.49 (s, 9H), 1.68-1.76 (m, 2H), 1.80-1.83 (m, 2H), 2.82-2.92 (m, 2H), 4.05 (s, 2H), 4.10-4.24 (m, 3H), 4.30 (q, 2H).

CAS-No.: 87120-72-7
3%
LC-MS (Analytical Method K, 0-3.0 min 5-50% B, 3.0-3.3 min 50-95%, 3.3-4.2 min 95% B): R$_t$ = 2.61 min; MS (ESIpos): m/z = 355 [M + H]$^+$ 02-22

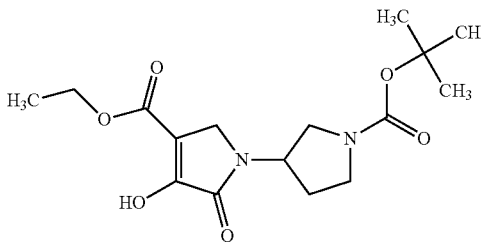

ethyl 1-[(±)-1-(tert-butoxycarbonyl)pyrrolidin-3-yl]-4-hydroxy-5-oxo-2,5-dihydro-1H-pyrrole-3-carboxylate ¹H NMR (400 MHz, DMSO-d6): δ [ppm]: 1.19 (t, 3H), 1.40 (s, 9H), 2.05 (s, 2H), 3.26-3.33 (m, 2H), 3.37-3.51 (m, 2H), 3.85-3.89 (m, 2H), 4.06-4.11 (m, 2H), 4.50-4.54 (m, 1H).

CAS-No.: 186550-13-0
88%
LC-MS (Analytical Method K, 0-2.0 min 5-95% B, 2.0-2.6 min 95% B): R$_t$ = 1.32 min; MS (ESIpos): m/z = 341 [M + H]$^+$ 02-23

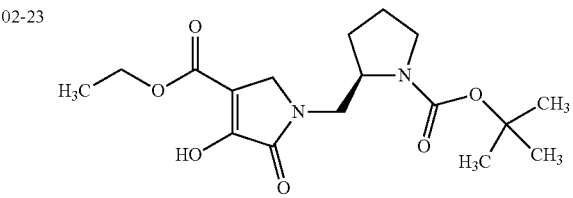

ethyl 1-{[(2R)-1-(tert-butoxycarbonyl)pyrrolidin-2-yl]methyl}-4-hydroxy-5-oxo-2,5-dihydro-1H-pyrrole-3-carboxylate ¹H NMR (300 MHz, CD3OD): δ [ppm]: 1.28 (t, 3H), 1.44 (s, 9H), 1.80-1.93 (m, 4H), 3.31-3.35 (m, 2H), 3.54-3.59 (m, 2H), 4.03-4.09 (m, 3H), 4.24 (q, 2H).

CAS-No.: 259537-92-3
80%
LC-MS (Analytical Method K, 0-1.25 min 10-95% B, 1.25-1.75 min 95% B): R$_t$ = 0.72 min; m/z = 255 [M + Boc]$^+$

| Int. | Structure<br>IUPAC-Name<br>¹H NMR | Synth. from<br>Yield<br>LC-MS |
|---|---|---|
| 02-24 | ethyl 4-hydroxy-5-oxo-1-[(±)-tetrahydrofuran-3-ylmethyl]-2,5-dihydro-1H-pyrrole-3-carboxylate | CAS-No.: 165253-31-6<br>40%<br>LC-MS (Analytical Method L, 0-1.20 min 10-95% B, 1.20-1.70 min 95% B): $R_t$ = 0.65 min; MS (ESIpos): m/z = 256 [M + H]⁺ |
| 02-25 | ethyl 4-hydroxy-5-oxo-1-[(±)-tetrahydrofuran-2-ylmethyl]-2,5-dihydro-1H-pyrrole-3-carboxylate<br>¹H NMR (400 MHz, CD3OD): δ [ppm] = 1.34 (t, 3H), 1.57-1.66 (m, 1H), 1.89-1.93 (m, 2H), 1.96-2.01 (m, 1H), 3.46-3.51 (m, 1H), 3.63-3.67 (m, 1H), 3.73-3.79 (m, 1H), 3.86-3.92 (m, 1H), 4.08-4.19 (m, 3H), 4.24-4.87 (m, 2H). | CAS-No.: 4795-29-3<br>2%<br>LC-MS (Analytical Method K, 0-2.0 min 5-95% B, 2.0-2.7 min 95% B): $R_t$ = 0.92 min; MS (ESIpos): m/z = 256 [M + H]⁺ |
| 02-26 | tert-butyl (2S)-2-{[4-(ethoxycarbonyl)-3-hydroxy-2-oxo-2,5-dihydro-1H-pyrrol-1-yl]methyl}morpholine-4-carboxylate<br>¹H NMR (500 MHz, Chloroform-d) δ [ppm]: 4.35 (q, 2H), 4.21-4.07 (m, 2H), 4.02-3.80 (m, 3H), 3.78-3.68 (m, 1H), 3.68-3.60 (m, 1H), 3.57-3.38 (m, 2H), 2.91 (s, 1H), 2.69-2.61 (m, 1H), 2.07 (s, 1H), 1.48 (s, 9H), 1.38 (t, 3H). | Intermediate: 01-03<br>72%<br>LC-MS (Analytical Method A)<br>$R_t$ = 1.05 min, MS (ESIpos): m/z = 271 (M − Boc + H)⁺. |
| 02-27 | ethyl 4-hydroxy-1-(1-methylpiperidin-4-yl)-5-oxo-2,5-dihydro-1H-pyrrole-3-carboxylate | CAS-No.: 41838-46-4<br>crude<br>LC-MS (Analytical Method H): $R_t$ = 0.44 min; MS (ESIpos): m/z = 269 [M + H]⁺ |

| Int. | Structure<br>IUPAC-Name<br>¹H NMR | Synth. from<br>Yield<br>LC-MS |
|---|---|---|
| 02-28 | ethyl 4-hydroxy-1-[(2S)-1-methoxypropan-2-yl]-5-oxo-2,5-dihydro-1H-pyrrole-3-carboxylate<br>¹H NMR (250 MHz, DMSO-d6) δ [ppm]: 1.14 (d, 3H), 1.23 (t, 3H), 3.24 (s, 3H), 3.40-3.54 (m, 2H), 3.82-4.03 (m, 2H), 4.17 (q, 2H), 4.22-4.38 (m, 1H), 11.24 (s, 1H). | CAS-No.: 99636-32-5<br>79%<br>LC-MS (Analytical Method A)<br>$R_t$ = 0.86 min, MS (ESIpos):<br>m/z = 244 [M + H]⁺. |
| 02-29 | ethyl 1-{[(±)-1-(tert-butoxycarbonyl)pyrrolidin-3-yl]methyl}-4-hydroxy-5-oxo-2,5-dihydro-1H-pyrrole-3-carboxylate<br>¹H NMR (400 MHz, CD3OD) δ [ppm]: 1.34 (t, 3H), 1.47 (s, 9H), 1.62-1.72 (m, 1H), 2.00-2.02 (m, 1H), 2.58-2.64 (m, 1H), 3.05-3.10 (m, 1H), 3.32-3.34 (m, 1H), 3.45-3.53 (m, 4H), 4.10 (s, 2H), 4.30 (q, 2H). | CAS-No.: 270912-72-6<br>2%<br>LC-MS (Analytical Method K, 0-3.0 min 20-65% B, 3.0-4.0 min 65-95% B, 4.0-5.0 min 95% B): $R_t$ = 2.10 min; MS (ESIpos): m/z = 355 [M + H]⁺ |
| 02-30 | ethyl 1-{[(±)-1-(tert-butoxycarbonyl)pyrrolidin-2-yl]methyl}-4-hydroxy-5-oxo-2,5-dihydro-1H-pyrrole-3-carboxylate<br>¹H NMR (400 MHz, CD3OD): δ [ppm]: 1.31 (t, 3H), 1.42 (s, 9H), 1.72-1.97 (m, 4H), 3.35-3.36 (m, 2H), 3.52-3.60 (m, 2H), 4.08-4.13 (m, 3H), 4.28 (q, 2H). | CAS-No.: 177911-87-4<br>1%<br>LC-MS (Analytical Method K, 0-3.0 min 5-50% B, 3.0-4.0 min 50-100% B, 4.0-4.6 100% B): $R_t$ = 2.40 min; MS (ESIpos): m/z = 256 [M + H]⁺ |
| 02-31 | ethyl 4-hydroxy-5-oxo-1-(tetrahydro-2H-pyran-4-ylmethyl)-2,5-dihydro-1H-pyrrole-3-carboxylate<br>¹H NMR (250 MHz, Chloroform-d) δ [ppm] 4.31 (q, 1H), 4.25-3.90 (m, 2H), 3.70 (q, 1H), 3.58-3.15 (m, 2H), 2.09-1.86 (m, 1H), 1.61-1.48 (m, 1H), 1.47-1.08 (m, 4H). | CAS-No.: 130290-79-8<br>56%<br>LC-MS (Analytical Method A)<br>$R_t$ = 0.84 min, MS (ESIpos):<br>m/z = 270 [M + H]⁺. |

| Int. | Structure<br>IUPAC-Name<br>¹H NMR | Synth. from<br>Yield<br>LC-MS |
|---|---|---|
| 02-32 | 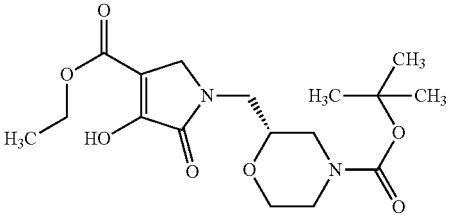<br>tert-butyl (2R)-2-{[4-(ethoxycarbonyl)-3-hydroxy-2-oxo-2,5-dihydro-1H-pyrrol-1-yl]methyl}morpholine-4-carboxylate<br>¹H NMR (500 MHz, Chloroform-d) δ [ppm]: 1.35 (t, 3H), 1.46 (s, 9H), 2.56-2.66 (m, 1H), 2.79-2.97 (m, 1H), 3.35-3.53 (m, 2H), 3.61 (s, 1H), 3.65-3.77 (m, 1H), 3.77-4.04 (m, 3H), 4.04-4.25 (m, 2H), 4.33 (q, 2H). | Intermediate: 01-06<br>91%<br>LC-MS (Analytical Method A)<br>$R_t$ = 1.05 min, MS (ESIpos):<br>m/z = 315 [M − tBu]⁺. |
| 02-33 | 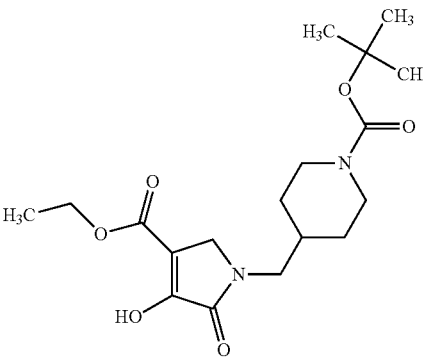<br>tert-butyl 4-{[4-(ethoxycarbonyl)-3-hydroxy-2-oxo-2,5-dihydro-1H-pyrrol-1-yl]methyl}piperidine-1-carboxylate | CAS-No.: 144222-22-0<br>22%<br>LC-MS (Analytical Method K, 0-1.1 min 10-100% B, 1.1-1.7 min 100% B): $R_t$ = 0.90 min;<br>MS (ESIpos): m/z = 269<br>[M + H − Boc]⁺ |
| 02-34 | 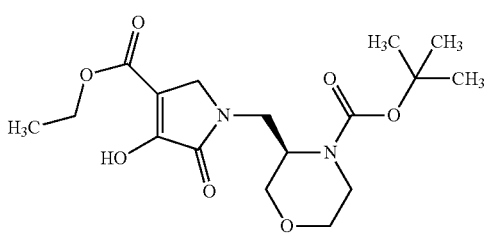<br>tert-butyl (3R)-3-{[4-(ethoxycarbonyl)-3-hydroxy-2-oxo-2,5-dihydro-1H-pyrrol-1-yl]methyl}morpholine-4-carboxylate<br>¹H NMR (500 MHz, Chloroform-d) δ [ppm]: 1.30-1.43 (m, 12H), 3.06-4.05 (m, 9H), 4.05-4.64 (m, 5H). | Intermediate: 01-16<br>50%<br>LC-MS (Analytical Method A)<br>$R_t$ = 0.98 min, MS (ESIPos):<br>m/z = 270.95 [M + H − Boc]⁺ |
| 02-35 | 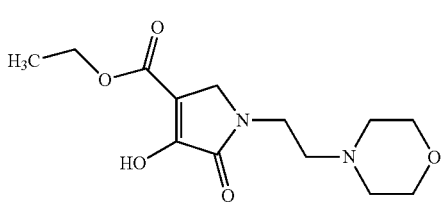<br>ethyl 4-hydroxy-1-[2-(morpholin-4-yl)ethyl]-5-oxo-2,5-dihydro-1H-pyrrole-3-carboxylate | CAS-No.: 2038-03-1<br>33%<br>LC-MS (Analytical Method G)<br>$R_t$ = 0.45 min, MS (ESIPos):<br>m/z = 285 [M + H]⁺ |

| Int. | Structure<br>IUPAC-Name<br>¹H NMR | Synth. from<br>Yield<br>LC-MS |
|---|---|---|
| 02-36 | ethyl 1-[(±)-butan-2-yl]-4-hydroxy-5-oxo-2,5-dihydro-1H-pyrrole-3-carboxylate<br>¹H NMR (250 MHz, DMSO-d6) δ [ppm]: 0.77 (t, 3H), 1.16 (d, 3H), 1.24 (t, 3H), 1.42-1.64 (m, 2H), 3.88 (d, 2H), 3.93-4.08 (m, 1H), 4.17 (q, 2H), 11.23 (s, 1H). | CAS-No.: 13952-84-6<br>28%<br>LC-MS (Analytical Method A)<br>$R_t$ = 0.97 min, MS (ESIpos):<br>m/z = 227.95 [M + H]⁺. |
| 02-37 | ethyl 1-(1,3-dimethoxypropan-2-yl)-4-hydroxy-5-oxo-2,5-dihydro-1H-pyrrole-3-carboxylate<br>¹H NMR (500 MHz, Chloroform-d) δ [ppm]: 1.37 (t, 3H), 3.35 (s, 6H), 3.58 (dd, 2H), 3.70 (dd, 2H), 4.14 (s, 2H), 4.34 (q, 2H), 4.55 (tt, 1H), 8.22 (s, 1H). | CAS-No.: 78531-29-0<br>74%<br>LC-MS (Analytical Method A):<br>$R_t$ = 0.88 min; MS (ESIpos):<br>m/z = 273.95 [M + H]⁺. |
| 02-38 | ethyl 4-hydroxy-5-oxo-1-[(pyridin-4-yl)methyl]-2,5-dihydro-1H-pyrrole-3-carboxylate-hydrogen chloride (1/1) | CAS-No.: 3731-53-1<br>97%<br>LC-MS (Analytical Method A):<br>$R_t$ = 0.41 min; MS (ESIpos):<br>m/z = 262.85 [M + H]⁺. |
| 02-39 | ethyl 4-hydroxy-5-oxo-1-[(pyridin-3-yl)methyl]-2,5-dihydro-1H-pyrrole-3-carboxylate-hydrogen chloride (1/1)<br>¹H NMR (250 MHz, DMSO-d6) δ [ppm]: 1.22 (t, 3H), 4.03 (s, 2H), 4.16 (q, 2H), 4.82 (s, 2H), 7.98 (dd, 1H), 8.40 (d, 2 Hz, 1H), 8.79-8.87 (m, 2H). | CAS-No.: 3731-52-0<br>20%<br>LC-MS (Analytical Method A):<br>$R_t$ = 0.45 min; MS (ESIpos):<br>m/z = 262.85 [M + H]⁺. |

| Int. | Structure<br>IUPAC-Name<br>¹H NMR | Synth. from<br>Yield<br>LC-MS |
|---|---|---|
| 02-40 | ethyl 4-hydroxy-5-oxo-1-[(pyridin-2-yl)methyl]-2,5-dihydro-1H-pyrrole-3-carboxylate-hydrogen chloride (1/1) | CAS-No.: 3731-51-9<br>67%<br>LC-MS (Analytical Method A):<br>R$_t$ = 0.76 min; MS (ESIpos):<br>m/z = 262.85 [M + H]⁺. |
| 02-41 | ethyl 1-[(4-fluorophenyl)methyl]-4-hydroxy-5-oxo-2,5-dihydro-1H-pyrrole-3-carboxylate<br>¹H NMR (400 MHz, DMSO-d6) δ [ppm]: 1.19 (t, 3H), 3.86 (s, 2H), 4.13 (q, 2H), 4.58 (s, 2H), 7.14-7.21 (m, 2H), 7.25-7.36 (m, 2H), 11.44 (br s, 1H). | Intermediate 01-34<br>65%<br>LC-MS (Method G): R$_t$ = 0.99 min; MS (ESIpos): m/z = 280 [M + H]⁺ |
| 02-42 | ethyl 1-(cyclobutylmethyl)-4-hydroxy-5-oxo-2,5-dihydro-1H-pyrrole-3-carboxylate<br>¹H NMR (500 MHz, DMSO-d6) δ [ppm]: 1.23 (t, 3H), 1.65-1.75 (m, 2H), 1.79-1.89 (m, 2H), 1.96-2.05 (m, 2H), 2.54-2.63 (m, 1H), 3.42 (d, 2H), 3.93 (s, 2H), 4.16 (q, 2H), 11.28 (s, 1H). | CAS-No.: 4415-83-2<br>67%<br>LC-MS (Analytical Method A):<br>R$_t$ = 1.02 min; MS (ESIpos):<br>m/z = 239.95 [M + H]⁺. |
| 02-43 | ethyl 4-hydroxy-1-{[(±)-oxan-2-yl]methyl}-5-oxo-2,5-dihydro-1H-pyrrole-3-carboxylate<br>¹H NMR (400 MHz, DMSO) δ [ppm]: 1.05-1.25 (m, 4H), 1.38-1.54 (m, 4H), 1.75-1.76 (m, 1H), 3.28-3.32 (m, 2H), 3.40-3.50 (m, 2H), 3.84-3.87 (m, 1H), 4.02 (s, 2H), 4.13-4.19 (m, 2H), 11.28 (br, 1H). | CAS-No.: 6628-83-7<br>38%<br>LC-MS (Analytical Method Q, 0-3.00 min 5-95% B): R$_t$ = 0.99 min; MS (ESIpos): m/z = 270 [M + H]⁺. |

| Int. | Structure / IUPAC-Name / ¹H NMR | Synth. from / Yield / LC-MS |
|---|---|---|
| 02-44 | ethyl 1-{[1-(tert-butoxycarbonyl)azetidin-3-yl]methyl}-4-hydroxy-5-oxo-2,5-dihydro-1H-pyrrole-3-carboxylate<br>¹H NMR (300 MHz, DMSO) δ [ppm]: 1.22 (t, 3H), 1.37 (s, 9H), 2.79-2.84 (m, 1H), 3.55-3.62 (m, 4H), 3.86-3.96 (m, 2H), 4.12 (s, 2H), 4.15-4.20 (m, 2H), 11.29 (br, 1H). | CAS-No.: 325775-44-8<br>32%<br>LC-MS (Analytical Method K, 0-3.00 min 5-95% B): $R_t$ = 1.19 min; MS (ESIpos): m/z = 341 [M + H]⁺. |
| 02-45 | ethyl 1-[1-(tert-butoxycarbonyl)azetidin-3-yl]-4-hydroxy-5-oxo-2,5-dihydro-1H-pyrrole-3-carboxylate<br>¹H NMR (400 MHz, CD₃OD) δ [ppm]: 1.32 (t, 3H), 1.44 (s, 9H), 4.13-4.19 (m, 6H), 4.22-4.31 (m, 2H), 4.88-4.91 (m, 1H). | CAS-No.: 193269-78-2<br>8%<br>LC-MS (Analytical Method Q, 0-5.00 min 5-95% B): $R_t$ = 2.38 min; MS (ESIpos): m/z = 271 [M + H − Bu]⁺. |
| 02-46 | ethyl 4-hydroxy-1-[(±)-oxan-3-yl]-5-oxo-2,5-dihydro-1H-pyrrole-3-carboxylate<br>¹H NMR (400 MHz, DMSO-d6) δ [ppm]: 1.22 (t, 3H), 1.53-1.75 (m, 2H), 1.75-1.88 (m, 2H), 3.28-3.44 (m, 3H), 3.65-3.77 (m, 2H), 3.85-3.95 (m, 1H), 3.95-4.00 (m, 1H), 4.00-4.06 (m, 1H), 4.16 (q, 2H). | CAS-No.: 675112-58-0<br>40%<br>LC-MS (Method G): $R_t$ = 0.78 min; MS (ESIpos): m/z = 256 [M + H]⁺ |
| 02-47 | ethyl 1-(1,1-dioxo-1lambda⁶-thian-4-yl)-4-hydroxy-5-oxo-2,5-dihydro-1H-pyrrole-3-carboxylate<br>¹H NMR (400 MHz, DMSO-d6) δ [ppm]: 1.22 (t, 3H), 1.94-2.13 (m, 2H), 2.14-2.27 (m, 2H), 3.08 (br d, 2H), 3.36-3.47 (m, 2H), 3.99 (s, 2H), 4.16 (q, 2H), 4.19-4.40 (m, 1H), 11.35 (br s, 1H). | CAS-No.: 210240-20-3<br>66%<br>LC-MS (Method G): $R_t$ = 0.63 min; MS (ESIpos): m/z = 304 [M + H]⁺ |

| Int. | Structure<br>IUPAC-Name<br>¹H NMR | Synth. from<br>Yield<br>LC-MS |
|---|---|---|
| 02-48 | 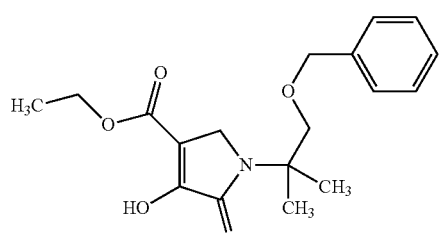<br>ethyl 1-[1-(benzyloxy)-2-methylpropan-2-yl]-4-hydroxy-5-oxo-2,5-dihydro-1H-pyrrole-3-carboxylate<br>¹H NMR (400 MHz, CD₃OD) δ [ppm]: 1.29 (t, 3H), 1.42 (s, 6H), 3.72 (s, 2H), 4.11 (s, 2H), 4.24-4.29 (m, 2H), 4.48 (s, 2H), 7.23-7.32 (m, 5H). | Intermediate 01-38<br>26%<br>LC-MS (Analytical Method T, 0-3.00 min 10-95% B):<br>$R_t$ = 0.85 min; MS (ESIpos): m/z = 334 [M + H]⁺. |
| 02-49 | 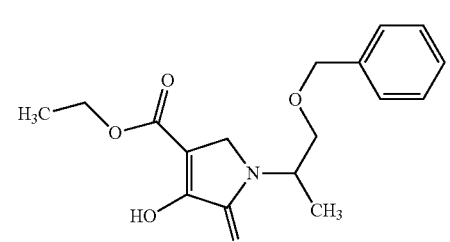<br>ethyl 1-[(±)-1-(benzyloxy)propan-2-yl]-4-hydroxy-5-oxo-2,5-dihydro-1H-pyrrole-3-carboxylate<br>¹H NMR (400 MHz, CD₃OD) δ [ppm]: 1.24 (d, 3H), 1.31 (t, 3H), 3.54-3.61 (m, 2H), 3.89-4.03 (m, 2H), 4.24-4.29 (m, 2H), 4.41-4.56 (m, 3H), 7.24-7.33 (m, 5H). | Intermediate 01-39<br>25%<br>LC-MS (Analytical Method K, 0-3.00 min 5-95% B): $R_t$ = 1.31 min; MS (ESIpos): m/z = 320 [M + H]⁺. |
| 02-50 | 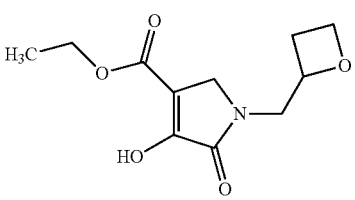<br>ethyl 4-hydroxy-1-{[(±)-oxetan-2-yl]methyl}-5-oxo-2,5-dihydro-1H-pyrrole-3-carboxylate<br>¹H NMR (400 MHz, DMSO) δ [ppm]: 1.20 (t, 3H), 2.38-2.50 (m, 1H), 2.57-2.65 (m, 1H), 3.53-3.57 (m, 1H), 3.67-3.72 (m, 1H), 4.00-4.18 (m, 4H), 4.35-4.40 (m, 1H), 4.47-4.52 (m, 1H), 4.86-4.92 (m, 1H), 11.35 (br, 1H). | CAS-No.: 882402-12-2<br>15%<br>LC-MS (Analytical Method Q, 0-3.00 min 5-95% B): $R_t$ = 0.70 min; MS (ESIpos): m/z = 242 [M + H]⁺. |
| 02-51 | 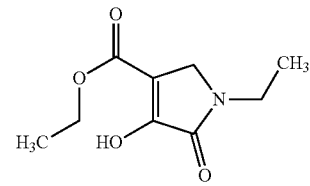<br>ethyl 1-ethyl-4-hydroxy-5-oxo-2,5-dihydro-1H-pyrrole-3-carboxylate<br>¹H NMR (400 MHz, DMSO-d6) δ [ppm]: 1.10 (3H), 1.21 (3H), 3.40 (2H), 3.94 (2H), 4.14 (2H), 8.74 (1H). | CAS-No.: 75-04-7<br>69%<br>LC-MS (Method G): $R_t$ = 0.72 min; MS (ESIpos): m/z = 200 [M + H]⁺ |

|  |  |
|---|---|
| Int. | Structure<br>IUPAC-Name<br>¹H NMR | Synth. from<br>Yield<br>LC-MS |

02-52 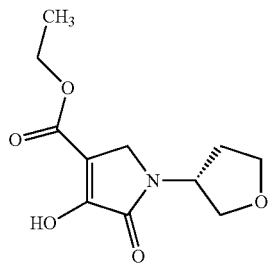

ethyl 4-hydroxy-5-oxo-1-[(3R)-oxolan-3-yl]-2,5-dihydro-1H-pyrrole-3-carboxylate

¹H NMR (250 MHz, DMSO-d6) δ [ppm]: 1.23 (t, 3H), 1.86-2.05 (m, 1H), 2.11-2.29 (m, 1H), 3.63-3.72 (m, 2H), 3.78 (dd, 1H), 3.87-3.97 (m, 1H), 3.98 (s, 2H), 4.17 (q, 2H), 4.58-4.80 (m, 1H), 11.27 (s, 1H).

CAS-No.: 104530-79-2
40%
LC-MS (Analytical Method A):
$R_t$ = 0.85 min; MS (ESIpos):
m/z = 242.0 [M + H]⁺.

02-53 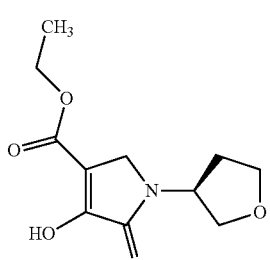

ethyl 4-hydroxy-5-oxo-1-[(3S)-oxolan-3-yl]-2,5-dihydro-1H-pyrrole-3-carboxylate

¹H NMR (500 MHz, DMSO-d6) δ [ppm]: 1.23 (t, 3H), 1.91-2.01 (m, 1H), 2.15-2.26 (m, 1H), 3.62-3.71 (m, 2H), 3.78 (dd, 1H), 3.90-3.97 (m, 1H), 3.98 (s, 2H), 4.17 (q, 2H), 4.66-4.75 (m, 1H), 11.27 (s, 1H).

CAS-No.: 111769-26-7
46%
LC-MS (Analytical Method A):
$R_t$ = 0.81 min; MS (ESIpos):
m/z = 242.0 [M + H]⁺.

02-54 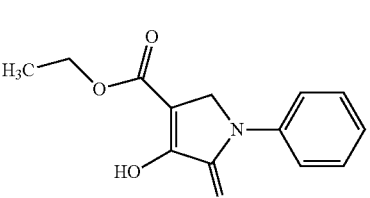

ethyl 4-hydroxy-5-oxo-1-phenyl-2H-pyrrole-3-carboxylate

CAS-No.: 62-53-3

02-55 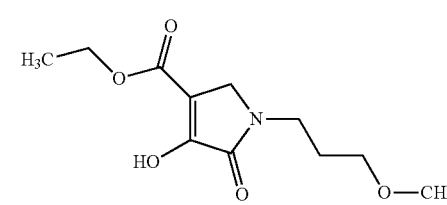

ethyl 4-hydroxy-1-(3-methoxypropyl)-5-oxo-2,5-dihydro-1H-pyrrole-3-carboxylate

¹H NMR (250 MHz, Chloroform-d) δ [ppm]: 1.34 (t, 3H), 1.88 (dt, 2H), 3.32 (s, 3H), 3.39 (t, 2H), 3.58 (t, 2H), 4.00 (s, 2H), 4.32 (q, 2H).

CAS-No.: 5332-73-0
72%
LC-MS (Analytical Method A):
$R_t$ = 0.86 min; MS (ESIpos):
m/z = 243.9 [M + H]⁺.

-continued

| Int. | Structure<br>IUPAC-Name<br>¹H NMR | Synth. from<br>Yield<br>LC-MS |
|---|---|---|
| 02-56 | ethyl 4-hydroxy-1-[(6-methylpyridin-3-yl)methyl]-5-oxo-2,5-dihydro-1H-pyrrole-3-carboxylate hydrochloride (1:1)<br>¹H NMR (250 MHz, DMSO-d6) δ [ppm]: 1.19 (t, 3H), 2.45 (s, 3H), 3.88 (s, 2H), 4.08 (q, 2H), 4.59 (s, 2H), 7.28 (d, 1H), 7.61 (d, 1H), 8.36 (s, 1H). | CAS-No.: 56622-54-9<br>31%<br>LC-MS (Analytical Method A):<br>R$_t$ = 0.45 min; MS (ESIpos):<br>m/z = 277.0 [M + H]+. |

Intermediate 02-57 ethyl 4-hydroxy-5-oxo-2,5-dihydro-1H-pyrrole-3-carboxylate

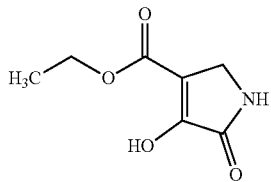

To a solution of ethyl-3-aminopropanoic acid hydrochloride (25.0 g, 0.16 mol) (CAS-No.: 4244-84-2) in ethanol (800 ml) were added diethyl oxalate (23.8 g, 0.163 mol) and sodium ethoxide (freshly prepared, 22.1 g, 0.33 mol) at 0° C. The resulting mixture was stirred at reflux for 2.5 h. After cooled to rt, the solvent was removed in vacuo and the residue was re-dissolved with water (500 ml). Diluted HCl (2 M) was added to adjust the pH value to 6 and the resulting solution was stirred at rt for 30 min. The precipitated solid was collected by filtration and the filter cake was dried in vacuo to give 15 g (44% yield) of the title compound.

LC-MS (Analytical Method L, 0-1.20 min 5-95% B, 1.20-1.70 min 95% B): R$_t$=0.54 min; MS (ESIpos): m/z=172 [M+H]⁺.

Intermediate 02-58 ethyl 4-hydroxy-1-methyl-5-oxo-2,5-dihydro-1H-pyrrole-3-carboxylate

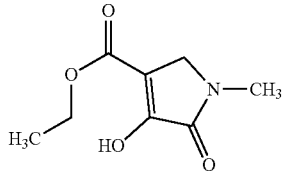

To a solution of methyl N-methyl-beta-alaninate (34 ml, 0.50 M, 17 mmol) in ethanol (2 mL) was added diethyl ethanedioate (2.50 g, 17.1 mmol) and sodium ethoxide (6.4 ml, 21% in ethanol, 17 mmol). The resulting mixture was refluxed at 93° C. under nitrogen for 3h and allowed to cool to room temperature. After evaporation of the solvent, the residue was taken up in dichloromethane/isopropanol 8.2, washed with water (3×), dried and evaporated to yield 438 mg oil containing a mixture of 73% of the target compound and 7% of methyl 4-hydroxy-1-methyl-5-oxo-2,5-dihydro-1H-pyrrole-3-carboxylate as by-product.

LC-MS (Method G): R$_t$=0.63 min; MS (ESIpos): m/z=186 [M+H]⁺; R$_t$=0.50 min; MS (ESIpos): m/z=172 [M+H]⁺

Intermediate 03-01

6-[(±)-butan-2-yl]-2-tert-butyl-6,7-dihydro-4H-pyrazolo[1,5-a]pyrrolo[3,4-d]pyrimidine-5,8-dione

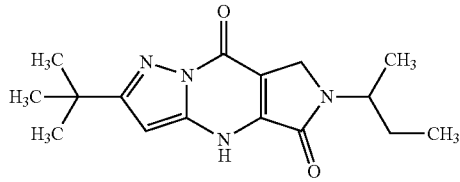

A mixture of ethyl 1-sec-butyl-4-hydroxy-5-oxo-2,5-dihydro-1H-pyrrole-3-carboxylate (700 mg, 81%, 2.5 mmol) (intermediate 02-36) and 3-(tert-butyl)-1H-pyrazol-5-amine (347 mg, 2.5 mmol) (CAS-No.: 82560-12-1) in glacial acetic acid (8 ml) was heated to reflux for 1 h. After this time the reaction mixture was allowed to cool to rt before being concentrated under reduced pressure. The concentrate was triturated with ethanol. The precipitate was isolated by vacuum filtration to afford 0.75 g (96% yield) of the title compound as a yellow powder.

¹H NMR (250 MHz, DMSO-d6) δ[ppm]: 0.81 (t, 3H), 1.22-1.26 (m, 3H), 1.31 (s, 9H), 1.45-1.73 (m, 2H), 4.03-4.33 (m, 3H), 6.08 (s, 1H), 13.13 (s, 1H).

LC-MS (Analytical Method A) R$_t$=1.00 min, MS (ESIpos): m/z=303.40 [M+H]⁺.

In analogy to the procedure described for Intermediate 03-01, the following intermediates were prepared using acetic acid and the appropriate building block and pyrazole starting materials.

| Int. | Structure<br>IUPAC-Name<br>¹H NMR | Synth. from<br>Yield<br>LC-MS |
|---|---|---|
| 03-02 | 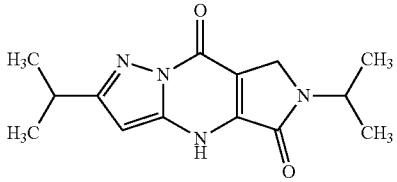<br>2,6-di(propan-2-yl)-6,7-dihydro-4H-pyrazolo[1,5-a]pyrrolo[3,4-d]pyrimidine-5,8-dione<br>¹H NMR (500 MHz, DMSO-d6) δ [ppm] 13.20 (s, 1H), 6.04 (s, 1H), 4.39-4.34 (m, 1H), 4.33 (s, 2H), 3.00 (hept, 1H), 1.26 (d, 6H), 1.25 (d, 6H) | Intermediate 02-01 and CAS No.: 56367-24-9<br>48%<br>LC-MS (Analytical Method A)<br>$R_t$ = 0.89 min, MS (ESIpos):<br>m/z = 275 [M + H]⁺. |
| 03-03 | 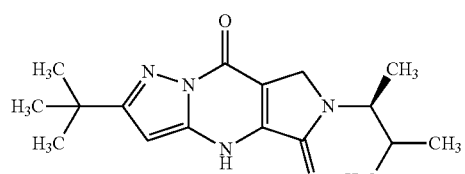<br>2-tert-butyl-6-[(2S)-3-methylbutan-2-yl]-6,7-dihydro-4H-pyrazolo[1,5-a]pyrrolo[3,4-d]pyrimidine-5,8-dione<br>¹H NMR (500 MHz, DMSO-d6) δ [ppm]: 13.24 (s, 1H), 6.09 (s, 1H), 4.34 (d, 1H), 4.24 (d, 1H), 3.93-3.83 (m, 1H), 1.92-1.89 (m, 1H), 1.32 (s, 9H), 1.26 (d, 3H), 0.97 (d, 3H), 0.78 (d, 3H). | Intermediate 02-02 and CAS No.: 82560-12-1<br>51%<br>LC-MS (Analytical Method A)<br>$R_t$ = 1.03 min, MS (ESIpos):<br>m/z = 317 [M + H]⁺. |
| 03-04 | 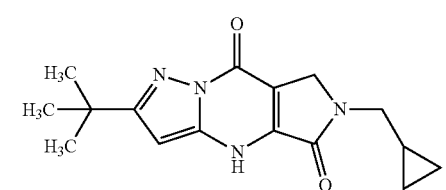<br>2-tert-butyl-6-(cyclopropylmethyl)-6,7-dihydro-4H-pyrazolo[1,5-a]pyrrolo[3,4-d]pyrimidine-5,8-dione<br>¹H NMR (500 MHz, DMSO-d6) δ [ppm]: 13.27 (s, 1H), 6.09 (s, 1H), 4.45 (s, 2H), 3.39 (d, 2H), 1.32 (s, 9H), 1.09 (qq, 1H), 0.60-0.46 (m, 2H), 0.43-0.25 (m, 2H). | Intermediate 02-03 and CAS No.: 82560-12-1<br>59%<br>LC-MS (Analytical Method A)<br>$R_t$ = 0.98 min, MS (ESIpos):<br>m/z = 301 [M + H]⁺. |
| 03-05 | 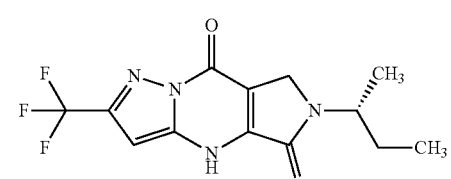<br>6-[(2R)-butan-2-yl]-2-(trifluoromethyl)-6,7-dihydro-4H-pyrazolo[1,5-a]pyrrolo[3,4-d]pyrimidine-5,8-dione<br>¹H NMR (500 MHz, DMSO-d6) δ [ppm]: 6.60 (s, 1H), 4.38 (d, 1H), 4.31 (d, 1H), 4.18-4.11 (m, 1H), 1.74-1.50 (m, 2H), 1.25 (d, 3H), 0.82 (t, 3H). | Intermediate 02-04 and CAS No.: 852443-61-9<br>53%<br>LC-MS (Analytical Method A)<br>$R_t$ = 1.00 min, MS (ESIpos):<br>m/z = 315 [M + H]⁺. |

| Int. | Structure<br>IUPAC-Name<br>¹H NMR | Synth. from<br>Yield<br>LC-MS |
|---|---|---|
| 03-06 | 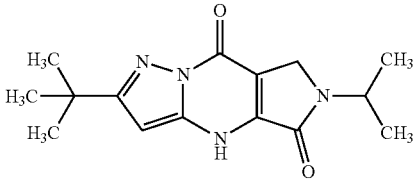<br>2-tert-butyl-6-(propan-2-yl)-6,7-dihydro-4H-pyrazolo[1,5-a]pyrrolo[3,4-d]pyrimidine-5,8-dione<br>¹H NMR (250 MHz, Chloroform-d) δ [ppm] 1.34 (d, 6H), 1.39 (s, 9H), 4.41 (s, 2H), 4.56 (hept, 1H), 6.16 (s, 1H). | Intermediate 02-01 and CAS No.: 82560-12-1<br>63%<br>LC-MS (Analytical Method A)<br>$R_t$ = 0.95 min, MS (ESIpos):<br>m/z = 289.05 [M + H]⁺. |
| 03-07 | 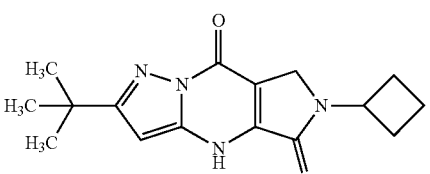<br>2-tert-butyl-6-cyclobutyl-6,7-dihydro-4H-pyrazolo[1,5-a]pyrrolo[3,4-d]pyrimidine-5,8-dione<br>¹H NMR (500 MHz, DMSO-d6) δ [ppm]: 13.22 (s, 1H), 6.07 (s, 1H), 4.67 (p, 1H), 4.46 (s, 2H), 2.44-2.31 (m, 2H), 2.19-2.08 (m, 2H), 1.79-1.65 (m, 2H), 1.31 (s, 9H). | Intermediate 02-05 and CAS No.: 82560-12-1<br>65%<br>LC-MS (Analytical Method A)<br>$R_t$ = 0.98 min, MS (ESIpos):<br>m/z = 301.00 [M + H]⁺. |
| 03-08 | 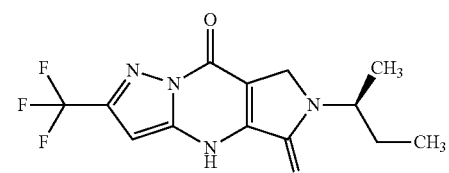<br>6-[(2S)-butan-2-yl]-2-(trifluoromethyl)-6,7-dihydro-4H-pyrazolo[1,5-a]pyrrolo[3,4-d]pyrimidine-5,8-dione<br>¹H NMR (500 MHz, DMSO-d6) δ [ppm]: 13.92 (s, 1H), 6.60 (s, 1H), 4.36 (q, 2H), 4.16 (h, 1H), 1.64 (dtt, 2H), 1.26 (d, 3H), 0.83 (t, 3H). | Intermediate 02-16 and CAS No.: 852443-61-9<br>38%<br>LC-MS (Analytical Method A)<br>$R_t$ = 0.99 min, MS (ESIpos):<br>m/z = 315 [M + H]⁺. |
| 03-09 | 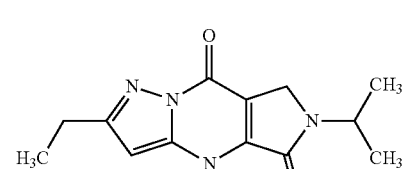<br>2-ethyl-6-(propan-2-yl)-6,7-dihydro-4H-pyrazolo[1,5-a]pyrrolo[3,4-d]pyrimidine-5,8-dione<br>¹H NMR (500 MHz, DMSO-d6) δ [ppm]: 13.24 (s, 1H), 6.06 (s, 1H), 4.41-4.31 (m, 3H), 2.69 (q, 2H), 1.27-1.22 (m, 9H). | Intermediate 02-01 and CAS No.: 1904-24-1<br>68%<br>LC-MS (Analytical Method A)<br>$R_t$ = 0.84 min, MS (ESIpos):<br>m/z = 261 [M + H]⁺. |

|  | Structure<br>IUPAC-Name | Synth. from |
|---|---|---|
| Int. | ¹H NMR | Yield<br>LC-MS |

03-10

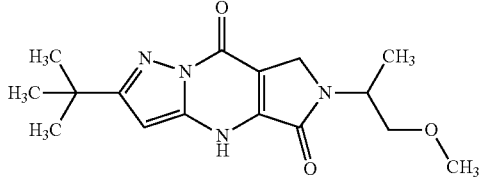

2-tert-butyl-6-[(±)-1-methoxypropan-2-yl]-6,7-dihydro-4H-pyrazolo[1,5-a]pyrrolo[3,4-d]pyrimidine-5,8-dione ¹H NMR (500 MHz, DMSO-d6) δ [ppm]: 13.26 (s, 1H), 6.09 (s, 1H), 4.48-4.39 (m, 1H), 4.39-4.24 (m, 2H), 3.57 (dd, 1H), 3.45 (dd, 1H), 3.27 (s, 3H), 1.32 (s, 9H), 1.22 (d, 3H).

Intermediate 02-09 and CAS No.: 82560-12-1
50%
LC-MS (Analytical Method A)
$R_t$ = 0.94 min, MS (ESIpos):
m/z = 319 [M + H]⁺.

03-11

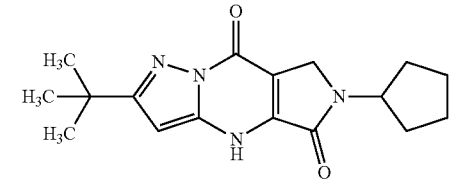

2-tert-butyl-6-cyclopentyl-6,7-dihydro-4H-pyrazolo[1,5-a]pyrrolo[3,4-d]pyrimidine-5,8-dione ¹H NMR (500 MHz, DMSO-d6) δ [ppm]: 13.24 (s, 1H), 6.07 (s, 1H), 4.49 (p, 1H), 4.36 (s, 2H), 1.94-1.85 (m, 2H), 1.79-1.67 (m, 4H), 1.63-1.55 (m, 2H), 1.31 (s, 9H).

Intermediate 02-06 and CAS No.: 82560-12-1
61%
LC-MS (Analytical Method A)
$R_t$ = 1.02 min, MS (ESIpos):
m/z = 315 [M + H]⁺

03-12

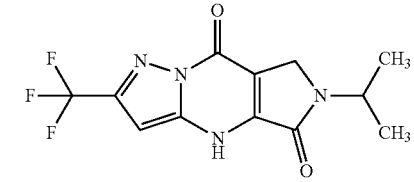

6-(propan-2-yl)-2-(trifluoromethyl)-6,7-dihydro-4H-pyrazolo[1,5-a]pyrrolo[3,4-d]pyrimidine-5,8-dione ¹H NMR (500 MHz, DMSO-d6) δ [ppm]: 13.90 (s, 1H), 6.60 (s, 1H), 4.41 (s, 2H), 4.40-4.33 (m, 1H), 1.27 (d, 6H).

Intermediate 02-01 and CAS No.: 852443-61-9
74%
LC-MS (Analytical Method A)
$R_t$ = 0.94 min, MS (ESIpos):
m/z = 301.0 [M + H]⁺.

03-13

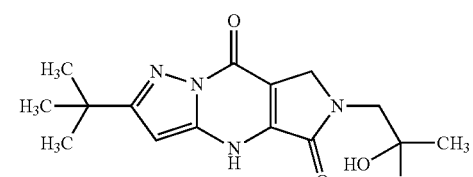

2-tert-butyl-6-(2-hydroxy-2-methylpropyl)-6,7-dihydro-4H-pyrazolo[1,5-a]pyrrolo[3,4-d]pyrimidine-5,8-dione ¹H NMR (500 MHz, DMSO-d6) δ [ppm]: 13.24 (s, 1H), 6.09 (s, 1H), 4.75 (s, 1H), 4.53 (s, 2H), 3.46 (s, 2H), 1.32 (s, 9H), 1.13 (s, 6H).

Intermediate 02-14 and CAS No.: 82560-12-1
30%
LC-MS (Analytical Method A)
$R_t$ = 0.87 min, MS (ESIpos):
m/z = 319 [M + H]⁺.

| Int. | Structure / IUPAC-Name / ¹H NMR | Synth. from / Yield / LC-MS |
|---|---|---|
| 03-14 | 2-tert-butyl-6-(tetrahydro-2H-pyran-4-yl)-6,7-dihydro-4H-pyrazolo[1,5-a]pyrrolo[3,4-d]pyrimidine-5,8-dione<br>¹H NMR (500 MHz, DMSO-d6) δ [ppm]: 13.29 (s, 1H), 6.08 (s, 1H), 4.38 (s, 2H), 4.22 (tt, 1H), 3.95 (dd, 2H), 3.49-3.42 (m, 2H), 1.86 (qd, 2H), 1.76-1.65 (m, 2H), 1.32 (s, 9H). | Intermediate 02-07 and CAS No.: 82560-12-1<br>57%<br>LC-MS (Analytical Method A)<br>R$_t$ = 0.92 min, MS (ESIpos): m/z = 331 [M + H]⁺. |
| 03-15 | 6-[2-(benzyloxy)ethyl]-2-tert-butyl-6,7-dihydro-4H-pyrazolo[1,5-a]pyrrolo[3,4-d]pyrimidine-5,8-dione<br>¹H NMR (500 MHz, DMSO-d6) δ [ppm]: 13.29 (s, 1H), 7.48-7.15 (m, 5H), 6.09 (s, 1H), 4.52 (s, 2H), 4.40 (s, 2H), 3.77-3.73 (m, 2H), 3.72-3.68 (m, 2H), 1.32 (s, 9H) | Intermediate 02-08 and CAS No.: 82560-12-1<br>62%<br>LC-MS (Analytical Method A)<br>R$_t$ = 1.08 min, MS (ESIpos): m/z = 381.5 [M + H]⁺ |
| 03-16 | 2-tert-butyl-6-[(2S)-1-methoxypropan-2-yl]-6,7-dihydro-4H-pyrazolo[1,5-a]pyrrolo[3,4-d]pyrimidine-5,8-dione<br>¹H NMR (250 MHz, DMSO-d6) δ [ppm]: 6.10 (s, 1H), 4.52-4.40 (m, 1H), 4.36 (d, 1H), 4.27 (d, 1H), 3.57 (dd, 2H), 3.27 (s, 3H), 1.31 (s, 9H), 1.22 (d, , 3H). | Intermediate 02-28 and CAS No.: 82560-12-1<br>51%<br>LC-MS (Analytical Method A)<br>R$_t$ = 0.93 min, MS (ESIpos): m/z = 319 [M + H]⁺. |
| 03-17 | 2-bromo-6-[(±)-1-methoxypropan-2-yl]-6,7-dihydro-4H-pyrazolo[1,5-a]pyrrolo[3,4-d]pyrimidine-5,8-dione<br>¹H NMR (500 MHz, DMSO-d6) δ [ppm]: 13.65 (s, 1H), 6.34 (s, 1H), 4.53-4.24 (m, 3H), 3.57 (dd, 1H), 3.45 (dd, 1H), 3.27 (s, 3H), 1.22 (d, 3H). | Intermediate 02-09 and CAS No.: 1203705-55-8<br>55%<br>LC-MS (Analytical Method A)<br>R$_t$ = 0.83 min, MS (ESIpos): m/z = 341/343 [M + H]⁺ |

| Int. | Structure<br>IUPAC-Name<br>¹H NMR | Synth. from<br>Yield<br>LC-MS |
|---|---|---|
| 03-18 | 6-[(2S)-1-methoxypropan-2-yl]-2-(trifluoromethyl)-6,7-dihydro-4H-pyrazolo[1,5-a]pyrrolo[3,4-d]pyrimidine-5,8-dione<br>¹H NMR (250 MHz, DMSO-d6) δ [ppm]: 6.61 (s, 1H), 4.53-4.22 (m, 3H), 3.62-3.55 (m, 2H), 3.27 (s, 3H), 1.23 (d, 3H). | Intermediate 02-28 and CAS No.: 852443-61-9<br>43%<br>LC-MS (Analytical Method A)<br>$R_t$ = 0.93 min, MS (ESIpos):<br>m/z = 331 [M + H]⁺. |
| 03-19 | 2-tert-butyl-6-[2-oxo-2-(pyrrolidin-1-yl)ethyl]-6,7-dihydro-4H-pyrazolo[1,5-a]pyrrolo[3,4-d]pyrimidine-5,8-dione<br>¹H NMR (250 MHz, Methanol-d4) δ [ppm]: 6.24 (s, 1H), 4.50 (m, 2H), 3.58 (m, 2H), 3.47 (m, 2H), 2.05 (m, 2H), 1.98 (m, 2H), 1.90 (m, 2H), 1.41 (s, 9H). | Intermediate 02-10 and CAS No.: 82560-12-1<br>58%<br>LC-MS (Analytical Method A)<br>$R_t$ = 0.89 min, MS (ESIpos):<br>m/z = 358 [M + H]⁺. |
| 03-20 | 6-[(2S)-1-methoxypropan-2-yl]-2-(propan-2-yl)-6,7-dihydro-4H-pyrazolo[1,5-a]pyrrolo[3,4-d]pyrimidine-5,8-dione<br>¹H NMR (250 MHz, DMSO-d6) δ [ppm]: 6.06 (s, 1H), 4.43 (m, 1H), 4.33 (d, 2H), 3.57 (m, 1H), 3.45 (m, 1H), 3.27 (s, 3H), 3.02 (m, 1H), 1.33-1.16 (m, 9H). | Intermediate 02-28 and CAS No.: 56367-24-9<br>55%<br>LC-MS (Analytical Method A)<br>$R_t$ = 0.91 min, MS (ESIpos):<br>m/z = 305 [M + H]⁺. |
| 03-21 | 6-[(2S)-1-methoxypropan-2-yl]-2-(tetrahydro-2H-pyran-4-yl)-6,7-dihydro-4H-pyrazolo[1,5-a]pyrrolo[3,4-d]pyrimidine-5,8-dione<br>¹H NMR (500 MHz, DMSO-d6) δ 6.09 (s, 1H), 4.45-4.24 (m, 3H), 3.94-3.88 (m, 2H), 3.56 (dd, 1H), 3.49-3.41 (m, 3H), 3.26 (s, 3H), 2.96 (tt, 1H), 1.89-1.83 (m, 2H), 1.76-1.65 (m, 2H), 1.22 (d, 3H). | Intermediate 02-28 and Intermediate 01-25<br>81%<br>LC-MS (Analytical Method A)<br>$R_t$ = 0.84 min, MS (ESIpos):<br>m/z = 347 [M + H]⁺. |

-continued

| Int. | Structure<br>IUPAC-Name<br>¹H NMR | Synth. from<br>Yield<br>LC-MS |
|---|---|---|
| 03-22 | 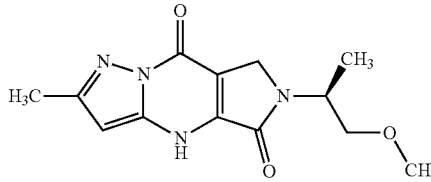<br>6-[(2S)-1-methoxypropan-2-yl]-2-methyl-6,7-dihydro-4H-pyrazolo[1,5-a]pyrrolo[3,4-d]pyrimidine-5,8-dione<br>¹H NMR (250 MHz, DMSO-d6) δ [ppm]: 13.23 (s, 1H), 6.04 (s, 1H), 4.54-4.22 (m, 3H), 3.57 (dd, 1H), 3.44 (dd, 1H), 3.32 (s, 3H), 2.32 (s, 3H), 1.22 (d, 3H). | Intermediate 02-28 and CAS No.: 113402-89-4<br>67%<br>LC-MS (Analytical Method A)<br>$R_t$ = 0.76 min, MS (ESIpos):<br>m/z = 277 [M + H]⁺. |
| 03-23 | 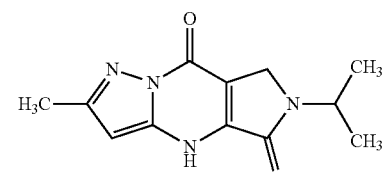<br>2-methyl-6-(propan-2-yl)-6,7-dihydro-4H-pyrazolo[1,5-a]pyrrolo[3,4-d]pyrimidine-5,8-dione<br>¹H NMR (500 MHz, DMSO-d6) δ [ppm] 13.19 (s, 1H), 6.03 (s, 1H), 4.39-4.30 (m, 3H), 2.31 (s, 3H), 1.25 (d, 6H). | Intermediate 02-01 and CAS No.: 113402-89-4<br>54%<br>LC-MS (Analytical Method A)<br>$R_t$ = 0.77 min, MS (ESIpos):<br>m/z = 247 [M + H]⁺. |
| 03-24 | 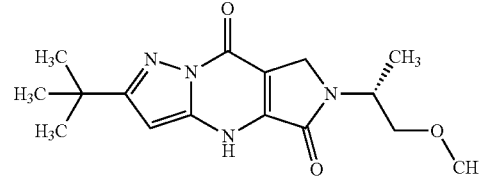<br>2-tert-butyl-6-[(2R)-1-methoxypropan-2-yl]-6,7-dihydro-4H-pyrazolo[1,5-a]pyrrolo[3,4-d]pyrimidine-5,8-dione<br>¹H NMR (500 MHz, DMSO-d6) δ [ppm]: 6.08 (s, 1H), 4.47-4.39 (m, 1H), 4.39-4.24 (m, 2H), 3.56 (dd, 1H), 3.44 (dd, 1H), 3.26 (s, 3H), 1.31 (s, 9H), 1.25-1.19 (m, 3H). | Intermediate 02-15 and CAS No.: 82560-12-1<br>60%<br>LC-MS (Analytical Method A)<br>$R_t$ = 0.96 min, MS (ESIpos):<br>m/z = 319.10 [M + H]⁺. |
| 03-25 | 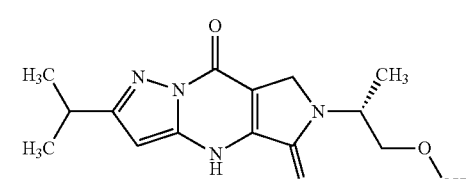<br>6-[(2R)-1-methoxypropan-2-yl]-2-(propan-2-yl)-6,7-dihydro-4H-pyrazolo[1,5-a]pyrrolo[3,4-d]pyrimidine-5,8-dione<br>¹H NMR (500 MHz, Chloroform-d) δ [ppm] 5.97 (s, 1H), 5.30 (s, 2H), 4.58-4.51 (m, 1H), 4.47-4.34 (m, 2H), 3.54-3.43 (m, 2H), 3.33 (s, 3H), 3.22-3.12 (m, 1H), 1.33-1.29 (m, 9H). | Intermediate 02-15 and CAS No.: 56367-24-9<br>95%<br>LC-MS (Analytical Method A)<br>$R_t$ = 0.90 min, MS (ESIpos):<br>m/z = 363.1 [M + H]⁺. |

| Int. | Structure / IUPAC-Name / ¹H NMR | Synth. from / Yield / LC-MS |
|---|---|---|
| 03-26 | 6-(propan-2-yl)-6,7-dihydro-4H-pyrazolo[1,5-a]pyrrolo[3,4-d]pyrimidine-5,8-dione<br>¹H NMR (500 MHz, DMSO-d6) δ [ppm]: 13.39 (s, 1H), 7.94 (d, 1H), 6.21 (d, 1H), 4.42-4.31 (m, 3H), 1.27 (d, 6H). | Intermediate 02-01 and CAS No.: 29212-73-5<br>63%<br>LC-MS (Analytical Method A)<br>$R_t$ = 0.88 min, MS (ESIpos):<br>m/z = 232.9 [M + H]⁺. |
| 03-27 | 2-ethyl-6-[(2S)-1-methoxypropan-2-yl]-6,7-dihydro-4H-pyrazolo[1,5-a]pyrrolo[3,4-d]pyrimidine-5,8-dione<br>¹H NMR (250 MHz, DMSO-d6) δ [ppm]: 6.06 (s, 1H), 4.48-4.38 (m, 1H), 4.33 (d, 2H), 3.63-3.45 (m, 3H), 3.27 (s, 3H), 2.69 (q, 2H), 1.24 (m, 6H). | Intermediate 02-28 and CAS No.: 1904-24-1<br>46%<br>LC-MS (Analytical Method A)<br>$R_t$ = 0.92 min, MS (ESIpos):<br>m/z = 291 [M + H]⁺. |
| 03-28 | 2-tert-butyl-6-(oxetan-3-yl)-6,7-dihydro-4H-pyrazolo[1,5-a]pyrrolo[3,4-d]pyrimidine-5,8-dione<br>¹H NMR (250 MHz, DMSO-d6) δ [ppm]: 13.27 (s, 1H), 6.10 (s, 1H), 5.37 (p, 1H), 4.90 (t, 2H), 4.85-4.73 (m, 2H), 4.68 (s, 2H), 1.32 (s, 9H). | Intermediate 02-11 and CAS No.: 82560-12-1<br>30%<br>LC-MS (Analytical Method A)<br>$R_t$ = 0.85 min, MS (ESIpos):<br>m/z = 303 [M + H]⁺. |
| 03-29 | 2-tert-butyl-6-(2-methoxyethyl)-6,7-dihydro-4H-pyrazolo[1,5-a]pyrrolo[3,4-d]pyrimidine-5,8-dione<br>¹H NMR (500 MHz, DMSO-d6) δ [ppm]: 13.26 (s, 1H), 6.08 (s, 1H), 4.39 (s, 2H), 3.69 (t, 2H), 3.58 (t, 2H), 3.28 (s, 3H), 1.31 (s, 9H). | Intermediate 02-12 and CAS No.: 82560-12-1<br>70%<br>LC-MS (Analytical Method A)<br>$R_t$ = 0.90 min, MS (ESIpos):<br>m/z = 305 [M + H]⁺. |

| Int. | Structure / IUPAC-Name / ¹H NMR | Synth. from / Yield / LC-MS |
|---|---|---|
| 03-30 | 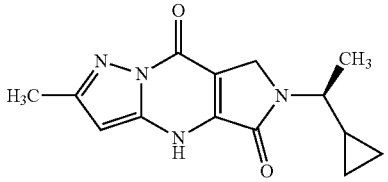<br>6-[(1S)-1-cyclopropylethyl]-2-methyl-6,7-dihydro-4H-pyrazolo[1,5-a]pyrrolo[3,4-d]pyrimidine-5,8-dione<br>¹H NMR (500 MHz, DMSO-d6) δ [ppm]: 13.18 (s, 1H), 6.03 (s, 1H), 4.43 (s, 2H), 3.57-3.48 (m, 1H), 2.31 (s, 3H), 1.30 (d, 3H), 1.23-1.14 (m, 1H), 0.61-0.52 (m, 1H), 0.46-0.35 (m, 2H), 0.29-0.19 (m, 1H). | Intermediate 02-13 and CAS No.: 113402-89-4<br>60%<br>LC-MS (Analytical Method A)<br>$R_t$ = 0.86 min, MS (ESIpos): m/z = 273.0 [M + H]⁺. |
| 03-31 | 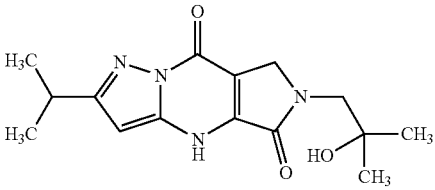<br>6-(2-hydroxy-2-methylpropyl)-2-(propan-2-yl)-6,7-dihydro-4H-pyrazolo[1,5-a]pyrrolo[3,4-d]pyrimidine-5,8-dione<br>¹H NMR (500 MHz, DMSO-d6) δ [ppm]: 13.22 (s, 1H), 6.06 (s, 1H), 4.75 (s, 1H), 4.53 (s, 2H), 3.46 (s, 2H), 3.02 (hept, 1H), 1.27 (d, 6H), 1.13 (s, 6H). | Intermediate 02-14 and CAS No.: 56367-24-9<br>18%<br>LC-MS (Analytical Method A)<br>$R_t$ = 0.87 min, MS (ESIpos): m/z = 305 [M + H]⁺. |
| 03-32 | 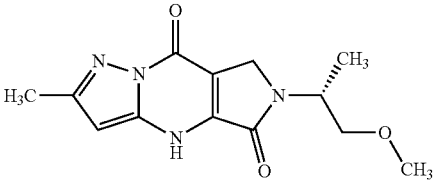<br>6-[(2R)-1-methoxypropan-2-yl]-2-methyl-6,7-dihydro-4H-pyrazolo[1,5-a]pyrrolo[3,4-d]pyrimidine-5,8-dione<br>¹H NMR (500 MHz, DMSO-d6) δ [ppm]: 13.23 (s, 1H), 6.04 (s, 1H), 4.47-4.40 (m, 1H), 4.37 (d, 1H), 4.28 (d, 1H), 3.57 (dd, 1H), 3.45 (dd, 1H), 3.27 (s, 3H), 2.32 (s, 3H), 1.22 (d, 3H). | Intermediate 02-15 and CAS No.: 113402-89-4<br>39%<br>LC-MS (Analytical Method A)<br>$R_t$ = 0.76 min, MS (ESIpos): m/z = 277.0 [M + H]⁺ |
| 03-33 | 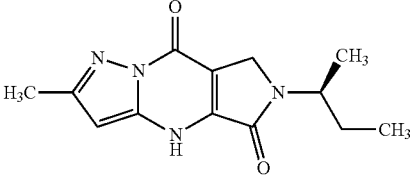<br>6-[(2S)-butan-2-yl]-2-methyl-6,7-dihydro-4H-pyrazolo[1,5-a]pyrrolo[3,4-d]pyrimidine-5,8-dione<br>¹H NMR (250 MHz, DMSO-d6) δ [ppm]: 13.19 (s, 1H), 6.04 (s, 1H), 4.39-4.19 (m, 2H), 4.13 (m, 1H), 2.32 (s, 3H), 1.61 (m, 2H), 1.24 (d, 3H), 0.82 (t, 3H). | Intermediate 02-16 and CAS No.: 113402-89-4<br>49%<br>LC-MS (Analytical Method A)<br>$R_t$ = 0.98 min, MS (ESIpos): m/z = 261 [M + H]⁺. |

| Int. | Structure<br>IUPAC-Name<br>¹H NMR | Synth. from<br>Yield<br>LC-MS |
|---|---|---|
| 03-34 | 2-tert-butyl-6-[(2S)-2-hydroxypropyl]-6,7-dihydro-4H-pyrazolo[1,5-a]pyrrolo[3,4-d]pyrimidine-5,8-dione<br>¹H NMR (500 MHz, DMSO-d6) δ [ppm]: 13.20 (s, 1H), 6.08 (s, 1H), 4.96-4.85 (m, 1H), 4.43 (s, 2H), 4.00-3.89 (m, 1H), 3.50-3.39 (m, 2H), 1.31 (s, 9H), 1.08 (d, 3H). | Intermediate 02-17 and CAS No.: 82560-12-1<br>31%<br>LC-MS (Analytical Method A)<br>$R_t$ = 0.97 min, MS (ESIpos):<br>m/z = 305 [M + H]⁺. |
| 03-35 | 6-[(1R)-1-cyclopropylethyl]-2-methyl-6,7-dihydro-4H-pyrazolo[1,5-a]pyrrolo[3,4-d]pyrimidine-5,8-dione<br>¹H NMR (250 MHz, DMSO-d6) δ [ppm]: 12.95 (s, 1H), 5.80 (s, 1H), 4.21 (s, 2H), 3.38-3.20 (m, 1H), 2.08 (s, 3H), 1.07 (d, 3H), 1.01-0.86 (m, 1H), 0.33 (m, 1H), 0.17 (m, 2H), 0.03 (m, 1H). | Intermediate 02-18 and CAS No.: 113402-89-4<br>53%<br>LC-MS (Analytical Method A)<br>$R_t$ = 0.98 min, MS (ESIpos):<br>m/z = 273 [M + H]⁺. |
| 03-36 | 2-cyclopropyl-6-(propan-2-yl)-6,7-dihydro-4H-pyrazolo[1,5-a]pyrrolo[3,4-d]pyrimidine-5,8-dione<br>¹H-NMR (400 MHz, DMSO-d6): δ [ppm]: 0.80-0.83 (m, 2H), 0.89-0.91 (m, 2H), 1.20 (d, 6H), 1.90-1.96 (m, 1H), 4.10 (s, 2H), 4.33-4.40 (m, 1H), 5.73 (s, 1H), 7.20 (br, 1H). | Intermediate 02-01 and CAS No.: 175137-46-9<br>43%<br>LC-MS (Analytical Method K, 0-2.5 min 5-30% B, 2.5-3.2 min 30-95% B, 3.2-4.2 min 95% B):<br>$R_t$ = 0.70 min; MS (ESIpos):<br>m/z = 273 [M + H]⁺. |
| 03-37 | ethyl 5,8-dioxo-6-(propan-2-yl)-5,6,7,8-tetrahydro-4H-pyrazolo[1,5-a]pyrrolo[3,4-d]pyrimidine-2-carboxylate<br>¹H-NMR (300 MHz, CD₃OD): δ [ppm] = 1.34 (d, 6H), 1.41 (t, 3H), 4.34-4.40 (m, 4H), 4.51-4.57 (m, 1H), 6.76 (s, 1H). | Intermediate 02-01 and CAS No.: 105434-90-0<br>79%<br>LC-MS (Analytical Method L, 0-1-1 min 10-100% B, 1.1-1.7 min 100% B): $R_t$ = 0.71 min; MS (ESIpos): m/z = 305 [M + H]⁺. |

| Int. | Structure<br>IUPAC-Name<br>¹H NMR | Synth. from<br>Yield<br>LC-MS |
|---|---|---|
| 03-38 | 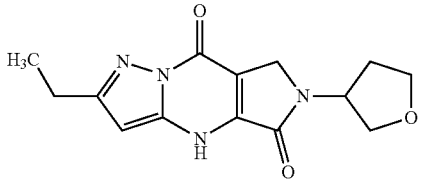<br>2-ethyl-6-[(±)-tetrahydrofuran-3-yl]-6,7-dihydro-4H-pyrazolo[1,5-a]pyrrolo[3,4-d]pyrimidine-5,8-dione<br>¹H-NMR (400 MHz, DMSO-d6): δ [ppm]: 1.21 (t, 3H), 2.01-2.12 (m, 1H), 2.23-2.31 (m, 1H), 2.66-2.71 (m, 2H), 3.68-3.77 (m, 2H), 3.85-3.88 (m, 1H), 3.97-4.03 (m, 1H), 4.33-4.43 (m, 2H), 4.82-4.87 (m, 1H), 6.06 (s, 1H), 13.28 (br, 1H). | Intermediate 02-19 and CAS No.: 1904-24-1<br>2%<br>LC-MS (Analytical Method K, 0-2.0 min 5-95% B, 2.0-2.7 min 95% B): R$_t$ = 0.73 min; MS (ESIpos): m/z = 289 [M + H]⁺ |
| 03-39 | 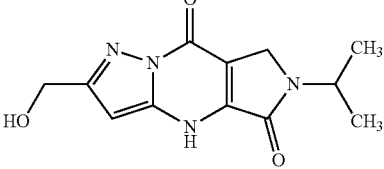<br>2-(hydroxymethyl)-6-(propan-2-yl)-6,7-dihydro-4H-pyrazolo[1,5-a]pyrrolo[3,4-d]pyrimidine-5,8-dione<br>¹H-NMR (400 MHz, CD3OD): δ [ppm]: 1.25 (d, 6H), 4.36 (s, 2H), 4.53-4.60 (m, 1H), 4.74 (s, 2H), 6.35 (s,1H). | Intermediate 02-01 and Intermediate 01-14<br>98%<br>LC-MS (Analytical Method K, 0-2.0 min 5-95% B, 2.0-2.7 min 95% B): R$_t$ = 0.64 min; MS (ESIpos): m/z = 263 [M + H]⁺. |
| 03-40 | 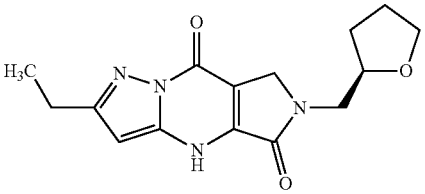<br>2-ethyl-6-[(2R)-tetrahydrofuran-2-ylmethyl]-6,7-dihydro-4H-pyrazolo[1,5-a]pyrrolo[3,4-d]pyrimidine-5,8-dione<br>¹H-NMR (400 MHz, CD3OD): δ [ppm]: 1.31 (t, 3H), 1.63-1.70 (m, 1H), 1.91-1.97 (m, 2H), 2.03-2.09 (m, 1H), 2.80 (q, 2H), 3.58-3.63 (m, 1H), 3.73-3.79 (m, 2H), 3.88-3.93 (m, 1H), 4.14-4.19 (m, 1H), 4.46-4.60 (m, 2H), 6.16 (s, 1H). | Intermediate 02-20 and CAS No.: 1904-24-1<br>1%<br>LC-MS (Analytical Method K, 0-2.0 min 5-95% B, 2.0-2.7 min 95% B): R$_t$= 0.82 min; MS (ESIpos): m/z = 303 [M + H]⁺. |
| 03-41 | 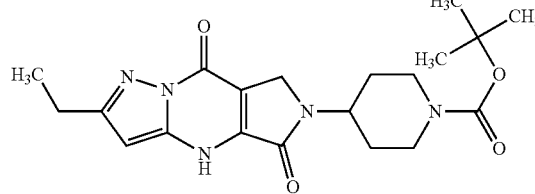<br>tert-butyl 4-(2-ethyl-5,8-dioxo-5,8-dihydro-4H-pyrazolo[1,5-a]pyrrolo[3,4-d]pyrimidin-6(7H)-yl)piperidine-1-carboxylate<br>¹H-NMR (400 MHz, CD3OD): δ [ppm]: 1.33 (t, 3H), 1.48 (s, 9H), 1.79-1.83 (m, 2H), 1.85-1.91 (m, 2H), 2.80 (q, 2H), 2.85-2.98 (m, 2H), 4.24-4.29 (m, 3H), 4.44 (s, 2H), 6.19 (s, 1H). | Intermediate 02-21<br>69%<br>LC-MS (Analytical Method K, 0-1.25 min 10-95% B, 1.25-1.75 min 95% B): R$_t$ = 0.73 min; MS (ESIpos): m/z = 402 [M + H]⁺ |

| Int. | Structure<br>IUPAC-Name<br>¹H NMR | Synth. from<br>Yield<br>LC-MS |
|---|---|---|
| 03-42 | 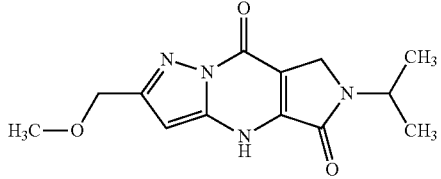<br>2-(methoxymethyl)-6-(propan-2-yl)-6,7-dihydro-4H-pyrazolo[1,5-a]pyrrolo[3,4-d]pyrimidine-5,8-dione<br>¹H-NMR (400 MHz, DMSO-d₆): δ [ppm]: 1.33 (d, 6H), 3.40 (s, 3H), 4.36 (s, 2H), 4.52-4.55 (m, 1H), 4.58 (s, 2H), 6.30 (s, 1H). | Intermediate 02-01 and Intermediate 01-12<br>21%<br>LC-MS (Analytical Method K, 0-1.2 min 5-95% B, 1.2-1.7 min 95% B): $R_t$ = 0.75 min; MS (ESIpos): m/z = 277 [M + H]⁺. |
| 03-43 | 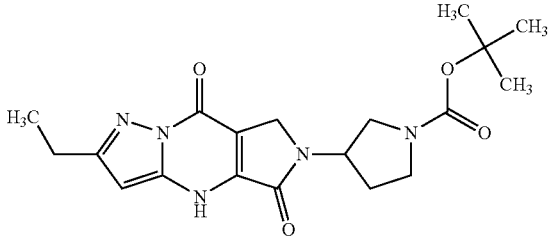<br>tert-butyl (±)-3-(2-ethyl-5,8-dioxo-5,8-dihydro-4H-pyrazolo[1,5-a]pyrrolo[3,4-d]pyrimidin-6(7H)-yl)pyrrolidine-1-carboxylate<br>¹H-NMR (300 MHz, DMSO-d6) δ [ppm]: 1.23 (t, 3H), 1.42 (s, 9H), 2.13-2.15 (m, 2H), 2.65 (q, 2H), 3.31-3.36 (m, 2H), 3.43-3.55 (m, 2H), 4.22-4.28 (m, 2H), 4.64-4.73 (m, 1H), 5.91 (s, 1H), 7.35 (br, 1H). | Intermediate 02-22 and CAS No.: 1904-24-1<br>66%<br>LC-MS (Analytical Method K, 0-2.0 min 5-95% B, 2.0-2.7 min 95% B): $R_t$ = 1.41 min; MS (ESIpos): m/z = 388 [M + H]⁺ |
| 03-44 | 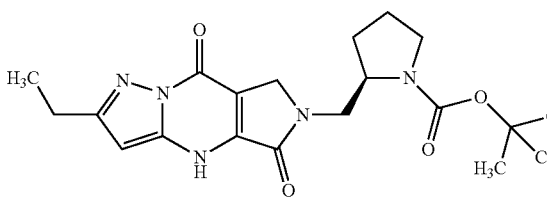<br>tert-butyl (2R)-2-[(2-ethyl-5,8-dioxo-5,8-dihydro-4H-pyrazolo[1,5-a]pyrrolo[3,4-d]pyrimidin-6(7H)-yl)methyl]pyrrolidine-1-carboxylate<br>¹H-NMR (400 MHz, CD3OD) δ [ppm]: 1.25-1.40 (m, 12H), 1.86-2.03 (m, 4H), 2.78 (q, 2H), 3.38-3.40 (m, 2H), 3.56-3.80 (m, 2H), 4.15-4.25 (m, 1H), 4.37-4.62 (m, 2H), 6.17 (s, 1H). | Intermediate 02-23 and CAS No.: 1904-24-1<br>38%<br>LC-MS (Analytical Method K, 0-1.1 min 5-100% B, 1.1-1.8 min 100% B): $R_t$ = 2.53 min; MS (ESIpos): m/z = 402 [M + H]⁺ |
| 03-45 | 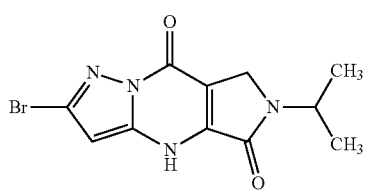<br>2-bromo-6-(propan-2-yl)-6,7-dihydro-4H-pyrazolo[1,5-a]pyrrolo[3,4-d]pyrimidine-5,8-dione<br>¹H NMR (400 MHz, DMSO-d6) δ [ppm]: 1.25 (d, 6H), 4.31-4.39 (m, 3H), 6.32 (s, 1H), 13.64 (br s, 1H). | Intermediate 02-01 and CAS No.: 1203705-55-8<br>71%<br>LC-MS (Analytical Method G): $R_t$ = 0.72 min; MS (ESIpos): m/z = 311 [M + H]⁺. |

| Int. | Structure<br>IUPAC-Name<br>¹H NMR | Synth. from<br>Yield<br>LC-MS |
|---|---|---|
| 03-46 | tert-butyl (±)-3-[(2-ethyl-5,8-dioxo-5,8-dihydro-4H-pyrazolo[1,5-a]pyrrolo[3,4-d]pyrimidin-6(7H)-yl)methyl]pyrrolidine-1-carboxylate<br>¹H-NMR (400 MHz, CD3OD) δ [ppm]: 1.21 (t, 3H), 1.35 (s, 9H), 1.61-1.63 (m, 1H), 1.93-1.95 (m, 1H), 2.57-2.60 (m, 1H), 2.68 (q, 2H), 3.00-3.02 (m, 1H), 3.20-3.24 (m, 1H), 3.38-3.41 (m, 2H), 3.53-3.55 (m, 2H), 4.35 (s, 2H), 6.06 (s, 1H). | Intermediate 02-29 and CAS No.: 1904-24-1<br>1%<br>LC-MS (Analytical Method K, 0-2.0 min 5-95% B, 2.0-2.6 min 95% B): $R_t$ = 1.22 min; MS (ESIpos): m/z = 402 [M + H]⁺. |
| 03-47 | 2-ethyl-6-[(±)-tetrahydrofuran-3-ylmethyl]-6,7-dihydro-4H-pyrazolo[1,5-a]pyrrolo[3,4-d]pyrimidine-5,8-dione<br>¹H-NMR (400 MHz, DMSO-d6): δ [ppm]: 1.19-1.26 (m, 3H), 1.53-1.62 (m, 1H), 1.96-2.00 (m, 1H), 2.62-2.70 (m, 3H), 3.32-3.33 (m, 1H), 3.42-3.45 (m, 1H), 3.50-3.52 (m, 1H), 3.56-3.60 (m, 1H), 3.62-3.69 (m, 2H), 4.30-4.39 (m, 2H), 6.01 (s, 1H), 7.13 (s, 1H). | Intermediate 02-24 and CAS No.: 1904-24-1<br>81%<br>LC-MS (Analytical Method K, 0-1.2 min 10-95% B, 1.2-1.7 min 95% B): $R_t$ = 0.76 min; MS (ESIpos): m/z = 303 [M + H]⁺. |
| 03-48 | 2-ethyl-6-[(±)-tetrahydrofuran-2-ylmethyl]-6,7-dihydro-4H-pyrazolo[1,5-a]pyrrolo[3,4-d]pyrimidine-5,8-dione<br>¹H-NMR (400 MHz, CD3OD) δ [ppm]: 1.31 (t, 3H), 1.61-1.69 (m, 1H), 1.89-1.97 (m, 2H), 2.03-2.11 (m, 1H), 2.82 (q, 2H), 3.58-3.63 (m, 1H), 3.73-3.79 (m, 2H), 3.88-3.93 (m, 1H), 4.14-4.20 (m, 1H), 4.46-4.59 (m, 2H), 6.16 (s, 1H). | Intermediate 02-25 and CAS No.: 1904-24-1<br>1%<br>LC-MS (Analytical Method K, 0-2.0 min 5-100% B, 2.0-2.8 min 100% B): $R_t$ = 1.09 min; MS (ESIpos): m/z = 303 [M + H]⁺ |
| 03-49 | 2-(2-methylpropyl)-6-(propan-2-yl)-6,7-dihydro-4H-pyrazolo[1,5-a]pyrrolo[3,4-d]pyrimidine-5,8-dione<br>¹H NMR (400 MHz, DMSO-d6) δ [ppm]: 0.91 (d, 6H), 1.24 (d, 6H), 1.91-2.03 (m, 1H), 2.52-2.55 (m, 1H), 4.30-4.40 (m, 3H), 6.02 (s, 1H), 13.27 (br s, 1H). | Intermediate 02-01 and CAS No.: 1000896-88-7<br>63%<br>LC-MS (Analytical Method G): $R_t$ = 0.87 min; MS (ESIpos): m/z = 289 [M + H]⁺. |

| Int. | Structure / IUPAC-Name / ¹H NMR | Synth. from / Yield / LC-MS |
|---|---|---|
| 03-50 | 2-ethyl-6-(tetrahydro-2H-pyran-4-ylmethyl)-6,7-dihydro-4H-pyrazolo[1,5-a]pyrrolo[3,4-d]pyrimidine-5,8-dione<br>¹H NMR (500 MHz, Chloroform-d) δ [ppm]: 11.42 (s, 1H), 6.12 (s, 1H), 4.49 (s, 2H), 4.04-3.95 (m, 2H), 3.58 (d, 2H), 3.39 (td, 2H), 2.85 (q, 2H), 2.12-1.99 (m, 1H), 1.62 (s, 2H), 1.45 (qd, 2H), 1.34 (t, 3H). | Intermediate 02-31 and CAS No.: 1904-24-1<br>47%<br>LC-MS (Analytical Method A)<br>$R_t$ = 0.80 min, MS (ESIpos):<br>m/z = 317 [M + H]⁺. |
| 03-51 | 2-cyclohexyl-6-(propan-2-yl)-6,7-dihydro-4H-pyrazolo[1,5-a]pyrrolo[3,4-d]pyrimidine-5,8-dione?<br>¹H NMR (400 MHz, DMSO-d6) δ [ppm]: 1.24 (d, 6H), 1.30-1.51 (m, 4H), 1.64-1.80 (m, 4H), 1.89-1.97 (m, 2H), 2.62-2.76 (m, 1H), 4.29-4.38 (m, 3H), 6.03 (s, 1H), 13.28 (br s, 1H). | Intermediate 02-01 and Intermediate 01-17<br>73%<br>LC-MS (Analytical Method G):<br>$R_t$ = 0.98 min; MS (ESIpos):<br>m/z = 315 [M + H]⁺ |
| 03-52 | tert-butyl (±)-2-[(2-ethyl-5,8-dioxo-5,8-dihydro-4H-pyrazolo[1,5-a]pyrrolo[3,4-d]pyrimidin-6(7H)-yl)methyl]pyrrolidine-1-carboxylate<br>¹H NMR (400 MHz, CD3OD) δ [ppm]: 1.28-1.40 (m, 12H), 1.83-2.05 (m, 4H), 2.80 (q, 2H), 3.40-3.42 (m, 2H), 3.57-3.82 (m, 2H), 4.18-4.25 (m, 1H), 4.39-4.64 (m, 2H), 6.18-6.19 (m, 1H). | Intermediate 02-30 and CAS No.: 1904-24-1<br>1%<br>LC-MS (Analytical Method K, 0-3.5 min 5-50% B, 3.5-4.2 min 50-95% B, 4.2-4.7 min 95% B):<br>$R_t$ = 2.51 min; MS (ESIpos):<br>m/z = 402 [M + H]⁺ |
| 03-53 | tert-butyl (2S)-2-[(2-ethyl-5,8-dioxo-5,8-dihydro-4H-pyrazolo[1,5-a]pyrrolo[3,4-d]pyrimidin-6(7H)-yl)methyl]morpholine-4-carboxylate<br>¹H NMR (500 MHz, DMSO-d6) δ [ppm]: 13.30 (s, 1H), 6.06 (s, 1H), 4.50-4.36 (m, 2H), 3.88-3.75 (m, 2H), 3.73-3.63 (m, 3H), 3.63-3.56 (m, 1H), 3.44-3.37 (m, 1H), 2.90 (s, 1H), 2.76-2.61 (m, 3H), 1.41 (s, 9H), 1.24 (t, 3H). | Intermediate 02-26 and CAS No.: 1904-24-1<br>50%<br>LC-MS (Analytical Method A)<br>$R_t$ = 0.98 min, MS (ESIpos):<br>m/z = 418.15 [M + H]⁺. |

| Int. | Structure<br>IUPAC-Name<br>¹H NMR | Synth. from<br>Yield<br>LC-MS |
|---|---|---|
| 03-54 | 2-ethyl-6-(1-methylpiperidin-4-yl)-6,7-dihydro-4H-pyrazolo[1,5-a]pyrrolo[3,4-d]pyrimidine-5,8-dione | Intermediate 02-27 and CAS No.: 1904-24-1<br>1%<br>LC-MS (Analytical Method H):<br>R$_t$ = 0.47 min; MS (ESIpos):<br>m/z = 316 [M + H]⁺. |
| 03-55 | tert-butyl (2R)-2-[(2-ethyl-5,8-dioxo-5,8-dihydro-4H-pyrazolo[1,5-a]pyrrolo[3,4-d]pyrimidin-6(7H)-yl)methyl]morpholine-4-carboxylate<br>¹H NMR (500 MHz, Chloroform-d) δ [ppm]: 1.33 (t, 3H), 1.46 (s, 9H), 2.57-2.77 (m, 1H), 2.84 (q, 2H), 2.88-3.04 (m, 1H), 3.48 (td, 1H), 3.63 (dd, 1H), 3.67-3.74 (m, 1H), 3.76-4.25 (m, 4H), 4.57 (d, 1H), 4.67 (d, 1H), 6.11 (s, 1H). | Intermediate 02-32 and CAS No.: 1904-24-1<br>28%<br>LC-MS (Analytical Method A)<br>R$_t$ = 0.97 min, MS (ESIpos):<br>m/z = 418 [M + H]⁺. |
| 03-56 | tert-butyl 4-[(2-ethyl-5,8-dioxo-5,8-dihydro-4H-pyrazolo[1,5-a]pyrrolo[3,4-d]pyrimidin-6(7H)-yl)methyl]piperidine-1-carboxylate | Intermediate 02-33 and CAS No.: 1904-24-1<br>2%<br>LC-MS (Analytical Method K, 0-1.1 min 10-100% B, 1.1-1.7 min 100% B): R$_t$ = 0.87 min; MS (ESIpos): m/z = 416 [M + H]⁺. |
| 03-57 | 2-ethyl-6-(tetrahydro-2H-pyran-4-yl)-6,7-dihydro-4H-pyrazolo[1,5-a]pyrrolo[3,4-d]pyrimidine-5,8-dione<br>¹H NMR (400 MHz, DMSO-d6) δ [ppm]: 1.23 (t, 3H), 1.70 (br dd, 2H), 1.85 (qd, 2H), 2.68 (q, 2H), 3.40-3.48 (m, 2H), 3.94 (dd, 2H), 4.21 (tt, 1H), 4.38 (s, 2H), 6.06 (s, 1H), 13.34 (br s, 1H). | Intermediate 02-07 and CAS No.: 1904-24-1<br>59%<br>LC-MS (Analytical Method G):<br>R$_t$ = 0.67 min; MS (ESIpos):<br>m/z = 303 [M + H]⁺. |

| Int. | Structure<br>IUPAC-Name<br>¹H NMR | Synth. from<br>Yield<br>LC-MS |
|---|---|---|
| 03-58 | 2-ethyl-6,7-dihydro-4H-pyrazolo[1,5-a]pyrrolo[3,4-d]pyrimidine-5,8-dione<br>¹H NMR (500 MHz, DMSO-d6) δ [ppm] 1.24 (t, 3H), 2.69 (q, 2H), 4.25 (s, 2H), 6.05 (s, 1H), 9.26 (s, 1H), 13.09 (s, 1H). | Intermediate 02-57 and CAS No.: 1904-24-1<br>55%<br>LC-MS (Analytical Method A):<br>R_t = 0.64 mins, MS (ESIPos):<br>m/z = 218.95 [M + H]⁺ |
| 03-59 | tert-butyl (3R)-3-[(2-ethyl-5,8-dioxo-5,8-dihydro-4H-pyrazolo[1,5-a]pyrrolo[3,4-d]pyrimidin-6(7H)-yl)methyl]morpholine-4-carboxylate<br>¹H NMR (500 MHz, Chloroform-d) δ [ppm]: 1.24-1.41 (m, 12H), 2.87 (q, 2H), 3.46-4.01 (m, 7H), 4.19-4.88 (m, 4H), 6.20 (s, 1H), 11.40 (s, 1H). | Intermediate 02-34 and CAS No.: 1904-24-1<br>4%<br>LC-MS (Analytical Method A)<br>R_t = 0.93 min, MS (ESIPos):<br>m/z = 418.05 [M + H]⁺ |
| 03-60 | ethyl 6-[(2S)-1-methoxypropan-2-yl]-5,8-dioxo-5,6,7,8-tetrahydro-4H-pyrazolo[1,5-a]pyrrolo[3,4-d]pyrimidine-2-carboxylate<br>¹H NMR (500 MHz, Chloroform-d) δ [ppm]: 1.40 (d, 3H), 1.42 (t, 3H), 3.36 (s, 3H), 3.59 (d, 2H), 4.46 (q, 2H), 4.52 (d, 1H), 4.59 (d, 1H), 4.66-4.75 (m, 1H), 6.84 (s, 1H). | Intermediate 02-28 and CAS No.: 105434-90-0<br>45%<br>LC-MS (Analytical Method A)<br>R_t = 0.86 min, MS (ESIpos):<br>m/z = 335 [M + H]⁺. |
| 03-61 | 6-cyclopentyl-2-(2-methylpropyl)-6,7-dihydro-4H-pyrazolo[1,5-a]pyrrolo[3,4-d]pyrimidine-5,8-dione<br>¹H NMR (400 MHz, DMSO-d6) δ [ppm]: 0.91 (d, 6H), 1.54-1.64 (m, 2H), 1.64-1.81 (m, 4H), 1.85-1.93 (m, 2H), 1.98 (dt, 1H), 2.52-2.55 (m, 3H), 4.36 (s, 2H), 4.45-4.54 (m, 1H), 6.02 (s, 1H). | Intermediate 02-06 and CAS No.: 1000896-88-7<br>23%<br>LC-MS (Analytical Method G):<br>R_t = 0.96 min; MS (ESIpos):<br>m/z = 315 [M + H]⁺. |

| Int. | Structure<br>IUPAC-Name<br>¹H NMR | Synth. from<br>Yield<br>LC-MS |
|---|---|---|
| 03-62 | 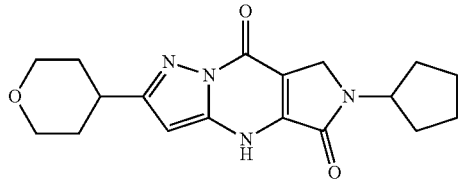<br>6-cyclopentyl-2-(tetrahydro-2H-pyran-4-yl)-6,7-dihydro-4H-pyrazolo[1,5-a]pyrrolo[3,4-d]pyrimidine-5,8-dione<br>¹H NMR (400 MHz, DMSO-d6) δ [ppm]: 1.55-1.79 (m, 8H), 1.83-1.93 (m, 4H), 2.95 (tt, 1H), 3.45 (td, 2H), 3.92 (dt, 2H), 4.36 (s, 2H), 4.49 (quin, 1H), 6.08 (s, 1H), 13.29 (br s, 1H). | Intermediate 02-06 and Intermediate 01-20<br>11%<br>LC-MS (Analytical Method G):<br>$R_t$ = 0.80 min; MS (ESIpos):<br>m/z = 343 [M + H]⁺. |
| 03-63 | 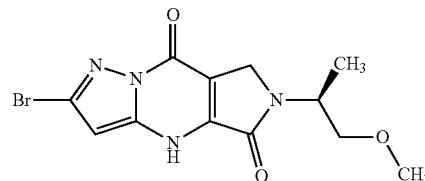<br>2-bromo-6-[(2S)-1-methoxypropan-2-yl]-6,7-dihydro-4H-pyrazolo[1,5-a]pyrrolo[3,4-d]pyrimidine-5,8-dione<br>¹H NMR (500 MHz, DMSO-d6) δ [ppm]: 1.22 (d, 3H), 3.27 (s, 3H), 3.44 (dd, 1H), 3.57 (dd, 1H), 4.28-4.48 (m, 3H), 6.34 (s, 1H), 13.66 (s, 1H). | Intermediate 02-28 and CAS No.: 1203705-55-8<br>67%<br>LC-MS (Analytical Method B):<br>$R_t$ = 0.84 min; MS (ESIpos):<br>m/z = 340.8 [M + H]⁺. |
| 03-64 | 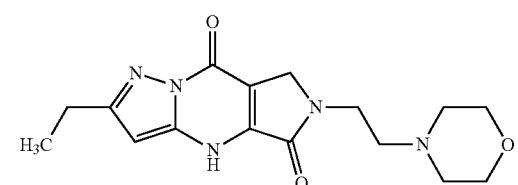<br>2-ethyl-6-[2-(morpholin-4-yl)ethyl]-6,7-dihydro-4H-pyrazolo[1,5-a]pyrrolo[3,4-d]pyrimidine-5,8-dione<br>¹H NMR (400 MHz, DMSO-d6) δ [ppm]: 1.23 (t, 3H), 1.89-1.92 (m, 4H), 2.68 (q, 2H), 3.43 (br s, 4H), 3.76 (t, 2H), 3.94 (t, 2H), 4.45 (s, 2H), 6.08 (s, 1H). | Intermediate 02-35 and CAS No.: 1904-24-1<br>70%<br>LC-MS (Analytical Method G):<br>$R_t$ = 0.46 min; MS (ESIpos):<br>m/z = 332 [M + H]⁺. |
| 03-65 | 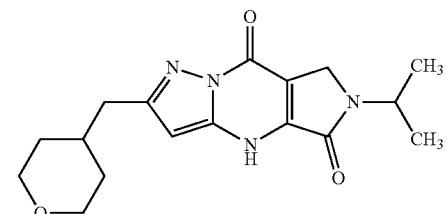<br>6-(propan-2-yl)-2-(tetrahydro-2H-pyran-4-ylmethyl)-6,7-dihydro-4H-pyrazolo[1,5-a]pyrrolo[3,4-d]pyrimidine-5,8-dione<br>¹H NMR (250 MHz, DMSO-d6) δ [ppm] 1.02-1.39 (m, 8H), 1.47-1.65 (m, 2H), 1.76-2.01 (m, 1H), 2.57 (d, 2H), 3.22 (s, 2H), 3.76-3.88 (m, 2H), 4.20 (s, 2H), 4.28-4.45 (m, 1H), 5.93 (s, 1H). | Intermediate 02-01 and Intermediate 01-26<br>46%<br>LC-MS (Analytical Method B):<br>$R_t$ = 0.87 min; MS (ESIpos):<br>m/z = 331 [M + H]⁺ |

-continued

| Int. | Structure<br>IUPAC-Name<br>¹H NMR | Synth. from<br>Yield<br>LC-MS |
|---|---|---|
| 03-66 | 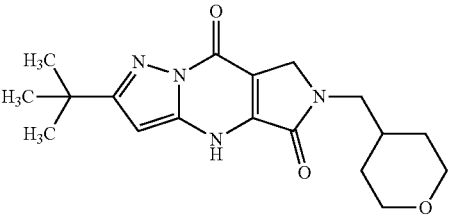<br>2-tert-butyl-6-(tetrahydro-2H-pyran-4-ylmethyl)-6,7-dihydro-4H-pyrazolo[1,5-a]pyrrolo[3,4-d]pyrimidine-5,8-dione<br>¹H NMR (500 MHz, DMSO-d6) δ [ppm]: 6.09 (s, 1H), 4.38 (s, 2H), 3.87-3.80 (m, 2H), 3.42 (d, 2H), 3.28 (td, 3H), 1.58-1.50 (m, 2H), 1.31 (s, 9H), 1.27-1.15 (m, 3H). | Intermediate 02-31 and CAS No.: 82560-12-1<br>63%<br>LC-MS (Analytical Method A): $R_t$ = 0.90 min; MS (ESIpos): m/z = 345 [M + H]⁺. |
| 03-67 | 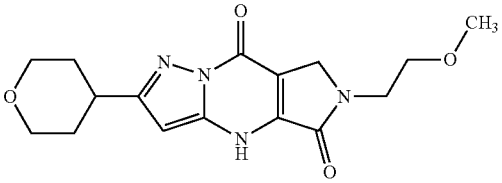<br>6-(2-methoxyethyl)-2-(oxan-4-yl)-6,7-dihydro-4H-pyrazolo[1,5-a]pyrrolo[3,4-d]pyrimidine-5,8-dione | Intermediate 02-12 and Intermediate 01-25<br>8%<br>LC-MS (Method G): $R_t$ = 0.65 min; MS (ESIpos): m/z = 333 [M + H]⁺ |
| 03-68 | 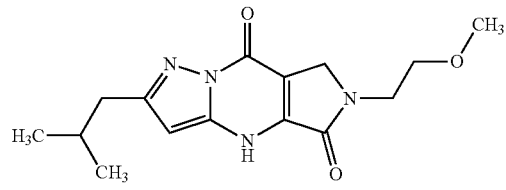<br>6-(2-methoxyethyl)-2-(2-methylpropyl)-6,7-dihydro-4H-pyrazolo[1,5-a]pyrrolo[3,4-d]pyrimidine-5,8-dione<br>¹H-NMR (400 MHz, DMSO-d6) δ [ppm]: 0.853 (1.64), 0.863 (0.60), 0.869 (1.72), 0.879 (0.59), 0.899 (15.90), 0.915 (16.00), 1.035 (0.47), 1.052 (0.96), 1.069 (0.52), 1.240 (0.62), 1.907 (3.95), 1.957 (1.65), 1.962 (0.84), 1.979 (0.96), 1.995 (0.74), 2.522 (4.52), 2.539 (4.13), 3.228 (0.87), 3.230 (1.12), 3.301 (0.40), 3.311 (0.59), 3.558 (1.38), 3.571 (3.33), 3.585 (2.23), 3.679 (1.88), 3.692 (2.74), 3.705 (1.18), 4.392 (6.60), 6.028 (4.87). | Intermediate 02-12 and CAS No.: 1000896-88-7<br>49%<br>LC-MS (Method G): $R_t$ = 0.79 min; MS (ESIpos): m/z = 305 [M + H]⁺ |
| 03-69 | 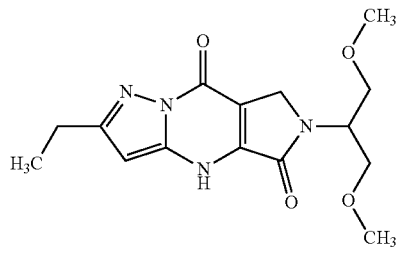<br>6-(1,3-dimethoxypropan-2-yl)-2-ethyl-6,7-dihydro-4H-pyrazolo[1,5-a]pyrrolo[3,4-d]pyrimidine-5,8-dione | Intermediate 02-37 and CAS No.: 1904-24-1<br>57%<br>LC-MS (Method G): $R_t$ = 1.02 min; MS (ESIpos): m/z = 457 [M + H]⁺ |

| Int. | Structure<br>IUPAC-Name<br>¹H NMR | Synth. from<br>Yield<br>LC-MS |
|---|---|---|
| 03-70 | 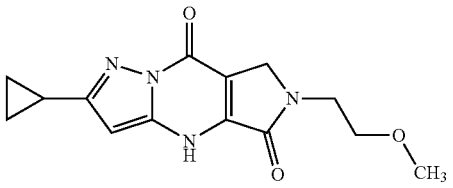<br>2-cyclopropyl-6-(2-methoxyethyl)-6,7-dihydro-4H-pyrazolo[1,5-a]pyrrolo[3,4-d]pyrimidine-5,8-dione<br>¹H NMR (250 MHz, Chloroform-d) δ [ppm]: 0.85-0.97 (m, 2H), 0.97-1.11 (m, 2H), 2.05-2.22 (m, 1H), 3.37 (s, 3H), 3.66 (t, 2H), 3.86 (t, 2H), 4.58 (s, 2H), 5.92 (s, 1H). | Intermediate 02-12 and CAS No.: 175137-46-9<br>60%<br>LC-MS (Analytical Method A):<br>$R_t$ = 0.82 min; MS (ESIpos):<br>m/z = 289 [M + H]⁺. |
| 03-71 | 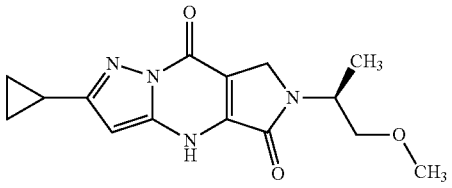<br>2-cyclopropyl-6-[(2S)-1-methoxypropan-2-yl]-6,7-dihydro-4H-pyrazolo[1,5-a]pyrrolo[3,4-d]pyrimidine-5,8-dione<br>¹H NMR (250 MHz, Chloroform-d) δ [ppm]: 0.87-0.97 (m, 2H), 0.98-1.10 (m, 2H), 1.37 (d, 3H), 2.06-2.22 (m, 1H), 3.35 (s, 3H), 3.56 (d, 2H), 4.36-4.48 (m, 1H), 4.53 (d, 1H), 4.63 (q, 1H), 5.92 (s, 1H). | Intermediate 02-28 and CAS No.: 175137-46-9<br>73%<br>LC-MS (Analytical Method A):<br>$R_t$ = 0.88 min; MS (ESIpos):<br>m/z = 303 [M + H]⁺. |
| 03-72 | 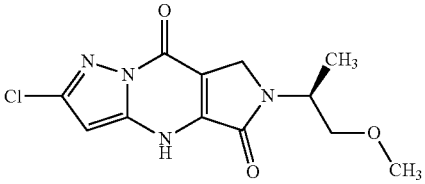<br>2-chloro-6-[(2S)-1-methoxypropan-2-yl]-6,7-dihydro-4H-pyrazolo[1,5-a]pyrrolo[3,4-d]pyrimidine-5,8-dione<br>¹H NMR (250 MHz, DMSO-d6) δ [ppm]: 1.22 (d, 3H), 3.27 (s, 3H), 3.40-3.65 (m, 2H), 4.25-4.52 (m, 3H), 6.29 (s, 1H), 13.70 (s, 1H). | Intermediate 02-28 and CAS No.: 916211-79-5<br>26%<br>LC-MS (Analytical Method A):<br>$R_t$ = 0.83 min; MS (ESIpos):<br>m/z = 296.8 [M + H]⁺. |
| 03-73 | 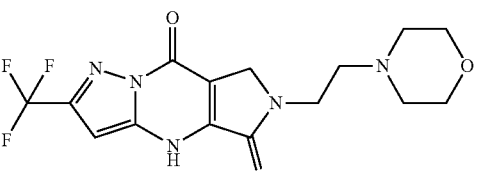<br>6-[2-(morpholin-4-yl)ethyl]-2-(trifluoromethyl)-6,7-dihydro-4H-pyrazolo[1,5-a]pyrrolo[3,4-d]pyrimidine-5,8-dione<br>¹H NMR (500 MHz, DMSO-d6) δ [ppm]: 3.02-3.19 (m, 2H), 3.44-3.58 (m, 4H), 3.80-3.96 (m, 4H), 3.99 (t, 2H), 4.53 (s, 2H), 6.65 (s, 1H), 11.28 (s, 1H). | Intermediate 02-35 and CAS No.: 852443-61-9<br>66%<br>LC-MS (Analytical Method A):<br>$R_t$ = 0.67 min; MS (ESIpos):<br>m/z = 371.9 [M + H]⁺. |

|  |  |  |
|---|---|---|
| Int. | Structure<br>IUPAC-Name<br>¹H NMR | Synth. from<br>Yield<br>LC-MS |
| 03-74 | 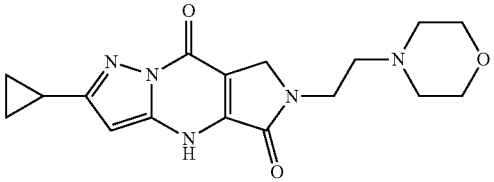<br>2-cyclopropyl-6-[2-(morpholin-4-yl)ethyl]-6,7-dihydro-4H-pyrazolo[1,5-a]pyrrolo[3,4-d]pyrimidine-5,8-dione<br>¹H NMR (250 MHz, DMSO-d6) δ [ppm]: 0.76-0.86 (m, 2H), 0.91-1.04 (m, 2H), 1.98-2.07 (m, 1H), 3.06-3.18 (m, 2H), 3.43-3.56 (m, 4H), 3.76-3.97 (m, 6H), 4.45 (s, 2H), 5.96 (s, 1H). | Intermediate 02-35 and CAS No.: 175137-46-9<br>70%<br>LC-MS (Analytical Method A):<br>$R_t$ = 0.62 min; MS (ESIpos):<br>m/z = 344.0 [M + H]⁺. |
| 03-75 | 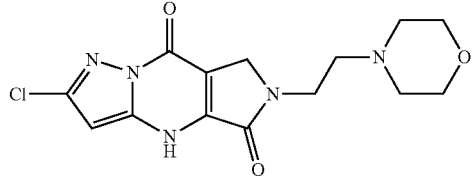<br>2-chloro-6-[2-(morpholin-4-yl)ethyl]-6,7-dihydro-4H-pyrazolo[1,5-a]pyrrolo[3,4-d]pyrimidine-5,8-dione<br>¹H NMR (250 MHz, DMSO-d6) δ [ppm]: 3.00-3.22 (m, 2H), 3.41-3.58 (m, 4H), 3.74-4.07 (m, 6H), 4.49 (s, 2H), 6.33 (s, 1H). | Intermediate 02-35 and CAS No.: 916211-79-5<br>64%<br>LC-MS (Analytical Method A):<br>$R_t$ = 0.46 min; MS (ESIpos):<br>m/z = 337.9 [M + H]⁺. |
| 03-76 | 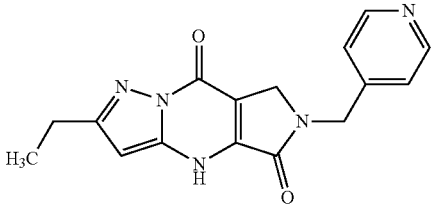<br>2-ethyl-6-[(pyridin-4-yl)methyl]-6,7-dihydro-4H-pyrazolo[1,5-a]pyrrolo[3,4-d]pyrimidine-5,8-dione<br>¹H NMR (500 MHz, DMSO-d6) δ [ppm]: 1.24 (t, 3H), 2.70 (q, 2H), 4.36 (s, 2H), 4.79 (s, 2H), 6.09 (s, 1H), 7.32 (d, 2H), 8.55 (d, 2H), 13.32 (s, 1H). | Intermediate 02-38 and CAS No.: 1904-24-1<br>10%<br>LC-MS (Analytical Method A):<br>$R_t$ = 0.55 min; MS (ESIpos):<br>m/z = 309.9 [M + H]⁺. |
| 03-77 | 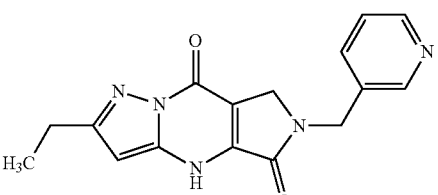<br>2-ethyl-6-[(pyridin-3-yl)methyl]-6,7-dihydro-4H-pyrazolo[1,5-a]pyrrolo[3,4-d]pyrimidine-5,8-dione<br>¹H (250 MHz, DMSO-d6) δ [ppm]: 1.23 (t, 3H), 2.64 (q, 2H), 4.13 (s, 2H), 4.73 (s, 2H), 5.90 (s, 1H), 7.34-7.42 (m, 1H), 7.67-7.72 (m, 1H), 8.50 (dd, 1H), 8.55 (d, 1H). | Intermediate 02-39 and CAS No.: 1904-24-1<br>10%<br>LC-MS (Analytical Method A):<br>$R_t$ = 0.63 min; MS (ESIpos):<br>m/z = 309.9 [M + H]⁺. |

|   | Structure<br>IUPAC-Name | Synth. from<br>Yield |
|---|---|---|
| Int. | ¹H NMR | LC-MS |

03-78

2-ethyl-6-[(pyridin-2-yl)methyl]-6,7-dihydro-4H-pyrazolo[1,5-a]pyrrolo[3,4-d]pyrimidine-5,8-dione ¹H NMR (500 MHz, DMSO-d6) δ [ppm]: 1.24 (t, 3H), 2.70 (q, 2H), 4.43 (s, 2H), 4.87 (s, 2H), 6.09 (s, 1H), 7.34 (dd, 1H), 7.38 (d, 1H), 7.79-7.84 (m, 1H), 8.55 (d, 1H).

Intermediate 02-40 and CAS No.: 1904-24-1
10%
LC-MS (Analytical Method A):
$R_t$ = 0.74 min; MS (ESIpos):
m/z = 309.9 [M + H]⁺.

03-79

2-cyclobutyl-6-[(2S)-1-methoxypropan-2-yl]-6,7-dihydro-4H-pyrazolo[1,5-a]pyrrolo[3,4-d]pyrimidine-5,8-dione ¹H NMR (250 MHz, Chloroform-d) [ppm]: 1.39 (d, 3H), 1.85-2.00 (m, 1H), 2.01-2.20 (m, 1H), 2.23-2.51 (m, 4H), 3.36 (s, 3H), 3.58 (d, 2H), 3.67-3.82 (m, 1H), 4.45 (d, 1H), 4.54 (d, 1H), 4.61-4.73 (m, 1H), 6.16 (s, 1H), 11.49 (s, 1H).

Intermediate 02-28 and CAS No.: 326827-21-8
69%
LC-MS (Amalytical Method A):
$R_t$ = 0.93 min; MS (ESIpos):
m/z = 317 [M + H]⁺.

03-80

2-bromo-6-[2-(morpholin-4-yl)ethyl]-6,7-dihydro-4H-pyrazolo[1,5-a]pyrrolo[3,4-d]pyrimidine-5,8-dione ¹H NMR (250 MHz, DMSO-d6) δ [ppm]: 3.06-3.18 (m, 2H), 3.43-3.53 (m, 4H), 3.84-4.00 (m, 6H), 4.49 (s, 2H), 6.38 (s, 1H).

Intermediate 02-35 and CAS No.: 1203705-55-8
92%
LC-MS (Analytical Method A):
$R_t$ = 0.48 min; MS (ESIpos):
m/z = 381.9 [M + H]⁺.

03-81

2-ethyl-6-[(4-fluorophenyl)methyl]-6,7-dihydro-4H-pyrazolo[1,5-a]pyrrolo[3,4-d]pyrimidine-5,8-dione ¹H NMR (400 MHz, DMSO-d6) δ [ppm]: 1.22 (t, 3H), 2.68 (q, 2H), 4.27 (s, 2H), 4.72 (s, 2H), 6.07 (s, 1H), 7.16-7.24 (m, 3H), 7.34-7.42 (m, 2H).

Intermediate 02-41 and CAS No.: 1904-24-1
73%
LC-MS (Method G): $R_t$ = 0.87 min; MS (ESIpos): m/z = 327 [M + H]⁺

| Int. | Structure<br>IUPAC-Name<br>¹H NMR | Synth. from<br>Yield<br>LC-MS |
|---|---|---|
| 03-82 | 6-(cyclobutylmethyl)-2-ethyl-6,7-dihydro-4H-pyrazolo[1,5-a]pyrrolo[3,4-d]pyrimidine-5,8-dione<br>¹H NMR (500 MHz, DMSO-d6) δ [ppm]: 1.23 (t, 3H), 1.72-1.80 (m, 2H), 1.82-1.90 (m, 2H), 2.00-2.10 (m, 2H), 2.62-2.72 (m, 3H), 3.56 (d, 2H), 4.32 (s, 2H), 6.05 (s, 1H), 13.26 (s, 1H). | Intermediate 02-42 and CAS No.: 1904-24-1<br>43%<br>LC-MS (Analytical Method A): $R_t$ = 0.95 min; MS (ESIpos): m/z = 287.0 [M + H]⁺. |
| 03-83 | 2-ethyl-6-{[(±)-oxan-2-yl]methyl}-6,7-dihydro-4H-pyrazolo[1,5-a]pyrrolo[3,4-d]pyrimidine-5,8-dione<br>¹H NMR (400 MHz, DMSO-d6) δ [ppm]: 1.23 (t, 3H), 1.37-1.61 (m, 5H), 1.70-1.83 (m, 1H), 2.67 (q, 2H), 3.46-3.62 (m, 4H), 3.82-3.92 (m, 1H), 4.39 (s, 2H), 6.03 (s, 1H). | Intermediate 02-43 and CAS No.: 1904-24-1<br>43%<br>LC-MS (Method G): $R_t$ = 0.80 min; MS (ESIpos): m/z = 317 [M + H]⁺. |
| 03-84 | 2-(5-methylpyridin-2-yl)-6-(propan-2-yl)-6,7-dihydro-4H-pyrazolo[1,5-a]pyrrolo[3,4-d]pyrimidine-5,8-dione<br>¹H NMR (500 MHz, DMSO-d6) δ [ppm]: 1.27 (d, 6H), 2.35 (s, 3H), 4.32-4.42 (m, 3H), 6.70 (s, 1H), 7.74 (dd, 1H), 8.05 (d, 1H), 8.48-8.52 (m, 1H), 13.46 (s, 1H). | Intermediate 02-01 and Intermediate 01-27<br>43%<br>LC-MS (Analytical Method A): $R_t$ = 0.90 min; MS (ESIpos): m/z = 324 [M + H]⁺. |
| 03-85 | tert-butyl 3-[(2-ethyl-5,8-dioxo-5,8-dihydro-4H-pyrazolo[1,5-a]pyrrolo[3,4-d]pyrimidin-6(7H)-yl)methyl]azetidine-1-carboxylate<br>¹H NMR (400 MHz, DMSO-d6) δ [ppm]: 1.23 (t, 3H), 1.37 (s, 9H), 2.68 (q, 2H), 2.89 (br t, 1H), 3.63 (br s, 2H), 3.74 (d, 2H), 3.92(br s, 2H), 4.33 (s, 2H), 6.04 (s, 1H), 12.51-13.72 (m, 1H). | Intermediate 02-44 and CAS No.: 1904-24-1<br>44%<br>LC-MS (Method G): $R_t$ = 0.91 min; MS (ESIneg): m/z = 386 [M − H]⁻ |

| Int. | Structure<br>IUPAC-Name<br>¹H NMR | Synth. from<br>Yield<br>LC-MS |
|---|---|---|
| 03-86 | 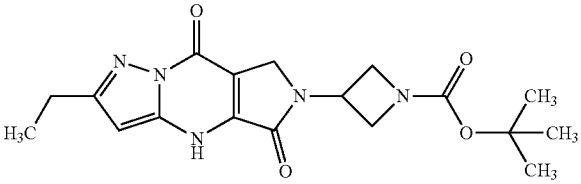<br>tert-butyl 3-(2-ethyl-5,8-dioxo-5,8-dihydro-4H-pyrazolo[1,5-a]pyrrolo[3,4-d]pyrimidin-6(7H)-yl)azetidine-1-carboxylate<br>¹H NMR (400 MHz, DMSO-d6) δ [ppm]: 1.23 (t, 3H), 1.41 (s, 9H), 2.68 (q, 2H), 4.06-4.23 (m, 4H), 4.58 (s, 2H), 4.95-5.04 (m, 1H), 6.05 (s, 1H), 12.67-13.66 (m, 1H). | Intermediate 02-45 and CAS No.: 1904-24-1<br>63%<br>LC-MS (Method G): $R_t$ = 0.90 min; MS (ESIpos): m/z = 374 [M + H]⁺ |
| 03-87 | 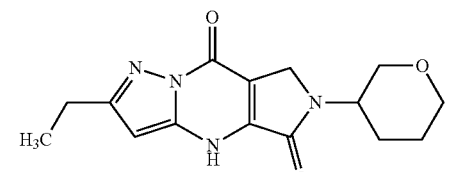<br>2-ethyl-6-[(±)-oxan-3-yl]-6,7-dihydro-4H-pyrazolo[1,5-a]pyrrolo[3,4-d]pyrimidine-5,8-dione<br>¹H NMR (400 MHz, DMSO-d6) δ [ppm]: 1.23 (t, 3H), 1.58-1.78 (m, 2H), 1.84-2.00 (m, 2H), 2.68 (q, 2H), 3.35-3.40 (m, 1H), 3.45-3.54 (m, 1H), 3.79 (br dd, 2H), 4.00-4.08 (m, 1H), 4.35-4.40 (m, 1H), 4.41-4.46 (m, 1H), 6.05 (s, 1H), 13.30 (br s, 1H). | Intermediate 02-46 and CAS No.: 1904-24-1<br>63%<br>LC-MS (Method G): $R_t$ = 0.70 min; MS (ESIpos): m/z = 303 [M + H]⁺ |
| 03-88 | 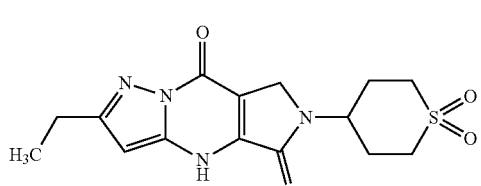<br>6-(1,1-dioxo-1lambda⁶-thian-4-yl)-2-ethyl-6,7-dihydro-4H-pyrazolo[1,5-a]pyrrolo[3,4-d]pyrimidine-5,8-dione<br>¹H NMR (400 MHz, DMSO-d6) δ [ppm]: 1.23 (t, 3H), 2.10 (br d, 2H), 2.22-2.40 (m, 2H), 2.68 (q, 2H), 3.13 (br d, 2H), 3.37-3.49 (m, 2H), 4.37-4.43 (m, 1H), 4.41 (s, 2H), 6.06 (s, 1H). | Intermediate 02-47 and CAS No.: 1904-24-1<br>72%<br>LC-MS (Method G): $R_t$ = 0.62 min; MS (ESIpos): m/z = 351 [M + H]⁺ |
| 03-89 | 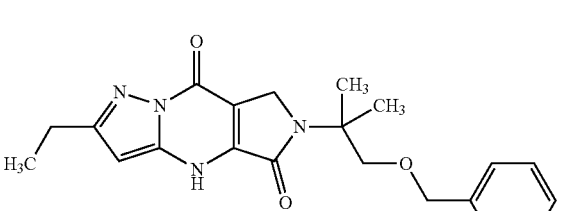<br>6-[1-(benzyloxy)-2-methylpropan-2-yl]-2-ethyl-6,7-dihydro-4H-pyrazolo[1,5-a]pyrrolo[3,4-d]pyrimidine-5,8-dione | Intermediate 02-48 and CAS No.: 1904-24-1<br>4%<br>LC-MS (Method H): $R_t$ = 0.61 min; MS (ESIpos): m/z = 381 [M + H]⁺ |

| Int. | Structure<br>IUPAC-Name<br>¹H NMR | Synth. from<br>Yield<br>LC-MS |
|---|---|---|
| 03-90 | 6-[(±)-1-(benzyloxy)propan-2-yl]-2-ethyl-6,7-dihydro-4H-pyrazolo[1,5-a]pyrrolo[3,4-d]pyrimidine-5,8-dione | Intermediate 02-49 and CAS No.: 1904-24-1<br>1%<br>LC-MS (Method H): $R_t$ = 0.60 min; MS (ESIpos): m/z = 367 [M + H]⁺ |
| 03-91 | ethyl 6-(oxan-4-yl)-5,8-dioxo-5,6,7,8-tetrahydro-4H-pyrazolo[1,5-a]pyrrolo[3,4-d]pyrimidine-2-carboxylate<br>¹H NMR (400 MHz, DMSO-d6) δ [ppm]: 1.33 (t, 3H), 1.70 (br dd, 2H), 1.86 (qd, 2H), 3.40-3.48 (m, 2H), 3.93 (br d, 1H), 3.96 (br d, 1H), 4.23 (tt, 1H), 4.34 (q, 2H), 4.44 (s, 2H), 6.57 (s, 1H). | Intermediate 02-07 and CAS No.: 105434-90-0<br>79%<br>LC-MS (Method G): $R_t$ = 0.69 min; MS (ESIpos): m/z = 347 [M + H]⁺ |
| 03-92 | ethyl 6-[2-(morpholin-4-yl)ethyl]-5,8-dioxo-5,6,7,8-tetrahydro-4H-pyrazolo[1,5-a]pyrrolo[3,4-d]pyrimidine-2-carboxylate<br>¹H NMR (400 MHz, DMSO-d6) δ [ppm]: 1.34 (t, 3H), 2.99-3.26 (m, 4H), 3.47 (br s, 2H), 3.88 (br s, 4H), 3.97 (br t, 2H), 4.35 (q, 2H), 4.50 (s, 2H), 6.59 (s, 1H). | Intermediate 02-35 and CAS No.: 105434-90-0<br>60%<br>LC-MS (Method G): $R_t$ = 0.52 min; MS (ESIpos): m/z = 376 [M + H]⁺ |
| 03-93 | ethyl 5,8-dioxo-6-[(pyridin-2-yl)methyl]-5,6,7,8-tetrahydro-4H-pyrazolo[1,5-a]pyrrolo[3,4-d]pyrimidine-2-carboxylate<br>¹H NMR (400 MHz, DMSO-d6) δ [ppm]: 1.34 (t, 3H), 4.35 (q, 2H), 4.48 (s, 2H), 4.88 (s, 2H), 6.57 (s, 1H), 7.29-7.36 (m, 1H), 7.38 (d, 1H), 7.81 (td, 1H), 8.52-8.57 (m, 1H). | Intermediate 02-40 and CAS No.: 105434-90-0<br>56%<br>LC-MS (Method G): $R_t$ = 0.66 min; MS (ESIpos): m/z = 354 [M + H]⁺ |
| 03-94 | 2-methyl-6-{[(±)-oxetan-2-yl]methyl}-6,7-dihydro-4H-pyrazolo[1,5-a]pyrrolo[3,4-d]pyrimidine-5,8-dione | Intermediate 02-50 and CAS No.: 113402-89-4<br>crude<br>LC-MS (Method G): $R_t$ = 0.80 min; MS (ESIpos): m/z = 275 [M + H]⁺ |

| Int. | Structure / IUPAC-Name / ¹H NMR | Synth. from / Yield / LC-MS |
|---|---|---|
| 03-95 | 2,6-diethyl-6,7-dihydro-4H-pyrazolo[1,5-a]pyrrolo[3,4-d]pyrimidine-5,8-dione<br>¹H-NMR (400 MHz, DMSO-d6) δ [ppm]: 1.173 (5.28), 1.192 (12.64), 1.206 (7.81), 1.210 (6.06), 1.225 (16.00), 1.244 (7.02), 2.518 (0.53), 2.647 (1.74), 2.666 (5.30), 2.685 (5.11), 2.704 (1.61), 3.334 (0.74), 3.519 (1.24), 3.537 (3.84), 3.555 (3.84), 3.573 (1.18), 4.366 (9.54), 6.045 (7.48). | Intermediate 02-51 and CAS No.: 1904-24-1<br>26%<br>LC-MS (Method G): $R_t$ = 0.64 min; MS (ESIpos): m/z = 247 [M + H]⁺ |
| 03-96 | 2-bromo-6-[(3R)-oxolan-3-yl]-6,7-dihydro-4H-pyrazolo[1,5-a]pyrrolo[3,4-d]pyrimidine-5,8-dione<br>¹H-NMR (250 MHz, DMSO-d6) δ [ppm] 1.99-2.15 (m, 1H), 2.19-2.34 (m, 1H), 3.65-3.79 (m, 2H), 3.86 (dd, 1H), 3.94-4.06 (m, 1H), 4.31-4.49 (m, 2H), 4.78-4.90 (m, 1H), 6.33 (s, 1H), 13.67 (s, 1H). | Intermediate 02-52 and CAS No.: 1203705-55-8<br>62%<br>LC-MS (Analytical Method A): $R_t$ = 0.85 min; MS (ESIpos): m/z = 339.0 [M + H]⁺. |
| 03-97 | 2-bromo-6-[(3S)-oxolan-3-yl]-6,7-dihydro-4H-pyrazolo[1,5-a]pyrrolo[3,4-d]pyrimidine-5,8-dione<br>¹H-NMR (250 MHz, DMSO-d6) δ [ppm]: 2.07 (ddd, 1H), 2.17-2.36 (m, 1H), 3.63-3.80 (m, 2H), 3.87 (dd, 1H), 3.94-4.07 (m, 1H), 4.40 (s, 1H), 4.41 (s, 1H), 4.78-4.92 (m, 1H), 6.33 (s, 1H), 13.67 (s, 1H). | Intermediate 02-53 and CAS No.: 1203705-55-8<br>72%<br>LC-MS (Analytical Method A): $R_t$ = 0.82; MS (ESIpos): m/z = 339.0 [M + H]⁺. |
| 03-98 | 2-ethyl-6-methyl-6,7-dihydro-4H-pyrazolo[1,5-a]pyrrolo[3,4-d]pyrimidine-5,8-dione<br>¹H-NMR (400 MHz, DMSO-d6) δ [ppm]: 1.206 (5.66), 1.225 (12.58), 1.244 (5.97), 2.648 (1.67), 2.667 (5.05), 2.686 (4.67), 2.705 (1.52), 2.900 (0.47), 3.094 (16.00), 4.344 (8.55), 6.049 (5.83), 13.285 (0.80). | Intermediate 02-58 and CAS No.: 1904-24-1<br>16%<br>LC-MS (Method G): $R_t$ = 0.58 min; MS (ESIpos): m/z = 233 [M + H]⁺ |

| Int. | Structure<br>IUPAC-Name<br>¹H NMR | Synth. from<br>Yield<br>LC-MS |
|---|---|---|
| 03-99 | 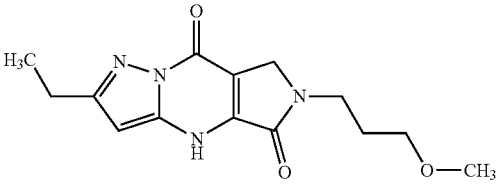<br>2-ethyl-6-(3-methoxypropyl)-6,7-dihydro-4H-pyrazolo[1,5-a]pyrrolo[3,4-d]pyrimidine-5,8-dione<br>¹H NMR (500 MHz, Chloroform-d) δ [ppm]: 1.34 (t, 3H), 2.08-1.94 (m, 2H), 2.85 (q, 2H), 3.34 (s, 3H), 3.47 (t, 2H), 3.81 (t, 2H), 4.49 (s, 2H), 6.18 (s, 1H), 12.07 (s, 1H). | Intermediate 02-55 and CAS No.: 1904-24-1<br>35%<br>LC-MS (Analytical Method A):<br>$R_t$ = 0.81 min; MS (ESIpos):<br>m/z = 290.9 [M + H]⁺. |
| 03-100 | 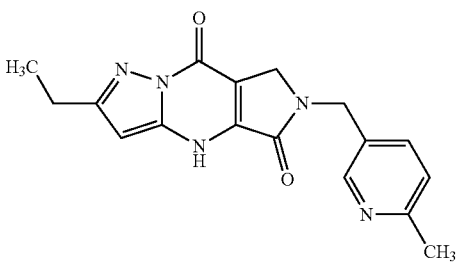<br>2-ethyl-6-[(6-methylpyridin-3-yl)methyl]-6,7-dihydro-4H-pyrazolo[1,5-a]pyrrolo[3,4-d]pyrimidine-5,8-dione<br>¹H NMR (500 MHz, DMSO-d6) δ [ppm]: 1.22 (t, 3H), 2.68 (q, 2H), 2.73 (s, 3H), 4.38 (s, 2H), 4.91 (s, 2H), 6.08 (s, 1H), 7.86 (d, 1H), 8.34-8.40 (m, 1H), 8.75-8.80 (m, 1H), 13.38 (s, 1H). | Intermediate 02-56 and CAS No.: 1904-24-1<br>40%<br>LC-MS (Analytical Method A):<br>$R_t$ = 0.56 min; MS (ESIpos):<br>m/z = 323.9 [M + H]⁺. |

Intermediate 03-101

2-ethyl-6-phenyl-6,7-dihydro-4H-pyrazolo[1,5-a]pyrrolo[3,4-d]pyrimidine-5,8-dione

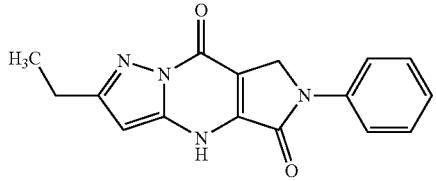

A solution of tert-butyl 3-amino-5-ethyl-1H-pyrazole-1-carboxylate (200 mg, 947 μmol) (intermediate 01-42) and ethyl 4-hydroxy-5-oxo-1-phenyl-2,5-dihydro-1H-pyrrole-3-carboxylate (234 mg, 947 μmol) (intermediate 02-54) was dissolved in trifluoroacetic acid (3.0 mL) and stirred at 85° C. overnight. After evaporation, the residue was taken up in toluene (5 mL) and reevaporated to yield 697 mg of the crude product as brown solid. Purification by preparative HPLC yielded 50 mg (17%) of the title compound.

Intermediate 03-102

6-[(4-fluorophenyl)methyl]-2-(pyridin-4-yl)-6,7-dihydro-4H-pyrazolo[1,5-a]pyrrolo[3,4-d]pyrimidine-5,8-dione

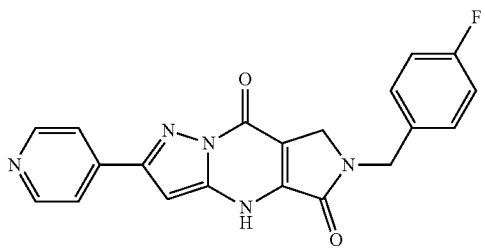

A solution of tert-butyl 5-amino-3-(pyridin-4-yl)-1H-pyrazole-1-carboxylate (200 mg, 768 μmol) (intermediate 01-31) and ethyl 1-(4-fluorobenzyl)-4-hydroxy-5-oxo-2,5-dihydro-1H-pyrrole-3-carboxylate (215 mg, 768 μmol) (intermediate 02-41) was dissolved in trifluoroacetic acid (2.4 mL) and stirred at 85° C. overnight. After evaporation, the residue was taken up in toluene (5 mL) and reevaporated to yield 821 mg of the crude product as brown solid. Purification by preparative HPLC yielded 60 mg (20%) of the title compound.

¹H-NMR (400 MHz, DMSO-d6) δ[ppm]: 0.851 (0.44), 1.231 (1.57), 1.786 (0.63), 1.987 (0.50), 2.074 (0.69), 2.331 (2.51), 2.336 (1.13), 2.518 (14.18), 2.523 (8.85), 2.539 (1.82), 2.635 (0.44), 2.673 (2.51), 2.678 (1.13), 3.454 (0.44), 3.468 (0.56), 4.318 (16.00), 4.581 (0.88), 4.743 (14.43), 6.846 (0.75), 6.859 (15.81), 7.167 (0.75), 7.176 (1.07), 7.184 (6.02), 7.189 (2.76), 7.194 (1.63), 7.200 (3.01), 7.206 (12.36), 7.211 (3.01), 7.222 (2.32), 7.228 (7.28), 7.236 (0.94), 7.363 (0.50), 7.382 (6.15), 7.388 (2.76), 7.396 (6.78), 7.405 (5.58), 7.413 (2.26), 7.419 (4.71), 7.965 (8.97), 7.969 (6.02), 7.976 (6.15), 7.980 (9.29), 8.667 (7.40), 8.682 (6.96).

LC-MS (Method G): Rt=0.73 min; MS (ESIpos): m/z=376 [M+H]+

In analogy to the procedure described for Intermediate 03-101 and 03-102, the following intermediates were prepared using trifluoroacetic acid and the appropriate building block and pyrazole starting materials.

| Int. | Structure<br>IUPAC-Name<br>¹H NMR | Synth. From<br>Yield<br>LC-MS |
|---|---|---|
| 03-103 | 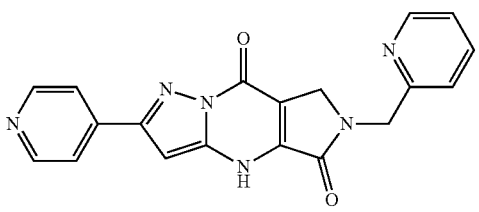<br>2-(pyridin-4-yl)-6-[ (pyridin-2-yl)methyl]-6,7-dihydro-4H-pyrazolo[1,5-a]pyrrolo[3,4-d]pyrimidine-5,8-dione<br>¹H-NMR (400 MHz, DMSO-d6) δ [ppm]: 1.752 (0.76), 2.331 (0.56), 2.518 (3.01), 2.522 (1.80), 2.539 (0.78), 2.673 (0.59), 4.358 (14.87), 4.838 (15.78), 6.791 (16.00), 7.165 (1.36), 7.293 (2.32), 7.295 (2.93), 7.307 (6.96), 7.309 (6.74), 7.326 (6.81), 7.329 (5.74), 7.605 (1.34), 7.608 (0.85), 7.615 (0.82), 7.620 (1.39), 7.749 (5.39), 7.753 (3.41), 7.760 (3.45), 7.764 (5.92), 7.769 (3.66), 7.773 (3.42), 7.788 (4.75), 7.792 (4.47), 7.807 (2.48), 7.812 (2.58), 7.936 (12.03), 7.940 (6.89), 7.947 (7.13), 7.951 (11.96), 8.513 (1.05), 8.528 (3.79), 8.531 (3.70), 8.536 (3.07), 8.540 (3.07), 8.543 (3.59), 8.545 (3.51), 8.547 (2.84), 8.631 (13.08), 8.636 (8.91), 8.643 (8.38), 8.646 (13.03), 13.621 (0.41). | Intermediate 02-40 and Intermediate 01-31<br>9%<br>LC-MS (Method H):<br>R$_t$ = 0.49 min; MS (ESIpos): m/z = 359 [M + H]+ |
| 03-104 | 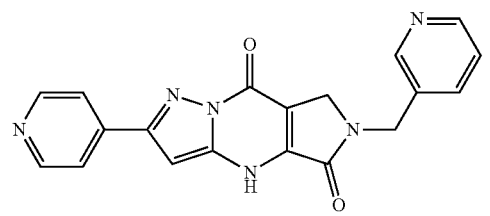<br>2-(pyridin-4-yl)-6-[ (pyridin-3-yl)methyl]-6,7-dihydro-4H-pyrazolo[1,5-a]pyrrolo[3,4-d]pyrimidine-5,8-dione<br>¹H-NMR (400 MHz, DMSO-d6) δ [ppm]: 1.752 (1.45), 2.331 (0.59), 2.518 (3.19), 2.522 (1.91), 2.539 (2.42), 2.673 (0.61), 4.239 (13.92), 4.762 (13.86), 6.772 (16.00), 7.166 (1.92), 7.372 (2.73), 7.374 (2.79), 7.384 (2.76), 7.386 (2.89), 7.392 (3.01), 7.394 (3.04), 7.404 (2.95), 7.406 (2.98), 7.604 (2.35), 7.608 (1.39), 7.615 (1.46), 7.619 (2.25), 7.714 (2.14), 7.719 (3.12), 7.724 (2.22), 7.734 (2.06), 7.739 (2.95), 7.743 (2.46), 7.749 (10.11), 7.753 (5.77), 7.760 (5.89), 7.764 (9.44), 7.921 (11.54), 7.925 (6.23), 7.932 (6.58), 7.936 (11.46), 8.136 (0.62), 8.502 (3.70), 8.507 (3.96), 8.514 (4.69), 8.518 (3.96), 8.524 (1.26), 8.527 (1.52), 8.571 (4.71), 8.574 (4.64), 8.620 (10.22), 8.624 (6.35), 8.631 (7.07), 8.636 (12.55), 8.651 (3.89), 13.619 (0.62). | Intermediate 02-39 and Intermediate 01-31<br>13%<br>LC-MS (Method H):<br>R$_t$ = 0.48 min; MS (ESIpos): m/z = 359 [M + H]+ |

-continued

| Int. | Structure<br>IUPAC-Name<br>¹H NMR | Synth. From<br>Yield<br>LC-MS |
|---|---|---|
| 03-105 | 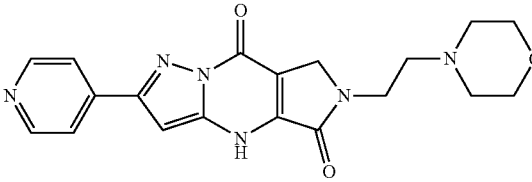<br><br>6-[2-(morpholin-4-yl)ethyl]-2-(pyridin-4-yl)-6,7-dihydro-4H-pyrazolo[1,5-a]pyrrolo[3,4-d]pyrimidine-5,8-dione<br>¹H-NMR (400 MHz, DMSO-d6) δ [ppm]: 1.223 (0.50), 1.232 (0.50), 1.751 (9.36), 2.103 (1.62), 2.322 (1.64), 2.327 (1.99), 2.331 (1.64), 2.518 (5.52), 2.522 (3.56), 2.539 (8.74), 2.555 (0.98), 2.601 (2.81), 2.617 (5.20), 2.632 (2.78), 2.664 (1.19), 2.669 (1.48), 2.673 (1.12), 2.944 (0.41), 2.994 (0.98), 3.360 (4.66), 3.498 (2.01), 3.555 (9.29), 3.566 (12.78), 3.577 (8.83), 3.643 (4.09), 3.659 (7.51), 3.674 (3.67), 3.924 (0.57), 4.375 (14.43), 5.872 (0.52), 6.765 (16.00), 7.156 (1.00), 7.604 (1.21), 7.608 (0.78), 7.615 (0.78), 7.619 (1.26), 7.749 (3.81), 7.752 (2.35), 7.759 (2.24), 7.764 (4.04), 7.930 (10.61), 7.934 (6.69), 7.940 (6.50), 7.945 (11.02), 8.136 (5.34), 8.512 (0.73), 8.527 (0.73), 8.629 (8.47), 8.632 (6.50), 8.643 (8.63). | Intermediate 02-35 and<br>Intermediate 01-31<br>13%<br>LC-MS (Method H):<br>R$_t$ = 0.48 min; MS<br>(ESIpos): m/z = 380<br>[M + H]⁺ |
| 03-106 | 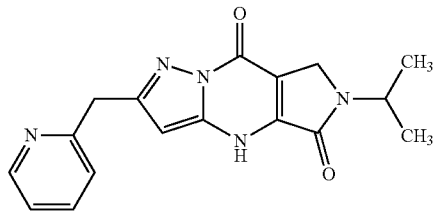<br><br>6-(propan-2-yl)-2-[(pyridin-2-yl)methyl]-6,7-dihydro-4H-pyrazolo[1,5-a]pyrrolo[3,4-d]pyrimidine-5,8-dione<br>¹H-NMR (400 MHz, DMSO-d6) δ [ppm]: 1.235 (15.95), 1.252 (16.00), 2.518 (1.52), 2.522 (0.99), 2.539 (2.39), 4.114 (1.55), 4.206 (8.96), 4.312 (0.49), 4.336 (8.69), 4.346 (1.73), 4.363 (1.07), 6.039 (7.56), 6.320 (0.99), 7.306 (1.05), 7.319 (1.14), 7.322 (1.17), 7.335 (1.12), 3247.399 (1.87), 7.419 (2.04), 7.793 (0.97), 7.797 (1.02), 7.812 (1.57), 7.817 (1.60), 7.832 (0.79), 7.836 (0.78), 8.133 (9.89), 8.532 (1.51), 8.535 (1.55), 8.537 (1.38), 8.543 (1.34), 8.545 (1.51), 8.547 (1.44). | Intermediate 02-01 and<br>Intermediate 01-32<br>19%<br>LC-MS (Method G):<br>R$_t$ = 0.55 min; MS<br>(ESIpos): m/z = 324<br>[M + H]⁺ |

Intermediate 03-108

2-acetyl-6-(propan-2-yl)-6,7-dihydro-4H-pyrazolo[1,5-a]pyrrolo[3,4-d]pyrimidine-5,8-dione

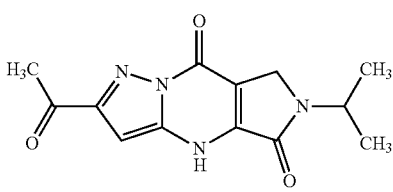

2-Bromo-6-(propan-2-yl)-6,7-dihydro-4H-pyrazolo[1,5-a]pyrrolo[3,4-d]pyrimidine-5,8-dione (1.00 g, 3.21 mmol) (intermediate 03-45), tributyl(1-ethoxyvinyl)stannane (1.32 g, 4.18 mmol), Pd(PPh$_3$)$_4$, (371 mg, 321 μmol), and K$_2$CO$_3$ (1.33 g, 9.64 mmol) were added into toluene (20 ml). The resulting mixture was stirred at 110° C. for 3 days under nitrogen. This reaction was cooled to room temperature and the solvent was removed in vacuo. The residue was dissolved in tetrahydrofuran and acidified to pH=3 with 2M HCl and the resulting mixture was stirred at rt for 30 min. The resulting solution was diluted with water (100 ml) then extracted with ethyl acetate (3×100 ml). The combined organic layer was dried (Na$_2$SO$_4$), filtered and the solvent was removed in vacuo. The residue was purified with column chromatography (silica gel, eluting with dichloromethane-methanol, 10:1) to afford 220 mg (23%) of the title compound.

LC-MS (Analytical Method K, 0-1.2 min 5-100% B, 1.2-1.6 min 100% B): R$_t$=0.65 min; MS (ESIpos): m/z=275 [M+H]⁺.

Intermediate 03-109

2-(2-hydroxypropan-2-yl)-6-(propan-2-yl)-6,7-dihydro-4H-pyrazolo[1,5-a]pyrrolo[3,4-d]pyrimidine-5,8-dione

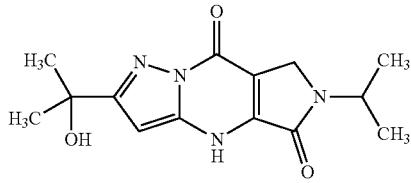

To a solution of 2-acetyl-6-isopropyl-6,7-dihydro-4H-pyrazolo[1,5-a]pyrrolo[3,4-d]pyrimidine-5,8-dione (100 mg, 0.36 mmol) (intermediate 03-108) in tetrahydrofuran (10 ml) was added methylmagnesium bromide (3 M in diethyl ether) (0.2 mL, 0.43 mmol) at 0° C. and the resulting mixture was stirred at rt for 2 h. Upon completion of the reaction, water was added and resulting mixture was extracted with ethyl acetate. The combined organic layer was dried over anhydrous Na$_2$SO$_4$ and concentrated in vacuo to give 120 mg (crude) of the title compound as a yellow solid.

LC-MS (Analytical Method K, 0-2.0 min 5-95% B, 2.0-2.6-min 95% B): R$_t$=0.79 min; MS (ESIpos): m/z=291 [M+H]$^+$.

Intermediate 03-110

5,8-dioxo-6-(propan-2-yl)-5,6,7,8-tetrahydro-4H-pyrazolo[1,5-a]pyrrolo[3,4-d]pyrimidine-2-carboxylic acid

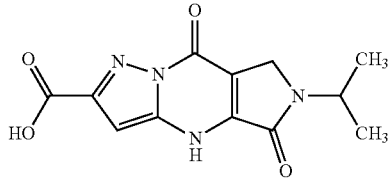

To a solution of ethyl 5,8-dioxo-6-(propan-2-yl)-5,6,7,8-tetrahydro-4H-pyrazolo[1,5-a]pyrrolo[3,4-d]pyrimidine-2-carboxylate (500 mg, 1.64 mmol) (intermediate 03-37) in tetrahydrofuran (5.0 ml, 62 mmol) and ethanol (5.0 ml, 86 mmol) was added a 2 N aqueous LiOH solution. The mixture was stirred for 1 h at 40° C. The solvent was removed under reduced pressure and acidified with conc. HCl solution to pH 3. The precipitate was filtered, washed with hexane and dried in vacuo to get 330 mg (73%) of the title compound.

$^1$H NMR (400 MHz, DMSO-d6) δ[ppm]: 1.21 (d, 6H), 4.15 (s, 2H), 4.38 (hept, 1H), 6.38 (s, 1H).

LC-MS (Analytical Method G): R$_t$=0.58 min; MS (ESIpos): m/z=277 [M+H]$^+$.

Intermediate 03-111

N-cyclopropyl-5,8-dioxo-6-(propan-2-yl)-5,6,7,8-tetrahydro-4H-pyrazolo[1,5-a]pyrrolo[3,4-d]pyrimidine-2-carboxamide

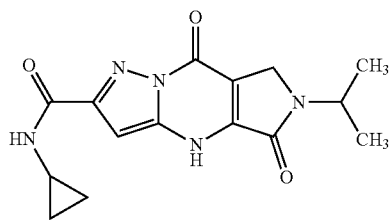

5,8-dioxo-6-(propan-2-yl)-5,6,7,8-tetrahydro-4H-pyrazolo[1,5-a]pyrrolo[3,4-d]pyrimidine-2-carboxylic acid (75.0 mg, 271 μmol) (intermediate 03-110) was dissolved in N,N-dimethylformamide (1.0 ml, 13 mmol). HATU (114 mg, 299 μmol) and N,N-diisopropylethylamine (95 μl, 540 μmol) were added and the resulting solution was stirred at rt for 15 min. Cyclopropanamine (38 μl, 540 μmol) was added and the reaction mixture stirred for 16 h at rt. The solution was diluted with ethyl acetate and water, extracted and concentrated. The residue was triturated with hexane and the resulting precipitate was collected by filtration, washed with hexane and dried in vacuum to get 33 mg (39%) of the title compound.

LC-MS (Analytical Method G): R$_t$=0.72 min; MS (ESIpos): m/z=316 [M+H]$^+$.

Intermediate 03-112 tert-butyl [5,8-dioxo-6-(propan-2-yl)-5,6,7,8-tetrahydro-4H-pyrazolo[1,5-a]pyrrolo[3,4-d]pyrimidin-2-yl]carbamate

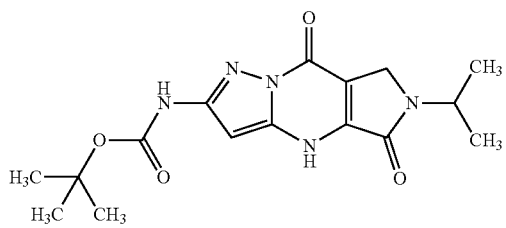

To a solution of 5,8-dioxo-6-(propan-2-yl)-5,6,7,8-tetrahydro-4H-pyrazolo[1,5-a]pyrrolo[3,4-d]pyrimidine-2-carboxylic acid (50.0 mg, 181 μmol) (intermediate 03-110) in N,N-dimethylformamide (0.75 ml) and tert-butanol (0.25 ml) was added triethylamine (50 μl, 360 μmol) followed by the addition of diphenyl phosphorazidate (59 μl, 270 μmol). The mixture was heated to 80° C. and stirred for 2 h. The solution was allowed to cool to rt before water was added. The mixture was extracted twice with ethyl acetate. The organic layer was washed with 1 N HCl solution, dried over a water repellant filter and concentrated. The residue was triturated with hexane, the solid was collected by filtration and dried in vacuo to get 31 mg (50%) of the title compound.

$^1$H NMR (400 MHz, Chloroform-d) δ [ppm]: 1.37 (d, 6H), 1.53 (s, 9H), 4.42 (s, 2H), 4.63 (dt, 1H), 6.68 (br s, 1H), 7.57 (br s, 1H), 11.63 (br s, 1H).

LC-MS (Analytical Method G): $R_t$=0.88 min; MS (ESI-pos): m/z=348 [M+H]$^+$.

Intermediate 04 ethyl {6-[(±)-butan-2-yl]-2-tert-butyl-5,8-dioxo-5,6,7,8-tetrahydro-4H-pyrazolo[1,5-a]pyrrolo[3,4-d]pyrimidin-4-yl}acetate

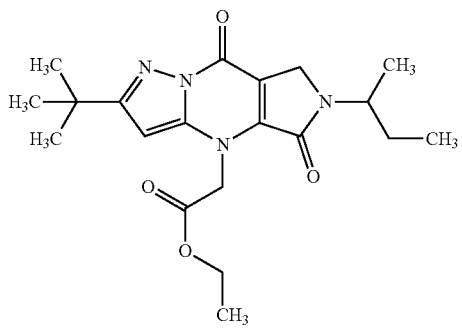 [SMILES: CCOC(=O)Cn1c2c(c(=O)n3nc(C(C)(C)C)cc13)CN(C(C)CC)C2=O]

A mixture of 6-sec-butyl-2-tert-butyl-6,7-dihydro-4H-pyrazolo[1,5-a]pyrrolo[3,4-d]pyrimidine-5,8-dione (0.75 g, 2.5 mmol) (intermediate 03-01), ethyl bromoacetate (0.55 ml, 5.0 mmol) and K$_2$CO$_3$ (377 mg, 2.7 mmol) in acetonitrile (14 ml) was stirred at 100° C. for 1.5 h. After this time the reaction was allowed to cool to rt, at which point it was diluted with water and extracted with ethyl acetate. The combined organics were dried (MgSO$_4$), filtered and concentrated under reduced pressure. The crude material was purified by Biotage Isolera™ chromatography (silica gel, eluting with heptanes-methyl tert-butyl ether, 1:0 to 0:1) to yield 900 mg (88% yield) of the title compound as a yellow solid.

$^1$H NMR (250 MHz, DMSO-d6) δ[ppm]: 0.79 (t, 17-1.26 (m, 6H), 1.31 (s, 9H), 1.46-1.75 (m, 2H), 3.95-4.45 (m, 5H), 5.36 (s, 2H), 6.59 (s, 1H).

LC-MS (Analytical Method F) $R_t$=3.26 min, MS (ESI-pos): m/z=389 [M+H]$^+$.

Intermediate 04 was formed as a mixture of two enantiomers. SFC Chiral Purification (Column: Lux A1 (21.2 mm×250 mm, 5 μm); eluent A: methanol, eluent B: CO2; gradient: isocratic 85% B; flow 50 ml/min; UV: 229 nm) provided enantiomer 1 (Intermediate 04-01) and enantiomer 2 (Intermediate 04-02).

Intermediate 04-01 ethyl {6-[butan-2-yl]-2-tert-butyl-5,8-dioxo-5,6,7,8-tetrahydro-4H-pyrazolo[1,5-a]pyrrolo[3,4-d]pyrimidin-4-yl}acetate (enantiomer 1)

SFC Chiral Purification (Column: Lux A1 (21.2 mm×250 mm, 5 μm); eluent A: methanol, eluent B: CO2; gradient: isocratic 85% B; flow 50 ml/min; UV: 229 nm) on 750 mg of Intermediate 04 gave 390 mg of the title compound as a yellow solid.

SFC Chiral Analysis (Column: Lux A1 (4.6 mm×250 mm, 5 μm); eluent A: methanol, eluent B: CO2; gradient: isocratic 85% B; flow 4 ml/min; UV: 210-400 nm): 96.8% e.e. $R_t$=1.70 min.

Intermediate 04-02 ethyl {6-[butan-2-yl]-2-tert-butyl-5,8-dioxo-5,6,7,8-tetrahydro-4H-pyrazolo[1,5-a]pyrrolo[3,4-d]pyrimidin-4-yl}acetate (enantiomer 2)

SFC Chiral Purification (Column: Lux A1 (21.2 mm×250 mm, 5 μm); eluent A: methanol, eluent B: CO2; gradient: isocratic 85% B; flow 50 ml/min; UV: 229 nm) on 750 mg of Intermediate 04 gave 388 mg of the title compound as a yellow solid.

SFC Chiral Analysis (Column: Lux A1 (4.6 mm×250 mm, 5 μm); eluent A: methanol, eluent B: CO2; gradient: isocratic 85% B; flow 4 ml/min; UV: 210-400 nm): 98% e.e. $R_t$=1.99 min.

In analogy to the procedure described for intermediate 04, the following intermediates were prepared using the appropriate building block and ethyl bromoacetate.

| Int. | Structure<br>IUPAC-Name<br>$^1$H NMR | Synth. From<br>Yield<br>LC-MS method |
|---|---|---|
| 04-03 | ![structure]<br>ethyl [5,8-dioxo-2,6-di(propan-2-yl)-5,6,7,8-tetrahydro-4H-pyrazolo[1,5-a]pyrrolo[3,4-d]pyrimidin-4-yl]acetate<br>$^1$H NMR (500 MHz, DMSO-d6) δ [ppm]: 6.52 (s, 1H), 5.36 (s, 2H), 4.37 (s, 2H), 4.33-4.25 (m, 1H), 4.18 (q, 2H), 3.01 (hept, 1H), 1.28-1.19 (m, 15H). | Intermediate 03-02<br>83%<br>LC-MS (Analytical Method A) $R_t$ = 1.05 min, MS (ESIpos): m/z = 361.2 [M + H]$^+$. |

| Structure IUPAC-Name | Synth. From Yield |
|---|---|
| Int. ¹H NMR | LC-MS method |

04-04 ethyl {2-tert-butyl-6-[(2S)-3-methylbutan-2-yl]-5,8-dioxo-5,6,7,8-tetrahydro-4H-pyrazolo[1,5-a]pyrrolo[3,4-d]pyrimidin-4-yl}acetate ¹H NMR (250 MHz, Chloroform-d) δ [ppm]: 5.97 (s, 1H), 5.37 (q, 2H), 4.50-4.19 (m, 4H), 4.13-3.93 (m, 1H), 1.96-1.78 (m, 1H), 1.42 (s, 9H), 1.35-1.18 (m, 6H), 1.04 (d, 3H), 0.87 (d, 3H).

Intermediate 03-03
88%
LC-MS (Analytical Method A) R$_t$ = 1.21 min, MS (ESIpos): m/z = 403 [M + H]⁺.

04-05 ethyl [2-tert-butyl-6-(cyclopropylmethyl)-5,8-dioxo-5,6,7,8-tetrahydro-4H-pyrazolo[1,5-a]pyrrolo[3,4-d]pyrimidin-4-yl]acetate ¹H NMR (250 MHz, Chloroform-d) δ [ppm]: 5.96 (s, 1H), 5.36 (s, 2H), 4.51 (s, 2H), 4.28 (q, 2H), 3.46 (d, 2H), 1.42 (s, 9H), 1.32 (m, 3H), 1.05 (m, 1H), 0.65 (m, 2H), 0.35 (m, 2H).

Intermediate 03-04
58%
LC-MS (Analytical Method A) R$_t$ = 1.12 min, MS (ESIpos): m/z = 387 [M + H]⁺.

04-06 ethyl {6-[(2R)-butan-2-yl]-5,8-dioxo-2-(trifluoromethyl)-5,6,7,8-tetrahydro-4H-pyrazolo[1,5-a]pyrrolo[3,4-d]pyrimidin-4-yl}acetate ¹H NMR (500 MHz, DMSO-d6) δ [ppm]: 7.27 (s, 1H), 5.47 (s, 2H), 4.44 (d, 1H), 4.37 (d, 1H), 4.18 (q, 2H), 4.13-4.08 (m, 1H), 1.70-1.54 (m, 2H), 1.26-1.18 (m, 6H), 0.80 (t, 3H).

Intermediate 03-05
90%
LC-MS (Analytical Method A) R$_t$ = 1.16 min, MS (ESIpos): m/z = 401 [M + H]⁺.

| Structure | Synth. From |
|---|---|
| IUPAC-Name | Yield |
| Int. ¹H NMR | LC-MS method |

04-07

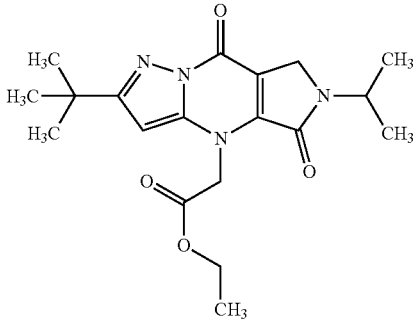

ethyl [2-tert-butyl-5,8-dioxo-6-(propan-2-yl)-5,6,7,8-tetrahydro-4H-pyrazolo[1,5-a]pyrrolo[3,4-d]pyrimidin-4-yl]acetate ¹H NMR (500 MHz, DMSO-d6) δ [ppm]: 6.59 (s, 1H), 5.36 (s, 2H), 4.37 (s, 2H), 4.34-4.24 (m, 1H), 4.18 (q, 2H), 1.31 (s, 9H), 1.26-1.20 (m, 9H).

Intermediate 03-06
99%
LC-MS (Analytical Method A) $R_t$ = 1.11 min, MS (ESIpos): m/z = 375 [M + H]⁺.

04-08

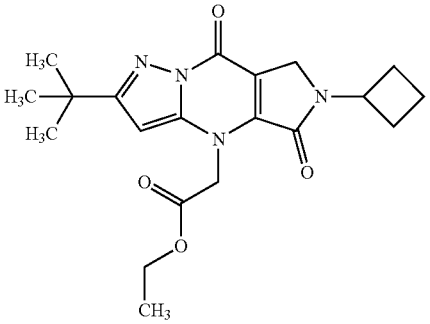

ethyl (2-tert-butyl-6-cyclobutyl-5,8-dioxo-5,6,7,8-tetrahydro-4H-pyrazolo[1,5-a]pyrrolo[3,4-d]pyrimidin-4-yl)acetate ¹H NMR (500 MHz, DMSO-d6) δ [ppm]: 6.59 (s, 1H), 5.33 (s, 2H), 4.65-4.56 (m, 1H), 4.50 (s, 2H), 4.17 (q, 2H), 2.42-2.31 (m, 2H), 2.20-2.10 (m, 2H), 1.80-1.63 (m, 2H), 1.31 (s, 9H), 1.21 (t, 3H).

Intermediate 03-07
98%
LC-MS (Analytical Method A) $R_t$ = 1.15 min, MS (ESIpos): m/z = 387.1 [M + H]⁺.

04-09

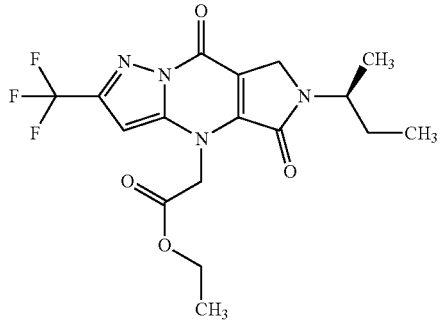

ethyl {6-[(2S)-butan-2-yl]-5,8-dioxo-2-(trifluoromethyl)-5,6,7,8-tetrahydro-4H-pyrazolo[1,5-a]pyrrolo[3,4-d]pyrimidin-4-yl}acetate ¹H NMR (500 MHz, Chloroform-d) δ [ppm]: 6.38 (s, 1H), 5.45 (m, 2H), 4.43-4.17 (m, 5H), 1.68 (m, 2H), 1.38-1.27 (m, 6H), 0.93 (t, 3H).

Intermediate 03-08
88%
LC-MS (Analytical Method A) $R_t$ = 1.15 min, MS (ESIpos): m/z = 401 [M + H]⁺.

| Int. | Structure / IUPAC-Name / ¹H NMR | Synth. From / Yield / LC-MS method |
|---|---|---|
| 04-10 | 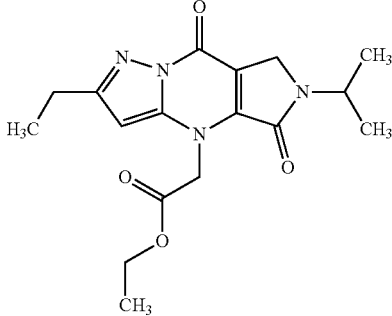<br>ethyl [2-ethyl-5,8-dioxo-6-(propan-2-yl)-5,6,7,8-tetrahydro-4H-pyrazolo[1,5-a]pyrrolo[3,4-d]pyrimidin-4-yl]acetate<br>¹H NMR (500 MHz, Methanol-d4) δ [ppm]: 6.33 (s, 1H), 4.86 (s, 2H), 4.50-4.42 (m, 1H), 4.41 (s, 2H), 4.26 (q, 2H), 2.79 (q, 2H), 1.37-1.31 (m, 9H), 1.30 (t, 3H). | Intermediate 03-09<br>81%<br>LC-MS (Analytical Method A) $R_t$ = 1.01 min, MS (ESIpos): m/z = 347 [M + H]⁺. |
| 04-11 | 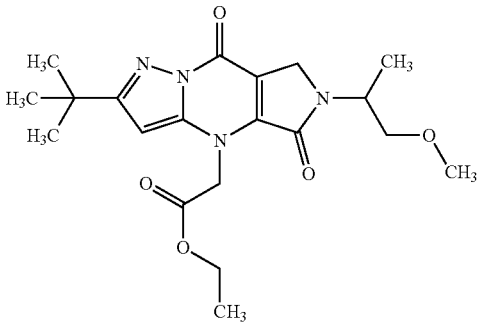<br>ethyl {2-tert-butyl-6-[(±)-1-methoxypropan-2-yl]-5,8-dioxo-5,6,7,8-tetrahydro-4H-pyrazolo[1,5-a]pyrrolo[3,4-d]pyrimidin-4-yl}acetate<br>¹H NMR (250 MHz, Chloroform-d) δ [ppm]: 5.95 (s, 1H), 5.46 (d, 1H), 5.27 (d, 1H), 4.59 (m, 1H), 4.47 (m, 2H), 4.29 (q, 2H), 3.52 (d, 2H), 3.36 (s, 3H), 1.46-1.21 (m, 16H). | Intermediate 03-10<br>88%<br>LC-MS (Analytical Method A) $R_t$ = 1.10 min, MS (ESIpos): m/z = 405 [M + H]⁺. |
| 04-12 | 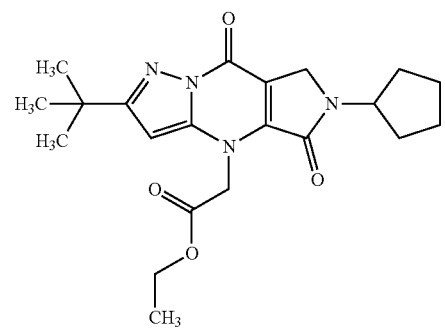<br>ethyl (2-tert-butyl-6-cyclopentyl-5,8-dioxo-5,6,7,8-tetrahydro-4H-pyrazolo[1,5-a]pyrrolo[3,4-d]pyrimidin-4-yl)acetate<br>¹H NMR (500 MHz, DMSO-d6) δ [ppm]: 6.59 (s, 1H), 5.36 (s, 2H), 4.48-4.40 (m, 1H), 4.40 (s, 2H), 4.18 (q, 2H), 1.97-1.82 (m, 2H), 1.80-1.64 (m, 4H), 1.65-1.52 (m, 2H), 1.31 (s, 9H), 1.21 (t, 3H). | Intermediate 03-11<br>95%<br>LC-MS (Analytical Method A) $R_t$ = 1.18 min, MS (ESIpos): m/z = 401 [M + H]⁺. |

| Structure | Synth. From |
|---|---|
| IUPAC-Name | Yield |
| Int. ¹H NMR | LC-MS method |

04-13

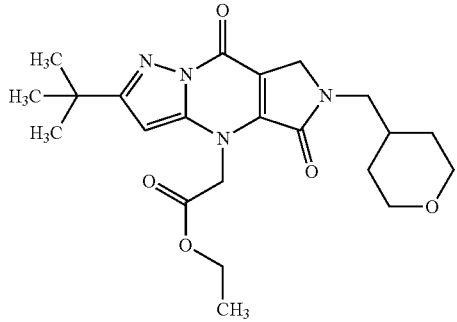

ethyl [2-tert-butyl-5,8-dioxo-6-(tetrahydro-2H-pyran-4-ylmethyl)-5,6,7,8-tetrahydro-4H-pyrazolo[1,5-a]pyrrolo[3,4-d]pyrimidin-4-yl]acetate
¹H NMR (250 MHz, Chloroform-d) δ [ppm]: 5.97 (s, 1H), 5.34 (s, 2H), 4.41 (s, 2H), 4.32 (d, 1H), 4.26 (d, 1H), 4.10-3.94 (m, 2H), 3.49 (d, 2H), 3.39 (m, 2H), 2.01 (m, 1H), 1.73-1.50 (m, 4H), 1.42 (s, 9H), 1.31 (t, 3H).

Intermediate 03-66
86%
LC-MS (Analytical Method A) 90% @ R$_t$ = 1.07 min, MS (ESIpos): m/z = 431 [M + H]⁺.

04-14

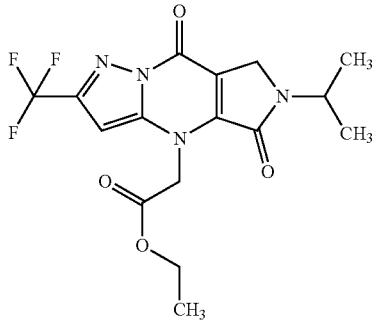

ethyl [5,8-dioxo-6-(propan-2-yl)-2-(trifluoromethyl)-5,6,7,8-tetrahydro-4H-pyrazolo[1,5-a]pyrrolo[3,4-d]pyrimidin-4-yl]acetate
¹H NMR (500 MHz, DMSO-d6) δ [ppm]: 7.28 (s, 1H), 5.48 (s, 2H), 4.46 (s, 2H), 4.32 (p, 1H), 4.20 (q, 2H), 1.26 (d, 6H), 1.23 (t, 3H).

Intermediate 03-12
72%
LC-MS (Analytical Method A) R$_t$ = 1.10 min, MS (ESIpos): m/z = 387 [M + H]⁺.

04-15

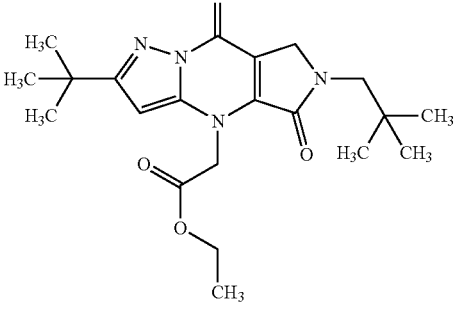

ethyl [2-tert-butyl-6-(2-hydroxy-2-methylpropyl)-5,8-dioxo-5,6,7,8-tetrahydro-4H-pyrazolo[1,5-a]pyrrolo[3,4-d]pyrimidin-4-yl]acetate
¹H NMR (250 MHz, Chloroform-d) δ [ppm]: 5.97 (s, 1H), 5.34 (s, 2H), 4.64 (s, 2H), 4.29 (q, 2H), 3.59 (s, 2H), 2.11 (s, 1H), 1.42 (s, 9H), 1.34-1.27 (m, 9H).

Intermediate 03-13
66%
LC-MS (Analytical Method A) R$_t$ = 1.03 min, MS (ESIpos): m/z = 405 [M + H]⁺.

| Int. | Structure<br>IUPAC-Name<br>¹H NMR | Synth. From<br>Yield<br>LC-MS method |
|---|---|---|
| 04-16 | 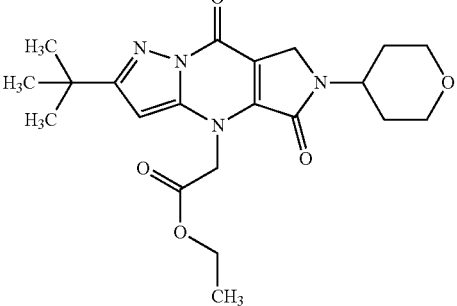<br>ethyl [2-tert-butyl-5,8-dioxo-6-(tetrahydro-2H-pyran-4-yl)-5,6,7,8-tetrahydro-4H-pyrazolo[1,5-a]pyrrolo[3,4-d]pyrimidin-4-yl]acetate<br>¹H NMR (500 MHz, Chloroform-d) δ [ppm]: 5.88 (s, 1H), 5.25 (s, 1H), 4.33-4.26 (m, 3H), 4.21 (q, 2H), 4.02 (m, 2H), 3.45? (m, 2H), 1.85-1.76 (m, 1H), 1.75 (s, 2H), 1.53 (s, 2H), 1.33 (s, 9H), 1.24-1.22 (m, 3H). | Intermediate 03-14<br>90%<br>LC-MS (Analytical Method A) $R_t$ = 1.06 min, MS (ESIpos): m/z = 417 [M + H]⁺. |
| 04-17 | 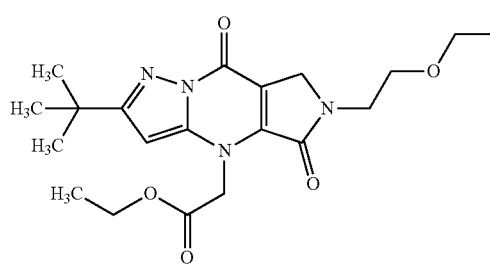<br>ethyl {6-[2-(benzyloxy)ethyl]-2-tert-butyl-5,8-dioxo-5,6,7,8-tetrahydro-4H-pyrazolo[1,5-a]pyrrolo[3,4-d]pyrimidin-4-yl}acetate<br>¹H NMR (250 MHz, DMSO-d6) δ [ppm]: 7.36-7.21 (m, 5H), 6.61 (s, 1H), 5.36 (s, 2H), 4.50 (s, 2H), 4.41 (s, 2H), 4.17 (q, 2H), 3.76-3.62 (m, 4H), 1.31 (s, 9H), 1.20 (t, 3H). | Intermediate 03-15<br>94%<br>LC-MS (Analytical Method A) $R_t$ = 1.29 min, MS (ESIpos): m/z = 467.5 [H + H]⁺. |
| 04-18 | 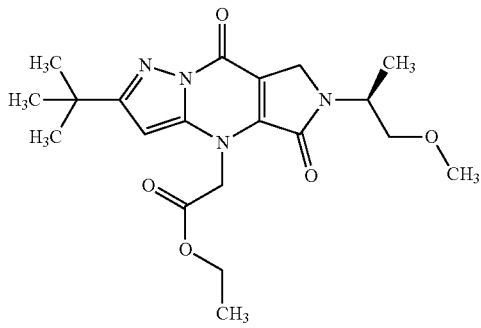<br>ethyl {2-tert-butyl-6-[(2S)-1-methoxypropan-2-yl]-5,8-dioxo-5,6,7,8-tetrahydro-4H-pyrazolo[1,5-a]pyrrolo[3,4-d]pyrimidin-4-yl}acetate | Intermediate 03-16<br>89%<br>LC-MS (Analytical Method A) $R_t$ = 1.10 min, MS (ESIpos): m/z = 405 [M + H]⁺. |

-continued

| Int. | Structure<br>IUPAC-Name<br>¹H NMR | Synth. From<br>Yield<br>LC-MS method |
|---|---|---|
| 04-19 | 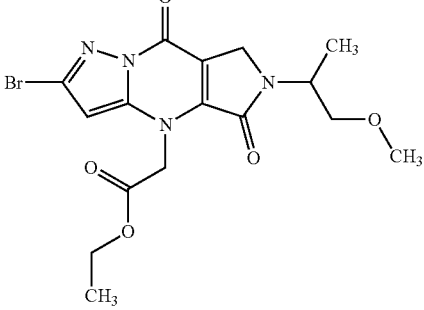<br>ethyl {2-bromo-6-[(±)-1-methoxypropan-2-yl]-5,8-dioxo-5,6,7,8-tetrahydro-4H-pyrazolo[1,5-a]pyrrolo[3,4-d]pyrimidin-4-yl}acetate<br>¹H NMR (500 MHz, DMSO-d6) δ [ppm]: 6.91 (s, 1H), 5.39 (s, 2H), 4.50-4.28 (m, 3H), 4.19 (q, 2H), 3.56 (dd, 1H), 3.44 (dd, 1H), 3.26 (s, 3H), 1.28-1.12 (m, 6H). | Intermediate 03-17<br>78%<br>LC-MS (Analytical Method A) R$_t$ = 1.01 min, MS (ESIpos): m/z = 427/429 [M + H]⁺. |
| 04-20 | 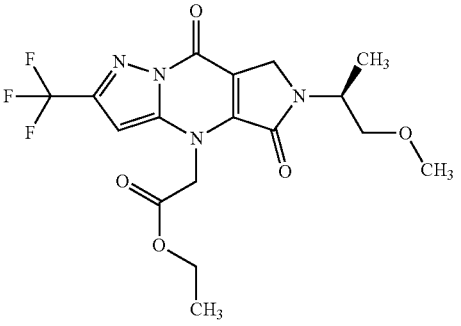<br>ethyl {6-[(2S)-1-methoxypropan-2-yl]-5,8-dioxo-2-(trifluoromethyl)-5,6,7,8-tetrahydro-4H-pyrazolo[1,5-a]pyrrolo[3,4-d]pyrimidin-4-yl}acetate<br>¹H NMR (250 MHz, Chloroform-d) δ [ppm]: 6.37 (s, 1H), 5.54 (d, 1H), 5.35 (d, 1H), 4.62-4.52 (m, 1H), 4.48 (d, 2H), 4.31 (q, 2H), 3.54 (d, 2H), 3.37 (s, 3H), 1.39-1.18 (m, 6H). | Intermediate 03-18<br>75%<br>LC-MS (Analytical Method A) R$_t$ = 1.09 min, MS (ESIpos): m/z = 417 [M + H]⁺. |
| 04-21 | 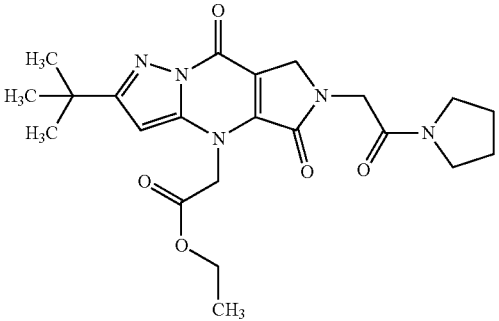<br>ethyl {2-tert-butyl-5,8-dioxo-6-[2-oxo-2-(pyrrolidin-1-yl)ethyl]-5,6,7,8-tetrahydro-4H-pyrazolo[1,5-a]pyrrolo[3,4-d]pyrimidin-4-yl}acetate<br>¹H NMR (250 MHz, Chloroform-d) δ [ppm]: 5.96 (s, 1H), 5.30 (s, 2H), 4.60 (s, 2H), 4.35-4.20 (m, 4H), 3.58-3.42 (m, 4H), 2.13-1.98 (m, 2H), 1.98-1.83 (m, 2H), 1.42 (s, 9H), 1.32-1.26 (m, 3H). | Intermediate 03-19<br>27%<br>LC-MS (Analytical Method A) R$_t$ = 1.04 min, MS (ESIpos): m/z = 444 [M + H]⁺. |

| Int. | Structure<br>IUPAC-Name<br>¹H NMR | Synth. From<br>Yield<br>LC-MS method |
|---|---|---|
| 04-22 | ethyl {6-[(2S)-1-methoxypropan-2-yl]-5,8-dioxo-2-(propan-2-yl)-5,6,7,8-tetrahydro-4H-pyrazolo[1,5-a]pyrrolo[3,4-d]pyrimidin-4-yl}acetate | Intermediate 03-20<br>72%<br>LC-MS (Analytical Method A) R$_t$ = 1.03 min, MS (ESIpos): m/z = 391 [M + H]⁺. |
| 04-23 | ethyl {6-[(2S)-1-methoxypropan-2-yl]-5,8-dioxo-2-(tetrahydro-2H-pyran-4-yl)-5,6,7,8-tetrahydro-4H-pyrazolo[1,5-a]pyrrolo[3,4-d]pyrimidin-4-yl}acetate<br>¹H NMR (500 MHz, Chloroform-d) δ [ppm]: 5.90 (s, 1H), 5.50-5.21 (m, 2H), 4.58-4.50 (m, 1H), 4.49-4.34 (m, 2H), 4.31-4.20 (m, 2H), 4.08-4.01 (m, 2H), 3.56-3.49 (m, 4H), 3.33 (s, 3H), 3.11 (tt, 1H), 1.99-1.92 (m, 2H), 1.89-1.80 (m, 2H), 1.33-1.27 (m, 6H). | Intermediate 03-21<br>67%<br>LC-MS (Analytical Method A) R$_t$ = 0.97 min, MS (ESIpos): m/z = 433.2 [H + H]⁺. |
| 04-24 | ethyl {6-[(2S)-1-methoxypropan-2-yl]-2-methyl-5,8-dioxo-5,6,7,8-tetrahydro-4H-pyrazolo[1,5-a]pyrrolo[3,4-d]pyrimidin-4-yl}acetate<br>¹H NMR (250 MHz, DMSO-d6) δ [ppm]: 6.41 (s, 1H), 5.38 (s, 2H), 4.48-4.28 (m, 3H), 4.23-4.12 (m, 2H), 3.56 (dd, 1H), 3.43 (dd, 1H), 3.26 (s, 3H), 2.33 (s, 3H), 1.26-1.17 (m, 6H). | Intermediate 03-22<br>74%<br>LC-MS (Analytical Method A) R$_t$ = 1.03 min, MS (ESIpos): m/z = 363 [M + H]⁺. |

| Int. | Structure / IUPAC-Name / ¹H NMR | Synth. From / Yield / LC-MS method |
|---|---|---|
| 04-25 | 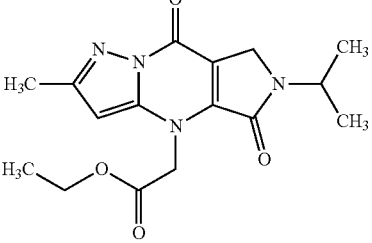<br>ethyl [2-methyl-5,8-dioxo-6-(propan-2-yl)-5,6,7,8-tetrahydro-4H-pyrazolo[1,5-a]pyrrolo[3,4-d]pyrimidin-4-yl]acetate<br>¹H NMR (500 MHz, DMSO-d6) δ [ppm]: 6.40 (s, 1H), 5.37 (s, 2H), 4.37 (s, 2H), 4.33-4.27 (m, 1H), 4.17 (q, 2H), 2.32 (s, 3H), 1.23 (d, 6H), 1.22 (d, 3H). | Intermediate 03-23<br>68%<br>LC-MS (Analytical Method A) R$_t$ = 0.97 min, MS (ESIpos): m/z = 333 [M + H]⁺. |
| 04-26 | 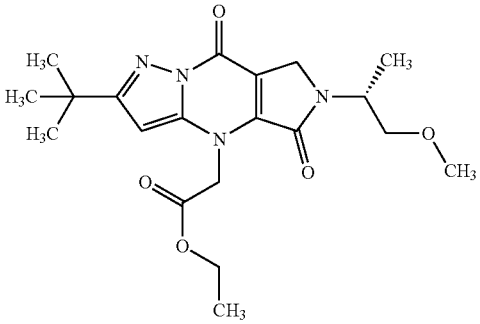<br>ethyl {2-tert-butyl-6-[(2R)-1-methoxypropan-2-yl]-5,8-dioxo-5,6,7,8-tetrahydro-4H-pyrazolo[1,5-a]pyrrolo[3,4-d]pyrimidin-4-yl}acetate<br>¹H NMR (500 MHz, Chloroform-d) δ [ppm]: 5.92 (s, 1H), 5.48-5.20 (m, 2H), 4.58-4.50 (m, 1H), 4.47-4.33 (m, 2H), 4.27 (q, 2H), 3.52-3.48 (m, 2H), 3.33 (s, 3H), 1.39 (s, 9H), 1.34-1.28 (m, 6H). | Intermediate 03-24<br>34%<br>LC-MS (Analytical Method A) R$_t$ 1.09 min, MS (ESIpos): m/z = 405 [M + H]⁺. |
| 04-27 | 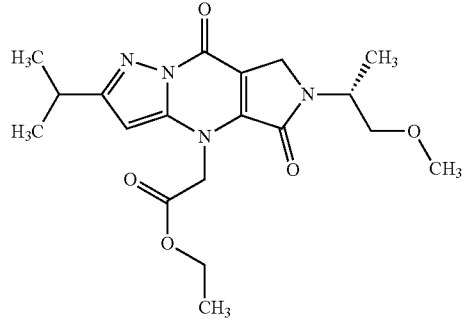<br>ethyl {6-[(2R)-1-methoxypropan-2-yl]-5,8-dioxo-2-(propan-2-yl)-5,6,7,8-tetrahydro-4H-pyrazolo[1,5-a]pyrrolo[3,4-d]pyrimidin-4-yl}acetate<br>¹H NMR (500 MHz, Chloroform-d) δ [ppm]: 5.89 (s, 1H), 5.47-5.20 (m, 2H), 4.58-4.50 (m, 1H), 4.47-4.34 (m, 2H), 4.29-4.20 (m, 3H), 3.51-3.41 (m, 2H), 3.33 (s, 3H), 1.36-1.23 (m, 12H). | Intermediate 03-25<br>15%<br>LC-MS (Analytical Method A) R$_t$ = 1.04 min, MS (ESIpos): m/z = 391 [M + H]⁺. |

| Int. | Structure<br>IUPAC-Name<br>¹H NMR | Synth. From<br>Yield<br>LC-MS method |
|---|---|---|
| 04-28 | 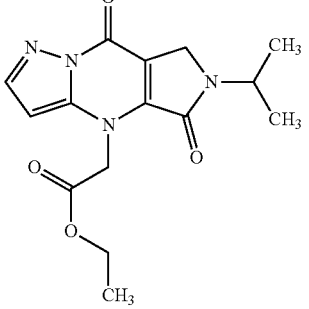<br>ethyl [5,8-dioxo-6-(propan-2-yl)-5,6,7,8-tetrahydro-4H-pyrazolo[1,5-a]pyrrolo[3,4-d]pyrimidin-4-yl]acetate<br>¹H NMR (500 MHz, DMSO-d6) δ [ppm]: 8.02 (d, 1H), 6.62 (d, 1H), 5.44 (s, 2H), 4.40 (s, 2H), 4.32 (hept, 1H), 4.18 (q, 2H), 1.25 (d, 6H), 1.22 (t, 3H). | Intermediate 03-26<br>37%<br>LC-MS (Analytical Method A) $R_t$ = 0.91 min, MS (ESIpos):<br>m/z = 319.0 [H + H]⁺. |
| 04-29 | 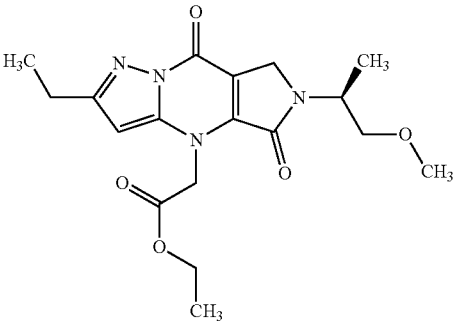<br>ethyl {2-ethyl-6-[(2S)-1-methoxypropan-2-yl]-5,8-dioxo-5,6,7,8-tetrahydro-4H-pyrazolo[1,5-a]pyrrolo[3,4-d]pyrimidin-4-yl}acetate<br>¹H NMR (250 MHz, Chloroform-d) δ [ppm]: 5.92 (s, 1H), 5.47 (d,), 5.36-5.17 (m, 1H), 4.57 (m, 1H), 4.43 (d, 1H), 4.36-4.13 (m, 3H), 3.52 (d, 1H), 3.35 (s, 3H), 2.84 (q, 2H), 1.38-1.27 (m, 9H). | Intermediate 03-27<br>70%<br>LC-MS (Analytical Method A) $R_t$ = 1.10 min, MS (ESIpos):<br>m/z = 377 [M + H]⁺. |
| 04-30 | 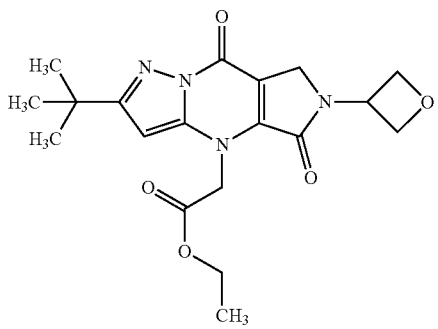<br>ethyl [2-tert-butyl-6-(oxetan-3-yl)-5,8-dioxo-5,6,7,8-tetrahydro-4H-pyrazolo[1,5-a]pyrrolo[3,4-d]pyrimidin-4-yl]acetate<br>¹H NMR (250 MHz, Chloroform-d) δ [ppm]: 5.98 (s, 1H), 5.48 (p, 1H), 5.30 (s, 2H), 4.98 (dd, 2H), 4.88 (dd, 2H), 4.69 (s, 2H), 4.29 (q, 2H), 1.42 (s, 9H), 1.32 (t, 3H). | Intermediate 03-28<br>75%<br>LC-MS (Analytical Method A) $R_t$ = 1.11 min, MS (ESIpos):<br>m/z = 389 [M + H]⁺. |

| Int. | Structure / IUPAC-Name / ¹H NMR | Synth. From / Yield / LC-MS method |
|---|---|---|
| 04-31 | ethyl [2-tert-butyl-6-(2-methoxyethyl)-5,8-dioxo-5,6,7,8-tetrahydro-4H-pyrazolo[1,5-a]pyrrolo[3,4-d]pyrimidin-4-yl]acetate<br>¹H NMR (500 MHz, DMSO-d6) δ [ppm]: 6.60 (s, 1H), 5.36 (s, 2H), 4.42 (s, 2H), 4.18 (q, 2H), 3.66 (t, 2H), 3.56 (t, 2H), 3.27 (s, 3H), 1.31 (s, 9H), 1.21 (t, 3H). | Intermediate 03-29<br>94%<br>LC-MS (Analytical Method A) $R_t$ = 1.05 min, MS (ESIpos): m/z = 391 [M + H]⁺. |
| 04-32 | ethyl {6-[(1S)-1-cyclopropylethyl]-2-methyl-5,8-dioxo-5,6,7,8-tetrahydro-4H-pyrazolo[1,5-a]pyrrolo[3,4-d]pyrimidin-4-yl}acetate<br>¹H NMR (500 MHz, DMSO-d6) δ [ppm]: 6.41 (s, 1H), 5.37 (s, 2H), 4.52-4.43 (m, 2H), 4.16 (q, 2H), 3.55-3.43 (m, 1H), 2.32 (s, 3H), 1.28 (d, 3H), 1.21-1.14 (m, 4H), 0.60-0.53 (m, 1H), 0.46-0.32 (m, 2H), 0.25-0.19 (m, 1H). | Intermediate 03-30<br>91%<br>LC-MS (Analytical Method A) $R_t$ = 1.02 min, MS (ESIpos): m/z = 359 [M + H]⁺. |
| 04-33 | ethyl [6-(2-hydroxy-2-methylpropyl)-5,8-dioxo-2-(propan-2-yl)-5,6,7,8-tetrahydro-4H-pyrazolo[1,5-a]pyrrolo[3,4-d]pyrimidin-4-yl]acetate<br>¹H NMR (250 MHz, Chloroform-d) δ [ppm]: 5.94 (s, 1H), 5.34 (s, 2H), 4.64 (s, 2H), 4.28 (q, 2H), 3.59 (s, 2H), 3.20 (m, 1H), 2.18 (br. m, 1H), 1.64 (br. m, 1H), 1.37-1.28 (m, 14H). | Intermediate 03-31<br>64%<br>LC-MS (Analytical Method A) $R_t$ = 1.05 min, MS (ESIpos): m/z = 391 [M + H]⁺. |

| Int. | Structure<br>IUPAC-Name<br>¹H NMR | Synth. From<br>Yield<br>LC-MS method |
|---|---|---|
| 04-34 | ethyl {6-[(2R)-1-methoxypropan-2-yl]-2-methyl-5,8-dioxo-5,6,7,8-tetrahydro-4H-pyrazolo[1,5-a]pyrrolo[3,4-d]pyrimidin-4-yl}acetate<br>¹H NMR (250 MHz, DMSO-d6) δ [ppm]: 6.41 (s, 1H), 5.38 (s, 2H), 4.52-4.28 (m, 3H), 4.18 (q, 2H), 3.62-3.52 (m, 1H), 3.43 (dd, 1H), 3.26 (s, 3H), 2.33 (s, 3H), 1.26-1.18 (m, 6H). | Intermediate 03-32<br>75%<br>LC-MS (Analytical Method A) R$_t$ = 0.98 min, MS (ESIpos):<br>m/z = 363.1 [H + H]⁺. |
| 04-35 | ethyl {6-[(2S)-butan-2-yl]-2-methyl-5,8-dioxo-5,6,7,8-tetrahydro-4H-pyrazolo[1,5-a]pyrrolo[3,4-d]pyrimidin-4-yl}acetate<br>¹H NMR (250 MHz, Chloroform-d) δ [ppm]: 5.91 (s, 1H), 5.42 (d, 1H), 5.32 (d, 1H), 4.35-4.20 (m, 5H), 2.47 (s, 3H), 1.75-1.61 (m, 2H), 1.36-1.27 (m, 6H), 0.92 (t, 3H). | Intermediate 03-33<br>94%<br>LC-MS (Analytical Method A) R$_t$ = 1.13 min, MS (ESIpos):<br>m/z = 347 [M + H]⁺. |
| 04-36 | ethyl {2-tert-butyl-6-[(2S)-2-hydroxypropyl]-5,8-dioxo-5,6,7,8-tetrahydro-4H-pyrazolo[1,5-a]pyrrolo[3,4-d]pyrimidin-4-yl}acetate<br>¹H NMR (250 MHz, DMSO-d6) δ [ppm]: 6.60 (s, 1H), 5.41-5.29 (m, 2H), 5.01-4.79 (m, 1H), 4.49-4.45 (m, 2H), 4.03 (q, 2H), 3.98-3.83 (m, 1H), 3.46-3.36 (m, 2H), 1.31 (s, 9H), 1.26-1.17 (m, 3H), 1.06 (d, 3H). | Intermediate 03-34<br>61%<br>LC-MS (Analytical Method A) R$_t$ = 1.10 min, MS (ESIpos):<br>m/z = 391 [M + H]⁺. |

-continued

| Int. | Structure<br>IUPAC-Name<br>¹H NMR | Synth. From<br>Yield<br>LC-MS method |
|---|---|---|
| 04-37 | ethyl {6-[(1R)-1-cyclopropylethyl]-2-methyl-5,8-dioxo-5,6,7,8-tetrahydro-4H-pyrazolo[1,5-a]pyrrolo[3,4-d]pyrimidin-4-yl}acetate<br>¹H NMR (250 MHz, Chloroform-d) δ [ppm]: 5.91 (s, 1H), 5.42 (d, 1H), 5.31 (d, 1H), 4.56 (d, 1H), 4.42 (d, 1H), 4.28 (q, 2H), 3.74-3.55 (m, 1H), 2.47 (s, 3H), 1.38-1.28 (m, 6H), 1.11-0.96 (m, 1H), 0.77-0.63 (m, 1H), 0.59-0.47 (m, 1H), 0.47-0.31 (m, 2H). | Intermediate 03-35<br>91%<br>LC-MS (Analytical Method A) $R_t$ = 1.15 min, MS (ESIpos): m/z = 359 [M + H]⁺. |
| 04-38 | tert-butyl [2-cyclopropyl-5,8-dioxo-6-(propan-2-yl)-5,6,7,8-tetrahydro-4H-pyrazolo[1,5-a]pyrrolo[3,4-d]pyrimidin-4-yl]acetate | Intermediate 03-36<br>49%<br>LC-MS (Analytical Method K, 0-1.1 min 5-100% B, 1.1-1.7 min 100% B):<br>$R_t$ = 1.02 min; MS (ESIpos): m/z = 387 [M + H]⁺. |
| 04-39 | tert-butyl [2-(methoxymethyl)-5,8-dioxo-6-(propan-2-yl)-5,6,7,8-tetrahydro-4H-pyrazolo[1,5-a]pyrrolo[3,4-d]pyrimidin-4-yl]acetate<br>¹H-NMR (400 MHz, CD3OD-d6) δ [ppm]: 1.33 (d, 6H), 1.46 (s, 9H), 3.41 (s, 3H), 4.39 (s, 2H), 4.41-4.46 (m, 1H), 4.55 (s, 2H), 5.31 (s, 2H), 6.41 (s, 1H). | Intermediate 03-42<br>26%<br>LC-MS (Analytical Method K, 0-1.2 min 5-95% B, 1.2-1.7 min 95% B): $R_t$ = 2.51 min; MS (ESIpos): m/z = 391 [M + H]⁺. |

| Int. | Structure<br>IUPAC-Name<br>¹H NMR | Synth. From<br>Yield<br>LC-MS method |
|---|---|---|
| 04-40 | methyl [2-bromo-5,8-dioxo-6-(propan-2-yl)-5,6,7,8-tetrahydro-4H-pyrazolo[1,5-a]pyrrolo[3,4-d]pyrimidin-4-yl]acetate<br>¹H-NMR (300 MHz, DMSO-d$_6$) δ [ppm]: 1.23 (d, 6H), 3.72 (s, 3H), 4.25-4.34 (m, 1H), 4.41 (s, 2H), 5.41 (br, 2H), 6.90 (s, 1H). | Intermediate 03-45<br>75%<br>LC-MS (Analytical Method L, 0-1.25 min 10-95% B, 1.25-1.75 min 95% B): R$_t$ = 1.26 min; MS (ESIpos): m/z = 383 [M + H]⁺. |
| 04-41 | methyl {2-ethyl-5,8-dioxo-6-[(±)-tetrahydrofuran-3-ylmethyl]-5,6,7,8-tetrahydro-4H-pyrazolo[1,5-a]pyrrolo[3,4-d]pyrimidin-4-yl}acetate<br>¹H-NMR (300 MHz, DMSO-d6) δ [ppm]: 2.00 (t, 3H), 1.52-1.62 (m, 1H), 1.95-2.01 (m, 1H), 2.60-2.73 (m, 3H), 3.39-3.43 (m, 1H), 3.46-3.58 (m, 2H), 3.60-3.79 (m, 6H), 4.44 (s, 2H), 5.57 (d, 2H), 6.49 (s, 1H). | Intermediate 03-47<br>27%<br>LC-MS (Analytical Method L, 0-2.5 min 10-40% B, 2.5-3.4 min 40-95% B, 3.4-4.15 min 95% B): R$_t$ = 1.56 min; MS (ESIpos): m/z = 375 [M + H]⁺. |
| 04-42 | methyl {2-ethyl-5,8-dioxo-6-[(±)-tetrahydrofuran-2-ylmethyl]-5,6,7,8-tetrahydro-4H-pyrazolo[1,5-a]pyrrolo[3,4-d]pyrimidin-4-yl}acetate<br>¹H-NMR (400 MHz, CDCl3) δ [ppm]: 1.31 (t, 3H), 1.55-1.62 (m, 1H), 1.87-1.94 (m, 2H), 2.00-2.07 (m, 1H), 2.84 (q, 2H), 3.45-3.50 (m, 1H), 3.72-3.91 (m, 5H), 4.07-4.11 (m, 1H), 4.47 (d, 1H), 4.65 (d, 1H), 5.35-5.37 (m, 2H), 5.91 (s, 1H). | Intermediate 03-48<br>47%<br>LC-MS (Analytical Method K, 0-2.0 min 5-95% B, 2.0-2.7 min 95% B): R$_t$ = 1.02 min; MS (ESIpos): m/z = 375 [M + H]⁺. |

| Int. | Structure IUPAC-Name ¹H NMR | Synth. From Yield LC-MS method |
|---|---|---|
| 04-43 | 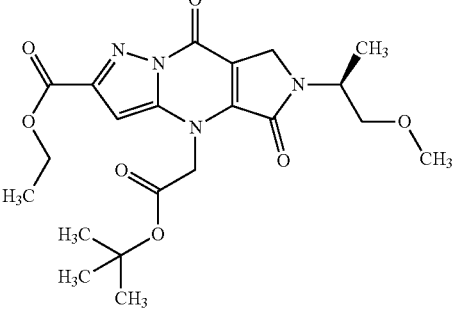<br>ethyl 4-(2-tert-butoxy-2-oxoethyl)-6-[(2S)-1-methoxypropan-2-yl]-6,8-dioxo-5,6,7,8-tetrahydro-4H-pyrazolo[1,5-a]pyrrolo[3,4-d]pyrimidine-2-carboxylate<br>¹H NMR (250 MHz, CDCl3) δ [ppm]: 1.32 (d, 3H), 1.43 (t, 3H), 1.48 (s, 9H), 3.34 (s, 3H), 3.51 (d, 2H), 4.37-4.61 (m, 5H), 5.20 (d, 1H), 5.39 (d, 1H), 6.62 (s, 1H). | Intermediate 03-60<br>53%<br>LC-MS (Analytical Method A): $R_t$ = 1.13 min; MS (ESIpos): m/z = 449 [M + H]⁺. |
| 04-44 | 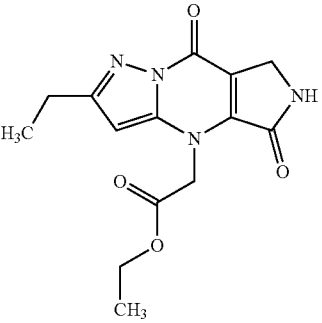<br>ethyl (2-ethyl-5,8-dioxo-5,6,7,8-tetrahydro-4H-pyrazolo[1,5-a]pyrrolo[3,4-d]pyrimidin-4-yl)acetate<br>¹H-NMR (300 MHz, DMSO-d6) δ [ppm]: 1.19-1.26 (m, 6H), 2.70 (q, 2H), 4.18 (q, 2H), 4.26 (s, 2H), 5.36 (s, 2H), 6.46 (s, 1H), 9.41 (br, 1H). | Intermediate 03-58<br>54%<br>LC-MS (Analytical Method K, 0-2.2 min 5-95% B, 2.2-3.1 min 95% B): $R_t$ = 1.14 min; MS (ESIpos): m/z = 305 [M + H]⁺. |
| 04-45 | 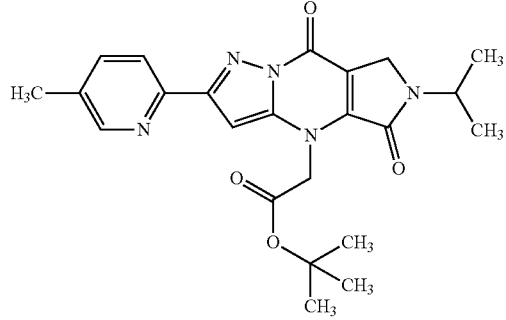<br>tert-butyl [2-(5-methylpyridin-2-yl)-5,8-dioxo-6-(propan-2-yl)-5,6,7,8-tetrahydro-4H-pyrazolo[1,5-a]pyrrolo[3,4-d]pyrimidin-4-yl]acetate<br>¹H-NMR (500 MHz, DMSO-d6) δ [ppm]: 1.25 (d, 6H), 1.42 (s, 9H), 2.37 (s, 3H), 4.31 (hept, 1H), 4.42 (s, 2H), 5.38 (s, 2H), 7.16 (s, 1H), 7.76 (dd, 1H), 8.06 (d, 1H), 8.52 (s, 1H). | Intermediate 03-84<br>54%<br>LC-MS (Analytical Method A): $R_t$ = 1.13 min; MS (ESIpos): m/z = 438 [M + H]⁺. |

-continued

| Int. | Structure<br>IUPAC-Name<br>¹H NMR | Synth. From<br>Yield<br>LC-MS method |
|---|---|---|
| 04-46 | 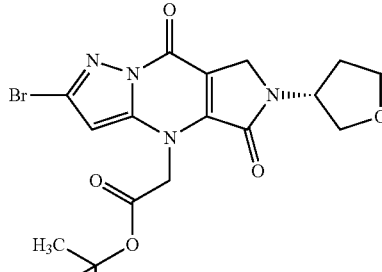<br>tert-butyl {2-bromo-5,8-dioxo-6-[(3R)-oxolan-3-yl]-5,6,7,8-tetrahydro-4H-pyrazolo[1,5-a]pyrrolo[3,4-d]pyrimidin-4-yl}acetate<br>¹H-NMR (250 MHz, Chloroform-d) δ [ppm]: 1.49 (s, 9H), 1.94-2.15 (m, 1H), 2.28-2.51 (m, 1H), 3.75-3.94 (m, 3H), 4.02-4.21 (m, 1H), 4.38 (d, 1H), 4.49 (d, 1H), 4.86-5.04 (m, 1H), 5.10-5.31 (m, 2H), 6.13 (s, 1H). | Intermediate 03-96<br>38%<br>LC-MS (Analytical Method A):<br>$R_t$ = 2.61min; MS (ESIpos): m/z = 453.0 [H + H]⁺. |

Intermediate 04-47 ethyl(6-{2-[(tert-butoxycarbonyl)amino]ethyl}-2-ethyl-5,8-dioxo-5,6,7,8-tetrahydro-4H-pyrazolo[1,5-a]pyrrolo[3,4-d]pyrimidin-4-yl)acetate

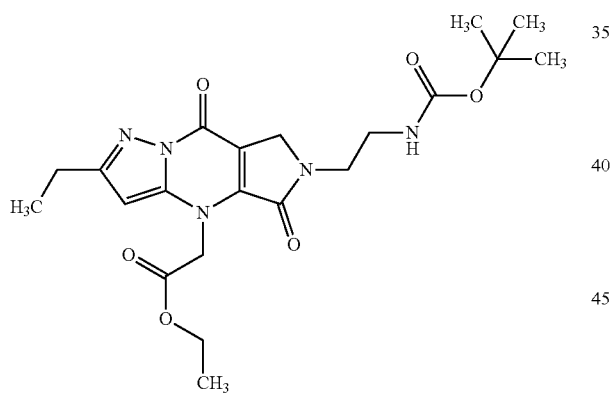

To a solution of ethyl(2-ethyl-5,8-dioxo-5,6,7,8-tetrahydro-4H-pyrazolo[1,5-a]pyrrolo[3,4-d]pyrimidin-4-yl)acetate (950 mg, 3.12 mmol) (intermediate 04-44) in N,N-dimethylformamide (20 ml) were added tert-butyl 2-bromoethylcarbamate (1.05 g, 4.68 mmol), and Cs₂CO₃ (3.05 g, 9.37 mmol). The reaction mixture was stirred at 60° C. for 25 min. After cooling to rt, the solvent was removed in vacuo and the residue was purified by silica gel column chromatography (petroleum ether: ethyl acetate=5:2) to give 520 mg (37% yield) of the title compound.

¹H-NMR (400 MHz, CDCl3) δ [ppm]: 1.11-1.23 (m, 6H), 1.33 (s, 9H), 2.75 (q, 2H), 3.34-3.35 (m, 2H), 3.62-3.63 (m, 2H), 4.18 (q, 2H), 4.39 (s, 2H), 5.26 (s, 2H), 5.85 (s, 1H).

LC-MS (Analytical Method O, 0-2.00 min 5-100% B, 2.00-2.80 min 100% B): $R_t$=1.13 min; MS (ESIpos): m/z=448 [M+H]⁺.

Intermediate 04-48 methyl [2-(3,6-dihydro-2H-pyran-4-yl)-5,8-dioxo-6-(propan-2-yl)-5,6,7,8-tetrahydro-4H-pyrazolo[1,5-a]pyrrolo[3,4-d]pyrimidin-4-yl]acetate

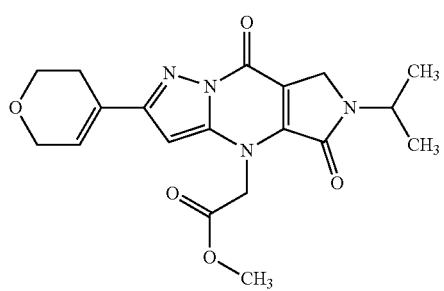 [SMILES: COC(=O)Cn1c2c(c(=O)n3nc(C4=CCOCC4)cc13)CN(C(C)C)C2=O]

To a solution of methyl [2-bromo-5,8-dioxo-6-(propan-2-yl)-5,6,7,8-tetrahydro-4H-pyrazolo[1,5-a]pyrrolo[3,4-d]pyrimidin-4-yl]acetate (1.9 g, 4.96 mmol) (intermediate 04-40) in dioxane/water (v:v=5:1, 12 ml) was added K₂CO₃ (1.70 g, 11.9 mmol), Pd(dppf)Cl₂ (320 mg, 0.5 mmol) and 4-(4,4,5,5-tetramethyl-1,3,2-dioxaborolan-2-yl)-3,6-dihydro-2H-pyran (2.08 g, 9.92 mmol). The resulting mixture was stirred at 60° C. for 40 min under nitrogen atmosphere. After allowing to cool to rt, water was added and the resulting solution was extracted with ethyl acetate. The combined organic layer was dried (Na₂SO₄), filtered and concentrated under reduced pressure. The residue was washed with petroleum ether/ethyl acetate (v:v=1:1) to give 1.3 g (84% yield) of the title compound.

¹H NMR (300 MHz, DMSO-d₆): δ [ppm]1.24 (d, 6H), 2.49-2.51 (m, 2H), 3.70 (s, 3H), 3.79-3.83 (m, 2H), 4.25-4.38 (m, 5H), 5.41 (br, 2H), 6.52 (s, 1H), 6.38 (s, 1H).

LC-MS (Analytical Method L, 0-1.25 min 10-95% B, 1.25-1.75 min 95% B): $R_t$=1.21 min; MS (ESIpos): m/z=387 [M+H]⁺.

Intermediate 04-49 methyl [5,8-dioxo-6-(propan-2-yl)-2-(tetrahydro-2H-pyran-4-yl)-5,6,7,8-tetrahydro-4H-pyrazolo[1,5-a]pyrrolo[3,4-d]pyrimidin-4-yl]acetate

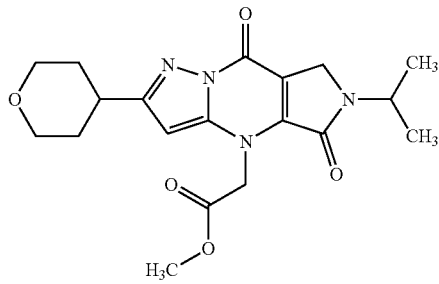 [SMILES: COC(=O)Cn1c2c(c(=O)n3nc(C4CCOCC4)cc13)CN(C(C)C)C2=O]

To a solution of methyl [2-(3,6-dihydro-2H-pyran-4-yl)-5,8-dioxo-6-(propan-2-yl)-5,6,7,8-tetrahydro-4H-pyrazolo[1,5-a]pyrrolo[3,4-d]pyrimidin-4-yl]acetate (1.3 g, 3.36 mmol) (intermediate 04-48) in methanol (10 ml) was added palladium/carbon (10%, 200 mg). The resulting mixture was stirred at rt for overnight under hydrogen atmosphere (about 2 atmospheres). Upon completion of the reaction, the catalyst was removed by filtration and the filtrate was concentrated in vacuo. The residue was purified with C18 reverse phase column chromatography (C18-silica gel, eluting with water (0.1% $NH_4HCO_3$)-acetonitrile, 9:1 to 2:3) to afford 1.05 g (69% yield) of the title compound as an off-white solid.

$^1$H NMR (300 MHz, $CD_3OD$): δ [ppm]1.30 (d, 6H), 1.83-1.94 (m, 4H), 3.00-3.09 (m, 1H), 3.52-3.59 (m, 2H), 3.82 (s, 3H), 3.99-4.03 (m, 2H), 4.35-4.45 (m, 3H), 5.43 (br, 2H), 6.39 (s, 1H).

LC-MS (Analytical Method L, 0-2.10 min 10-95% B, 2.10-2.70 min 95% B): $R_t$=1.15 min; MS (ESIpos): m/z=389 [M+H]$^+$.

Intermediate 05-01

{6-[(±)-butan-2-yl]-2-tert-butyl-5,8-dioxo-5,6,7,8-tetrahydro-4H-pyrazolo[1,5-a]pyrrolo[3,4-d]pyrimidin-4-yl}acetic acid

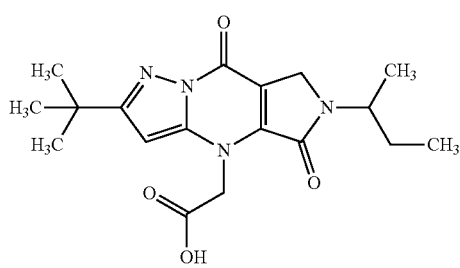 [SMILES: CCC(C)N1Cc2c(n(CC(=O)O)c3cc(C(C)(C)C)nn3c2=O)C1=O]

To a solution of ethyl {6-[(±)-butan-2-yl]-2-tert-butyl-5,8-dioxo-5,6,7,8-tetrahydro-4H-pyrazolo[1,5-a]pyrrolo[3,4-d]pyrimidin-4-yl}acetate (158 mg, 0.35 mmol) (intermediate 04) in methanol/tetrahydrofuran (1:1 v/v; 6 ml) was added 2 M aqueous lithium hydroxide solution (2.5 ml), and the reaction was stirred for 4 h. The reaction mixture was concentrated under reduced pressure, and the residue acidified to pH 4 with 2 M aqueous hydrogen chloride solution and extracted with dichloromethane (3×5 ml). The combined organics were dried ($MgSO_4$), filtered and concentrated under reduced pressure to afford 86.6 mg (47% yield) of the title compound as a pink gum.

LC-MS (Analytical Method A) $R_t$=1.03 min, MS (ESI-pos): m/z=361 [M+H]$^+$.

In analogy to the procedure described for Intermediate 05-01, the following intermediates were prepared from the appropriate ester starting materials.

| Int. | Structure<br>IUPAC-Name<br>$^1$H NMR | Synth. From<br>Yield<br>LC-MS method |
|---|---|---|
| 05-02 | ![structure]<br>{6-[butan-2-yl]-2-tert-butyl-5,8-dioxo-5,6,7,8-tetrahydro-4H-pyrazolo[1,5-a]pyrrolo[3,4-d]pyrimidin-4-yl}acetic acid (enantiomer 1) | Intermediate 04-01<br>83%<br>LC-MS (Analytical Method A):<br>$R_t$ = 1.00 min; m/z (ESI) = 361 [M + H]$^+$. |

| | Structure<br>IUPAC-Name | Synth. From |
|---|---|---|
| Int. | ¹H NMR | Yield<br>LC-MS method |
| 05-03 | {6-[butan-2-yl]-2-tert-butyl-5,8-dioxo-5,6,7,8-tetrahydro-4H-pyrazolo[1,5-a]pyrrolo[3,4-d]pyrimidin-4-yl}acetic acid (enantiomer 2) | Intermediate 04-02<br>52%<br>LC-MS (Analytical Method A):<br>R$_t$ = 0.99 min; m/z (ESI) = 361 [M + H]⁺. |
| 05-04 | [5,8-dioxo-2,6-di(propan-2-yl)-5,6,7,8-tetrahydro-4H-pyrazolo[1,5-a]pyrrolo[3,4-d]pyrimidin-4-yl]acetic acid<br>¹H NMR (500 MHz, DMSO-d6) δ [ppm]: 13.34 (s, 1H), 6.50 (s, 1H), 5.28 (s, 2H), 4.36 (s, 2H), 4.34-4.25 (m, 1H), 3.01 (hept, 1H), 1.26 (d, 6H), 1.24 (d, 6H). | Intermediate 04-03<br>47%<br>LC-MS (Analytical Method A)<br>R$_t$ = 0.90 min, MS (ESIpos):<br>m/z = 333.6 [M + H]⁺. |
| 05-05 | {2-tert-butyl-6-[(2S)-3-methylbutan-2-yl]-5,8-dioxo-5,6,7,8-tetrahydro-4H-pyrazolo[1,5-a]pyrrolo[3,4-d]pyrimidin-4-yl}acetic acid | Intermediate 04-04<br>80%<br>LC-MS (Analytical Method A)<br>R$_t$ = 1.02 min, MS (ESIpos):<br>m/z = 375 [M + H]⁺. |
| 05-06 | [2-tert-butyl-6-(cyclopropylmethyl)-5,8-dioxo-5,6,7,8-tetrahydro-4H-pyrazolo[1,5-a]pyrrolo[3,4-d]pyrimidin-4-yl]acetic acid<br>¹H NMR (500 MHz, Chloroform-d) δ [ppm]: 6.03 (s, 1H), 5.36 (br. s, 2H), 4.52 (s, 2H), 3.52 (s, 1H), 3.46 (d, 2H), 1.42 (s, 9H), 1.05 (m, 1H), 0.66 (m, 2H), 0.35 (m, 2H). | Intermediate 04-05<br>92%<br>LC-MS (Analytical Method A)<br>R$_t$ = 0.97 min, MS (ESIpos):<br>m/z = 359 [M + H]⁺. |

| Int. | Structure<br>IUPAC-Name<br>¹H NMR | Synth. From<br>Yield<br>LC-MS method |
|---|---|---|
| 05-07 | {6-[(2R)-butan-2-yl]-5,8-dioxo-2-(trifluoromethyl)-5,6,7,8-tetrahydro-4H-pyrazolo[1,5-a]pyrrolo[3,4-d]pyrimidin-4-yl}acetic acid<br>¹H NMR (250 MHz, DMSO-d6) δ [ppm]: 7.27 (s, 1H), 5.40 (s, 2H), 4.52-4.29 (m, 2H), 4.17-4.08 (m, 1H), 1.70-1.52 (m, 2H), 1.24 (d, 3H), 0.80 (t, 3H). | Intermediate 04-06<br>72%<br>LC-MS (Analytical Method A)<br>$R_t$ = 0.97 min, MS (ESIpos):<br>m/z = 373.0 [M + H]⁺. |
| 05-08 | [2-tert-butyl-5,8-dioxo-6-(propan-2-yl)-5,6,7,8-tetrahydro-4H-pyrazolo[1,5-a]pyrrolo[3,4-d]pyrimidin-4-yl]acetic acid<br>¹H NMR (500 MHz, DMSO-d6) δ [ppm]: 13.33 (s, 1H), 6.57 (s, 1H), 5.28 (s, 2H), 4.36 (s, 2H), 4.34-4.25 (m, 1H), 1.31 (s, 9H), 1.24 (d, 6H). | Intermediate 04-07<br>75%<br>LC-MS (Analytical Method D)<br>$R_t$ = 3.27 min, MS (ESIpos):<br>m/z = 347.05 [M + H]⁺. |
| 05-09 | (2-tert-butyl-6-cyclobutyl-5,8-dioxo-5,6,7,8-tetrahydro-4H-pyrazolo[1,5-a]pyrrolo[3,4-d]pyrimidin-4-yl)acetic acid<br>¹H NMR (500 MHz, DMSO-d6) δ [ppm]: 6.58 (s, 1H), 5.26 (s, 2H), 4.66-4.57 (m, 1H), 4.49 (s, 2H), 2.42-2.32 (m, 2H), 2.19-2.11 (m, 2H), 1.77-1.65 (m, 2H), 1.31 (s, 9H). | Intermediate 04-08<br>85%<br>LC-MS (Analytical Method A)<br>$R_t$ = 0.98 min, MS (ESIpos):<br>m/z = 359.05 [M + H]⁺. |
| 05-10 | {6-[(2S)-butan-2-yl]-5,8-dioxo-2-(trifluoromethyl)-5,6,7,8-tetrahydro-4H-pyrazolo[1,5-a]pyrrolo[3,4-d]pyrimidin-4-yl}acetic acid | Intermediate 04-09<br>85%<br>LC-MS (Analytical Method A)<br>$R_t$ = 0.97 min, MS (ESIpos):<br>m/z = 373 [M + H]⁺. |

| Int. | Structure<br>IUPAC-Name<br>¹H NMR | Synth. From<br>Yield<br>LC-MS method |
|---|---|---|
| 05-11 | 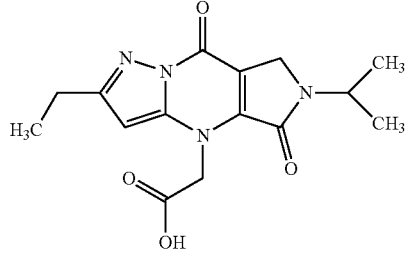<br>[2-ethyl-5,8-dioxo-6-(propan-2-yl)-5,6,7,8-tetrahydro-4H-pyrazolo[1,5-a]pyrrolo[3,4-d]pyrimidin-4-yl]acetic acid<br>¹H NMR (500 MHz, DMSO-d6) δ [ppm]: 13.34 (s, 1H), 6.46 (s, 1H), 5.29 (s, 2H), 4.37 (s, 2H), 4.35-4.26 (m, 1H), 2.70 (q, 2H), 1.27-1.23 (m, 9H). | Intermediate 04-10<br>62%<br>LC-MS (Analytical Method A)<br>$R_t$ = 0.83 min, MS (ESIpos):<br>m/z = 319 [M + H]⁺. |
| 05-12 | 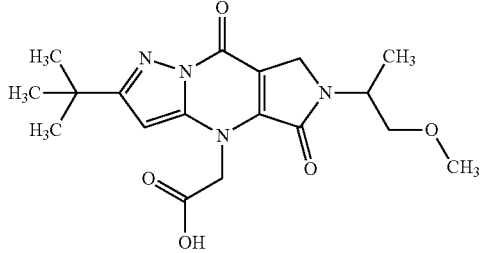<br>{2-tert-butyl-6-[(±)-1-methoxypropan-2-yl]-5,8-dioxo-5,6,7,8-tetrahydro-4H-pyrazolo[1,5-a]pyrrolo[3,4-d]pyrimidin-4-yl}acetic acid | Intermediate 04-11<br>70%<br>LC-MS (Analytical Method A)<br>$R_t$ = 0.90 min, MS (ESIpos):<br>m/z = 377 [M + H]⁺. |
| 05-13 | 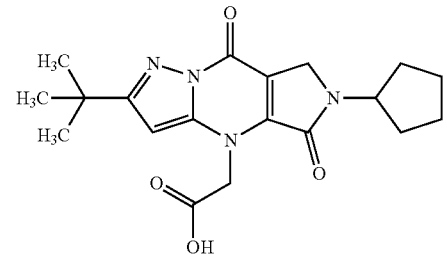<br>(2-tert-butyl-6-cyclopentyl-5,8-dioxo-5,6,7,8-tetrahydro-4H-pyrazolo[1,5-a]pyrrolo[3,4-d]pyrimidin-4-yl)acetic acid<br>¹H NMR (500 MHz, DMSO-d6) δ [ppm]: 13.31 (s, 1H), 6.59 (s, 1H), 5.29 (s, 2H), 4.45 (p, 1H), 4.40 (s, 2H), 1.95-1.86 (m, 2H), 1.79-1.66 (m, 4H), 1.64-1.57 (m, 2H), 1.32 (s, 9H). | Intermediate 04-12<br>67%<br>LC-MS (Analytical Method A)<br>$R_t$ = 1.02 min, MS (ESIpos):<br>m/z = 373 [M + H]⁺. |
| 05-14 | 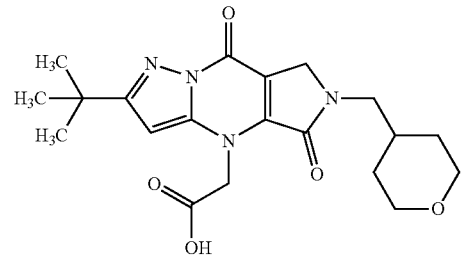<br>[2-tert-butyl-5,8-dioxo-6-(tetrahydro-2H-pyran-4-ylmethyl)-5,6,7,8-tetrahydro-4H-pyrazolo[1,5-a]pyrrolo[3,4-d]pyrimidin-4-yl]acetic acid<br>¹H NMR (500 MHz, Chloroform-d) δ [ppm]: 5.93 (s, 1H), 5.25 (s, 2H), 4.31 (s, 2H), 4.03-3.80 (m, 2H), 3.39 (d, 2H), 3.29 (m, 2H), 1.90 (m, 1H), 1.49 (m, 2H), 1.31 (s, 11H). | Intermediate 04-13<br>91%<br>LC-MS (Analytical Method F)<br>$R_t$ = 2.14, MS (ESIpos):<br>m/z = 403 [M + H]⁺. |

| Int. | Structure<br>IUPAC-Name<br>¹H NMR | Synth. From<br>Yield<br>LC-MS method |
|---|---|---|
| 05-15 | [5,8-dioxo-6-(propan-2-yl)-2-(trifluoromethyl)-5,6,7,8-tetrahydro-4H-pyrazolo[1,5-a]pyrrolo[3,4-d]pyrimidin-4-yl]acetic acid<br>¹H NMR (250 MHz, DMSO-d6) δ [ppm]: 7.28 (s, 1H), 5.41 (s, 2H), 4.46 (s, 2H), 4.43-4.25 (m, 1H), 1.26 (d, 6H). | Intermediate 04-14<br>63%<br>LC-MS (Analytical Method A)<br>$R_t$ = 0.92 min, MS (ESIpos):<br>m/z = 359 [M + H]⁺. |
| 05-16 | [2-tert-butyl-6-(2-hydroxy-2-methylpropyl)-5,8-dioxo-5,6,7,8-tetrahydro-4H-pyrazolo[1,5-a]pyrrolo[3,4-d]pyrimidin-4-yl]acetic acid | Intermediate 04-15<br>72%<br>LC-MS (Analytical Method A)<br>$R_t$ = 0.88 min, MS (ESIpos):<br>m/z = 377 [M + H]⁺. |
| 05-17 | [2-tert-butyl-5,8-dioxo-6-(tetrahydro-2H-pyran-4-yl)-5,6,7,8-tetrahydro-4H-pyrazolo[1,5-a]pyrrolo[3,4-d]pyrimidin-4-yl]acetic acid | Intermediate 04-16<br>81%<br>LC-MS (Analytical Method A)<br>$R_t$ = 0.89 min, MS (ESIpos):<br>m/z = 389 [M + H]⁺. |
| 05-18 | {6-[2-(benzyloxy)ethyl]-2-tert-butyl-5,8-dioxo-5,6,7,8-tetrahydro-4H-pyrazolo[1,5-a]pyrrolo[3,4-d]pyrimidin-4-yl}acetic acid<br>¹H NMR (500 MHz, DMSO-d6) δ [ppm]: 13.38 (s, 1H), 7.36-7.19 (m, 5H), 6.60 (s, 1H), 5.28 (s, 2H), 4.50 (s, 2H), 4.40 (s, 2H), 3.74-3.64 (m, 4H), 1.31 (s, 9H). | Intermediate 04-17<br>65%<br>LC-MS (Analytical Method A)<br>$R_t$ = 1.16 min, MS (ESIpos):<br>m/z = 439.1 [M + H]⁺. |

| Int. | Structure / IUPAC-Name / ¹H NMR | Synth. From / Yield / LC-MS method |
|---|---|---|
| 05-19 | {2-tert-butyl-6-[(2S)-1-methoxypropan-2-yl]-5,8-dioxo-5,6,7,8-tetrahydro-4H-pyrazolo[1,5-a]pyrrolo[3,4-d]pyrimidin-4-yl}acetic acid | Intermediate 04-18<br>77%<br>LC-MS (Analytical Method A)<br>$R_t$ = 0.94 min, MS (ESIpos):<br>m/z = 377 [M + H]⁺. |
| 05-20 | {2-bromo-6-[(±)-1-methoxypropan-2-yl]-5,8-dioxo-5,6,7,8-tetrahydro-4H-pyrazolo[1,5-a]pyrrolo[3,4-d]pyrimidin-4-yl}acetic acid<br>¹H NMR (500 MHz, DMSO-d6) δ [ppm]: 6.91 (s, 1H), 5.31 (s, 2H), 4.55-4.25 (m, 3H), 3.56 (dd, 1H), 3.44 (dd, 1H), 3.26 (s, 3H), 1.21 (d, 3H). | Intermediate 04-19<br>75%<br>LC-MS (Analytical Method A)<br>$R_t$ = 0.81 min, MS (ESIpos):<br>m/z = 399.0/400.8 [M + H]⁺. |
| 05-21 | {6-[(2S)-1-methoxypropan-2-yl]-5,8-dioxo-2-(trifluoromethyl)-5,6,7,8-tetrahydro-4H-pyrazolo[1,5-a]pyrrolo[3,4-d]pyrimidin-4-yl}acetic acid<br>¹H NMR (500 MHz, Methanol-d4) δ [ppm]: 6.92 (s, 1H), 5.60-5.42 (m, 2H), 4.59-4.51 (m, 1H), 4.49 (d, 2H), 3.65 (m, 1H), 3.56 (m, 1H), 3.37 (s, 3H), 1.34 (d, 3H). | Intermediate 04-20<br>78%<br>LC-MS (Analytical Method A)<br>$R_t$ = 0.88 min, MS (ESIpos):<br>m/z = 389 [M + H]⁺. |
| 05-22 | {2-tert-butyl-5,8-dioxo-6-(2-oxo-2-(pyrrolidin-1-yl)ethyl]-5,6,7,8-tetrahydro-4H-pyrazolo[1,5-a]pyrrolo[3,4-d]pyrimidin-4-yl}acetic acid | Intermediate 04-21<br>74%<br>LC-MS (Analytical Method A)<br>$R_t$ = 0.88 min MS (ESIpos):<br>m/z = 416 [M + H]⁺. |

| Int. | Structure / IUPAC-Name / ¹H NMR | Synth. From / Yield / LC-MS method |
|---|---|---|
| 05-23 | {6-[(2S)-1-methoxypropan-2-yl]-5,8-dioxo-2-(propan-2-yl)-5,6,7,8-tetrahydro-4H-pyrazolo[1,5-a]pyrrolo[3,4-d]pyrimidin-4-yl}acetic acid | Intermediate 04-22<br>53%<br>LC-MS (Analytical Method A)<br>$R_t$ = 0.90 min, MS (ESIpos):<br>m/z = 363 [M + H]⁺. |
| 05-24 | {6-[(2S)-1-methoxypropan-2-yl]-5,8-dioxo-2-(tetrahydro-2H-pyran-4-yl)-5,6,7,8-tetrahydro-4H-pyrazolo[1,5-a]pyrrolo[3,4-d]pyrimidin-4-yl}acetic acid<br>¹H NMR (500 MHz, DMSO-d6) δ [ppm]: 13.37 (s, 1H), 6.55 (s, 1H), 5.29 (s, 2H), 4.44-4.27 (m, 3H), 3.96-3.90 (m, 2H), 3.59-3.42 (m, 4H), 3.26 (s, 3H), 2.98 (tt, 1H), 1.93-1.86 (m, 2H), 1.78-1.64 (m, 2H), 1.21 (d, 3H). | Intermediate 04-23<br>87%<br>LC-MS (Analytical Method A)<br>$R_t$ = 0.81 min, MS (ESIpos):<br>m/z = 405 [M + H]⁺. |
| 05-25 | {6-[(2S)-1-methoxypropan-2-yl]-2-methyl-5,8-dioxo-5,6,7,8-tetrahydro-4H-pyrazolo[1,5-a]pyrrolo[3,4-d]pyrimidin-4-yl}acetic acid<br>¹H NMR (500 MHz, DMSO-d6) δ [ppm]: 13.38 (s, 1H), 6.40 (s, 1H), 5.30 (s, 2H), 4.47-4.26 (m, 3H), 3.56 (dd, 1H), 3.44 (dd, 1H), 3.26 (s, 3H), 2.33 (s, 3H), 1.21 (d, 3H). | Intermediate 04-24<br>55%<br>LC-MS (Analytical Method A)<br>$R_t$ = 0.77 min, MS (ESIpos):<br>m/z = 335 [M + H]⁺. |
| 05-26 | [2-methyl-5,8-dioxo-6-(propan-2-yl)-5,6,7,8-tetrahydro-4H-pyrazolo[1,5-a]pyrrolo[3,4-d]pyrimidin-4-yl]acetic acid<br>¹H NMR (500 MHz, DMSO-d6) δ [ppm]: 6.38 (s, 1H), 5.28 (s, 2H), 4.36 (s, 2H), 4.34-4.23 (m, 1H), 2.32 (s, 3H), 1.24 (d, 6H). | Intermediate 04-25<br>58%<br>LC-MS (Analytical Method A)<br>$R_t$ = 0.76 min, MS (ESIpos):<br>m/z = 305 [M + H]⁺. |

| Int. | Structure / IUPAC-Name / ¹H NMR | Synth. From / Yield / LC-MS method |
|---|---|---|
| 05-27 | {2-tert-butyl-6-[(2R)-1-methoxypropan-2-yl]-5,8-dioxo-5,6,7,8-tetrahydro-4H-pyrazolo[1,5-a]pyrrolo[3,4-d]pyrimidin-4-yl}acetic acid<br>¹H NMR (500 MHz, Chloroform-d) δ [ppm]: 6.00 (s, 1H), 5.50-5.19 (m, 2H), 4.59-4.51 (m, 1H), 4.47-4.34 (m, 2H), 3.54-3.46 (m, 2H), 3.33 (s, 3H), 1.39 (s, 9H), 1.30 (d, 3H). | Intermediate 04-26<br>84%<br>LC-MS (Analytical Method A)<br>$R_t$ = 0.95 min, MS (ESIpos):<br>m/z = 377 [M + H]⁺. |
| 05-28 | {6-[(2R)-1-methoxypropan-2-yl]-5,8-dioxo-2-(propan-2-yl)-5,6,7,8-tetrahydro-4H-pyrazolo[1,5-a]pyrrolo[3,4-d]pyrimidin-4-yl}acetic acid<br>¹H NMR (500 MHz, Chloroform-d) δ [ppm]: 5.97 (s, 1H), 5.30 (s, 2H), 4.58-4.51 (m, 1H), 4.47-4.34 (m, 2H), 3.54-3.43 (m, 2H), 3.33 (s, 3H), 3.22-3.12 (m, 1H), 1.33-1.29 (m, 9H). | Intermediate 04-27<br>95%<br>LC-MS (Analytical Method A)<br>$R_t$ = 0.90 min, MS (ESIpos):<br>m/z = 363 [M + H]⁺. |
| 05-29 | [5,8-dioxo-6-(propan-2-yl)-5,6,7,8-tetrahydro-4H-pyrazolo[1,5-a]pyrrolo[3,4-d]pyrimidin-4-yl]acetic acid<br>¹H NMR (250 MHz, DMSO-d6) δ [ppm]: 13.39 (s, 1H), 8.01 (d, 1H), 6.61 (d, 1H), 5.36 (s, 2H), 4.40 (s, 2H), 4.36-4.24 (m, 1H), 1.26 (d, 6H). | Intermediate 04-28<br>57%<br>LC-MS (Analytical Method A)<br>$R_t$ = 0.71 min, MS (ESIpos):<br>m/z = 291 [M + H]⁺. |

| Int. | Structure<br>IUPAC-Name<br>¹H NMR | Synth. From<br>Yield<br>LC-MS method |
|---|---|---|
| 05-30 | 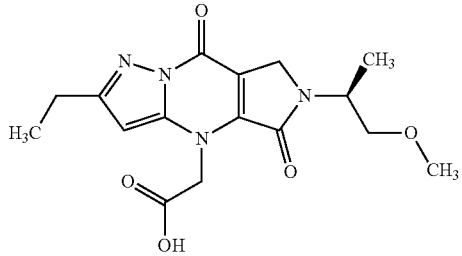<br>{2-ethyl-6-[(2S)-1-methoxypropan-2-yl]-5,8-dioxo-5,6,7,8-tetrahydro-4H-pyrazolo[1,5-a]pyrrolo[3,4-d]pyrimidin-4-yl}acetic acid<br>¹H NMR (500 MHz, Chloroform-d) δ [ppm]: 5.92 (s, 1H), 5.40 (d, 1H), 5.23 (d, 1H), 4.51-4.43 (m, 1H), 4.37 (d, 1H), 4.30 (d, 1H), 4.05 (q, 1H), 3.46-3.43 (m, 1H), 3.26 (s, 3H), 2.75 (q, 2H), 1.24 (t, 6H). | Intermediate 04-29<br>83%<br>LC-MS (Analytical Method A)<br>$R_t$ = 0.84 min, MS (ESIpos):<br>m/z = 349 [M + H]⁺. |
| 05-31 | 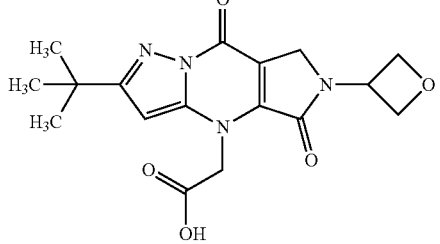<br>[2-tert-butyl-6-(oxetan-3-yl)-5,8-dioxo-5,6,7,8-tetrahydro-4H-pyrazolo[1,5-a]pyrrolo[3,4-d]pyrimidin-4-yl]acetic acid<br>¹H NMR (250 MHz, Chloroform-d) δ [ppm]: 5.96 (s, 1H), 5.43-5.32 (m, 1H), 5.23 (s, 2H), 4.84 (m, 4H), 4.58 (s, 2H), 1.32 (s, 9H). | Intermediate 04-30<br>59%<br>LC-MS (Analytical Method A)<br>$R_t$ = 0.86, MS (ESIpos):<br>m/z = 361 [M + H]⁺. |
| 05-32 | 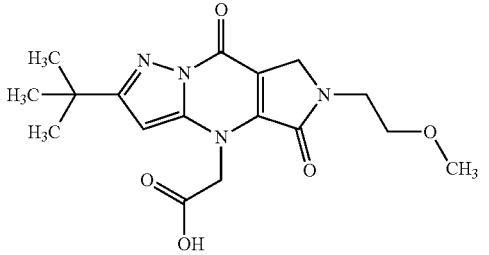<br>[2-tert-butyl-6-(2-methoxyethyl)-5,8-dioxo-5,6,7,8-tetrahydro-4H-pyrazolo[1,5-a]pyrrolo[3,4-d]pyrimidin-4-yl]acetic acid<br>¹H NMR (250 MHz, DMSO-d6) δ [ppm]: 6.59 (s, 1H), 5.28 (s, 2H), 4.41 (s, 2H), 3.67 (t, 2H), 3.57 (t, 2H), 3.27 (s, 3H), 1.31 (s, 9H). | Intermediate 04-31<br>94%<br>LC-MS (Analytical Method A)<br>$R_t$ = 0.89 min, MS (ESIpos):<br>m/z = 363.05 [M + H]⁺. |
| 05-33 | 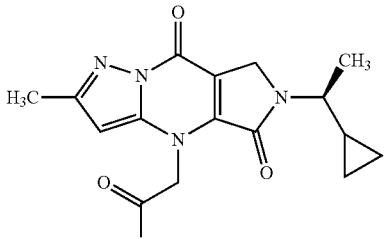<br>{6-[(1S)-1-cyclopropylethyl]-2-methyl-5,8-dioxo-5,6,7,8-tetrahydro-4H-pyrazolo[1,5-a]pyrrolo[3,4-d]pyrimidin-4-yl}acetic acid<br>¹H NMR (250 MHz, DMSO-d6) δ [ppm]: 6.39 (s, 1H), 5.29 (s, 2H), 4.47 (s, 2H), 3.55-3.40 (m, 1H), 2.32 (s, 3H), 1.33-1.08 (m, 4H), 0.64-0.12 (m, 4H). | Intermediate 04-32<br>89%<br>LC-MS (Analytical Method A)<br>$R_t$ = 0.85 min, MS (ESIpos):<br>m/z = 331 [M + H]⁺. |

| Int. | Structure / IUPAC-Name / ¹H NMR | Synth. From / Yield / LC-MS method |
|---|---|---|
| 05-34 | [6-(2-hydroxy-2-methylpropyl)-5,8-dioxo-2-(propan-2-yl)-5,6,7,8-tetrahydro-4H-pyrazolo[1,5-a]pyrrolo[3,4-d]pyrimidin-4-yl]acetic acid | Intermediate 04-33<br>34%<br>LC-MS (Analytical Method A)<br>$R_t$ = 0.89 min, MS (ESIpos):<br>m/z = 363 [M + H]⁺. |
| 05-35 | {6-[(2R)-1-methoxypropan-2-yl]-2-methyl-5,8-dioxo-5,6,7,8-tetrahydro-4H-pyrazolo[1,5-a]pyrrolo[3,4-d]pyrimidin-4-yl}acetic acid<br>¹H NMR (500 MHz, DMSO-d6) δ [ppm]: 13.38 (s, 1H), 6.40 (s, 1H), 5.30 (s, 2H), 4.49-4.20 (m, 3H), 3.56 (dd, 1H), 3.44 (dd, 1H), 3.26 (s, 3H), 2.33 (s, 3H), 1.21 (d, 3H). | Intermediate 04-34<br>59%<br>LC-MS (Analytical Method A)<br>$R_t$ = 0.80 min, MS (ESIpos):<br>m/z = 335 [M + H]⁺. |
| 05-36 | {6-[(2S)-butan-2-yl]-2-methyl-5,8-dioxo-5,6,7,8-tetrahydro-4H-pyrazolo[1,5-a]pyrrolo[3,4-d]pyrimidin-4-yl}acetic acid<br>¹H NMR (250 MHz, Chloroform-d) δ [ppm]: 7.70 (s, 1H), 5.99 (s, 1H), 5.48 (d, 1H), 5.36 (d, 1H), 4.37-4.27 (m, 3H), 2.47 (s, 3H), 1.77-1.55 (m, 2H), 1.31 (d, 3H), 0.92 (t, 3H). | Intermediate 04-35<br>70%<br>LC-MS (Analytical Method A)<br>$R_t$ = 0.97 min, MS (ESIpos):<br>m/z = 319 [M + H]⁺. |
| 05-37 | {2-tert-butyl-6-[(2S)-2-hydroxypropyl]-5,8-dioxo-5,6,7,8-tetrahydro-4H-pyrazolo[1,5-a]pyrrolo[3,4-d]pyrimidin-4-yl}acetic acid<br>¹H NMR (500 MHz, DMSO-d6) δ [ppm]: 6.60 (s, 1H), 5.34-5.23 (m, 2H), 4.47-4.43 (m, 2H), 3.95-3.89 (m, 1H), 3.46-3.40 (m, 2H), 1.31 (s, 9H), 1.06 (d, 3H). | Intermediate 04-36<br>99%<br>LC-MS (Analytical Method A)<br>$R_t$ = 0.98 min, MS (ESIpos):<br>m/z = 363.0 [M + H]⁺. |

| Int. | Structure<br>IUPAC-Name<br>¹H NMR | Synth. From<br>Yield<br>LC-MS method |
|---|---|---|
| 05-38 | 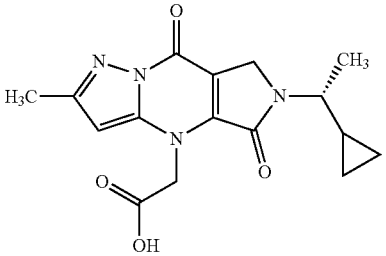<br>{6-[(1R)-1-cyclopropylethyl]-2-methyl-5,8-dioxo-5,6,7,8-tetrahydro-4H-pyrazolo[1,5-a]pyrrolo[3,4-d]pyrimidin-4-yl}acetic acid<br>¹H NMR (250 MHz, Chloroform-d) δ [ppm]: 6.74 (s, 1H), 5.68 (s, 1H), 5.24 (d, 1H), 5.11 (d, 1H), 3.53-3.31 (m, 1H), 4.33 (d, 1H), 4.20 (d, 1H), 2.24 (s, 3H), 1.13 (d, 3H), 0.89-0.72 (m, 1H), 0.55-0.39 (m, 1H), 0.39-0.22 (m, 1H), 0.22-0.09 (m, 2H). | Intermediate 04-37<br>57%<br>LC-MS (Analytical Method A)<br>$R_t$ = 0.99 min, MS (ESIpos):<br>m/z = 331 [M + H]⁺. |
| 05-39 | 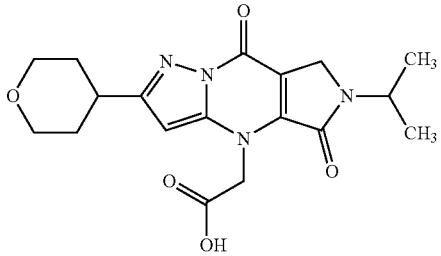<br>[5,8-dioxo-6-(propan-2-yl)-2-(tetrahydro-2H-pyran-4-yl)-5,6,7,8-tetrahydro-4H-pyrazolo[1,5-a]pyrrolo[3,4-d]pyrimidin-4-yl]acetic acid | Intermediate 04-49<br>34%<br>LC-MS (Analytical Method G):<br>$R_t$ = 0.71 min; MS (ESIpos):<br>m/z = 375 [M + H]⁺. |
| 05-40 | 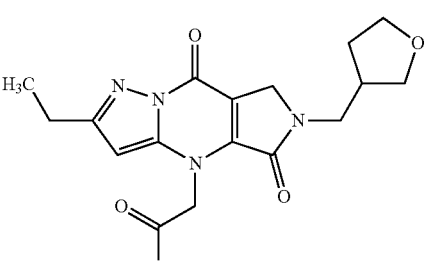<br>{2-ethyl-5,8-dioxo-6-[(±)-tetrahydrofuran-3-ylmethyl]-5,6,7,8-tetrahydro-4H-pyrazolo[1,5-a]pyrrolo[3,4-d]pyrimidin-4-yl}acetic acid<br>¹H NMR (400 MHz, DMSO-d6) δ [ppm]: 1.24 (t, 3H), 1.56 (dq, 1H), 1.90-2.01 (m, 1H), 2.55-2.65 (m, 1H), 2.69 (q, 2H), 3.40-3.45 (m, 1H), 3.50 (d, 2H), 3.58-3.79 (m, 3H), 4.38-4.48 (m, 2H), 5.28 (br s, 2H), 6.49 (s, 1H), 13.39 (br s, 1H). | Intermediate 04-41<br>77%<br>LC-MS (Analytical Method G):<br>$R_t$ = 0.64 min; MS (ESIpos):<br>m/z = 361 [M + H]⁺. |

| Int. | Structure<br>IUPAC-Name<br>¹H NMR | Synth. From<br>Yield<br>LC-MS method |
|---|---|---|
| 05-41 | 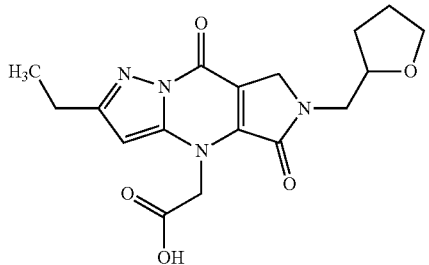<br>{2-ethyl-5,8-dioxo-6-[(±)-tetrahydrofuran-2-ylmethyl]-5,6,7,8-tetrahydro-4H-pyrazolo[1,5-a]pyrrolo[3,4-d]pyrimidin-4-yl}acetic acid<br>¹H NMR (400 MHz, DMSO-d6) δ [ppm]: 1.24 (t, 3H), 1.49-1.59 (m, 1H), 1.76-2.01 (m, 3H), 2.69 (q, 2H), 3.46-3.54 (m, 1H), 3.56-3.69 (m, 2H), 3.75-3.83 (m, 1H), 4.06 (qd, 1H), 4.39-4.50 (m, 2H), 5.28 (br s, 2H), 6.48 (s, 1H), 13.42 (br s, 1H). | Intermediate 04-42<br>65%<br>LC-MS (Analytical Method G):<br>$R_t$ = 0.68 min; MS (ESIpos):<br>m/z = 361 [M + H]⁺. |
| 05-42 | 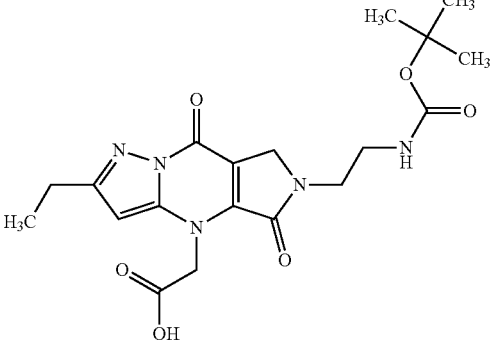<br>(6-{2-[(tert-butoxycarbonyl)amino]ethyl}-2-ethyl-5,8-dioxo-5,6,7,8-tetrahydro-4H-pyrazolo[1,5-a]pyrrolo[3,4-d]pyrimidin-4-yl)acetic acid<br>¹H-NMR (400 MHz, CDCl3) δ [ppm]: 1.33 (t, 3H), 1.59 (s, 9H), 2.73-2.79 (m, 2H), 3.19-3.35 (m, 2H), 3.62-3.73 (m, 2H), 4.12-4.33 (m, 2H), 4.87-5.36 (m, 2H), 5.98 (s, 1H). | Intermediate 04-47<br>45%<br>LC-MS (Analytical Method N, 0-1.30 min 10-95% B, 1.30-1.70 min 95% B): $R_t$ = 0.58 min; MS (ESIpos): m/z = 420 [M + H]⁺. |
| 05-43 | 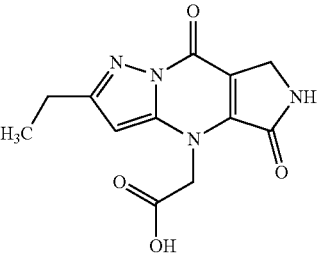<br>(2-ethyl-5,8-dioxo-5,6,7,8-tetrahydro-4H-pyrazolo[1,5-a]pyrrolo[3,4-d]pyrimidin-4-yl)acetic acid<br>¹H NMR (400 MHz, DMSO-d6) δ [ppm]: 1.24 (t, 3H), 2.69 (q, 2H), 4.26 (s, 2H), 5.27 (br s, 2H), 6.46 (s, 1H), 9.42 (s, 1H), 13.38 (br s, 1H). | Intermediate 04-44<br>85%<br>LC-MS (Method G): $R_t$ = 0.54 min; MS (ESIpos): m/z = 277 [M + H]⁺. |

| Int. | Structure<br>IUPAC-Name<br>¹H NMR | Synth. From<br>Yield<br>LC-MS method |
|---|---|---|
| 05-44 | 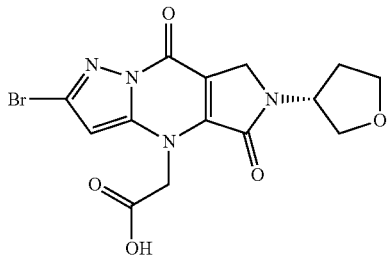<br>{2-bromo-5,8-dioxo-6-[(3R)-oxolan-3-yl]-5,6,7,8-tetrahydro-4H-pyrazolo[1,5-a]pyrrolo[3,4-d]pyrimidin-4-yl}acetic acid<br>¹H NMR (500 MHz, DMSO-d6) δ [ppm]: 2.01-2.11 (m, 1H), 2.21-2.32 (m, 1H), 3.66-3.79 (m, 2H), 3.86 (dd, 1H), 3.96-4.04 (m, 1H), 4.44 (d, 1H), 4.49 (d, 1H), 4.73-4.86 (m, 1H), 5.31 (s, 2H), 6.92 (s, 1H), 13.46 (s, 1H). | Intermediate 04-46<br>72%<br>LC-MS (Analytical Method A):<br>R$_t$ = 0.81 min; MS (ESIpos):<br>m/z = 397 [M + H]⁺. |

Intermediate 05-45

[2-cyclopropyl-5,8-dioxo-6-(propan-2-yl)-5,6,7,8-tetrahydro-4H-pyrazolo[1,5-a]pyrrolo[3,4-d]pyrimidin-4-yl]acetic acid

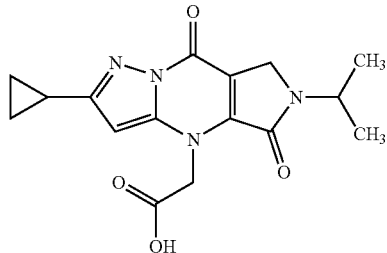 [SMILES: CC(C)N1Cc2c(n(CC(=O)O)c3cc(C4CC4)nn3c2=O)C1=O]

To a solution of tert-butyl(2-cyclopropyl-6-isopropyl-5,8-dioxo-5,6,7,8-tetrahydro-4H-pyrazolo[1,5-a]pyrrolo[3,4-d]pyrimidin-4-yl)acetate (120 mg, 0.331 mmol) (intermediate 04-38) in dichloromethane (3 ml) was added trifluoroacetic acid (1 ml) and the resulting mixture was stirred at rt for 18 h. Upon completion of the reaction, the solvent was removed in vacuo to give 120 mg (crude) of the title compound as a yellow solid. It was used directly for next step without further purification.

LC-MS (Analytical Method K, 0-1.1 min 5-100% B, 1.1-1.7 min 100% B): R$_t$=0.74 min; MS (ESIpos): m/z=331 [M+H]⁺.

| Int. | Structure<br>IUPAC-Name<br>¹H NMR | Synth. From<br>Yield<br>LC-MS method |
|---|---|---|
| 05-46 | 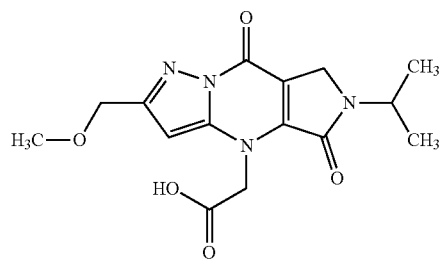<br>[2-(methoxymethyl)-5,8-dioxo-6-(propan-2-yl)-5,6,7,8-tetrahydro-4H-pyrazolo[1,5-a]pyrrolo[3,4-d]pyrimidin-4-yl]acetic acid | Intermediate 04-39<br>crude<br>LC-MS (Analytical Method K, 0-1.2 min 5-95% B, 1.2-1.7 min 95% B): R$_t$ = 0.66 min; MS (ESIpos): m/z = 335 [M + H]⁺. |

| Int. | Structure<br>IUPAC-Name<br>¹H NMR | | Synth. From<br>Yield<br>LC-MS method |
|---|---|---|---|
| 05-47 | 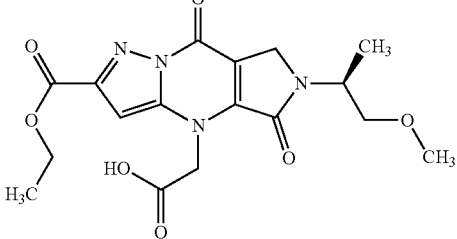 {2-(ethoxycarbonyl)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}acetic acid<br>¹H NMR (500 MHz, Chloroform-d) δ [ppm]: 1.32 (d, 3H), 1.42 (t, 3H), 3.35 (s, 3H), 3.51-3.54 (m, 2H), 4.42-4.49 (m, 4H), 4.53-4.60 (m, 1H), 5.30-5.44 (m, 1H), 5.52 (d, 1H), 6.72 (s, 1H). | | Intermediate 04-43<br>crude<br>LC-MS (Analytical Method A) $R_t$ = 0.85 min, MS (ESIpos): m/z = 393 [M + H]⁺. |
| 05-48 | 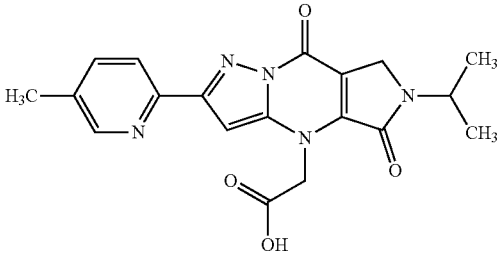 [2-(5-methylpyridin-2-yl)-5,8-dioxo-6-(propan-2-yl)-5,6,7,8-tetrahydro-4H-pyrazolo[1,5-a]pyrrolo[3,4-d]pyrimidin-4-yl]acetic acid-trifluoroacetic acid (1/1)<br>¹H NMR (500 MHz, DMSO-d6) δ [ppm]: 1.26 (d, 6H), 2.38 (s, 3H), 4.32 (hept, 1H), 4.42 (s, 2H), 5.44 (s, 2H), 7.18 (s, 1H), 7.82-7.88 (m, 1H), 8.10 (d, 1H), 8.52-8.57 (m, 1H). | | Intermediate 04-45<br>91%<br>LC-MS (Analytical Method A): $R_t$ = 0.87 min; MS (ESIpos): m/z = 382 [M + H]⁺. |

Intermediate 06-01 tert-butyl(2R)-2-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}pyrrolidine-1-carboxylate

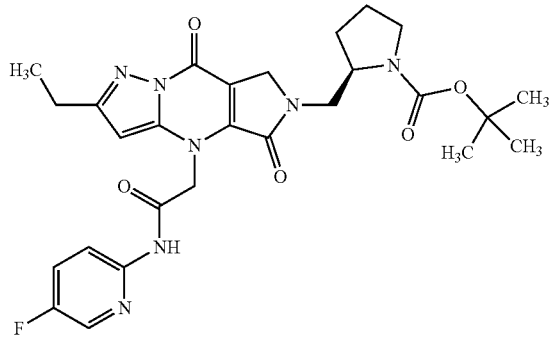 [SMILES: CCc1cc2n(CC(=O)Nc3ccc(F)cn3)c3c(c(=O)n2n1)CN(C[C@H]1CCCN1C(=O)OC(C)(C)C)C3=O]

To a solution of tert-butyl(2R)-2-[(2-ethyl-5,8-dioxo-5,8-dihydro-4H-pyrazolo[1,5-a]pyrrolo[3,4-d]pyrimidin-6(7H)-yl)methyl]pyrrolidine-1-carboxylate (1.30 g, 3.3 mmol) (intermediate 03-44) in N,N-dimethylformamide (25 ml) were added Na$_2$CO$_3$ (1.37 g, 12.9 mmol), and 2-bromo-N-(5-fluoropyridin-2-yl)acetamide (906 mg, 3.9 mmol). The resulting mixture was stirred at 80° C. for 1 hour. After cooled to rt, water was added and the resulting mixture was extracted with ethyl acetate. The combined organic layer was concentrated in vacuo and the residue was purified by column chromatography (silica gel, eluting with dichloromethane-methanol, 10:1) to get 699 mg (38% yield) of the title compound as a yellow solid.

$^1$H-NMR (400 MHz, CD$_3$OD) δ [ppm]: 1.30 (t, 3H), 1.47 (s, 9H), 1.74-1.86 (m, 4H), 2.80 (q, 2H), 2.81-2.92 (m, 2H), 4.20-4.23 (m, 3H), 4.42 (s, 2H), 5.54 (s, 2H), 6.33 (s, 1H), 7.53-7.58 (m, 1H), 8.04-8.06 (m, 1H), 8.21 (d, 1H).

LC-MS (Analytical Method K, 0-2.0 min 5-95% B, 2.0-2.6 min 95% B): R$_t$=1.30 min; MS (ESIpos): m/z=554 [M+H]$^+$.

Intermediate 06-02

2-[2-tert-butyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]ethyl trifluoromethanesulfonate

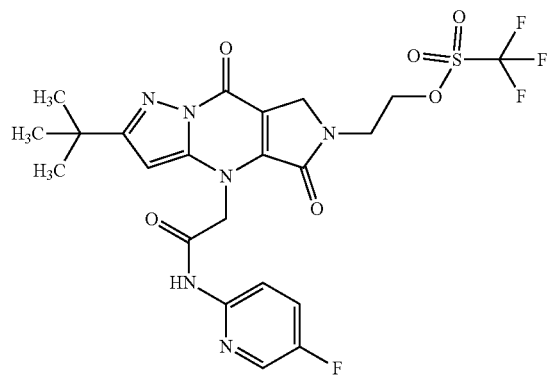 [SMILES: CC(C)(C)c1cc2n(CC(=O)Nc3ccc(F)cn3)c3c(c(=O)n2n1)CN(CCOS(=O)(=O)C(F)(F)F)C3=O]

A suspension of 2-[2-tert-butyl-6-(2-hydroxyethyl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide (200 mg, 0.40 mmol) (example 135) in dichloromethane (2 ml) was cooled to −78° C. and pyridine (97 μl, 1.20 mmol) was added followed by trifluoromethanesulfonic anhydride (88 μl, 0.52 mmol) and the reaction was stirred at this temperature for 1 h. The reaction mixture was poured onto water, the organic layer was separated, washed with sat. aqueous ammonium chloride and the organic layer was passed through a hydrophobic frit and used directly without purification as a solution in dichloromethane.

Intermediate 06-03 phenyl 4-{2-[(5-fluoropyridin-2-yl)amino]-2-oxoethyl}-6-[(±)-1-methoxypropan-2-yl]-5,8-dioxo-5,6,7,8-tetrahydro-4H-pyrazolo[1,5-a]pyrrolo[3,4-d]pyrimidine-2-carboxylate

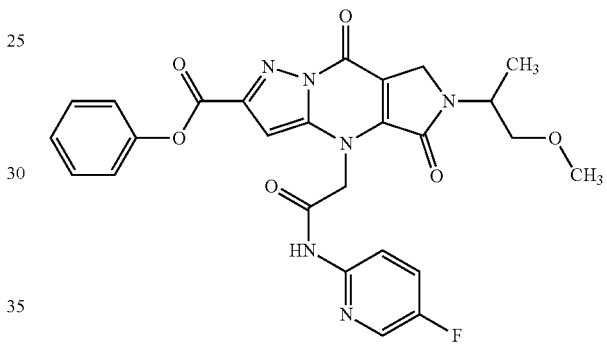

A suspension of 2-[2-bromo-6-(1-methoxypropan-2-yl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide (50 mg, 0.10 mmol) (example 36), phenyl formate (33 ul, 0.30 mmol), triethylamine (0.05 ml, 0.37 mmol) and Pd(OAc)$_2$ (3.4 mg, 0.016 mmol) in anhydrous acetonitrile (1 ml) was degassed by nitrogen bubbling for 10 min. t-Bu$_3$Ph.HBF$_4$ (18 mg, 0.06 mmol) was then added and the reaction was heated by microwave irradiation at 70° C. for 1 h, then at 90° C. for a total of 4 h. The solvent was removed under a steady stream of air and the residue partitioned between ethyl acetate and aqueous citric acid solution (5% w/v). The organic layer was washed with water, dried (MgSO$_4$), filtered and concentrated under reduced pressure. The residual material was purified by Biotage Isolera™ chromatography (silica gel, eluting with heptanes-ethyl acetate, 3:2 to 0:1) to afford 16 mg (32% yield) of the title compound as a beige solid.

$^1$H NMR (500 MHz, DMSO-d6) δ[ppm]: 11.11 (s, 1H), 8.38 (d, 1H), 8.09-7.95 (m, 1H), 7.75 (ddd, 1H), 7.53-7.47 (m, 2H), 7.40 (s, 1H), 7.37-7.31 (m, 3H), 5.63 (s, 2H), 4.52 (d, 1H), 4.44-4.33 (m, 2H), 3.58 (dd, 1H), 3.46 (dd, 1H), 3.27 (s, 3H), 1.23 (d, 3H).

LC-MS (Analytical Method A) R$_t$=1.12 min, MS (ESIpos): m/z=535 [M+H]$^+$.

Intermediate 06-04

2-[2-acetyl-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

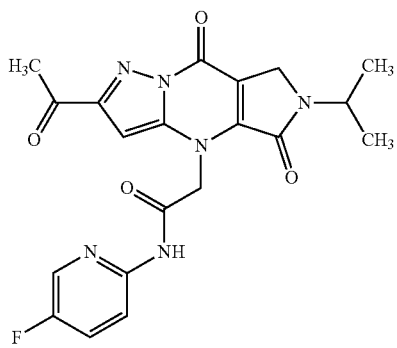 [SMILES: CC(=O)c1cc2n(CC(=O)Nc3ccc(F)cn3)c3c(c(=O)n2n1)CN(C(C)C)C3=O]

To a solution of 2-acetyl-6-isopropyl-6,7-dihydro-4H-pyrazolo[1,5-a]pyrrolo[3,4-d]pyrimidine-5,8-dione (160 mg, 0.58 mmol) (intermediate 03-108), in N,N-dimethylformamide (15 ml) was added 2-bromo-N-(5-fluoropyridin-2-yl)acetamide (163 mg, 0.7 mmol) and Na$_2$CO$_3$ (123 mg, 1.17 mmol). The resulting mixture was stirred at 60° C. for 2 h. After being cooled to rt, water was added and the resulting mixture was extracted with ethyl acetate. The combined organic layer was washed with water, brine and dried (Na$_2$SO$_4$). The solvent was removed in vacuo and the residue was purified by column chromatography (silica gel, eluting with dichloromethane-methanol, 10:1) to afford 200 mg (80% yield) of the title compound as a pink oil.

LC-MS (Analytical Method K, 0-1.1 min 5-100% B, 1.1-1.8 min 100% B): R$_t$=1.10 min; MS (ESIpos): m/z=427 [M+H]$^+$.

Intermediate 06-05 ethyl 4-{2-[(5-fluoropyridin-2-yl)amino]-2-oxoethyl}-6-[(2S)-1-methoxypropan-2-yl]-5,8-dioxo-5,6,7,8-tetrahydro-4H-pyrazolo[1,5-a]pyrrolo[3,4-d]pyrimidine-2-carboxylate

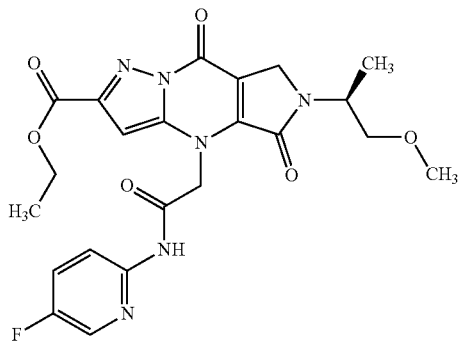 [SMILES: CCOC(=O)c1cc2n(CC(=O)Nc3ccc(F)cn3)c3c(c(=O)n2n1)CN([C@@H](C)COC)C3=O]

To a solution of {2-(ethoxycarbonyl)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}acetic acid (630 mg, 75% purity, 1.20 mmol) (intermediate 05-47) and 5-fluoropyridin-2-amine (162 mg, 1.45 mmol) in dichloromethane (2 ml), was added N,N-diisopropylethylamine (630 µl, 3.6 mmol) and T$_3$P (1.4 ml, 50% in ethyl acetate, 2.4 mmol). The reaction was stirred for 1 h at rt, the reaction mixture washed with 2 M NaOH (2 ml) and the aqueous layer further extracted with dichloromethane. The combined organics were dried (MgSO$_4$), filtered and concentrated under reduced pressure. The crude material was purified by Biotage Isolera™ chromatography (silica gel, eluting with heptanes-acetone, 19:1 to 7:13) to afford 474 mg (70% yield, 86% purity) of the title compound as a brown gum.

1H NMR (500 MHz, Chloroform-d) δ [ppm]: =1.33 (d, 3H), 1.41 (t, 3H), 3.34 (s, 3H), 3.53 (d, 2H), 4.41-4.46 (m, 3H), 4.51 (t, 1H), 4.63 (dt, 1H), 5.29-5.47 (m, 1H), 5.49-5.67 (m, 1H), 6.88 (s, 1H), 7.42 (ddd, 1H), 8.02-8.22 (m, 2H), 9.30 (s, 1H).

LC-MS (Analytical Method A) R$_t$=1.03 min, MS (ESIpos): m/z=487 [M+H]$^+$.

Intermediate 06-06 tert-butyl(3R)-3-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}morpholine-4-carboxylate

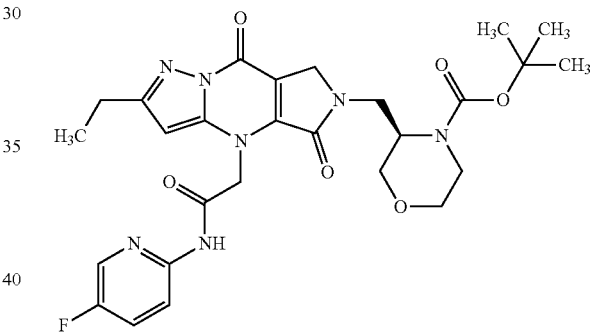

A suspension of tert-butyl(3R)-3-[(2-ethyl-5,8-dioxo-5,8-dihydro-4H-pyrazolo[1,5-a]pyrrolo[3,4-d]pyrimidin-6(7H)-yl)methyl]morpholine-4-carboxylate (200 mg, 89% purity, 426 µmol) (intermediate 03-59), 2-chloro-N-(5-fluoropyridin-2-yl)acetamide (201 mg, 80% purity, 853 µmol) and K$_2$CO$_3$ (118 mg, 853 µmol) in acetonitrile (4.2 ml) was heated at 80° C. for 1 h. After this time the reaction mixture was concentrated in vacuo, with the residual material partitioned between 20% isopropanol/dichloromethane and water. The organic layer was removed and the aqueous layer re-extracted with further aliquots of 20% isopropanol/dichloromethane. The combined organic layers were dried (MgSO$_4$), filtered and concentrated in vacuo. The residual material was purified by Biotage Isolera™ chromatography (silica gel, eluting with dichloromethane-methanol, 1:0 to 9:1) to afford 121 mg (41% yield, 83% purity) of the title compound as a brown solid.

$^1$H NMR (250 MHz, Chloroform-d) δ [ppm]: 1.04-1.42 (m, 12H), 2.85 (q, 2H), 3.33-3.99 (m, 8H), 4.21-4.50 (m, 2H), 4.55-4.86 (m, 1H), 5.12-5.58 (m, 2H), 6.24 (s, 1H), 7.34-7.50 (m, 1H), 8.05-8.24 (m, 2H).

LC-MS (Analytical Method A) R$_t$=1.07 min, MS (ESIPos): m/z=570 [M+H]$^+$.

243

Intermediate 06-07

2-{2-bromo-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide

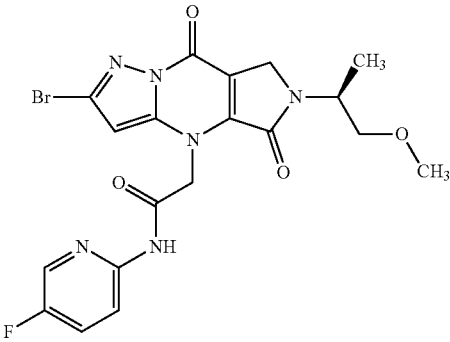 [SMILES: COC[C@H](C)N1Cc2c(n(CC(=O)Nc3ccc(F)cn3)c3cc(Br)nn3c2=O)C1=O]

A suspension of 2-bromo-6-[(2S)-1-methoxypropan-2-yl]-6,7-dihydro-4H-pyrazolo[1,5-a]pyrrolo[3,4-d]pyrimidine-5,8-dione (2.00 g, 5.86 mmol) (intermediate 03-63), 2-chloro-N-(5-fluoropyridin-2-yl)acetamide (1.22 g, 6.45 mmol), and K₂CO₃ (891 mg, 6.45 mmol) in acetonitrile (27 ml) was stirred at reflux for 3 h. Further 2-chloro-N-(5-fluoropyridin-2-yl)acetamide (608 mg, 3.22 mmol) was added and the reaction was stirred at this temperature for 4 h. After this time, further K₂CO₃ (446 mg, 3.22 mmol) and KI (146 mg, 0.88 mmol) were added and the reaction was stirred at this temperature for 2 h. The reaction mixture was allowed to cool to rt and concentrated under reduced pressure. The residual material was partitioned between ethyl acetate and water, with the organic layer separated and the aqueous phase back-extracted with further ethyl acetate. The combined organic phases were washed with saturated aqueous sodium chloride solution, dried (MgSO₄), filtered and concentrated in vacuo. The resulting material was purified by column chromatography on a Biotage Isolera Four [Biotage SNAP Cartridge KP-Sil 50 g; 0-50% ethyl acetate in dichloromethane], and the product containing fractions were combined to afford the title compound (1.21 g, 38%) as brown solid.

$^1$H NMR (500 MHz, Methanol-d4) δ [ppm]: 1.33 (d, 3H), 3.36 (s, 3H), 3.54 (dd, 1H), 3.63 (dd, 1H), 4.42-4.57 (m, 3H), 5.50-5.69 (m, 2H), 6.64 (s, 1H), 7.56-7.63 (m, 1H), 8.03-8.14 (m, 1H), 8.23-8.25 (m, 1H).

LC-MS (Analytical Method A) R$_t$=1.04 min, MS (ESI-Pos): m/z=493 [M+H]⁺.

244

Intermediate 06-08

2-(2-ethyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide

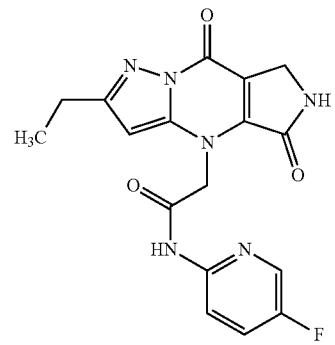 [SMILES: CCc1cc2n(CC(=O)Nc3ccc(F)cn3)c3c(c(=O)n2n1)CNC3=O]

To a solution of 2-(2-ethyl-5,8-dioxo-5,6,7,8-tetrahydro-4H-pyrazolo[1,5-a]pyrrolo[3,4-d]pyrimidin-4-yl)acetic acid (500 mg, 1.80 mmol) (intermediate 05-43) in dichloromethane (10 mL) were added 5-fluoropyridin-2-amine (304 mg, 2.72 mmol), N,N-diisopropylethylamine (466 mg, 3.62 mmol) and T3P (50 wt % in ethyl acetate, 3.5 mL, 5.4 mmol). The resulting mixture was stirred at room temperature for 2 hours. Upon completion of the reaction, water was added. The resulting solution was extracted with dichloromethane. The combined organic layer was dried over anhydrous sodium sulfate and concentrated in vacuo. The residue was purified with silica gel column chromatography (petroleum ether: ethyl acetate=5:2) to give 480 mg (72%) of the product as a yellow solid.

LC-MS (Analytical Method K, 0-2.00 min 5-95% B): R$_1$=0.75 min; MS (ESIpos): m/z=371 [M+H]⁺.

Intermediate 06-09 tert-butyl [2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]acetate

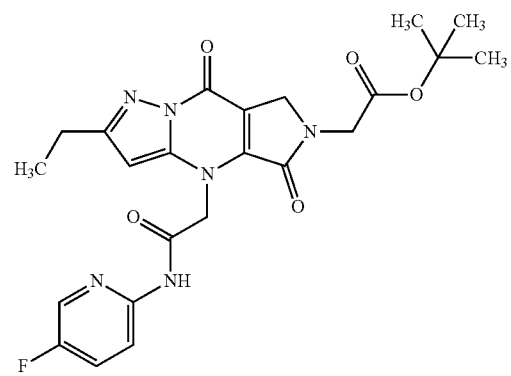 [SMILES: CCc1cc2n(CC(=O)Nc3ccc(F)cn3)c3c(c(=O)n2n1)CN(CC(=O)OC(C)(C)C)C3=O]

To a solution of 2-(2-ethyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide (480 mg, 1.30 mmol) (intermediate 06-08) in N,N-dimethylformamide (12 mL) were added tert-butyl 2-bromoacetate (379 mg, 1.95 mmol) and cesium carbonate (1.3 g, 3.89 mmol). The resulting mixture was stirred at 60° C. for 30 minutes under nitrogen atmosphere. After cooled to room temperature, water was added and the resulting solution was extracted with ethyl acetate. The combined organic layer was dried over anhydrous sodium sulfate and concentrated in vacuo. The residue was purified by silica gel column chromatography (ethyl acetate: petroleum ether=1:3) to give 450 mg (72%) of the product as a yellow solid.

LC-MS (Analytical Method R, 0-2.00 min 5-95% B): $R_t$=1.10 min; MS (ESIpos): m/z=485 [M+H]$^+$.

Intermediate 06-10

[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]acetic acid

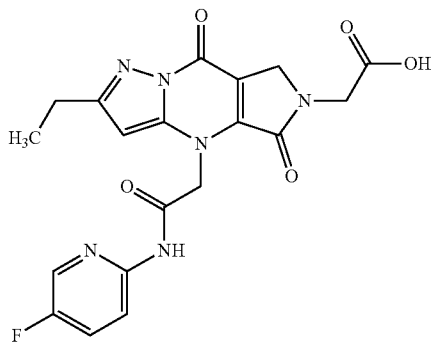 [SMILES: CCc1cc2n(CC(=O)Nc3ccc(F)cn3)c3c(c(=O)n2n1)CN(CC(=O)O)C3=O]

To a solution of tert-butyl 2-(2-ethyl-4-(2-((5-fluoropyridin-2-yl)amino)-2-oxoethyl)-5,8-dioxo-5,8-dihydro-4H-pyrazolo[1,5-a]pyrrolo[3,4-d]pyrimidin-6(7H)-yl)acetate (450 mg, 0.928 mmol) (intermediate 06-09) in dichloromethane (10 mL) was added trifluoroacetic acid (2.5 mL). The resulting mixture was stirred at room temperature for 1 hour. Upon completion of the reaction, the solvent was removed in vacuo and water was added. Sodium bicarbonate solution was added to adjust the pH value to 5 and the resulting solution was purified by Prep-HPLC [Mobile Phase A: Water (0.1% TFA), Mobile Phase B: Acetonitrile; Gradient: 7% B to 27% B in 8 min] to give 252 mg (60%) of the product as a white solid.

$^1$H-NMR (400 MHz, DMSO-d$_6$): δ [ppm]=1.24 (t, 3H), 2.67-2.72 (m, 2H), 4.27 (s, 2H), 4.42 (s, 2H), 5.45 (br, 2H), 6.48 (s, 1H), 7.71-7.76 (m, 1H), 7.95-8.05 (m, 1H), 8.37 (d, 1H), 11.11 (s, 1H), 13.12 (br, 1H).

LC-MS (Analytical Method Q, 0-3.00 min 5-95% B): $R_t$=0.88 min; MS (ESIpos): m/z=429 [M+H]$^+$.

Intermediate 06-11

2-{2-bromo-5,8-dioxo-6-[(3R)-oxolan-3-yl]-5,6,7,8-tetrahydro-4H-pyrazolo[1,5-a]pyrrolo[3,4-d]pyrimidin-4-yl}-N-(5-fluoropyridin-2-yl)acetamide

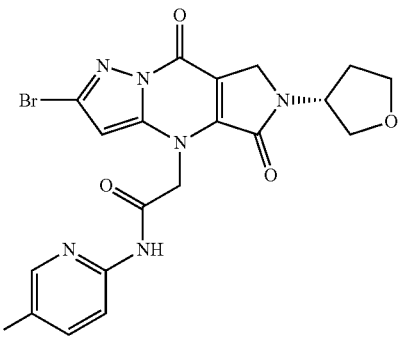

To a solution of {2-bromo-5,8-dioxo-6-[(3R)-oxolan-3-yl]-5,6,7,8-tetrahydro-4H-pyrazolo[1,5-a]pyrrolo[3,4-d]pyrimidin-4-yl}acetic acid (355 mg, 90% purity, 804 µmol) (intermediate 05-44) and 5-fluoropyridin-2-amine (135 mg, 1.21 mmol) in dichloromethane (5 ml), was added diisopropylethylamine (700 µl, 4.0 mmol) and T3P (50% in ethyl acetate, 948 µl, 1.6 mmol). The reaction was stirred for 1h, the reaction was quenched with sat. aq. NaHCO$_3$, and the layers separated. The aqueous layer was extracted with dichloromethane, and the combined organics were dried (MgSO$_4$), filtered and concentrated under reduced pressure. The crude material was purified by Biotage Isolera™ chromatography (silica gel, eluting with heptanes-ethyl acetate-methanol, 1:3:0 to 0:1:0 to 0:4:1 to afford 180 mg (43% yield) of the title compound as an off-white powder.

$^1$H-NMR (250 MHz, Chloroform-d) δ [ppm]: 1.97-2.13 (m, 1H), 2.33-2.52 (m, 1H), 3.78-3.98 (m, 3H), 4.04-4.20 (m, 1H), 4.42 (d, 1H), 4.53 (d, 1H), 4.95-5.12 (m, 1H), 5.37 (s, 2H), 6.42 (s, 1H), 7.43 (ddd, 1H), 8.04-8.20 (m, 2H), 8.98 (s, 1H).

LC-MS (Analytical Method A) $R_t$=1.00 min; MS (ESIpos): m/z=491 [M+H]$^+$.

Intermediate 06-12

2-{2-bromo-5,8-dioxo-6-[(3S)-oxolan-3-yl]-5,6,7,8-tetrahydro-4H-pyrazolo[1,5-a]pyrrolo[3,4-d]pyrimidin-4-yl}-N-(5-fluoropyridin-2-yl)acetamide

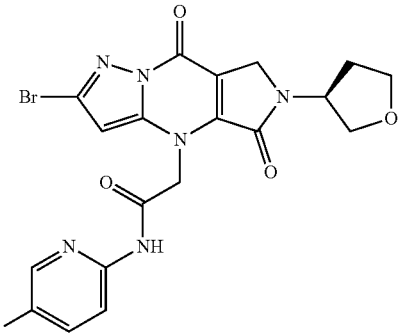

A suspension of 2-bromo-6-[(3S)-oxolan-3-yl]-6,7-dihydro-4H-pyrazolo[1,5-a]pyrrolo[3,4-d]pyrimidine-5,8-dione (1.29 g, 3.80 mmol) (intermediate 03-97), 2-bromo-N-(5-fluoropyridin-2-yl)acetamide (1.33 g, 5.71 mmol) and potassium carbonate (789 mg, 5.71 mmol) in acetonitrile (16 ml) was stirred at 80° C. for 2 h. After this time, the reaction mixture was allowed to cool to rt, and the acetonitrile was removed under reduced pressure. The resulting residue was taken up in ethyl acetate and water, the phases were separated, and the aqueous phase was re-extracted with ethyl acetate. The combined organics were dried (MgSO₄), filtered and concentrated in vacuo. The crude material was purified by Biotage Isolera™ chromatography (silica gel, eluting with heptanes-ethyl acetate, 1:0 to 1:1), then further purified by Biotage Isolera™ chromatography (C-18 silica gel, eluting with water-MeCN (+0.1% formic acid), 1:0 to 0:1) to afford 518.2 mg (28% yield) of the title compound as a white powder.

$^1$H-NMR (500 MHz, Chloroform-d) δ [ppm]: 2.00-2.10 (m, 1H), 2.36-2.48 (m, 1H), 3.80-3.88 (m, 2H), 3.91 (dd, 1H), 4.07-4.18 (m, 1H), 4.43 (d, 1H), 4.52 (d, 1H), 4.96-5.05 (m, 1H), 5.38 (s, 2H), 6.42 (s, 1H), 7.43 (ddd, 1H), 8.11 (s, 1H), 8.14 (d, 1H), 9.08 (s, 1H).

LC-MS (Analytical Method D) $R_t$=3.40 min; MS (ESI-pos): m/z=491 [M+H]⁺.

EXPERIMENTAL SECTION—EXAMPLES

Example 1

2-[2-tert-butyl-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

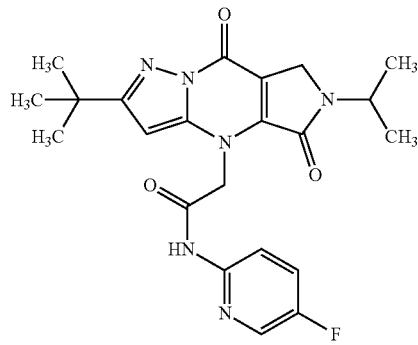

(2-tert-Butyl-6-isopropyl-5,8-dioxo-5,6,7,8-tetrahydro-4H-pyrazolo[1,5-a]pyrrolo[3,4-d]pyrimidin-4-yl)acetic acid (600 mg, 1.73 mmol) (intermediate 05-08), 5-fluoropyridin-2-amine (214 mg, 1.91 mmol) and N,N-diisopropylethylamine (0.91 ml, 5.2 mmol) were dissolved in dichloromethane (31 ml). T₃P (2.02 ml, 3.46 mmol, 50% in ethyl acetate) was added and the reaction mixture stirred at rt for 1 h. The reaction mixture washed with saturated aqueous NaHCO₃ solution (40 ml) and the aqueous layer further extracted with dichloromethane (2×40 ml). The combined organics were dried (MgSO₄), filtered and concentrated under reduced pressure. The crude material was purified by Biotage Isolera™ chromatography (silica gel, eluting with heptanes-ethyl acetate, 1:0 to 0:1). The fractions containing desired product were combined and concentrated under reduced pressure to yield a pink powder solid. This solid was heated in methanol (40 ml), collected by filtration and dried under vacuum to yield 327 mg (42% yield) of the title compound as a white-pink powder.

$^1$H NMR (250 MHz, DMSO-d6) δ [ppm]1.23 (d, 6H), 1.31 (s, 9H), 4.17-4.49 (m, 3H), 5.46 (s, 2H), 6.57 (s, 1H), 7.58-7.85 (m, 1H), 7.88-8.18 (m, 1H), 8.37 (d, 1H), 11.07 (s, 1H).

LC-MS (Analytical Method F): $R_t$=2.92 mins; m/z (ESI-pos)=441 [M+H]⁺.

In analogy to the procedure described for Example 1 the following examples were prepared using the appropriate carboxylic acid and amine as starting materials.

| Example | Structure<br>IUPAC-Name<br>$^1$H NMR | Synth. from<br>Yield<br>LC-MS |
|---|---|---|
| 2 | ![structure]<br>2-[2-tert-butyl-5,8-dioxo-6-(propan-2-yl)-5,6,7,8-tetrahydro-4H-pyrazolo[1,5-a]pyrrolo[3,4-d]pyrimidin-4-yl]-N-(pyridin-2-yl)acetamide formic acid-(1:1)<br>$^1$H NMR (250 MHz, DMSO-d6) δ [ppm]: 1.23 (d, 6H), 1.31 (s, 9H), 4.17-4.47 (m, 3H), 5.47 (s, 2H), 6.56 (s, 1H), 7.00-7.22 (m, 1H), 7.64-7.84 (m, 1H), 7.84-8.03 (m, 1H), 8.29-8.44 (m, 1H), 10.94 (s, 1H). | Intermediate 05-08<br>50%<br>LC-MS (Analytical Method F): $R_t$ = 2.64 mins, m/z (ESI) = 422.2 [M + H]⁺. |

| Example | Structure<br>IUPAC-Name<br>¹H NMR | Synth. from<br>Yield<br>LC-MS |
|---|---|---|
| 3 | 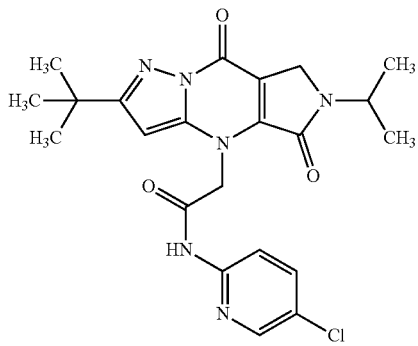<br>2-[2-tert-butyl-5,8-dioxo-6-(propan-2-yl)-5,6,7,8-tetrahydro-4H-pyrazolo[1,5-a]pyrrolo[3,4-d]pyrimidin-4-yl]-N-(5-chloropyridin-2-yl)acetamide<br>¹H NMR (250 MHz, DMSO-d6) δ [ppm]: 1.23 (d, 6H), 1.30 (s, 9H), 4.19-4.45 (m, 3H), 5.46 (s, 2H), 6.58 (s, 1H), 7.78-8.05 (m, 2H), 8.32-8.50 (m, 1H), 11.15 (s, 1H). | Intermediate 05-08<br>48%<br>LC-MS (Analytical Method F): $R_t$ = 3.2 mins, m/z (ESI) = 457.2 [M + H]⁺. |
| 4 | 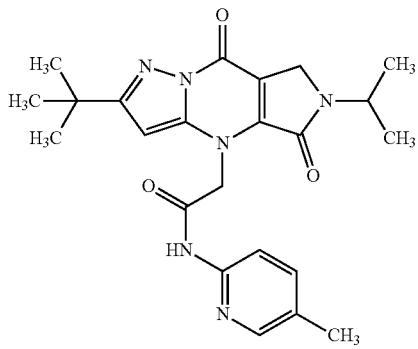<br>2-[2-tert-butyl-5,8-dioxo-6-(propan-2-yl)-5,6,7,8-tetrahydro-4H-pyrazolo[1,5-a]pyrrolo[3,4-d]pyrimidin-4-yl]-N-(5-methylpyridin-2-yl)acetamide<br>¹H NMR (250 MHz, DMSO-d6) δ [ppm]: 1.23 (d, 6H), 1.30 (s, 9H), 2.25 (s, 3H), 4.15-4.45 (m, 3H), 5.45 (s, 2H), 6.55 (s, 1H), 7.59 (dd, 1H), 7.85 (d, 1H), 8.19 (d, 1H), 10.85 (s, 1H). | Intermediate 05-08<br>48%<br>LC-MS (Analytical Method F): $R_t$ = 2.81 mins, m/z (ESI) = 437 [M + H]⁺. |

| Example | Structure<br>IUPAC-Name<br>¹H NMR | Synth. from<br>Yield<br>LC-MS |
|---|---|---|
| 5 | 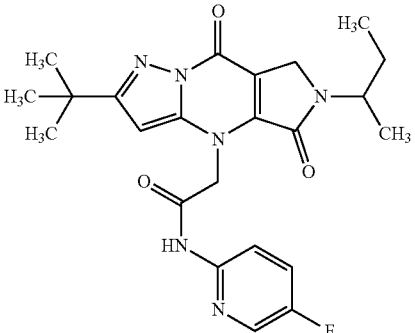<br>2-{6-[2-butan-2-yl]-2-tert-butyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide enantiomer 1<br>¹H NMR (250 MHz, Methanol-d4) δ [ppm]: 0.80 (t, 3H), 1.21 (d, 3H), 1.28 (s, 9H), 1.46-1.71 (m, 2H), 4.01-4.42 (m, 3H), 5.46 (s, 2H), 6.31 (s, 1H), 7.35-7.55 (m, 1H), 7.94 (s, 1H), 8.12 (d, 1H). | Intermediate 05-02<br>14%<br>LC-MS (Analytical Method F): $R_t$ = 3.12 mins, m/z (ESI) = 455 [M + H]⁺. |
| 6 | 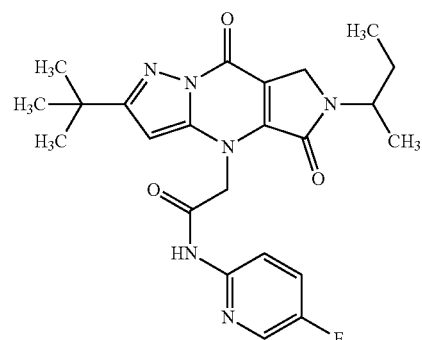<br>2-{6-[2-butan-2-yl]-2-tert-butyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide enantiomer 2<br>¹H NMR (500 MHz, Methanol-d4) δ [ppm]: 0.90 (t, 3H), 1.31 (d, 3H), 1.38 (s, 9H), 1.60-1.78 (m, 2H), 4.06-4.48 (m, 3H), 5.56 (s, 2H), 6.41 (s, 1H), 7.37-7.61 (m, 1H), 8.05 (s, 1H), 8.22 (d, 1H). | Intermediate 05-03<br>17%<br>LC-MS (Analytical Method F): R t = 3.12 mins, m/z (ESI) = 455 [M + H]⁺. |

| | Structure<br>IUPAC-Name | Synth. from<br>Yield |
|---|---|---|
| Example | ¹H NMR | LC-MS |

7

2-[5,8-dioxo-2,6-di(propan-2-yl)-5,6,7,8-tetrahydro-
4H-pyrazolo[1,5-a]pyrrolo[3,4-d]pyrimidin-4-yl]-N-
(5-fluoropyridin-2-yl)acetamide
¹H NMR (500 MHz, DMSO-d6) δ [ppm]: 11.08 (s, 1H),
8.44-8.28 (m, 1H), 8.06-7.90 (m, 1H), 7.73 (ddd,
1H), 6.49 (s, 1H), 5.46 (s, 2H), 4.36 (s, 2H), 4.29
(hept, 1H), 3.00 (hept, 1H), 1.26 (d, 6H), 1.23 (d, 6H).

Intermediate 05-04
51%
LC-MS (Analytical
Method F) R$_t$ = 2.68
min, MS (ESIpos):
m/z = 427 [M + H]⁺.

8

N-(5-chloropyridin-2-yl)-2-[5,8-dioxo-2,6-di(propan-
2-yl)-5,6,7,8-tetrahydro-4H-pyrazolo[1,5-
a]pyrrolo[3,4-d]pyrimidin-4-yl]acetamide
¹H NMR (500 MHz, DMSO-d6) δ [ppm]: 11.15 (s, 1H),
8.41 (d, 1H), 8.05-7.94 (m, 1H), 7.89 (dd, 1H), 6.50
(s, 1H), 5.47 (s, 2H), 4.36 (s, 2H), 4.33-4.23 (m, 1H),
3.00 (hept, 1H), 1.25 (d, 6H), 1.23 (d, 6H).

Intermediate 05-04
46%
LC-MS (Analytical
Method F) R$_t$ = 2.98
min, MS (ESIpos):
m/z = 443 [M + H]⁺.

-continued

| Example | Structure<br>IUPAC-Name<br>¹H NMR | Synth. from<br>Yield<br>LC-MS |
|---|---|---|
| 9 | 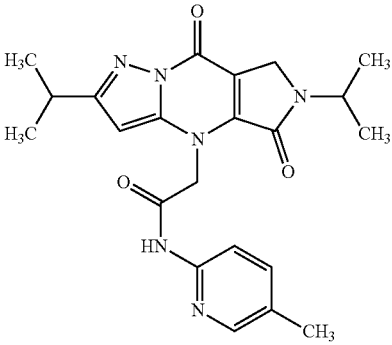<br>2-[5,8-dioxo-2,6-di(propan-2-yl)-5,6,7,8-tetrahydro-4H-pyrazolo[1,5-a]pyrrolo[3,4-d]pyrimidin-4-yl]-N-(5-methylpyridin-2-yl)acetamide<br>¹H NMR (500 MHz, DMSO-d6) δ [ppm]: 10.86 (s, 1H), 8.19 (d, 1H), 7.85 (d, 1H), 7.59 (dd, 1H), 6.47 (s, 1H), 5.45 (s, 2H), 4.36 (s, 2H), 4.28 (h, 1H), 3.00 (hept, 1H), 2.25 (s, 3H), 1.26 (d, 6H), 1.23 (d, 6H). | Intermediate 05-04<br>47%<br>LC-MS (Analytical Method F) $R_t$ = 2.56 min, MS (ESIpos): m/z = 423 [M + H]⁺. |
| 10 | 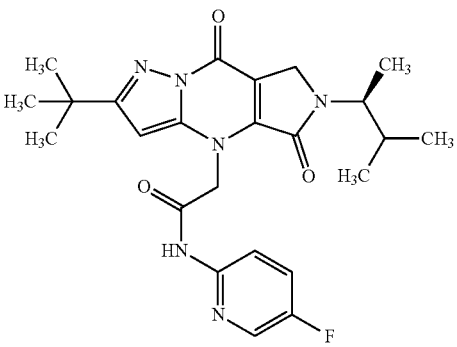<br>2-{2-tert-butyl-6-[(2S)-3-methylbutan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR 1H NMR (500 MHz, Chloroform-d) δ [ppm]: 9.13 (s, 1H), 8.06 (d, 2H), 7.34 (ddd, 1H), 6.20 (s, 1H), 5.23 (d, 2H), 4.37-4.16 (m, 2H), 4.10-3.93 (m, 1H), 1.84-1.66 (m, 1H), 1.33 (s, 9H), 1.24 (d, 3H), 0.95 (d, 3H), 0.78 (d, 3H). | Intermediate 05-05<br>17%<br>LC-MS (Analytical Method F) $R_t$ = 3.31 min, MS (ESIpos): m/z = 469 [M + H]⁺. |

| Example | Structure<br>IUPAC-Name<br>¹H NMR | Synth. from<br>Yield<br>LC-MS |
|---|---|---|
| 11 | 2-{2-tert-butyl-6-[(2S)-3-methylbutan-2-yl]-5,8-dioxo-5,6,7,8-tetrahydro-4H-pyrazolo[1,5-a]pyrrolo[3,4-d]pyrimidin-4-yl}-N-(5-methylpyridin-2-yl)acetamide<br>¹H NMR (500 MHz, Chloroform-d) δ [ppm]: 8.87 (s, 1H), 8.02 (s, 1H), 7.91 (s, 1H), 7.42 (dd, 1H), 6.15 (s, 1H), 5.26 (d, 2H), 4.33-4.18 (m, 2H), 4.03 (dq, 1H), 2.21 (s, 3H), 1.82-1.71 (m, 1H), 1.32 (s, 9H), 1.23 (d, 3H), 0.94 (d, 3H), 0.78 (d, 3H). | Intermediate 05-05<br>10%<br>LC-MS (Analytical Method F) R$_t$ = 3.22 min, MS (ESIpos): m/z = 465 [M + H]⁺. |
| 12 | 2-{2-tert-butyl-6-[(2S)-3-methylbutan-2-yl]-5,8-dioxo-5,6,7,8-tetrahydro-4H-pyrazolo[1,5-a]pyrrolo[3,4-d]pyrimidin-4-yl}-N-(5-chloropyridin-2-yl)acetamide<br>¹H NMR (500 MHz, Chloroform-d) δ [ppm]: 9.15 (s, 1H), 8.16 (d, 1H), 8.02 (s, 1H), 7.57 (dd, 1H), 6.19 (s, 1H), 5.23 (d, 2H), 4.31 (d, 1H), 4.23 (d, 1H), 4.08-3.98 (m, 1H), 1.83-1.69 (m, 1H), 1.33 (s, 9H), 1.24 (d, 3H), 0.95 (d, 3H), 0.78 (d, 3H). | Intermediate 05-05<br>9%<br>LC-MS (Analytical Method F) R$_t$ = 3.58 min, MS (ESIpos): m/z = 485 [M + H]⁺. |

-continued

| Example | Structure<br>IUPAC-Name<br>¹H NMR | Synth. from<br>Yield<br>LC-MS |
|---|---|---|
| 13 | 2-[2-tert-butyl-6-(cyclopropylmethyl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, Chloroform-d) δ [ppm]: 9.07 (s, 1H), 8.07 (d, 2H), 7.34 (ddd, 1H), 6.19 (s, 1H), 5.23 (s, 2H), 4.45 (s, 2H), 3.42 (d, 2H), 1.33 (s, 9H), 0.98 (ddt, 1H), 0.56 (dd, 2H), 0.28 (q, 2H). | Intermediate 05-06<br>27%<br>LC-MS (Analytical Method F) $R_t$ = 3.04 min, MS (ESIpos): m/z = 453 [M + H]⁺. |
| 14 | 2-{6-[(2R)-butan-2-yl]-5,8-dioxo-2-(trifluoromethyl)-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, DMSO-d6) δ [ppm]: 11.11 (s, 1H), 8.37 (d, 1H), 8.07-7.90 (m, 1H), 7.73 (ddd, 1H), 7.28 (s, 1H), 5.80-5.34 (m, 2H), 4.43 (d, 1H), 4.36 (d, 1H), 4.17-4.00 (m, 1H), 1.71-1.50 (m, 2H), 1.23 (d, 3H), 0.80 (t, 3H). | Intermediate 05-07<br>43%<br>LC-MS (Analytical Method F) $R_t$ = 3.14 min, MS (ESIpos): m/z = 467 [M + H]⁺. |

| Example | Structure<br>IUPAC-Name<br>¹H NMR | Synth. from<br>Yield<br>LC-MS |
|---|---|---|
| 15 | 2-{6-[(2R)-butan-2-yl]-5,8-dioxo-2-(trifluoromethyl)-5,6,7,8-tetrahydro-4H-pyrazolo[1,5-a]pyrrolo[3,4-d]pyrimidin-4-yl}-N-(5-chloropyridin-2-yl)acetamide<br>¹H NMR (500 MHz, DMSO-d6) δ [ppm]: 11.18 (s, 1H), 8.42 (d, 1H), 8.07-7.93 (m, 1H), 7.89 (dd, 1H), 7.29 (s, 1H), 5.62-5.51 (m, 2H), 4.43 (d, 1H), 4.36 (d, 1H), 4.17-3.96 (m, 1H), 1.73-1.49 (m, 2H), 1.23 (d, 3H), 0.79 (t, 3H). | Intermediate 05-07<br>33%<br>LC-MS (Analytical Method F) R$_t$ = 3.42 min, MS (ESIpos): m/z = 483 [M + H]⁺. |
| 16 | 2-{6-[(2R)-butan-2-yl]-5,8-dioxo-2-(trifluoromethyl)-5,6,7,8-tetrahydro-4H-pyrazolo[1,5-a]pyrrolo[3,4-d]pyrimidin-4-yl}-N-(5-methylpyridin-2-yl)acetamide<br>¹H NMR (500 MHz, DMSO-d6) δ [ppm]: 10.89 (s, 1H), 8.19 (d, 1H), 7.85 (d, 1H), 7.59 (dd, 1H), 7.27 (s, 1H), 5.74-5.37 (m, 2H), 4.43 (d, 1H), 4.36 (d, 1H), 4.03-4.13 (m, 1H), 2.25 (s, 3H), 1.72-1.52 (m, 2H), 1.23 (d, 3H), 0.80 (t, 3H). | Intermediate 05-07<br>22%<br>LC-MS (Analytical Method F) R$_t$ = 3.07 min, MS (ESIpos): m/z = 463 [M + H]⁺. |

| | Structure<br>IUPAC-Name | Synth. from |
|---|---|---|
| Example | ¹H NMR | Yield<br>LC-MS |

| 17 | 2-(2-tert-butyl-6-cyclobutyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide<br>¹H NMR (500 MHz, Chloroform-d) δ [ppm]: 9.11 (s, 1H), 8.21-8.07 (m, 2H), 7.42 (ddd, 1H), 6.24 (s, 1H), 5.31 (s, 2H), 4.88-4.73 (m, 1H), 4.47 (s, 2H), 2.43-2.21 (m, 4H), 1.91-1.77 (m, 2H), 1.40 (s, 9H). | Intermediate 05-09<br>32%<br>LC-MS (Analytical Method F) R$_t$ = 3.07 min, MS (ESIpos): m/z + 453 [M + H]⁺. |

| 18 | 2-(2-tert-butyl-6-cyclobutyl-5,8-dioxo-5,6,7,8-tetrahydro-4H-pyrazolo[1,5-a]pyrrolo[3,4-d]pyrimidin-4-yl)-N-(5-chloropyridin-2-yl)acetamide<br>¹H NMR (500 MHz, Chloroform-d) δ [ppm]: 9.15 (s, 1H), 8.24 (d, 1H), 8.09 (d, 1H), 7.65 (dd, 1H), 6.24 (s, 1H), 5.31 (s, 2H), 4.86-4.76 (m, 1H), 4.47 (s, 2H), 2.39-2.24 (m, 4H), 1.88-1.76 (m, 2H), 1.40 (s, 9H). | Intermediate 05-09<br>20%<br>LC-MS (Analytical Method F) R$_t$ = 3.36 min, MS (ESIpos): m/z = 469 [M + H]⁺. |

| Example | Structure IUPAC-Name ¹H NMR | Synth. from Yield LC-MS |
|---|---|---|
| 19 | 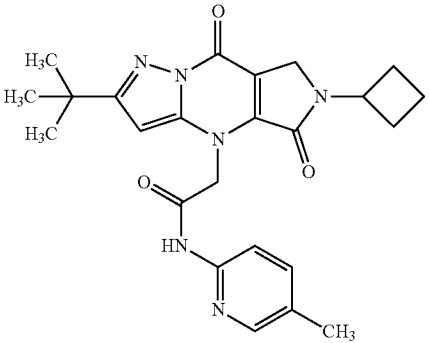<br>2-(2-tert-butyl-6-cyclobutyl-5,8-dioxo-5,6,7,8-tetrahydro-4H-pyrazolo[1,5-a]pyrrolo[3,4-d]pyrimidin-4-yl)-N-(5-methylpyridin-2-yl)acetamide<br>¹H NMR (500 MHz, DMSO-d6) δ [ppm]: 10.77 (s, 1H), 8.12 (d, 1H), 7.78 (d, 1H), 7.51 (dd, 1H), 6.49 (s, 1H), 5.35 (s, 2H), 4.64-4.46 (m, 1H), 4.42 (s, 2H), 2.35-2.24 (m, 2H), 2.18 (s, 3H), 2.11-2.03 (m, 2H), 1.69-1.58 (m, 2H), 1.24 (s, 9H). | Intermediate 05-09<br>39%<br>LC-MS (Analytical Method F) $R_t$ = 2.97 min, MS (ESIpos): m/z = 449 [M + H]⁺. |
| 20 | 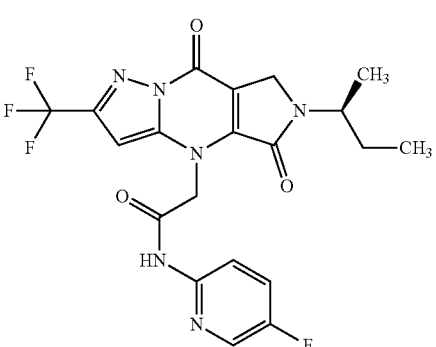<br>2-{6-[(2S)-butan-2-yl]-5,8-dioxo-2-(trifluoromethyl)-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, Chloroform-d) δ [ppm]: 9.05 (s, 1H), 8.26-7.78 (m, 2H), 7.36 (ddd, 1H), 6.60 (s, 1H), 5.37 (d, 2H), 4.53-4.03 (m, 3H), 1.64-1.72 (m, 2H), 1.26 (d,3H), 0.86 (t, 3H). | Intermediate 05-10<br>26%<br>LC-MS (Analytical Method F) $R_t$ = 3.07 min, MS (ESIpos): m/z = 467 [M + H]⁺. |

| Example | Structure<br>IUPAC-Name<br>¹H NMR | Synth. from<br>Yield<br>LC-MS |
|---|---|---|
| 21 | 2-{6-[(2S)-butan-2-yl]-5,8-dioxo-2-(trifluoromethyl)-5,6,7,8-tetrahydro-4H-pyrazolo[1,5-a]pyrrolo[3,4-d]pyrimidin-4-yl}-N-(5-methylpyridin-2-yl)acetamide<br>¹H NMR (500 MHz, Chloroform-d) δ [ppm]: 8.89 (s, 1H), 8.04 (s, 1H), 7.89 (s, 1H), 7.44 (dd, 1H), 6.57 (s, 1H), 5.39 (d, 2H), 4.36-4.21 (m, 3H), 2.23 (s, 3H), 1.59 (q, 2H), 1.24 (d, 3H), 0.85 (t, 3H). | Intermediate 05-10<br>34%<br>LC-MS (Analytical Method F) $R_t$ = 3.08 min, MS (ESIpos): m/z = 463 [M + H]⁺. |
| 22 | 2-{6-[(2S)-butan-2-yl]-5,8-dioxo-2-(trifluoromethyl)-5,6,7,8-tetrahydro-4H-pyrazolo[1,5-a]pyrrolo[3,4-d]pyrimidin-4-yl}-N-(5-chloropyridin-2-yl)acetamide<br>¹H NMR (500 MHz, Chloroform-d) δ [ppm]: 9.02 (s, 1H), 8.18 (d, 1H), 8.00 (s, 1H), 7.59 (dd, 1H), 6.60 (s, 1H), 5.36 (d, 2H), 4.38-4.13 (m, 3H), 1.64-1.73 (m, 2H), 1.26 (d, 3H), 0.86 (t, 3H). | Intermediate 05-10<br>5%<br>LC-MS (Analytical Method F) $R_t$ = 3.42 min, MS (ESIpos): m/z = 483 [M + H]⁺. |

-continued

| | Structure<br>IUPAC-Name | Synth. from<br>Yield |
|---|---|---|
| Example | ¹H NMR | LC-MS |

23

N-(5-fluoropyridin-2-yl)-2-[2-methyl-5,8-dioxo-6-(propan-2-yl)-5,6,7,8-tetrahydro-4H-pyrazolo[1,5-a]pyrrolo[3,4-d]pyrimidin-4-yl]acetamide ¹H NMR (500 MHz, DMSO-d6) δ [ppm]: 11.03 (s, 1H), 8.30 (d, 1H), 8.06-7.87 (m, 1H), 7.66 (ddd, 1H), 6.29 (s, 1H), 5.41 (s, 2H), 4.30 (s, 2H), 4.27-4.17 (m, 1H), 2.24 (s, 3H), 1.17 (d, 6H).

Intermediate 05-26
55%
LC-MS (Analytical Method F) $R_t$ = 1.86 min, MS (ESIpos): m/z = 399 [M + H]⁺.

24

2-[2-ethyl-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide ¹H NMR (500 MHz, DMSO-d6) δ [ppm]: 11.10 (s, 1H), 8.38 (d, 1H), 8.00 (s, 1H), 7.74 (td, 1H), 6.44 (s, 1H), 5.48 (s, 2H), 4.37 (s, 2H), 4.25-4.33 (m, 1H), 2.69 (q, 2H), 1.28-1.19 (m, 9H).

Intermediate 05-11
47%
LC-MS (Analytical Method D): $R_t$ = 1.00 mins, MS (ESIPos): m/z = 413 [M + H]⁺.

| Example | Structure / IUPAC-Name / ¹H NMR | Synth. from / Yield / LC-MS |
|---|---|---|
| 25 | 2-{2-tert-butyl-6-[(±)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, Chloroform-d) δ [ppm]: 9.14 (s, 1H), 8.06 (d, 2H), 7.34 (ddd, 1H), 6.18 (s, 1H), 5.30 (d, 1H), 5.17 (d, 1H), 4.59-4.68 (m, 1H), 4.40 (d, 1H), 4.33 (d, 1H), 3.45 (d, 2H), 3.26 (s, 3H), 1.32 (s, 9H), 1.25 (d, 3H). | Intermediate 05-12<br>11%<br>LC-MS (Analytical Method F) $R_t$ = 2.84 min, MS (ESIpos): m/z = 471 [M + H]⁺. |
| 26 | 2-(2-tert-butyl-6-cyclopentyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide<br>¹H NMR (500 MHz, DMSO-d6) δ [ppm]: 11.08 (s, 1H), 8.38 (d, 1H), 8.09-7.94 (m, 1H), 7.74 (ddd, 1H), 6.58 (s, 1H), 5.46 (s, 2H), 4.51-4.42 (m, 1H), 4.40 (s, 2H), 1.97-1.84 (m, 2H), 1.79-1.66 (m, 4H), 1.63-1.55 (m, 2H), 1.32 (s, 9H). | Intermediate 05-13<br>35%<br>LC-MS (Analytical Method F) $R_t$ = 3.23 min, MS (ESIpos): m/z = 467.2 [M + H]⁺. |

| Example | Structure<br>IUPAC-Name<br>¹H NMR | Synth. from<br>Yield<br>LC-MS |
|---|---|---|
| 27 | 2-[2-tert-butyl-6-(oxetan-3-yl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, Chloroform-d) δ [ppm]: 8.85 (s, 1H), 8.18 (d,2H), 7.52-7.38 (m, 1H), 6.25 (s, 1H), 5.48-5.56 (m, 1H), 5.32 (s, 2H), 5.00 (dd, 2H), 4.89 (dd, 2H), 4.73 (s, 2H), 1.43 (s, 9H). | Intermediate 05-31<br>19%<br>LC-MS (Analytical Method F) $R_t$ = 2.51 min, MS(ESpos): m/z = 455 [M + H]⁺. |
| 28 | 2-[2-tert-butyl-5,8-dioxo-6-(tetrahydro-2H-pyran-4-ylmethyl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, Chloroform-d) δ [ppm]: 9.11 (s, 1H), 8.17 (d, 2H), 7.45 (ddd, 1H), 6.29 (s, 1H), 5.33 (s, 2H), 4.46 (s, 2H), 4.06-3.94 (m, 2H), 3.60-3.47 (m, 2H), 3.40 (td, 2H), 2.03 (ddt, 1H), 1.61-1.53 (m, 2H), 1.60-1.41 (m, 11H). | Intermediate 05-14<br>38%<br>LC-MS (Analytical Method D) $R_t$ = 4.43 min, MS (ESIpos): m/z = 497 [M + H]⁺. |

| Example | Structure IUPAC-Name ¹H NMR | Synth. from Yield LC-MS |
|---|---|---|
| 29 | N-(5-chloropyridin-2-yl)-2-[5,8-dioxo-6-(propan-2-yl)-2-(trifluoromethyl)-5,6,7,8-tetrahydro-4H-pyrazolo[1,5-a]pyrrolo[3,4-d]pyrimidin-4-yl]acetamide<br>¹H NMR (500 MHz, DMSO-d6) δ [ppm]: 11.20 (s, 1H), 8.43 (d, 1H), 8.04-7.95 (m, 1H), 7.90 (dd, 1H), 7.30 (s, 1H), 5.58 (s, 2H), 4.46 (s, 2H), 4.31 (hept, 1H), 1.25 (d, 6H). | Intermediate 05-15<br>40%<br>LC-MS (Analytical Method F) $R_t$ = 3.22 min, MS (ESIpos): m/z = 469 [M + H]⁺. |
| 30 | 2-[5,8-dioxo-6-(propan-2-yl)-2-(trifluoromethyl)-5,6,7,8-tetrahydro-4H-pyrazolo[1,5-a]pyrrolo[3,4-d]pyrimidin-4-yl]-N-(5-methylpyridin-2-yl)acetamide<br>¹H NMR (500 MHz, DMSO-d6) δ [ppm]: 10.91 (s, 1H), 8.20 (d, 1H), 7.86 (d, 1H), 7.59 (dd, 1H), 7.28 (s, 1H), 5.57 (s, 2H), 4.46 (s, 2H), 4.31 (hept, 1H), 2.26 (s, 3H), 1.25 (d, 6H) | Intermediate 05-15<br>37%<br>LC-MS (Analytical Method F) $R_t$ = 2.84 min, MS (ESIpos): m/z = 449 [M + H]⁺. |

| Example | Structure<br>IUPAC-Name<br>¹H NMR | Synth. from<br>Yield<br>LC-MS |
|---|---|---|
| 31 | 2-[5,8-dioxo-6-propan-2-yl)-2-(trifluoromethyl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, DMSO-d6) δ [ppm]: 11.04 (s, 1H), 8.30 (d, 1H), 8.01-7.87 (m, 1H), 7.66 (td, 1H), 7.22 (s, 1H), 5.50 (s, 2H), 4.38 (s, 2H), 4.24 (hept, 1H), 1.18 (d, 6H). | Intermediate 05-15<br>12%<br>LC-MS (Analytical Method F) R$_t$ = 2.93 min, MS (ESIpos): m/z = 453 [M + H]⁺. |
| 32 | 2-[2-tert-butyl-6-(2-hydroxy-2-methylpropyl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, Chloroform-d) δ [ppm]: 9.18 (s, 1H), 8.16 (d, 2H), 7.44 (ddd, 1H), 6.30 (s, 1H), 5.32 (s, 2H), 4.69 (s, 2H), 3.66 (s, 2H), 1.97 (s, 1H), 1.43 (s, 9H), 1.32 (s, 6H). | Intermediate 05-16<br>21%<br>LC-MS (Analytical Method D) R$_t$ = 4.25 min, MS (ESIpos): m/z = 471 [M + H]⁺. |

| Example | Structure<br>IUPAC-Name<br>¹H NMR | Synth. from<br>Yield<br>LC-MS |
|---|---|---|
| 33 | 2-[2-tert-butyl-5,8-dioxo-6-(tetrahydro-2H-pyran-4-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, Chloroform-d) δ [ppm]: 8.95 (s, 1H), 8.07 (d, 2H), 7.43-7.28 (m, 1H), 6.17 (s, 1H), 5.22 (s, 2H), 4.36 (dt, 1H), 4.32 (s, 2H), 4.07-3.97 (m, 2H), 3.45 (td, 2H), 1.90-1.69 (m, 4H), 1.32 (s, 9H). | Intermediate 05-17<br>27%<br>LC-MS (Analytical Method F) R$_t$ = 2.69 min, MS (ESIpos): m/z = 483 [M + H]⁺. |
| 34 | 2-{6-[2-(benzyloxy)ethyl]-2-tert-butyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, DMSO-d6) δ [ppm]: 11.07 (s, 1H), 8.37 (d, 1H), 8.07-7.93 (m, 1H), 7.80-7.67 (m, 1H), 7.39-7.14 (m, 5H), 6.59 (s, 1H), 5.45 (s, 2H), 4.50 (s, 2H), 4.41 (s, 2H), 3.74-3.59 (m, 4H), 1.31 (s, 9H). | Intermediate 05-18<br>58%<br>LC-MS (Analytical Method A) R$_t$ = 1.21 min, MS (ESIpos): m/z = 533 [M + H]⁺. |

| | Structure<br>IUPAC-Name | Synth. from<br>Yield |
|---|---|---|
| Example | ¹H NMR | LC-MS |

35

2-{2-tert-butyl-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide ¹H NMR (500 MHz, Chloroform-d) δ [ppm] 9.21 (s, 1H), 8.17 (d, 2H), 7.47-7.35 (m, 1H), 6.28 (s, 1H), 5.55-5.11 (m, 2H), 4.72-4.60 (m, 1H), 4.51 (d, 1H), 4.43 (d, 1H), 3.55 (d, 2H), 3.36 (s, 3H), 1.43 (s, 9H), 1.36 (d, 3H).

Intermediate 05-19
30%
LC-MS (Analytical Method F) R$_t$ = 2.84 min, MS (ESIpos): m/z = 471 [M + H]⁺.

36

2-{2-bromo-6-[(±)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide ¹H NMR (500 MHz, DMSO-d6) δ [ppm]: 11.10 (s, 1H), 8.38 (d, 1H), 8.06-7.92 (m, 1H), 7.74 (ddd, 1H), 6.90 (s, 1H), 5.49 (s, 2H), 4.51-4.25 (m, 3H), 3.56 (dd, 1H), 3.43 (dd, 1H), 3.26 (s, 3H), 1.20 (d, 3H)

Intermediate 05-20
81%
LC-MS (Analytical Method F) R$_t$ = 2.52 min, MS (ESIpos): m/z = 493/495 [M + H]⁺.

| | Structure<br>IUPAC-Name | Synth. from<br>Yield |
|---|---|---|
| Example | ¹H NMR | LC-MS |

37

N-(5-fluoropyridin-2-yl)-2-{6-[(2S)-1-methoxypropan-2-yl]-5,8-dioxo-2-(trifluoromethyl)-5,6,7,8-tetrahydro-4H-pyrazolo[1,5-a]pyrrolo[3,4-d]pyrimidin-4-yl}acetamide ¹H NMR (500 MHz, Chloroform-d) δ [ppm]: 9.00 (br. s, 1H), 8.17-7.86 (br. m, 2H), 7.35 (m, 1H), 6.59 (s, 1H), 5.39 (br. m, 1H), 5.26 (br. m, 1H), 4.56 (m, 1H), 4.46 (d, 1H), 4.37 (d, 1H), 3.46 (d, 2H), 3.26 (s, 3H), 1.27 (d, 3H).

Intermediate 05-21
6%
LC-MS (Analytical Method F) R$_t$ = 2.85 min, MS (ESIpos): m/z = 483 [M + H]⁺.

38

2-{2-tert-butyl-5,8-dioxo-6-[2-oxo-2-(pyrrolidin-1-yl)ethyl]-5,6,7,8-tetrahydro-4H-pyrazolo[1,5-a]pyrrolo[3,4-d]pyrimidin-4-yl}-N-(5-fluoropyridin-2-yl)acetamide ¹H NMR (500 MHz, Chloroform-d) δ [ppm]: 9.33 (s, 1H), 8.14 (d, 2H), 7.47-7.33 (m, 1H), 6.20 (s, 1H), 5.31 (s, 2H), 4.61 (s, 2H), 4.39 (s, 2H), 3.66-3.36 (m, 4H), 2.11-2.02 (m, 2H), 2.01-1.80 (m, 2H), 1.42 (s, 9H).

Intermediate 05-22
23%
LC-MS (Analytical Method F) R$_t$ = 2.62 min, MS (ESIpos): m/z = 510 [M + H]⁺.

| Example | Structure / IUPAC-Name / ¹H NMR | Synth. from / Yield / LC-MS |
|---|---|---|
| 39 | N-(5-fluoropyridin-2-yl)-2-{6-[(2S)-1-methoxypropan-2-yl]-5,8-dioxo-2-(propan-2-yl)-5,6,7,8-tetrahydro-4H-pyrazolo[1,5-a]pyrrolo[3,4-d]pyrimidin-4-yl}acetamide<br>¹H NMR (500 MHz, Chloroform-d) δ [ppm]: 1.34 (dd, 9H), 3.18 (hept, 1H), 3.34 (s, 3H), 3.53 (d, 2H), 4.41 (d, 1H), 4.49 (d, 1H), 4.59-4.69 (m, 1H), 5.26 (s, 1H), 5.37 (s, 1H), 6.23 (s, 1H), 7.42 (ddd, 1H), 8.10-8.22 (m, 2H), 9.18 (s, 1H). | Intermediate 05-23<br>30%<br>LC-MS (Analytical Method D) R$_t$ = 3.63 min, MS (ESIpos): m/z = 457 [M + H]⁺. |
| 40 | N-(5-fluoropyridin-2-yl)-2-{6-[(2S)-1-methoxypropan-2-yl]-5,8-dioxo-2-(tetrahydro-2H-pyran-4-yl)-5,6,7,8-tetrahydro-4H-pyrazolo[1,5-a]pyrrolo[3,4-d]pyrimidin-4-yl}acetamide<br>¹H NMR (500 MHz, Chloroform-d) δ [ppm]: 1.36 (d, 3H), 1.91 (qd, 2H), 1.96-2.03 (m, 2H), 3.14 (tt, 1H), 3.36 (s, 3H), 3.51-3.60 (m, 4H), 4.04-4.12 (m, 2H), 4.44 (d, 1H), 4.52 (d, 1H), 4.62-4.72 (m, 1H), 5.15-5.34 (m, 1H), 5.36-5.52 (m, 1H), 6.27 (s, 1H), 7.44 (ddd, 1H), 8.17 (d, 2H), 9.20 (s, 1H). | Intermediate 05-24<br>53%<br>LC-MS (Analytical Method D) R$_t$ = 3.40 min, MS (ESIpos): m/z = 499 [M + H]⁺. |

| Example | Structure IUPAC-Name ¹H NMR | Synth. from Yield LC-MS |
|---|---|---|
| 41 | 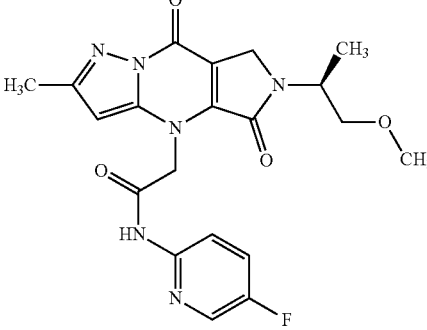<br>N-(5-fluoropyridin-2-yl)-2-{6-[(2S)-1-methoxypropan-2-yl]-2-methyl-5,8-dioxo-5,6,7,8-tetrahydro-4H-pyrazolo[1,5-a]pyrrolo[3,4-d]pyrimidin-4-yl}acetamide<br>¹H NMR (500 MHz, DMSO-d6) δ [ppm]: 11.10 (s, 1H), 8.38 (d, 1H), 8.10-7.87 (m, 1H), 7.74 (ddd, 1H), 6.37 (s, 1H), 5.48 (s, 2H), 4.47-4.23 (m, 3H), 3.56 (dd, 1H), 3.44 (dd, 1H), 3.26 (s, 3H), 2.32 (s, 3H), 1.21 (d, 3H). | Intermediate 05-25<br>48%<br>LC-MS (Analytical Method F) $R_t$ = 2.16 min, MS (ESIpos): m/z = 429.1 [M + H]⁺. |
| 42 | 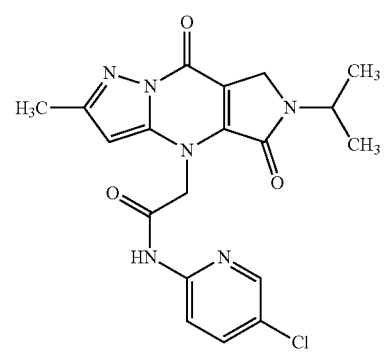<br>N-(5-chloropyridin-2-yl)-2-[2-methyl-5,8-dioxo-6-(propan-2-yl)-5,6,7,8-tetrahydro-4H-pyrazolo[1,5-a]pyrrolo[3,4-d]pyrimidin-4-yl]acetamide<br>¹H NMR (500 MHz, DMSO-d6) δ [ppm]: 11.05 (s, 1H), 8.35 (d, 1H), 7.91 (d, 1H), 7.82 (dd, 1H), 6.30 (s, 1H), 5.41 (s, 2H), 4.30 (s, 2H), 4.22 (hept, 1H), 2.24 (s, 3H), 1.16 (d, 6H). | Intermediate 05-26<br>39%<br>LC-MS (Analytical Method F) $R_t$ = 2.54 min, MS (ESIpos): m/z = 415 [M + H]⁺. |

-continued

| | Structure<br>IUPAC-Name | Synth. from |
|---|---|---|
| Example | ¹H NMR | Yield<br>LC-MS |

43

2-{2-tert-butyl-6-[(2R)-1-methoxypropan-2-yl]-5,8-
dioxo-5,6,7,8-tetrahydro-4H-pyrazolo[1,5-
a]pyrrolo[3,4-d]pyrimidin-4-yl}-N-(5-fluoropyridin-
2-yl)acetamide
¹H NMR (500 MHz, DMSO-d6) δ [ppm]: 11.08 (s, 1H),
8.37 (d, 1H), 8.05-7.95 (m, 1H), 7.83-7.68 (m, 1H),
6.57 (s, 1H), 5.45 (s, 2H), 4.42-4.25 (m, 3H), 3.55
(dd, 1H), 3.43 (dd, 1H), 3.25 (s, 3H), 1.31 (s, 9H), 1.19
(d, 3H).

Intermediate 05-27
44%
LC-MS (Analytical
Method F) R$_t$ = 2.84
min, MS (ESIpos):
m/z = 471 [M + H]⁺.

44

N-(5-fluoropyridin-2-yl)-2-{6-[(2R)-1-
methoxypropan-2-yl]-5,8-dioxo-2-(propan-2-yl)-
5,6,7,8-tetrahydro-4H-pyrazolo[1,5-a]pyrrolo[3,4-
d]pyrimidin-4-yl}acetamide
¹H NMR (500 MHz, DMSO-d6) δ [ppm]: 11.09 (s, 1H),
8.37 (d, 1H), 8.06-7.95 (m, 1H), 7.83-7.65 (m, 1H),
6.49 (s, 1H), 5.46 (s, 2H), 4.54-4.16 (m, 3H), 3.55
(dd, 1H), 3.43 (dd, 1H), 3.25 (s, 3H), 3.01 (hept, 1H),
1.26 (d, 6H), 1.19 (d, 3H).

Intermediate 05-28
50%
LC-MS (Analytical
Method F) R$_t$ = 2.60
min, MS (ESIpos):
m/z = 457 [M + H]⁺.

| Example | Structure IUPAC-Name ¹H NMR | Synth. from Yield LC-MS |
|---|---|---|
| 45 | 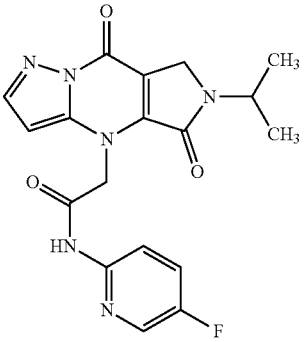<br>2-[5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, DMSO-d6) δ [ppm]: 11.11 (s, 1H), 8.38 (d, 1H), 8.09-7.91 (m, 2H), 7.74 (ddd, 1H), 6.59 (d, 1H), 5.54 (s, 2H), 4.40 (s, 2H), 4.32 (hept, 1H), 1.25 (d, 6H). | Intermediate 05-29<br>33%<br>LC-MS (Analytical Method F) $R_t$ = 2.11 min, MS (ESIpos): m/z = 385 [M + H]⁺. |
| 46 | 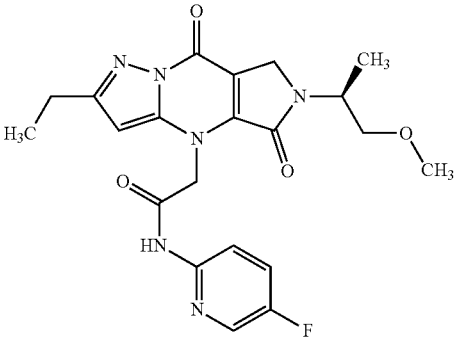<br>N-(5-fluoropyridin-2-yl)-2-{6-[(2R)-1-methoxypropan-2-yl]-5,8-dioxo-2-(propan-2-yl)-5,6,7,8-tetrahydro-4H-pyrazolo[1,5-a]pyrrolo[3,4-d]pyrimidin-4-yl}acetamide<br>¹H NMR (500 MHz, DMSO-d6) δ [ppm]: 11.09 (s, 1H), 8.37 (d, 1H), 8.06-7.95 (m, 1H), 7.83-7.65 (m, 1H), 6.49 (s, 1H), 5.46 (s, 2H), 4.54-4.16 (m, 3H), 3.55 (dd, 1H), 3.43 (dd, 1H), 3.25 (s, 3H), 3.01 (hept, 1H), 1.26 (d, 6H), 1.19 (d, 3H). | Intermediate 05-30<br>20%<br>LC-MS (Analytical Method D) $R_t$ = 3.46 min, MS (ESIpos): m/z = 443 [M + H]⁺. |

| Example | Structure<br>IUPAC-Name<br>¹H NMR | Synth. from<br>Yield<br>LC-MS |
|---------|-----------------------------------|-------------------------------|
| 47 | 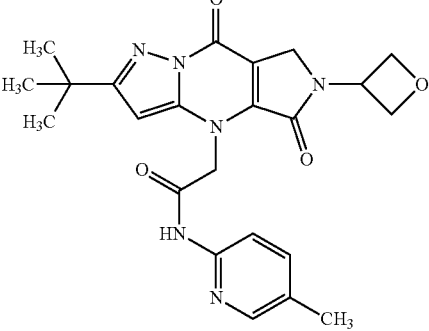<br>2-[2-tert-butyl-6-(oxetan-3-yl)-5,8-dioxo-5,6,7,8-tetrahydro-4H-pyrazolo[1,5-a]pyrrolo[3,4-d]pyrimidin-4-yl]-N-(5-methylpyridin-2-yl)acetamide<br>¹H NMR (500 MHz, Chloroform-d) δ [ppm]: 8.62 (s, 1H), 8.02 (s, 1H), 7.90 (s, 1H), 7.43 (dd, 1H), 6.11 (s, 1H), 5.43 (p, 1H), 5.23 (s, 2H), 4.88 (t, 2H), 4.78 (t, 2H), 4.61 (s, 2H), 2.21 (s, 3H), 1.32 (s, 9H). | Intermediate 05-31<br>14%<br>LC-MS (Analytical Method D) $R_t$ = 2.80 min, MS (ESIpos): m/z = 451 [M + H]⁺. |
| 48 | 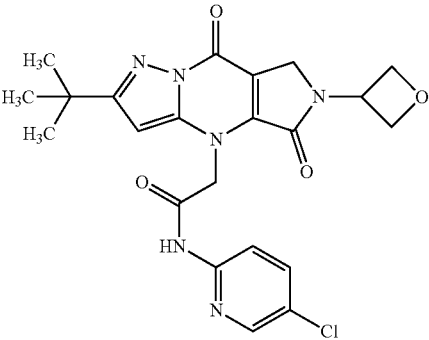<br>2-[2-tert-butyl-6-(oxetan-3-yl)-5,8-dioxo-5,6,7,8-tetrahydro-4H-pyrazolo[1,5-a]pyrrolo[3,4-d]pyrimidin-4-yl]-N-(5-chloropyridin-2-yl)acetamide<br>¹H NMR (500 MHz, Chloroform-d) δ [ppm]: 8.70 (s, 1H), 8.17 (d, 1H), 8.00 (s, 1H), 7.58 (dd, 1H), 6.14 (s, 1H), 5.47-5.55 (m, 1H), 5.21 (s, 2H), 4.89 (t, 2H), 4.78 (t, 2H), 4.62 (s, 2H), 1.32 (s, 9H). | Intermediate 05-31<br>16%<br>LC-MS (Analytical Method D) $R_t$ = 2.80 min, MS (ESIpos): m/z = 471 [M + H]⁺. |

| Example | Structure<br>IUPAC-Name<br>¹H NMR | Synth. from<br>Yield<br>LC-MS |
|---|---|---|
| 49 | 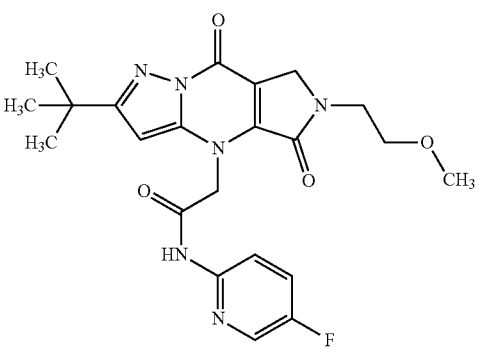<br>2-[2-tert-butyl-6-(2-methoxyethyl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, DMSO-d6) δ [ppm]: 11.07 (s, 1H), 8.37 (d, 1H), 8.03-7.95 (m, 1H), 7.76-7.67 (m, 1H), 6.58 (s, 1H), 5.45 (s, 2H), 4.42 (s, 2H), 3.65 (t, 2H), 3.56 (t, 2H), 3.27 (s, 3H), 1.31 (s, 9H). | Intermediate 05-32<br>58%<br>LC-MS (Analytical Method F) $R_t$ = 2.67 min, MS (ESIpos): m/z = 457 [M + H]⁺. |
| 50 | 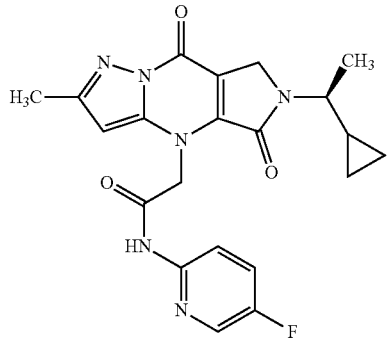<br>2-{6-[(1S)-1-cyclopropylethyl]-2-methyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, DMSO-d6) δ [ppm]: 11.09 (s, 1H), 8.37 (d, 1H), 8.06-7.94 (m, 1H), 7.79-7.66 (m, 1H), 6.36 (s, 1H), 5.61-5.33 (m, 2H), 4.56-4.41 (m, 2H), 3.53-3.43 (m, 1H), 2.31 (s, 3H), 1.28 (d, 3H), 1.23-1.13 (m, 1H), 0.60-0.53 (m, 1H), 0.49-0.40 (m, 1H), 0.40-0.31 (m, 1H), 0.27-0.17 (m, 1H). | Intermediate 05-33<br>55%<br>LC-MS (Analytical Method F) $R_t$ = 2.57 min, MS (ESIpos): m/z = 425 [M + H]⁺. |

| Structure IUPAC-Name | Synth. from Yield |
|---|---|
| Example ¹H NMR | LC-MS |

51

N-(5-fluoropyridin-2-yl)-2-[6-(2-hydroxy-2-methylpropyl)-5,8-dioxo-2-(propan-2-yl)-5,6,7,8-tetrahydro-4H-pyrazolo[1,5-a]pyrrolo[3,4-d]pyrimidin-4-yl]acetamide ¹H NMR (500 MHz, Chloroform-d) δ [ppm]: 9.20 (s, 1H), 8.16 (d, 2H), 7.44 (ddd, 1H), 6.26 (s, 1H), 5.33 (s, 2H), 4.69 (s, 2H), 3.66 (s, 2H), 3.21 (hept, 1H), 2.02 (d, 1H), 1.37 (d, 6H), 1.32 (s, 6H).

Intermediate 05-34
64%
LC-MS (Analytical Method D) $R_t$ = 2.14 min, MS (ESIpos): m/z = 457 [M + H]⁺.

52

N-(5-fluoropyridin-2-yl)-2-{6-[(2R)-1-methoxypropan-2-yl]-2-methyl-5,8-dioxo-5,6,7,8-tetrahydro-4H-pyrazolo[1,5-a]pyrrolo[3,4-d]pyrimidin-4-yl}acetamide ¹H NMR (500 MHz, DMSO-d₆) δ [ppm]: 11.11 (s, 1H), 8.38 (d, 1H), 8.06-7.95 (m, 1H), 7.74 (ddd, 1H), 6.37 (s, 1H), 5.48 (s, 2H), 4.50-4.13 (m, 3H), 3.56 (dd, 1H), 3.44 (dd, 1H), 3.26 (s, 3H), 2.32 (s, 3H), 1.21 (d, 3H)

Intermediate 05-35
26%
LC-MS (Analytical Method F) $R_t$ = 1.87 min, MS (ESIpos): m/z = 429 [M + H]⁺.

| Example | Structure / IUPAC-Name / ¹H NMR | Synth. from / Yield / LC-MS |
|---|---|---|
| 53 | 2-{6-[(2S)-butan-2-yl]-2-methyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, Chloroform-d) δ [ppm]: 9.03 (s, 1H), 8.06 (d, 2H), 7.34 (ddd, 1H), 6.13 (s, 1H), 5.31 (d, 1H), 5.18 (d, 1H), 4.35-4.26 (m, 2H), 4.23 (d, 1H), 2.38 (s, 3H), 1.63-1.53 (m, 2H), 1.23 (d, 3H), 0.84 (t, 3H). | Intermediate 05-36<br>15%<br>LC-MS (Analytical Method D) $R_t$ = 2.47 min, MS (ESIpos): m/z = 413 [M + H]⁺. |
| 54 | 2-{2-tert-butyl-6-[(2S)-2-hydroxypropyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, DMSO-d6) δ [ppm]: 11.06 (s, 1H), 8.37 (d, 1H), 8.05-7.95 (m, 1H), 7.75-7.70 (m, 1H), 6.58 (s, 1H), 5.51-5.43 (m, 2H), 4.94-4.89 (m, 1H), 4.51-4.39 (m, 2H), 3.97-3.88 (m, 1H), 3.46-3.34 (m, 2H), 1.31 (s, 9H), 1.05 (d, 3H). | Intermediate 05-37<br>7%<br>LC-MS (Analytical Method F) $R_t$ = 2.44 min, MS (ESIpos): m/z = 457 [M + H]⁺. |

| Example | Structure / IUPAC-Name / ¹H NMR | Synth. from / Yield / LC-MS |
|---|---|---|
| 55 | 2-{6-[(1R)-1-cyclopropylethyl]-2-methyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, Chloroform-d) δ [ppm]: 9.14 (s, 1H), 8.06 (d, 2H), 7.33 (ddd, 1H), 6.13 (s, 1H), 5.24 (s, 2H), 4.49 (d, 1H), 4.37 (d, 1H), 3.70-3.59 (m, 1H), 2.38 (s, 3H), 1.29 (d, 3H), 1.01-0.89 (m, 1H), 0.66-0.56 (m, 1H), 0.47-0.38 (m, 1H), 0.36-0.24 (m, 2H). | Intermediate 05-38<br>16%<br>LC-MS (Analytical Method D) $R_t$ = 2.57 min, MS (ESIpos): m/z = 425 [M + H]⁺. |
| 56 | 2-[2-cyclopropyl-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H-NMR (300 MHz, DMSO) δ [ppm]: 0.75-0.80 (m, 2H), 0.98-1.01 (m, 2H), 1.23 (d, 6H), 1.97-2.01 (m, 1H), 4.25-4.29 (m, 1H), 4.36 (s, 2H), 5.43 (br, 2H), 6.35 (s, 1H), 7.74 (t, 1H), 7.99-8.01 (m, 1H), 8.37 (d, 1H), 11.09 (br, 1H). | Intermediate 05-45<br>39 %<br>LC-MS (Analytical Method K, 0-2.1 min 10-95% B, 2.1-2.7 min 95% B): $R_t$ = 1.15 min; MS (ESIpos): m/z = 425 [M + H]⁺ |

| Example | Structure IUPAC-Name ¹H NMR | Synth. from Yield LC-MS |
|---|---|---|
| 57 | 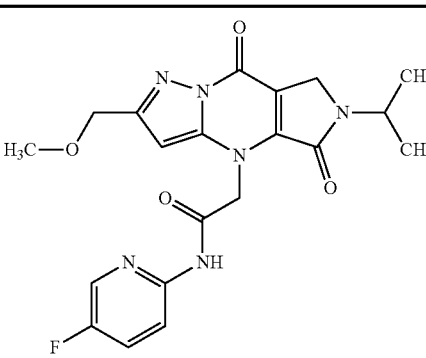<br>N-(5-fluoropyridin-2-yl)-2-[2-(methoxymethyl)-5,8-dioxo-6-(propan-2-yl)-5,6,7,8-tetrahydro-4H-pyrazolo[1,5-a]pyrrolo[3,4-d]pyrimidin-4-yl]acetamide<br>¹H-NMR (300 MHz, CD3OD) δ [ppm]: 1.31 (d, 6H), 3.40 (s, 3H), 4.42-4.50 (m, 3H), 4.57 (s, 2H), 5.59 (s, 2H), 6.47 (s, 1H), 7.52-7.59 (m, 1H), 8.03-8.05 (m, 1H), 8.21-8.22 (m, 1H). | Intermediate 05-46<br>20%<br>LC-MS Analytical Method K, 0-2.9 min 5-40% B, 2.9-3.3 min 40-95% B, 3.3-4.2 min 95% B): $R_t$ = 2.27 min; MS (ESIpos): m/z = 429 [M + H]⁺. |
| 58 | 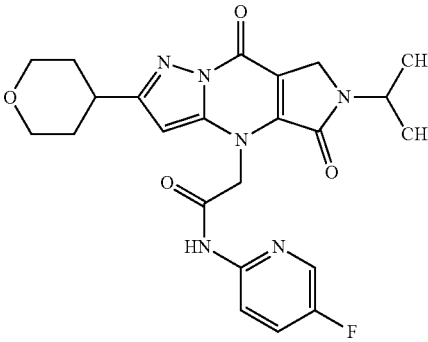<br>2-[5,8-dioxo-6-(propan-2-yl)-2-(tetrahydro-2H-pyran-4-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.23 (d, 6H), 1.61-1.82 (m, 2H), 1.86 (br dd, 2H), 2.96 (tt, 1H), 3.39-3.50 (m, 2H), 3.87-3.95 (m, 2H), 4.23-4.34 (m, 1H), 4.37 (s, 2H), 5.46 (br s, 2H), 6.54 (s, 1H), 7.74 (td, 1H), 8.00 (br d, 1H), 8.38 (d, 1H), 11.11 (br s, 1H). | Intermediate 05-39<br>7%<br>LC-MS (Analytical Method J): $R_t$ = 0.88 min; MS (ESIpos): m/z = 469 [M + H]⁺ |

| | Structure<br>IUPAC-Name | Synth. from<br>Yield |
|---|---|---|
| Example | ¹H NMR | LC-MS |
| 59 | 2-[5,8-dioxo-6-(propan-2-yl)-2-(tetrahydro-2H-pyran-4-yl)-5,6,7,8-tetrahydro-4H-pyrazolo[1,5-a]pyrrolo[3,4-d]pyrimidin-4-yl]-N-(5-methylpyridin-2-yl)acetamide<br>¹H NMR (400 MHz, DMSO-d6) δ [ppm]: 1.23 (d, 6H), 1.61-1.76 (m, 2H), 1.86 (br dd, 2H), 2.25 (s, 3H), 2.96 (tt, 1H), 3.36-3.48 (m, 2H), 3.91 (dt, 2H), 4.25-4.34 (m, 1H), 4.37 (s, 2H), 5.45 (br s, 2H), 6.52 (s, 1H), 7.59 (dd, 1H), 7.85 (br d, 1H), 8.16-8.22 (m, 1H), 10.89 (s, 1H). | Intermediate 05-39<br>7%<br>LC-MS (Analytical Method J): $R_t$ = 0.90 min; MS (ESIpos): m/z = 465 [M + H]⁺ |
| 60 | N-(5-chloropyridin-2-yl)-2-{2-ethyl-5,8-dioxo-6-[(±)-tetrahydrofuran-3-ylmethyl]-5,6,7,8-tetrahydro-4H-pyrazolo[1,5-a]pyrrolo[3,4-d]pyrimidin-4-yl}acetamide<br>¹H NMR (400 MHz, DMSO-d6) δ [ppm]: 1.23 (t, 3H), 1.50-1.60 (m, 1H), 1.90-2.01 (m, 1H), 2.59-2.72 (m, 3H), 3.41 (dd, 1H), 3.48 (d, 2H), 3.57-3.65 (m, 1H), 3.65-3.78 (m, 2H), 4.39-4.48 (m, 2H), 5.47 (br s, 2H), 6.47 (s, 1H), 7.87-7.92 (m, 1H), 7.98 (br d, 1H), 8.40-8.43 (m, 1H), 11.18 (s, 1H). | Intermediate 05-40<br>5%<br>LC-MS (Analytical Method J): $R_t$ = 0.92 min; MS (ESIpos): m/z = 471 [M + H]⁺. |

| Example | Structure<br>IUPAC-Name<br>¹H NMR | Synth. from<br>Yield<br>LC-MS |
|---|---|---|
| 61 | 2-{2-ethyl-5,8-dioxo-6-[(±)-tetrahydrofuran-3-ylmethyl]-5,6,7,8-tetrahydro-4H-pyrazolo[1,5-a]pyrrolo[3,4-d]pyrimidin-4-yl}-N-(5-methylpyridin-2-yl)acetamide<br>¹H NMR (400 MHz, DMSO-d6) δ [ppm]: 1.23 (t, 3H), 1.45-1.63 (m, 1H), 1.90-2.03 (m, 1H), 2.23-2.27 (m, 3H), 2.59-2.72 (m, 3H), 3.37-3.52 (m, 3H), 3.58-3.77 (m, 3H), 4.38-4.48 (m, 2H), 4.93 (br s, 1H), 5.45 (br s, 1H), 6.45 (s, 1H), 7.58 (dd, 1H), 7.84 (br d, 1H), 8.16-8.20 (m, 1H), 10.89 (s, 1H). | Intermediate 05-40<br>11%<br>LC-MS (Analytical Method J): $R_t$ = 0.86 min; MS (ESIpos): m/z = 451 [M + H]⁺. |
| 62 | N-(5-chloropyridin-2-yl)-2-{2-ethyl-5,8-dioxo-6-[(±)-tetrahydrofuran-2-ylmethyl]-5,6,7,8-tetrahydro-4H-pyrazolo[1,5-a]pyrrolo[3,4-d]pyrimidin-4-yl}acetamide<br>¹H NMR (400 MHz, DMSO-d6) δ [ppm]: 1.23 (t, 3H), 1.46-1.60 (m, 1H), 1.75-2.01 (m, 3H), 2.69 (q, 2H), 3.45-3.52 (m, 1H), 3.55-3.68 (m, 2H), 3.75-3.82 (m, 1H), 4.06 (qd, 1H), 4.39-4.51 (m, 2H), 5.47 (br s, 2H), 6.47 (s, 1H), 7.88-7.93 (m, 1H), 7.98 (br d, 1H), 8.41-8.43 (m, 1H), 11.18 (s, 1H). | Intermediate 05-41<br>80%<br>LC-MS (Analytical Method H): $R_t$ = 1.02 min; MS (ESIpos): m/z = 471 [M + H]⁺. |

| | Structure<br>IUPAC-Name | Synth. from<br>Yield |
|---|---|---|
| Example | ¹H NMR | LC-MS |

63

2-{2-ethyl-5,8-dioxo-6-[(±)-tetrahydrofuran-2-ylmethyl]-5,6,7,8-tetrahydro-4H-pyrazolo[1,5-a]pyrrolo[3,4-d]pyrimidin-4-yl}-N-(5-methylpyridin-2-yl)acetamide ¹H NMR (400 MHz, DMSO-d6) δ [ppm]: 1.23 (t, 3H), 1.44-1.62 (m, 1H), 1.74-2.01 (m, 3H), 2.24 (s, 3H), 2.64-2.72 (m, 2H), 3.43-3.52 (m, 1H), 3.56-3.68 (m, 2H), 3.75-3.83 (m, 1H), 4.06 (qd, 1H), 4.39-4.51 (m, 2H), 5.45 (br s, 2H), 6.44 (s, 1H), 7.59 (dd, 1H), 7.85 (br d, 1H), 8.18 (s, 1H), 10.89 (s, 1H).

Intermediate 05-41
72%
LC-MS (Analytical Method J): $R_t$ = 0.91 min; MS (ESIpos): m/z = 451 [M + H]⁺.

64

2-[2-ethyl-5,8-dioxo-6-(propan-2-yl)-5,6,7,8-tetrahydro-4H-pyrazolo[1,5-a]pyrrolo[3,4-d]pyrimidin-4-yl]-N-(pyridin-2-yl)acetamide Intermediate 05-11
30%
LC-MS (Analytical Method P): $R_t$ = 0.86 min; MS (ESIpos): m/z = 395 [M + H]⁺.

65

2-[2-ethyl-5,8-dioxo-6-(propan-2-yl)-5,6,7,8-tetrahydro-4H-pyrazolo[1,5-a]pyrrolo[3,4-d]pyrimidin-4-yl]-N-(5-methylpyridin-2-yl)acetamide Intermediate 05-11
22%
LC-MS (Analytical Method P): $R_t$ = 0.92 min; MS (ESIpos): m/z = 409 [M + H]⁺.

| Example | Structure<br>IUPAC-Name<br>¹H NMR | Synth. from<br>Yield<br>LC-MS |
|---|---|---|
| 66 | N-(5-chloropyridin-2-yl)-2-[2-ethyl-5,8-dioxo-6-(propan-2-yl)-5,6,7,8-tetrahydro-4H-pyrazolo[1,5-a]pyrrolo[3,4-d]pyrimidin-4-yl]acetamide | Intermediate 05-11<br>24%<br>LC-MS (Analytical Method P): R$_t$ = 1.03 min; MS (ESIpos): m/z = 429 [M + H]⁺. |
| 67 | N-(5-bromopyridin-2-yl)-2-[2-ethyl-5,8-dioxo-6-(propan-2-yl)-5,6,7,8-tetrahydro-4H-pyrazolo[1,5-a]pyrrolo[3,4-d]pyrimidin-4-yl]acetamide<br>¹H NMR (500 MHz, DMSO-d6) δ [ppm]: 11.17 (s, 1H), 8.50 (d, 1H), 8.01 (dd, 1H), 7.95 (s, 1H), 6.46 (s, 1H), 5.48 (s, 2H), 4.37 (s, 2H), 4.30 (hept, 1H), 2.69 (q, 2H), 1.26-1.21 (m, 9H). | Intermediate 05-11<br>57%<br>LC-MS (Analytical Method D) R$_t$ = 3.84 min, MS (ESIpos): m/z = 473.10/474.85 [M + H]⁺. |

| Example | Structure IUPAC-Name ¹H NMR | Synth. from Yield LC-MS |
|---|---|---|
| 68 | tert-butyl {2-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]ethyl}carbamate<br>¹H-NMR (400 MHz, DMSO-d6) δ [ppm]: :1.21 (t, 3H), 1.37 (s, 9H), 2.70 (q, 2H), 3.18 (q, 2H), 3.52 (q, 2H), 4.41 (s, 2H), 5.48 (br, 2H), 6.47 (s, 1H), 6.95-6.98 (m, 1H), 7.70-7.76 (m, 1H), 7.99-8.00 (m, 1H), 8.37-8.38 (m, 1H), 11.10 (br, 1H). | Intermediate 05-42<br>15%<br>LC-MS (Analytical Method N, 0-2.00 min 10-95% B, 2.00-2.70 min 95% B): $R_t$ = 1.28 min; MS (ESIpos): m/z = 514 [M + H]⁺. |
| 69 | N-(5-fluoropyridin-2-yl)-2-[2-(5-methylpyridin-2-yl)-5,8-dioxo-6-{propan-2-yl}-5,6,7,8-tetrahydro-4H-pyrazolo[1,5-a]pyrrolo[3,4-d]pyrimidin-4-yl]acetamide<br>¹H-NMR (500 MHz, DMSO-d6) δ [ppm]: 1.25 (d, 6H), 2.35 (s, 3H), 4.32 (hept, 1H), 4.42 (s, 2H), 5.62 (s, 2H), 7.13 (s, 1H), 7.69-7.79 (m, 2H), 7.94-8.04 (m, 1H), 8.06 (d, 1H), 8.38 (d, 1H), 8.46-8.52 (m, 1H), 11.12 (s, 1H). | Intermediate 05-48<br>61%<br>LC-MS (Analytical Method F): $R_t$ = 2.55 min; MS (ESIpos): m/z = 476.2 [M + H]⁺. |

Example 70 ethyl 4-{2-[(5-fluoropyridin-2-yl)amino]-2-oxo-ethyl}-5,8-dioxo-6-(propan-2-yl)-5,6,7,8-tetrahydro-4H-pyrazolo[1,5-a]pyrrolo[3,4-d]pyrimidine-2-carboxylate

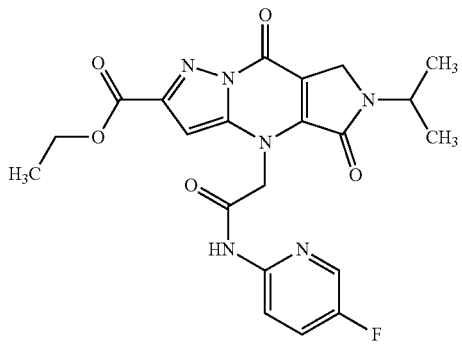 [SMILES: CCOC(=O)c1cc2n(CC(=O)Nc3ccc(F)cn3)c3c(c(=O)n2n1)CN(C(C)C)C3=O]

To a solution of ethyl 6-isopropyl-5,8-dioxo-5,6,7,8-tetrahydro-4H-pyrazolo[1,5-a]pyrrolo[3,4-d]pyrimidine-2-carboxylate (10 g, 32.9 mmol) (intermediate 03-37), in N,N-dimethylformamide (30 ml) was added 2-bromo-N-(5-fluoropyridin-2-yl)acetamide (10.2 g, 0.6 mmol) and the resulting mixture was stirred at 60° C. for 1 h. After cooling to rt, the crude product was purified by reverse phase column chromatography (C18-silica gel, eluting with water (0.1% NH$_4$HCO$_3$)-acetonitrile, 9:1 to 2:3) to give 10.21 g (67% yield) of the title compound as a pink solid.

$^1$H-NMR (300 MHz, DMSO-d6) δ[ppm]: 1.24 (d, 6H), 1.32 (t, 3H), 4.26-4.33 (m, 3H), 4.44 (s, 2H), 5.59 (s, 2H), 7.16 (s, 1H), 7.69-7.77 (m, 1H), 7.99-8.00 (m, 1H), 8.37-8.38 (m, 1H), 11.11 (br, 1H).

LC-MS (Water (Analytical Method L, 0-3.0 min 20-65% B, 3.0-4.0 min 65-95% B, 4.0-5.0 min 95% B): R$_t$=1.38 min; MS (ESIpos): m/z=457 [M+H]$^+$.

Example 71

2-{2-ethyl-5,8-dioxo-6-[(±)-tetrahydrofuran-3-yl]-5,6,7,8-tetrahydro-4H-pyrazolo[1,5-a]pyrrolo[3,4-d]pyrimidin-4-yl}-N-(5-fluoropyridin-2-yl)acetamide

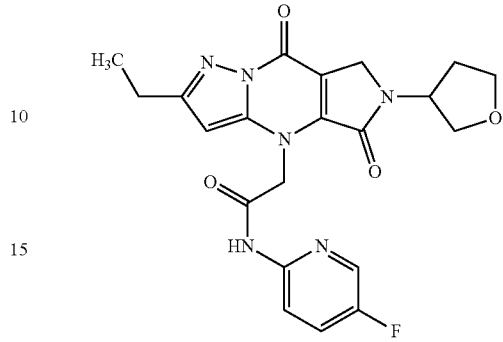

To a solution of 2-ethyl-6-[(±)-tetrahydrofuran-3-yl]-6,7-dihydro-4H-pyrazolo[1,5-a]pyrrolo[3,4-d]pyrimidine-5,8-dione (400 mg, 1.387 mmol) (intermediate 03-38) in N,N-dimethylformamide (10 ml), Na$_2$CO$_3$ (588 mg, 5.55 mmol) and 2-bromo-N-(5-fluoropyridin-2-yl)acetamide (388 mg, 1.66 mol) were added respectively. The mixture was stirred for 1 h at 80° C. After being cooled to rt, the mixture was added to water (20 ml). The mixture was extracted with ethyl acetate. The organics were concentrated in vacuo and the residue was purified with column chromatography (silica gel, eluting with dichloromethane-methanol, 10:1) to give 208.9 mg (34% yield) of the title compound as an off-white solid.

$^1$H-NMR (400 MHz, CDCl3) δ [ppm]: 1.31 (t, 3H), 2.01-2.09 (m, 1H), 2.36-2.46 (m, 1H), 2.82 (q, 2H), 3.82-3.93 (m, 3H), 4.08-4.14 (m, 1H), 4.40-4.54 (m, 2H), 5.01-5.03 (m, 1H), 5.38 (br, 2H), 6.21 (s, 1H), 7.41-7.45 (m, 1H), 8.15-8.16 (m, 1H), 9.21 (br, 1H).

LC-MS (Analytical Method K, 0-2.0 min 5-95% B, 2.0-2.7 min 95% B): R$_t$=1.04 min; MS (ESIpos): m/z=441 [M+H]$^+$.

In analogy to the procedure described for Example 71 the following examples were prepared using the appropriate intermediate and haloacetamide as starting materials.

| Example | Structure<br>IUPAC-Name<br>$^1$H NMR | Synth. from<br>Yield<br>LC-MS |
|---|---|---|
| 72 | ![structure]<br>N-(5-fluoropyridin-2-yl)-2-[2-(hydroxymethyl)-5,8-dioxo-6-(propan-2-yl)-5,6,7,8-tetrahydro-4H-pyrazolo[1,5-a]pyrrolo[3,4-d]pyrimidin-4-yl]acetamide<br>$^1$H-NMR (400 MHz, DMSO-d6) δ [ppm]: 1.36 (d, 6H), 4.28-4.34 (m, 1H), 4.39 (s, 2H), 4.55 (d, 2H), 5.39 (t, 1H), 5.54 (brs, 2H), 6.51 (s, 1H), 7.71-7.76 (m, 1H), 8.00-8.01 (m, 1H), 8.38 (s, 1H), 11.06 (br, 1H). | Intermediate 03-39<br>31%<br>LC-MS (Analytical Method K, 0-2.0 min 5-95% B, 2.0-2.7 min 95% B): R$_t$ = 0.94 min; MS (ESIpos): m/z = 415 [M + H]$^+$. |

| Example | Structure<br>IUPAC-Name<br>¹H NMR | Synth. from<br>Yield<br>LC-MS |
|---|---|---|
| 73 | 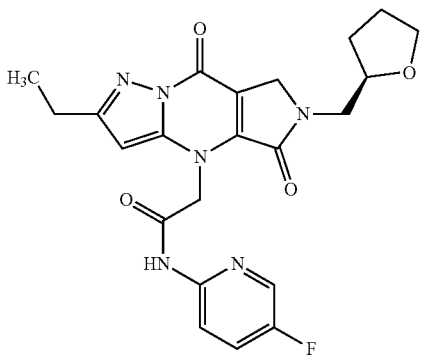<br>2-{2-ethyl-5,8-dioxo-6-[(2R)-tetrahydrofuran-2-ylmethyl]-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (400 MHz, CDCl3) δ [ppm]: 1.34 (t, 3H), 1.59-1.62 (m, 1H), 1.92-1.97 (m, 2H), 2.06-2.11 (m, 1H), 2.84 (q, 2H), 3.52-3.58 (m, 1H), 3.76-3.80 (m, 1H), 3.86-3.92 (m, 2H), 4.14-4.16 (m, 1H), 4.53 (d, 1H), 4.71 (d, 1H), 5.36 (br s, 2H), 6.25 (s, 1H), 7.41-7.46 (m, 1H), 8.15-8.16 (m, 2H), 9.32 (br s, 1H). | Intermediate 03-40<br>45%<br>LC-MS (Analytical Method K, 0-2.0 min 5-95% B, 2.0-2.7 min 95% B): $R_t$ = 1.12 min; MS (ESIpos): m/z = 455 [M + H]⁺ |
| 74 | 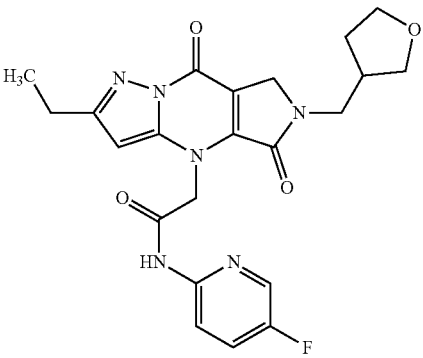<br>2-{2-ethyl-5,8-dioxo-6-[(±)-tetrahydrofuran-3-ylmethyl]-5,6,7,8-tetrahydro-4H-pyrazolo[1,5-a]pyrrolo[3,4-d]pyrimidin-4-yl}-N-{5-fluoropyridin-2-yl)acetamide<br>¹H-NMR (300 MHz, DMSO-d6): δ [ppm]: 1.23 (t, 3H), 1.52-1.58 (m, 1H), 1.92-1.98 (m, 1H), 2.62-2.73 (m, 3H), 3.32-3.43 (m, 1H), 3.47-3.50 (m, 2H), 3.57-3.78 (m, 3H), 4.43 (s, 2H), 5.46 (br s, 2H), 6.46 (s, 1H), 7.70-7.75 (m, 1H), 7.98-8.00 (m, 1H), 8.37 (d, 1H), 11.09 (br s, 1H) | Intermediate 03-47<br>44%<br>LC-MS (Analytical Method L, 0-2.0 min 10-95% B, 2.0-2.7 min 95% B): $R_t$ = 1.07 min; MS (ESIpos): m/z = 455 [M + H]⁺ |

-continued

| Example | Structure<br>IUPAC-Name<br>¹H NMR | Synth. from<br>Yield<br>LC-MS |
|---|---|---|
| 75 | 2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H-NMR (300 MHz, DMSO-d6) δ [ppm]: 1.24 (d, 6H), 4.26-4.32 (m, 1H), 4.41 (s, 2H), 5.50 (br s, 2H), 6.90 (s, 1H), 7.70-7.77 (m, 1H), 8.00-8.02 (m, 1H), 8.38 (m, 1H), 11.11 (br s, 1H) | Intermediate 03-45<br>58%<br>LC-MS (Analytical Method L, 0-2.0 min 5-95% B, 2.0-2.6 min 95% B): $R_t$ = 1.68 min; MS (ESIpos): m/z = 463 [M + H]⁺ |
| 76 | tert-butyl 4-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]piperidine-1-carboxylate<br>¹H-NMR (400 MHz, CD₃OD): δ [ppm]: 1.30 (t, 3H), 1.47 (s, 9H), 1.74-1.86 (m, 4H), 2.80 (q, 2H), 2.81-2.92 (m, 2H), 4.20-4.23 (m, 3H), 4.42 (s, 2H), 5.54 (s, 2H), 6.33 (s, 1H), 7.53-7.58 (m, 1H), 8.04-8.06 (m, 1H), 8.21 (d, 1H). | Intermediate 03-41<br>53%<br>LC-MS (Analytical Method K, 0-2.0 min 5-95% B, 2.0-2.6 min 95% B): $R_t$ = 1.49 min; MS (ESIpos): m/z = 554 [M + H]⁺ |

| Example | Structure<br>IUPAC-Name<br>¹H NMR | Synth. from<br>Yield<br>LC-MS |
|---|---|---|
| 77 | 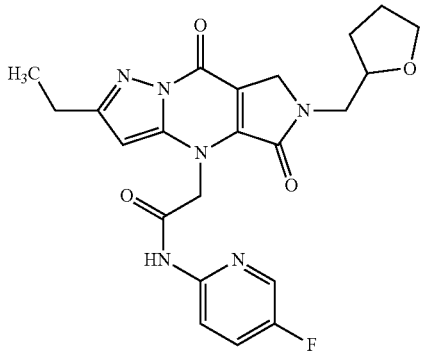<br>2-{2-ethyl-5,8-dioxo-6-[(±-tetrahydrofuran-2-ylmethyl]-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (400 MHz, CD₃OD) δ [ppm]: 1.30 (t, 3H), 1.59-1.64 (m, 1H), 1.88-1.95 (m, 2H), 1.99-2.05 (m, 1H), 2.76 (q, 2H), 3.52-3.58 (m, 1H), 3.71-3.77 (m, 2H), 3.86-3.91 (m, 1H), 4.12-4.15 (m, 1H), 4.46-4.61 (m, 2H), 5.54 (br s, 2H), 6.32 (s, 1H), 7.52-7.57 (m, 1H), 8.04-8.05 (m, 1H), 8.20-8.21 (m, 1H). | Intermediate 03-48<br>53%<br>LC-MS (Analytical Method M, 0-2.0 min 5-95% B, 2.0-2.6 min 95% B): R$_t$ = 1.20 min; MS (ESIpos): m/z = 455 [M + H]⁺ |
| 78 | 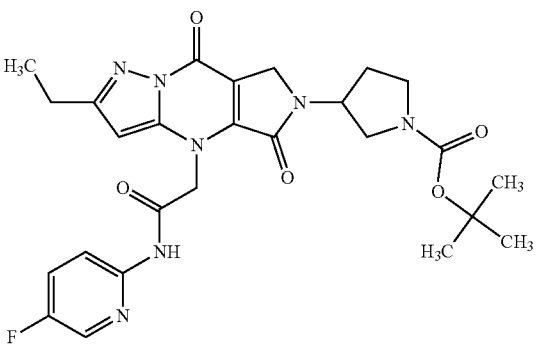<br>tert-butyl (±)-3-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]pyrrolidine-1-carboxylate<br>¹H-NMR (300 MHz, CDCl3) δ [ppm]: 1.25 (t, 3H), 1.48 (s, 9H), 2.28 (m, 2H), 2.80 (q, 2H), 3.43-3.77 (m, 4H), 4.43 (s, 2H), 4.85-4.91 (m, 1H), 5.44 (s, 2H), 6.20 (s, 1H), 7.28-7.42 (m, 1H), 8.06-8.11 (m, 2H), 9.52 (br s, 1H). | Intermediate 03-43<br>62%<br>LC-MS (Analytical Method K, 0-2.0 min 5-95% B, 2.0-2.7 min 95% B): R$_t$ = 1.35 min; MS (ESIpos): m/z = 540 [M + H]⁺ |

| | Structure<br>IUPAC-Name | Synth. from<br>Yield |
|---|---|---|
| Example | ¹H NMR | LC-MS |

79

N-cyclopropyl-4-{2-[(5-fluoropyridin-2-yl)amino]-2-
oxoethyl}-5,8-dioxo-6-(propan-2-yl)-5,6,7,8-tetrahydro-
4H-pyrazolo[1,5-a]pyrrolo[3,4-d]pyrimidine-2-
carboxamide ¹H NMR (400 MHz, DMSO-d6) δ [ppm]: 0.63-0.69 (m, 4H),
1.24 (d, 6H), 2.80-2.92 (m, 1H), 4.31 (hep, 1H), 4.42 (s,
2H), 5.58 (br s, 2H), 6.98 (s, 1H), 7.74 (td, 1H), 8.00 (br d,
1H), 8.38 (d, 1H), 8.64 (d, 1H), 11.12 (s, 1H).

Intermediate
03-111
21%
LC-MS
(Analytical
Method H): $R_t$ =
0.93 min; MS
(ESIpos): m/z =
468 [M + H]⁺.

80 tert-butyl (±)-3-{[2-ethyl-4-{2-[(5-fluoropyridin-2-
yl)amino]-2-oxoethyl}-5,8-dioxo-5,8-dihydro-4H-
pyrazolo[1,5-a]pyrrolo[3,4-d]pyrimidin-6(7H)-
yl]methyl}pyrrolidine-1-carboxylate ¹H-NMR (400 MHz, CD₃OD) δ [ppm]: 1.30 (t, 3H), 1.41-
1.44 (m, 9H), 1.66-1.72 (m, 1H), 2.00-2.04 (m, 1H), 2.62-
2.68 (m, 1H), 2.75 (q, 2H), 3.05-3.12 (m, 1H), 3.27-3.30 (m,
1H), 3.42-3.50 (m, 2H), 3.60-3.62 (m, 2H), 4.46 (s, 2H),
5.48-5.58 (m, 2H), 6.33 (s, 1H), 7.52-7.57 (m, 1H), 8.04-
8.05 (m, 1H), 8.20-8.21 (m, 1H).

Intermediate
03-46
55%
LC-MS
(Analytical
Method M, 0-2.0
min 5-95% B,
2.0-2.6 min 95%
B): $R_t$ = 1.50
min; MS
(ESIpos): m/z =
554 [M + H]⁺.

| Example | Structure<br>IUPAC-Name<br>¹H NMR | Synth. from<br>Yield<br>LC-MS |
|---|---|---|
| 81 | 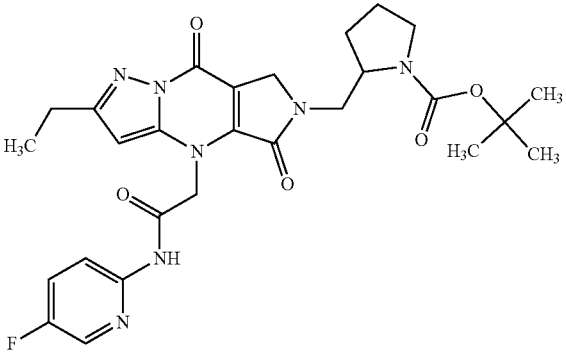<br>tert-butyl (±)-2-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}pyrrolidine-1-carboxylate<br>¹H-NMR (400 MHz, CD₃OD) δ [ppm]: 1.25 (t, 3H), 1.30-1.46 (m, 9H), 1.80-2.03 (m, 4H), 2.76 (q, 2H), 3.34-3.36 (m, 2H), 3.59-3.71 (m, 2H), 4.13-4.18 (m, 1H), 4.39-4.59 (m, 2H), 5.55 (br s, 2H), 6.33 (s, 1H), 7.52-7.57 (m, 1H), 8.04-8.05 (m, 1H), 8.20 (s, 1H). | Intermediate 03-52<br>75%<br>LC-MS (Analytical Method M, 0-2.0 min 5-95% B, 2.0-2.6 min 95% B): $R_t$ = 1.45 min; MS (ESIpos): m/z = 554 [M + H]⁺. |
| 82 | 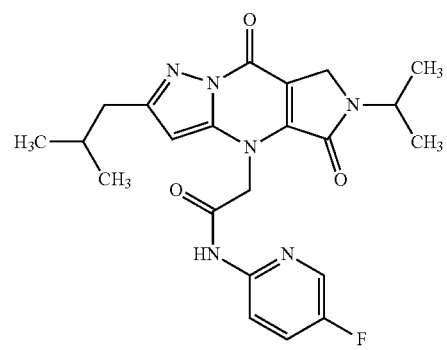<br>N-(5-fluoropyridin-2-yl)-2-[2-(2-methylpropyl)-5,8-dioxo-6-(propan-2-yl)-5,6,7,8-tetrahydro-4H-pyrazolo[1,5-a]pyrrolo[3,4-d]pyrimidin-4-yl]acetamide<br>¹H NMR (400 MHz, DMSO-d6) δ [ppm]: 0.91 (d, 6H), 1.23 (d, 6H), 1.97 (dquin, 1H), 2.52-2.55 (m, 2H), 4.29 (dt, 1H), 4.36 (s, 2H), 5.47 (br s, 2H), 6.42 (s, 1H), 7.74 (td, 1H), 8.00 (br d, 1H), 8.37 (d, 1H), 10.29-11.81 (m, 1H). | Intermediate 03-49<br>34%<br>LC-MS (Analytical Method J): $R_t$ = 1.05 min; MS (ESIpos): m/z = 441 [M + H]⁺. |

| Example | Structure / IUPAC-Name / ¹H NMR | Synth. from / Yield / LC-MS |
|---|---|---|
| 83 | 2-[2-ethyl-5,8-dioxo-6-(tetrahydro-2H-pyran-4-ylmethyl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, Chloroform-d) δ [ppm] 9.06 (s, 1H), 8.15 (d, 2H), 7.42 (ddd, 1H), 6.24 (s, 1H), 5.31 (d, 2H), 4.43 (s, 2H), 3.99 (dd, 2H), 3.54 (d, 2H), 3.37 (td, 2H), 2.83 (q, 2H), 2.09-1.94 (m, 1H), 1.59 (d, 2H), 1.43 (qd, 2H), 1.33 (t, 3H). | Intermediate 03-50<br>30%<br>LC-MS (Analytical Method D) $R_t$ = 3.39 min, MS (ESIpos): m/z = 469 [M + H]⁺. |
| 84 | 4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxylic acid<br>¹H NMR (400 MHz, DMSO-d6) δ [ppm]: 1.24 (d, 6H), 4.31 (dt, 1H), 4.43 (s, 2H), 5.58 (br s, 2H), 7.07 (s, 1H), 7.74 (td, 1H), 8.00 (br d, 1H), 8.38 (d, 1H), 11.11 (s, 1H), 13.43 (br s, 1H). | Intermediate 03-110<br>2%<br>LC-MS (Analytical Method G): $R_t$ = 0.80 min; MS (ESIpos): m/z = 429 [M + H]⁺. |

| Example | Structure<br>IUPAC-Name<br>¹H NMR | Synth. from<br>Yield<br>LC-MS |
|---|---|---|
| 85 | 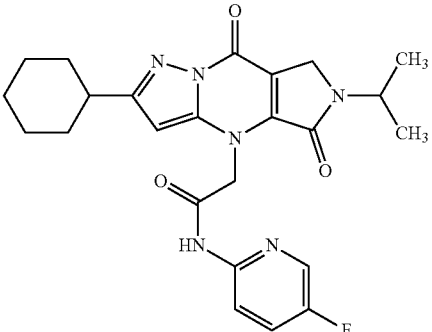<br>2-[2-cyclohexyl-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.23 (d, 6H), 1.31-1.50 (m, 5H), 1.63-1.83 (m, 3H), 1.94 (br d, 2H), 2.64-2.72 (m, 1H), 4.29 (dt, 1H), 4.36 (s, 2H), 5.45 (br s, 2H), 6.48 (s, 1H), 7.74 (td, 1H), 7.99 (br s, 1H), 8.38 (d, 1H), 11.10 (br s, 1H). | Intermediate 03-51<br>31%<br>LC-MS (Analytical Method H): $R_t$ = 1.17 min; MS (ESIpos): m/z = 467 [M + H]⁺. |
| 86 | 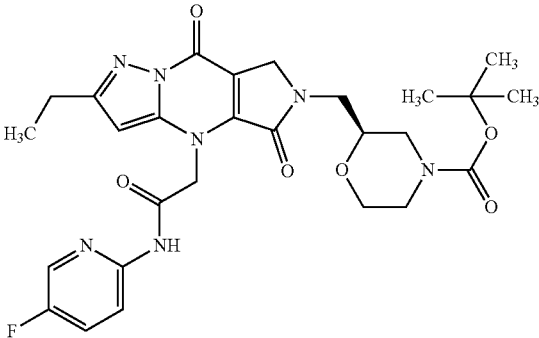<br>tert-butyl (2S)-2-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}morpholine-4-carboxylate<br>¹H NMR (500 MHz, DMSO-d6) δ [ppm]: 11.11 (s, 1H), 8.38 (d, 1H), 8.04-7.97 (m, 1H), 7.77-7.70 (m, 1H), 6.46 (s, 1H), 5.47 (s, 2H), 4.52-4.41 (m, 2H), 3.87-3.74 (m, 2H), 3.72-3.53 (m, 4H), 3.44-3.37 (m, 1H), 2.88 (s, 1H), 2.74-2.57 (m, 3H), 1.40 (s, 9H), 1.24 (t, 3H). | Intermediate 03-53<br>60%<br>LC-MS (Analytical Method D) $R_t$ = 3.89 min, MS (ESIpos): m/z = 570.10 [M + H]⁺. |

| Example | Structure / IUPAC-Name / ¹H NMR | Synth. from / Yield / LC-MS |
|---|---|---|
| 87 | 2-[2-ethyl-6-(1-methylpiperidin-4-yl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.23 (t, 3H), 1.60-1.76 (m, 2H), 1.76-1.92 (m, 2H), 1.98 (br t, 2H), 2.18 (s, 3H), 2.63-2.74 (m, 2H), 2.85 (br d, 2H), 3.86 (tt, 1H), 4.39 (s, 2H), 5.46 (br s, 2H), 6.46 (s, 1H), 7.74 (td, 1H), 8.00 (br d, 1H), 8.38 (d, 1H), 11.11 (s, 1H). | Intermediate 03-54<br>7%<br>LC-MS (Analytical Method G): $R_t$ = 0.72 min; MS (ESIpos): m/z = 468 [M + H]⁺. |
| 88 | N-(5-fluoropyridin-2-yl)-2-[2-(2-hydroxypropan-2-yl)-5,8-dioxo-6-(propan-2-yl)-5,6,7,8-tetrahydro-4H-pyrazolo[1,5-a]pyrrolo[3,4-d]pyrimidin-4-yl]acetamide<br>¹H-NMR (400 MHz, DMSO-d6) δ [ppm]: 1.24 (d, 6H), 1.46 (s, 6H), 4.26-4.30 (m, 1H), 4.38 (s, 2H), 5.25 (s, 1H), 5.51 (br s, 2H), 6.52 (s, 1H), 7.71-7.76 (m, 1H), 7.99-8.01 (m, 1H), 8.38 (s, 1H), 11.12 (br s, 1H). | Intermediate 03-109<br>4%<br>LC-MS (Analytical Method N, 0-2.0 min 10-95% B, 2.0-2.7 min 95% B): $R_t$ = 1.18 min; MS (ESIpos): m/z = 443 [M + H]⁺. |

| Example | Structure / IUPAC-Name / 1H NMR | Synth. from / Yield / LC-MS |
|---|---|---|
| 89 | 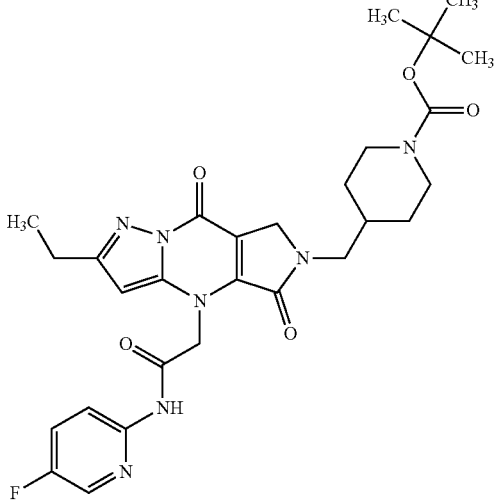<br>tert-butyl 4-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}piperidine-1-carboxylate<br>1H NMR (400 MHz, DMSO-d6) δ [ppm]: 0.92-1.09 (m, 2H), 1.23 (t, 3H), 1.37 (s, 9H), 1.56 (br d, 2H), 1.87-2.01 (m, 1H), 2.69 (q, 3H), 3.35-3.40 (m, 2H), 3.90 (br d, 2H), 4.41 (s, 2H), 5.45 (br s, 2H), 6.46 (s, 1H), 7.73 (td, 1H), 8.00 (br d, 1H), 8.37 (d, 1H), 11.10 (s, 1H). | Intermediate 03-56<br>37%<br>LC-MS (Analytical Method K, 0-2.0 min 5-95% B, 2.0-2.7 min 95% B): $R_t$ = 1.43 min; MS (ESIpos): m/z = 568 [M + H]$^+$ |
| 90 | 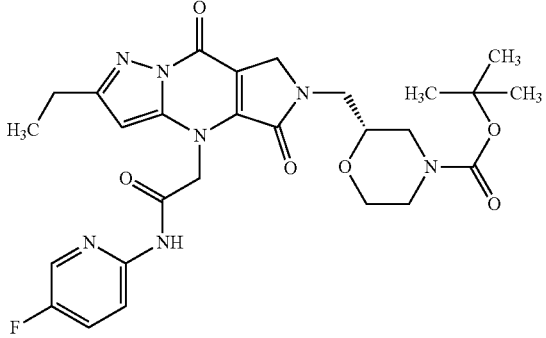<br>tert-butyl (2R)-2-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}morpholine-4-carboxylate<br>1H NMR (500 MHz, Chloroform-d) δ [ppm]: 1.33 (t, 3H), 1.47 (s, 9H), 2.66 (s, 1H), 2.83 (q, 2H), 2.93 (s, 1H), 3.42-3.51 (m, 1H), 3.52-3.73 (m, 2H), 3.72-4.10 (m, 4H), 4.46-4.58 (m, 1H), 4.56-4.72 (m, 1H), 5.31 (s, 2H), 6.23 (s, 1H), 7.36-7.45 (m, 1H), 8.00-8.23 (m, 2H), 9.08 (s, 1H). | Intermediate 03-55<br>26%<br>LC-MS (Analytical Method D) $R_t$ = 3.88 min, MS (ESIpos): m/z = 570 [M + H]$^+$. |

| Example | Structure<br>IUPAC-Name<br>¹H NMR | Synth. from<br>Yield<br>LC-MS |
|---|---|---|
| 91 | 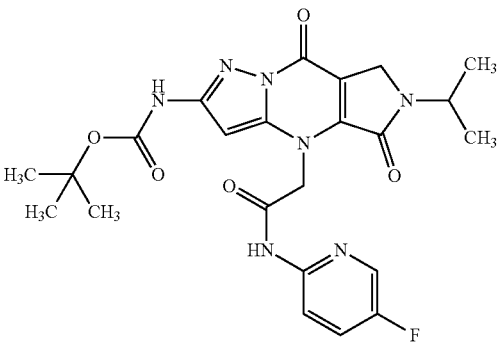<br>tert-butyl [4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]carbamate<br>¹H NMR (400 MHz, Chloroform-d) δ [ppm]: 1.30 (d, 6H), 1.52 (s, 9H), 4.36 (s, 2H), 4.51-4.61 (m, 1H), 5.55 (br s, 2H), 6.80 (br s, 1H), 7.40 (ddd, 1H), 8.02-8.20 (m, 3H), 9.31-9.46 (m, 1H). | Intermediate 03-112<br>24%<br>LC-MS (Analytical Method H): R$_t$ = 1.08 min; MS (ESIpos): m/z = 500 [M + H]⁺ |
| 92 | 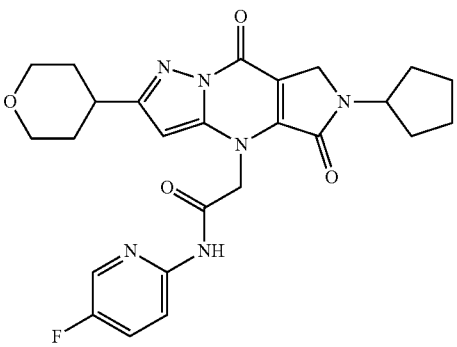<br>2-[6-cyclopentyl-5,8-dioxo-2-(tetrahydro-2H-pyran-4-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, Chloroform-d) δ [ppm]: 1.59-2.09 (m, 12H), 3.03-3.15 (m, 1H), 3.52 (td, 2H), 4.00-4.09 (m, 2H), 4.40 (s, 2H), 4.67 (quin, 1H), 5.36 (br s, 2H), 6.23 (s, 1H), 7.37-7.46 (m, 1H), 8.14 (br d, 2H), 9.34 (br s, 1H). | Intermediate 03-62<br>50%<br>LC-MS (Analytical Method G): R$_t$ = 1.02 min; MS (ESIpos): m/z = 495 [M + H]⁺ |

| | Structure<br>IUPAC-Name | Synth. from<br>Yield |
|---|---|---|
| Example | ¹H NMR | LC-MS |
| 93 | 2-[6-cyclopentyl-2-(2-methylpropyl)-5,8-dioxo-5,6,7,8-tetrahydro-4H-pyrazolo[1,5-a]pyrrolo[3,4-d]pyrimidin-4-yl]-N-{5-fluoropyridin-2-yl)acetamide<br>¹H NMR (400 MHz, Chloroform-d) δ [ppm]: 0.94 (d, 6H), 1.60-1.85 (m, 6H), 1.97-2.11 (m, 3H), 2.66 (d, 2H), 4.39 (s, 2H), 4.66 (quin, 1H), 5.37 (br s, 2H), 6.18 (s, 1H), 7.37-7.46 (m, 1H), 8.06-8.21 (m, 2H), 9.44 (br s, 1H) | Intermediate 03-61<br>25%<br>LC-MS (Analytical Method G): R$_t$ = 1.17 min; MS (ESIpos): m/z = 467 [M + H]⁺ |
| 94 | 2-[2-ethyl-5,8-dioxo-6-(tetrahydro-2H-pyran-4-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.23 (t, 3H), 1.68 (br dd, 2H), 1.84 (qd, 2H), 2.69 (q, 2H), 3.36-3.44 (m, 2H), 3.93 (dd, 2H), 4.15 (tt, Hz, 1H), 4.42 (s, 2H), 5.46 (br s, 2H), 6.46 (s, 1H), 7.74 (td, 1H), 8.00 (br d, 1H), 8.37 (d, 1H), 11.11 (s, 1H) | Intermediate 03-57<br>20%<br>LC-MS (Analytical Method G): R$_t$ = 0.87 min; MS (ESIpos): m/z = 455 [M + H]⁺ |

| Example | Structure IUPAC-Name ¹H NMR | Synth. from Yield LC-MS |
|---|---|---|
| 95 | 2-{2-ethyl-6-[2-(morpholin-4-yl)ethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm]: 1.23 (t, 3H), 2.36-2.44 (m, 4H), 2.52-2.57 (m, 4H), 2.63-2.76 (m, 2H), 3.49-3.54 (t, 2H), 3.61 (t, 2H), 4.46 (s, 2H), 5.38-5.54 (m, 2H), 6.46 (s, 1H), 7.68-7.78 (m, 1H), 7.96-8.03 (m, 1H), 8.37 (d, 1H), 11.11 (br s, 1H). | Intermediate 03-64<br>15%<br>LC-MS (Analytical Method G): $R_t$ = 0.69 min; MS (ESIpos): m/z = 484 [M + H]⁺. |
| 96 | 2-[5,8-dioxo-6-(propan-2-yl)-2-(tetrahydro-2H-pyran-4-ylmethyl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, Chloroform-d) δ [ppm]: 1.33 (d, 6H), 1.35-1.46 (m, 2H), 1.59-1.65 (m, 2H), 1.94-2.07 (m, 1H), 2.73 (d, 2H), 3.36 (td, 2H), 3.94 (dd, 2H), 4.38 (s, 2H), 4.53-4.66 (m, 1H), 5.33 (s, 2H), 6.21 (s, 1H), 7.42 (ddd, 1H), 8.08-8.19 (m, 2H), 9.17 (s, 1H). | Intermediate 03-65<br>60%<br>LC-MS (Analytical Method D) $R_t$ = 3.77 min, MS (ESIpos): m/z = 483 [M + H]⁺. |

| Example | Structure<br>IUPAC-Name<br>¹H NMR | Synth. from<br>Yield<br>LC-MS |
|---|---|---|
| 97 | N-(5-fluoropyridin-2-yl)-2-[6-(2-methoxyethyl)-2-(oxan-4-yl)-5,8-dioxo-5,6,7,8-tetrahydro-4H-pyrazolo[1,5-a]pyrrolo[3,4-d]pyrimidin-4-yl]acetamide<br>¹H-NMR (400 MHz, CHLOROFORM-d) δ [ppm]: 0.810 (0.62), 0.871 (4.03), 0.887 (4.10), 1.183 (2.34), 1.376 (0.64), 1.608 (1.53), 1.785 (3.31), 1.813 (3.62), 1.875 (5.33), 1.984 (1.42), 2.108 (1.56), 2.582 (1.48), 2.598 (1.39), 3.041 (1.97), 3.284 (16.00), 3.324 (3.74), 3.431 (3.24), 3.457 (5.18), 3.486 (3.58), 3.555 (6.01), 3.749 (5.38), 3.967 (4.55), 3.992 (3.61), 4.325 (2.10), 4.484 (8.74), 4.598 (0.44), 4.954 (0.46), 5.302 (2.98), 6.030 (0.46), 6.113 (1.16), 6.152 (3.99), 7.365 (3.43), 8.067 (7.27), 9.265 (0.56), 9.374 (1.94). | Intermediate 03-67<br>14%<br>LC-MS (Method G): $R_t$ = 0.83 min; MS (ESIpos): m/z = 485 [M + H]⁺ |
| 98 | N-(5-fluoropyridin-2-yl)-2-[6-(2-methoxyethyl)-2-(2-methylpropyl)-5,8-dioxo-5,6,7,8-tetrahydro-4H-pyrazolo[1,5-a]pyrrolo[3,4-d]pyrimidin-4-yl]acetamide<br>¹H-NMR (400 MHz, CHLOROFORM-d) δ [ppm]: 0.000 (0.82), 0.834 (0.44), 0.877 (2.10), 0.900 (14.41), 0.916 (14.30), 1.207 (1.35), 1.978 (0.57), 1.996 (0.94), 2.013 (1.11), 2.029 (0.86), 2.047 (0.44), 2.129 (3.08), 2.574 (0.43), 2.592 (0.54), 2.612 (4.37), 2.629 (4.11), 3.304 (16.00), 3.353 (1.52), 3.524 (0.43), 3.565 (2.16), 3.577 (3.71), 3.589 (2.66), 3.768 (2.35), 3.780 (3.29), 3.792 (1.88), 4.509 (7.44), 5.284 (1.24), 6.158 (3.44), 7.349 (0.82), 7.356 (0.85), 7.373 (1.31), 7.391 (0.87), 7.398 (0.82), 8.044 (0.44), 8.097 (3.13), 8.104 (3.14), 9.173 (0.92). | Intermediate 03-68<br>39%<br>LC-MS (Method G): $R_t$ = 1.02 min; MS (ESIpos): m/z = 457 [M + H]⁺ |

| | Structure<br>IUPAC-Name | Synth. from<br>Yield |
|---|---|---|
| Example | ¹H NMR | LC-MS |

99

2-[6-(1,3-dimethoxypropan-2-yl)-2-ethyl-5,8-dioxo-5,6,7,8-tetrahydro-4H-pyrazolo[1,5-a]pyrrolo[3,4-d]pyrimidin-4-yl]-N-(5-fluoropyridin-2-yl)acetamide ¹H-NMR (500 MHz, Methanol-d4) [ppm]: 1.20 (t, 3H), 2.67 (q, 2H), 3.24 (s, 6H), 3.52 (dd, 2H), 3.63 (dd, 2H), 4.38 (s, 2H), 4.46 (tt, 1H), 5.45 (s, 2H), 6.23 (s, 1H), 7.44 (ddd, 1H), 7.91-7.98 (m, 1H), 8.10 (d, 1H).

Intermediate 03-69
5%
LC-MS (Analytical Method D): $R_t$ = 3.77 min; MS (ESIpos): m/z = 473 [M + H]⁺.

100

2-[2-cyclopropyl-6-(2-methoxyethyl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide ¹H-NMR (250 MHz, Chloroform-d) δ = 0.89-0.99 (m, 2H), 1.00-1.11 (m, 2H), 2.04-2.19 (m, 1H), 3.35 (s, 3H), 3.56-3.69 (m, 2H), 3.82 (t, 2H), 4.54 (s, 2H), 5.28 (s, 2H), 6.04 (s, 1H), 7.33-7.52 (m, 1H), 8.04-8.21 (m, 2H), 9.11 (s, 1H).

Intermediate 03-70
13%
LC-MS Analytical Method D): $R_t$ = 3.68 min; MS (ESIpos): m/z = 441 [M + H]⁺.

| Example | Structure<br>IUPAC-Name<br>¹H NMR | Synth. from<br>Yield<br>LC-MS |
|---|---|---|
| 101 | 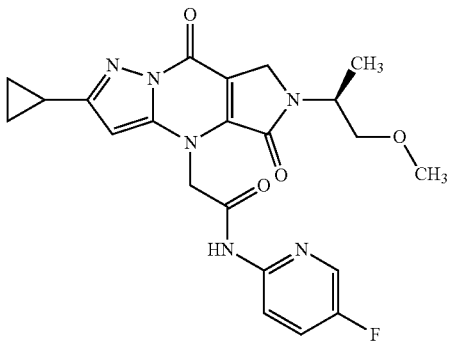<br>2-{2-cyclopropyl-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (500 MHz, Chloroform-d) δ [ppm]: 0.91-0.98 (m, 2H), 1.00-1.09 (m, 2H), 1.33 (d, 3H), 2.11 (tt, 1H), 3.34 (s, 3H), 3.52 (d, 2H), 4.40 (d, 1H), 4.48 (d, 1H), 4.60-4.66 (m, 1H), 5.23 (s, 1H), 5.35 (s, 1H), 6.05 (s, 1H), 7.42 (ddd, 1H), 8.02-8.25 (m, 2H), 9.17 (s, 1H). | Intermediate 03-71<br>18%<br>LC-MS Analytical Method F): $R_t$ = 2.50 min; MS (ESIpos): m/z = 455 [M + H]⁺. |
| 102 | 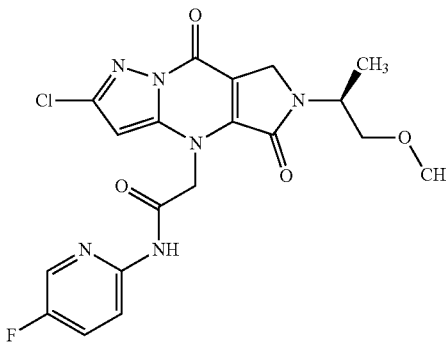<br>2-{2-chloro-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (500 MHz, DMSO-d6) δ [ppm]: 1.20 (d, 3H), 3.25 (s, 3H), 3.43 (dd, 1H), 3.55 (dd, 1H), 4.33 (d, 1H), 4.36-4.41 (m, 1H), 4.45 (d, 1H), 5.49 (s, 2H), 6.86 (s, 1H), 7.75 (td, 1H), 8.00 (s, 1H), 8.38 (d, 1H), 11.11 (s, 1H). | Intermediate 03-72<br>17%<br>LC-MS Analytical Method D): $R_t$ = 3.84 min; MS (ESIpos): m/z = 448.95 [M + H]⁺. |

-continued

| Example | Structure IUPAC-Name ¹H NMR | Synth. from Yield LC-MS |
|---|---|---|
| 103 | 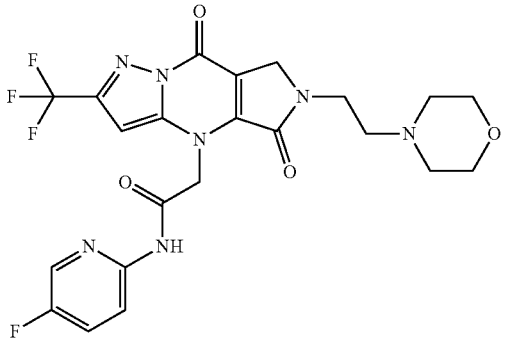<br>N-(5-fluoropyridin-2-yl)-2-{6-[2-(morpholin-4-yl)ethyl]-5,8-dioxo-2-(trifluoromethyl)-5,6,7,8-tetrahydro-4H-pyrazolo[1,5-a]pyrrolo[3,4-d]pyrimidin-4-yl}acetamide<br>¹H-NMR (500 MHz, DMSO-d6) δ [ppm]: 2.41 (s, 4H), 2.56 (t, 2H), 3.45-3.56 (m, 4H), 3.64 (t, 2H), 4.55 (d, 2H), 5.58 (s, 2H), 7.32 (d, 1H), 7.66-7.79 (m, 1H), 8.00 (s, 1H), 8.38 (d, 1H), 11.12 (s, 1H). | Intermediate 03-73<br>37%<br>LC-MS Analytical Method D): $R_t$ = 3.03 min; MS (ESIpos): m/z = 524.0 [M + H]⁺. |
| 104 | 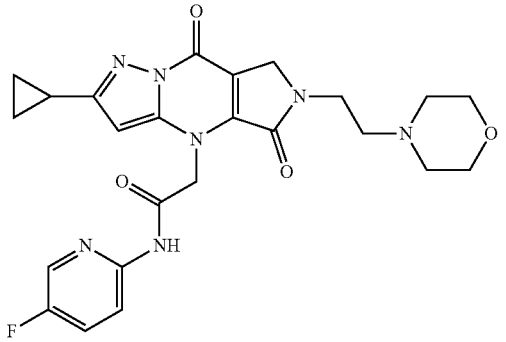<br>2-{2-cyclopropyl-6-[2-(morpholin-4-yl)ethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (500 MHz, DMSO-d6) δ [ppm]: 0.73-0.83 (m, 2H), 0.96-1.04 (m, 2H), 1.96-2.05 (m, 1H), 2.41 (s, 4H), 2.53-2.56 (m, 2H), 3.47-3.57 (m, 4H), 3.61 (t, 2H), 4.46 (s, 2H), 5.43 (s, 2H), 6.36 (s, 1H), 7.66-7.82 (m, 1H), 8.00 (s, 1H), 8.38 (d, 1H), 11.08 (s, 1H). | Intermediate 03-74<br>37%<br>LC-MS Analytical Method D): $R_t$ = 2.86 min; MS (ESIpos): m/z = 496.0 [M + H]⁺. |

| Example | Structure IUPAC-Name ¹H NMR | Synth. from Yield LC-MS |
|---|---|---|
| 105 | 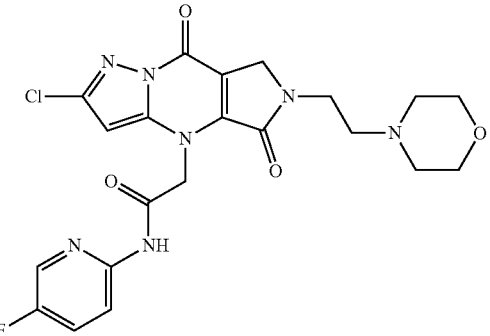<br>2-{2-chloro-6-[2-(morpholin-4-yl)ethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (500 MHz, DMSO-d6) δ [ppm]: 2.39 (d, 4H), 2.53-2.57 (m, 2H), 3.48-3.55 (m, 4H), 3.63 (t, 2H), 4.50 (d, 2H), 5.48 (s, 2H), 6.88 (s, 1H), 7.67-7.80 (m, 1H), 8.00 (s, 1H), 8.38 (t, 1H), 11.10 (s, 1H). | Intermediate<br>34%<br>LC-MS Analytical Method D): $R_t$ = 2.81 min; MS (ESIpos): m/z = 490.0 [M + H]⁺. |
| 106 | 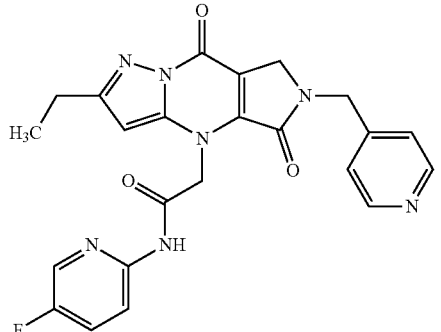<br>2-{2-ethyl-5,8-dioxo-6-[(pyridin-4-yl)methyl]-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (500 MHz, DMSO-d6) δ [ppm]: 1.24 (t, 3H), 2.70 (q, 2H), 4.41 (s, 2H), 4.76 (s, 2H), 5.48 (s, 2H), 6.49 (s, 1H), 7.29 (d, 2H), 7.75 (td, 1H), 8.01 (s, 1H), 8.38 (d, 1H), 8.52-8.59 (m, 2H), 11.12 (s, 1H). | Intermediate 03-76<br>11%<br>LC-MS Analytical Method D): $R_t$ = 3.02 min; MS (ESIpos): m/z = 462.0 [M + H]⁺. |

| Example | Structure<br>IUPAC-Name<br>¹H NMR | Synth. from<br>Yield<br>LC-MS |
|---|---|---|
| 107 | 2-{2-ethyl-5,8-dioxo-6-[(pyridin-3-yl)methyl]-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (500 MHz, DMSO-d6) δ [ppm]: 1.23 (t, 3H), 2.69 (q, 2H), 4.38 (s, 2H), 4.75 (s, 2H), 5.47 (s, 2H), 6.47 (s, 1H), 7.39 (dd, 1H), 7.72-7.76 (m, 2H), 8.01 (s, 1H), 8.38 (d, 1H), 8.52 (dd, 1H), 8.56 (d, 1H), 11.12 (s, 1H). | Intermediate 03-77<br>16%<br>LC-MS Analytical Method D): $R_t$ = 3.24 min; MS (ESIpos): m/z = 462.0 [M + H]⁺. |
| 108 | 2-{2-ethyl-5,8-dioxo-6-[(pyridin-2-yl)methyl]-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (500 MHz, DMSO-d6) δ [ppm]: 1.24 (t, 3H), 2.70 (q, 2H), 4.47 (s, 2H), 4.82 (s, 2H), 5.48 (s, 2H), 6.48 (s, 1H), 7.28-7.37 (m, 2H), 7.70-7.76 (m, 1H), 7.80 (td, 1H), 8.01 (d, 1H), 8.37 (d, 1H), 8.54 (ddd, 1H), 11.11 (s, 1H). | Intermediate 03-78<br>26%<br>LC-MS Analytical Method D): $R_t$ = 3.61 min; MS (ESIpos): m/z = 462.0 [M + H]⁺. |

| Example | Structure<br>IUPAC-Name<br>¹H NMR | Synth. from<br>Yield<br>LC-MS |
|---|---|---|
| 109 | 2-[2-ethyl-6-(3-methoxypropyl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide<br>¹H-NMR (500 MHz, Chloroform-d) δ 1.33 (t, 3H), 1.90-2.00 (m, 2H), 2.83 (q, 2H), 3.32 (s, 3H), 3.44 (t, 2H), 3.74 (t, 2H), 4.43 (s, 2H), 5.32 (s, 2H), 6.23 (s, 1H), 7.42 (ddd, 1H), 8.06-8.21 (m, 2H), 9.13 (s, 1H). | Intermediate 03-99<br>47%<br>LC-MS Analytical Method F): $R_t$ = 2.32 min; MS (ESIpos): m/z = 443 [M + H]⁺. |
| 110 | 2-{2-cyclobutyl-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (500 MHz, Chloroform-d) δ [ppm]: 1.33 (d, 3H), 1.85-1.98 (m, 1H), 2.07 (dq, 1H), 2.25-2.45 (m, 4H), 3.34 (s, 3H), 3.53 (d, 2H), 3.67-3.78 (m, 1H), 4.41 (d, 1H), 4.49 (d, 1H), 4.58-4.71 (m, 1H), 5.18-5.31 (m, 1H), 5.34-5.47 (m, 1H), 6.28 (s, 1H), 7.42 (ddd, 1H), 8.10-8.20 (m, 2H), 9.19 (s, 1H). | Intermediate 03-79<br>54%<br>LC-MS Analytical Method D): $R_t$ = 4.06 min; MS (ESIpos): m/z = 469 [M + H]⁺. |

| Example | Structure<br>IUPAC-Name<br>¹H NMR | Synth. from<br>Yield<br>LC-MS |
|---|---|---|
| 111 | 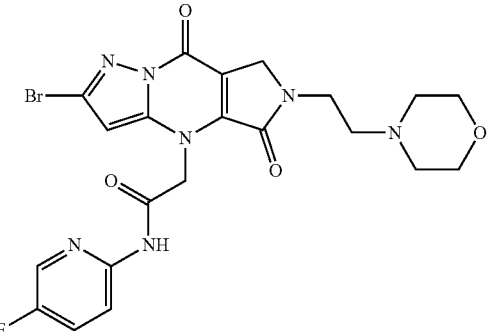<br>2-{2-bromo-6-[2-(morpholin-4-yl)ethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (500 MHz, CDCl3-d) δ [ppm]: 2.49 (s, 4H), 2.64 (t, 2H), 3.65-3.67 (m, 4H), 3.76 (t, 2H), 4.52 (s, 2H), 5.36 (s, 2H), 6.45 (s, 1H), 7.43 (ddd, 1H), 8.12-8.14 (m, 2H), 9.18 (s, 1H). | Intermediate 03-80<br>54%<br>LC-MS (Analytical Method A): $R_t$ = 0.83 min; MS (ESIpos): m/z = 533.95 [M + H]⁺. |
| 112 | 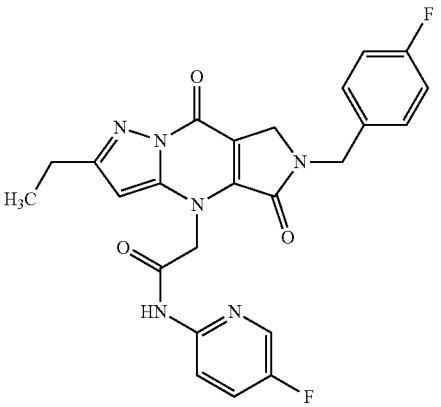<br>2-{2-ethyl-6-[(4-fluorophenyl)methyl]-5,8-dioxo-5,6,7,8-tetrahydro-4H-pyrazolo[1,5-a]pyrrolo[3,4-d]pyrimidin-4'-yl}-N-(5-fluoropyridin-2-yl)acetamide<br>¹H NMR (400 MHz, DMSO-d6) δ [ppm]: 1.22 (t, 3H), 2.68 (q, 2H), 4.31 (s, 2H), 4.68 (s, 2H), 5.47 (br s, 2H), 6.47 (s, 1H), 7.14-7.22 (m, 2H), 7.32-7.40 (m, 2H), 7.70-7.79 (m, 1H), 8.01 (br dd, 1H), 8.38 (d, 1H), 11.12 (s, 1H). | Intermediate 03-81<br>8%<br>LC-MS (Method J): $R_t$ = 1.04 min; MS (ESIpos): m/z = 479 [M + H]⁺ |

| Example | Structure IUPAC-Name ¹H NMR | Synth. from Yield LC-MS |
|---|---|---|
| 113 | 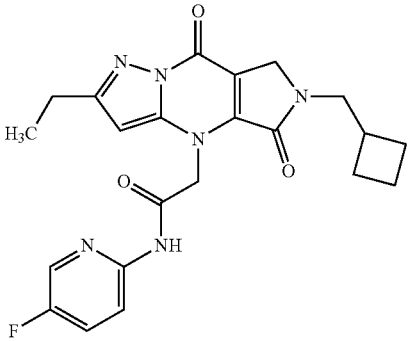<br>2-[6-(cyclobutylmethyl)-2-ethyl-5,8-dioxo-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, DMSO-d6) δ [ppm]: 1.23 (t, 3H), 1.70-1.79 (m, 2H), 1.80-1.90 (m, 2H), 2.00-2.08 (m, 2H), 2.61-2.68 (m, 1H), 2.69 (q, 2H), 3.53 (d, 2H), 4.36 (s, 2H), 5.47 (s, 2H), 6.45 (s, 1H), 7.71-7.77 (m, 1H), 7.97-8.03 (m, 1H), 8.38 (d, 1H), 11.10 (s, 1H). | Intermediate 03-82<br>18%<br>LC-MS (Analytical Method D): R$_t$ = 3.82 min; MS (ESIpos): m/z = 439 [M + H]⁺. |
| 114 | 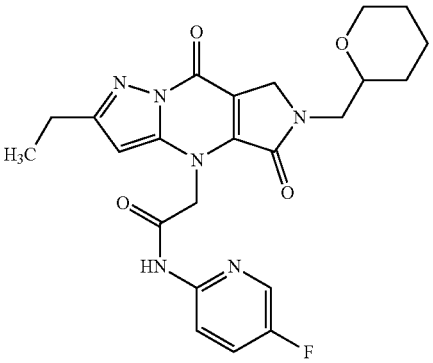<br>2-(2-ethyl-6-{[(±)-oxan-2-yl]methyl}-5,8-dioxo-5,6,7,8-tetrahydro-4H-pyrazolo[1,5-a]pyrrolo[3,4-d]pyrimidin-4-yl)-N-(5-fluoropyridin-2-yl)acetamide<br>¹H NMR (400 MHz, DMSO-d6) δ [ppm]: 1.12-1.23 (m, 2H), 1.23 (t, 3H), 1.37-1.49 (m, 3H), 1.55 (br d, 1H), 1.75 (br s, 1H), 2.62-2.77 (q, 2H), 3.46-3.58 (m, 3H), 3.87 (br d, 1H), 4.43 (s, 2H), 5.46 (br s, 2H), 6.46 (s, 1H), 7.74 (td, 1H), 8.00 (br d, 1H), 8.37 (d, 1H), 11.11 (s, 1H). | Intermediate 03-83<br>27%<br>LC-MS (Method H): R$_t$ = 1.01 min; MS (ESIpos): m/z = 469 [M + H]⁺ |

| Example | Structure IUPAC-Name ¹H NMR | Synth. from Yield LC-MS |
|---|---|---|
| 115 | tert-butyl 3-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}azetidine-1-carboxylate<br>¹H NMR (400 MHz, DMSO-d6) δ [ppm]: 1.23 (t, 3H), 1.36 (s, 9H), 2.68 (q, 2H), 2.83-2.93 (m, 1H), 3.60 (br s, 2H), 3.71 (d, 2H), 3.91 (br s, 2H), 4.38 (s, 2H), 5.45 (br s, 2H), 6.46 (s, 1H), 7.73 (td, 1H), 8.00 (br dd, 1H), 8.37 (d, 1H), 11.11 (s, 1H). | Intermediate 03-85<br>57%<br>LC-MS (Method H): $R_t$ = 1.08 min; MS (ESIpos): m/z = 341 [M + H]⁺ |
| 116 | tert-butyl 3-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]azetidine-1-carboxylate<br>¹H NMR (400 MHz, DMSO-d6) δ [ppm]: 1.23 (t, 3H), 1.39 (s, 9H), 2.69 (q, 2H), 4.03-4.24 (m, 4H), 4.65 (s, 2H), 4.88-5.03 (m, 1H), 5.43 (br s, 2H), 6.48 (s, 1H), 7.73 (td, 1H), 7.99 (br d, 1H), 8.37 (d, 1H), 11.11 (s, 1H). | Intermediate 03-86<br>76%<br>LC-MS (Method H): $R_t$ = 525.20 min; MS (ESIpos): m/z = 527 [M + H]⁺ |

-continued

| Example | Structure IUPAC-Name ¹H NMR | Synth. from Yield LC-MS |
|---|---|---|
| 117 | 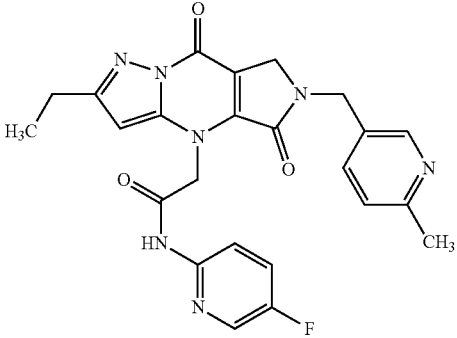<br>2-{2-ethyl-6-[(6-methylpyridin-3-yl)methyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, DMSO-d6) δ [ppm]: 1.22 (t, 3H), 2.44 (s, 3H), 2.65-2.71 (m, 2H), 4.34 (s, 2H), 4.68 (s, 2H), 5.46 (s, 2H), 6.46 (s, 1H), 7.24 (d, 1H), 7.62 (dd, 1H), 7.74 (td, 1H), 8.00 (s, 1H), 8.37 (d, 1H), 8.42 (d, 1H), 11.11 (s, 1H). | Intermediate 03-100 and CAS No.: 1904-24-1 3% LC-MS Analytical Method F): R$_t$ = 1.51 min; MS (ESIpos): m/z = 476 [M + H]+. |
| 118 | 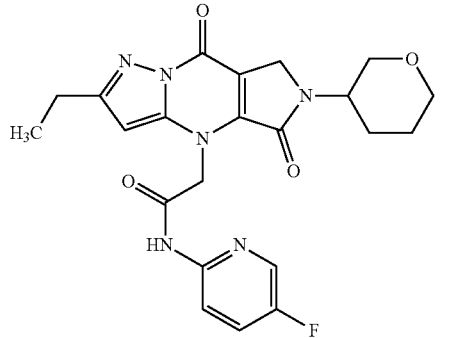<br>2-{2-ethyl-6-[(±)-oxan-3-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm]: 1.23 (t, 3H), 1.53-1.67 (m, 1H), 1.68-1.77 (m, 1H), 1.83-1.95 (m, 2H), 2.68 (q, 2H), 3.34-3.39 (m, 1H), 3.49 (t, 1H), 3.72-3.79 (m, 2H), 3.93-4.04 (m, 1H), 4.40-4.50 (m, 2H), 5.46 (br d, 2H), 6.46 (s, 1H), 7.69-7.79 (m, 1H), 8.00 (br d, 1H), 8.38 (d, 1H), 11.11 (s, 1H). | Intermediate 03-87 19% LC-MS (Method H): R$_t$ = 0.90 min; MS (ESIpos): m/z = 455 [M + H]⁺ |

| Example | Structure / IUPAC-Name / $^1$H NMR | Synth. from / Yield / LC-MS |
|---|---|---|
| 119 | 2-[6-(1,1-dioxo-1lambda$^6$-thian-4-yl)-2-ethyl-5,8-dioxo-5,6,7,8-tetrahydro-4H-pyrazolo[1,5-a]pyrrolo[3,4-d]pyrimidin-4-yl]-N-(5-fluoropyridin-2-yl)acetamide<br>$^1$H NMR (400 MHz, DMSO-d6) δ [ppm]: 1.23 (t, 3H), 2.07 (br d, 2H), 2.24-2.36 (m, 2H), 2.69 (q, 2H), 3.12 (br d, 2H), 3.35-3.46 (m, 2H), 4.27-4.37 (m, 1H), 4.46 (s, 2H), 5.45 (br s, 2H), 6.47 (s, 1H), 7.73 (td, 1H), 7.96-8.04 (m, 1H), 8.37 (d, 1H), 11.11 (s, 1H). | Intermediate 03-88<br>19%<br>LC-MS (Method H): $R_t$ = 0.82 min; MS (ESIpos): m/z = 503 [M + H]$^+$ |
| 120 | 2-{6-[1-(benzyloxy)-2-methylpropan-2-yl]-2-ethyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>$^1$H NMR (400 MHz, DMSO-d6) δ [ppm]: 1.23 (t, 3H), 1.45 (s, 6H), 2.69 (q, 2H), 3.70 (s, 2H), 4.47 (s, 2H), 4.48 (s, 2H), 5.44 (br s, 2H), 6.43 (s, 1H), 7.17-7.29 (m, 5H), 7.73 (td, 1H), 7.97-8.04 (m, 1H), 8.38 (d, 1H), 11.09 (s, 1H). | Intermediate 03-89<br>21%<br>LC-MS (Method H): $R_t$ = 1.20 min; MS (ESIpos): m/z = 533 [M + H]$^+$ |

| Example | Structure / IUPAC-Name / ¹H NMR | Synth. from / Yield / LC-MS |
|---|---|---|
| 121 | 2-{6-[(±)-1-(benzyloxy)propan-2-yl]-2-ethyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm]: 1.20-1.26 (m, 6H), 2.69 (q, 2H), 3.51-3.66 (m, 2H), 4.19-4.30 (m, 1H), 4.34-4.55 (m, 4H), 5.47 (br s, 2H), 6.46 (s, 1H), 7.21-7.33 (m, 5H), 7.68-7.79 (m, 1H), 7.93-8.06 (m, 1H), 8.38 (br d, 1H), 11.12 (br s, 1H). | Intermediate 03-90<br>32%<br>LC-MS (Method H): $R_t$ = 1.13 min; MS (ESIpos): m/z = 519 [M + H]⁺ |
| 122 | ethyl 4-{2-[(5-fluoropyridin-2-yl)amino]-2-oxoethyl}-6-(oxan-4-yl)-5,8-dioxo-5,6,7,8-tetrahydro-4H-pyrazolo[1,5-a]pyrrolo[3,4-d]pyrimidine-2-carboxylate<br>¹H NMR (400 MHz, DMSO-d6) δ [ppm]: 1.33 (t, 3H), 1.68 (br dd, 2H), 1.85 (qd, 2H), 3.35-3.44 (m, 2H), 3.93 (br dd, 2H), 4.16 (tt, 1H), 4.35 (q, 2H), 4.49 (s, 2H), 5.50-5.64 (m, 2H), 7.19 (s, 1H), 7.73 (td, 1H), 8.00 (br d, 1H), 8.38 (d, 1H), 11.11 (s, 1H). | Intermediate 03-91<br>51%<br>LC-MS (Method H): $R_t$ = 0.91 min; MS (ESIpos): m/z = 500 [M + H]⁺ |

| | Structure<br>IUPAC-Name | Synth. from |
|---|---|---|
| Example | ¹H NMR | Yield<br>LC-MS |
| 123 | ethyl 4-{2-[(5-fluoropyridin-2-yl)amino]-2-oxoethyl}-6-[2-(morpholin-4-yl)ethyl]-5,8-dioxo-5,6,7,8-tetrahydro-4H-pyrazolo[1,5-a]pyrrolo[3,4-d]pyrimidine-2-carboxylate<br>¹H NMR (400 MHz, DMSO-d6) δ [ppm]: 1.33 (t, 3H), 2.34-2.44 (m, 4H), 2.54 (br t, 2H), 3.52 (br t, 4H), 3.63 (br t, 2H), 4.35 (q, 2H), 4.53 (s, 2H), 5.58 (br s, 2H), 7.19 (s, 1H), 7.74 (td, 1H), 7.99 (br s, 1H), 8.38 (d, 1H), 11.09 (s, 1H). | Intermediate 03-92<br>53%<br>LC-MS (Method H): R$_t$ = 0.89 min; MS (ESIpos): m/z = 529 [M + H]⁺ |
| 124 | ethyl 4-{2-[(5-fluoropyridin-2-yl)amino]-2-oxoethyl}-5,8-dioxo-6-[(pyridin-2-yl)methyl]-5,6,7,8-tetrahydro-4H-pyrazolo[1,5-a]pyrrolo[3,4-d]pyrimidine-2-carboxylate<br>¹H NMR (400 MHz, DMSO-d6) δ [ppm]: 1.33 (t, 3H), 4.35 (q, 2H), 4.53 (s, 2H), 4.83 (s, 2H), 5.59 (br s, 2H), 7.20 (s, 1H), 7.30-7.37 (m, 2H), 7.70-7.77 (m, 1H), 7.79 (td, 1H), 8.00 (br d, 1H), 8.37 (d, 1H), 8.52-8.55 (m, 1H), 11.11 (s, 1H). | Intermediate 03-93<br>51%<br>LC-MS (Method H): R$_t$ = 0.93 min; MS (ESIpos): m/z = 506 [M + H]⁺ |

| Example | Structure IUPAC-Name ¹H NMR | Synth. from Yield LC-MS |
|---|---|---|
| 125 | 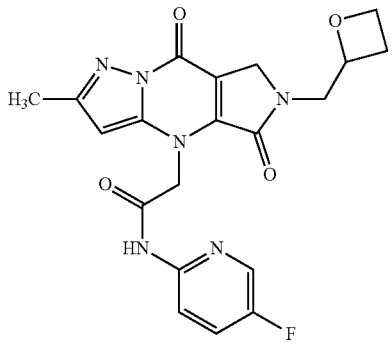<br>N-(5-fluoropyridin-2-yl)-2-(2-methyl-6-{[(±)-oxetan-2-yl]methyl}-5,8-dioxo-5,6,7,8-tetrahydro-4H-pyrazolo[1,5-a]pyrrolo[3,4-d]pyrimidin-4-yl)acetamide<br>¹H NMR (400 MHz, DMSO-d6) δ [ppm]: 2.31 (s, 3H), 2.33-2.46 (m, 1H), 2.59-2.70 (m, 1H), 3.36-3.59 (m, 1H), 3.65 (dd, 1H), 3.82 (dd, 1H), 4.37-4.56 (m, 3H), 4.89-5.01 (m, 1H), 5.47 (br s, 2H), 6.40 (s, 1H), 7.73 (ddd, 1H), 8.00 (br d, 1H), 8.37 (d, 1H), 11.12 (br s, 1H). | Intermediate 03-94<br>31%<br>LC-MS (Method H): $R_t$ = 0.77 min; MS (ESIpos): m/z = 427 [M + H]⁺ |
| 126 | 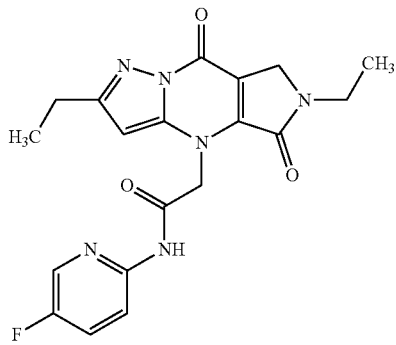<br>2-(2,6-diethyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide<br>¹H-NMR (400 MHz, DMSO-d6) δ [ppm]: 1.157 (5.18), 1.175 (12.09), 1.193 (5.32), 1.209 (7.09), 1.228 (16.00), 1.247 (7.30), 2.326 (0.43), 2.518 (2.16), 2.522 (1.32), 2.655 (1.80), 2.674 (5.67), 2.694 (5.29), 2.712 (1.66), 3.483 (1.21), 3.502 (3.72), 3.519 (3.72), 3.538 (1.17), 4.405 (8.19), 5.466 (1.26), 6.454 (8.15), 7.708 (0.89), 7.716 (0.98), 7.731 (1.42), 7.738 (1.52), 7.752 (1.09), 7.759 (1.16), 7.992 (0.74), 8.370 (3.74), 8.377 (3.68), 11.109 (1.83). | Intermediate 03-95<br>31%<br>LC-MS (Method G): $R_t$ = 0.87 min; MS (ESIpos): m/z = 399 [M + H]⁺ |

| Example | Structure<br>IUPAC-Name<br>¹H NMR | Synth. from<br>Yield<br>LC-MS |
|---|---|---|
| 127 | 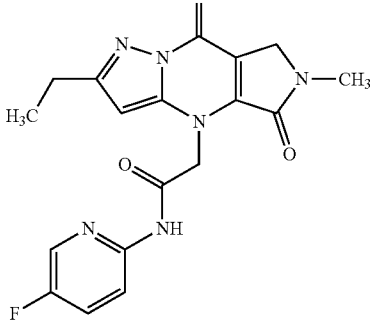<br>2-(2-ethyl-6-methyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide<br>¹H-NMR (400 MHz, DMSO-d6) δ [ppm]: 1.208 (6.65), 1.227 (16.00), 1.246 (6.98), 2.322 (0.51), 2.327 (0.69), 2.331 (0.51), 2.518 (2.84), 2.523 (1.78), 2.655 (1.63), 2.665 (0.72), 2.674 (5.33), 2.693 (4.81), 2.712 (1.50), 2.908 (0.68), 3.059 (14.90), 4.381 (6.24), 5.461 (1.06), 6.466 (6.98), 7.707 (0.77), 7.715 (0.84), 7.730 (1.18), 7.738 (1.26), 7.751 (0.91), 7.759 (0.96), 7.989 (0.61), 8.004 (0.55), 8.370 (3.28), 8.377 (3.20), 11.104 (1.65). | Intermediate 03-98<br>39%<br>LC-MS (Method G): $R_t$ = 0.81 min; MS (ESIpos): m/z = 385 [M + H]⁺ |
| 129 | 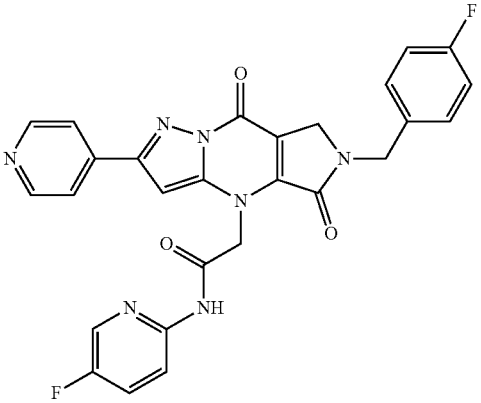<br>2-{6-[(4-fluorophenyl)methyl]-5,8-dioxo-2-(pyridin-4-yl)-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (400 MHz, DMSO-d6) δ [ppm]: 2.518 (2.45), 2.522 (1.66), 2.539 (2.02), 2.887 (0.49), 3.364 (3.12), 4.381 (11.09), 4.427 (0.79), 4.701 (10.08), 4.722 (1.25), 5.549 (1.07), 5.683 (0.58), 7.169 (0.85), 7.176 (5.44), 7.181 (2.24), 7.186 (1.61), 7.193 (2.68), 7.199 (10.94), 7.204 (2.52), 7.208 (2.09), 7.216 (2.19), 7.221 (6.23), 7.230 (0.99), 7.354 (0.86), 7.360 (0.89), 7.367 (5.40), 7.373 (2.61), 7.381 (6.34), 7.392 (16.00), 7.403 (4.71), 7.435 (0.47), 7.681 (0.59), 7.720 (1.54), 7.729 (1.69), 7.742 (2.59), 7.751 (2.52), 7.764 (2.06), 7.772 (1.93), 7.787 (0.58), 7.903 (11.42), 7.906 (6.68), 7.913 (6.48), 7.918 (11.70), 8.021 (1.66), 8.034 (1.51), 8.200 (6.43), 8.329 (0.45), 8.336 (0.54), 8.385 (6.23), 8.393 (6.27), 8.406 (1.13), 8.414 (0.76), 8.665 (0.56), 8.688 (12.22), 8.692 (6.72), 8.699 (6.10), 8.703 (10.54), 8.718 (0.48), 8.724 (0.54), 8.734 (0.45), 8.739 (0.44), 11.209 (2.57). | Intermediate 03-102<br>13%<br>LC-MS (Method G): $R_t$ = 0.92 min; MS (ESIpos): m/z = 528 [M + H]⁺ |

| Example | Structure IUPAC-Name ¹H NMR | Synth. from Yield LC-MS |
|---|---|---|
| 130 | 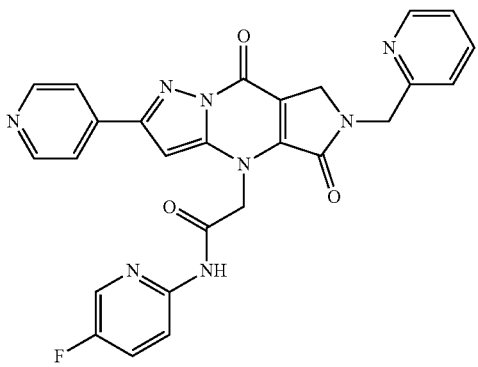<br>2-{5,8-dioxo-2-(pyridin-4-yl)-6-[(pyridin-2-yl)methyl]-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (400 MHz, DMSO-d6) δ [ppm]: 1.231 (0.43), 1.752 (0.47), 2.331 (0.76), 2.518 (3.78), 2.522 (2.33), 2.539 (1.16), 2.673 (0.72), 3.443 (5.86), 4.037 (0.47), 4.048 (0.47), 4.480 (0.42), 4.529 (13.65), 4.570 (0.40), 4.716 (0.47), 4.837 (13.49), 4.950 (0.47), 5.092 (0.63), 5.558 (1.70), 7.166 (0.61), 7.248 (0.92), 7.305 (2.62), 7.308 (3.07), 7.320 (3.16), 7.324 (3.04), 7.327 (3.29), 7.336 (2.78), 7.339 (3.06), 7.351 (4.92), 7.370 (5.33), 7.399 (16.00), 7.712 (1.68), 7.719 (2.06), 7.727 (1.72), 7.735 (3.62), 7.742 (3.15), 7.748 (2.15), 7.750 (2.06), 7.755 (3.42), 7.763 (2.40), 7.771 (1.77), 7.779 (4.39), 7.784 (3.85), 7.799 (5.46), 7.803 (5.50), 7.818 (2.87), 7.822 (2.73), 7.887 (0.54), 7.913 (11.23), 7.916 (7.29), 7.923 (6.94), 7.928 (11.37), 8.014 (1.83), 8.028 (1.70), 8.125 (1.05), 8.135 (1.05), 8.148 (0.98), 8.158 (0.85), 8.316 (3.00), 8.324 (2.95), 8.335 (1.43), 8.375 (7.74), 8.383 (7.48), 8.393 (1.16), 8.534 (3.34), 8.536 (4.01), 8.538 (4.01), 8.540 (3.78), 8.546 (3.60), 8.548 (4.18), 8.550 (3.85), 8.552 (3.53), 8.693 (7.20), 8.707 (6.73), 8.822 (0.51), 8.840 (0.61), 10.448 (1.05), 11.205 (3.44). | Intermediate 03-103<br>11%<br>LC-MS (Method H): $R_t$ = 0.85 min; MS (ESIpos): m/z = 511 [M + H]⁺ |

| Example | Structure<br>IUPAC-Name<br>¹H NMR | Synth. from<br>Yield<br>LC-MS |
|---|---|---|
| 131 | 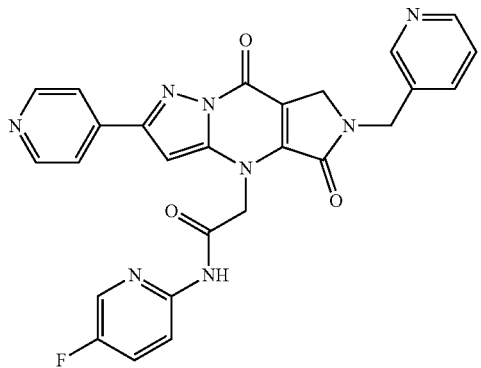<br>2-{5,8-dioxo-2-(pyridin-4-yl)-6-[(pyridin-3-yl)methyl]-5,6,7,8-tetrahydro-4H-pyrazolo[1,5-a]pyrrolo[3,4-d]pyrimidin-4-yl}-N-(5-fluoropyridin-2-yl)acetamide<br>¹H-NMR (400 MHz, DMSO-d6) δ [ppm]: 1.230 (0.51), 1.753 (0.63), 2.287 (0.60), 2.518 (2.64), 2.523 (1.69), 2.540 (1.96), 2.729 (0.76), 2.887 (0.86), 3.395 (1.11), 3.439 (16.00), 3.540 (0.61), 3.596 (0.58), 4.043 (0.89), 4.445 (8.41), 4.761 (7.59), 5.508 (0.70), 5.565 (0.95), 6.125 (0.63), 7.152 (0.54), 7.379 (2.04), 7.381 (2.12), 7.395 (9.90), 7.411 (2.10), 7.412 (2.12), 7.718 (1.45), 7.727 (3.28), 7.735 (3.39), 7.742 (3.14), 7.747 (6.86), 7.750 (5.34), 7.756 (3.71), 7.758 (4.19), 7.761 (3.08), 7.771 (4.64), 7.778 (3.24), 7.790 (0.45), 7.797 (0.42), 7.880 (0.55), 7.895 (0.72), 7.904 (8.28), 7.908 (4.67), 7.915 (4.72), 7.919 (8.12), 8.018 (1.08), 8.031 (1.02), 8.126 (2.29), 8.136 (2.28), 8.149 (2.07), 8.159 (1.90), 8.316 (7.01), 8.324 (6.82), 8.335 (1.28), 8.350 (0.74), 8.383 (4.69), 8.390 (4.72), 8.407 (0.55), 8.512 (2.69), 8.516 (2.72), 8.524 (2.64), 8.528 (2.54), 8.573 (3.52), 8.577 (3.66), 8.668 (0.57), 8.689 (6.26), 8.692 (4.03), 8.700 (3.71), 8.704 (5.84), 10.445 (1.68). | Intermediate 03-104<br>5%<br>LC-MS (Method H): $R_t$ = 0.82 min; MS (ESIpos): m/z = 511 [M + H]⁺ |

| Example | Structure<br>IUPAC-Name<br>¹H NMR | Synth. from<br>Yield<br>LC-MS |
|---|---|---|
| 132 | 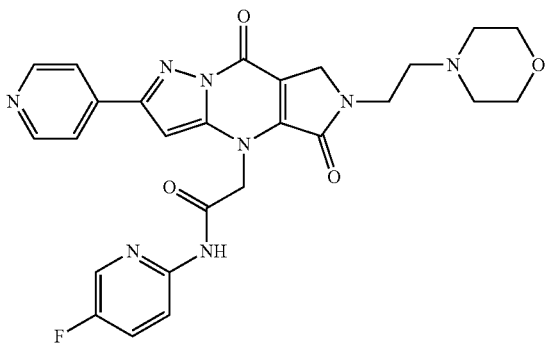<br>N-(5-fluoropyridin-2-yl)-2-{6-[2-(morpholin-4-yl)ethyl]-5,8-dioxo-2-(pyridin-4-yl)-5,6,7,8-tetrahydro-4H-pyrazolo[1,5-a]pyrrolo[3,4-d]pyrimidin-4-yl}acetamide<br>¹H-NMR (400 MHz, DMSO-d6) δ [ppm]: 0.836 (1.25), 0.854 (2.82), 0.872 (1.27), 1.132 (1.79), 1.137 (0.57), 1.150 (3.95), 1.168 (1.82), 1.231 (0.44), 1.753 (1.40), 2.287 (2.40), 2.323 (0.84), 2.327 (1.08), 2.332 (0.83), 2.409 (9.36), 2.518 (3.65), 2.523 (2.64), 2.540 (6.93), 2.553 (7.53), 2.568 (3.81), 2.665 (0.63), 2.669 (0.86), 2.674 (0.61), 2.727 (0.68), 2.888 (0.82), 3.121 (0.70), 3.251 (1.02), 3.396 (7.40), 3.416 (2.49), 3.434 (1.91), 3.451 (1.43), 3.469 (1.19), 3.514 (8.74), 3.525 (13.16), 3.536 (9.35), 3.560 (3.16), 3.571 (2.17), 3.581 (2.77), 3.596 (8.63), 3.618 (3.68), 3.633 (6.64), 3.649 (3.42), 3.679 (0.68), 3.697 (0.67), 3.717 (1.21), 3.731 (0.63), 3.740 (0.64), 3.746 (0.67), 3.774 (0.63), 3.781 (0.67), 3.791 (0.66), 3.799 (0.70), 3.809 (0.41), 3.817 (0.71), 3.834 (0.66), 3.859 (0.55), 3.924 (0.52), 4.033 (0.57), 4.043 (2.94), 4.051 (0.71), 4.060 (0.66), 4.078 (0.67), 4.097 (0.61), 4.109 (0.57), 4.116 (0.61), 4.120 (0.58), 4.138 (0.44), 4.143 (0.68), 4.161 (0.86), 4.171 (0.47), 4.188 (0.45), 4.225 (1.18), 4.486 (0.57), 4.523 (14.44), 4.547 (1.85), 4.583 (0.58), 4.646 (1.19), 4.659 (1.15), 5.549 (1.24), 7.046 (0.51), 7.124 (0.87), 7.155 (0.61), 7.383 (16.00), 7.620 (0.96), 7.704 (0.42), 7.712 (1.62), 7.719 (3.22), 7.726 (2.30), 7.734 (2.88), 7.741 (4.63), 7.746 (3.00), 7.749 (2.71), 7.754 (2.61), 7.762 (3.55), 7.769 (2.18), 7.774 (0.98), 7.776 (1.00), 7.789 (0.66), 7.797 (0.64), 7.880 (0.51), 7.885 (0.51), 7.896 (0.55), 7.907 (12.91), 7.912 (7.98), 7.919 (7.75), 7.922 (13.07), 7.933 | Intermediate 03-105<br>8%<br>LC-MS (Method H): $R_t$ = 0.81 min; MS (ESIpos): m/z = 533 [M + H]⁺ |

| Example | Structure IUPAC-Name ¹H NMR | Synth. from Yield LC-MS |
|---|---|---|
| 133 | 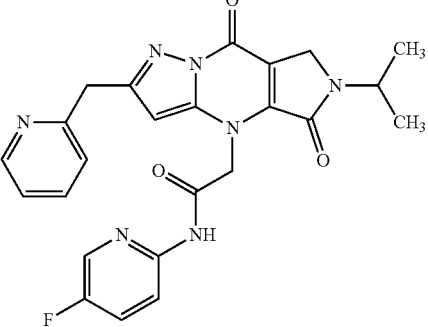

2-{5,8-dioxo-6-(propan-2-yl)-2-[(pyridin-2-yl)methyl]-5,6,7,8-tetrahydro-4H-pyrazolo[1,5-a]pyrrolo[3,4-d]pyrimidin-4-yl}-N-(5-fluoropyridin-2-yl)acetamide
¹H-NMR (400 MHz, DMSO-d6) δ [ppm]: 1.219 (15.66), 1.236 (16.00), 2.518 (2.05), 2.522 (1.29), 2.539 (0.43), 2.669 (0.55), 4.087 (0.42), 4.254 (0.67), 4.271 (1.69), 4.283 (8.19), 4.304 (1.26), 4.321 (0.58), 4.374 (7.01), 4.832 (1.17), 4.897 (0.46), 4.904 (2.08), 5.463 (1.24), 6.469 (7.17), 7.433 (0.77), 7.450 (1.04), 7.464 (0.83), 7.534 (1.48), 7.554 (1.59), 7.706 (0.80), 7.714 (0.89), 7.729 (1.25), 7.736 (1.50), 7.750 (1.03), 7.757 (1.26), 7.947 (0.80), 7.966 (1.72), 7.982 (1.09), 8.343 (0.72), 8.351 (0.72), 8.368 (3.39), 8.375 (3.48), 8.380 (1.79), 8.590 (1.47), 8.601 (1.48), 10.832 (0.45), 11.092 (1.81). | Intermediate 03-106 27% LC-MS (Method G): $R_t$ = 0.76 min; MS (ESIpos): m/z = 476 [M + H]⁺ |

Example 135

2-[2-tert-butyl-6-(2-hydroxyethyl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide

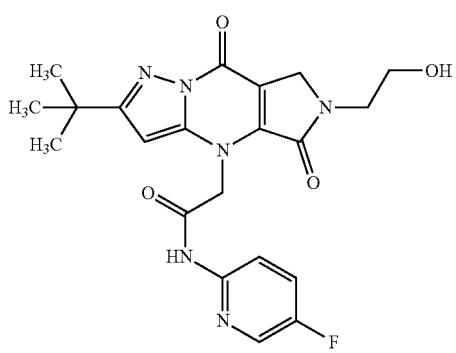 [SMILES: CC(C)(C)c1cc2n(CC(=O)Nc3ccc(F)cn3)c3c(c(=O)n2n1)CN(CCO)C3=O]

2-{6-[2-(Benzyloxy)ethyl]-2-tert-butyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide (710 mg, 1.33 mmol) (example 34) was dissolved in acetic acid (10 ml) and Pd/C (10%, 142 mg) was added. The reaction was stirred under a hydrogen atmosphere for 24 h then filtered through Celite®, washing with DCM. The filtrate was concentrated under reduced pressure and dried overnight in the vacuum oven to afford 660 mg (96% yield) of the title compound as a pale yellow solid.

¹H NMR (500 MHz, DMSO-d6) δ[ppm]11.07 (s, 1H), 8.37 (d, 1H), 8.06-7.88 (m, 1H), 7.83-7.69 (m, 1H), 6.58 (s, 1H), 5.55-5.38 (m, 2H), 4.45 (s, 2H), 3.62 (t, 2H), 3.54 (t, 2H), 1.31 (s, 9H).
LC-MS (Analytical Method A) $R_t$=0.97 min, MS (ESIpos): m/z=443.1 [M+H]⁺.

Example 136

2-[2-ethyl-6-(1-hydroxy-2-methylpropan-2-yl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide

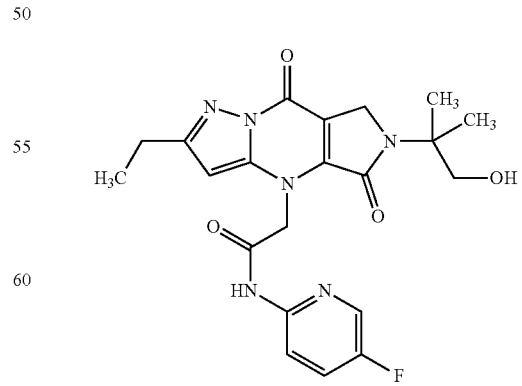

2-{6-[1-(benzyloxy)-2-methylpropan-2-yl]-2-ethyl-5,8-dioxo-5,6,7,8-tetrahydro-4H-pyrazolo[1,5-a]pyrrolo[3,4-d]

pyrimidin-4-yl}-N-(5-fluoropyridin-2-yl)acetamide (30.0 mg, 56.3 µmol) (example 120) was solved in methanol (1 mL) and palladium on carbon (5.99 mg, 10% purity, 5.63 µmol) and ammonium formiate (35.5 mg, 563 µmol) were added. The suspension was stirred at 100° C. for 2 h. Further ammonium formiate (17.8 mg, 282 µmol) was added and stirring was continued at 100° C. for 2 h. After addition of another portion of ammonium formiate (35.5 mg, 563 µmol) the reaction mixture was aged for further 4 h at 100° C. for 4 h. After filtration over celite, the filtrate was concentrated under vacuum and the residual material dissolved in acetonitrile/water (7:3) and purified with preparative HPLC (Method F, gradient C) to afford 28 mg (>99% yield) of the title compound.

LC-MS (Method H): $R_t$=0.88 min; MS (ESIpos): m/z=443 [M+H]$^+$ $^1$H NMR (400 MHz, DMSO-d6) δ[ppm]: 1.23 (t, 3H), 1.40 (s, 6H), 2.63-2.74 (m, 2H), 3.62 (d, 2H), 4.48 (s, 2H), 4.97 (t, 1H), 5.47 (br s, 2H), 6.41 (s, 1H), 7.74 (td, 1H), 7.97-8.05 (m, 1H), 8.38 (d, 1H), 11.09 (s, 1H).

Example 137

2-{2-ethyl-6-[(±)-1-hydroxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide

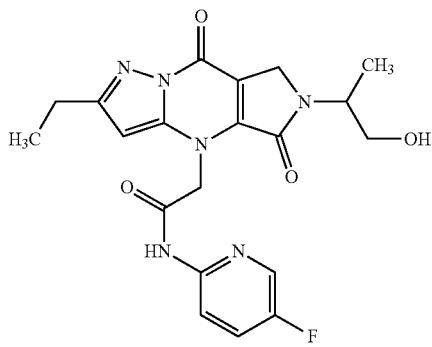 [SMILES: CCc1cc2n(CC(=O)Nc3ccc(F)cn3)c3c(c(=O)n2n1)CN(C(C)CO)C3=O]

2-{6-[(±)-1-(benzyloxy)propan-2-yl]-2-ethyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide (45.0 mg, 86.8 µmol) (example 121) was dissolved in methanol (1 mL) and palladium on carbon (9.23 mg, 10% purity, 8.68 µmol) and ammonium formiate (82.1 mg, 1.30 mmol) were added and the resulting suspension stirred at 100° C. for 3 h. After filtration of the reaction mixture over celite, the filtrate was aged with another portion of ammonium formiate (54.7 mg, 868 µmol) and palladium on carbon (9.23 mg, 10% purity, 8.68 µmol) for 3 h at 100° C. The reaction mixture was filtered over celite and the filtrate concentrated under pressure. The residual material dissolved in acetonitrile/water (7:3) and purified with preparative HPLC (Method F, gradient C) to afford 14.8 mg (38% yield) of the title compound.

LC-MS (Method H): $R_t$=0.80 min; MS (ESIpos): m/z=429 [M+H]$^+$ $^1$H NMR (400 MHz, DMSO-d6) δ[ppm]: 1.14-1.20 (m, 3H), 1.23 (t, 3H), 2.69 (q, 2H), 3.46-3.58 (m, 2H), 4.19 (br d, 1H), 4.37 (d, 2H), 4.93 (t, 1H), 5.48 (br s, 2H), 6.45 (s, 1H), 7.70-7.78 (m, 1H), 8.01 (br d, 1H), 8.37 (d, 1H), 11.11 (s, 1H).

Example 138

2-{2-tert-butyl-6-[2-(morpholin-4-yl)ethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide

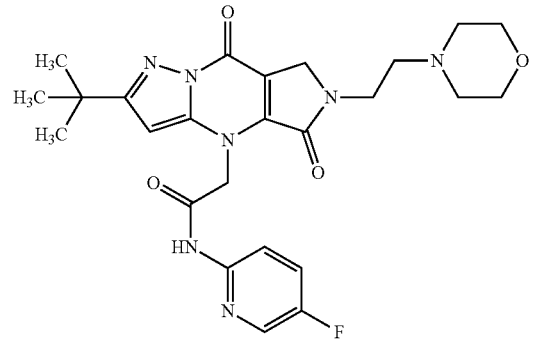 [SMILES: CC(C)(C)c1cc2n(CC(=O)Nc3ccc(F)cn3)c3c(c(=O)n2n1)CN(CCN1CCOCC1)C3=O]

2-[2-tert-butyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]ethyl trifluoromethanesulfonate (52 mg, 0.09 mmol) (intermediate 06-02) was dissolved in dichloromethane (1 ml) and to the resulting green solution was added morpholine (16 µl, 0.18 mmol) resulting in a colour change from green to orange. After stirring for 15 min at rt, the reaction was washed with sat. NaHCO$_3$, passed through a hydrophobic frit, concentrated under reduced pressure and purified by Biotage Isolera™ chromatography (silica gel, eluting with dichloromethane-methanol, 1:0 to 19:1). The material was freeze-dried to afford 20 mg (41% yield) of the title compound as a pale pink solid.

$^1$H NMR (500 MHz, DMSO-d6) δ[ppm]10.99 (s, 1H), 8.30 (d, 1H), 8.03-7.87 (m, 1H), 7.67 (ddd, 1H), 6.52 (s, 1H), 5.38 (s, 2H), 4.38 (s, 2H), 3.54 (t, 2H), 3.48-3.42 (m, 4H), 2.47 (t, 2H), 2.37-2.28 (m, 4H), 1.24 (s, 9H).

LC-MS (Analytical Method F) $R_t$=1.85 min, MS (ESIpos): m/z=512 [M+H]$^+$.

Example 139

2-{2-tert-butyl-6-[2-(dimethylamino)ethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide

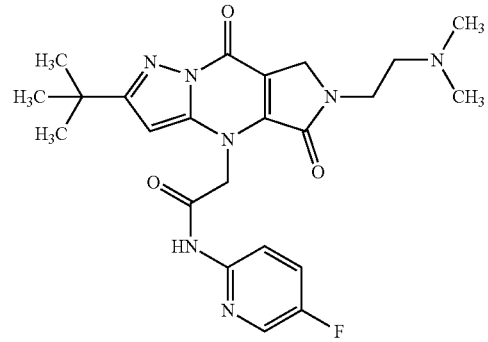 [SMILES: CN(C)CCN1Cc2c(n(CC(=O)Nc3ccc(F)cn3)c3cc(C(C)(C)C)nn3c2=O)C1=O]

2-[2-tert-Butyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]ethyl trifluoromethanesulfonate (52 mg, 0.09 mmol) (intermediate 06-02) was dissolved in dichloromethane (1 ml) and N,N-diisopropylethylamine (0.04 ml, 0.23 mmol) was added, followed by dimethylamine hydrochloride (8 mg, 0.10 mmol; azeotroped with toluene three times prior to use). The resulting orange solution was stirred for 10 min at rt and then the reaction was washed with sat. aq. NaHCO$_3$ solution, passed through a hydrophobic frit, concentrated under reduced pressure and purified by Biotage Isolera™ chromatography (silica gel, eluting with dichloromethane-methanol, 1:0 to 4:1). The material was freeze-dried to afford 27 mg (61% yield) of the title compound as a pale pink solid.

$^1$H NMR (500 MHz, DMSO-d6) δ[ppm]11.00 (s, 1H), 8.30 (d, 1H), 7.99-7.86 (m, 1H), 7.67 (ddd, 1H), 6.52 (s, 1H), 5.38 (s, 2H), 4.38 (s, 2H), 3.62-3.53 (m, 2H), 2.79-2.52 (m, 2H), 2.23 (s, 6H), 1.24 (s, 9H).

LC-MS (Analytical Method F) R$_t$=1.81 min, MS (ESI-pos): m/z=470.2 [M+H]$^+$.

Example 140

4-{2-[(5-fluoropyridin-2-yl)amino]-2-oxoethyl}-6-[(±)-1-methoxypropan-2-yl]-N,N-dimethyl-5,8-dioxo-5,6,7,8-tetrahydro-4H-pyrazolo[1,5-a]pyrrolo[3,4-d]pyrimidine-2-carboxamide

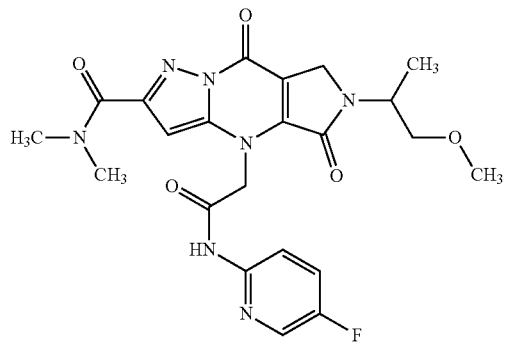

Phenyl 4-{2-[(5-fluoropyridin-2-yl)amino]-2-oxoethyl}-6-(1-methoxypropan-2-yl)-5,8-dioxo-5,6,7,8-tetrahydro-4H-pyrazolo[1,5-a]pyrrolo[3,4-d]pyrimidine-2-carboxylate (15 mg, 0.03 mmol) (intermediate 06-03) was dissolved in anhydrous acetonitrile (1 ml). Dimethylamine (2 M in tetrahydrofuran, 0.07 ml, 0.14 mmol) was added and the reaction was stirred at rt for 30 mins. Solvent was removed under a steady stream of air and the residue was purified by Biotage Isolera™ chromatography (silica gel, eluting with ethyl acetate-methanol, 1:0 to 9:1) and freeze-dried to afford 13 mg (93% yield) of the title compound as a pale pink solid.

$^1$H NMR (500 MHz, DMSO-d6) δ[ppm]11.10 (s, 1H), 8.38 (d, 1H), 8.06-7.96 (m, 1H), 7.74 (ddd, 1H), 6.88 (s, 1H), 5.56 (s, 2H), 4.51-4.30 (m, 3H), 3.57 (dd, 1H), 3.45 (dd, 1H), 3.26 (s, 3H), 3.25 (s, 3H), 3.02 (s, 3H), 1.21 (d, 3H).

LC-MS (Analytical Method F) R$_t$=2.10 min, MS (ESI-pos): m/z=486.2 [M+H]$^+$.

Example 141

N-(5-fluoropyridin-2-yl)-2-{2-(hydroxymethyl)-6-[(±)-1-methoxypropan-2-yl]-5,8-dioxo-5,6,7,8-tetrahydro-4H-pyrazolo[1,5-a]pyrrolo[3,4-d]pyrimidin-4-yl}acetamide

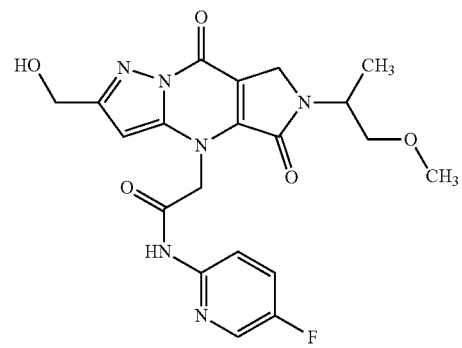 [SMILES: COCC(C)N1Cc2c(n(CC(=O)Nc3ccc(F)cn3)c3cc(CO)nn3c2=O)C1=O]

Phenyl 4-{2-[(5-fluoropyridin-2-yl)amino]-2-oxoethyl}-6-(1-methoxypropan-2-yl)-5,8-dioxo-5,6,7,8-tetrahydro-4H-pyrazolo[1,5-a]pyrrolo[3,4-d]pyrimidine-2-carboxylate (40 mg, 0.05 mmol, 70% purity) (intermediate 06-03) was dissolved in anhydrous tetrahydrofuran (1 ml) and the solution was cooled to 0° C. NaBH$_4$ (3 mg, 0.07 mmol) was then added and the reaction mixture was allowed to warm to rt and was then stirred for 1 h. Solvent was removed under a steady stream of air and the residue was dissolved in ethyl acetate and washed with water. The aqueous layer was extracted with ethyl acetate (twice) and the combined organic extracts were dried (MgSO$_4$), filtered, concentrated under reduced pressure and purified by Biotage Isolera™ chromatography (silica gel, eluting with ethyl acetate-methanol, 1:0 to 4:1). The resulting glassy solid was freeze-dried to afford 4 mg (15% yield) of the title compound as a white powder.

$^1$H NMR (500 MHz, DMSO-d6) δ[ppm]11.04 (s, 1H), 8.30 (d, 1H), 7.98-7.88 (m, 1H), 7.66 (ddd, 1H), 6.43 (s, 1H), 5.46 (s, 2H), 5.31 (t, 1H), 4.47 (d, 2H), 4.40-4.21 (m, 3H), 3.49 (dd, 1H), 3.37 (dd, 1H), 3.19 (s, 3H), 1.13 (d, 3H).

LC-MS (Analytical Method F) R$_t$=1.87 min, MS (ESI-pos): m/z=445.1 [M+H]$^+$.

Example 142 tert-butyl 3-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-2,5-dihydro-1H-pyrrole-1-carboxylate

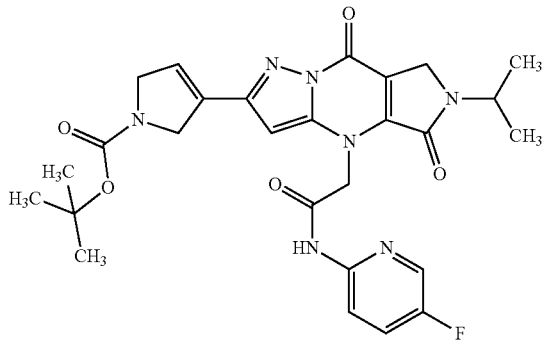 [SMILES: CC(C)N1Cc2c(n(CC(=O)Nc3ccc(F)cn3)c3cc(C4=CCN(C(=O)OC(C)(C)C)C4)nn3c2=O)C1=O]

To a solution of 2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (2.0 g, 4.3 mmol) (example 75) in dioxane/water (12 ml, v:v=5:1) was added K$_2$CO$_3$ (1.17 g, 8.48 mmol), Pd(dppf)Cl$_2$ (326 mg, 0.4 mmol) and tert-butyl 3-(4,4,5,5-tetramethyl-1,3,2-dioxaborolan-2-yl)-2H-pyrrole-1(5H)-carboxylate (1.5 g, 5.08 mmol). The resulting mixture was stirred at 60° C. for 40 min under nitrogen atmosphere. After being cooled to rt, water was added and the resulting solution was extracted with ethyl acetate. The combined organic layer was dried (Na$_2$SO$_4$), filtered and the solvent was removed in vacuo. The residue was washed with petroleum ether/ethyl acetate (v:v=1:1) to afford 1.5 g (62% yield) of the product as a yellow solid.

$^1$H-NMR (300 MHz, DMSO-d6): δ [ppm]: 1.24 (d, 6H), 1.44 (s, 9H), 4.23-4.30 (m, 3H), 4.32-4.39 (m, 4H), 5.49 (br s, 2H), 6.48-6.50 (m, 1H), 6.93 (s, 1H), 7.70-7.76 (m, 1H), 7.99-8.01 (m, 1H), 8.37-8.38 (m, 1H), 11.14 (br s, 1H).

LC-MS (Analytical Method N, 0-1.25 min 10-95% B, 1.25-1.75 min 95% B): R$_t$=1.59 min; MS (ESIpos): m/z=552 [M+H]$^+$.

Example 143 tert-butyl 4-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-3,6-dihydropyridine-1(2H)-carboxylate

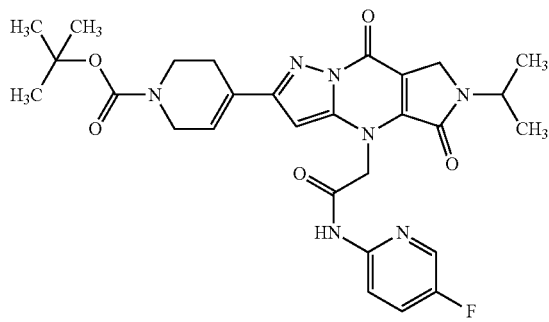 [SMILES: CC(C)N1Cc2c(n(CC(=O)Nc3ccc(F)cn3)c3cc(C4=CCN(C(=O)OC(C)(C)C)CC4)nn3c2=O)C1=O]

To a solution of 2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (2 g, 4.3 mmol) (example 75) of dioxane/water (10 ml, v:v=1:1) was added tert-butyl 4-(4,4,5,5-tetramethyl-1,3,2-dioxaborolan-2-yl)-5,6-dihydropyridine-1(2H)-carboxylate (1.87 g, 6.1 mmol), K$_2$CO$_3$ (1.19 g, 8.7 mmol) and Pd(dppf)Cl$_2$ (326 mg, 0.43 mmol). The mixture was stirred at 60° C. for 1 h under nitrogen atmosphere. After being cooled to rt, water was added and the resulting solution was extracted with ethyl acetate. The combined organic layer was dried (Na$_2$SO$_4$), filtered and the solvent was removed in vacuo to give 1.6 g (crude) of the product as a brown solid. It was used directly for next step without further purification in the hydrogenation to example 140.

$^1$H-NMR (300 MHz, CD$_3$OD): δ [ppm]=1.31 (d, 6H), 1.48 (s, 9H), 2.65-2.66 (m, 2H), 3.62-3.63 (m, 2H), 4.08-4.09 (m, 2H), 4.42-4.49 (m, 3H), 5.57 (br s, 2H), 6.52 (s, 1H), 6.62 (s, 1H), 7.52-7.59 (m, 1H), 8.04-8.09 (m, 1H), 8.21 (br, 1H)

LC-MS (Analytical Method N, 0-2.1 min 10-95% B, 2.1-2.7 min 95% B): R$_t$=1.60 min; MS (ESIpos): m/z=566 [M+H]$^+$.

Example 144

2-[2-(4,5-dihydrofuran-3-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

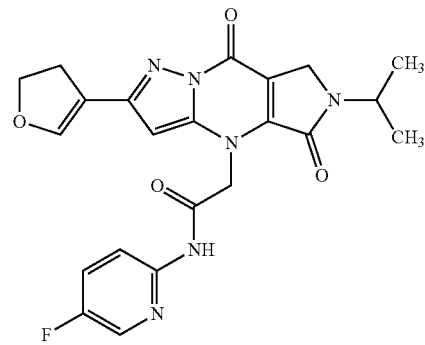 [SMILES: CC(C)N1Cc2c(n(CC(=O)Nc3ccc(F)cn3)c3cc(C4=COCC4)nn3c2=O)C1=O]

To a degassed mixture of 2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (230 mg, 496 µmol) (example 75) and 2-(4,5-dihydrofuran-3-yl)-4,4,5,5-tetramethyl-1,3,2-dioxaborolane (122 mg, 621 µmol) in dioxane/water (1:1, 2 ml) was added potassium carbonate (137 mg, 0993 µmol) and 1,1'-bis(diphenylphosphino)ferrocenepalladium(II) chloride: (36.3 mg, 49.6 µmol). The mixture was stirred for 1 h under a nitrogen atmosphere. The reaction was re-treated with 1,1'-bis(diphenylphosphino)ferrocenepalladium(II) chloride: (36.3 mg, 49.6 µmol), and heated for a further 2h then diluted with water (5 ml), and extracted with ethyl acetate (3×5 ml). The combined organics were dried (MgSO$_4$), filtered and concentrated under reduced pressure. The material was re-subjected to the reaction conditions, and heated for a further 1 h, at which time LC-MS showed complete conversion. The reaction was worked up as previously described. The crude material was purified by Biotage Isolera™ chromatography (silica gel, eluting with heptanes-acetone, 4:1 to 1:4), the pure fractions were combined and concentrated. The material was further purified by trituration from diethyl ether, the precipitate was collected by vacuum filtration and dried under vacuum to afford 48 mg (21% yield) of the title compound as an off-white powder.

1H-NMR (500 MHz, Chloroform-d) δ [ppm]: 1.33 (d, 6H), 3.15 (td, 2H), 4.38 (s, 2H), 4.50-4.71 (m, 3H), 5.30 (s, 2H), 6.30 (s, 1H), 7.08 (t, 1H), 7.40-7.45 (m, 1H), 8.16 (d, 2H), 9.13 (s, 1H).

LC-MS (Analytical Method D) Rt=3.94 min, MS (ESIpos): m/z=453 [M+H]$^+$.

Example 145

2-[2-(1,1-dioxo-1,2,3,6-tetrahydro-1lambda$^6$-thiopyran-4-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

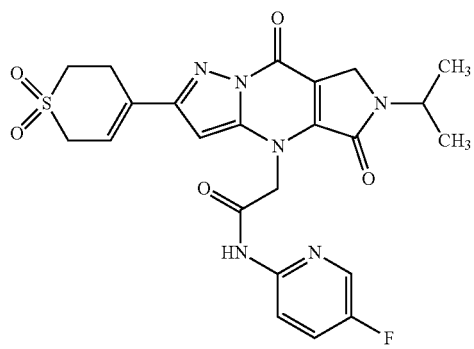 [SMILES: CC(C)N1Cc2c(n(CC(=O)Nc3ccc(F)cn3)c3cc(C4=CCS(=O)(=O)CC4)nn3c2=O)C1=O]

To a solution of 2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (70.0 mg, 151 µmol) (example 75) in 1,4-dioxane (1.2 ml, 14 mmol) and water (300 µl, 17 mmol) was added potassium carbonate (50.1 mg, 363 µmol), 1,1'-bis(diphenylphosphino)ferrocenepalladium(II) chloride (11.1 mg, 15.1 µmol) and 4-(4,4,5,5-tetramethyl-1,3,2-dioxaborolan-2-yl)-3,6-dihydro-1lambda6-thiopyran-1,1(2H)-dione (78.0 mg, 302 µmol). The vial was flushed with nitrogen, sealed and heated to 60° C. for 1 h. The mixture was filtrated through a celite packed filter and the filtrate was evaporated to dryness. The residue was dissolved with dimethyl sulfoxide (2.5 mL), filtrated and purified with preparative HPLC (Method F, gradient C). The product fractions were pooled and the acetonitrile was evaporated under reduced pressure. The aqueous solution was extracted with ethyl acetate. The combined organic phases were washed with brine and dried with a water repellant filter. The filtrate was evaporated to dryness. The residue was dissolved with ethyl acetate (2 mL) and diethyl ether (15 mL) was added to the solution. The formed solid was collected by vacuum filtration, washed with a little amount of diethyl ether and dried on air to afford 59 mg (75% yield) of the title compound.

LC-MS (Method H): R$_t$=0.88 min; MS (ESIpos): m/z=515 [M+H]$^+$ $^1$H NMR (400 MHz, DMSO-d6) δ[ppm]: 1.23 (d, 6H), 3.06-3.16 (m, 2H), 3.34-3.40 (m, 2H), 3.96 (br d, 2H), 4.30 (hept, 1H), 4.39 (s, 2H), 5.49 (br s, 2H), 6.43 (t, 1H), 6.93 (s, 1H), 7.74 (td, 1H), 8.00 (br d, 1H), 8.38 (d, 1H), 11.13 (s, 1H).

Example 146

2-[2-cyano-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

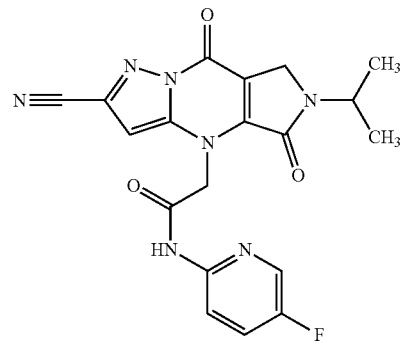 [SMILES: CC(C)N1Cc2c(n(CC(=O)Nc3ccc(F)cn3)c3cc(C#N)nn3c2=O)C1=O]

2-[2-Bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (60.0 mg, 130 µmol) (example 75), Pd$_2$(dba)$_3$ (5.93 mg, 6.48 µmol), zinc powder (2.12 mg, 32.4 µmol), zinc cyanide (16.7 mg, 142 µmol) and DPPF (7.18 mg, 13.0 µmol) were dissolved in anhydrous N,N-dimethylacetamide (1.0 ml, 11 mmol) under an atmosphere of nitrogen. The reaction mixture was heated by microwave irradiation at 120° C. for 16 h. After cooling to rt the reaction mixture was quenched with water. The solution was filtered, concentrated, dissolved with acetonitrile and purified with preparative HPLC (Method F, gradient C) to afford 6.3 mg (12% yield) of the final product.

$^1$H NMR (400 MHz, DMSO-d6) δ[ppm]: 1.20-1.27 (m, 6H), 4.22-4.35 (m, 1H), 4.39-4.48 (m, 2H), 5.38-5.64 (m, 2H), 7.43 (s, 1H), 7.74 (td, 1H), 8.00 (br d, 1H), 8.33-8.40 (m, 1H), 11.09-11.20 (m, 1H).

LC-MS (Analytical Method G): R$_t$=0.95 min; MS (ESIpos): m/z=410 [M+H]$^+$.

In analogy to the procedure described for Example 146 the following examples were prepared using the appropriate bromides as starting materials.

| Example | Structure IUPAC-Name ¹H NMR | Synth. from Yield LC-MS |
|---|---|---|
| 147 | 2-{2-cyano-6-[2-(morpholin-4-yl)ethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (250 MHz, DMSO-d6) δ [ppm]: 2.35-2.45 (m, 4H), 2.53-2.59 (m, 2H), 3.45-3.55 (m, 4H), 3.64 (t, 2H), 4.55 (s, 2H), 5.55 (s, 2H), 7.44 (s, 1H), 7.74 (td, 1H), 7.99 (s, 1H), 8.38 (d, 1H), 11.13 (s, 1H). | Example 75<br>18%<br>LC-MS (Analytical Method D): R$_t$ = 2.80 min; MS (ESIpos): m/z = 481 [M + H]⁺. |
| 148 | 2-{2-cyano-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, Chloroform-d) δ [ppm]: 9.07 (s, 1H), 8.16 (d, 1H), 8.10 (s, 1H), 7.47-7.41 (m, 1H), 6.78 (s, 1H), 5.41 (d, 2H), 4.63 (q, 1H), 4.58-4.41 (m, 2H), 3.54 (d, 2H), 3.34 (s, 3H), 1.35 (d, 3H). | Intermediate 06-07<br>26%<br>LC-MS (Analytical Method D): R$_t$ = 3.65 min; MS (ESIpos): m/z = 440.05 [M + H]⁺. |

Example 149

2-[5,8-dioxo-6-(propan-2-yl)-2-(pyridin-4-yl)-5,6,7,8-tetrahydro-4H-pyrazolo[1,5-a]pyrrolo[3,4-d]pyrimidin-4-yl]-N-(5-fluoropyridin-2-yl)acetamide

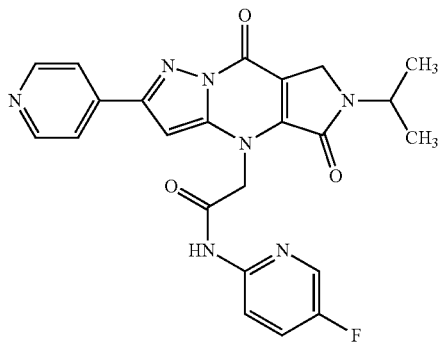 [SMILES: CC(C)N1Cc2c(n(CC(=O)Nc3ccc(F)cn3)c3cc(-c4ccncc4)nn3c2=O)C1=O]

2-[2-Bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (60.0 mg, 130 µmol) (example 75) and pyridin-4-ylboronic acid (22.3 mg, 181 µmol) were dissolved in dry 1,4-dioxane (1.0 ml, 12 mmol). K$_2$CO$_3$ (35.8 mg, 259 µmol), Pd(dppf)Cl$_2$ (9.48 mg, 13.0 µmol) and water (100 µL) were added successively. The reaction mixture was heated at 60° C. for 16 h. The reaction mixture was cooled to rt and filtered with a syringe filter. The filtrate was evaporated, the residue was dissolved in acetonitrile/water (7:3) and purified with preparative HPLC (Method E, gradient B) to afford 9 mg (14% yield) of the title compound.

$^1$H NMR (400 MHz, DMSO-d6) δ[ppm]: 1.25 (d, 6H), 4.31 (hep, 1H), 4.44 (s, 2H), 5.55 (br s, 2H), 7.37 (s, 1H), 7.74 (td, 1H), 7.92 (d, 2H), 8.02 (br d, 1H), 8.39 (d, 1H), 8.67-8.73 (m, 2H), 11.19 (s, 1H)

LC-MS (Analytical Method G): R$_t$=0.80 min; MS (ESI-pos): m/z=462 [M+H]$^+$.

Example 150

2-[5,8-dioxo-2-phenyl-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

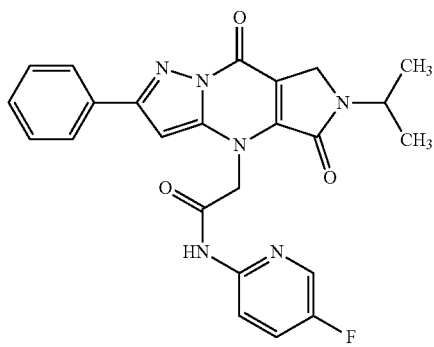 [SMILES: CC(C)N1Cc2c(n(CC(=O)Nc3ccc(F)cn3)c3cc(-c4ccccc4)nn3c2=O)C1=O]

2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (75.0 mg, 162 µmol) (example 75) and phenylboronic acid (29.6 mg, 243 µmol) were dissolved in 1,4-dioxane (1.0 ml, 12 mmol). Solid K$_2$CO$_3$ (44.7 mg, 324 µmol), Pd(dppf)Cl$_2$ (11.8 mg, 16.2 µmol) and water (500 µl) were added successively. The reaction mixture was heated at 60° C. for 16 h. The mixture was filtered and the filtrate was purified by preparative HPLC (Method F, gradient C). The product fractions were collected and the acetonitrile was removed under reduced pressure. The aqueous phase was extracted with ethyl acetate and the combined organic phases were washed with brine. The organics were evaporated and the residue was crystalized with hexane. The collected solid was dried under vacuum to afford 41 mg (55% yield) of the title compound.

$^1$H NMR (400 MHz, DMSO-d6) δ 1.25 (d, 6H), 4.26-4.35 (m, 1H), 4.42 (s, 2H), 5.54 (br s, 2H), 7.20 (s, 1H), 7.40-7.46 (m, 1H), 7.47-7.53 (m, 2H), 7.74 (td, 1H), 7.95-8.00 (m, 2H), 8.00-8.07 (m, 1H), 8.39 (d, 1H), 11.16 (s, 1H)

LC-MS (Analytical Method H): R$_t$=1.09 min; MS (ESI-pos): m/z=461 [M+H]$^+$.

Example 151

N-(5-fluoropyridin-2-yl)-2-{6-[(2S)-1-methoxypropan-2-yl]-2-(6-methylpyridin-3-yl)-5,8-dioxo-5,6,7,8-tetrahydro-4H-pyrazolo[1,5-a]pyrrolo[3,4-d]pyrimidin-4-yl}acetamide

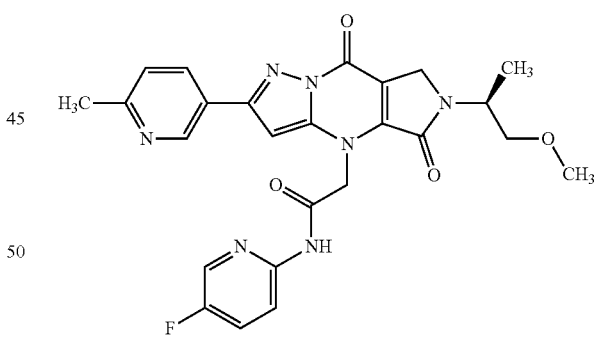

A sealed tube was charged with 2-{2-bromo-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide (100 mg, 0.20 mmol) (intermediate 06-07), (6-methylpyridin-3-yl)boronic acid (97 mg, 0.71 mmol) and K$_2$CO$_3$ (140 mg, 1.01 mmol) in THF:water (6:4 v:v; 3 mL). The reaction mixture was degassed with nitrogen for 15 min. Pd(dppf)Cl$_2$ (37 mg, 0.05 mmol) was then added and the solution was stirred at 80° C. for 2 h. After this time, the reaction mixture was partitioned between ethyl acetate and saturated aqueous NaCl solution. The organic layer was removed, dried (MgSO$_4$), filtered and concentrated in vacuo. The residual material dissolved in acetonitrile/water (7:3) and purified with preparative HPLC (Method B) to afford 22 mg (21% yield) of the title compound.

$^1$H NMR (500 MHz, Methanol-d4) δ [ppm]1.34 (d, 3H), 2.59 (s, 3H), 3.37 (s, 3H), 3.55 (dd, 1H), 3.65 (dd, 1H), 4.49 (d, 2H), 4.51-4.57 (m, 1H), 5.54-5.77 (m, 2H), 7.01 (s, 1H), 7.41 (d, 1H), 7.56 (ddd, 1H), 8.05-8.13 (m, 1H), 8.24 (d, 1H), 8.33 (dd, 1H), 9.02 (d, 1H).

LC-MS (Analytical Method F) R$_t$=3.14 min, MS (ESI-pos): m/z=506 [M+H]$^+$.

Example 152

N-(5-fluoropyridin-2-yl)-2-{6-[(2S)-1-methoxypropan-2-yl]-2-(3-methylpyridin-4-yl)-5,8-dioxo-5,6,7,8-tetrahydro-4H-pyrazolo[1,5-a]pyrrolo[3,4-d]pyrimidin-4-yl}acetamide

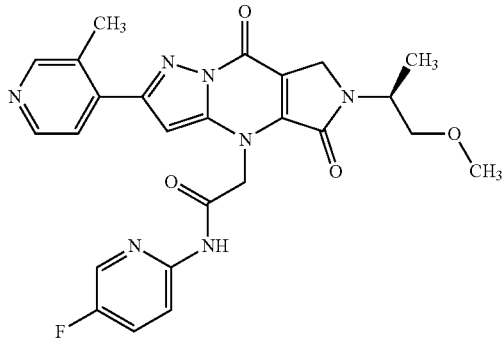 [SMILES: COC[C@H](C)N1Cc2c(n(CC(=O)Nc3ccc(F)cn3)c3cc(-c4ccncc4C)nn3c2=O)C1=O]

A sealed tube was charged with 2-{2-bromo-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide (100 mg, 0.20 mmol) (intermediate 06-07), (3-methylpyridin-4-yl)boronic acid (97 mg, 0.71 mmol) and K$_2$CO$_3$ (140 mg, 1.01 mmol) in tetrahydrofuran: water (6:4 v:v; 3 mL). The reaction mixture was degassed with nitrogen for 15 min. Pd(dppf)Cl$_2$ (37 mg, 0.05 mmol) was then added and the solution was stirred at 80° C. for 2 h. After this time, the reaction mixture was partitioned between ethyl acetate and saturated aqueous NaCl solution. The organic layer was removed, dried (MgSO$_4$), filtered and concentrated in vacuo. The residual material dissolved in acetonitrile/water (7:3) and purified with preparative HPLC (Method B) to afford 16.6 mg (16% yield) of the title compound.

$^1$H NMR (500 MHz, Methanol-d4) δ [ppm]: 1.35 (d, 3H), 2.60 (s, 3H), 3.38 (s, 3H), 3.56 (dd, 1H), 3.66 (dd, 1H), 4.51 (d, 2H), 4.52-4.59 (m, 1H), 5.58-5.79 (m, 2H), 6.91 (s, 1H), 7.58 (ddd, 1H), 7.74 (d, 1H), 8.04-8.13 (m, 1H), 8.23 (d, 1H), 8.46 (d, 1H), 8.52 (s, 1H).

LC-MS (Analytical Method F) R$_t$=3.12 min, MS (ESI-pos): m/z=506 [M+H]$^+$.

In analogy to the procedure described for Example 152 the following examples were prepared using the appropriate bromides and pyridine boronic acids/esters as starting materials.

| Example | Structure<br>IUPAC-Name<br>$^1$H NMR | Synth. from<br>Yield<br>LC-MS |
|---|---|---|
| 153 | N-(5-fluoropyridin-2-yl)-2-{6-[(2S)-1-methoxypropan-2-yl]-2-(2-methylpyridin-4-yl)-5,8-dioxo-5,6,7,8-tetrahydro-4H-pyrazolo[1,5-a]pyrrolo[3,4-d]pyrimidin-4-yl}acetamide<br>$^1$H NMR (500 MHz, DMSO-d6) δ [ppm]: 1.22 (d, 3H), 2.55 (s, 3H), 3.27 (s, 3H), 3.45 (dd, 1H), 3.57 (dd, 1H), 4.30-4.43 (m, 2H), 4.48 (d, 1H), 5.55 (s, 2H), 7.34 (s, 1H), 7.67-7.78 (m, 2H), 7.81 (s, 1H), 8.03 (d, 1H), 8.39 (d, 1H), 8.56 (d, 1H), 11.18 (s, 1H). | Intermediate 06-07<br>16%<br>LC-MS (Analytical Method D): R$_t$ = 2.96 min; MS (ESIpos): m/z = 506.10 [M + H]$^+$. |

| Example | Structure IUPAC-Name ¹H NMR | Synth. from Yield LC-MS |
|---|---|---|
| 154 | N-(5-fluoropyridin-2-yl)-2-[2-(6-methylpyridin-3-yl)-5,8-dioxo-6-(propan-2-yl)-5,6,7,8-tetrahydro-4H-pyrazolo[1,5-a]pyrrolo[3,4-d]pyrimidin-4-yl]acetamide<br>¹H NMR (500 MHz, DMSO-d6) δ [ppm]: 1.26 (d, 6H), 2.53 (s, 3H), 4.32 (hept, 1H), 4.43 (s, 2H), 5.54 (s, 2H), 7.26 (s, 1H), 7.40 (d, 1H), 7.74 (td, 1H), 7.94-8.08 (m, 1H), 8.22 (dd, 1H), 8.39 (d, 1H), 9.02 (d, 1H), 11.17 (s, 1H). | Example 75<br>27%<br>LC-MS (Analytical Method D): $R_t$ = 3.28 min; MS (ESIpos): m/z = 476.1 [M + H]⁺. |
| 155 | N-(5-fluoropyridin-2-yl)-2-[2-(4-methylpyridin-3-yl)-5,8-dioxo-6-(propan-2-yl)-5,6,7,8-tetrahydro-4H-pyrazolo[1,5-a]pyrrolo[3,4-d]pyrimidin-4-yl]acetamide<br>¹H NMR (500 MHz, DMSO-d6) δ [ppm]: 1.22 (d, 3H), 2.55 (s, 3H), 3.27 (s, 3H), 3.45 (dd, 1H), 3.57 (dd, 1H), 4.30-4.43 (m, 2H), 4.48 (d, 1H), 5.55 (s, 2H), 7.34 (s, 1H), 7.67-7.78 (m, 2H), 7.81 (s, 1H), 8.03 (d, 1H), 8.39 (d, 1H), 8.56 (d, 1H), 11.18 (s, 1H). | Example 75<br>38%<br>LC-MS (Analytical Method D): $R_t$ = 2.96 min; MS (ESIpos): m/z = 506.10 [M + H]⁺. |

| | Structure<br>IUPAC-Name | Synth. from |
|---|---|---|
| Example | ¹H NMR | Yield<br>LC-MS |

| 156 | 2-[2-(4,6-dimethylpyridin-3-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, Chloroform-d) δ [ppm]: 1.35 (d, 6H), 2.53 (s, 3H), 2.55 (s, 3H), 4.41 (s, 2H), 4.61 (hept, 1H), 5.44 (s, 2H), 6.55 (s, 1H), 7.07 (s, 1H), 7.42 (ddd, 1H), 8.14 (d, 2H), 8.67 (s, 1H), 9.28 (s, 1H). | Example 75<br>14%<br>LC-MS (Analytical Method D): $R_t$ = 3.02 min; MS (ESIpos): m/z = 490 [M + H]⁺. |

| 157 | 2-[2-(2,6-dimethylpyridin-3-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (250 MHz, Chloroform-d) δ 1.34 (d, 6H), 2.56 (s, 3H), 2.71 (s, 3H), 4.41 (s, 2H), 4.52-4.70 (m, 1H), 5.44 (s, 2H), 6.57 (s, 1H), 7.06 (d, 1H), 7.41 (ddd, 1H), 7.90 (d, 1H), 8.14 (d, 2H), 9.25 (s, 1H). | Example 75<br>64%<br>LC-MS (Analytical Method D): $R_t$ = 2.94 min; MS (ESIpos): m/z = m/z = 490 [M + H]⁺. |

| Example | Structure<br>IUPAC-Name<br>¹H NMR | Synth. from<br>Yield<br>LC-MS |
|---|---|---|
| 158 | 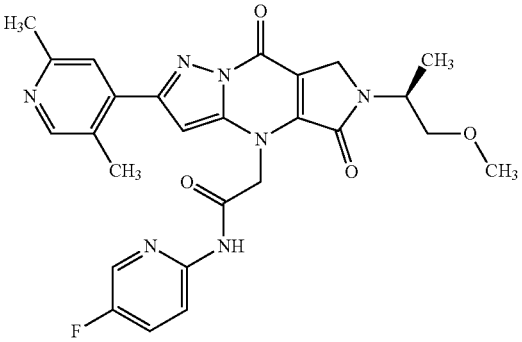<br>2-{2-(2,5-dimethylpyridin-4-yl)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, Chloroform-d) δ 1.35 (d, 3H), 2.48 (s, 3H), 2.55 (s, 3H), 3.35 (s, 3H), 3.54 (d, 2H), 4.45 (d, 1H), 4.53 (d, 1H), 4.62-4.69 (m, 1H), 5.31-5.44 (m, 1H), 5.44-5.59 (m, 1H), 6.62 (s, 1H), 7.41 (ddd, 1H), 7.52 (s, 1H), 8.06-8.21 (m, 2H), 8.40 (s, 1H), 9.35 (s, 1H). | Intermediate 06-07<br>64%<br>LC-MS (Analytical Method D): R$_t$ = 1.72; MS (ESIpos): m/z = 520 [M + H]⁺. |
| 159 | 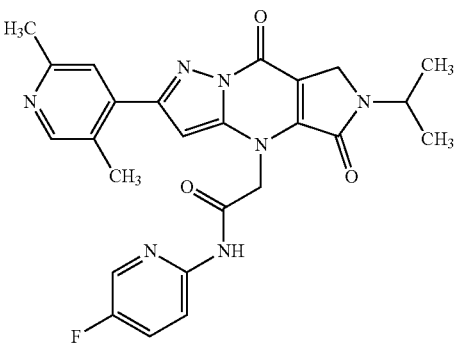<br>2-[2-(2,5-dimethylpyridin-4-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (500 MHz, Chloroform-d) δ 1.36 (d, 6H), 2.51 (s, 3H), 2.56 (s, 3H), 4.42 (s, 2H), 4.56-4.69 (m, 1H), 5.41 (s, 2H), 6.65 (s, 1H), 7.43 (ddd, 1H), 7.54 (s, 1H), 8.14 (s, 1H), 8.16 (d, 1H), 8.42 (s, 1H), 9.17 (s, 1H). | Example 75<br>18%<br>LC-MS (Analytical Method D): R$_t$ = 3.03 min; MS (ESIpos): m/z = 490 [M + H]⁺. |

Example 160

N-(5-fluoropyridin-2-yl)-2-[2-(5-methylpyridin-2-yl)-5,8-dioxo-6-[(3R)-oxolan-3-yl]-5,6,7,8-tetrahydro-4H-pyrazolo[1,5-a]pyrrolo[3,4-d]pyrimidin-4-yl]acetamide

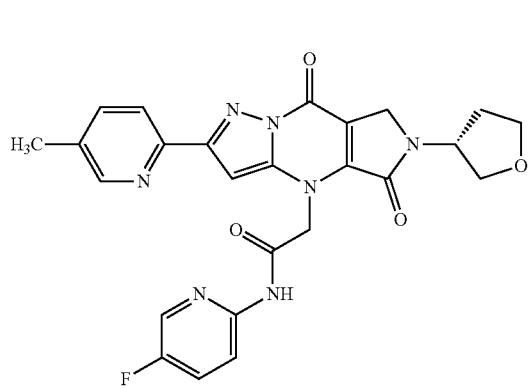 [SMILES: Cc1ccc(-c2cc3n(CC(=O)Nc4ccc(F)cn4)c4c(c(=O)n3n2)CN([C@@H]2CCOC2)C4=O)nc1]

A mixture of 2-{2-bromo-5,8-dioxo-6-[(3R)-oxolan-3-yl]-5,6,7,8-tetrahydro-4H-pyrazolo[1,5-a]pyrrolo[3,4-d]pyrimidin-4-yl}-N-(5-fluoropyridin-2-yl)acetamide (180 mg, 366 μmol) (intermediate 06-11), 5-methyl-2-(tributylstannyl)pyridine (224 mg, 586 μmol), tetrakis(triphenylphosphine)palladium(0) (29.6 mg, 25.6 μmol) and toluene (3.5 ml) under nitrogen was subjected to microwave irradiation at 120° C. for 2 hour. After cooling, KF on celite (250 mg) was added, and the reaction stirred for 1h. The reaction mixture was then filtered through celite, washing with ethyl acetate followed by dichloromethane/methanol and concentrated under reduced pressure. The crude material was purified by Biotage Isolera™ chromatography (silica gel, eluting with heptanes-ethyl acetate-methanol, 3:1:0 to 0:1:0 to 0:4:1). The product containing fractions were concentrated, and the residue further purified by trituration form MeCN to afford 27.3 mg (14% yield) of the title compound as a white powder.

$^1$H NMR (500 MHz, Chloroform-d) δ [ppm]: 2.02-2.12 (m, 1H), 2.38 (s, 3H), 2.40-2.47 (m, 1H), 3.81-3.89 (m, 2H), 3.93 (dd, 1H), 4.10-4.17 (m, 1H), 4.46 (d, 1H), 4.55 (d, 1H), 5.02 (d, 1H), 5.47 (s, 2H), 7.02 (s, 1H), 7.38-7.45 (m, 1H), 7.60 (dd, 1H), 8.08-8.18 (m, 2H), 8.29 (d, 1H), 8.46 (s, 1H), 8.70 (s, 1H).

LC-MS (Analytical Method F) $R_t$=2.25 min; MS (ESI-pos): m/z=504 [M+H]$^+$.

Example 161

N-(5-fluoropyridin-2-yl)-2-{2-(5-methylpyridin-2-yl)-5,8-dioxo-6-[(3S)-oxolan-3-yl]-5,6,7,8-tetrahydro-4H-pyrazolo[1,5-a]pyrrolo[3,4-d]pyrimidin-4-yl}acetamide

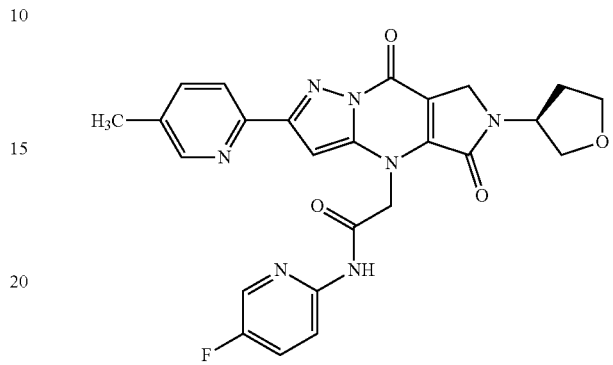

A mixture of 2-{2-bromo-5,8-dioxo-6-[(3S)-oxolan-3-yl]-5,6,7,8-tetrahydro-4H-pyrazolo[1,5-a]pyrrolo[3,4-d]pyrimidin-4-yl}-N-(5-fluoropyridin-2-yl)acetamide (250 mg, 509 μmol) (intermediate 06-12), 5-methyl-2-(tributylstannyl)pyridine (311 mg, 814 μmol), tetrakis(triphenylphosphine)palladium(0) (41 mg, 35.6 μmol) and toluene (5 ml) under nitrogen was heated to 120° C. for 18h. The reaction was re-treated with tetrakis(triphenylphosphine)palladium (0) (41 mg, 35.6 μmol) and subjected to microwave irradiation at 120° C. for 1 hour. After cooling, KF on celite (250 mg) was added, and the reaction stirred for 1h. The reaction mixture was then filtered through celite, washing with ethyl acetate, followed by methanol/dichloromethane and concentrated under reduced pressure. The crude material was purified by Biotage Isolera™ chromatography (silica gel, eluting with heptanes-ethyl acetate-methanol, 3:1:0 to 0:1:0 to 0:4:1). The product containing fractions were concentrated, and the residue further purified by trituration from MeCN to afford 45.6 mg (17% yield) of the title compound as an off-white powder.

$^1$H NMR (500 MHz, Chloroform-d) δ [ppm]2.02-2.11 (m, 1H), 2.38 (s, 3H), 2.39-2.48 (m, 1H), 3.82-3.89 (m, 2H), 3.92 (dd, 1H), 4.10-4.18 (m, 1H), 4.46 (d, 1H), 4.54 (d, 1H), 4.98-5.05 (m, 1H), 5.48 (s, 2H), 7.01 (s, 1H), 7.40 (ddd, 1H), 7.60 (dd, 1H), 8.08-8.16 (m, 2H), 8.28 (d, 1H), 8.45 (d, 1H), 8.78 (s, 1H).

LC-MS (Analytical Method F) Rt=2.25 min, MS (ESI-pos): m/z=504 [M+H]$^+$.

In analogy to the procedure described for Examples 160 and 161 the following examples were prepared using the appropriate bromides and pyridyl stannanes as starting materials.

| Example | Structure<br>IUPAC-Name<br>¹H NMR | Synth. from<br>Yield<br>LC-MS |
|---|---|---|
| 162 | N-(5-fluoropyridin-2-yl)-2-{6-[(2S)-1-methoxypropan-2-yl]-2-(5-methylpyridin-2-yl)-5,8-dioxo-5,6,7,8-tetrahydro-4H-pyrazolo[1,5-a]pyrrolo[3,4-d]pyrimidin-4-yl}acetamide<br>¹H NMR (250 MHz, DMSO-d6) δ [ppm] 1.20 (d, 3H), 2.34 (s, 3H), 3.25 (s, 3H), 3.39-3.47 (m, 1H), 3.52-3.60 (m, 1H), 4.25-4.53 (m, 3H), 5.61 (s, 2H), 7.12 (s, 1H), 7.66-7.80 (m, 2H), 7.93-8.09 (m, 2H), 8.34-8.39 (m, 1H), 8.46-8.50 (m, 1H), 11.14 (s, 1H). | Intermediate 06-07<br>33%<br>LC-MS (Analytical Method F): R$_t$ = 2.51 min; MS (ESIpos): m/z = 506.2 [M + H]⁺. |
| 163 | N-(5-fluoropyridin-2-yl)-2-[2-(3-methylpyridin-2-yl)-5,8-dioxo-6-(propan-2-yl)-5,6,7,8-tetrahydro-4H-pyrazolo[1,5-a]pyrrolo[3,4-d]pyrimidin-4-yl]acetamide<br>¹H NMR (500 MHz, DMSO-d6) δ [ppm]: 1.26 (d, 6H), 2.72 (s, 3H), 4.24-4.37 (m, 1H), 4.42 (s, 2H), 5.62 (s, 2H), 7.10 (s, 1H), 7.35 (dd, Hz, 1H), 7.70-7.76 (m, 1H), 7.76-7.79 (m, 1H), 7.95-8.08 (m, 1H), 8.38 (d, 1H), 8.47-8.54 (m, 1H), 11.13 (s, 1H). | Example 75<br>14%<br>LC-MS (Analytical Method F): R$_t$ = 2.28 min; MS (ESIpos): m/z = 476.2 [M + H]⁺. |

| | |
|---|---|
| Example | Structure<br>IUPAC-Name<br>¹H NMR | Synth. from<br>Yield<br>LC-MS |

164

N-(5-fluoropyridin-2-yl)-2-{6-[(2S)-1-methoxypropan-2-yl]-2-(3-methylpyridin-2-yl)-5,8-dioxo-5,6,7,8-tetrahydro-4H-pyrazolo[1,5-a]pyrrolo[3,4-d]pyrimidin-4-yl}acetamide
¹H NMR (500 MHz, DMSO-d6) δ 1.22 (d, 3H), 2.71 (s, 3H), 3.27 (s, 3H), 3.45 (dd, 1H), 3.58 (dd, 1H), 4.29-4.52 (m, 3H), 5.62 (s, 2H), 7.10 (s, 1H), 7.35 (dd, 1H), 7.69-7.82 (m, 2H), 7.94-8.09 (m, 1H), 8.37 (d, 1H), 8.48-8.54 (m, 1H), 11.14 (s, 1H).

Intermediate 06-07
15%
LC-MS (Analytical Method F): R_t = 2.22 min; MS (ESIpos): m/z = 506.3 [M + H]⁺.

165

N-(5-fluoropyridin-2-yl)-2-[2-(5-fluoropyridin-2-yl)-5,8-dioxo-6-(propan-2-yl)-5,6,7,8-tetrahydro-4H-pyrazolo[1,5-a]pyrrolo[3,4-d]pyrimidin-4-yl]acetamide
¹H NMR (500 MHz, Chloroform-d) δ [ppm] 1.37 (d, 6H), 4.44 (s, 2H), 4.55-4.69 (m, 1H), 5.50 (s, 2H), 7.04 (s, 1H), 7.40-7.47 (m, 1H), 7.50-7.57 (m, 1H), 8.11-8.23 (m, 2H), 8.43 (dd, 1H), 8.51 (d, 1H), 8.95 (s, 1H).

Example 75
22%
LC-MS (Analytical Method F): R_t = 2.84 min; MS (ESIpos): m/z = 480 [M + H]⁺.

Example 166

2-[2-(3,5-dimethylpyridin-2-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

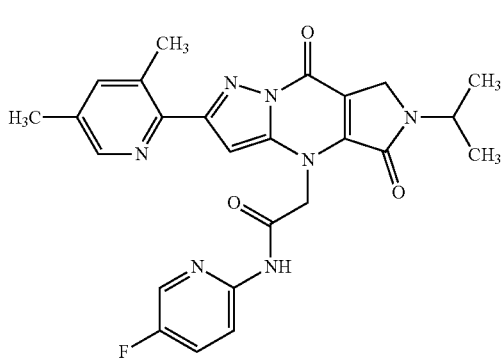 [SMILES: Cc1cnc(-c2cc3n(CC(=O)Nc4ccc(F)cn4)c4c(c(=O)n3n2)CN(C(C)C)C4=O)c(C)c1]

A mixture of 2-bromo-3,5-dimethylpyridine (64 mg, 345 µmol) and hexamethylditin (72 µl, 350 µmol) in 1,4-dioxane (3 ml) was degassed with a stream of nitrogen, then tetrakis(triphenylphosphine)palladium(0) (12 mg, 10.8 µmol) was added. The reaction was subjected to microwave irradiation at 110° C. for 2h. 2-[2-Bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (100 mg, 216 µmol) (example 75) was added, and the reaction irradiated at 110° C. for a further 2h. KF and celite (1:1 mixture, 250 mg) were added, and the solution stirred for one hour, before being filtered, washing with ethyl acetate/methanol, and concentrated under reduced pressure. The crude mixture was taken up in toluene (3 ml), and degassed with a stream of $N_2$ for 5 mins. Tetrakis(triphenylphosphine)palladium(0) (12 mg, 10.8 µmol) was added, and the reaction irradiated to 120° C. in the microwave for 1 h, the irradiation was then repeated until conversion was complete. KF and celite (1:1 mixture, 250 mg) were added, and the solution stirred for one hour, before being filtered, washing with ethyl acetate/methanol, and concentrated under reduced pressure. The crude material was purified by preparative HPLC, then further purified by trituration from MeCN to afford 27.7 mg (26% yield) of the title compound as an off-white powder.

$^1$H NMR (500 MHz, Chloroform-d) δ [ppm]1.34 (d, 6H), 2.35 (s, 3H), 2.75 (s, 3H), 4.39 (s, 2H), 4.51-4.64 (m, 1H), 5.46 (s, 2H), 6.95 (s, 1H), 7.37-7.44 (m, 2H), 8.09-8.17 (m, 2H), 8.33 (s, 1H), 8.91 (s, 1H).

LC-MS (Analytical Method F) $R_t$=2.30 min; MS (ESI-pos): m/z=490 [M+H]$^+$.

Example 167

2-[2-(cyclopropylamino)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

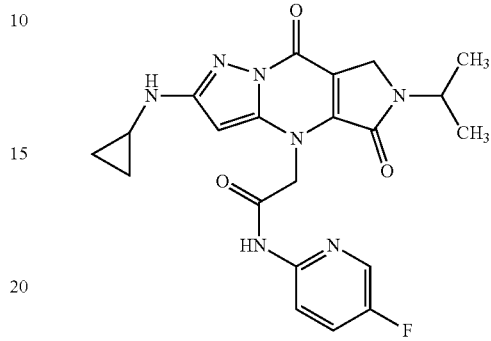

To a suspension of 2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (200 mg, 432 µmol) (example 75), BrettPhos-G3 (39.1 mg, 43.2 µmol), tBu-BrettPhos (20.9 mg, 43.2 µmol) and LiCl (220 mg, 5.18 mmol) in dry 1,4-dioxane (2.0 ml, 23 mmol) was added cyclopropanamine (60 µl, 860 µmol). The mixture was flushed with nitrogen and a solution of LiHMDS (2.2 ml, 1.0 M, 2.2 mmol) in tetrahydrofuran was added. The reaction mixture was heated for 1 h at 80° C. The mixture was quenched with 1M aqueous HCl solution and extracted with ethyl acetate. The organic phase was washed with brine, dried over a water repellant filter and concentrated. The residue was dissolved in dimethyl sulfoxide and purified by preparative HPLC (Method F, gradient C). The acetonitrile of the product containing fractions was evaporated under reduced pressure. The aqueous solution was extracted with ethyl acetate; the organics were washed with brine, filtrated over a water repellant filter and concentrated. The residue was dissolved with a few drops of ethyl acetate. To the solution were added 50 ml of diethyl ether and the formed solid was collected by filtration to afford 22 mg (11% yield) of the title compound.

$^1$H NMR (400 MHz, DMSO-d6) δ[ppm]: 0.36-0.43 (m, 2H), 0.60-0.66 (m, 2H), 1.22 (d, 6H), 4.23-4.30 (m, 1H), 4.31 (s, 2H), 5.42 (br s, 2H), 5.78 (s, 1H), 6.58 (d, 1H), 7.74 (td, 3.04 Hz, 1H), 8.00 (br s, 1H), 8.37 (d, 1H), 11.09 (s, 1H)

LC-MS (Analytical Method H): $R_t$=0.91 min; MS (ESI-pos): m/z=441 [M+H]$^+$.

In analogy to the procedure described for Example 167 the following examples were prepared using the appropriate bromide and amine as starting materials.

| Example | Structure / IUPAC-Name / ¹H NMR | Synth. from / Yield / LC-MS |
|---|---|---|
| 168 | 2-[2-(cyclopentylamino)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (600 MHz, DMSO-d6) δ [ppm]: 1.22 (d, 6H), 1.39-1.46 (m, 2H), 1.48-1.56 (m, 2H), 1.60-1.70 (m, 2H), 1.86-1.92 (m, 2H), 3.86 (m, 1H), 4.25-4.29 (m, 1H), 4.30 (s, 2H), 5.39 (br s, 2H), 5.62 (s, 1H), 6.19 (d, 1H), 7.75 (td, 1H), 7.95-8.08 (m, 1H), 8.37 (d, 1H), 11.10 (s, 1H). | Example 75<br>50%<br>LC-MS (Analytical Method H): $R_t$ = 1.04 min; MS (ESIpos): m/z = 468 [M + H]⁺. |
| 169 | N-(5-fluoropyridin-2-yl)-2-{2-[(2-methoxyethyl)amino]-5,8-dioxo-6-(propan-2-yl)-5,6,7,8-tetrahydro-4H-pyrazolo[1,5-a]pyrrolo[3,4-d]pyrimidin-4-yl}acetamide<br>¹H NMR (400 MHz, DMSO-d6) δ [ppm]: 1.22 (d, 6H), 3.25 (s, 3H), 3.27-3.33 (m, 2H), 3.43-3.48 (m, 2H), 4.24-4.33 (m, 3H), 5.39 (br s, 2H), 5.67 (s, 1H), 6.26 (t, 1H), 7.75 (ddd, 1H), 7.92-8.10 (m, 1H), 8.37 (d, 1H), 11.10 (br s, 1H). | Example 75<br>24%<br>LC-MS (Analytical Method H): $R_t$ = 0.87 min; MS (ESIpos): m/z = 458 [M + H]⁺. |

| Example | Structure<br>IUPAC-Name<br>¹H NMR | Synth. from<br>Yield<br>LC-MS |
|---|---|---|
| 170 | 2-{2-[(2,2-difluoroethyl)amino]-5,8-dioxo-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm]: 1.22 (d, 6H), 3.52-3.64 (m, 2H), 4.23-4.30 (m, 1H), 4.31 (s, 2H), 5.41 (br s, 2H), 5.76 (s, 1H), 6.12 (tt, 1H), 6.68 (t, 1H), 7.74 (td, 1H), 8.01 (br d, 1H), 8.37 (d, 1H), 11.10 (s, 1H). | Example 75<br>13%<br>LC-MS (Analytical Method H): $R_t$ = 0.92 min; MS (ESIpos): m/z = 464 [M + H]⁺. |
| 171 | 2-[5,8-dioxo-6-(propan-2-yl)-2-(propan-2-ylamino)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.14 (d, 6H), 1.22 (d, 6H), 3.65-3.74 (m, 1H), 4.23-4.29 (m, 1H), 4.30 (s, 2H), 5.39 (br s, 2H), 5.61 (s, 1H), 6.04 (d, 1H), 7.72-7.78 (m, 1H), 8.01 (br d, 1H), 8.37 (d, 1H), 11.09 (s, 1H). | Example 75<br>11%<br>LC-MS (Analytical Method H): $R_t$ = 0.96 min; MS (ESIpos): m/z = 442 [M + H]⁺. |

| Example | Structure IUPAC-Name ¹H NMR | Synth. from Yield LC-MS |
|---|---|---|
| 172 | 2-[2-(dimethylamino)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.22 (d, 6H), 2.89 (s, 6H), 4.23-4.30 (m, 1H), 4.32 (s, 2H), 5.29-5.45 (m, 2H), 6.09 (s, 1H), 7.74 (ddd, 1H), 8.01 (br d, 1H), 8.37 (d, 1H), 11.07 (s, 1H). | Example 75<br>12%<br>LC-MS (Analytical Method G): R$_t$ = 0.91 min; MS (ESIpos): m/z = 428 [M + H]⁺ |
| 173 | 2-[2-{ethylamino)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.13 (t, 3H), 1.22 (d, 6H), 3.10-3.21 (m, 2H), 4.22-4.28 (m, 1H), 4.30 (s, 2H), 5.39 (br s, 2H), 5.65 (s, 1H), 6.15 (t, 1H), 7.74 (ddd, 1H), 8.01 (br d, 1H), 8.37 (d, 1H), 11.09 (br s, 1H). | Example 75<br>28%<br>LC-MS (Analytical Method H): R$_t$ = 0.89 min; MS (ESIpos): m/z = 428 [M + H]⁺ |

| Example | Structure<br>IUPAC-Name<br>¹H NMR | Synth. from<br>Yield<br>LC-MS |
|---|---|---|
| 174 | N-(5-fluoropyridin-2-yl)-2-[2-(methylamino)-5,8-dioxo-6-(propan-2-yl)-5,6,7,8-tetrahydro-4H-pyrazolo[1,5-a]pyrrolo[3,4-d]pyrimidin-4-yl]acetamide<br>¹H NMR (400 MHz, DMSO-d6) δ [ppm]: 1.22 (d, 6H), 2.74 (d, 3H), 4.24-4.29 (m, 1H), 4.30 (s, 2H), 5.39 (br s, 2H), 5.68 (s, 1H), 6.12 (q, 1H), 7.74 (ddd, 1H), 7.94-8.07 (m, 1H), 8.37 (d, 1H), 11.08 (s, 1H). | Example 75<br>17%<br>LC-MS (Analytical Method H): R$_t$ = 0.82 min; MS (ESIpos): m/z = 414 [M + H]⁺. |
| 175 | 2-{2-[(cyclopropylmethyl)amino]-5,8-dioxo-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm] 0.15-0.22 (m, 2H), 0.38-0.44 (m, 2H), 0.97-1.10 (m, 1H), 1.22 (d, 6H), 3.01 (t, 2H), 4.23-4.28 (m, 1H), 4.30 (s, 2H), 5.40 (br s, 2H), 5.67 (s, 1H), 6.28 (t, 1H), 7.68-7.80 (m, 1H), 8.01 (br d, 1H), 8.37 (d, 1H), 11.10 (s, 1H). | Example 75<br>25%<br>LC-MS (Analytical Method H): R$_t$ = 0.98 min; MS (ESIpos): m/z = 454 [M + H]⁺. |

| Example | Structure / IUPAC-Name / ¹H NMR | Synth. from / Yield / LC-MS |
|---|---|---|
| 176 | 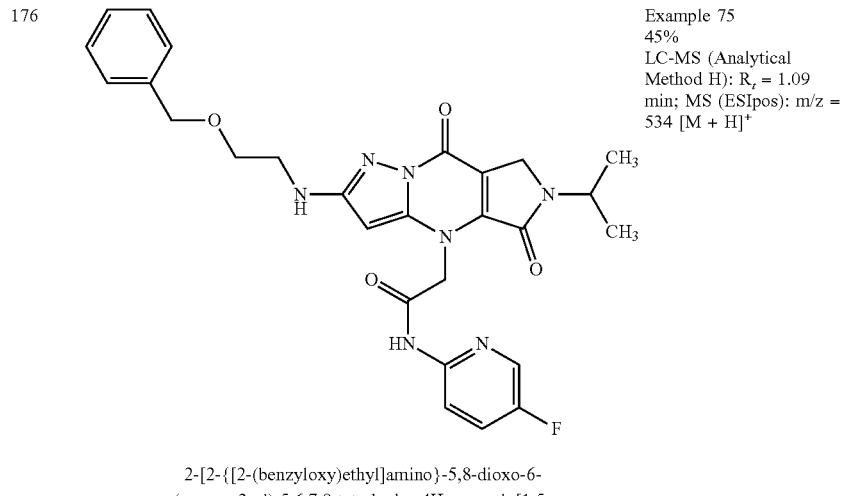<br>2-[2-{[2-(benzyloxy)ethyl]amino}-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.22 (d, 6H), 3.37 (q, 2H), 3.54-3.60 (m, 2H), 4.23-4.33 (m, 3H), 4.49 (s, 2H), 5.33-5.46 (m, 2H), 5.69 (s, 1H), 6.30 (t, 1H), 7.23-7.35 (m, 5H), 7.74 (td, 1H), 8.01 (br s, 1H), 8.37 (d, 1H), 11.10 (s, 1H). | Example 75<br>45%<br>LC-MS (Analytical Method H): $R_t$ = 1.09 min; MS (ESIpos): m/z = 534 [M + H]⁺ |
| 177 | 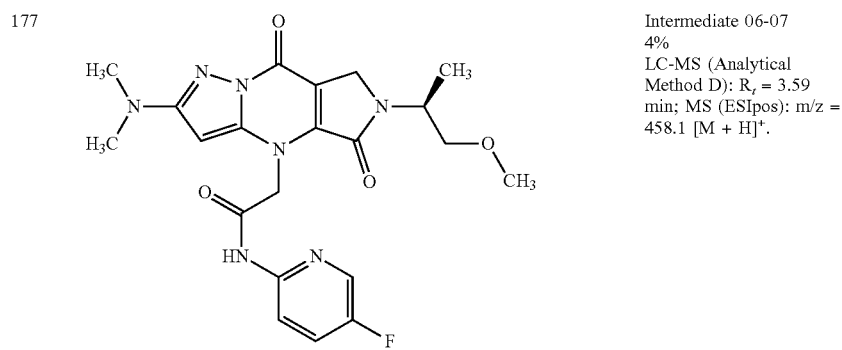<br>2-{2-(dimethylamino)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, Chloroform-d) δ [ppm]: 1.32 (d, 3H), 3.03 (s, 6H), 3.34 (s, 3H), 3.48-3.55 (m, 2H), 4.38 (d, 1H), 4.45 (d, 1H), 4.55-4.68 (m, 1H), 5.18 (s, 1H), 5.23-5.41 (m, 1H), 5.73 (s, 1H), 7.38-7.45 (m, 1H), 8.10-8.19 (m, 2H), 9.30 (s, 1H). | Intermediate 06-07<br>4%<br>LC-MS (Analytical Method D): $R_t$ = 3.59 min; MS (ESIpos): m/z = 458.1 [M + H]⁺. |

| Example | Structure IUPAC-Name ¹H NMR | Synth. from Yield LC-MS |
|---|---|---|
| 178 | 2-{2-(cyclopentylamino)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, Chloroform-d) δ [ppm] 1.32 (d, 3H), 1.42-1.53 (m, 2H), 1.59-1.65 (m, 2H), 1.67-1.78 (m, 2H), 1.98-2.08 (m, 2H), 3.33 (s, 3H), 3.49-3.55 (m, 2H), 3.92-4.03 (m, 1H), 4.25 (d, 1H), 4.37 (d, 1H), 4.45 (d, 1H), 4.57-4.67 (m, 1H), 5.10-5.21 (m, 1H), 5.23-5.42 (m, 1H), 5.71 (s, 1H), 7.42 (ddd, 1H), 8.14 (d, 2H), 9.25 (s, 1H). | Intermediate 06-07<br>65%<br>LC-MS (Analytical Method D): R$_t$ = 3.72 min; MS (ESIpos): m/z = 498 [M + H]⁺. |
| 179 | N-(5-fluoropyridin-2-yl)-2-(6-[(2S)-1-methoxypropan-2-yl]-2-(methylamino)-5,8-dioxo-5,6,7,8-tetrahydro-4H-pyrazolo[1,5-a]pyrrolo[3,4-d]pyrimidin-4-yl}acetamide<br>¹H NMR (500 MHz, DMSO-d6) δ 1.18 (d, 3H), 2.75 (d, 3H), 3.25 (s, 3H), 3.42 (dd, 1H), 3.53 (dd, 1H), 4.19-4.41 (m, 3H), 5.39 (s, 2H), 5.67 (s, 1H), 6.11 (q, 1H), 7.65-7.81 (m, 1H), 8.01 (s, 1H), 8.37 (d, 1H), 11.07 (s, 1H). | Intermediate 06-07<br>7%<br>LC-MS (Analytical Method F): R$_t$ = 2.02 min; MS (ESIpos): m/z = 444.3 [M + H]⁺. |

Example 180

N-(5-fluoropyridin-2-yl)-2-[2-(morpholin-4-yl)-5,8-dioxo-6-(propan-2-yl)-5,6,7,8-tetrahydro-4H-pyrazolo[1,5-a]pyrrolo[3,4-d]pyrimidin-4-yl]acetamide

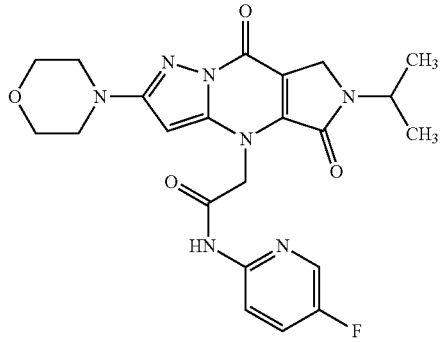 [SMILES: CC(C)N1Cc2c(n(CC(=O)Nc3ccc(F)cn3)c3cc(N4CCOCC4)nn3c2=O)C1=O]

To a suspension of 2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (50.0 mg, 108 µmol) (example 75), chloro(2-dicyclohexylphosphino-2',6'-di-i-propoxy-1,1'-biphenyl)(2'-amino-1,1'-biphenyl-2-yl)palladium(II) (8.38 mg, 10.8 µmol), 2-dicyclohexylphosphino-2',6'-di-i-propoxy-1,1'-biphenyl (5.04 mg, 10.8 µmol) and lithium bis(trimethylsilyl)amide (540 µl, 1.0 M, 540 µmol) in dry 1,4-dioxane (750 µl, 8.8 mmol), lithium chloride (54.9 mg, 1.30 mmol) and morpholine (19 µl, 220 µmol) were added. The mixture was flushed with nitrogen and heated for 90 min at 90° C. After cooling to room temperature, a 1 M aqueous hydrogen chloride solution was added. The solution was extracted with ethyl acetate. The combined organic layers were washed with brine, dried with a water repellant filter and concentrated. The residual material dissolved in dimethyl sulfoxide (2 mL) and purified with preparative HPLC (Method D) to afford 2.0 mg (3% yield) of the title compound.

LC-MS (Method J): $R_t$=0.85 min; MS (ESIpos): m/z=470 [M+H]$^+$ $^1$H NMR (400 MHz, DMSO-d6) δ[ppm]: 1.22 (d, 6H), 3.21-3.27 (m, 4H), 3.66-3.72 (m, 4H), 4.22-4.31 (m, 1H), 4.33 (s, 2H), 5.29-5.52 (m, 2H), 6.21 (s, 1H), 7.70-7.78 (m, 1H), 7.94-8.08 (m, 1H), 8.37 (d, 1H), 11.09 (br s, 1H).

Example 181

N-(5-fluoropyridin-2-yl)-2-[2-(4-methylpiperazin-1-yl)-5,8-dioxo-6-(propan-2-yl)-5,6,7,8-tetrahydro-4H-pyrazolo[1,5-a]pyrrolo[3,4-d]pyrimidin-4-yl]acetamide

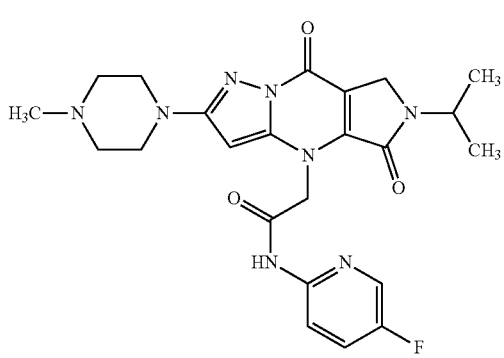 [SMILES: CC(C)N1Cc2c(n(CC(=O)Nc3ccc(F)cn3)c3cc(N4CCN(C)CC4)nn3c2=O)C1=O]

To a suspension of 2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (50.0 mg, 108 µmol) (example 75), chloro(2-dicyclohexylphosphino-2',6'-di-i-propoxy-1,1'-biphenyl)(2'-amino-1,1'-biphenyl-2-yl)palladium(II) (8.38 mg, 10.8 µmol), 2-dicyclohexylphosphino-2',6'-di-i-propoxy-1,1'-biphenyl (5.04 mg, 10.8 µmol) and lithium bis(trimethylsilyl)amide (1 M in THF) (540 µl, 540 µmol) in dry dioxane was added lithium chloride (54.9 mg, 1.30 mmol) and 1-methylpiperazine (24 µl, 220 µmol). The mixture was flushed with nitrogen and was heated for 16 h at 120° C. The mixture was quenched with 1 M aqueous hydrogen chloride solution and extracted with ethyl acetate. The aqueous phase was basified with saturated sodium hydrogencarbonate solution and extracted with ethyl acetate. The combined organic phases were washed with brine, dried with a water repellant filter and concentrated under reduced pressure. The residual material dissolved in dimethyl sulfoxide (2 mL) and purified with preparative HPLC (Method D) to afford 3.9 mg (7% yield) of the title compound.

LC-MS (Method J): $R_t$=0.86 min; MS (ESIpos): m/z=483 [M+H]$^+$ $^1$H NMR (400 MHz, DMSO-d6) δ[ppm]: 1.22 (d, 6H), 2.20 (s, 3H), 2.39 (br t, 4H), 3.23-3.31 (m, 4H), 4.23-4.31 (m, 1H), 4.32 (s, 2H), 5.37 (br s, 2H), 6.19 (s, 1H), 7.74 (td, 1H), 7.94-8.10 (m, 1H), 8.37 (d, 1H), 11.08 (s, 1H).

Example 182

4-{2-[(5-fluoropyridin-2-yl)amino]-2-oxoethyl}-N,N-dimethyl-5,8-dioxo-6-(propan-2-yl)-5,6,7,8-tetrahydro-4H-pyrazolo[1,5-a]pyrrolo[3,4-d]pyrimidine-2-carboxamide

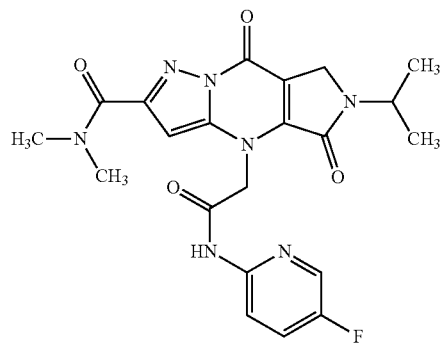 [SMILES: CC(C)N1Cc2c(n(CC(=O)Nc3ccc(F)cn3)c3cc(C(=O)N(C)C)nn3c2=O)C1=O]

To an ice-cooled solution of N-methylmethanamine hydrochloride (1:1) (53.6 mg, 657 µmol) in dry toluene (2.0 ml) under nitrogen atmosphere was added a solution of trimethylaluminum (2 M in toluene, 330 µl, 660 µmol) dropwise over a period of 5 min. The mixture stirred for 1 h at 0° C. and additional 2 h at rt. After this time ethyl 4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxylate (100 mg, 219 µmol) (example 70) was added in one portion to the prepared aluminum amine solution. The mixture stirred for 16 h at 50° C. The reaction was quenched with water and the solvent was evaporated. The residue was purified with preparative HPLC (Method F, gradient C) to afford 35 mg (33% yield) of the title compound.

¹H NMR (500 MHz, DMSO-d6) δ[ppm]: 1.24 (d, 6H), 3.01 (s, 3H), 3.24 (s, 3H), 4.31 (hep, 1H), 4.42 (s, 2H), 5.55 (br s, 2H), 6.88 (s, 1H), 7.74 (td, 1H), 8.00 (br d, 1H), 8.38 (d, 1H), 11.12 (br s, 1H)

LC-MS (Analytical Method H): $R_t$=0.86 min; MS (ESIpos): m/z=456 [M+H]⁺.

In analogy to the procedure described for Example 182, the following analogues were prepared from the appropriate ester building block and amine starting materials.

| Example | Structure / IUPAC-Name / ¹H NMR | Synth. From / Yield / LC-MS |
|---|---|---|
| 183 | 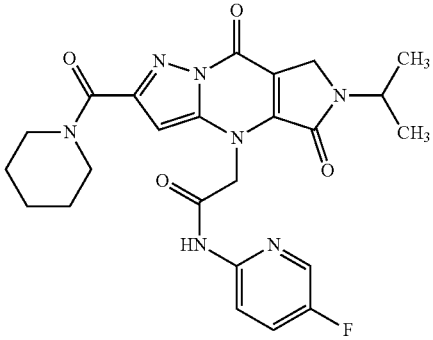<br>2-[5,8-dioxo-2-(piperidin-1-ylcarbonyl)-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm] 1.24 (d, 6H), 1.33 (t, 2H), 1.45-1.59 (m, 2H), 1.63 (br d, 1H), 3.56-3.66 (m, 1H), 3.66-3.74 (m, 1H), 4.27-4.39 (m, 2H), 4.43 (d, 2H), 5.56 (br d, 2H), 6.86 + 7.18 (s, 1H), 7.69-7.79 (m, 1H), 7.99 (br s, 1H), 8.38 (d, 1H), 11.11 (br s, 1H). | Example 70<br>22%<br>LC-MS (Analytical Method H): $R_t$ = 1.25 min; MS (ESIpos): m/z = 496 [M + H]⁺ |
| 184 | 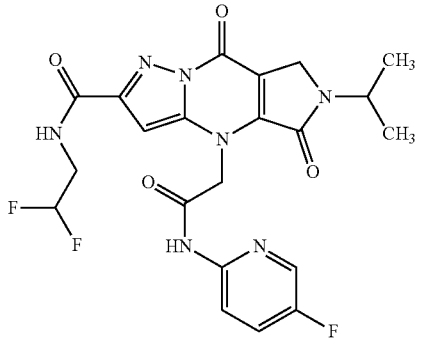<br>N-(2,2-difluoroethyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.24 (d, 6H), 3.56-3.73 (m, 2H), 4.25-4.37 (m, 1H), 4.44 (s, 2H), 5.59 (br s, 2H), 6.13 (tt, 1H), 7.06 (s, 1H), 7.73 (td, 1H), 8.00 (br d, 1H), 8.38 (d, 1H), 8.98 (t, 1H), 11.12 (br s, 1H). | Example 70<br>7%<br>LC-MS (Analytical Method H): $R_t$ = 0.95 min; MS (ESIneg): m/z = 490 [M − H]⁻ |

| Example | Structure IUPAC-Name ¹H NMR | Synth. From Yield LC-MS |
|---|---|---|
| 185 | 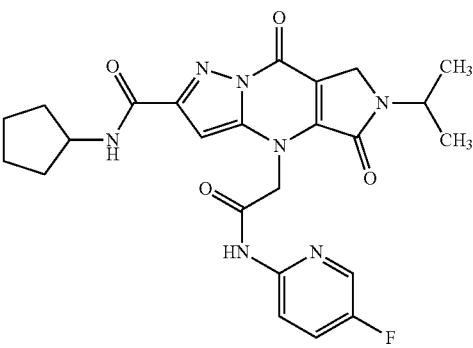<br>N-cyclopentyl-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.24 (d, 6H), 1.47-1.71 (m, 6H), 1.78-1.91 (m, 2H), 4.20-4.27 (m, 1H), 4.31 (quin, 1H), 4.43 (s, 2H), 5.58 (br s, 2H), 6.97 (s, 1H), 7.74 (td, 1H), 8.00 (br d, 1H), 8.38 (d, 1H), 8.42 (d, 1H), 11.13 (s, 1H). | Example 70<br>8%<br>LC-MS (Analytical Method G): R$_t$ = 1.07 min; MS (ESIpos): m/z = 496 [M + H]⁺. |
| 186 | 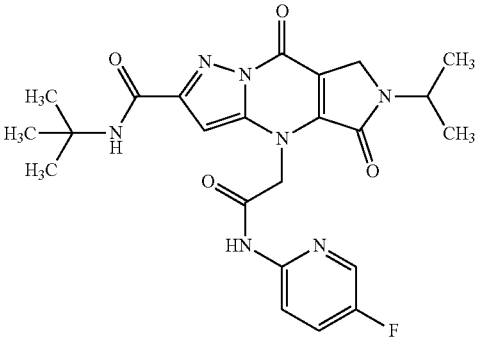<br>N-tert-butyl-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ 1.24 (d, 6H), 1.40 (s, 9H), 4.31 (hep, 1H), 4.43 (s, 2H), 5.58 (br s, 2H), 6.95 (s, 1H), 7.55 (s, 1H), 7.70-7.78 (m, 1H), 8.00 (br d, 1H), 8.38 (d, 1H), 11.13 (br s, 1H). | Example 70<br>5%<br>LC-MS (Analytical Method H): R$_t$ = 1.07 min; MS (ESIpos): m/z = 484 [M + H]⁺ |

| Example | Structure / IUPAC-Name / ¹H NMR | Synth. From / Yield / LC-MS |
|---|---|---|
| 187 | 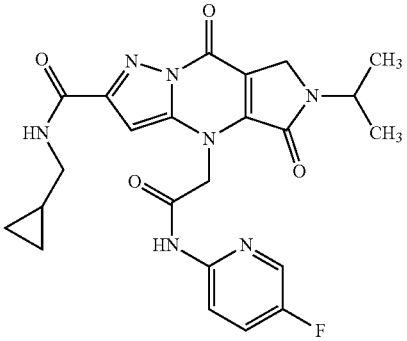<br>N-(cyclopropylmethyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 0.24 (br d, 2H), 0.41 (br d, 2H), 1.05 (br s, 1H), 1.24 (br d, 6H), 3.12 (br t, 2H), 4.24-4.37 (m, 1H), 4.43 (s, 2H), 5.59 (br s, 2H), 7.00 (s, 1H), 7.74 (td, 1H), 8.00 (br d, 1H), 8.38 (d, 1H), 8.69 (br t, 1H), 11.13 (br s, 1H). | Example 70<br>35%<br>LC-MS (Analytical Method J): $R_t$ = 0.95 min; MS (ESIpos): m/z = 482 [M + H]⁺ |
| 188 | 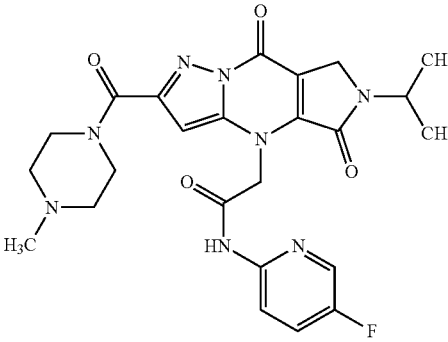<br>N-(5-fluoropyridin-2-yl)-2-{2-[(4-methylpiperazin-1-yl)carbonyl]-5,8-dioxo-6-(propan-2-yl)-5,6,7,8-tetrahydro-4H-pyrazolo[1,5-a]pyrrolo[3,4-d]pyrimidin-4-yl}acetamide<br>¹H NMR (400 MHz, DMSO-d6) δ [ppm]: 1.24 (d, 6H), 2.26 (br s, 3H), 2.37-2.45 (m, 3H), 3.50-3.76 (m, 3H), 3.76-3.99 (m, 2H), 4.25-4.35 (m, 1H), 4.42 (s, 2H), 5.55 (br s, 2H), 6.91 (s, 1H), 7.69-7.77 (m, 1H), 8.00 (br d, 1H), 8.38 (d, 1H), 11.12 (s, 1H). | Example 70<br>26%<br>LC-MS (Analytical Method J): $R_t$ = 0.82 min; MS (ESIpos): m/z = 511 [M + H]⁺ |

| Example | Structure IUPAC-Name ¹H NMR | Synth. From Yield LC-MS |
|---|---|---|
| 189 | 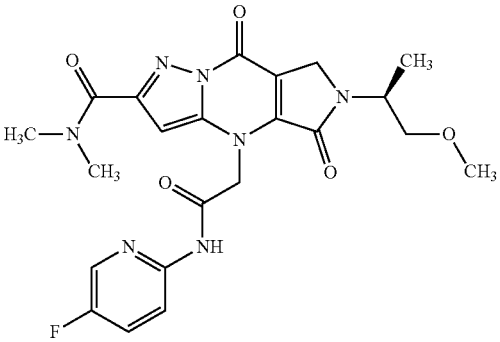<br>4-{2-[(5-fluoropyridin-2-yl)amino]-2-oxoethyl}-6-[(2S)-1-methoxypropan-2-yl]-N,N-dimethyl-5,8-dioxo-5,6,7,8-tetrahydro-4H-pyrazolo[1,5-a]pyrrolo[3,4-d]pyrimidine-2-carboxamide<br>¹H NMR (500 MHz, Chloroform-d) δ [ppm]: 1.34 (d, 3H), 3.14 (s, 3H), 3.34 (s, 3H), 3.40 (s, 3H), 3.53 (d, 2H), 4.42 (d, 1H), 4.50 (d, 1H), 4.57-4.67 (m, 1H), 5.38 (s, 1H), 5.54 (s, 1H), 6.75 (s, 1H), 7.40 (ddd, 1H), 8.10 (s, 1H), 8.14 (d, 1H), 9.08 (s, 1H). | Intermediate 06-05<br>35%<br>LC-MS (Analytical Method D) $R_t$ = 3.50 min, MS (ESIpos): m/z = 486 [M + H]$^+$. |
| 190 | 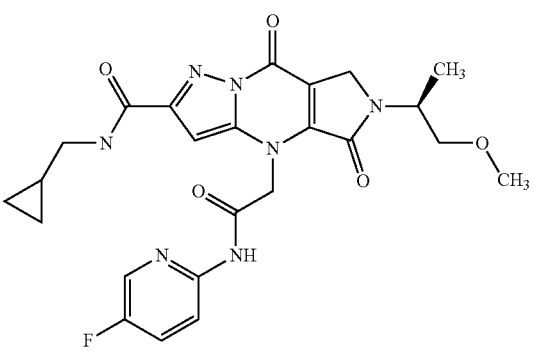<br>N-(cyclopropylmethyl)-4-{2-[(5-fluoropyridin-2-yl)amino]-2-oxoethyl}-6-[(2S)-1-methoxypropan-2-yl]-5,8-dioxo-5,6,7,8-tetrahydro-4H-pyrazolo[1,5-a]pyrrolo[3,4-d]pyrimidine-2-carboxamide<br>¹H NMR (500 MHz, Chloroform-d) δ [ppm]: 0.24-0.32 (m, 2H), 0.50-0.59 (m, 2H), 0.99-1.11 (m, 1H), 1.34 (d, 3H), 3.31-3.35 (m, 2H), 3.35 (s, 3H), 3.54 (d, 2H), 4.44 (d, 1H), 4.53 (d, 1H), 4.62 (q, 1H), 5.44 (s, 1H), 5.64 (s, 1H), 6.93 (s, 1H), 7.39 (ddd, 1H), 7.47 (t, 1H), 8.08 (s, 1H), 8.12 (d, 1H), 9.13 (s, 1H). | Intermediate 06-05<br>36%<br>LC-MS (Analytical Method D) $R_t$ = 3.79 min, MS (ESIpos): m/z = 512 [M + H]$^+$. |

| Example | Structure IUPAC-Name ¹H NMR | Synth. From Yield LC-MS |
|---|---|---|
| 191 | 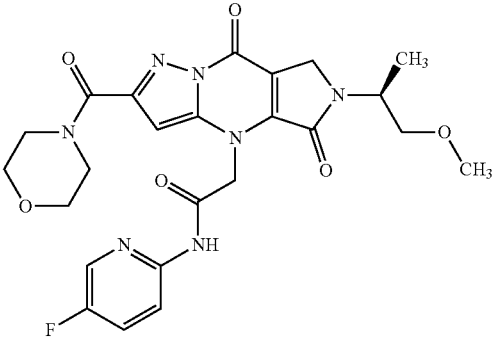<br>N-(5-fluoropyridin-2-yl)-2-{6-[(2S)-1-methoxypropan-2-yl]-2-(morpholin-4-ylcarbonyl)-5,8-dioxo-5,6,7,8-tetrahydro-4H-pyrazolo[1,5-a]pyrrolo[3,4-d]pyrimidin-4-yl}acetamide<br>¹H NMR (500 MHz, Chloroform-d) δ [ppm]: 1.34 (d, 3H), 3.35 (s, 3H), 3.54 (d, 2H), 3.71-3.76 (m, 2H), 3.77-3.81 (m, 2H), 3.82-3.87 (m, 2H), 4.13-4.18 (m, 2H), 4.42 (d, 1H), 4.50 (d, 1H), 4.59-4.66 (m, 1H), 5.38 (s, 1H), 5.57 (s, 1H), 6.79 (s, 1H), 7.40 (ddd, 1H), 8.09 (s, 1H), 8.13 (d, 1H), 9.13 (s, 1H). | Intermediate 06-05<br>38%<br>LC-MS (Analytical Method D) $R_t$ = 3.45 min, MS (ESIpos): m/z = 528 [M + H]⁺. |
| 192 | 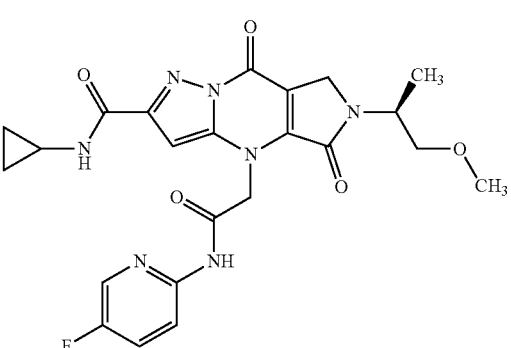<br>N-cyclopropyl-4-{2-[(5-fluoropyridin-2-yl)amino]-2-oxoethyl}-6-[(2S)-1-methoxypropan-2-yl]-5,8-dioxo-5,6,7,8-tetrahydro-4H-pyrazolo[1,5-a]pyrrolo[3,4-d]pyrimidine-2-carboxamide<br>¹H NMR (500 MHz, Chloroform-d) δ [ppm]: 0.65-0.72 (m, 2H), 0.83-0.88 (m, 2H), 1.34 (d, 3H), 2.91-3.01 (m, 1H), 3.34 (s, 3H), 3.53 (d, 2H), 4.43 (d, 1H), 4.52 (d, 1H), 4.57-4.66 (m, 1H), 5.48 (s, 1H), 5.66 (s, 1H), 7.00 (s, 1H), 7.37-7.46 (m, 2H), 8.10 (s, 1H), 8.13 (d, 1H), 9.18 (s, 1H). | Intermediate 06-05<br>11%<br>LC-MS (Analytical Method D) $R_t$ = 3.60 min, MS (ESIpos): m/z = 498 [M + H]⁺. |

| Example | Structure<br>IUPAC-Name<br>¹H NMR | Synth. From<br>Yield<br>LC-MS |
|---|---|---|
| 193 | 4-{2-[(5-fluoropyridin-2-yl)amino]-2-oxoethyl}-6-[(2S)-1-methoxypropan-2-yl]-N-methyl-5,8-dioxo-5,6,7,8-tetrahydro-4H-pyrazolo[1,5-a]pyrrolo[3,4-d]pyrimidine-2-carboxamide<br>¹H NMR (500 MHz, Chloroform-d) δ [ppm]: 1.34 (d, 3H), 3.01 (d, 3H), 3.34 (s, 3H), 3.53 (d, 2H), 4.44 (d, 1H), 4.52 (d, 1H), 4.57-4.67 (m, 1H), 5.45 (s, 1H), 5.64 (s, 1H), 6.93 (s, 1H), 7.34-7.44 (m, 2H), 8.08 (s, 1H), 8.12 (d, 1H), 9.13 (s, 1H). | Intermediate 06-05<br>36%<br>LC-MS (Analytical Method D) $R_t$ = 3.46 min, MS (ESIpos): m/z = 472 [M + H]⁺. |
| 194 | 2-{2-(azetidin-1-ylcarbonyl)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (500 MHz, Chloroform-d) δ [ppm]: 1.34 (d, 3H), 2.39 (quin, 2H), 3.34 (s, 3H), 3.51-3.55 (m, 2H), 4.24-4.33 (m, 2H), 4.41 (d, 1H), 4.49 (d, 1H), 4.56-4.66 (m, 1H), 4.75-4.82 (m, 2H), 5.47 (s, 1H), 5.66 (s, 1H), 6.93 (s, 1H), 7.38 (ddd, 1H), 8.10 (s, 1H), 8.12 (d, 1H), 9.40 (s, 1H). | Intermediate 06-05<br>32%<br>LC-MS (Analytical Method D) $R_t$ = 3.59 min, MS (ESIpos): m/z = 498 [M + H]⁺. |

| Example | Structure IUPAC-Name ¹H NMR | Synth. From Yield LC-MS |
|---|---|---|
| 195 | 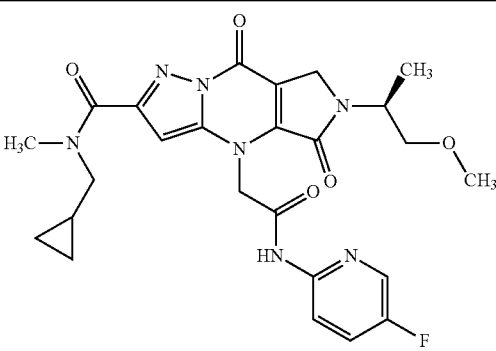<br>N-(cyclopropylmethyl)-4-{2-[(5-fluoropyridin-2-yl)amino]-2-oxoethyl}-6-[(2S)-1-methoxypropan-2-yl]-N-methyl-5,8-dioxo-5,6,7,8-tetrahydro-4H-pyrazolo[1,5-a]pyrrolo[3,4-d]pyrimidine-2-carboxamide<br>¹H NMR (500 MHz, Chloroform-d) δ [ppm]: 0.13-0.61 (m, 4H), 0.98-1.16 (m, 1H), 1.34 (d, 3H), 3.11-3.45 (m, 6H), 3.45-3.72 (m, 4H), 4.37-4.45 (m, 1H), 4.45-4.54 (m, 1H), 4.57-4.67 (m, 1H), 5.38 (s, 1H), 5.55 (s, 1H), 6.68-6.80 (m, 1H), 7.36-7.44 (m, 1H), 8.11 (d, 2H), 9.17 (s, 1H). | Intermediate 06-05<br>13%<br>LC-MS (Analytical Method F): R$_t$ = 2.59 min; MS (ESIpos): m/z = 526 [M + H]⁺. |
| 196 | 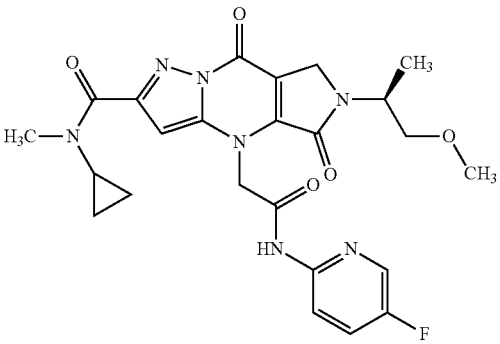<br>N-cyclopropyl-4-{2-[(5-fluoropyridin-2-yl)amino]-2-oxoethyl}-6-[(2S)-1-methoxypropan-2-yl]-N-methyl-5,8-dioxo-5,6,7,8-tetrahydro-4H-pyrazolo[1,5-a]pyrrolo[3,4-d]pyrimidine-2-carboxamide<br>¹H NMR (500 MHz, Chloroform-d) δ [ppm]: 0.44-0.97 (m, 4H), 1.34 (d, 7.0, 3H), 2.86-3.21 (m, 3H), 3.25-3.30 (m, 1H), 3.30-3.36 (m, 3H), 3.53 (d, 2H), 4.43 (d, 1H), 4.51 (d, 1H), 4.56-4.67 (m, 1H), 5.23-5.45 (m, 1H), 5.47-5.65 (m, 1H), 6.63-6.84 (m, 1H), 7.35-7.45 (m, 1H), 8.04-8.19 (m, 2H), 9.11-9.35 (m, 1H). | Intermediate 06-05<br>16%<br>LC-MS (Analytical Method F): R$_t$ = 2.32 min; MS (ESIpos): m/z = 512 [M + H]⁺. |

| Example | Structure IUPAC-Name ¹H NMR | Synth. From Yield LC-MS |
|---|---|---|
| 197 | N-(2,2-difluoroethyl)-4-{2-[(5-fluoropyridin-2-yl)amino]-2-oxoethyl}-6-[(2S)-1-methoxypropan-2-yl]-5,8-dioxo-5,6,7,8-tetrahydro-4H-pyrazolo[1,5-a]pyrrolo[3,4-d]pyrimidine-2-carboxamide<br>¹H NMR (500 MHz, Chloroform-d) δ [ppm]: 1.34 (d, 3H), 3.35 (s, 3H), 3.54 (d, 2H), 3.77-3.89 (m, 2H), 4.45 (d, 1H), 4.53 (d, 1H), 4.62 (q, 1H), 5.39 (s, 1H), 5.57 (s, 1H), 5.79-6.08 (m, 1H), 6.91 (s, 1H), 7.38-7.45 (m, 1H), 7.55 (t, 1H), 8.10 (s, 1H), 8.15 (d, 1H), 8.88 (s, 1H). | Intermediate 06-05<br>25%<br>LC-MS (Analytical Method F): R$_t$ = 2.41 min; MS (ESIpos): m/z = 522 [M + H]⁺. |
| 198 | N-(5-fluoropyridin-2-yl)-2-{6-[(2S)-1-methoxypropan-2-yl]-5,8-dioxo-2-(piperidine-1-carbonyl)-5,6,7,8-tetrahydro-4H-pyrazolo[1,5-a]pyrrolo[3,4-d]pyrimidin-4-yl}acetamide<br>¹H NMR (500 MHz, Chloroform-d) δ [ppm]: 1.34 (d, 3H), 1.58-1.64 (m, 2H), 1.64-1.74 (m, 4H), 3.34 (s, 3H), 3.53 (d, 2H), 3.72-3.78 (m, 2H), 3.85-3.94 (m, 2H), 4.41 (d, 1H), 4.49 (d, 1H), 4.58-4.69 (m, 1H), 5.30-5.43 (m, 1H), 5.49-5.62 (m, 1H), 6.71 (s, 1H), 7.40 (ddd, 1H), 8.10 (s, 1H), 8.13 (d, 1H), 9.20 (s, 1H). | Intermediate 06-05<br>30%<br>LC-MS (Analytical Method F): R$_t$ = 2.53 min; MS (ESIpos): m/z = 526 [M + H]⁺. |

| Example | Structure<br>IUPAC-Name<br>¹H NMR | Synth. From<br>Yield<br>LC-MS |
|---|---|---|
| 199 | 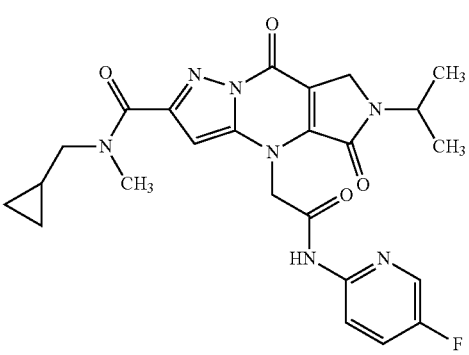<br>N-(cyclopropylmethyl)-4-{2-[(5-fluoropyridin-2-yl)amino]-2-oxoethyl}-N-methyl-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (250 MHz, Chloroform-d) δ [ppm]: 0.11-0.25 (m, 1H), 0.27-0.38 (m, 1H), 0.46-0.61 (m, 2H), 0.97-1.16 (m, 1H), 1.32 (d, 6H), 3.17-3.45 (m, 3H), 3.45-3.70 (m, 2H), 4.32-4.41 (m, 2H), 4.51-4.66 (m, 1H), 5.51 (s, 2H), 6.73 (d, 1H), 7.33-7.47 (m, 1H), 8.01-8.18 (m, 2H), 9.40 (s, 1H). | Example 70<br>26%<br>LC-MS (Analytical Method F): R$_t$ = 3.62 min; MS (ESIpos): m/z = 496.1 [M + H]⁺. |
| 200 | 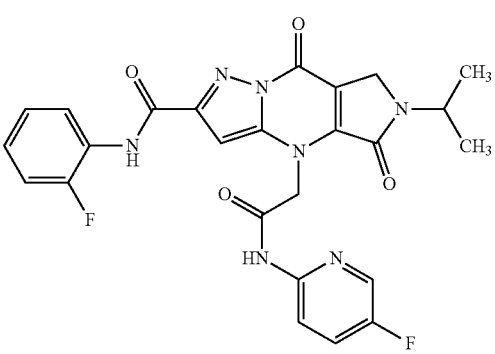<br>N-(2-fluorophenyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.25 (d, 6H), 4.32 (quin, 1H), 4.46 (s, 2H), 5.62 (br s, 2H), 7.14-7.19 (m, 1H), 7.20-7.35 (m, 3H), 7.69-7.78 (m, 2H), 7.96-8.06 (m, 1H), 8.38 (d, 1H), 10.19 (s, 1H), 11.14 (br s, 1H). | Example 70<br>11%<br>LC-MS (Analytical Method H): R$_t$ = 1.11 min; MS (ESIpos): m/z = 522 [M + H]⁺. |

| Example | Structure / IUPAC-Name / ¹H NMR | Synth. From / Yield / LC-MS |
|---|---|---|
| 201 | 4-{2-[(5-fluoropyridin-2-yl)amino]-2-oxoethyl}-5,8-dioxo-6-{propan-2-yl}-N-(pyridin-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.25 (d, 6H), 4.32 (hep, 1H), 4.46 (s, 2H), 5.61 (br s, 2H), 7.21 (ddd, 1H), 7.28 (s, 1H), 7.74 (td, 1H), 7.84-7.94 (m, 1H), 8.01 (br d, 1H), 8.17 (d, 1H), 8.36-8.43 (m, 2H), 9.96 (s, 1H), 11.15 (s, 1H). | Example 70<br>30%<br>LC-MS (Method H): Rt = 1.01 min; MS (ESIpos): m/z = 505 [M + H]⁺ |
| 202 | 4-{2-[(5-fluoropyridin-2-yl)amino]-2-oxoethyl}-N-(2-methoxyphenyl)-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.25 (br d, 6H), 3.94 (s, 3H), 4.28-4.36 (m, 1H), 4.46 (s, 2H), 5.62 (br s, 2H), 6.96-7.03 (m, 1H), 7.15 (br d, 2H), 7.21 (s, 1H), 7.74 (td, 1H), 8.00 (br s, 1H), 8.25 (d, 1H), 8.39 (d, 1H), 9.50 (s, 1H), 11.14 (br s, 1H). | Example 70<br>4%<br>LC-MS (Method H): R$_t$ = 1.16 min; MS (ESIpos): m/z = 534 [M + H]⁺ |

| Example | Structure / IUPAC-Name / ¹H NMR | Synth. From / Yield / LC-MS |
|---|---|---|
| 203 | 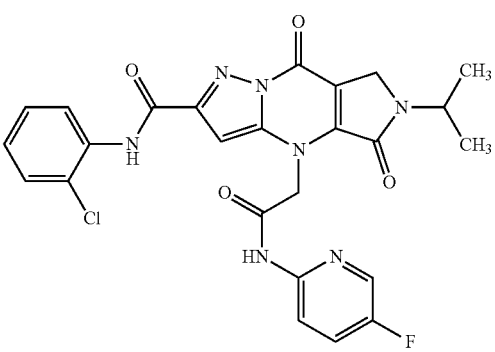<br>N-(2-chlorophenyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.25 (d, 6H), 4.27-4.37 (m, 1H), 4.46 (s, 2H), 5.62 (br s, 2H), 7.21 (s, 1H), 7.24-7.30 (m, 1H), 7.37-7.45 (m, 1H), 7.57 (dd, 1H), 7.74 (td, 1H), 7.91 (dd, 1H), 7.97-8.05 (m, 1H), 8.38 (d, 1H), 10.07 (s, 1H), 11.14 (s, 1H). | Example 70<br>44%<br>LC-MS (Method H): $R_t$ = 1.20 min; MS (ESIpos): m/z = 538 [M + H]⁺ |
| 204 | 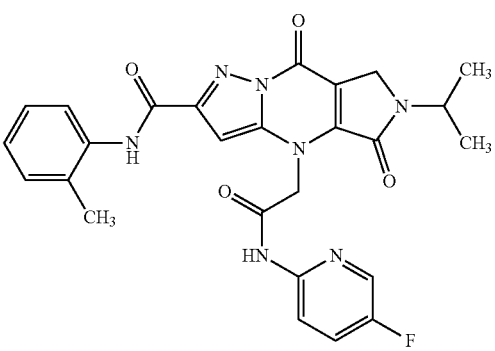<br>4-{2-[(5-fluoropyridin-2-yl)amino]-2-oxoethyl}-N-(2-methylphenyl)-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.26 (d, 6H), 2.25 (s, 3H), 4.32 (hep, 1H), 4.46 (s, 2H), 5.62 (br s, 2H), 7.12-7.15 (m, 1H), 7.15-7.24 (m, 2H), 7.25-7.30 (m, 1H), 7.42 (d, 1H), 7.74 (td, 1H), 8.01 (br d, 1H), 8.38 (d, 1H), 10.07 (s, 1H), 11.14 (s, 1H). | Example 70<br>16%<br>LC-MS (Method H): $R_t$ = 1.12 min; MS (ESIneg): m/z = 516 [M − H]⁻ |

| Example | Structure / IUPAC-Name / ¹H NMR | Synth. From / Yield / LC-MS |
|---|---|---|
| 205 | N-(2,6-difluorophenyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.25 (d, 6H), 4.32 (hep, 1H), 4.47 (s, 2H), 5.62 (br s, 2H), 7.15-7.23 (m, 3H), 7.36-7.47 (m, 1H), 7.74 (td, 1H), 8.01 (br d, 1H), 8.38 (d, 1H), 10.43 (s, 1H), 11.13 (s, 1H). | Example 70<br>37%<br>LC-MS (Method H): R$_t$ = 1.06 min; MS (ESIpos): m/z = 540 [M + H]⁺ |
| 206 | N-(3-fluorophenyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.25 (d, 6H), 4.32 (hep, 1H), 4.46 (s, 2H), 5.62 (br s, 2H), 6.95 (td, 1H), 7.17 (s, 1H), 7.35-7.42 (m, 1H), 7.68-7.82 (m, 3H), 8.01 (br d, 1H), 8.39 (d, 1H), 10.76 (s, 1H), 11.15 (s, 1H). | Example 70<br>34%<br>LC-MS (Method H): Rt = 1.13 min; MS (ESIpos): m/z = 522 [M + H]⁺ |

| | |
|---|---|
| Example | Structure<br>IUPAC-Name<br>¹H NMR | Synth. From<br>Yield<br>LC-MS |

| | | |
|---|---|---|
| 207 | 4-{2-[(5-fluoropyridin-2-yl)amino]-2-oxoethyl}-5,8-dioxo-6-(propan-2-yl)-N-(pyridin-3-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.25 (d, 6H), 4.27-4.39 (m, 1H), 4.46 (s, 2H), 5.62 (br s, 2H), 7.16-7.20 (m, 1H), 7.40 (dd, 1H), 7.71-7.79 (m, 1H), 8.01 (br d, 1H), 8.24 (ddd, 1H), 8.33 (dd, 1H), 8.36-8.43 (m, 1H), 9.01 (d, 1H), 10.81 (s, 1H), 11.15 (s, 1H). | Example 70<br>14%<br>LC-MS (Method H): R$_t$ = 0.93 min; MS (ESIpos): m/z = 505 [M + H]⁺ |
| 208 | N-(4-fluorophenyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.25 (d, 6H), 4.32 (hep, 1H), 4.45 (s, 2H), 5.61 (br s, 2H), 7.14-7.17 (m, 1H), 7.20 (t, 2H), 7.74 (td, 1H), 7.83-7.89 (m, 2H), 8.01 (br d, 1H), 8.39 (d, J = 3.04 Hz, 1H), 10.62 (s, 1H), 11.14 (s, 1H). | Example 70<br>13%<br>LC-MS (Method H): R$_t$ = 1.10 min; MS (ESIpos): m/z = 522 [M + H]⁺ |

| Example | Structure / IUPAC-Name / ¹H NMR | Synth. From / Yield / LC-MS |
|---|---|---|
| 209 | 4-{2-[(5-fluoropyridin-2-yl)amino]-2-oxoethyl}-N-(1,3-oxazol-2-yl)-5,8-dioxo-6-(propan-2-yl)-5,6,7,8-tetrahydro-4H-pyrazolo[1,5-a]pyrrolo[3,4-d]pyrimidine-2-carboxamide | Example 70<br>2%<br>LC-MS (Method H): R$_t$ = 0.56 min; MS (ESIpos): m/z = 495 [M + H]$^+$ |
| 210 | 4-{2-[(5-fluoropyridin-2-yl)amino]-2-oxoethyl}-5,8-dioxo-6-{propan-2-yl}-N-(pyrimidin-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.25 (d, 6H), 4.21-4.42 (m, 1H), 4.46 (s, 2H), 5.61 (br s, 2H), 7.25 (s, 1H), 7.30 (t, 1H), 7.74 (td, 1H), 8.01 (br d, 1H), 8.38 (d, 1H), 8.75 (d, 2H), 10.31 (br s, 1H), 11.06-11.21 (m, 1H). | Example 70<br>22%<br>LC-MS (Method H): R$_t$ = 0.83 min; MS (ESIpos): m/z = 506 [M + H]$^+$ |

| | Structure<br>IUPAC-Name | Synth. From<br>Yield |
|---|---|---|
| Example | ¹H NMR | LC-MS |

211

4-{2-[(5-fluoropyridin-2-yl)amino]-2-oxoethyl}-N-
(1,2-oxazol-3-yl)-5,8-dioxo-6-(propan-2-yl)-5,6,7,8-
tetrahydro-4H-pyrazolo[1,5-a]pyrrolo[3,4-
d]pyrimidine-2-carboxamide
¹H NMR (400 MHz, DMSO-d6) δ [ppm]: 1.25 (d, 6H),
4.26-4.33 (m, 1H), 4.42-4.47 (m, 2H), 5.60 (br s, 2H),
6.96 (d, 1H), 7.21 (s, 1H), 7.71-7.77 (m, 1H), 8.00 (br
s, 1H), 8.38 (d, 1H), 8.85 (d, 1H), 11.15 (s, 1H), 11.44
(s, 1H).

Example 70
10%
LC-MS (Method H): R$_t$ =
0.87 min; MS
(ESIpos): m/z = 495
[M + H]⁺

212

4-{2-[(5-fluoropyridin-2-yl)amino]-2-oxoethyl}-5,8-
dioxo-6-{propan-2-yl}-N-(pyridazin-3-yl)-5,6,7,8-
tetrahydro-4H-pyrazolo[1,5-a]pyrrolo[3,4-
d]pyrimidine-2-carboxamide
¹H NMR (400 MHz, DMSO-d6) δ [ppm]: 1.26 (d, 6H),
4.32 (hep, 1H), 4.47 (s, 2H), 5.62 (br s, 2H), 7.31 (s,
1H), 7.71-7.76 (m, 1H), 7.76-7.81 (m, 1H), 8.02 (br d,
1H), 8.36-8.40 (m, 2H), 9.06 (dd, 1H), 10.73 (br s,
1H), 11.16 (br s, 1H).

Example 70
3%
LC-MS (Method H): R$_t$ =
0.86 min; MS
(ESIpos): m/z = 506
[M + H]⁺

| Example | Structure IUPAC-Name ¹H NMR | Synth. From Yield LC-MS |
|---|---|---|
| 213 | 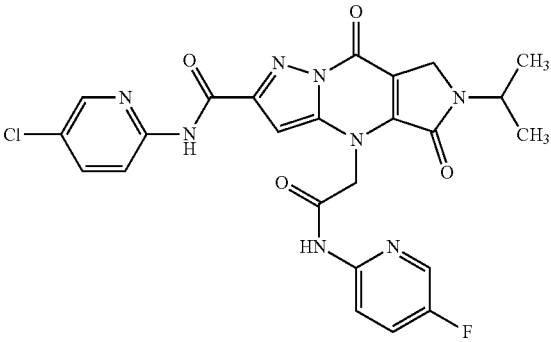<br>N-(5-chloropyridin-2-yl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.25 (d, 6H), 4.32 (hep, 1H), 4.46 (s, 2H), 5.61 (br s, 2H), 7.28 (s, 1H), 7.74 (td, 1H), 8.00 (d, 1H), 8.02 (d, 1H), 8.20 (d, 1H), 8.39 (d, 1H), 8.47 (d, 1H), 10.27 (s, 1H), 11.15 (s, 1H). | Example 70<br>1%<br>LC-MS (Method H): R$_t$ = 1.12 min; MS (ESIpos): m/z = 539 [M + H]⁺ |
| 214 | 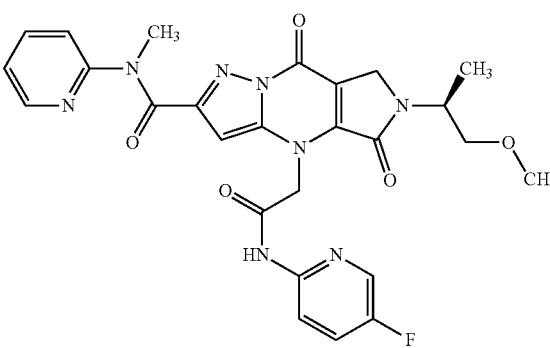<br>4-{2-[(5-fluoropyridin-2-yl)amino]-2-oxoethyl}-6-[(2S)-1-methoxypropan-2-yl]-N-methyl-5,8-dioxo-N-(pyridin-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.18 (d, 3H), 3.23 (s, 3H), 3.41 (dd, 1H), 3.48 (s, 3H), 3.53 (dd, 1H), 4.24-4.45 (m, 3H), 5.48 (br s, 2H), 6.69 (s, 1H), 7.12 (ddd, 1H), 7.28 (d, 1H), 7.67-7.80 (m, 2H), 8.00 (br d, 1H), 8.27-8.30 (m, 1H), 8.39 (d, 1H), 11.07 (s, 1H). | Intermediate 06-05<br>20%<br>LC-MS (Method H): R$_t$ = 0.90 min; MS (ESIpos): m/z = 549 [M + H]⁺ |

| Example | Structure IUPAC-Name ¹H NMR | Synth. From Yield LC-MS |
|---|---|---|
| 215 | 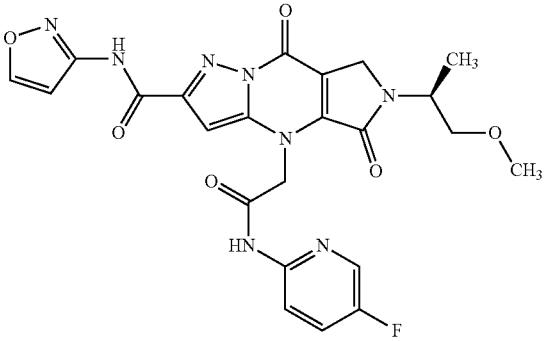<br>4-{2-[(5-fluoropyridin-2-yl)amino]-2-oxoethyl}-6-[(2S)-1-methoxypropan-2-yl]-N-(1,2-oxazol-3-yl)-5,8-dioxo-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.21 (d, 3H), 3.26 (s, 3H), 3.44 (dd, 1H), 3.57 (dd, 1H), 4.28-4.44 (m, 2H), 4.46-4.53 (m, 1H), 5.60 (brs, 2H), 6.96 (d, 1H), 7.21 (s, 1H), 7.74 (td, 1H), 7.95-8.07 (m, 1H), 8.38 (d, 1H), 8.86 (d, 1H), 10.87-11.36 (m, 1H). | Intermediate 06-05<br>17%<br>LC-MS (Method H): $R_t$ = 0.85 min; MS (ESIpos): m/z = 525 [M + H]⁺ |
| 216 | 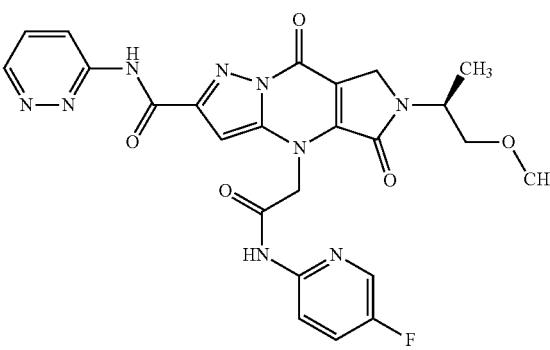<br>4-{2-[(5-fluoropyridin-2-yl)amino]-2-oxoethyl}-6-[(2S)-1-methoxypropan-2-yl]-5,8-dioxo-N-(pyridazin-3-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.22 (d, 3H), 3.26 (s, 3H), 3.45 (dd, 1H), 3.57 (dd, 1H), 4.35-4.45 (m, 2H), 4.47-4.54 (m, 1H), 5.62 (br s, 2H), 7.31 (s, 1H), 7.69-7.83 (m, 2H), 8.02 (br d, 1H), 8.32-8.41 (m, 2H), 9.06 (dd, 1H), 10.44-10.94 (m, 1H), 11.16 (br s, 1H). | Intermediate 06-05<br>3%<br>LC-MS (Method H): $R_t$ = 0.85 min; MS (ESIpos): m/z = 536 [M + H]⁺ |

| Example | Structure IUPAC-Name ¹H NMR | Synth. From Yield LC-MS |
|---|---|---|
| 217 | 4-{2-[(5-fluoropyridin-2-yl)amino]-2-oxoethyl}-6-[(2S)-1-methoxypropan-2-yl]-5,8-dioxo-N-(pyrimidin-2-yl)-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.21 (d, 3H), 3.26 (s, 3H), 3.44 (dd, 1H), 3.57 (dd, 1H), 4.31-4.45 (m, 2H), 4.45-4.53 (m, 1H), 5.61 (br s, 2H), 7.26 (s, 1H), 7.30 (t, 1H), 7.70-7.78 (m, 1H), 7.97-8.05 (m, 1H), 8.38 (d, 1H), 8.76 (d, 2H), 10.12-10.36 (m, 1H), 11.14 (br s, 1H). | Intermediate 06-05<br>3%<br>LC-MS (Method H): $R_t$ = 0.83 min; MS (ESIpos): m/z = 536 [M + H]⁺ |
| 218 | 4-{2-[(5-fluoropyridin-2-yl)amino]-2-oxoethyl}-6-[(2S)-1-methoxypropan-2-yl]-N-methyl-5,8-dioxo-N-[(pyridin-3-yl)methyl]-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.20 (br d, 3H), 2.54 (s, 1H), 2.92 (s, 1H), 3.22-3.26 (m, 4H), 3.43 (ddd, 1H), 3.49-3.60 (m, 1H), 4.30-4.49 (m, 3H), 4.73 (s, 1H), 5.01 (s, 1H), 5.56 (br s, 2H), 6.99 (s, 1H), 7.35-7.42 (m, 1H), 7.71-7.82 (m, 2H), 8.01 (br d, 1H), 8.38 (d, 1H), 8.47-8.54 (m, 1H), 8.57 (br s, 1H), 11.12 (br s, 1H). | Intermediate 06-05<br>6%<br>LC-MS (Method H): $R_t$ = 0.89 min; MS (ESIpos): m/z = 563 [M + H]⁺ |

| Example | Structure IUPAC-Name ¹H NMR | Synth. From Yield LC-MS |
|---|---|---|
| 219 | 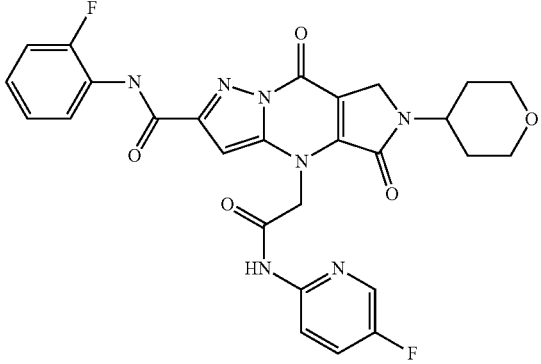<br>N-(2-fluorophenyl)-4-{2-[(5-fluoropyridin-2-yl)amino]-2-oxoethyl}-6-(oxan-4-yl)-5,8-dioxo-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 2.41 (br s, 4H), 2.56 (br t, 2H), 3.53 (br t, 4H), 3.65 (br t, 2H), 4.55 (s, 2H), 5.61 (br s, 2H), 7.19 (s, 1H), 7.22-7.35 (m, 3H), 7.70-7.77 (m, 2H), 8.01 (br d, 1H), 8.38 (d, 1H), 10.20 (s, 1H), 11.12 (s, 1H). | Example 122<br>14%<br>LC-MS (Method H): R$_t$ = 1.03 min; MS (ESIpos): m/z = 564 [M + H]⁺ |
| 220 | 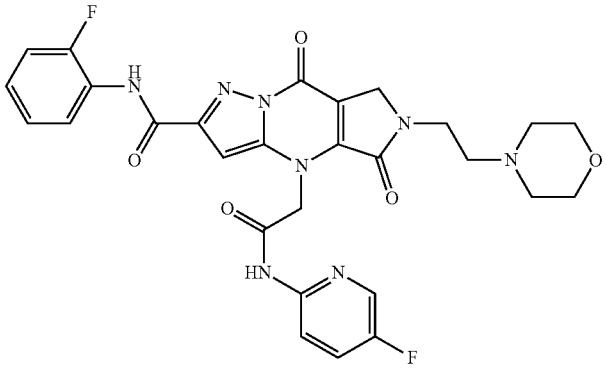<br>N-(2-fluorophenyl)-4-{2-[(5-fluoropyridin-2-yl)amino]-2-oxoethyl}-6-[2-(morpholin-4-yl)ethyl]-5,8-dioxo-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 2.41 (br s, 4H), 2.56 (br t, 2H), 3.53 (br t, 4H), 3.65 (br t, 2H), 4.55 (s, 2H), 5.61 (br s, 2H), 7.19 (s, 1H), 7.22-7.35 (m, 3H), 7.70-7.77 (m, 2H), 8.01 (br d, 1H), 8.38 (d, 1H), 10.20 (s, 1H), 11.12 (s, 1H). | Example 123<br>6%<br>LC-MS (Method H): R$_t$ = 1.01 min; MS (ESIpos): m/z = 594 [M + H]⁺ |

| Example | Structure IUPAC-Name ¹H NMR | Synth. From Yield LC-MS |
|---|---|---|
| 221 | 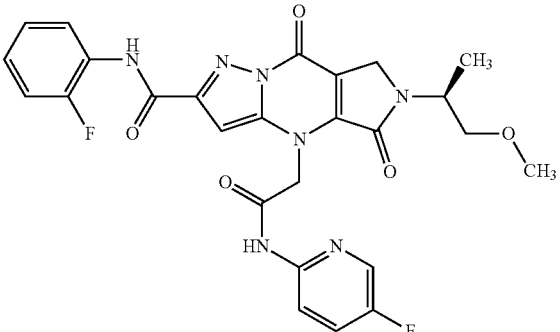<br>N-(2-fluorophenyl)-4-{2-[(5-fluoropyridin-2-yl)amino]-2-oxoethyl}-6-[(2S)-1-methoxypropan-2-yl]-5,8-dioxo-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 1.21 (d, 3H), 3.26 (s, 3H), 3.45 (dd, 1H), 3.57 (dd, 1H), 4.33-4.45 (m, 2H), 4.45-4.54 (m, 1H), 5.62 (br s, 2H), 7.14-7.19 (m, 1H), 7.19-7.36 (m, 3H), 7.69-7.79 (m, 2H), 8.01 (br d, 1H), 8.38 (d, 1H), 10.19 (s, 1H), 11.14 (s, 1H). | Intermediate 06-05<br>4%<br>LC-MS (Method H): $R_t$ = 1.09 min; MS (ESIpos): m/z = 553 [M + H]⁺ |
| 222 | 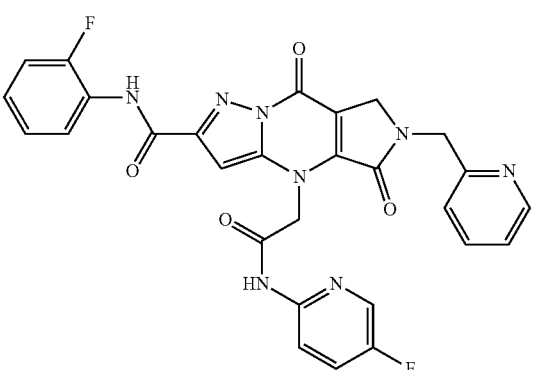<br>N-(2-fluorophenyl)-4-{2-[(5-fluoropyridin-2-yl)amino]-2-oxoethyl}-5,8-dioxo-6-[(pyridin-2-yl)methyl]-5,6,7,8-tetrahydro-4H-pyrazolo[1,5-a]pyrrolo[3,4-d]pyrimidine-2-carboxamide<br>¹H NMR (400 MHz, DMSO-d6) δ [ppm]: 4.55 (s, 2H), 4.85 (s, 2H), 5.62 (br s, 2H), 7.21-7.39 (m, 6H), 7.70-7.77 (m, 2H), 7.81 (td, 1H), 7.96-8.05 (m, 1H), 8.38 (d, 1H), 8.51-8.57 (m, 1H), 10.21 (s, 1H), 11.14 (s, 1H). | Example 124<br>16%<br>LC-MS (Method H): $R_t$ = 1.05 min; MS (ESIpos): m/z = 571 [M + H]⁺ |

Example 223

2-[2-(azetidin-1-ylcarbonyl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

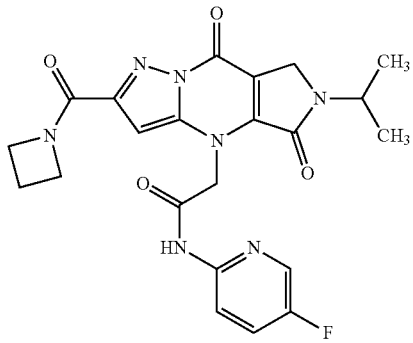 [SMILES: CC(C)N1Cc2c(n(CC(=O)Nc3ccc(F)cn3)c3cc(C(=O)N4CCC4)nn3c2=O)C1=O]

4-{2-[(5-Fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxylic acid (75.0 mg, 60% purity, 105 μmol) (example 84) was dissolved in dichloromethane (750 μl). $T_3P$ in ethyl acetate (120 μl, 50% purity, 210 μmol) and N,N-diisopropylethylamine (55 μl, 320 μmol) were added and the resulting solution was stirred at rt for 15 min. Azetidine (9.9 μl, 150 μmol) was added and the reaction mixture stirred for 1 h at rt. The solution was diluted with acetonitrile and water and purified via preparative HPLC (Method F, gradient C) to afford 10 mg (20% yield) of the title compound.

$^1$H NMR (400 MHz, DMSO-d6) δ[ppm]: 1.24 (d, 6H), 2.26-2.44 (m, 3H), 4.06 (t, 2H), 4.24-4.38 (m, 1H), 4.41 (s, 2H), 4.57 (t, 2H), 5.57 (br s, 2H), 6.98 (s, 1H), 7.73 (td, 1H), 7.99 (br s, 1H), 8.38 (d, 1H).

LC-MS (Analytical Method H): $R_t$=0.95 min; MS (ESI-pos): m/z=468 [M+H]$^+$.

In analogy to the procedure described for Example 223, the following analogue was prepared from the appropriate carboxylic acid building block and amine starting material.

Example 225

N-(5-fluoropyridin-2-yl)-2-[2-(morpholin-4-ylcarbonyl)-5,8-dioxo-6-(propan-2-yl)-5,6,7,8-tetrahydro-4H-pyrazolo[1,5-a]pyrrolo[3,4-d]pyrimidin-4-yl]acetamide

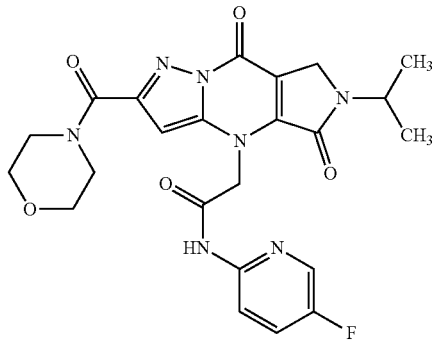 [SMILES: CC(C)N1Cc2c(n(CC(=O)Nc3ccc(F)cn3)c3cc(C(=O)N4CCOCC4)nn3c2=O)C1=O]

4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxylic acid (100 mg, 60% purity, 140 μmol) (example 84) was dissolved in N,N-dimethylformamide (1.0 ml, 13 mmol). HATU (79.9 mg, 210 μmol) N,N-diisopropylethylamine (37 μl, 210 μmol) were added and the resulting solution was stirred at rt for 15 min. Morpholine (18 μl, 210 μmol) was added and the reaction mixture stirred for 1 h at rt. The solution was diluted with acetonitrile and water and purified with preparative HPLC (Method C) to get 17 mg (94% purity, 23% yield) of the title compound.

$^1$H NMR (400 MHz, DMSO-d6) δ[ppm]: 1.24 (d, 6H), 3.57-3.64 (m, 2H), 3.66 (br s, 4H), 3.85-3.95 (m, 2H), 4.26-4.39 (m, 1H), 4.42 (s, 2H), 5.56 (br s, 2H), 6.93 (s, 1H), 7.74 (td, 1H), 8.00 (br d, 1H), 8.38 (d, 1H), 11.12 (s, 1H).

LC-MS (Analytical Method I): $R_t$=0.83 min; MS (ESI-pos): m/z=498 [M+H]$^+$

| Example | Structure<br>IUPAC-Name<br>$^1$H NMR | Synth. From<br>Yield<br>LC-MS |
|---|---|---|
| 224 | 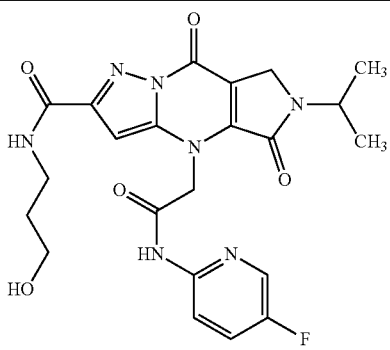<br>4-{2-[(5-fluoropyridin-2-yl)amino]-2-oxoethyl}-N-(3-hydroxypropyl)-5,8-dioxo-6-(propan-2-yl)-5,6,7,8-tetrahydro-4H-pyrazolo[1,5-a]pyrrolo[3,4-d]pyrimidine-2-carboxamide<br>$^1$H NMR (400 MHz, DMSO-d6) δ [ppm]: 1.24 (d, 6H), 1.67 (quin, 2H), 3.26-3.31 (m, 2H), 3.44 (q, 2H), 4.31 (dt, 1H), 4.43 (s, 2H), 4.50 (t, 1H), 5.58 (br s, 2H), 6.99 (s, 1H), 7.74 (td, 1H), 7.99 (br s, 1H), 8.38 (d, 1H), 8.61 (t, 1H), 11.12 (s, 1H). | Example 84<br>3%<br>LC-MS (Analytical Method H): $R_t$ = 0.83 min; MS (ESIpos): m/z = 486 [M + H]$^+$. |

Example 226 tert-butyl(±)-3-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]pyrrolidine-1-carboxylate

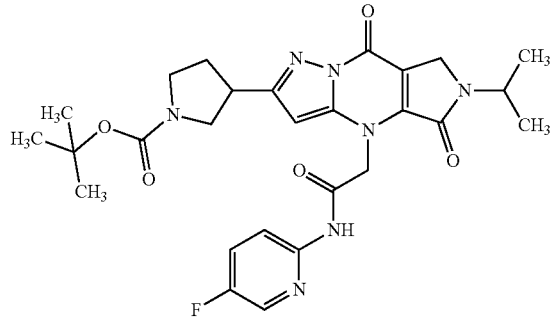 [SMILES: CC(C)N1Cc2c(n(CC(=O)Nc3ccc(F)cn3)c3cc(C4CCN(C(=O)OC(C)(C)C)C4)nn3c2=O)C1=O]

To a solution of tert-butyl 3-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-2,5-dihydro-1H-pyrrole-1-carboxylate (1.5 g, 2.72 mmol) (example 142), in methanol/ethyl acetate (30 ml, v:v=1:1) was added palladium/carbon (10%, 200 mg). The resulting mixture was stirred at rt for 18 h under hydrogen atmosphere (about 2 atmospheres). Upon completion of the reaction, the catalyst was removed by filtration and the filtrate was concentrated in vacuo. The residue was purified with reverse phase column chromatography (C-18 silica gel, eluting with water (0.1% NH$_4$HCO$_3$)-acetonitrile, 9:1 to 2:3) to afford 656 mg (44% yield) of the title compound as an off-white solid.

$^1$H-NMR (300 MHz, DMSO-d6) δ[ppm]: 1.23 (d, 6H), 1.39 (s, 9H), 1.99-2.06 (m, 1H), 2.22-2.25 (m, 1H), 3.32-3.55 (m, 4H), 3.67-3.70 (m, 1H), 4.27-4.38 (m, 3H), 5.47 (br, 2H), 6.58 (s, 1H), 7.70-7.77 (m, 1H), 7.99-8.00 (br, 1H), 8.37 (s, 1H), 11.11 (br, 1H)

LC-MS (Analytical Method N, 0-2.1 min 10-95% B, 2.1-2.7 min 95% B): R$_t$=1.52 min; MS (ESIpos): m/z=554 [M+H]$^+$.

Example 227 tert-butyl 4-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]piperidine-1-carboxylate

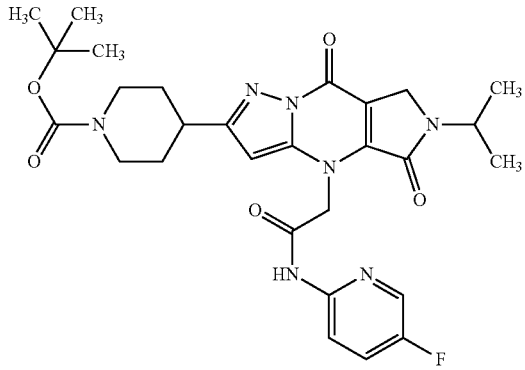 [SMILES: CC(C)N1Cc2c(n(CC(=O)Nc3ccc(F)cn3)c3cc(C4CCN(C(=O)OC(C)(C)C)CC4)nn3c2=O)C1=O]

To a solution of tert-butyl 4-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-3,6-dihydropyridine-1(2H)-carboxylate (1.2 g, 2.1 mmol) (example 143), in methanol/ethyl acetate (30 ml, v:v=1:1) was added palladium/carbon (10%, 200 mg). The resulting mixture was stirred at rt overnight under hydrogen atmosphere (about 2 atm). Upon completion of the reaction, the catalyst was removed by filtration and the filtrate was concentrated in vacuo. The residue was purified with reverse phase column chromatography (0-18 silica gel, eluting with water (0.1% NH$_4$HCO$_3$)-acetonitrile, 9:1 to 2:3) to afford 663.4 mg (56% yield) of the title compound as an off-white solid.

$^1$H-NMR (300 MHz, CD$_3$OD): δ [ppm]=1.30 (d, 6H), 1.48 (s, 9H), 1.59-1.73 (m, 2H), 1.96-2.03 (m, 2H), 2.86-3.02 (m, 3H), 4.11-4.15 (m, 2H), 4.40-4.46 (m, 3H), 5.55 (br, 2H), 6.39 (s, 1H), 7.51-7.57 (m, 1H), 8.03-8.04 (m, 1H), 8.19 (s, 1H)

LC-MS (Analytical Method N, 0-3.4 min 25-55% B, 3.4-4.0 min 55-95% B, 4.0-5.0 min 95% B): R$_t$=2.54 min; MS (ESIpos): m/z=568 [M+H]$^+$.

Example 228

2-{5,8-dioxo-2-[(±)-oxolan-3-yl]-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide

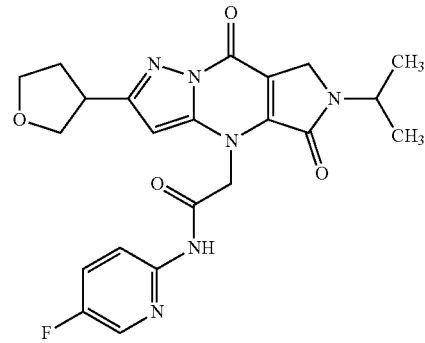 [SMILES: CC(C)N1Cc2c(n(CC(=O)Nc3ccc(F)cn3)c3cc(C4CCOC4)nn3c2=O)C1=O]

To a de-gassed solution of 2-[2-(4,5-dihydrofuran-3-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (48.0 mg, 106 μmol) (example 144) in EtOH (2 ml) was added Pd/C (10%, 4.8 mg). The mixture was stirred at room temperature under an atmosphere of hydrogen for 22 hours. The reaction was re-treated with Pd/C (10%, 4.8 mg) and stirred under an atmosphere of hydrogen for 4h. The reaction mixture was filtered through GF/F paper and the filtrate concentrated under reduced pressure. The crude material was purified by preparative-TLC (silica gel, eluting four times with dichloromethane-methanol, 97:3) to afford 36.8 mg (76% yield) of the title compound as an off-white powder.

$^1$H NMR (500 MHz, Chloroform-d) δ [ppm]: 1.33 (d, 6H), 2.16-2.25 (m, 1H), 2.35-2.46 (m, 1H), 3.69 (dt, 1H), 3.86-3.94 (m, 2H), 4.04 (td, 1H), 4.10-4.22 (m, 1H), 4.38 (s, 2H), 4.54-4.64 (m, 1H), 5.34 (s, 2H), 6.26 (s, 1H), 7.42 (ddd, 1H), 8.10-8.18 (m, 2H), 9.11 (s, 1H).

LC-MS (Analytical Method D) R$_t$=3.74 min; MS (ESIpos): m/z=455 [M+H]$^+$.

Example 229

2-[2-(1,1-dioxo-1lambda⁶-thian-4-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

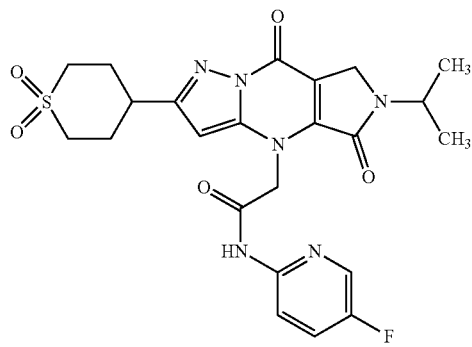 [SMILES: CC(C)N1Cc2c(n(CC(=O)Nc3ccc(F)cn3)c3cc(C4CCS(=O)(=O)CC4)nn3c2=O)C1=O]

2-[2-(1,1-dioxo-1,2,3,6-tetrahydro-1lambda⁶-thiopyran-4-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (45.0 mg, 87.5 µmol) (example 145) was dissolved in ethanol (2.3 ml, 87 µmol)/ethyl acetate (2.3 ml, 23 mmol) and the mixture flushed with nitrogen. This procedure was repeated twice, before the palladium on carbon (14.0 mg, 10% purity, 13.1 µmol) was added. The flask was again evacuated and flushed with hydrogen (3 cycles). The suspension stirred under hydrogen atmosphere for 6 h at room temperature. After filtration over a celite packed filter and washing with ethyl acetate, the filtrate was evaporated to dryness. The oily residue was dissolved with a few drops acetonitrile and diethyl ether (5 mL) was added to the solution. The formed precipitate was collected by vacuum filtration, washed with a little amount of diethyl ether and dried on air to afford 26.0 mg (56% yield) of the title compound.

LC-MS (Method H): $R_t$=0.87 min; MS (ESIpos): m/z=517 [M+H]⁺

¹H NMR (400 MHz, DMSO-d6) δ[ppm]: 1.23 (d, 6H), 2.07-2.20 (m, 2H), 2.24-2.35 (m, 2H), 3.07-3.19 (m, 3H), 3.26-3.30 (m, 1H), 3.35-3.39 (m, 1H), 4.29 (hep, 1H), 4.37 (s, 2H), 5.47 (br s, 2H), 6.64 (s, 1H), 7.74 (td, 1H), 8.00 (br d, 1H), 8.38 (d, 1H), 11.11 (s, 1H).

¹³C NMR (101 MHz, DMSO-d6) δ[ppm]: 20.2 (s, CH₃), 29.6 (s, CH₂), 34.1 (s, CH), 41.2 (s, CH₂), 43.8 (s, CH), 49.1 (s, CH₂), 49.9 (s, CH₂), 87.9 (s, CH), 111.0 (s, C), 114.5 (d, CH), 125.5 (d, CH), 135.6 (d, CH), 139.4 (s, C), 145.4 (s, C), 148.1 (s, C), 152.7 (s, C), 155.8 (d, C), 158.8 (s, C), 161.3 (s, C), 165.5 (s, C).

Example 230 tert-butyl 3-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]azetidine-1-carboxylate

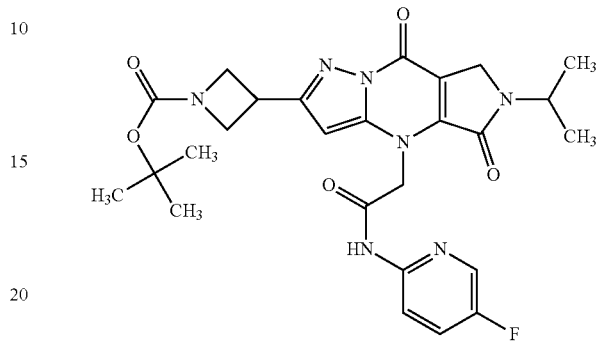

2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (160 mg, 345 µmol) (example 75), 4,4'-bis(1,1-dimethylethyl)-2,2'-bipyridine-N1,N1']bis[3,5-difluoro-2-[5-(trifluoromethyl)-2-pyridinyl-N]phenyl-C]iridium(III) hexafluorophosphate (7.75 mg, 6.91 µmol), tris(trimethylsilyl)silane (110 µl, 350 µmol) and lithium carbonate (102 mg, 1.38 mmol) were dissolved in the reaction vial in benzotrifluoride (8.0 ml). In a separate vial, the nickel catalyst was prepared by dissolving nickel (II) chloride dimethoxyethane adduct (380 µg, 1.7 µmol) and 4,4'-di-tert-butyl-2,2'-bipyridine (460 µg, 1.7 µmol) in benzotrifluoride (100-fold amount in 10 mL) followed by stirring for 5 min. The catalyst solution (0.1 mL) was syringed to the sealed reaction vial and argon was bubbled through the solution for another 5 min then tert-butyl 3-bromoazetidine-1-carboxylate (170 µl, 1.0 mmol) was added. The reaction vial was placed in a water bath (to keep the temp. below 35° C.) and was subsequently irradiated by two 40W Kessil LED Aquarium lamps. After quenching the reaction mixture with half saturated sodium bicarbonate solution and separated three times with ethyl acetate, dried over sodium sulfate and concentrated in vacuo. The crude was purified with preparative HPLC (Method F, gradient C, 60 ml/min) to afford 96.5 mg (49% yield) of the title compound.

LC-MS (Method H): $R_t$=1.09 min; MS (ESIneg): m/z=538 [M−H]⁻

¹H NMR (400 MHz, DMSO-d6) δ[ppm]: 1.23 (d, 6H), 1.38 (s, 9H), 3.84-4.03 (m, 3H), 4.16-4.26 (m, 2H), 4.26-4.34 (m, 1H), 4.39 (s, 2H), 5.48 (br s, 2H), 6.69 (s, 1H), 7.64-7.77 (m, 1H), 8.00 (br d, 1H), 8.37 (d, 1H), 11.11 (s, 1H).

Example 231

N-(5-fluoropyridin-2-yl)-2-{2-[(±)-1-methyl-5-oxopyrrolidin-2-yl]-5,8-dioxo-6-(propan-2-yl)-5,6,7,8-tetrahydro-4H-pyrazolo[1,5-a]pyrrolo[3,4-d]pyrimidin-4-yl}acetamide

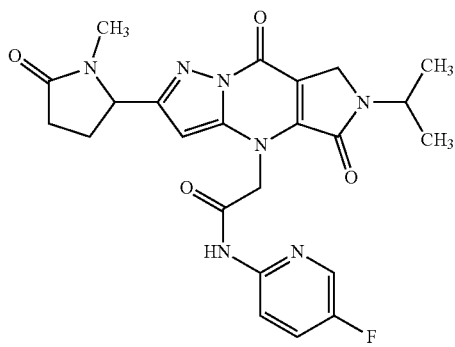 [SMILES: CC(C)N1Cc2c(n(CC(=O)Nc3ccc(F)cn3)c3cc(C4CCC(=O)N4C)nn3c2=O)C1=O]

2-[2-bromo-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (120 mg, 259 µmol) (example 75), [4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate (29.1 mg, 25.9 µmol), lithium carbonate (38.3 mg, 518 µmol) and 4,4'-dimethoxybenzophenone (14 µl, 65 µmol) were dissolved in the reaction vial in 1-methylpyrrolidin-2-one (5.1 ml, 53 mmol). In a separate vial, the nickel catalyst was prepared by dissolving nickel(II) nitrate hexahydrate (3.77 mg, 13.0 µmol) and 4,4'-di-tert-butyl-2,2'-bipyridine (3.48 mg, 13.0 µmol) in 1-methylpyrrolidin-2-one (100-fold amount in 10 mL) followed by heating (50° C.) for 10 min. The nickel catalyst solution (0.1 mL) was syringed to the sealed reaction vial followed by sparging with argon for 10 min. The sealed vial was placed in a water bath (to keep the temp. below 35° C.) and was subsequently irradiated by two 40W Kessil LED Aquarium lamps. After concentration the reaction mixture was purified over Biotage Isolera Four (Biotage SNAP Cartridge KP-Sil 10 g; 0-8% methanol in dichloromethane). The fractions containing a mixture of the products were separated with preparative HPLC (Method G) to afford 22 mg (31% yield) of the title compound (example 231) and 5 mg (4% yield) of example 232.

$^1$H NMR (400 MHz, Chloroform-d) δ [ppm]: 1.32 (d, 3H), 1.33 (d, 3H), 2.04-2.15 (m, 1H), 2.46-2.66 (m, 3H), 2.74 (s, 3H), 4.39 (s, 2H), 4.59 (hep, 1H), 4.84-4.90 (m, 1H), 5.29-5.51 (m, 1H), 5.59 (br s, 1H), 6.29 (s, 1H), 7.40 (ddd, 1H), 8.12 (br d, 2H), 9.53 (br s, 1H).

Example 232

2-{5,8-dioxo-2-[(2-oxopyrrolidin-1-yl)methyl]-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide

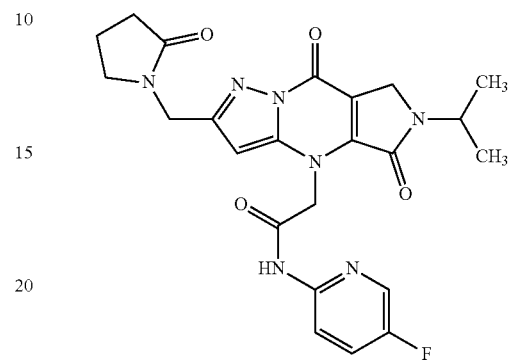

The synthesis and purification of example 232 is described under example 231. The synthesis afforded 5 mg (4% yield) of the title compound (example 232) and 22 mg (31% yield) of example 231.

$^1$H NMR (400 MHz, Chloroform-d) δ [ppm]: 1.32 (d, 6H), 2.01 (quin, 2H), 2.43 (t, 2H), 3.42 (t, 2H), 4.37 (s, 2H), 4.57 (hep, 1H), 4.62 (s, 2H), 5.43 (br s, 2H), 6.31 (s, 1H), 7.40 (ddd, 1H), 8.06-8.12 (m, 1H), 8.12 (d, 1H), 9.32 (br s, 1H).

Example 233

2-{2-ethyl-5,8-dioxo-6-[(2R)-pyrrolidin-2-ylmethyl]-5,6,7,8-tetrahydro-4H-pyrazolo[1,5-a]pyrrolo[3,4-d]pyrimidin-4-yl}-N-(5-fluoropyridin-2-yl)acetamide hydrochloride (1:1)

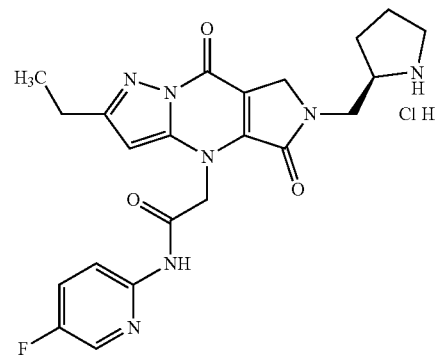

Hydrochloric acid (4M in dioxane) was added to a stirred solution of tert-butyl(2R)-2-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}pyrrolidine-1-carboxylate (50.0 mg, 90.3 µmol) (intermediate 06-01) in dichloromethane. The solvent was evaporated and the resulting solid was triturated with diethylether, collected by filtration and dried in vacuo to get 34 mg (76% yield) of the desired product.

¹H NMR (400 MHz, DMSO-d6) δ[ppm]: 1.23 (t, 3H), 1.53-1.73 (m, 1H), 1.77-2.18 (m, 3H), 2.69 (q, 2H), 3.01-3.14 (m, 1H), 3.24 (br s, 1H), 3.75-3.89 (m, 3H), 4.45-4.57 (m, 2H), 5.47 (br s, 2H), 6.51 (s, 1H), 7.74 (td, 1H), 8.00 (br d, 1H), 8.38 (d, 1H), 8.94 (br s, 1H), 9.46 (br s, 1H), 11.15 (br s, 1H)

LC-MS (Analytical Method G): $R_t$=0.72 min; MS (ESIpos): m/z=454 [M+H]⁺.

In analogy to the procedure described for Example 233, the following examples were prepared from the appropriate tert butyl carbonate protected amine.

| Example | Structure / IUPAC-Name / ¹H NMR | Synth. from / Yield / LC-MS |
|---|---|---|
| 234 | <br>2-[5,8-dioxo-2-(piperidin-4-yl)-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide hydrochloride (1:1)<br>¹H NMR (400 MHz, DMSO-d6) δ [ppm]: 1.23 (d, 6H), 1.80-1.92 (m, 2H), 2.12 (br d, 2H), 2.97-3.09 (m, 3H), 3.31 (br d, 2H), 4.24-4.48 (m, 3H), 5.49 (br s, 2H), 6.53 (s, 1H), 7.74 (td, 1H), 7.99 (br s, 1H), 8.38 (d, 1H), 8.66 (br d, 1H), 8.91 (br d, 1H), 11.14 (s, 1H). | Example 227<br>crude<br>LC-MS (Analytical Method G): $R_t$ = 0.71 min; MS (ESIpos): m/z = 468 [M + H]⁺ |
| 235 | <br>2-{5,8-dioxo-6-(propan-2-yl)-2-[(±)-pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide hydrochloride (1:1)<br>¹H NMR (400 MHz, DMSO-d6) δ [ppm]: 1.23 (d, 6H), 2.06 (dq, 1H), 2.30-2.42 (m, 1H), 3.20-3.36 (m, 3H), 3.58-3.70 (m, 2H), 4.29 (dt, 1H), 4.39 (s, 2H), 5.48 (br s, 2H), 6.65 (s, 1H), 7.74 (td, 1H), 8.00 (br d, 1H), 8.38 (d, 1H), 9.22 (br s, 2H), 11.16 (s, 1H). | Example 226<br>crude<br>LC-MS (Analytical Method G): $R_t$ = 0.74 min; MS (ESIpos): m/z = 454 [M + H]⁺ |

| Structure<br>IUPAC-Name<br>Example ¹H NMR | Synth. from<br>Yield<br>LC-MS |
|---|---|
| 236<br><br>2-[2-ethyl-5,8-dioxo-6-[(±)-pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide hydrochloride (1:1)<br>¹H NMR (400 MHz, DMSO-d6) δ [ppm]: 1.23 (t, 3H), 2.13-2.29 (m, 2H), 2.69 (q, 2H), 3.18-3.31 (m, 1H), 3.31-3.50 (m, 4H), 4.45-4.59 (m, 2H), 4.81 (dt, 1H), 5.46 (br s, 2H), 6.49 (s, 1H), 7.74 (td, 1H), 8.00 (br d, 1H), 8.38 (d, 1H), 9.33 (br s, 2H). | Example 78<br>crude<br>LC-MS (Analytical Method G): R$_t$ = 0.67 min; MS (ESIpos): m/z = 440 [M + H]⁺. |
| 237<br><br>2-[2-ethyl-5,8-dioxo-6-(piperidin-4-yl)-5,6,7,8-tetrahydro-4H-pyrazolo[1,5-a]pyrrolo[3,4-d]pyrimidin-4-yl]-N-(5-fluoropyridin-2-yl)acetamide hydrochloride (1:1)<br>¹H NMR (400 MHz, DMSO-d6) δ [ppm]: 1.23 (t, 3H), 1.86-2.07 (m, 3H), 2.64-2.73 (m, 2H), 3.02 (q, 2H), 3.32-3.41 (m, 2H), 4.16-4.37 (m, 4H), 4.40 (s, 2H), 5.46 (br s, 1H), 6.49 (s, 1H), 7.74 (td, 1H), 7.99 (br d, 1H), 8.38 (d, 1H), 8.62 (br d, 1H), 8.90 (br d, 1H). | Example 76<br>crude<br>LC-MS (Analytical Method G): R$_t$ = 0.69 min; MS (ESIpos): m/z = 454 [M + H]⁺. |

| Example | Structure<br>IUPAC-Name<br>¹H NMR | Synth. from<br>Yield<br>LC-MS |
|---|---|---|
| 238 | 2-{2-ethyl-5,8-dioxo-6-[(±)-pyrrolidin-3-ylmethyl]-5,6,7,8-tetrahydro-4H-pyrazolo[1,5-a]pyrrolo[3,4-d]pyrimidin-4-yl}-N-(5-fluoropyridin-2-yl)acetamide hydrochloride (1:1)<br>¹H NMR (400 MHz, DMSO-d6) δ [ppm]: 1.23 (t, 3H), 1.55-1.68 (m, 2H), 1.95-2.08 (m, 1H), 2.64-2.74 (m, 3H), 2.81-2.92 (m, 1H), 3.03-3.14 (m, 1H), 3.16-3.34 (m, 2H), 3.58-3.74 (m, 1H), 4.38-4.52 (m, 2H), 5.46 (br s, 2H), 6.48 (s, 1H), 7.74 (td, 1H), 7.99 (br s, 1H), 8.38 (d, 1H), 9.04 (br s, 2H), 11.13 (s, 1H). | Example 80<br>crude<br>LC-MS (Analytical Method G): R$_t$ = 0.72 min; MS (ESIpos): m/z = 454 [M + H]⁺. |
| 239 | 2-{2-ethyl-5,8-dioxo-6-[(±)-pyrrolidin-2-ylmethyl]-5,6,7,8-tetrahydro-4H-pyrazolo[1,5-a]pyrrolo[3,4-d]pyrimidin-4-yl}-N-(5-fluoropyridin-2-yl)acetamide hydrochloride (1:1)<br>¹H NMR (400 MHz, DMSO-d6) δ [ppm]: 1.24 (t, 3H), 1.58-1.68 (m, 2H), 1.83-2.02 (m, 2H), 2.08 (br d, 1H), 2.70 (q, 2H), 3.07-3.16 (m, 1H), 3.24 (br d, 1H), 3.74-3.87 (m, 3H), 4.51 (s, 2H), 5.47 (br s, 1H), 6.51 (s, 1H), 7.74 (td, 1H), 8.00 (br d, 1H), 8.38 (d, 1H), 8.83 (br s, 1H), 9.34 (br s, 1H), 11.15 (s, 1H). | Example 81<br>94%<br>LC-MS (Analytical Method G): R$_t$ = 0.72 min; MS (ESIpos): m/z = 454 [M + H]⁺. |

| | Structure<br>IUPAC-Name | Synth. from |
|---|---|---|
| Example | ¹H NMR | Yield<br>LC-MS |
| 240 | 2-[2-ethyl-5,8-dioxo-6-(piperidin-4-ylmethyl)-5,6,7,8-tetrahydro-4H-pyrazolo[1,5-a]pyrrolo[3,4-d]pyrimidin-4-yl]-N-(5-fluoropyridin-2-yl)acetamide hydrochloride (1:1)<br>¹H NMR (400 MHz, DMSO-d6) δ [ppm]: 1.23 (t, 3H), 1.34 (q, 2H), 1.67-1.77 (m, 2H), 2.04 (ddd, 1H), 2.69 (q, 2H), 2.73-2.86 (m, 2H), 3.23 (br d, 2H), 3.40 (br d, 2H), 4.42 (s, 2H), 5.46 (br s, 2H), 6.47 (s, 1H), 7.74 (td, 1H), 7.99 (br d, 1H), 8.38 (d, 1H), 8.61 (br d, 1H), 8.90 (br d, 1H), 11.13 (s, 1H). | Example 89<br>crude<br>LC-MS (Analytical Method G): $R_t$ = 0.76 min; MS (ESIpos): m/z = 468 [M + H]⁺ |
| 241 | 2-[2-amino-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide hydrochloride (1:1)<br>¹H NMR (400 MHz, DMSO-d6) δ [ppm]: 1.22 (d, 6H), 4.23-4.28 (m, 1H), 4.29 (s, 2H), 5.40 (br s, 2H), 5.59 (s, 1H), 5.66 (s, 2H), 7.75 (td, 1H), 8.01 (br d, 1H), 8.37 (d, 1H), 11.10 (s, 1H). | Example 91<br>92%<br>LC-MS (Analytical Method H): $R_t$ = 0.79 min; MS (ESIpos): m/z = 400 [M + H]⁺. |

| Example | Structure IUPAC-Name ¹H NMR | Synth. from Yield LC-MS |
|---|---|---|
| 242 | 2-{6-[(azetidin-3-yl)methyl]-2-ethyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide-hydrogen chloride (1/1)<br>¹H NMR (400 MHz, DMSO-d6) δ [ppm]: 1.17-1.27 (m, 3H), 2.65-2.73 (m, 2H), 3.14 (dt, 1H), 3.65-3.90 (m, 4H), 3.94-4.05 (m, 2H), 4.39-4.50 (m, 2H), 5.46 (br s, 2H), 6.47 + 6.49 (s, 1H), 7.74 (td, 1H), 7.93-8.13 (m, 2H), 8.38 (d, 1H), 8.77-9.00 (m, 1H), 11.13 (s, 1H). | Example 115<br>93%<br>LC-MS (Method G): R$_t$ = 0.69 min; MS (ESIpos): m/z = 440 [M + H]⁺ |
| 243 | 2-[6-(azetidin-3-yl)-2-ethyl-5,8-dioxo-5,6,7,8-tetrahydro-4H-pyrazolo[1,5-a]pyrrolo[3,4-d]pyrimidin-4-yl]-N-(5-fluoropyridin-2-yl)acetamide hydrogen chloride (1/1)<br>¹H NMR (400 MHz, DMSO-d6) δ [ppm]: 1.23 (t, 3H), 2.64-2.75 (m, 2H), 4.29-4.52 (m, 4H), 4.69 (s, 2H), 5.11 (quin, 1H), 5.44 (br s, 2H), 6.51 + 6.52 (s, 1H), 7.68-7.79 (m, 1H), 7.92-8.08 (m, 1H), 8.16 (br s, 1H), 8.38 (d,), 9.11 (br s, 1H), 11.14 (s, 1H). | Example 116<br>83%<br>LC-MS (Method G): R$_t$ = 0.68 min; MS (ESIpos): m/z = 426 [M + H]⁺ |

| Example | Structure IUPAC-Name ¹H NMR | Synth. from Yield LC-MS |
|---|---|---|
| 244 | 2-[2-(azetidin-3-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide hydrogen chloride (1/1)<br>¹H NMR (400 MHz, DMSO-d6) δ [ppm]: 1.24 (d, 6H), 3.99-4.35 (m, 6H), 4.41 (s, 2H), 5.50 (br s, 2H), 6.64 (s, 1H), 7.74 (td, 1H), 8.00 (br d, 1H), 8.38 (d, 1H), 8.80-9.02 (m, 1H), 9.13 (br s, 1H), 11.18 (s, 1H). | Example 230<br>79%<br>LC-MS (Method H): $R_t$ = 0.88 min; MS (ESIpos): m/z = 440 [M + H]⁺ |

Example 245

2-[6-(2-aminoethyl)-2-ethyl-5,8-dioxo-5,6,7,8-tetrahydro-4H-pyrazolo[1,5-a]pyrrolo[3,4-d]pyrimidin-4-yl]-N-(5-fluoropyridin-2-yl)acetamide To a solution of tert-butyl {2-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]ethyl}carbamate (200 mg, 0.45 mmol) (example 68) in dichloromethane (4 ml) was added trifluoroacetic acid (1 ml) and the resulting mixture was stirred at rt for 2 h. Upon completion of the reaction, the solvent was removed in vacuo and the residue was purified by preparative HPLC [Column: Kinetex 5 μm EVO C18 100A, 150×21.2 mm; mobile phase A: water (0.1% NH₄HCO₃), mobile phase B: acetonitrile; gradient: 8% B to 40% B in 8 min] to give 74.8 mg (45%) of the title compound as a white solid.

¹H-NMR (400 MHz, DMSO-d6) δ[ppm]: 1.23 (t, 3H), 2.69 (q, 2H), 2.82 (t, 2H), 3.49 (t, 2H), 4.45 (s, 2H), 5.48 (s, 2H), 6.46 (s, 1H), 7.71-7.76 (m, 1H), 7.99-8.00 (m, 1H), 8.37-8.38 (m, 1H), 11.11 (br, 1H).

LC-MS (Analytical Method O, 0-2.00 min 5-100% B, 2.00-2.80 min 100% B): $R_t$=0.75 min; MS (ESIpos): m/z=414 [M+H]⁺.

Example 246

2-{2-ethyl-6-[(2S)-morpholin-2-ylmethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide Tert-butyl(2R)-2-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}morpholine-4-carboxylate (65 mg, 0.10 mmol) (example 90) was dissolved in dichloromethane (2 ml). Trifluoroacetic acid (1 ml) was added, and the reaction stirred for 1 h. The solvent was removed in vacuo and the crude material purified by preparative HPLC (Method A). The product containing fractions were combined, concentrated and freeze-dried from acetonitrile-water to afford 18.2 mg (40% yield) of the title compound as a white powder.

¹H NMR (500 MHz, Chloroform-d) δ [ppm]: 1.33 (t, 3H), 2.56-2.65 (m, 1H), 2.79-2.87 (m, 4H), 2.98 (d, 1H), 3.53-3.67 (m, 2H), 3.69-3.79 (m, 2H), 3.87 (d, 1H), 4.54 (d, 1H), 4.63 (d, 1H), 5.31 (s, 2H), 6.23 (s, 1H), 7.39-7.45 (m, 1H), 8.08-8.20 (m, 2H), 9.12 (s, 1H).

LC-MS (Analytical Method F) $R_t$=1.46 min, MS (ESIpos): m/z=470.2 [M+H]⁺.

Example 247

2-{2-ethyl-6-[(2R)-morpholin-2-ylmethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide

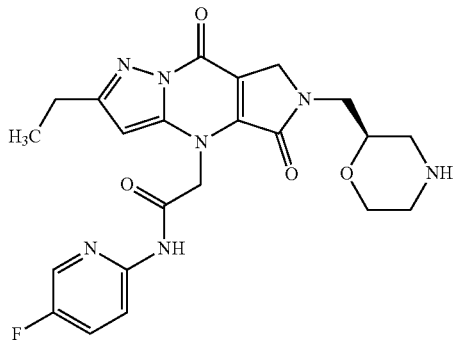 [SMILES: CCc1cc2n(CC(=O)Nc3ccc(F)cn3)c3c(c(=O)n2n1)CN(C[C@H]1CNCCO1)C3=O]

To a solution of tert-butyl(2S)-2-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}morpholine-4-carboxylate (1.7 g, 2.7 mmol, 89% purity) (example 86) in methanol (50 ml) under nitrogen was added acetyl chloride (1.9 ml, 27.0 mmol) dropwise at 0° C. The reaction was allowed to reach rt and was stirred at this temperature for 17 h. After this time, the reaction mixture was concentrated under reduced pressure, and the resulting material was purified by reverse phase Biotage Isolera™ chromatography (C18-silica gel, eluting with water (0.1% formic acid)-acetonitrile, 1:0 to 0:1) The product containing fractions were combined and concentrated under reduced pressure to afford 618 mg (47% yield) of the title compound.

$^1$H NMR (500 MHz, DMSO-d6) δ[ppm]: 11.10 (s, 1H), 8.38 (d, 1H), 8.00 (s, 1H), 7.79-7.68 (m, 1H), 6.46 (s, 1H), 5.46 (s, 2H), 4.44 (s, 2H), 3.79-3.71 (m, 1H), 3.67-3.58 (m, 1H), 3.54-3.47 (m, 1H), 3.47-3.40 (m, 3H), 2.78 (d, 1H), 2.74-2.57 (m, 4H), 2.42-2.33 (m, 1H), 1.24 (t, 3H).

LC-MS (Analytical Method D) R$_t$=2.65 min, MS (ESI-pos): m/z=470.15 [M+H]$^+$.

Example 248

2-{2-ethyl-6-[(3R)-morpholin-3-ylmethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide

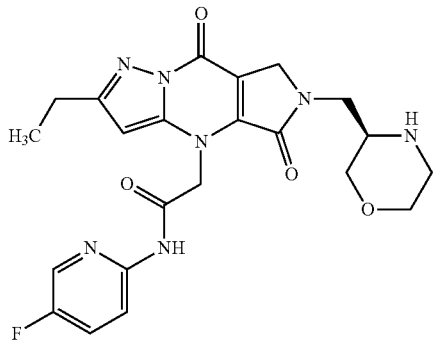

To a solution of tert-butyl(3R)-3-{[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]methyl}morpholine-4-carboxylate (121 mg, 84% purity, 178 μmol) (intermediate 06-06) in dichloromethane (2 ml) was added trifluoroacetic acid (1 ml). The resulting solution was stirred at rt for 1 h. After this time, the reaction mixture was concentrated in vacuo, with the residual material dissolved in methanol and loaded onto a SCX cartridge. The cartridge was flushed with further methanol, prior to release of the desired product by 2 M NH$_3$ in methanol. This fraction was concentrated in vacuo to afford 93 mg (97% yield, 87% purity) of the title compound as a pale yellow solid. A portion of this material (30 mg) was further purified by preparative HPLC (Method A), with the product containing fractions combined and freeze-dried to afford 12 mg as a pale yellow powder.

$^1$H NMR (500 MHz, DMSO-d6) δ[ppm]: 1.24 (t, 3H), 2.65-2.73 (m, 3H), 2.78 (d, 1H), 3.01 (d, 1H), 3.08-3.15 (m, 2H), 3.61 (d, 1H), 3.66 (dd, 2H), 4.37-4.50 (m, 2H), 5.47 (s, 2H), 6.46 (s, 1H), 7.74 (td, 1H), 7.94-8.06 (m, 1H), 8.18 (s, 1H), 8.38 (d, 1H), 11.10 (s, 1H).

LC-MS (Analytical Method D): R$_t$=2.92 min; MS (ESI-pos): m/z=470 [M+H]$^+$.

Example 249

N-(5-fluoropyridin-2-yl)-2-{2-[(±)-1-methylpyrrolidin-3-yl]-5,8-dioxo-6-(propan-2-yl)-5,6,7,8-tetrahydro-4H-pyrazolo[1,5-a]pyrrolo[3,4-d]pyrimidin-4-yl}acetamide

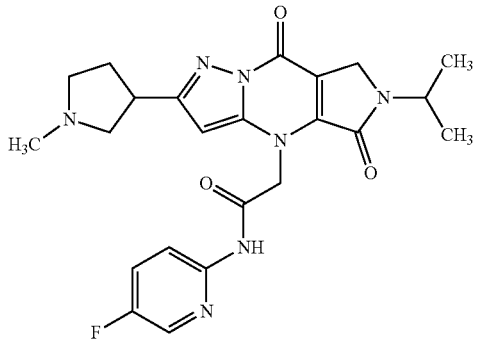 [SMILES: CC(C)N1Cc2c(n(CC(=O)Nc3ccc(F)cn3)c3cc(C4CCN(C)C4)nn3c2=O)C1=O]

To a solution of 2-{5,8-dioxo-6-(propan-2-yl)-2-[(±)-pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide hydrochloride (1:1) (60.0 mg, 122 μmol) (example 235) in dichloromethane (0.75 ml) was added formaldehyde (11 μl, 37% purity, 150 μmol). After 5 min NaBH(OAc)$_3$ (57.1 mg, 269 μmol) was added to the solution in one portion. The mixture stirred at rt for 16 h. The solvent was evaporated under reduced pressure and the residue was purified by preparative HPLC (Method F, gradient C) to afford 8 mg (13% yield) of the title compound.

$^1$H NMR (400 MHz, DMSO-d6) δ[ppm]: 1.23 (d, 6H), 1.90-2.02 (m, 1H), 2.16-2.24 (m, 1H), 2.27 (s, 3H), 2.54-2.64 (m, 2H), 2.87 (t, 1H), 3.39-3.49 (m, 1H), 4.29 (dt, 1H), 4.37 (s, 2H), 5.47 (br s, 2H), 6.51 (s, 1H), 7.74 (td, 1H), 8.00 (br d, 1H), 8.38 (d, 1H), 11.10 (s, 1H)

LC-MS (Analytical Method H): R$_t$=0.93 min; MS (ESI-pos): m/z=468 [M+H]$^+$.

In analogy to the procedure described for Example 249, the following examples were prepared from the appropriate secondary amine and aldehyde or ketone starting materials.

| Example | Structure<br>IUPAC-Name<br>¹H NMR | Synth. From<br>Yield<br>LC-MS |
|---|---|---|
| 250 | 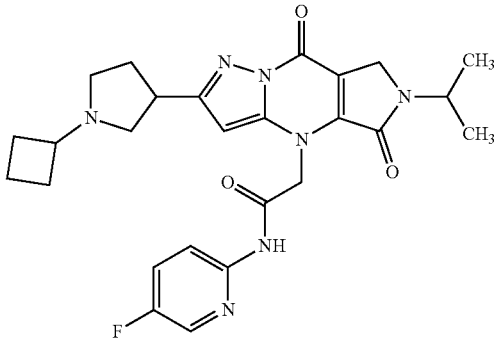<br>2-{2-[(±)-1-cyclobutylpyrrolidin-3-yl]-5,8-dioxo-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm]: 1.23 (d, 6H), 1.59-1.69 (m, 2H), 1.84 (s, 2H), 1.86-2.04 (m, 4H), 2.14-2.24 (m, 1H), 2.41-2.47 (m, 1H), 2.56-2.64 (m, 1H), 2.83-2.96 (m, 2H), 3.35-3.45 (m, 1H), 4.29 (quin, 1H), 4.37 (s, 2H), 5.47 (br s, 2H), 6.51 (s, 1H), 7.74 (td, 1H), 7.99 (br s, 1H), 8.38 (d, 1H), 11.12 (s, 1H). | Example 235<br>47%<br>LC-MS (Analytical Method H): $R_t$ = 1.08 min; MS (ESIpos): m/z = 508 [M + H]⁺ |
| 251 | 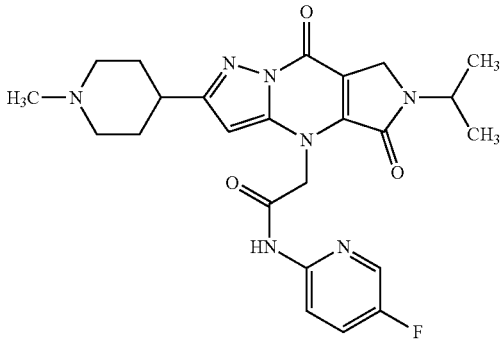<br>N-(5-fluoropyridin-2-yl)-2-[2-(1-methylpiperidin-4-yl)-5,8-dioxo-6-(propan-2-yl)-5,6,7,8-tetrahydro-4H-pyrazolo[1,5-a]pyrrolo[3,4-d]pyrimidin-4-yl]acetamide<br>¹H NMR (400 MHz, DMSO-d6) δ [ppm]: 1.23 (d, 6H), 1.66 (qd, 2H), 1.87-2.02 (m, 4H), 2.17 (s, 3H), 2.57-2.64 (m, 1H), 2.81 (br d, 2H), 4.29 (quin, 1H), 4.36 (s, 2H), 5.45 (br s, 2H), 6.51 (s, 1H), 7.74 (td, 1H), 8.00 (br d, 1H), 8.38 (d, 1H), 11.10 (s, 1H). | Example 234<br>17%<br>LC-MS (Analytical Method H): $R_t$ = 0.96 min; MS (ESIpos): m/z = 482 [M + H]⁺ |

| Example | Structure IUPAC-Name ¹H NMR | Synth. From Yield LC-MS |
|---|---|---|
| 252 | 2-[2-(1-cyclobutylpiperidin-4-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.23 (d, 6H), 1.56-1.67 (m, 4H), 1.71-1.84 (m, 4H), 1.91-2.01 (m, 4H), 2.59-2.72 (m, 2H), 2.82 (br d, 2H), 4.29 (quin, 1H), 4.36 (s, 2H), 5.45 (br s, 2H), 6.52 (s, 1H), 7.74 (td, 1H), 8.00 (br d, 1H), 8.38 (d, 1H), 11.11 (br s, 1H). | Example 234<br>34%<br>LC-MS (Analytical Method H): R$_t$ = 1.12 min; MS (ESIpos): m/z = 522 [M + H]⁺ |
| 253 | 2-{2-ethyl-6-[(±)-1-methylpyrrolidin-3-yl]-5,8-dioxo-5,6,7,8-tetrahydro-4H-pyrazolo[1,5-a]pyrrolo[3,4-d]pyrimidin-4-yl}-N-{5-fluoropyridin-2-yl}acetamide<br>¹H NMR (400 MHz, DMSO-d6) δ [ppm]: 1.23 (t, 3H), 1.82-1.93 (m, 1H), 2.10-2.26 (m, 2H), 2.27 (s, 3H), 2.41-2.47 (m, 1H), 2.68 (q, 2H), 2.73 (dd, 1H), 2.78-2.88 (m, 1H), 4.44 (d, 2H), 4.67-4.74 (m, 1H), 5.46 (br s, 2H), 6.46 (s, 1H), 7.70-7.77 (m, 1H), 8.00 (br d, 1H), 8.37 (d, 1H), 11.11 (br s, 1H). | Example 236<br>24%<br>LC-MS (Analytical Method H): R$_t$ = 0.90 min; MS (ESIpos): m/z = 454 [M + H]⁺. |

| Example | Structure<br>IUPAC-Name<br>¹H NMR | Synth. From<br>Yield<br>LC-MS |
|---|---|---|
| 254 | 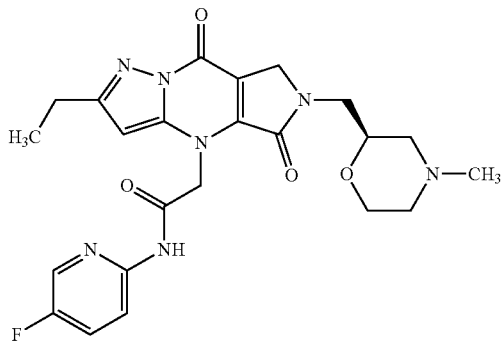<br>2-{6-[(±)-1-cyclobutylpyrrolidin-3-yl]-2-ethyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm]: 1.23 (t, 3H), 1.59-1.72 (m, 2H), 1.82-2.02 (m, 5H), 2.09-2.24 (m, 2H), 2.40-2.46 (m, 1H), 2.65-2.72 (m, 3H), 2.75-2.83 (m, 1H), 2.90 (quin, 1H), 4.46 (s, 2H), 4.65-4.72 (m, 1H), 5.46 (br s, 2H), 6.46 (s, 1H), 7.70-7.77 (m, 1H), 8.00 (br d, 1H), 8.37 (d, 1H), 11.11 (br s, 1H). | Example 236<br>17%<br>LC-MS (Analytical Method H): $R_t$ = 1.06 min; MS (ESIpos): m/z = 494 [M + H]⁺. |

Example 255

2-(2-ethyl-6-{[(2R)-4-methylmorpholin-2-yl]methyl}-5,8-dioxo-5,6,7,8-tetrahydro-4H-pyrazolo[1,5-a]pyrrolo[3,4-d]pyrimidin-4-yl)-N-(5-fluoropyridin-2-yl)acetamide A mixture of 2-{2-ethyl-6-[(2R)-morpholin-2-ylmethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide (50 mg, 0.107 mmol) (example 247), 37% formaldehyde solution in water (40 μl, 0.533 mmol), camphor-10-sulfonic acid (12 mg, 0.053 mmol) and acetic acid (11 μl, 0.187 mmol) in methanol (1 ml) was stirred at rt for 45 min. NaBH(OAc)₃ (68 mg, 0.320 mmol) was then added, and the reaction mixture was stirred at rt for 20 h. The solution was concentrated under reduced pressure, and the residue was dissolved in dichloromethane. The organic phase was washed with saturated aqueous NaHCO₃ solution (5 ml), and the aqueous phase was extracted with dichloromethane (2×5 ml). The combined organic phases were dried (MgSO₄), filtered and concentrated in vacuo. The resulting material was purified by preparative HPLC (Method B), and the product containing fractions were concentrated and freeze-dried to afford 24.3 mg (46% yield) of the title compound as a white powder.

¹H NMR (500 MHz, DMSO-d6) δ[ppm]: 1.24 (t, 3H), 1.70-1.77 (m, 1H), 1.93-2.01 (m, 1H), 2.15 (s, 3H), 2.53-2.58 (m, 1H), 2.63-2.73 (m, 3H), 3.46-3.55 (m, 2H), 3.55-3.62 (m, 1H), 3.69-3.76 (m, 1H), 3.77-3.83 (m, 1H), 4.45 (s, 2H), 5.46 (s, 2H), 6.46 (s, 1H), 7.70-7.78 (m, 1H), 7.97-8.05 (m, 1H), 8.38 (d, 1H), 11.10 (s, 1H).

LC-MS (Analytical Method D) $R_t$=2.73 min, MS (ESIpos): m/z=484 [M+H]⁺.

Example 256

2-(2-ethyl-5,8-dioxo-6-{[(2R)-4-(propan-2-yl)morpholin-2-yl]methyl}-5,6,7,8-tetrahydro-4H-pyrazolo[1,5-a]pyrrolo[3,4-d]pyrimidin-4-yl)-N-(5-fluoropyridin-2-yl)acetamide

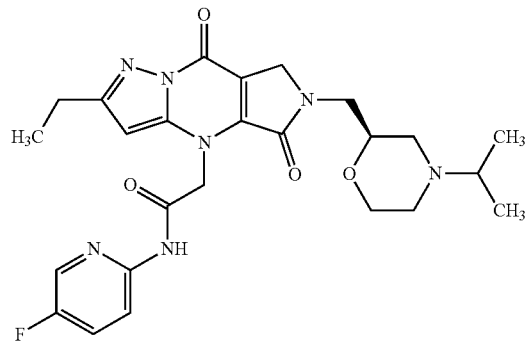 [SMILES: CCc1cc2n(CC(=O)Nc3ccc(F)cn3)c3c(c(=O)n2n1)CN(C[C@H]1CN(C(C)C)CCO1)C3=O]

A mixture of 2-{2-ethyl-6-[(2R)-morpholin-2-ylmethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide (50 mg, 0.11 mmol) (example 247), acetone (78 μl) and acetic acid (11 μl) in 1,2-dichloroethane (0.5 ml) was stirred at rt for 45 minutes. NaBH(OAc)₃ (68 mg, 0.32 mmol) was then added, and the reaction mixture was stirred at rt for 17 h. After this time, the reaction mixture was neutralised with saturated aqueous NaHCO₃ solution (5 ml) and the phases were separated. The aqueous phase was extracted with dichloromethane (2×5 ml), and the combined organics were dried (MgSO₄), filtered and concentrated under reduced pressure. The crude material was purified by preparative HPLC (Method B), and the product containing fractions were freeze-dried to afford 21.1 mg (37% yield) of the title compound as a white solid.

¹H NMR (500 MHz, DMSO-d6) δ[ppm]: 0.94 (d, 6H), 1.24 (t, 3H), 1.89-1.98 (m, 1H), 2.14-2.22 (m, 1H), 2.53-2.61 (m, 2H), 2.66-2.73 (m, 3H), 3.64-3.73 (m, 1H), 3.77-3.86 (m, 1H), 4.44 (s, 2H), 5.46 (s, 2H), 6.46 (s, 1H), 7.70-7.77 (m, 1H), 7.96-8.05 (m, 1H), 8.37 (d, 1H), 11.10 (s, 1H).

LC-MS (Analytical Method D) R$_t$=2.74 min, MS (ESIpos): m/z=512 [M+H]⁺.

In analogy to the procedure described for Example 256, the following examples were prepared from the appropriate secondary amine and aldehyde or ketone starting materials.

| Example | Structure IUPAC-Name ¹H NMR | Synth. From Yield LC-MS |
|---|---|---|
| 257 | 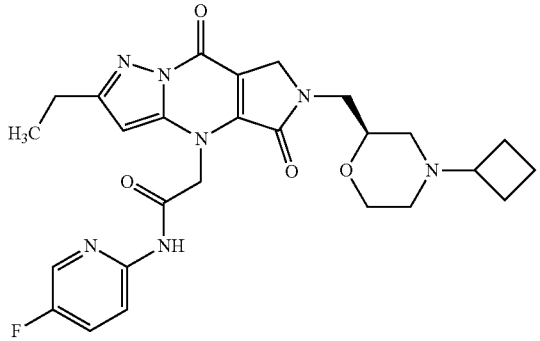<br>2-(6-{[(2R)-4-cyclobutylmorpholin-2-yl]methyl}-2-ethyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide<br>¹H NMR (500 MHz, DMSO-d6) δ [ppm]: 1.24 (t, 3H), 1.54-1.66 (m, 3H), 1.69-1.97 (m, 5H), 2.53-2.58 (m, 1H), 2.62-2.74 (m, 4H), 3.66-3.73 (m, 1H), 3.78-3.84 (m, 1H), 4.44 (s, 2H), 5.46 (s, 2H), 6.46 (s, 1H), 7.70-7.77 (m, 1H), 7.97-8.04 (m, 1H), 8.37 (d, 1H), 11.10 (s, 1H). | Example 247<br>14%<br>LC-MS (Analytical Method D) R$_t$ = 2.79 min, MS (ESIpos): m/z = 524 [M + H]⁺. |
| 258 | 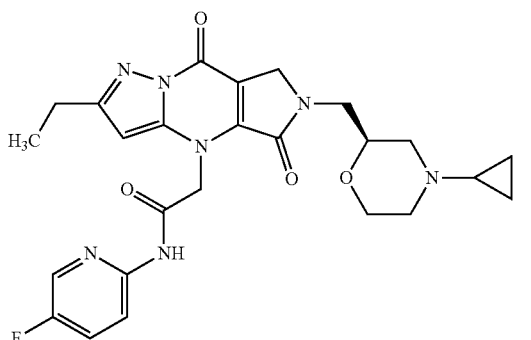<br>2-(6-{[(2R)-4-cyclopropylmorpholin-2-yl]methyl}-2-ethyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide<br>¹H NMR (500 MHz, DMSO-d6) δ [ppm]: 0.28-0.34 (m, 2H), 0.36-0.43 (m, 2H), 1.24 (t, 3H), 1.56-1.67 (m, 1H), 2.00-2.07 (m, 1H), 2.23-2.32 (m, 1H), 2.66-2.73 (m, 3H), 2.78-2.84 (m, 1H), 3.40-3.44 (m, 1H), 3.49-3.68 (m, 3H), 3.76-3.83 (m, 1H), 4.42-4.47 (m, 2H), 5.46 (s, 2H), 6.46 (s, 1H), 7.69-7.79 (m, 1H), 7.96-8.08 (m, 1H), 8.38 (d, 1H), 11.10 (s, 1H). | Example 247<br>13%<br>LC-MS (Analytical Method D) R$_t$ = 2.79 min, MS (ESIpos): m/z = 510 [M + H]⁺. |

| Example | Structure<br>IUPAC-Name<br>¹H NMR | Synth. From<br>Yield<br>LC-MS |
|---|---|---|
| 259 | 2-(2-ethyl-5,8-dioxo-6-{[(2R)-4-(3,3,3-trifluoropropyl)morpholin-2-yl]methyl}-5,6,7,8-tetrahydro-4H-pyrazolo[1,5-a]pyrrolo[3,4-d]pyrimidin-4-yl)-N-(5-fluoropyridin-2-yl)acetamide<br>¹H NMR (500 MHz, Methanol-d4) δ [ppm]: 1.33 (t, 3H), 1.93-1.99 (m, 1H), 2.17-2.25 (m, 1H), 2.35-2.48 (m, 2H), 2.58-2.65 (m, 2H), 2.71-2.77 (m, 1H), 2.80 (q, 2H), 2.84-2.90 (m, 1H), 3.58-3.74 (m, 3H), 3.78-3.86 (m, 1H), 3.89-3.96 (m, 1H), 4.50-4.62 (m, 2H), 5.54 (s, 2H), 6.36 (s, 1H), 7.54-7.60 (m, 1H), 8.04-8.11 (m, 1H), 8.23-8.25 (m, 1H). | Example 247<br>13%<br>LC-MS (Analytical Method D) R$_t$ = 2.79 min, MS (ESIpos): m/z = 566 [M + H]⁺. |
| 260 | 2-(2-ethyl-5,8-dioxo-6-{[(3R)-4-(propan-2-yl)morpholin-3-yl]methyl}-5,6,7,8-tetrahydro-4H-pyrazolo[1,5-a]pyrrolo[3,4-d]pyrimidin-4-yl)-N-(5-fluoropyridin-2-yl)acetamide<br>¹H NMR (500 MHz, DMSO-d6) δ [ppm]: 0.97 (d, 3H), 1.05 (d, 3H), 1.24 (t, 3H), 2.39-2.44 (m, 1H), 2.66-2.72 (m, 2H), 2.89-2.96 (m, 1H), 3.19-3.26 (m, 1H), 3.44-3.50 (m, 2H), 3.54-3.63 (m, 2H), 3.64-3.72 (m, 2H), 4.49 (d, 2H), 5.32-5.59 (m, 2H), 6.46 (s, 1H), 7.74 (td, 1H), 8.00 (s, 1H), 8.38 (d, 1H), 11.09 (s, 1H). | Example 248<br>44%<br>LC-MS (Analytical Method D): R$_t$ = 3.09 min; MS (ESIpos): m/z = 512 [M + H]⁺. |

-continued

| Example | Structure<br>IUPAC-Name<br>¹H NMR | Synth. From<br>Yield<br>LC-MS |
|---|---|---|
| 261 | 2-(2-ethyl-5,8-dioxo-6-{[(3R)-4-(3,3,3-trifluoropropyl)morpholin-3-yl]methyl}-5,6,7,8-tetrahydro-4H-pyrazolo[1,5-a]pyrrolo[3,4-d]pyrimidin-4-yl)-N-(5-fluoropyridin-2-yl)acetamide<br>¹H NMR (500 MHz, DMSO-d6) δ [ppm]: 1.21-1.27 (m, 5H), 2.69 (q, 2H), 2.75-2.89 (m, 2H), 2.89-3.04 (m, 2H), 3.48-3.77 (m, 6H), 4.49 (s, 2H), 5.46 (s, 2H), 6.46 (s, 2H), 7.73 (td, 1H), 7.99 (s, 1H), 8.37 (d, 1H), 11.09 (s, 1H). | Example 248<br>22%<br>LC-MS (Analytical Method D): $R_t$ = 3.59 min; MS (ESIpos): m/z = 566 [M + H]⁺. |
| 262 | N-(5-fluoropyridin-2-yl)-2-[2-(1-methylazetidin-3-yl)-5,8-dioxo-6-(propan-2-yl)-5,6,7,8-tetrahydro-4H-pyrazolo[1,5-a]pyrrolo[3,4-d]pyrimidin-4-yl]acetamide<br>¹H NMR (400 MHz, DMSO-d6) δ [ppm]: 1.23 (d, 6H), 2.16 (s, 1H), 2.25 (s, 3H), 3.17 (t, 2H), 3.51-3.70 (m, 3H), 4.29 (dt, 1H), 4.38 (s, 2H), 5.49 (br s, 1H), 6.63 (s, 1H), 7.74 (td, 1H), 8.00 (br s, 1H), 8.38 (d, 1H), 11.11 (s, 1H). | Example 244<br>20%<br>LC-MS (Method H): $R_t$ = 0.89 min; MS (ESIpos): m/z = 454 [M + H]⁺ |

Example 263

2-[2-(1-acetylpiperidin-4-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

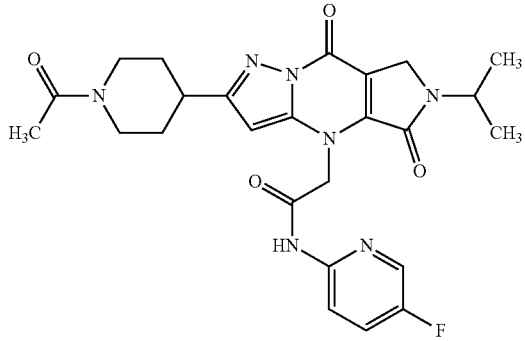 [SMILES: CC(=O)N1CCC(c2cc3n(CC(=O)Nc4ccc(F)cn4)c4c(c(=O)n3n2)CN(C(C)C)C4=O)CC1]

To a solution of 2-[5,8-dioxo-2-(piperidin-4-yl)-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide hydrochloride (1:1) (40.0 mg, 79.4 µmol) (example 234) in N-methylpyrrolidone (750 µl, 7.8 mmol) and N,N-diisopropylethylamine (29 µl, 170 µmol) was added acetyl chloride (5.9 µl, 83 µmol). The mixture stirred for 1 h at rt. The solution was concentrated and dissolved with acetonitrile/water (7:3), filtrated and purified by preparative HPLC (Method F, gradient C) to afford 17 mg (43% yield) of the title compound.

$^1$H NMR (400 MHz, DMSO-d6) δ[ppm]: 1.23 (d, 6H), 1.35-1.55 (m, 1H), 1.62 (qd, 1H), 1.87-2.00 (m, 2H), 2.01 (s, 3H), 2.63-2.73 (m, 1H), 2.97 (tt, 1H), 3.12-3.21 (m, 1H), 3.86 (br d, 1H), 4.29 (quin, 1H), 4.37 (s, 2H), 4.38-4.43 (m, 1H), 5.45 (br s, 2H), 6.55 (s, 1H), 7.74 (td, 1H), 8.00 (br d, 1H), 8.38 (d, 1H), 11.11 (s, 1H)

LC-MS (Analytical Method H): $R_t$=0.88 min; MS (ESIpos): m/z=510 [M+H]$^+$.

In analogy to the procedure described for Example 263, the following examples were prepared from the appropriate secondary amine and acyl chloride starting materials.

| Example | Structure / IUPAC-Name / $^1$H NMR | Synth. from / Yield / LC-MS |
|---|---|---|
| 264 | 2-{2-[1-(difluoroacetyl)piperidin-4-yl]-5,8-dioxo-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide<br>$^1$H NMR (400 MHz, DMSO-d6) δ [ppm]: 1.23 (d, 6H), 1.45-1.71 (m, 3H), 1.96-2.08 (m, 2H), 2.93 (br t, 1H), 3.06 (tt, 1H), 3.23-3.32 (m, 1H), 3.93 (br d, 1H), 4.25-4.36 (m, 2H), 4.37 (s, 2H), 5.45 (br s, 2H), 6.57 (s, 1H), 6.76 (t, 1H), 7.74 (td, 1H), 8.00 (br d, 1H), 8.38 (d, 1H). | Example 234<br>46%<br>LC-MS (Analytical Method G): $R_t$ = 0.96 min; MS (ESIpos): m/z = 546 [M + H]$^+$. |

| Example | Structure<br>IUPAC-Name<br>¹H NMR | Synth. from<br>Yield<br>LC-MS |
|---|---|---|
| 265 | 2-{6-[(±)-1-acetylpyrrolidin-3-yl]-2-ethyl-5,8-dioxo-5,6,7,8-tetrahydro-4H-pyrazolo[1,5-a]pyrrolo[3,4-d]pyrimidin-4-yl}-N-{5-fluoropyridin-2-yl)acetamide<br>¹H NMR (400 MHz, DMSO-d6) δ [ppm]: 1.19-1.26 (m, 3H), 1.95 + 1.97 (s, 3H), 2.06-2.26 (m, 2H), 2.64-2.73 (m, 2H), 3.26-3.31 (m) + 3.37-3.50 (m, 1H), 3.50-3.76 (m, 3H), 4.38-4.52 (m, 2H), 4.63 (quin) + 4.75 (quin, 1H), 5.47 (br s, 2H), 6.47 + 6.48 (s, 1H), 7.74 (td, 1H), 8.00 (br d, 1H), 8.38 (d, 1H), 11.12 (br s, 1H). | Example 236<br>41%<br>LC-MS (Analytical Method H): R$_t$ = 0.82 min; MS (ESIpos): m/z = 482 [M + H]⁺ |
| 266 | 2-{6-[(±)-1-(difluoroacetyl)pyrrolidin-3-yl]-2-ethyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm]: 1.23 (t, 3H), 2.13-2.34 (m, 2H), 2.65-2.72 (m, 2H), 3.43-3.51 (m, 1H), 3.57-3.74 (m, 2H), 3.80-3.90 (m, 1H), 4.42-4.53 (m, 2H), 4.70 + 4.79 (quin, 1H), 5.46 (br s, 2H), 6.47 + 6.48 (s, 1H), 6.56 + 6.59 (t, 1H), 7.74 (td, 1H), 8.00 (br d, 1H), 8.38 (d, 1H), 11.12 (br s, 1H). | Example 236<br>41%<br>LC-MS (Analytical Method H): R$_t$ = 0.89 min; MS (ESIpos): m/z = 518 [M + H]⁺. |

| Example | Structure<br>IUPAC-Name<br>¹H NMR | Synth. from<br>Yield<br>LC-MS |
|---|---|---|
| 267 | 2-(6-{[(2R)-4-acetylmorpholin-2-yl]methyl}-2-ethyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide<br>¹H NMR (250 MHz, DMSO-d6) δ [ppm]: 1.26 (t, 3H), 2.00 (s, 3H), 2.72 (q, 2H), 3.37-3.55 (m, 1H), 3.55-4.34 (m, 7H), 4.47 (s, 2H), 5.49 (s, 2H), 6.34 (s, 1H), 7.60-7.76 (m, 1H), 7.91-8.01 (m, 1H), 8.28-8.38 (m, 1H), 10.81 (s, 1H). | Example 247<br>32%<br>LC-MS (Analytical Method D) $R_t$ = 3.35 min, MS (ESIpos): m/z = 512 [M + H]⁺. |
| 268 | 2-{6-[(1-acetylazetidin-3-yl)methyl]-2-ethyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm]: 1.23 (t, 3H), 1.71 (s, 3H), 2.62-2.73 (m, 2H), 2.87-2.98 (m, 1H), 3.58 (dd, 1H), 3.66-3.81 (m, 2H), 3.83-3.93 (m, 2H), 4.17 (t, 1H), 4.35-4.44 (m, 2H), 5.46 (br s, 2H), 6.47 (s, 1H), 7.73 (td, 1H), 7.94-8.02 (m, 1H), 8.37 (d, 1H), 11.13 (br s, 1H). | Example 242<br>18%<br>LC-MS (Method H): $R_t$ = 0.81 min; MS (ESIpos): m/z = 482 [M + H]⁺ |

| Example | Structure<br>IUPAC-Name<br>¹H NMR | Synth. from<br>Yield<br>LC-MS |
|---|---|---|
| 269 | ![structure]<br>2-[6-(1-acetylazetidin-3-yl)-2-ethyl-5,8-dioxo-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.23 (t, 3H), 1.79 (s, 3H), 2.69 (q, 2H), 4.07-4.20 (m, 2H), 4.33-4.46 (m, 2H), 4.60-4.66 (m, 1H), 4.66 (br s, 1H), 4.94-5.04 (m, 1H), 5.44 (br s, 2H), 6.49 (s, 1H), 7.73 (td, 1H), 7.99 (br d, 1H), 8.37 (d, 1H), 11.11 (br s, 1H). | Example 243<br>34%<br>LC-MS (Method H): R$_t$ = 0.81 min; MS (ESIpos): m/z = 468 [M + H]⁺ |

Example 270

N-(5-fluoropyridin-2-yl)-2-{2-[(±)-1-(methylsulfonyl)pyrrolidin-3-yl]-5,8-dioxo-6-(propan-2-yl)-5,6,7,8-tetrahydro-4H-pyrazolo[1,5-a]pyrrolo[3,4-d]pyrimidin-4-yl}acetamide

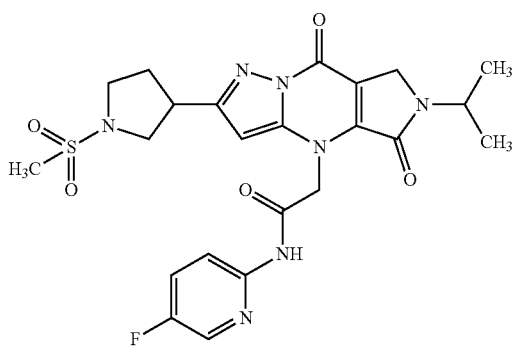 [SMILES: CC(C)N1Cc2c(n(CC(=O)Nc3ccc(F)cn3)c3cc(C4CCN(S(C)(=O)=O)C4)nn3c2=O)C1=O]

To a solution of 2-{5,8-dioxo-6-(propan-2-yl)-2-[(±)-pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide hydrochloride (1:1) (40.0 mg, 81.6 μmol) (example 235) in THF (750 μl) and triethylamine (23 μl, 160 μmol) was added methanesulfonyl chloride (6.6 μl, 86 μmol). The mixture stirred for 16 h at rt. Further methanesulfonyl chloride (6.6 μl, 86 μmol) was added. The reaction mixture stirred another 1 h at rt. Water was added and the aqueous phase was extracted with ethyl acetate.

The organics were washed with brine, dried with a water repellant filter and concentrated in vacuo. The residue was dissolved with a few drops of ethyl acetate. To the solution hexane was added. The formed precipitate was collected by filtration and dried in vacuo to get 24 mg (54% yield) of the title compound.

¹H NMR (400 MHz, DMSO-d6) δ[ppm]: 1.23 (d, 6H), 2.12 (dq, 1H), 2.91 (s, 3H), 3.33-3.44 (m, 3H), 3.53-3.74 (m, 3H), 4.29 (dt, 1H), 4.38 (s, 2H), 5.47 (br s, 2H), 6.63 (s, 1H), 7.74 (td, 1H), 7.99 (br s, 1H), 8.38 (d, 1H), 11.13 (s, 1H).

LC-MS (Analytical Method G): R$_t$=0.92 min; MS (ESIpos): m/z=532 [M+H]⁺.

In analogy to the procedure described for Example 270, the following examples were prepared from the appropriate secondary amine and sulfonyl chloride starting materials.

| Example | Structure IUPAC-Name ¹H NMR | Synth. From Yield LC-MS |
|---|---|---|
| 271 | 2-[5,8-dioxo-6-(propan-2-yl)-2-{(±)-1-[(2,2,2-trifluoroethyl)sulfonyl]pyrrolidin-3-yl}-5,6,7,8-tetrahydro-4H-pyrazolo[1,5-a]pyrrolo[3,4-d]pyrimidin-4-yl]-N-(5-fluoropyridin-2-yl)acetamide<br>¹H NMR (400 MHz, DMSO-d6) δ [ppm]: 1.23 (d, 6H), 2.11 (dq, 1H), 2.29-2.39 (m, 1H), 3.41-3.54 (m, 3H), 3.61 (quin, 1H), 3.80 (dd, 1H), 4.29 (quin, 1H), 4.39 (s, 2H), 4.51-4.68 (m, 2H), 5.47 (br s, 2H), 6.61 (s, 1H), 7.74 (td, 1H), 8.00 (br d, 1H), 8.38 (d, 1H), 11.13 (s, 1H). | Example 235<br>10%<br>LC-MS (Analytical Method G): R$_t$ = 1.08 min; MS (ESIpos): m/z = 600 [M + H]⁺ |
| 272 | 2-{2-ethyl-6-[(±)-1-(methylsulfonyl)pyrrolidin-3-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm]: 1.23 (t, 3H), 2.13-2.27 (m, 2H), 2.69 (q, 2H), 2.97 (s, 3H), 3.34-3.41 (m, 2H), 3.44-3.56 (m, 2H), 4.50 (s, 2H), 4.74 (quin, 1H), 5.46 (br s, 2H), 6.48 (s, 1H), 7.74 (td, 1H), 8.00 (br d, 1H), 8.38 (d, 1H), 11.12 (s, 1H). | Example 236<br>43%<br>LC-MS (Analytical Method H): R$_t$ = 0.87 min; MS (ESIpos): m/z = 518 [M + H]⁺ |

| | |
|---|---|
| Structure<br>IUPAC-Name<br>Example ¹H NMR | Synth. From<br>Yield<br>LC-MS |
| 273<br><br>2-{2-ethyl-6-[1-(methanesulfonyl)azetidin-3-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide<br>¹H NMR (400 MHz, DMSO-d6) δ [ppm]: 1.24 (t, 3H), 2.69 (q, 2H), 3.15 (s, 3H), 4.09 (t, 2H), 4.29 (dd, 2H), 4.72 (s, 2H), 4.99-5.10 (m, 1H), 5.43 (br s, 2H), 6.50 (s, 1H), 7.73 (td, 1H), 7.99 (br d, 1H), 8.37 (d, 1H), 11.12 (s, 1H). | Example 243<br>26%<br>LC-MS (Method H): $R_t$ = 0.86 min; MS (ESIpos): m/z = 504 [M + H]⁺ |

Example 274

(±)-3-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]-N-(propan-2-yl)pyrrolidine-1-carboxamide

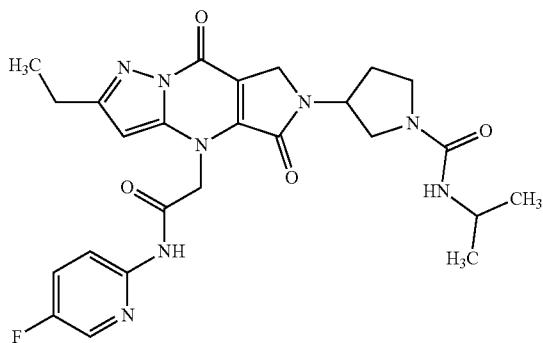 [SMILES: CCc1cc2n(CC(=O)Nc3ccc(F)cn3)c3c(c(=O)n2n1)CN(C1CCN(C(=O)NC(C)C)C1)C3=O]

To a solution of 2-{2-ethyl-5,8-dioxo-6-[(±)-pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide hydrochloride (1:1) (50.0 mg, 105 µmol) (example 236) in N,N-dimethylformamide (750 µl) was added 2-isocyanatopropane (12 µl, 130 µmol). The reaction mixture stirred for 40 h at rt. Another equivalent of 2-isocyanatopropane (12 µl, 130 µmol) was added and stirred for 1 h. The solution was quenched with water, filtrated and purified by preparative HPLC (Method F, gradient C) to get 8 mg (15% yield) of the title compound.

¹H NMR (400 MHz, DMSO-d6) δ[ppm]: 1.06 (dd, 6H), 1.23 (t, 3H), 2.10-2.22 (m, 2H), 2.63-2.73 (m, 3H), 3.24-3.31 (m, 1H), 3.34-3.39 (m, 1H), 3.43-3.58 (m, 2H), 3.68-3.80 (m, 1H), 4.35-4.47 (m, 2H), 4.63 (m, 1H), 5.46 (br s, 2H), 5.85 (d, 1H), 6.47 (s, 1H), 7.74 (td, 1H), 8.00 (br d, 1H), 8.38 (d, 1H).

LC-MS (Analytical Method H): $R_t$=0.91 min; MS (ESIpos): m/z=525 [M+H]⁺

Example 275

N-(5-fluoropyridin-2-yl)-2-{2-[(±)-1-hydroxyethyl]-5,8-dioxo-6-(propan-2-yl)-5,6,7,8-tetrahydro-4H-pyrazolo[1,5-a]pyrrolo[3,4-d]pyrimidin-4-yl}acetamide

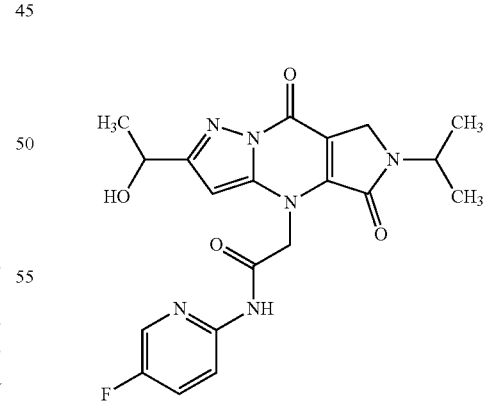

To a solution of 2-(2-acetyl-6-isopropyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide (200 mg, 0.47 mmol) (intermediate 06-04), in methanol (50 ml) was added NaBH₄ (35.5 mg, 0.94 mmol) at 0° C. and the resulting mixture was stirred at rt for 2 h. Upon completion of the reaction, water was added and the solvent was removed in vacuo. The residue was diluted with water and the resulting mixture was extracted with ethyl acetate. The combined organic layer was concentrated in vacuo and the residue was purified by preparative HPLC [column: XBridge Prep C18 OBD Column, 5 um, 19×150 mm, mobile phase A: water (0.1% NH$_4$HCO$_3$), mobile phase B: acetonitrile; Gradient: 20% B to 33% B in 8 min] to afford 13 mg (6% yield) of the title compound as a white solid.

$^1$H-NMR (400 MHz, DMSO-d6) δ[ppm]: 1.24 (d, 6H), 1.41 (d, 3H), 4.26-4.33 (m, 1H), 4.38 (s, 2H), 4.76-4.83 (m, 1H), 5.41 (d, 1H), 5.50-5.54 (m, 2H), 6.52 (s, 1H), 7.71-7.76 (m, 1H), 7.99-8.01 (m, 1H), 8.37-8.38 (m, 1H), 11.11 (br, 1H).

LC-MS (Analytical Method M, 0-2.0 min 5-95% B, 2.0-2.6 min 95% B): R$_t$=1.05 min; MS (ESIpos): m/z=429 [M+H]$^+$.

Example 276

N-(5-fluoropyridin-2-yl)-2-{2-[(2-hydroxyethyl)amino]-5,8-dioxo-6-(propan-2-yl)-5,6,7,8-tetrahydro-4H-pyrazolo[1,5-a]pyrrolo[3,4-d]pyrimidin-4-yl}acetamide

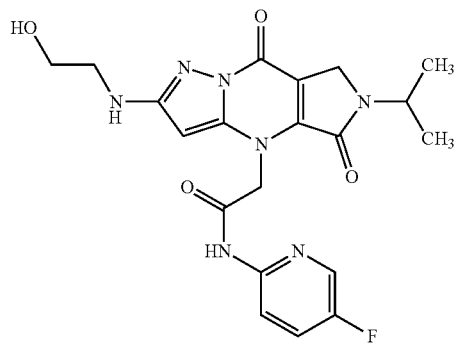

To a solution of 2-[2-{[2-(benzyloxy)ethyl]amino}-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (50.0 mg, 93.7 μmol) (example 176) in ethanol (2.5 ml) flushed with nitrogen was added palladium on activated carbon (10% purity, 9.97 mg, 9.37 μmol). The solution was flushed with hydrogen and stirred for 8 h. The reaction mixture was flushed with nitrogen and filtrated through Celite®. The filtrate was evaporated and the residue dissolved in a few drops of ethyl acetate. To the solution was added diethyl ether, the formed precipitate was collected by filtration and dried on air to get 22 mg (51% yield) of the title compound.

$^1$H NMR (400 MHz, DMSO-d6) δ[ppm]: 1.22 (d, 6H), 3.22 (q, 2H), 3.52 (q, 2H), 4.24-4.34 (m, 3H), 4.69 (br t, 1H), 5.39 (br s, 2H), 5.68 (s, 1H), 6.19 (t, 1H), 7.74 (td, 1H), 8.01 (br d, 1H), 8.37 (d, 1H), 11.11 (s, 1H)

LC-MS (Analytical Method H): R$_t$=0.78 min; MS (ESIpos): m/z=444 [M+H]$^+$.

Example 236 was formed as a mixture of two enantiomers. Chiral Purification (Instrument: Labomatic HD5000, Labocord-5000; Gilson GX-241, Labcol Vario 4000; Column: Chiralpak IC 5μ 250×30 mm; eluent A: methanol+0.1 Vol-% diethylamine (99%), eluent B: ethanol; gradient: isocratic 50% B; flow 40 ml/min; UV: 254 nm) provided enantiomer 1 (Example 172) and enantiomer 2 (Example 173).

Example 277

2-{2-ethyl-5,8-dioxo-6-[pyrrolidin-3-yl]-5,6,7,8-tetrahydro-4H-pyrazolo[1,5-a]pyrrolo[3,4-d]-pyrimidin-4-yl}-N-(5-fluoropyridin-2-yl)acetamide (enantiomer 1)

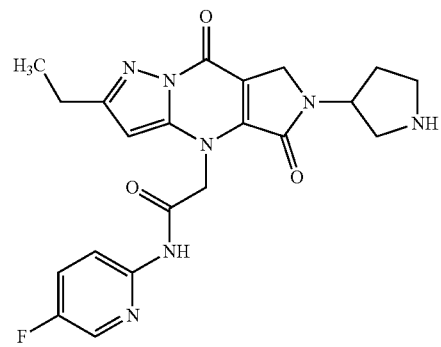 [SMILES: CCc1cc2n(CC(=O)Nc3ccc(F)cn3)c3c(c(=O)n2n1)CN(C1CCNC1)C3=O]

and

Example 278

2-{2-ethyl-5,8-dioxo-6-[pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide (enantiomer 2)

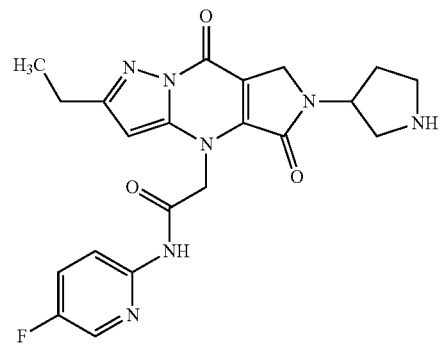 [SMILES: CCc1cc2n(CC(=O)Nc3ccc(F)cn3)c3c(c(=O)n2n1)CN(C1CCNC1)C3=O]

The racemic mixture of 2-{2-ethyl-5,8-dioxo-6-[(±)-pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide hydrochloride (1:1) (59.0 mg, 124 μmol) (example 236) was dissolved in 1.5 ml Dichlormethane/Methanol (1:1) and the enantiomers were separated via chiral preparative HPLC to get 19 mg (35%) of 2-{2-ethyl-5,8-dioxo-6-[pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide (enantiomer 1) and 21 mg (38%) of 2-{2-ethyl-5,8-dioxo-6-[pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide (enantiomer 2)

¹H NMR (400 MHz, DMSO-d6) δ[ppm]1.23 (t, 3H), 1.87-2.16 (m, 2H), 2.62-2.73 (m, 3H), 2.82-3.00 (m, 2H), 3.02-3.13 (m, 2H), 4.45 (s, 2H), 4.58-4.70 (m, 1H), 5.36-5.53 (m, 2H), 6.46 (s, 1H), 7.70-7.77 (m, 1H), 8.00 (br d, 1H), 8.38 (d, 1H), 11.12 (br s, 1H).

Chiral analytical HPLC (Instrument: Agilent HPLC 1260; Column: Chiralpak IC 3μ 100×4.6 mm; eluent A: methanol+0.1 Vol-% diethylamine (99%), eluent B: ethanol; gradient isocratic 50% B; flow 1.4 ml/min; temperature: 25° C.; DAD: 254 nm):

Enantiomer 1: $R_t$=6.31 min; ee: >99.9%
Enantiomer 2: $R_t$=11.82 min; ee: >99.9%

Example 77 was formed as a mixture of two enantiomers. Chiral Purification (Instrument: Labomatic HD5000, Labocord-5000; Gilson GX-241, Labcol Vario 4000; Column: Chiralpak IC 5 μm 250×30 mm; eluent A: methanol+0.1 Vol-% diethylamine (99%), eluent B: ethanol; gradient isocratic 50% B; flow 40 ml/min; UV: 254 nm) provided the S-Isomer (Example 279) and R-Isomer (Example 73).

Example 279

2-{2-ethyl-5,8-dioxo-6-[(2S)-tetrahydrofuran-2-ylmethyl]-5,6,7,8-tetrahydro-4H-pyrazolo[1,5-a]pyrrolo[3,4-d]pyrimidin-4-yl}-N-(5-fluoropyridin-2-yl)acetamide

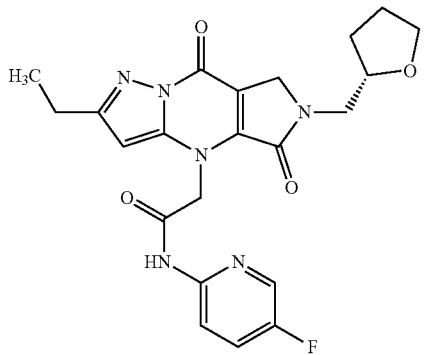 [SMILES: CCc1cc2n(CC(=O)Nc3ccc(F)cn3)c3c(c(=O)n2n1)CN(C[C@@H]1CCCO1)C3=O]

and

Example 73

2-{2-ethyl-5,8-dioxo-6-[(2R)-tetrahydrofuran-2-ylmethyl]-5,6,7,8-tetrahydro-4H-pyrazolo[1,5-a]pyrrolo[3,4-d]pyrimidin-4-yl}-N-(5-fluoropyridin-2-yl)acetamide

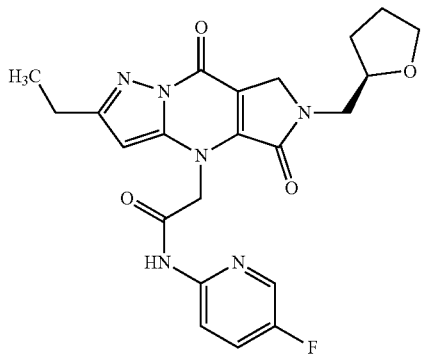 [SMILES: CCc1cc2n(CC(=O)Nc3ccc(F)cn3)c3c(c(=O)n2n1)CN(C[C@H]1CCCO1)C3=O]

The racemic mixture of 2-{2-ethyl-5,8-dioxo-6-[(±)-tetrahydrofuran-2-ylmethyl]-5,6,7,8-tetrahydro-4H-pyrazolo[1,5-a]pyrrolo[3,4-d]pyrimidin-4-yl}-N-(5-fluoropyridin-2-yl)acetamide (100 mg, 220 μmol) (example 77) was dissolved in 4.5 ml Dichlormethane/Methanol (1:1) and the enantiomers were separated via chiral preparative HPLC to get 32 mg (32%) of 2-{2-ethyl-5,8-dioxo-6-[(2S)-tetrahydrofuran-2-ylmethyl]-5,6,7,8-tetrahydro-4H-pyrazolo[1,5-a]pyrrolo[3,4-d]pyrimidin-4-yl}-N-(5-fluoropyridin-2-yl)acetamide and 41 mg (41%) of 2-{2-ethyl-5,8-dioxo-6-[(2R)-tetrahydrofuran-2-ylmethyl]-5,6,7,8-tetrahydro-4H-pyrazolo[1,5-a]pyrrolo[3,4-d]pyrimidin-4-yl}-N-(5-fluoropyridin-2-yl)acetamide.

¹H NMR (400 MHz, DMSO-d6) δ[ppm]: 1.23 (t, 3H), 1.47-1.58 (m, 1H), 1.75-1.99 (m, 3H), 2.69 (q, 2H), 3.44-3.53 (m, 1H), 3.56-3.69 (m, 2H), 3.75-3.82 (m, 1H), 4.06 (qd, 1H), 4.39-4.45 (m, 1H), 4.46-4.52 (m, 1H), 5.46 (br s, 2H), 6.46 (s, 1H), 7.74 (td, 1H), 8.00 (br d, 1H), 8.37 (d, 1H), 11.11 (s, 1H)

Chiral analytical HPLC (Instrument: Agilent HPLC 1260; Column: Chiralpak IC 3 μm 100×4.6 mm; eluent A: methanol+0.1 Vol-% diethylamine (99%), eluent B: ethanol; gradient isocratic 50% B; flow 1.4 ml/min; temperature: 25° C.; DAD: 254 nm):

S-Isomer: $R_t$=3.65 min; ee: 98.6%
R-Isomer: $R_t$=4.24 min; ee: 95.4%

Example 228 was formed as a mixture of two enantiomers. SFC Chiral Purification (Column: Lux $C_4$ (21.2 mm×250 mm, 5 μm); eluent A: methanol, eluent B: CO2, with 0.2% v/v $NH_3$ modifier; gradient: isocratic 50% B; flow 50 ml/min; UV: 233 nm) provided enantiomer 1 (Example 280) and enantiomer 2 (Example 281).

Example 280

2-{5,8-dioxo-2-[oxolan-3-yl]-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide (enantiomer 1)

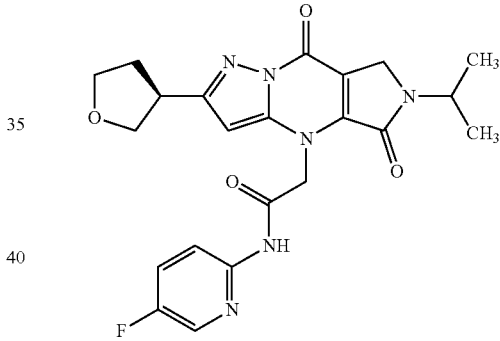

and

Example 281

2-{5,8-dioxo-2-[oxolan-3-yl]-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide (enantiomer 2)

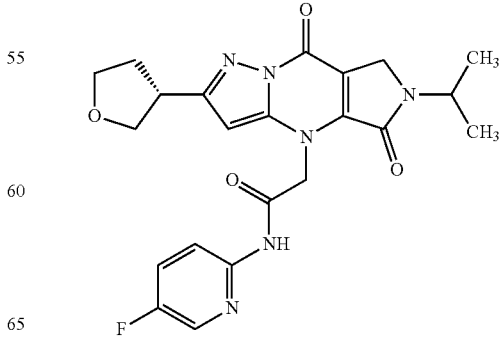

The racemic mixture of 2-{5,8-dioxo-2-[(±)-oxolan-3-yl]-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide (28.7 mg, 96% purity, 60.4 µmol) (example 228) was dissolved to 14 mg/ml in methanol and was then purified by chiral preparative SFC to afford 13.4 mg (47%) of 2-{5,8-dioxo-2-[oxolan-3-yl]-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide (enantiomer 1) and 12.4 mg (43%) of 2-{5,8-dioxo-2-[oxolan-3-yl]-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide (enantiomer 2).

$^1$H NMR (500 MHz, Chloroform-d) δ 1.33 (d, 6H), 2.16-2.25 (m, 1H), 2.37-2.46 (m, 1H), 3.65-3.75 (m, 1H), 3.85-3.96 (m, 2H), 4.04 (td, 1H), 4.15 (dd, 1H), 4.38 (s, 2H), 4.54-4.65 (m, 1H), 5.33 (s, 2H), 6.26 (s, 1H), 7.43 (ddd, 1H), 8.09-8.23 (m, 2H), 9.07 (s, 1H).

SFC Chiral Analysis (Column: Lux $C_4$ (4.6 mm×250 mm, 5 µm); eluent A: methanol, eluent B: $CO_2$, with 0.2% v/v $NH_3$ modifier; gradient: isocratic 50% B; flow 4 ml/min; UV: 210-400 nm):

Enantiomer 1: $R_t$=3.78 min; ee: 96.8%

Enantiomer 2: $R_t$=3.19 min; ee: 99.8%

Example 282

2-[2-(acetylamino)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide

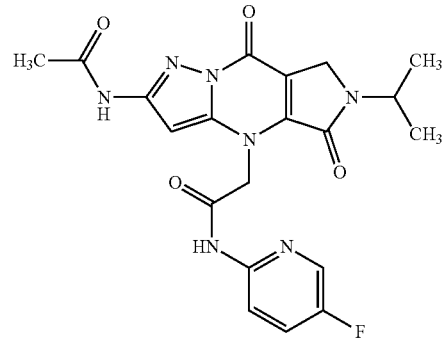

To a solution of 2-[2-amino-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide hydrochloride (1:1) (50.0 mg, 125 µmol) (example 241) in N-methylpyrrolidone (750 µl) was added N,N-diisopropylethylamine (65 µl, 380 µmol) and acetyl chloride (9.3 µl, 130 µmol). The reaction mixture stirred for 1.5 h at rt. The mixture was quenched with water and purified by preparative HPLC (Method F, gradient C) to afford 13.2 mg (23% yield) of the title compound.

$^1$H NMR (400 MHz, DMSO-d6) δ[ppm]1.24 (d, 6H), 2.05 (s, 3H), 4.30 (m, 1H), 4.37 (s, 2H), 5.54 (br s, 2H), 6.78 (s, 1H), 7.71-7.78 (m, 1H), 7.92-8.07 (m, 1H), 8.38 (d, 1H), 11.04 (s, 1H), 11.15 (s, 1H)

LC-MS (Analytical Method H): $R_t$=0.85 min; MS (ESI-pos): m/z=442 [M+H]$^+$.

In analogy to the procedure described for Example 282, the following examples were prepared from the appropriate amine and acyl chloride starting materials.

| Example | Structure<br>IUPAC-Name<br>$^1$H NMR | Synth. from<br>Yield<br>LC-MS |
|---|---|---|
| 283 | ![structure]<br>2,2-difluoro-N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]acetamide<br>$^1$H NMR (400 MHz, DMSO-d6) δ [ppm]: 1.24 (d, 6H), 4.31 (quin, 1H), 4.39 (s, 2H), 5.58 (br s, 2H), 6.38 (t, 1H), 6.88 (s, 1H), 7.71-7.78 (m, 1H), 8.00 (br d, 1H), 8.38 (d, 1H), 11.14 (s, 1H), 11.77-12.16 (m, 1 H). | Example 241<br>11%<br>LC-MS (Analytical Method H): $R_t$ = 0.63 min; MS (ESIpos): m/z = 478 [M + H]$^+$ |

| Example | Structure<br>IUPAC-Name<br>¹H NMR | Synth. from<br>Yield<br>LC-MS |
|---|---|---|
| 284 | N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]tetrahydro-2H-pyran-4-carboxamide<br>¹H NMR (400 MHz, DMSO-d6) δ [ppm]: 1.24 (d, 6H), 1.56-1.72 (m, 4H), 2.61-2.69 (m, 1H), 3.28-3.32 (m, 2H), 3.87 (dt, 2H), 4.26-4.35 (m, 1H), 4.37 (s, 2H), 5.54 (br s, 2H), 6.83 (s, 1H), 7.71-7.77 (m, 1H), 8.00 (br d, 1H), 8.38 (d, 1H), 11.06 (s, 1H), 11.09-11.21 (m, 1H) | Example 241<br>28%<br>LC-MS (Analytical Method H): R$_t$ = 0.90 min; MS (ESIpos): m/z = 512 [M + H]⁺. |
| 285 | N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-2-methoxyacetamide<br>¹H NMR (400 MHz, DMSO-d6) δ [ppm]: 1.24 (d, 6H), 3.33 (s, 3H), 4.04 (s, 2H), 4.30 (quin, 1H), 4.38 (s, 2H), 5.56 (br s, 2H), 6.83 (s, 1H), 7.71-7.78 (m, 1H), 7.94-8.06 (m, 1H), 8.38 (d, 1H), 10.87 (s, 1H), 11.15 (br s, 1H). | Example 241<br>41%<br>LC-MS (Analytical Method H): R$_t$ = 0.87 min; MS (ESIpos): m/z = 472 [M + H]⁺. |

| Example | Structure / IUPAC-Name / ¹H NMR | Synth. from / Yield / LC-MS |
|---|---|---|
| 286 | N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-1H-1,2,3-triazole-5-carboxamide<br>¹H NMR (400 MHz, DMSO-d6) δ [ppm]: 1.25 (d, 6H), 4.31 (dt, 1H), 4.40 (s, 2H), 5.59 (br s, 2H), 6.95 (s, 1H), 7.74 (td, 1H), 8.01 (br d, 1H), 8.39 (d, 1H), 8.62 (br s, 1H), 11.18 (s, 1H), 11.26-11.51 (m, 1H), 15.26-15.97 (m, 1H) | Example 241<br>25%<br>LC-MS (Analytical Method G): $R_t$ = 0.85 min; MS (ESIpos): m/z = 495 [M + H]⁺ |
| 287 | 2-(benzyloxy)-N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]acetamide<br>¹H NMR (400 MHz, DMSO-d6) δ [ppm]: 1.24 (d, 6H), 4.16 (s, 2H), 4.31 (dt, 6.62 Hz, 1H), 4.38 (s, 2H), 4.58 (s, 2H), 5.56 (br s, 2H), 6.85 (s, 1H), 7.26-7.32 (m, 1H), 7.33-7.40 (m, 4H), 7.74 (td, 1H), 8.00 (br d, 1H), 8.38 (d, 1H), 10.93 (s, 1H), 11.16 (s, 1H). | Example 241<br>38%<br>LC-MS (Analytical Method H): $R_t$ = 1.09 min; MS (ESIpos): m/z = 548 [M + H]⁺ |

| Example | Structure IUPAC-Name ¹H NMR | Synth. from Yield LC-MS |
|---|---|---|
| 288 | ![structure] N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-N²,N²-dimethylglycinamide | Example 241 9% LC-MS (Method J): $R_t$ = 0.87 min; MS (ESIpos): m/z = 485 [M + H]⁺ |

Example 289

N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-2-hydroxyacetamide

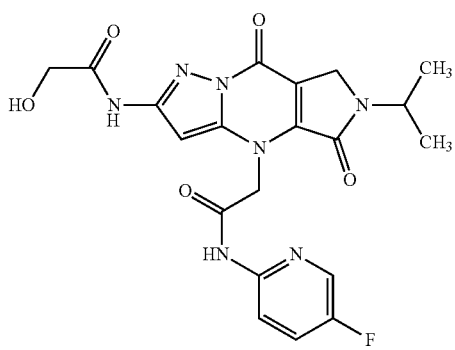

The prepared solution of 2-(benzyloxy)-N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]acetamide (20.0 mg, 36.5 µmol) (example 287) in ethanol (1.0 mL) was evaporated and flushed with nitrogen (3 cycles). Then palladium on carbon (3.89 mg, 10% purity, 3.65 µmol) was added, the flask was evaporated and flushed with hydrogen. The mixture stirred for 14 h at room temperature and then filtrated through a filter packed with celite. The celite was washed with ethanol and the filtrate was concentrated. The residue was dissolved with a few drops of ethyl acetate and diethyl ether (15 mL) were added to the solution. The formed precipitate was collected by filtration and dried on air to afford 3 mg (17% yield) of the title compound.

LC-MS (Method H): $R_t$=0.80 min; MS (ESIpos): m/z=458 [M+H]+

¹H NMR (400 MHz, DMSO-d6) δ[ppm]: 1.24 (br d, 6H), 4.03 (s, 2H), 4.30 (dt, 1H), 4.38 (s, 2H), 5.56 (br s, 3H), 6.83 (s, 1H), 7.74 (td, 1H), 7.99 (br s, 1H), 8.38 (d, 1H), 10.54 (br s, 1H), 11.16 (br s, 1H).

Example 290

2-[5,8-dioxo-6-(propan-2-yl)-2-{[(propan-2-yl)carbamoyl]amino}-5,6,7,8-tetrahydro-4H-pyrazolo[1,5-a]pyrrolo[3,4-d]pyrimidin-4-yl]-N-(5-fluoropyridin-2-yl)acetamide

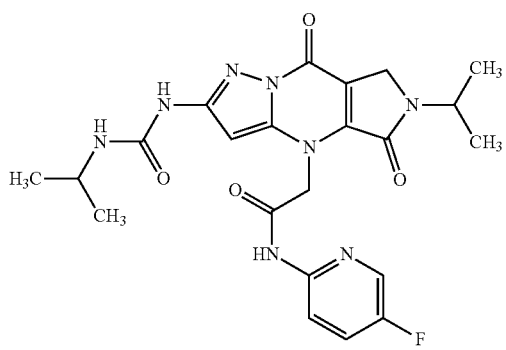

To a solution of 2-[2-amino-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide (50.0 mg, 125 µmol) (example 241) in N,N-diisopropylethylamine (65 µl, 380 µmol) was added 2-isocyanatopropane (25 µl, 250 µmol). The reaction mixture stirred for 16 h at room temperature. Further 2-isocyanatopropane (25 µl, 250 µmol) was added and the mixture stirred for additional 24 h at room temperature. Another portion of 2-isocyanatopropane (25 µl, 250 µmol) was added and the solution stirred for further 3 days. The solution was filtrated and purified with preparative HPLC (Method F, gradient C) to afford 7.5 mg (11% yield) of the title compound.

LC-MS (Method H): $R_t$=0.94 min; MS (ESIpos): m/z=485 [M+H]+

$^1$H NMR (400 MHz, DMSO-d6) δ[ppm]: 1.10 (d, 6H), 1.23 (d, 6H), 3.75 (dq, 1H), 4.24-4.33 (m, 1H), 4.35 (s, 2H), 5.50 (br s, 2H), 6.48-6.56 (m, 2H), 7.71-7.78 (m, 1H), 8.00 (br d, 1H), 8.38 (d, 1H), 9.14 (s, 1H), 11.15 (s, 1H).

Example 291

2-{2-ethyl-6-[2-(morpholin-4-yl)-2-oxoethyl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide

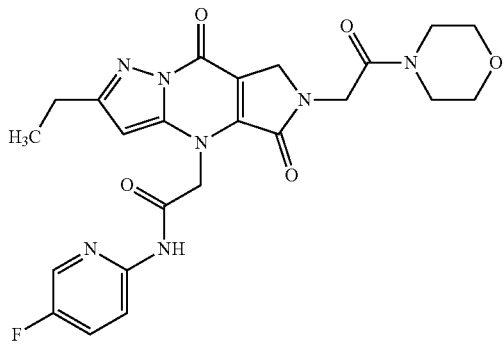 [SMILES: CCc1cc2n(CC(=O)Nc3ccc(F)cn3)c3c(c(=O)n2n1)CN(CC(=O)N1CCOCC1)C3=O]

To a solution of [2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]acetic acid (30.0 mg, 70.0 μmol) (intermediate 06-10) in dry N,N-dimethylformamide (750 μL) was added HATU (39.9 mg, 105 μmol) and N,N-diisopropylethylamine (18 μl, 110 μmol). The solution stirred for 10 min at room temperature. Morpholine (9.2 μl, 110 μmol) was added and the reaction mixture stirred for 16 h at room temperature. The reaction mixture was diluted with dimethyl sulfoxide to a volume of 2 mL The residual material dissolved in acetonitrile/water (7:3) and purified with preparative HPLC (Method D) to afford 16.8 mg (48% yield) of the title compound.

LC-MS (Method J): $R_t$=0.78 min; MS (ESIpos): m/z=498 [M+H]$^+$ $^1$H NMR (400 MHz, DMSO-d6) δ[ppm]: 1.24 (t, 3H), 2.69 (q, 2H), 3.46 (br dd, 4H), 3.53-3.64 (m, 4H), 4.38 (s, 2H), 4.46 (s, 2H), 5.45 (br s, 2H), 6.49 (s, 1H), 7.74 (td, 1H), 8.00 (br d, 1H), 8.37 (d, 1H), 11.11 (s, 1H).

In analogy to the procedure described for Example 291, the following examples were prepared from the appropriate amine and carboxylic acid starting materials.

| Example | Structure<br>IUPAC-Name<br>$^1$H NMR | Synth. from<br>Yield<br>LC-MS |
|---|---|---|
| 292 | ![structure]<br>2-(2-ethyl-5,8-dioxo-6-{2-oxo-2-[(propan-2-yl)amino]ethyl}-5,6,7,8-tetrahydro-4H-pyrazolo[1,5-a]pyrrolo[3,4-d]pyrimidin-4-yl)-N-(5-fluoropyridin-2-yl)acetamide<br>$^1$H NMR (400 MHz, DMSO-d6) δ [ppm]: 1.06 (d, 6H), 1.23 (t, 3H), 2.69 (q, 2H), 3.84 (dq, 1H), 4.12 (s, 2H), 4.42 (s, 2H), 5.46 (br s, 2H), 6.48 (s, 1H), 7.74 (td, 1H), 7.97-8.06 (m, 2H), 8.37 (d, 1H), 11.11 (s, 1H). | Intermediate 06-10<br>36%<br>LC-MS (Method J): $R_t$ = 0.84 min; MS (ESIpos): m/z = 470 [M + H]$^+$. |

-continued

| Example | Structure IUPAC-Name $^1$H NMR | Synth. from Yield LC-MS |
|---|---|---|
| 293 | 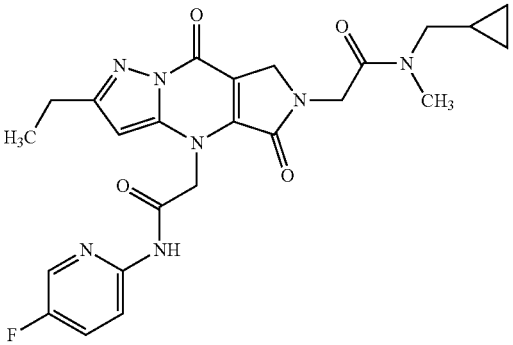<br>N-(cyclopropylmethyl)-2-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]-N-methylacetamide<br>$^1$H NMR (400 MHz, DMSO-d6) δ [ppm]: 0.17-0.23 (m, 1H), 0.26-0.33 (m, 1H), 0.40-0.46 (m, 1H), 0.48-0.55 (m, 1H), 0.89-1.07 (m, 1H), 1.24 (t, 3H), 2.69 (q, 2H), 2.89 + 3.05 (s, 3H), 3.14-3.25 (m, 2H), 4.37 + 4.39 (s, 2H), 4.45 + 4.46 (s, 2H), 5.46 (br s, 2H), 6.49 (s, 1H), 7.74 (td, Hz, 1H), 8.00 (br d, 1H), 8.37 (d, 1H), 11.11 (s, 1H) (rotamers present) | Intermediate 06-10<br>33%<br>LC-MS (Method J): $R_t$ = 0.92 min; MS (ESIpos): m/z = 496 [M + H]$^+$. |
| 294 | 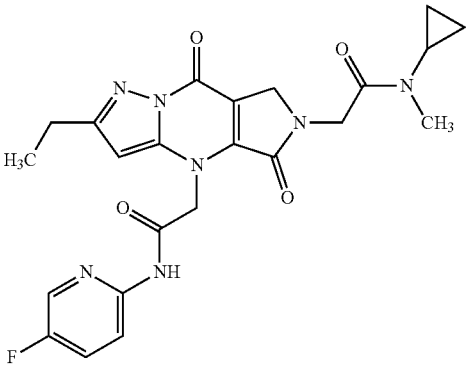<br>N-cyclopropyl-2-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]-N-methylacetamide<br>$^1$H NMR (400 MHz, DMSO-d6) δ [ppm]: 0.80-0.88 (m, 3H), 1.24 (t, 4H), 2.70 (q, 2H), 2.77-2.80 (m, 1H), 2.81 (s, 3H), 4.41 (s, 2H), 4.57 (s, 2H), 5.45 (br s, 2H), 6 49 (s, 1H), 7.74 (td, 1H), 8.00 (br d,), 8.37 (d, 1H), 11.12 (br s, 1H). | Intermediate 06-10<br>22%<br>LC-MS (Method J): $R_t$ = 0.87 min; MS (ESIpos): m/z = 482 [M + H]$^+$. |

Experimental Section—Biological Assays

Examples were tested in selected biological assays one or more times. When tested more than once, data are reported as either average values or as median values, wherein
- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

1) Intracellular Calcium Measurement to Assess Antagonist Activity at Human P2X3 Receptors (hP2X3 FLIPR)

A fluorescent imaging plate reader (FLEX/FLIPR station; Molecular Devices) was used to monitor intracellular calcium levels using the calcium-chelating dye Fluo-4 (Molecular Probes). The excitation and emission wavelengths used to monitor fluorescence were 470-495 nm and 515-575 nm, respectively. The human astrocytoma 1312N1 cells expressing purinergic receptors P2X3 (human) were plated at a density of 15,000 cells/well in collagen—coated 384-well plates approximately 20 hours before beginning the assay. On the day of the assay, 20 µl of loading buffer (Hank's balanced salt solution, 20 mM HEPES, 0.5 mM $CaCl_2$), 0.5 mM $MgCl_2$, 0.1% BSA, 5 mM probenecid, 10 mM D-glucose monohydrate, 2 µM Fluo-4, and 5 units/mL, hexokinase, pH=7.4) was added and cells dye-loaded for 90 min at 37° C. The dye supernatant was removed and replaced with 45 µl probenecid buffer (Hank's balanced salt solution, 20 mM HEPES, 0.5 mM $CaCl_2$, 0.5 mM $MgCl_2$, 0.1% BSA, 5 mM probenecid, 10 mM D-glucose monohydrate, pH=7.4). The test compounds were added in a volume of 5 µl and allowed to incubate for 30 min at 37° C. The final assay DMSO concentration is 1%. The agonist, α,β-Me-ATP, was added in a volume of 20 µl at a concentration representing the $EC_{50}$ value. The fluorescence was measured for an interval of 90 sec at 2 sec intervals and analyzed based on the increase in peak relative fluorescence units (RFU) compared to the basal fluorescence. Peak fluorescence was used to determine the response to agonist obtained at each concentration of test compound by the following equation:

$$\text{Response} = 100 * (RFU_{(test\ compound)} - RFU_{(control)}) / (RFU_{(DMSO)} - RFU_{(control)})$$

The Examples were tested in triplicates per plate and mean values were plotted in Excel XLFit to determine $IC_{50}$ values at the human P2X3 and human P2X2/3 receptors, percentage of maximal inhibition and the Hill coefficients.

2) Intracellular Calcium Measurement to Assess Antagonist Activity at Human P2X3 Receptors (hP2X3 CHO)

The determination of antagonistic activity at the P2X3 receptor of the compounds of the invention was performed by use of a recombinant cell line. This cell line derives originally from the Chinese hamster ovary (CHO) cell line (Tjio J. H.; Puck T. T., 1958, J. Exp. Med. 108: 259-271). The cell line is stably transfected with the human P2X3 receptor and a calcium-sensitive photoprotein, mitochondrial photina, which, after reconstitution with the cofactor coelenterazine, emits light in dependence of calcium binding [Bovolenta S, Foti M, Lohmer S, Corazza S., J Biomol Screen. 2007 August; 12(5):694-704]. The strength of the photina luminescence signal corresponds to the level of receptor activation upon agonist binding. An inhibitor would decrease the signal depending on its potency and concentration. Bioluminescence was detected using a suitable luminometer [Milligan G, Marshall F, Rees S, Trends in Pharmacological Sciences 17,235-237 (1996)].

Test Procedure:

On the day before the assay, the cells were plated out in culture medium (DMEM/F12 (PAN, P04-41451), 10% FCS) in 384-well microtiter plates and kept in a cell incubator (96% humidity, 5% v/v $CO_2$, 30° C.). On the day of the assay medium was replaced by 2 mM Ca-tyrode buffer containing 5 µg/ml coelenterazine. Plates were incubated for 3 hours at 37° C. (96% humidity, 5% v/v $CO_2$). After incubation the test substances in various concentrations were placed for 10 minutes in the wells of the microtiter plate before the agonist α,β-methylene-ATP at $EC_{50}$ concentration was added. The resulting light signal was measured immediately in the luminometer.

3) And 4) Intracellular Calcium Measurement to Compare Antagonist Activity at Human P2X3 Receptors (hP2X3 $1321N_1$) and at Human P2X2/3 Receptors (hP2X23 $1321N_1$)

The comparison of antagonistic activity at the P2X3 versus the P2X2/3 receptor of the compounds of the invention were performed by use of recombinant cell lines. These cell lines derived originally from the human astrocytoma cell line 1312N1 (Macintyre E H, Pontén J, Vatter A E. Acta Pathol Microbiol Scand A. 1972; 80(2):267-83). The cell lines are stably transfected with the human P2X3 receptor forming homotrimeric P2X3 receptors or are co-transfected with P2X2 and P2X3 forming heterotrimeric P2X2/3 receptors. Stimulation of the receptors with the agonist ATP leads to a conformational change of the receptors and influx of extracellular calcium ions through the open ion channel. The cytoplasmatic calcium transient is detected via the calcium sensitive dye Fluo8. The strength of Fluo8 fluorescence signal corresponds to the level of receptor activation. An inhibitor would decrease the signal depending on its potency and concentration. Fluorescence was measured by use of a suitable fluorescence reader.

Test Procedure:

On the day before the assay, the cells were plated in culture medium (DMEM high glucose, 10% FCS, 1% MEM non-essential amino acids, 4 mM Glutamax) in 384-well poly-D-lysine coated microtiter plates and kept in a cell incubator (96% humidity, 5% v/v $CO_2$, 37° C.). On the day of the assay medium was exchanged by Fluo8 containing buffer and incubated for 60 minutes. Test compounds were added at various concentrations and plates were incubated for 10 minutes. In the fluorescence reader a 3 seconds baseline measurement was performed and the agonist ATP was applied at $EC_{50}$ concentration of the respective receptor during constant fluorescence measurement for 120 seconds.

Results:

| Example No. | 1) hP2X3 $IC_{50}$ [nM] (1321N1) | 2) hP2X3 $IC_{50}$ [nM] (CHO) | 3) hP2X3 $IC_{50}$ [nM] (1321N1) | 4) hP2X2/3 $IC_{50}$ [nM] (1321N1) | hP2X23/ hP2X3* Selectivity (1321N1) |
|---|---|---|---|---|---|
| 1 | 22 | 35 | 35 | 4900 | 138 |
| 2 | 219 | 135 | 185 | >22000 | >119 |
| 3 | 32 | 147 | 37 | 2850 | 78 |
| 4 | 147 | 345 | 177 | 9600 | 54 |
| 5 | nd | 65 | 27 | 7700 | 282 |
| 6 | 13 | 75 | 19 | 1750 | 95 |
| 7 | 28 | 71 | 48 | 8000 | 167 |
| 8 | 50 | 51 | 48 | 3650 | 76 |
| 9 | 107 | 220 | 263 | >19900 | >76 |
| 10 | 24 | 38 | 317 | >32000 | >101 |
| 11 | 376 | 750 | 657 | Y > 20600 | >31 |
| 12 | 59 | 110 | 225 | 8800 | 39 |
| 13 | 21 | 51 | 27 | 5650 | 212 |
| 14 | 30 | 60 | 59 | 11500 | 194 |
| 15 | 21 | 49 | 53 | 4650 | 88 |
| 16 | 100 | 320 | >16600 | >100000 | >6 |
| 17 | 31 | 72 | 53 | >18100 | >345 |
| 18 | 69 | 106 | 124 | 2500 | 20 |
| 19 | 379 | 430 | 740 | 8050 | 11 |
| 20 | 312 | 375 | 537 | >22000 | >41 |
| 21 | 164 | 180 | 233 | 12400 | 53 |
| 22 | 56 | 81 | 82 | 2850 | 35 |
| 23 | 80 | 64 | 153 | >20550 | >11134 |
| 24 | 35 | 60 | 76 | 10000 | 132 |
| 25 | 10 | 23 | 11 | 7150 | 624 |
| 26 | 22 | 20 | 46 | 2450 | 54 |
| 27 | 95 | 118 | 205 | >21000 | >102 |
| 28 | 146 | 305 | 410 | 12250 | 30 |
| 29 | 62 | 41 | 36 | 4150 | 115 |
| 30 | 344 | 170 | 393 | >21500 | >55 |

| Example No. | 1) hP2X3 IC$_{50}$ [nM] (1321N1) | 2) hP2X3 IC$_{50}$ [nM] (CHO) | 3) hP2X3 IC$_{50}$ [nM] (1321N1) | 4) hP2X2/3 IC$_{50}$ [nM] (1321N1) | hP2X23/hP2X3* Selectivity (1321N1) |
|---|---|---|---|---|---|
| 31 | 130 | 120 | 277 | >32000 | >116 |
| 32 | 139 | 121 | 170 | 12000 | 71 |
| 33 | 276 | 165 | 297 | >21500 | >72 |
| 34 | 4 | nd | nd | nd | nd |
| 35 | 12 | 20 | 16 | 5650 | 353 |
| 36 | 34 | 44 | 57 | >20950 | >368 |
| 37 | 82 | 135 | 200 | >32000 | >160 |
| 38 | 161 | 175 | 627 | >21000 | >34 |
| 39 | 14 | 29 | 25 | 7550 | 308 |
| 40 | 20 | 26 | 31 | >23500 | >758 |
| 41 | 55 | 51 | 82 | >32000 | >393 |
| 42 | 35 | nd | nd | nd | nd |
| 43 | 19 | 20 | 31 | 6500 | 213 |
| 44 | 16 | 39 | 34 | 8200 | 241 |
| 45 | 377 | 394 | 370 | >32000 | >86 |
| 46 | 28 | 59 | 36 | 14000 | 385 |
| 47 | 1221 | 1100 | nd | nd | nd |
| 48 | 182 | 555 | 263 | 8100 | 31 |
| 49 | 23 | 62 | 33 | 3900 | 119 |
| 50 | 117 | 215 | 155 | 8700 | 56 |
| 51 | 311 | 160 | 253 | 11550 | 46 |
| 52 | 52 | 43 | 71 | >23000 | >324 |
| 53 | 133 | 195 | 200 | >22000 | >110 |
| 54 | 215 | 155 | 263 | >32000 | >122 |
| 55 | 104 | 195 | 117 | 10800 | 93 |
| 56 | nd | 73 | 185 | 9950 | 54 |
| 57 | nd | 125 | 265 | >32000 | >121 |
| 58 | nd | 24 | 36 | 9850 | 277 |
| 59 | nd | 83 | 145 | 13000 | 90 |
| 60 | nd | 105 | 480 | >19800 | >41 |
| 61 | nd | 695 | 1933 | >23000 | >12 |
| 62 | nd | 55 | 240 | 5150 | 21 |
| 63 | nd | 355 | 370 | 7400 | 20 |
| 64 | nd | 430 | 433 | >32000 | >74 |
| 65 | nd | 200 | 207 | 10500 | 51 |
| 66 | nd | 81 | 56 | 5450 | 98 |
| 67 | nd | 185 | 217 | 6350 | 29 |
| 68 | nd | 17 | 10 | 1665 | 160 |
| 69 | nd | 8 | 4 | 1700 | 447 |
| 70 | nd | 16 | 36 | 1800 | 51 |
| 71 | nd | 111 | 125 | >23000 | >184 |
| 72 | nd | 120 | 235 | >32000 | >136 |
| 73 | nd | 122 | 104 | 9500 | 91 |
| 74 | nd | 570 | 437 | >32000 | >73 |
| 75 | nd | 29 | 89 | 4400 | 50 |
| 76 | nd | 470 | 1667 | >21500 | >13 |
| 77 | nd | 102 | 185 | 9050 | 49 |
| 78 | nd | 21 | 62 | 6100 | 98 |
| 79 | nd | 94 | 61 | 4800 | 79 |
| 80 | nd | 32 | 63 | 1955 | 31 |
| 81 | nd | 103 | 42 | 2600 | 61 |
| 82 | nd | 6 | 8 | 1875 | 239 |
| 83 | nd | 370 | 665 | >32000 | >48 |
| 84 | nd | 1403 | nd | nd | nd |
| 85 | nd | 4 | 6 | 1950 | 328 |
| 86 | nd | 70 | 140 | 2350 | 17 |
| 87 | nd | 1645 | nd | nd | nd |
| 88 | nd | 115 | 56 | >23500 | >423 |
| 89 | nd | 64 | 135 | 6550 | 49 |
| 90 | nd | 94 | 130 | 3450 | 27 |
| 91 | nd | 27 | 33 | 1900 | 58 |
| 92 | nd | 64 | 26 | 5050 | 192 |
| 93 | nd | 6 | 8 | 2350 | 295 |
| 94 | nd | 290 | 410 | >23000 | >56 |
| 95 | nd | 178 | 273 | >22500 | >82 |
| 96 | nd | 20 | 26 | 8800 | 345 |
| 97 | nd | 66 | 47 | 9750 | 207 |
| 98 | nd | 8 | 12 | 2600 | 211 |
| 99 | nd | 21 | 15 | 9100 | 607 |
| 100 | nd | 52 | 20 | 4850 | 243 |
| 101 | nd | 28 | 13 | 6950 | 535 |
| 102 | nd | 114 | 81 | >22500 | >278 |
| 103 | nd | 143 | nd | nd | nd |
| 104 | nd | 69 | 120 | >32000 | >267 |
| 105 | nd | 78 | 92 | >32000 | >348 |
| 106 | nd | 69 | 46 | 10450 | 227 |
| 107 | nd | 18 | 17 | 5000 | 294 |
| 108 | nd | 18 | 16 | 3200 | 200 |
| 109 | nd | 133 | 280 | >32000 | >114 |
| 110 | nd | 7 | 12 | 3050 | 254 |
| 111 | nd | 225 | nd | nd | nd |
| 112 | nd | 17 | 11 | 2550 | 232 |
| 113 | nd | 113 | nd | nd | nd |
| 114 | nd | 17 | 76 | 7550 | 99 |
| 115 | nd | 205 | nd | nd | nd |
| 116 | nd | 585 | nd | nd | nd |
| 117 | nd | 27 | nd | 6150 | nd |
| 118 | nd | 131 | nd | nd | nd |
| 119 | nd | 470 | nd | nd | nd |
| 120 | nd | 5 | nd | 345 | nd |
| 121 | nd | 51 | nd | 1157 | nd |
| 122 | nd | 94 | nd | nd | nd |
| 123 | nd | 21 | nd | nd | nd |
| 124 | nd | 10 | nd | nd | nd |
| 125 | nd | 240 | nd | nd | nd |
| 126 | nd | 57 | nd | nd | nd |
| 127 | nd | 43 | nd | nd | nd |
| 129 | nd | 53 | nd | nd | nd |
| 130 | nd | 14 | nd | nd | nd |
| 131 | nd | 14 | nd | nd | nd |
| 132 | nd | 18 | nd | nd | nd |
| 133 | nd | 22 | nd | nd | nd |
| 135 | 40 | 59 | 119 | 6850 | 58 |
| 136 | nd | 56 | nd | nd | nd |
| 137 | nd | 155 | nd | nd | nd |
| 138 | 56 | 32 | 86 | 9150 | 107 |
| 139 | 237 | 420 | 400 | >32000 | >80 |
| 140 | 57 | 55 | 115 | >20900 | >183 |
| 141 | 125 | nd | nd | nd | nd |
| 142 | nd | 11 | 7 | 1140 | 165 |
| 143 | nd | 20 | 34 | 6600 | 197 |
| 144 | nd | 36 | nd | nd | nd |
| 145 | nd | 33 | nd | nd | nd |
| 146 | nd | 97 | 124 | 6950 | 56 |
| 147 | nd | 225 | nd | nd | nd |
| 148 | nd | 225 | nd | nd | nd |
| 149 | nd | 11 | 13 | 2115 | 169 |
| 150 | nd | 12 | 16 | 2250 | 139 |
| 151 | nd | 6 | 5 | 580 | 106 |
| 152 | nd | 9 | 4 | 1460 | 328 |
| 153 | nd | 10 | 6 | 2350 | 408 |
| 154 | nd | 21 | 8 | 765 | 96 |
| 155 | nd | 19 | 4 | 3850 | 987 |
| 156 | nd | 12 | 4 | 295 | 78 |
| 157 | nd | 26 | 54 | >32000 | >593 |
| 158 | nd | 10 | 3 | 1400 | 424 |
| 159 | nd | 13 | 3 | 1800 | 581 |
| 160 | nd | 16 | 6 | 2200 | 367 |
| 161 | nd | 24 | nd | 1350 | nd |
| 162 | nd | 6 | nd | 1200 | nd |
| 163 | nd | 398 | nd | nd | nd |
| 164 | nd | 20 | nd | 3700 | nd |
| 165 | nd | 13 | nd | 1460 | nd |
| 166 | nd | 5 | nd | nd | nd |
| 167 | nd | 36 | 18 | 2300 | 128 |
| 168 | nd | 17 | 9 | 2350 | 250 |
| 169 | nd | 108 | 120 | >20750 | >173 |
| 170 | nd | 59 | 120 | >20400 | >170 |
| 171 | nd | 27 | 33 | 4900 | 148 |
| 172 | nd | 35 | 42 | 6350 | 150 |
| 173 | nd | 58 | 104 | 8900 | 85 |
| 174 | nd | 59 | nd | nd | nd |
| 175 | nd | 73 | 37 | 6950 | 190 |
| 176 | nd | 88 | 68 | 7700 | 114 |
| 177 | nd | 30 | 29 | 11500 | 397 |
| 178 | nd | 14 | 2 | 2200 | 917 |
| 179 | nd | 120 | nd | nd | nd |
| 180 | nd | 175 | 170 | >32000 | >188 |

| Example No. | 1) hP2X3 IC$_{50}$ [nM] (1321N1) | 2) hP2X3 IC$_{50}$ [nM] (CHO) | 3) hP2X3 IC$_{50}$ [nM] (1321N1) | 4) hP2X2/3 IC$_{50}$ [nM] (1321N1) | hP2X23/ hP2X3* Selectivity (1321N1) |
|---|---|---|---|---|---|
| 181 | nd | 63 | 32 | 5550 | 173 |
| 182 | nd | 109 | 165 | >32000 | >194 |
| 183 | nd | 23 | 20 | 2300 | 118 |
| 184 | nd | 38 | 46 | 3200 | 70 |
| 185 | nd | 22 | 40 | 3350 | 84 |
| 186 | nd | 124 | 1850 | >32000 | >17 |
| 187 | nd | 21 | 21 | 2300 | 112 |
| 188 | nd | 91 | 120 | >32000 | >267 |
| 189 | nd | 35 | 81 | >23500 | >291 |
| 190 | nd | 10 | 16 | 5900 | 361 |
| 191 | nd | 29 | 27 | >32000 | >1199 |
| 192 | nd | 56 | 37 | >19600 | >530 |
| 193 | nd | 155 | 125 | >22500 | >180 |
| 194 | nd | 18 | 9 | 3200 | 368 |
| 195 | nd | 20 | 22 | 8900 | 399 |
| 196 | nd | 10 | 15 | 4150 | 277 |
| 197 | nd | 19 | 34 | 9800 | 291 |
| 198 | nd | 35 | 16 | 9300 | 581 |
| 199 | nd | 11 | 5 | 7000 | 1321 |
| 200 | nd | 44 | 38 | 3950 | 105 |
| 201 | nd | 37 | nd | 3875 | nd |
| 202 | nd | 135 | nd | nd | nd |
| 203 | nd | 25 | nd | nd | nd |
| 204 | nd | 36 | nd | nd | nd |
| 205 | nd | 17 | nd | 5000 | nd |
| 206 | nd | 47 | nd | nd | nd |
| 207 | nd | 17 | nd | 2675 | nd |
| 208 | nd | 28 | nd | nd | nd |
| 209 | nd | 123 | nd | nd | nd |
| 210 | nd | 28 | nd | nd | nd |
| 211 | nd | 26 | nd | nd | nd |
| 212 | nd | 22 | nd | nd | nd |
| 213 | nd | 93 | nd | nd | nd |
| 214 | nd | 22 | nd | 6450 | nd |
| 215 | nd | 63 | nd | nd | nd |
| 216 | nd | 20 | nd | 5600 | nd |
| 217 | nd | 70 | nd | nd | nd |
| 218 | nd | 15 | nd | 11467 | nd |
| 219 | nd | 180 | nd | nd | nd |
| 220 | nd | 45 | nd | nd | nd |
| 221 | nd | 30 | nd | nd | nd |
| 222 | nd | 15 | nd | 1350 | nd |
| 223 | nd | 23 | 56 | 8925 | 158 |
| 224 | nd | 145 | nd | nd | nd |
| 225 | nd | 37 | 67 | >32000 | >481 |
| 226 | nd | 22 | 39 | 3050 | 78 |
| 227 | nd | 24 | 71 | 9300 | 132 |
| 228 | nd | 95 | 20 | >23500 | >1175 |
| 229 | nd | 39 | 27 | >32000 | >1185 |
| 230 | nd | 115 | nd | nd | nd |
| 231 | nd | 95 | nd | >23500 | nd |
| 232 | nd | 53 | nd | nd | nd |
| 233 | nd | 335 | 1063 | >32000 | >30 |
| 234 | nd | 125 | 370 | >32000 | >86 |
| 235 | nd | 155 | 340 | >66000 | >194 |
| 236 | nd | 615 | 1280 | >32000 | >25 |
| 237 | nd | 1950 | nd | nd | nd |
| 238 | nd | 550 | 650 | >32000 | >49 |
| 239 | nd | 220 | 650 | >32000 | >49 |
| 240 | nd | 628 | 1267 | >32000 | >25 |
| 241 | nd | 625 | nd | nd | nd |
| 242 | nd | 585 | nd | nd | nd |
| 243 | nd | 230 | nd | nd | nd |
| 244 | nd | 330 | 280 | 7900 | 28 |
| 245 | nd | 425 | 345 | >21000 | >61 |
| 246 | nd | 830 | 2200 | >32000 | >15 |
| 247 | nd | 360 | 937 | >32000 | >34 |
| 248 | nd | 185 | 740 | >32000 | >43 |
| 249 | nd | 305 | 109 | 9200 | 85 |
| 250 | nd | 162 | 118 | 4300 | 36 |
| 251 | nd | 235 | 195 | >32000 | >164 |
| 252 | nd | 460 | 350 | >32000 | >91 |
| 253 | nd | 493 | 793 | >32000 | >40 |
| 254 | nd | 1153 | nd | nd | nd |
| 255 | nd | 400 | 440 | 11300 | 26 |
| 256 | nd | 42 | 53 | 1590 | 30 |
| 257 | nd | 54 | 57 | 660 | 12 |
| 258 | nd | 66 | 52 | 1080 | 21 |
| 259 | nd | 33 | 71 | 1170 | 16 |
| 260 | nd | 108 | 141 | >20650 | >146 |
| 261 | nd | 41 | 39 | 5550 | 142 |
| 262 | nd | 127 | nd | nd | nd |
| 263 | nd | 35 | 25 | 4700 | 191 |
| 264 | nd | 36 | 17 | 7400 | 427 |
| 265 | nd | 533 | 470 | >32000 | >68 |
| 266 | nd | 270 | 317 | >32000 | >101 |
| 267 | nd | 557 | 325 | 8000 | 25 |
| 268 | nd | 580 | nd | nd | nd |
| 269 | nd | 1500 | nd | nd | nd |
| 270 | nd | 29 | 57 | 6650 | 118 |
| 271 | nd | 81 | 36 | >20500 | >569 |
| 272 | nd | 433 | 610 | >32000 | >52 |
| 273 | nd | 565 | nd | nd | nd |
| 274 | nd | 187 | 125 | >32000 | >256 |
| 275 | nd | 173 | 210 | >32000 | >152 |
| 276 | nd | 130 | 91 | >20200 | >223 |
| 277 | nd | 150 | 110 | 7300 | 66 |
| 278 | nd | 650 | 675 | >32000 | >47 |
| 279 | nd | 210 | 270 | >23000 | >85 |
| 280 | nd | 57 | nd | nd | nd |
| 281 | nd | 42 | nd | nd | nd |
| 282 | nd | 110 | 323 | >32000 | >99 |
| 283 | nd | 165 | 347 | >32000 | >92 |
| 284 | nd | 57 | 47 | 9350 | 201 |
| 285 | nd | 110 | 143 | 12000 | 84 |
| 286 | nd | 22 | 33 | 8200 | 248 |
| 287 | nd | 32 | 48 | 1800 | 38 |
| 289 | nd | 245 | 587 | >32000 | >55 |
| 290 | nd | 115 | 105 | 4650 | 44 |
| 291 | nd | 415 | nd | nd | nd |
| 292 | nd | 112 | 120 | >32000 | >267 |
| 293 | nd | 240 | nd | nd | nd |
| 294 | nd | 247 | nd | nd | nd |

*for selectivity calculations the data in column 4) were used for hP2X2/3 and the data in column 3) for hP2X3

The invention claimed is:

1. A compound of formula (I):

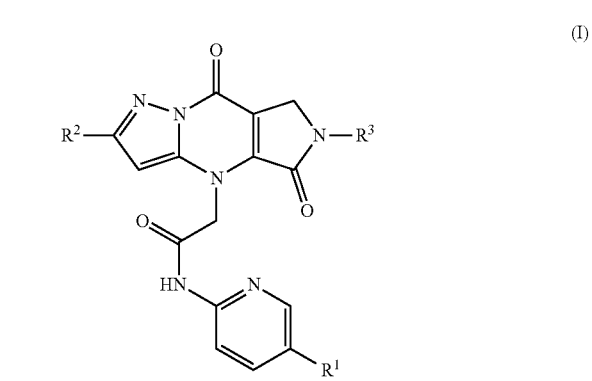

wherein

R$^1$ is H, C$_1$-C$_6$-alkyl, C$_3$-C$_5$-cycloalkyl, —(C$_1$-C$_3$-alkyl)-(C$_3$-C$_5$-cycloalkyl) or halogen, wherein said C$_1$-C$_6$-alkyl, C$_3$-C$_5$-cycloalkyl and —(C$_1$-C$_3$-alkyl)-(C$_3$-C$_5$-cycloalkyl) are optionally substituted with one or more fluorine atoms;

$R^2$ is
- H,
- —OH,
- halogen,
- —CN,
- —CO$_2$H,
- —C(O)R$^5$,
- —C(O)OR$^5$,
- —C(O)NH$_2$,
- —C(O)N(R$^4$)(R$^5$),
- NH$_2$,
- —N(R$^4$)(R$^5$),
- —N(R$^4$)C(O)R$^5$,
- —N(R$^4$)—C(O)OR$^5$,
- —N(R$^4$)C(O)N(R$^4$)(R$^5$),
- —N(R$^4$)SO$_2$R$^5$,
- —SO$_2$R$^8$,
- —SO$_2$NH$_2$,
- —SO$_2$N(R$^8$)(R$^9$),
- C$_1$-C$_6$-alkyl, optionally substituted with 1 to 3 substituents R$^{2a}$ which are the same or different,
- C$_2$-C$_6$-alkenyl, optionally substituted with 1 to 3 substituents R$^{2a}$ which are the same or different,
- C$_2$-C$_6$-alkynyl, optionally substituted with 1 to 3 substituents R$^{2a}$ which are the same or different,
- C$_3$-C$_7$-cycloalkyl, optionally substituted with one or more substituents R$^{2b}$ which are the same or different,
- —OC$_1$-C$_6$-alkyl, optionally substituted with 1 to 3 substituents R$^{2a}$ which are the same or different,
- —OC$_3$-C$_7$-cycloalkyl, optionally substituted with one or more substituents R$^{2b}$ which are the same or different,
- 4- to 6-membered heterocycloalkyl, wherein said 4- to 6-membered heterocycloalkyl contains 1 or 2 heteroatoms or heteroatom-containing groups independently selected from the group consisting of N, NH, N(R$^{2c}$), O, S, SO and SO$_2$, and wherein said 4- to 6-membered heterocycloalkyl is optionally substituted at one or more carbon atoms with 1 to 4 substituents R$^{2d}$ which are the same or different, and wherein optionally in said 4- to 6-membered heterocycloalkyl one —CH$_2$— group adjacent to a nitrogen atom, if present, is replaced by a —C(=O)— group,
- 5- to 6-membered heterocycloalkenyl, wherein said 5- to 6-membered heterocycloalkenyl contains 1 or 2 heteroatoms or heteroatom-containing groups independently selected from the group consisting of N, NH, N(R$^{2c}$), O, S, SO and SO$_2$, and wherein said 5- to 6-membered heterocycloalkenyl is optionally substituted at one or more carbon atoms with 1 to 4 substituents R$^{2d}$ which are the same or different, and wherein optionally in said 5- to 6-membered heterocycloalkenyl one —CH$_2$— group adjacent to a nitrogen atom, if present, is replaced by a —C(=O)— group,
- 6- to 9-membered heterobicycloalkyl, wherein said 6- to 9-membered heterobicycloalkyl contains 1 or 2 heteroatoms or heteroatom-containing groups independently selected from the group consisting of N, NH, N(R$^{2c}$), O, S, SO and SO$_2$, and wherein said 6- to 9-membered heterobicycloalkyl is optionally substituted at one or more carbon atoms with 1 to 4 substituents R$^{2d}$ which are the same or different, and wherein optionally in said 6- to 9-membered heterobicycloalkyl one —CH$_2$— group adjacent to a nitrogen atom, if present, is replaced by a —C(=O)— group,
- phenyl, optionally substituted with 1 to 3 substituents R$^{2d}$ which are the same or different, or
- 5- or 6-membered heteroaryl, wherein said 5-membered heteroaryl contains 1, 2 or 3 heteroatoms or heteroatom-containing groups independently selected from the group consisting of S, N, NH, N(R$^{2c}$) and O, and wherein said 6-membered heteroaryl contains 1 or 2 N, and wherein said 5- or 6-membered heteroaryl is optionally substituted at one or more carbon atoms with 1 to 3 substituents R$^{2d}$ which are the same or different;

$R^{2a}$ is
- C$_3$-C$_5$-cycloalkyl, optionally substituted with 1 to 3 substituents R$^{10}$ which are the same or different,
- F,
- Cl,
- OH,
- O(R$^6$),
- —CN,
- —C(O)NH$_2$,
- —C(O)N(R$^4$)(R$^5$),
- —N(R$^4$)(R$^5$),
- —N(R$^4$)C(O)R$^5$,
- 4- to 6-membered heterocycloalkyl containing 1 or 2 heteroatoms or heteroatom-containing groups independently selected from the group consisting of N, NH, N(R$^7$), O, S, SO and SO$_2$, and wherein said 4- to 6-membered heterocycloalkyl is optionally substituted at one or more carbon atoms with 1 to 4 substituents R$^{10}$ which are the same or different, and wherein optionally in said 4- to 6-membered heterocycloalkyl one —CH$_2$— group adjacent to a nitrogen atom, if present, is replaced by a —C(=O)— group,
- 5- to 6-membered heterocycloalkenyl containing 1 or 2 heteroatoms or heteroatom-containing groups independently selected from the group consisting of N, NH, N(R$^7$), O, S, SO and SO$_2$, and wherein said 5- to 6-membered heterocycloalkenyl is optionally substituted at one or more carbon atoms with 1 to 4 substituents R$^{10}$ which are the same or different, and wherein optionally in said 5- to 6-membered heterocycloalkenyl one —CH$_2$— group adjacent to a nitrogen atom, if present, is replaced by a —C(=O)— group,
- 6- to 9-membered heterobicycloalkyl containing 1 or 2 heteroatoms or heteroatom-containing groups independently selected from the group consisting of N, NH, N(R$^7$), O, S, SO and SO$_2$, and wherein said 6- to 9-membered heterobicycloalkyl is optionally substituted at one or more carbon atoms with 1 to 4 substituents R$^{10}$ which are the same or different, and wherein optionally in said 6- to 9-membered heterobicycloalkyl one —CH$_2$— group adjacent to a nitrogen atom, if present, is replaced by a —C(=O)— group, or
- 5- or 6-membered heteroaryl wherein said 5-membered heteroaryl contains 1, 2 or 3 heteroatoms or heteroatom-containing groups independently selected from the group consisting of S, N, NH, N(R$^7$) and O, and wherein said 6-membered heteroaryl contains 1 or 2 N, and wherein said 5- or 6-membered heteroaryl is optionally substituted at one or more carbon atoms with 1 to 3 substituents R$^{10}$ which are the same or different;

$R^{2b}$ is $C_1$-$C_4$-alkyl, Cl, F, OH, —C(O)N($R^4$)($R^5$), N($R^4$)($R^5$), —N($R^4$)C(O)$R^5$ or 4-to 6-membered heterocycloalkyl containing 1 or 2 heteroatoms or heteroatom-containing groups independently selected from the group consisting of NH, N, N($R^7$), O and $SO_2$, and wherein said $C_1$-$C_4$-alkyl and 4- to 6-membered heterocycloalkyl are optionally substituted at one or more carbon atoms with 1 to 4 substituents $R^{10}$ which are the same or different;

$R^{2c}$ is $C_1$-$C_4$-alkyl, $C_3$-$C_5$-cycloalkyl, —($C_1$-$C_3$-alkyl)-($C_3$-$C_5$-cycloalkyl), —C(O)$R^5$, —C(O)O$R^5$, —$SO_2R^8$, or 4- to 6-membered heterocycloalkyl containing 1 or 2 heteroatoms or heteroatom-containing groups independently selected from the group consisting of N, NH, N($R^7$), O and $SO_2$; and
  wherein said $C_1$-$C_4$-alkyl, $C_3$-$C_5$-cycloalkyl, ($C_1$-$C_3$-alkyl)-($C_3$-$C_5$-cycloalkyl) and 4-to 6-membered heterocycloalkyl are optionally substituted at one or more carbon atoms with 1 to 4 substituents $R^{10}$ which are the same or different;

$R^{2d}$ is F, Cl, OH, CN, —C(O)N($R^4$)($R^5$), N($R^4$)($R^5$), —N($R^4$)C(O)$R^5$, $C_1$-$C_4$-alkyl, $C_3$-$C_5$-cycloalkyl, —O$C_1$-$C_4$-alkyl, —O$C_3$-$C_5$-cycloalkyl or 4- to 6-membered heterocycloalkyl containing 1 or 2 heteroatoms or heteroatom-containing groups selected from the group consisting of N, NH, N($R^7$), O and $SO_2$; and
  wherein said $C_1$-$C_4$-alkyl, $C_3$-$C_5$-cycloalkyl, —O$C_1$-$C_4$-alkyl, —O$C_3$-$C_5$-cycloalkyl and 4- to 6-membered heterocycloalkyl are optionally substituted at one or more carbon atoms with 1 to 4 substituents $R^{10}$ which are the same or different;

$R^3$ is
  $C_1$-$C_6$-alkyl, optionally substituted with 1 to 3 substituents $R^{3a}$ which are the same or different,
  $C_3$-$C_7$-cycloalkyl, optionally substituted with one or more substituents $R^{3b}$ which are the same or different,
  4- to 6-membered heterocycloalkyl, wherein said 4- to 6-membered heterocycloalkyl is linked through a carbon atom and contains 1 or 2 heteroatoms or heteroatom-containing groups independently selected from the group consisting of N, NH, N($R^{3c}$), O, S, SO and $SO_2$, and wherein said 4- to 6-membered heterocycloalkyl is optionally substituted at one or more carbon atoms with 1 to 4 substituents $R^{3d}$ which are the same or different,
  6- to 9-membered heterobicycloalkyl, wherein said 6- to 9-membered heterobicycloalkyl is linked through a carbon atom and contains 1 or 2 heteroatoms or heteroatom-containing groups independently selected from the group consisting of N, NH, N($R^{3c}$), O, S, SO and $SO_2$, and wherein said 6- to 9-membered heterobicycloalkyl is optionally substituted at one or more carbon atoms with 1 to 4 substituents $R^{3d}$ which are the same or different,
  phenyl, optionally substituted with 1 to 3 substituents $R^{3d}$ which are the same or different, or
  5- or 6-membered heteroaryl, wherein said 5-membered heteroaryl is linked through a carbon atom and contains 1, 2 or 3 heteroatoms or heteroatom-containing groups independently selected from the group consisting of S, N, NH, N($R^{3c}$) and O, and wherein said 6-membered heteroaryl is linked through a carbon atom and contains 1 or 2 N, and wherein said 5- or 6-membered heteroaryl is optionally substituted at one or more carbon atoms with 1 to 3 substituents $R^{3d}$ which are the same or different;

$R^{3a}$ is
  $C_3$-$C_5$-cycloalkyl, optionally substituted at one or more carbon atoms with 1 to 3 substituents $R^{10}$ which are the same or different,
  F,
  Cl,
  OH,
  O($R^6$),
  —CN,
  —C(O)$NH_2$,
  —C(O)N($R^4$)($R^5$),
  —N($R^4$)($R^5$),
  $NH_2$,
  —N($R^4$)C(O)$R^5$,
  —N($R^4$)—C(O)O$R^5$,
  4- to 6-membered heterocycloalkyl containing 1 or 2 heteroatoms or heteroatom-containing groups independently selected from the group consisting of N, NH, N($R^7$), O, S, SO and $SO_2$, and wherein said 4- to 6-membered heterocycloalkyl is optionally substituted at one or more carbon atoms with 1 to 4 substituents $R^{10}$ which are the same or different, and wherein optionally in said 4- to 6-membered heterocycloalkyl one —$CH_2$— group adjacent to a nitrogen atom, if present, is replaced by a —C(=O)— group,
  5- to 6-membered heterocycloalkenyl containing 1 or 2 heteroatoms or heteroatom-containing groups independently selected from the group consisting of N, NH, N($R^7$), O, S, SO and $SO_2$, and wherein said 5- to 6-membered heterocycloalkenyl is optionally substituted at one or more carbon atoms with 1 to 4 substituents $R^{10}$ which are the same or different, and wherein optionally in said 5- to 6-membered heterocycloalkenyl one —$CH_2$— group adjacent to a nitrogen atom, if present, is replaced by a —C(=O)— group,
  6- to 9-membered heterobicycloalkyl containing 1 or 2 heteroatoms or heteroatom-containing groups independently selected from the group consisting of N, NH, N($R^7$), O and $SO_2$, and wherein said 6- to 9-membered heterobicycloalkyl is optionally substituted at one or more carbon atoms with 1 to 4 substituents $R^{10}$ which are the same or different, and wherein optionally in said 6- to 9-membered heterobicycloalkyl one —$CH_2$— group adjacent to a nitrogen atom, if present, is replaced by a —C(=O)— group,
  phenyl, optionally substituted with 1 to 3 substituents $R^{10}$ which are the same or different, or
  5- or 6-membered heteroaryl, wherein said 5-membered heteroaryl contains 1, 2 or 3 heteroatoms or heteroatom-containing groups independently selected from the group consisting of S, N, NH, N($R^7$) and O, and wherein said 6-membered heteroaryl contains 1 or 2 N, and wherein said 5- or 6-membered heteroaryl is optionally substituted at one or more carbon atoms with 1 to 3 substituents $R^{10}$ which are the same or different;

$R^{3b}$ is $C_1$-$C_4$-alkyl, Cl, F, OH, —C(O)N($R^4$)($R^5$), —N($R^4$)C(O)($R^5$), —N($R^4$)($R^5$) or 4- to 6-membered heterocycloalkyl containing 1 or 2 heteroatoms or heteroatom-containing groups independently selected from the group consisting of NH, N, N($R^7$), O and $SO_2$, and wherein said $C_1$-$C_4$-alkyl and 4- to 6-membered heterocycloalkyl are optionally substituted with one or more substituents $R^{10}$ which are the same or different;

$R^{3c}$ is $C_1$-$C_4$-alkyl, $C_3$-$C_5$-cycloalkyl, —C(O)$R^5$, —C(O)O$R^5$, —SO$_2$$R^8$, —C(O)N($R^4$)($R^5$), or 4- to 6-membered heterocycloalkyl containing 1 or 2 heteroatoms or heteroatom-containing groups independently selected from the group consisting of N, NH, N($R^7$), O and SO$_2$; and wherein said $C_1$-$C_4$-alkyl, $C_3$-$C_5$-cycloalkyl and 4- to 6-membered heterocycloalkyl are optionally substituted with one or more substituents $R^{10}$ which are the same or different;

$R^{3d}$ is $C_1$-$C_4$-alkyl, $C_3$-$C_5$-cycloalkyl, F, Cl, OH, O($R^6$), CN, —C(O)N($R^4$)($R^5$), —N($R^4$)($R^5$), —N($R^4$)C(O)$R^5$, or 4- to 6-membered heterocycloalkyl containing 1 or 2 heteroatoms or heteroatom-containing groups independently selected from the group consisting of N, NH, N($R^7$), O and SO$_2$; and wherein said $C_1$-$C_4$-alkyl, $C_3$-$C_5$-cycloalkyl and 4- to 6-membered heterocycloalkyl are optionally substituted at one or more carbon atoms with 1 to 4 substituents $R^{10}$ which are the same or different;

$R^4$ is H, $C_1$-$C_4$-alkyl or —($C_1$-$C_3$-alkyl)$_n$-($C_3$-$C_5$-cycloalkyl), wherein said $C_1$-$C_4$-alkyl and —($C_1$-$C_3$-alkyl)$_n$($C_3$-$C_5$-cycloalkyl) are optionally substituted with OH or 1 to 5 fluorine atoms;

$R^5$ is
$C_1$-$C_6$-alkyl, optionally substituted with 1 to 3 substituents $R^{5a}$ which are the same or different,
$C_3$-$C_6$-cycloalkyl, optionally substituted with 1 to 3 substituents $R^{5b}$ which are the same or different,
—($C_1$-$C_3$-alkyl)$_n$-(4- to 6-membered heterocycloalkyl), wherein said 4- to 6-membered heterocycloalkyl contains 1 or 2 heteroatoms or heteroatom-containing groups independently selected from the group consisting of NH, N, N($R^{5c}$), O, S, SO and SO$_2$, and wherein optionally in said 4- to 6-membered heterocycloalkyl one —CH$_2$— group adjacent to a nitrogen atom, if present, is replaced by a —C(=O)— group, and wherein said —($C_1$-$C_3$-alkyl)$_n$-(4- to 6-membered heterocycloalkyl) is optionally substituted at one or more carbon atoms with 1 to 4 substituents $R^{5d}$ which are the same or different;
5- to 6-membered heterocycloalkenyl, wherein said 5- to 6-membered heterocycloalkenyl contains 1 or 2 heteroatoms or heteroatom-containing groups independently selected from the group consisting of N, NH, N($R^{5c}$), O, S, SO and SO$_2$, and wherein said 5- to 6-membered heterocycloalkenyl is optionally substituted at one or more carbon atoms with 1 to 4 substituents $R^{5d}$ which are the same or different, and wherein optionally in said 5- to 6-membered heterocycloalkenyl one —CH$_2$— group adjacent to a nitrogen atom, if present, is replaced by a —C(=O)— group;
—($C_1$-$C_3$-alkyl)$_n$-(6- to 9-membered heterobicycloalkyl), wherein said 6- to 9-membered heterobicycloalkyl contains 1 or 2 heteroatoms or heteroatom-containing groups independently selected from the group consisting of NH, N, N($R^{5c}$), O, S, SO and SO$_2$, and wherein optionally in said 6- to 9-membered heterobicycloalkyl one —CH$_2$— group adjacent to a nitrogen atom, if present, is replaced by a —C(=O)— group, and wherein said —($C_1$-$C_3$-alkyl)$_n$-(6- to 9-membered heterobicycloalkyl) is optionally substituted at one or more carbon atoms with 1 to 4 substituents $R^{5d}$ which are the same or different;
—($C_1$-$C_3$-alkyl)$_n$-phenyl, optionally substituted with 1 to 3 substituents $R^{5d}$ which are the same or different, or
—($C_1$-$C_3$-alkyl)$_n$-(5- or 6-membered heteroaryl), wherein said 5-membered heteroaryl contains 1, 2 or 3 heteroatoms or heteroatom-containing groups independently selected from the group consisting of S, N, NH, N($R^{5c}$), and O, and wherein said 6-membered heteroaryl contains 1 or 2 N, and wherein said —($C_1$-$C_3$-alkyl)$_n$-(5- or 6-membered heteroaryl) is optionally substituted at one or more carbon atoms with 1 to 3 substituents $R^{5d}$ which are the same or different;

or $R^4$ and $R^5$ are taken together with the nitrogen to which $R^4$ and $R^5$ are attached to form a
4- to 6-membered heterocycloalkyl, optionally containing 1 additional heteroatom or heteroatom-containing group independently selected from the group consisting of NH, N($R^{14}$), O and SO$_2$, and wherein optionally in said 4- to 6-membered heterocycloalkyl one —CH$_2$— group adjacent to a nitrogen atom, if present, is replaced by a —C(=O)— group, and wherein said 4- to 6-membered heterocycloalkyl is optionally substituted at one or more carbon atoms with 1 to 4 substituents $R^{13}$ which are the same or different, or
6- to 9-membered heterobicycloalkyl, optionally containing 1 additional heteroatom or heteroatom-containing group independently selected from the group consisting of NH, N($R^{14}$), O and SO$_2$, and wherein said 6- to 9-membered heterobicycloalkyl is optionally substituted at one or more carbon atoms with 1 to 4 substituents $R^{13}$ which are the same or different;

$R^{5a}$ is OH, F, Cl, $C_3$-$C_5$-cycloalkyl, O$C_1$-$C_4$-alkyl, —C(O)N($R^{11}$)($R^{12}$), —N($R^{11}$)($R^{12}$) or —N($R^{11}$)C(O)$R^{12}$, wherein said $C_3$-$C_5$-cycloalkyl and O$C_1$-$C_4$-alkyl are optionally substituted with OH, 1 to 5 fluorine atoms or phenyl, optionally substituted with 1 to 3 substituents $R^{5d}$ which are the same or different;

$R^{5b}$ is OH, F, Cl, $C_1$-$C_4$-alkyl, O$C_1$-$C_4$-alkyl, —C(O)N($R^{11}$)($R^{12}$), —N($R^{11}$)($R^{12}$) or —N($R^{11}$)C(O)$R^{12}$, wherein said $C_1$-$C_4$-alkyl and O$C_1$-$C_4$-alkyl are optionally substituted with OH or 1 to 5 fluorine atoms;

$R^{5c}$ is $C_1$-$C_4$-alkyl —($C_1$-$C_3$-alkyl)$_n$-($C_3$-$C_5$-cycloalkyl), or —C(O)($R^{11}$)($R^{12}$), wherein said $C_1$-$C_4$-alkyl and —($C_1$-$C_3$-alkyl)$_n$-($C_3$-$C_5$-cycloalkyl) are optionally substituted with OH or 1 to 5 fluorine atoms;

$R^{5d}$ is OH, F, Cl, $C_1$-$C_4$-alkyl, O$C_1$-$C_4$-alkyl, $C_3$-$C_5$-cycloalkyl, —C(O)N($R^{11}$)($R^{12}$), —N($R^{11}$)($R^{12}$) or —N($R^{11}$)C(O)$R^{12}$, wherein said $C_1$-$C_4$-alkyl, O$C_1$-$C_4$-alkyl and $C_3$-$C_5$-cycloalkyl are optionally substituted with OH or 1 to 5 fluorine atoms;

$R^6$ is $C_1$-$C_6$-alkyl, —($C_1$-$C_3$-alkyl)$_n$-($C_3$-$C_5$-cycloalkyl), —($C_1$-$C_3$-alkyl)$_n$-phenyl or —($C_1$-$C_3$-alkyl)$_n$-(6-membered heteroaryl) which are optionally substituted at one or more carbon atoms with one or more substituents independently selected from the group consisting of F, Cl, OH and —O$C_1$-$C_4$-alkyl;

$R^7$ is
—C(O)$R^{12}$,
—C(O)O$R^{12}$,
$C_1$-$C_6$-alkyl, or
—($C_1$-$C_3$-alkyl)$_n$-($C_3$-$C_5$-cycloalkyl); and
wherein said $C_1$-$C_6$-alkyl and —($C_1$-$C_3$-alkyl)$_n$-($C_3$-$C_5$-cycloalkyl) are optionally substituted with one or more substituents independently selected from the group consisting of F, OH and $OC_1$-$C_4$-alkyl;

$R^8$ is
- $C_1$-$C_6$-alkyl,
- —($C_1$-$C_3$-alkyl)$_n$-($C_3$-$C_6$-cycloalkyl),
- 4- to 6-membered heterocycloalkyl, wherein said 4- to 6-membered heterocycloalkyl contains 1 or 2 heteroatoms or heteroatom-containing groups selected from the group consisting of NH, N, N($R^{14}$) and O,
- —($C_1$-$C_3$-alkyl)$_n$-phenyl, or
- —($C_1$-$C_3$-alkyl)$_n$-(5- or 6-membered heteroaryl) wherein said 5-membered heteroaryl is linked through a carbon atom and contains 1, 2 or 3 heteroatoms or heteroatom-containing groups independently selected from the group consisting of S, N, NH, N($R^{14}$) and O, and wherein said 6-membered heteroaryl is linked through a carbon atom and contains 1 or 2 N; and wherein said $C_1$-$C_6$-alkyl, —($C_1$-$C_3$-alkyl)$_n$-($C_3$-$C_5$-cycloalkyl), 4- to 6-membered heterocycloalkyl, —($C_1$-$C_3$-alkyl)$_n$-phenyl and —($C_1$-$C_3$-alkyl)$_n$-(5- or 6-membered heteroaryl) are optionally substituted on one or more carbon atoms with 1 to 4 substituents $R^{13}$ which are the same or different;

$R^9$ is H, $C_1$-$C_4$-alkyl or —($C_1$-$C_3$-alkyl)$_n$-($C_3$-$C_5$-cycloalkyl), wherein said $C_1$-$C_4$-alkyl and —($C_1$-$C_3$-alkyl)$_n$($C_3$-$C_5$-cycloalkyl) are optionally substituted with 1 to 5 fluorine atoms;

or $R^8$ and $R^9$ are taken together with the nitrogen to which $R^8$ and $R^9$ are attached to form a 4- to 6-membered heterocycloalkyl, wherein said 4- to 6-membered heterocycloalkyl optionally contains 1 additional heteroatom or heteroatom-containing groups selected from the group consisting of NH, N($R^{14}$) and O, and wherein said 4- to 6-membered heterocycloalkyl is optionally substituted at one or more carbon atoms with 1 to 4 substituents $R^{13}$ which are the same or different;

$R^{10}$ is F, Cl, $C_1$-$C_4$-alkyl, $OC_1$-$C_4$-alkyl, —C(O)N($R^{11}$)($R^{12}$), —N($R^{11}$)($R^{12}$), or —N($R^{11}$)C(O)$R^{12}$, wherein said $C_1$-$C_4$-alkyl and $OC_1$-$C_4$-alkyl are optionally substituted with 1 to 5 fluorine atoms;

$R^{11}$ is H, $C_1$-$C_4$-alkyl or —($C_1$-$C_3$-alkyl)$_n$-($C_3$-$C_5$-cycloalkyl), wherein said $C_1$-$C_4$-alkyl and —($C_1$-$C_3$-alkyl)$_n$($C_3$-$C_5$-cycloalkyl) are optionally substituted with 1 to 5 fluorine;

$R^{12}$ is $C_1$-$C_4$-alkyl, —($C_1$-$C_3$-alkyl)$_n$-($C_3$-$C_5$-cycloalkyl) or 4- to 6-membered heterocycloalkyl wherein said 4- to 6-membered heterocycloalkyl contains 1 or 2 heteroatoms or heteroatom-containing groups selected from the group consisting of NH, N, N($R^9$) and O, wherein said $C_1$-$C_4$-alkyl and —($C_1$-$C_3$-alkyl)$_n$($C_3$-$C_5$-cycloalkyl) are optionally substituted with 1 to 5 fluorine;

or $R^{11}$ and $R^{12}$ are taken together with the nitrogen to which $R^{11}$ and $R^{12}$ are attached to form a 4-to 6-membered heterocycloalkyl, wherein said 4- to 6-membered heterocycloalkyl optionally contains 1 additional heteroatom or heteroatom-containing groups selected from the group consisting of NH, N($R^{14}$) and O, and wherein said 4- to 6-membered heterocycloalkyl is optionally substituted at one or more carbon atoms with 1 to 4 substituents $R^{13}$ which are the same or different;

$R^{13}$ is F, Cl, $C_1$-$C_4$-alkyl, $C_3$-$C_5$-cycloalkyl or $OC_1$-$C_4$-alkyl, wherein said $C_1$-$C_4$-alkyl, $C_3$-$C_5$-cycloalkyl and $OC_1$-$C_4$-alkyl are optionally substituted with OH or 1 to 5 fluorine atoms;

$R^{14}$ is $C_1$-$C_4$-alkyl, —($C_1$-$C_3$-alkyl)$_n$-($C_3$-$C_5$-cycloalkyl) or —C(O)($R^{11}$)($R^{12}$), wherein said $C_1$-$C_4$-alkyl and —($C_1$-$C_3$-alkyl)$_n$($C_3$-$C_5$-cycloalkyl) are optionally substituted with OH or 1 to 5 fluorine atoms;

n is 0 or 1;

or a stereoisomer, an N-oxide, a salt thereof, or a mixture of any of the foregoing.

2. The compound according to claim 1, wherein:

$R^1$ is H, $C_1$-$C_3$-alkyl or halogen, wherein said $C_1$-$C_3$-alkyl is optionally substituted with one or more fluorine atoms;

$R^2$ is
- H,
- halogen,
- —CN,
- —$CO_2H$,
- —C(O)$OR^5$,
- —C(O)$NH_2$,
- —C(O)N($R^4$)($R^5$),
- $NH_2$,
- —N($R^4$)($R^5$),
- —N($R^4$)C(O)$R^5$,
- —N($R^4$)—C(O)$OR^5$,
- $C_1$-$C_6$-alkyl, optionally substituted with 1 to 3 substituents $R^{2a}$ which are the same or different,
- $C_3$-$C_7$-cycloalkyl, optionally substituted with one or more substituents $R^{2b}$ which are the same or different,
- —$OC_1$-$C_6$-alkyl, optionally substituted with 1 to 3 substituents $R^{2a}$ which are the same or different,
- —$OC_3$-$C_7$-cycloalkyl, optionally substituted with one or more substituents $R^{2b}$ which are the same or different,
- 4- to 6-membered heterocycloalkyl, wherein said 4- to 6-membered heterocycloalkyl contains 1 or 2 heteroatoms or heteroatom-containing groups independently selected from the group consisting of N, NH, N($R^{2c}$), O, S, SO and $SO_2$, and wherein said 4- to 6-membered heterocycloalkyl is optionally substituted at one or more carbon atoms with 1 to 4 substituents $R^{2d}$ which are the same or different,
- 5- to 6-membered heterocycloalkenyl, wherein said 5- to 6-membered heterocycloalkenyl contains 1 or 2 heteroatoms or heteroatom-containing groups independently selected from the group consisting of N, NH, N($R^{2c}$), O, S, SO and $SO_2$, and wherein said 5- to 6-membered heterocycloalkenyl is optionally substituted at one or more carbon atoms with 1 to 4 substituents $R^{2d}$ which are the same or different,
- 6- to 9-membered heterobicycloalkyl, wherein said 6- to 9-membered heterobicycloalkyl contains 1 or 2 heteroatoms or heteroatom-containing groups independently selected from the group consisting of N, NH, N($R^{2c}$), O, S, SO and $SO_2$, and wherein said 6- to 9-membered heterobicycloalkyl is optionally substituted at one or more carbon atoms with 1 to 4 substituents $R^{2d}$ which are the same or different,
- phenyl, optionally substituted with 1 to 3 substituents $R^{2d}$ which are the same or different, or 5- or 6-membered heteroaryl, wherein said 5-membered heteroaryl contains 1, 2 or 3 heteroatoms or heteroatom-containing groups independently selected from the group consisting of S, N, NH, N($R^{2c}$) and O, and wherein said 6-membered heteroaryl contains 1 or 2 N, and wherein said 5- or 6-membered heteroaryl is optionally substituted at one or more carbon atoms with 1 to 3 substituents $R^{2d}$ which are the same or different;

$R^{2a}$ is $C_3$-$C_5$-cycloalkyl, optionally substituted with 1 to 3 substituents $R^{10}$ which are the same or different,

F,

Cl,

OH,

O($R^6$),

—N($R^4$)($R^5$), or 4- to 6-membered heterocycloalkyl containing 1 or 2 heteroatoms or heteroatom-containing groups independently selected from the group consisting of N, NH, N($R^7$), O, S, SO and $SO_2$, and wherein said 4- to 6-membered heterocycloalkyl is optionally substituted at one or more carbon atoms with 1 to 4 substituents $R^{10}$ which are the same or different;

$R^{2b}$ is $C_1$-$C_4$-alkyl, Cl, F or OH, wherein said $C_1$-$C_4$-alkyl is optionally substituted at one or more carbon atoms with 1 to 3 substituents $R^{10}$ which are the same or different;

$R^{2c}$ is $C_1$-$C_4$-alkyl, $C_3$-$C_5$-cycloalkyl, —C(O)$R^5$, —C(O)O$R^5$ or —$SO_2R^8$, wherein said $C_1$-$C_4$-alkyl and $C_3$-$C_5$-cycloalkyl are optionally substituted at one or more carbon atoms with 1 to 3 substituents $R^{10}$ which are the same or different;

$R^{2d}$ is $C_1$-$C_4$-alkyl, optionally substituted at one or more carbon atoms with 1 to 3 substituents $R^{10}$ which are the same or different;

$R^3$ is $C_1$-$C_6$-alkyl, optionally substituted with 1 to 3 substituents $R^{3a}$ which are the same or different, $C_3$-$C_6$-cycloalkyl, optionally substituted with one or more substituents $R^{3b}$ which are the same or different, or 4- to 6-membered heterocycloalkyl, wherein said 4- to 6-membered heterocycloalkyl is linked through a carbon atom and contains 1 or 2 heteroatoms or heteroatom-containing groups independently selected from the group consisting of N, NH, N($R^{3c}$), O, S, SO and $SO_2$, and wherein said 4- to 6-membered heterocycloalkyl is optionally substituted at one or more carbon atoms with 1 to 4 substituents $R^{3d}$ which are the same or different, $R^{3a}$ is $C_3$-$C_5$-cycloalkyl, optionally substituted at one or more carbon atoms with 1 to 3 substituents $R^{10}$ which are the same or different,

F,

Cl,

OH,

O($R^6$),

—C(O)$NH_2$,

—C(O)N($R^4$)($R^5$),

—N($R^4$)($R^5$), $NH_2$,

—N($R^4$)C(O)$R^5$,

—N($R^4$)—C(O)O$R^5$, or 4- to 6-membered heterocycloalkyl containing 1 or 2 heteroatoms or heteroatom-containing groups independently selected from the group consisting of N, NH, N($R^7$), O, S, SO and $SO_2$, and wherein said 4- to 6-membered heterocycloalkyl is optionally substituted at one or more carbon atoms with 1 to 4 substituents $R^{10}$ which are the same or different, $R^{3b}$ is $C_1$-$C_3$-alkyl, Cl or F;

$R^{3c}$ is $C_1$-$C_4$-alkyl, $C_3$-$C_5$-cycloalkyl, —C(O)$R^5$, —C(O)O$R^5$, —$SO_2R^8$ or —C(O)N($R^4$)($R^5$); and wherein said $C_1$-$C_4$-alkyl and $C_3$-$C_5$-cycloalkyl are optionally substituted with one or more substituents $R^{10}$ which are the same or different;

$R^{3d}$ is $C_1$-$C_4$-alkyl;

$R^4$ is H or $C_1$-$C_4$-alkyl;

$R^5$ is $C_1$-$C_6$-alkyl, optionally substituted with 1 to 3 substituents $R^{5a}$ which are the same or different, $C_3$-$C_6$-cycloalkyl, optionally substituted with 1 to 3 substituents $R^{5b}$ which are the same or different, —($C_1$-$C_3$-alkyl)$_n$-phenyl, optionally substituted with 1 to 3 substituents $R^{5d}$ which are the same or different, or —($C_1$-$C_3$-alkyl)$_n$-(5- or 6-membered heteroaryl), wherein said 5-membered heteroaryl contains 1, 2 or 3 heteroatoms or heteroatom-containing groups independently selected from the group consisting of S, N, NH, N($R^{5c}$), and O, and wherein said 6-membered heteroaryl contains 1 or 2 N, and wherein said —($C_1$-$C_3$-alkyl)$_n$-(5- or 6-membered heteroaryl) is optionally substituted at one or more carbon atoms with 1 to 3 substituents $R^{5d}$ which are the same or different;

or $R^4$ and $R^5$ are taken together with the nitrogen to which $R^4$ and $R^5$ are attached to form a 4- to 6-membered heterocycloalkyl, optionally containing 1 additional heteroatom or heteroatom-containing group independently selected from the group consisting of NH, N($R^{14}$) and O, and wherein said 4- to 6-membered heterocycloalkyl is optionally substituted at one or more carbon atoms with 1 to 4 substituents $R^{13}$ which are the same or different;

$R^{5a}$ is OH, F, Cl, $C_3$-$C_5$-cycloalkyl, O$C_1$-$C_4$-alkyl, wherein said $C_3$-$C_5$-cycloalkyl and O$C_1$-$C_4$-alkyl are optionally substituted with OH, 1 to 5 fluorine atoms or phenyl, optionally substituted with 1 to 3 substituents $R^{5d}$ which are the same or different;

$R^{5b}$ is OH, F, Cl, $C_1$-$C_4$-alkyl or O$C_1$-$C_4$-alkyl;

$R^{5c}$ is $C_1$-$C_4$-alkyl;

$R^{5d}$ is OH, F, Cl, $C_1$-$C_4$-alkyl or O$C_1$-$C_4$-alkyl;

$R^6$ is $C_1$-$C_6$-alkyl, —($C_1$-$C_3$-alkyl)$_n$-($C_3$-$C_5$-cycloalkyl) or —($C_1$-$C_3$-alkyl)$_n$-phenyl;

$R^7$ is

—C(O)$R^{12}$,

—C(O)O$R^{12}$, $C_1$-$C_6$-alkyl, or

—($C_1$-$C_3$-alkyl)$_n$-($C_3$-$C_5$-cycloalkyl); and wherein said $C_1$-$C_6$-alkyl and —($C_1$-$C_3$-alkyl)$_n$-($C_3$-$C_5$-cycloalkyl) are optionally substituted with one or more fluorine atoms;

$R^8$ is $C_1$-$C_3$-alkyl, optionally substituted at one or more carbon atoms with 1 to 3 substituents $R^{13}$ which are the same or different;

$R^9$ is H or $C_1$-$C_3$-alkyl;

or $R^8$ and $R^9$ are taken together with the nitrogen to which $R^8$ and $R^9$ are attached to form a 4- to 6-membered heterocycloalkyl, wherein said 4- to 6-membered heterocycloalkyl optionally contains 1 additional heteroatom or heteroatom-containing groups selected from the group consisting of NH, $N(R^{14})$ and O;
$R^{10}$ is F, Cl, $C_1$-$C_3$-alkyl or $OC_1$-$C_3$-alkyl;
$R^{11}$ is H or $C_1$-$C_3$-alkyl;
$R^{12}$ is $C_1$-$C_4$-alkyl;
or
$R^{11}$ and $R^{12}$ are taken together with the nitrogen to which $R^{11}$ and $R^{12}$ are attached to form a 4- to 6-membered heterocycloalkyl, wherein said 4- to 6-membered heterocycloalkyl optionally contains 1 additional heteroatom or heteroatom-containing groups selected from the group consisting of NH, $N(R^{14})$ and O;
$R^{13}$ is F, Cl or $C_1$-$C_3$-alkyl;
$R^{14}$ is $C_1$-$C_3$-alkyl;
n is 0;
or a stereoisomer, an N-oxide, a salt thereof, or a mixture of any of the foregoing.

3. The compound according to claim 1, wherein:
$R^1$ is H, F, Cl, Br or methyl;
$R^2$ is
H,
Br,
—CN,
—$CO_2H$,
—$C(O)OR^5$,
—$C(O)N(R^4)(R^5)$,
$NH_2$,
—$N(R^4)(R^5)$,
—$N(R^4)C(O)R^5$,
—$N(R^4)$-$C(O)OR^5$,
$C_1$-$C_4$-alkyl, optionally substituted with 1 to 3 substituents $R^{2a}$ which are the same or different,
$C_3$-$C_6$-cycloalkyl,
5- to 6-membered heterocycloalkyl, wherein said 5- to 6-membered heterocycloalkyl contains 1 heteroatom or heteroatom-containing group independently selected from the group consisting of NH, $N(R^{2c})$ and O,
5- to 6-membered heterocycloalkenyl, wherein said 5- to 6-membered heterocycloalkenyl contains 1 heteroatom-containing group $N(R^{2c})$,
phenyl, optionally substituted with 1 to 3 substituents $R^{2d}$ which are the same or different, or
6-membered heteroaryl, containing 1 N and optionally substituted with 1 substituent $R^{2d}$;
$R^{2a}$ is
F,
OH,
$O(R^6)$,
$N(R^4)(R^5)$, or
6-membered heterocycloalkyl containing 1 O atom;
$R^{2c}$ is methyl, cyclobutyl, —$C(O)R^5$, —$C(O)OR^5$ or —$SO_2R^8$;
$R^{2d}$ is methyl;
$R^3$ is
$C_1$-$C_5$-alkyl, optionally substituted with 1 substituent $R^{3a}$,
$C_4$-$C_5$-cycloalkyl, or
4- to 6-membered heterocycloalkyl, wherein said 4- to 6-membered heterocycloalkyl is linked through a carbon atom and contains 1 heteroatom or heteroatom-containing group selected from the group consisting of NH, $N(R^{3c})$ and O, $R^{3a}$ is
cyclopropyl,
OH,
$O(R^6)$,
—$C(O)N(R^4)(R^5)$,
—$N(R^4)(R^5)$,
$NH_2$,
—$N(R^4)$—$C(O)OR^5$, or
5- to 6-membered heterocycloalkyl containing 1 or 2 heteroatoms or heteroatom-containing groups independently selected from the group consisting of N, NH, $N(R^7)$ and O,
$R^{3a}$ is methyl, cyclobutyl, —$C(O)R^5$, —$C(O)OR^5$, —$SO_2R^8$ or —$C(O)N(R^4)(R^5)$;
$R^4$ is H or methyl;
$R^5$ is
$C_1$-$C_6$-alkyl, optionally substituted with 1 to 2 substituents $R^{5a}$ which are the same or different,
$C_3$-$C_5$-cycloalkyl,
phenyl, optionally substituted with 1 substituent $R^{5d}$, or
5-membered heteroaryl containing 1, 2 or 3 heteroatoms or heteroatom-containing groups independently selected from the group consisting of N and NH;
or
$R^4$ and $R^5$ are taken together with the nitrogen to which $R^4$ and $R^5$ are attached to form a
4- to 6-membered heterocycloalkyl, optionally containing 1 additional heteroatom or heteroatom-containing group independently selected from the group consisting of $N(R^{14})$ and O;
$R^{5a}$ is OH, F, cyclopropyl or methoxy, wherein said methoxy is optionally substituted with phenyl;
$R^{5d}$ is F;
$R^6$ is methyl or —$CH_2$-phenyl;
$R^7$ is
—$C(O)R^{12}$,
—$C(O)OR^{12}$,
$C_1$-$C_3$-alkyl, optionally substituted with one to three F, or
$C_3$-$C_4$-cycloalkyl;
$R^8$ is $C_1$-$C_3$-alkyl, optionally substituted at one carbon atom with 1 to 3 substituents $R^{13}$;
$R^{12}$ is $C_1$-$C_4$-alkyl;
$R^{13}$ is F;
$R^{14}$ is methyl;
n is 0;
or a stereoisomer, an N-oxide, a salt thereof, or a mixture of any of the foregoing.

4. The compound according to claim 1, wherein:
$R^1$ is F, Cl or methyl;
or a stereoisomer, an N-oxide, a salt thereof, or a mixture of any of the foregoing.

5. The compound according to claim 1, which is selected from the group consisting of:
2-(2,6-diethyl-5,8-dioxo-5,6,7,8-tetrahydro-4H-pyrazolo [1,5-a]pyrrolo[3,4-d]pyrimidin-4-yl)-N-(5-fluoropyridin-2-yl)acetamide,
2-(2-ethyl-6-methyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide,
2-{2-cyano-6-[2-(morpholin-4-yl)ethyl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide,
2-{6-[(4-fluorophenyl)methyl]-5,8-dioxo-2-(pyridin-4-yl)-5,6,7,8-tetrahydro-4H-pyrazolo [1,5-a]pyrrolo[3,4-d]pyrimidin-4-yl}-N-(5-fluoropyridin-2-yl)acetamide,
2-{5,8-dioxo-2-(pyridin-4-yl)-6-[(pyridin-2-yl)methyl]-5,6,7,8-tetrahydro-4H-pyrazolo [1,5-a]pyrrolo[3,4-d] pyrimidin-4-yl}-N-(5-fluoropyridin-2-yl)acetamide, 2-{5,8-dioxo-2-(pyridin-4-yl)-6-[(pyridin-3-yl)methyl]-5,6,7,8-tetrahydro-4H-pyrazolo [1,5-a]pyrrolo[3,4-d]pyrimidin-4-yl}-N-(5-fluoropyridin-2-yl)acetamide, N-(5-fluoropyridin-2-yl)-2-{6-[2-(morpholin-4-yl)ethyl]-5,8-dioxo-2-(pyridin-4-yl)-5,6,7,8-tetrahydro-4H-pyrazolo[1,5-a]pyrrolo[3,4-d]pyrimidin-4-yl}acetamide, 2-{5,8-dioxo-6-(propan-2-yl)-2-[(pyridin-2-yl)methyl]-5,6,7,8-tetrahydro-4H-pyrazolo [1,5-a]pyrrolo[3,4-d]pyrimidin-4-yl}-N-(5-fluoropyridin-2-yl)acetamide, 2-[2-tert-butyl-6-(2-hydroxyethyl)-5,8-dioxo-5,6,7,8-tetrahydro-4H-pyrazolo[1,5-a]pyrrolo[3,4-d]pyrimidin-4-yl]-N-(5-fluoropyridin-2-yl)acetamide, 2-[2-ethyl-6-(1-hydroxy-2-methylpropan-2-yl)-5,8-dioxo-5,6,7,8-tetrahydro-4H-pyrazolo [1,5-a]pyrrolo[3,4-d]pyrimidin-4-yl]-N-(5-fluoropyridin-2-yl)acetamide, 2-{2-ethyl-6-[(2S)-1-hydroxypropan-2-yl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 2-{2-tert-butyl-6-[2-(morpholin-4-yl)ethyl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 2-{2-tert-butyl-6-[2-(dimethylamino)ethyl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 4-{2-[(5-fluoropyridin-2-yl)amino]-2-oxoethyl}-6-[(2S)-1-methoxypropan-2-yl]-N,N-dimethyl-5,8-dioxo-5,6,7,8-tetrahydro-4H-pyrazolo[1,5-a]pyrrolo[3,4-d]pyrimidine-2-carboxamide, N-(5-fluoropyridin-2-yl)-2-{2-(hydroxymethyl)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}acetamide, tert-butyl 3-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-2,5-dihydro-1H-pyrrole-1-carboxylate, tert-butyl 4-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-3,6-dihydropyridine-1(2H)-carboxylate, 2-[2-(4,5-dihydrofuran-3-yl)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, 2-[2-(1,1-dioxido-3,6-dihydro-2H-thiopyran-4-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide, 2-[2-cyano-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide, 2-{2-cyano-6-[(2S)-1-methoxypropan-2-yl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 2-[5,8-dioxo-6-(propan-2-yl)-2-(pyridin-4-yl)-5,6,7,8-tetrahydro-4H-pyrazolo[1,5-a]pyrrolo[3,4-d]pyrimidin-4-yl]-N-(5-fluoropyridin-2-yl)acetamide, 2-[5,8-dioxo-2-phenyl-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, N-(5-fluoropyridin-2-yl)-2-{6-[(2S)-1-methoxypropan-2-yl]-2-(6-methylpyridin-3-yl)-5,8-dioxo-5,6,7,8-tetrahydro-4H-pyrazolo[1,5-a]pyrrolo[3,4-d]pyrimidin-4-yl}acetamide, N-(5-fluoropyridin-2-yl)-2-{6-[(2S)-1-methoxypropan-2-yl]-2-(3-methylpyridin-4-yl)-5,8-dioxo-5,6,7,8-tetrahydro-4H-pyrazolo[1,5-a]pyrrolo[3,4-d]pyrimidin-4-yl}acetamide, N-(5-fluoropyridin-2-yl)-2-{6-[(2S)-1-methoxypropan-2-yl]-2-(2-methylpyridin-4-yl)-5,8-dioxo-5,6,7,8-tetrahydro-4H-pyrazolo[1,5-a]pyrrolo[3,4-d]pyrimidin-4-yl}acetamide, N-(5-fluoropyridin-2-yl)-2-[2-(6-methylpyridin-3-yl)-5,8-dioxo-6-(propan-2-yl)-5,6,7,8-tetrahydro-4H-pyrazolo[1,5-a]pyrrolo[3,4-d]pyrimidin-4-yl]acetamide, N-(5-fluoropyridin-2-yl)-2-[2-(4-methylpyridin-3-yl)-5,8-dioxo-6-(propan-2-yl)-5,6,7,8-tetrahydro-4H-pyrazolo[1,5-a]pyrrolo[3,4-d]pyrimidin-4-yl]acetamide, 2-[2-(4,6-dimethylpyridin-3-yl)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, 2-[2-(2,6-dimethylpyridin-3-yl)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, 2-{2-(2,5-dimethylpyridin-4-yl)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide, 2-[2-(2,5-dimethylpyridin-4-yl)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, N-(5-fluoropyridin-2-yl)-2-{2-(5-methylpyridin-2-yl)-5,8-dioxo-6-[(3R)-oxolan-3-yl]-5,6,7,8-tetrahydro-4H-pyrazolo [1,5-a]pyrrolo[3,4-d]pyrimidin-4-yl}acetamide, N-(5-fluoropyridin-2-yl)-2-{2-(5-methylpyridin-2-yl)-5,8-dioxo-6-[(3S)-oxolan-3-yl]-5,6,7,8-tetrahydro-4H-pyrazolo [1,5-a]pyrrolo[3,4-d]pyrimidin-4-yl}acetamide, N-(5-fluoropyridin-2-yl)-2-{6-[(2S)-1-methoxypropan-2-yl]-2-(5-methylpyridin-2-yl)-5,8-dioxo-5,6,7,8-tetrahydro-4H-pyrazolo[1,5-a]pyrrolo[3,4-d]pyrimidin-4-yl}acetamide, N-(5-fluoropyridin-2-yl)-2-[2-(3-methylpyridin-2-yl)-5,8-dioxo-6-(propan-2-yl)-5,6,7,8-tetrahydro-4H-pyrazolo[1,5-a]pyrrolo[3,4-d]pyrimidin-4-yl]acetamide, N-(5-fluoropyridin-2-yl)-2-{6-[(2S)-1-methoxypropan-2-yl]-2-(3-methylpyridin-2-yl)-5,8-dioxo-5,6,7,8-tetrahydro-4H-pyrazolo[1,5-a]pyrrolo[3,4-d]pyrimidin-4-yl}acetamide, N-(5-fluoropyridin-2-yl)-2-[2-(5-fluoropyridin-2-yl)-5,8-dioxo-6-(propan-2-yl)-5,6,7,8-tetrahydro-4H-pyrazolo [1,5-a]pyrrolo[3,4-d]pyrimidin-4-yl]acetamide, 2-[2-(3,5-dimethylpyridin-2-yl)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, 2-[2-(cyclopropylamino)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, 2-[2-(cyclopentylamino)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, N-(5-fluoropyridin-2-yl)-2-{2-[(2-methoxyethyl)amino]-5,8-dioxo-6-(propan-2-yl)-5,6,7,8-tetrahydro-4H-pyrazolo [1,5-a]pyrrolo[3,4-d]pyrimidin-4-yl}acetamide, 2-{2-[(2,2-difluoroethyl)amino]-5,8-dioxo-6-(propan-2-yl)-5,6,7,8-tetrahydro-4H-pyrazolo [1,5-a]pyrrolo[3,4-d]pyrimidin-4-yl}-N-(5-fluoropyridin-2-yl)acetamide, 2-[5,8-dioxo-6-(propan-2-yl)-2-(propan-2-ylamino)-5,6,7,8-tetrahydro-4H-pyrazolo [1,5-a]pyrrolo[3,4-d]pyrimidin-4-yl]-N-(5-fluoropyridin-2-yl)acetamide, 2-[2-(dimethylamino)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, 2-[2-(ethylamino)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide, N-(5-fluoropyridin-2-yl)-2-[2-(methylamino)-5,8-dioxo-6-(propan-2-yl)-5,6,7,8-tetrahydro-4H-pyrazolo[1,5-a]pyrrolo[3,4-d]pyrimidin-4-yl]acetamide, 2-{2-[(cyclopropylmethyl)amino]-5,8-dioxo-6-(propan-2-yl)-5,6,7,8-tetrahydro-4H-pyrazolo [1,5-a]pyrrolo[3,4-d]pyrimidin-4-yl}-N-(5-fluoropyridin-2-yl)acetamide, 2-[2-{[2-(benzyloxy)ethyl]amino}-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, 2-{2-(dimethylamino)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide, 2-{2-(cyclopentylamino)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide, N-(5-fluoropyridin-2-yl)-2-{6-[(2S)-1-methoxypropan-2-yl]-2-(methylamino)-5,8-dioxo-5,6,7,8-tetrahydro-4H-pyrazolo[1,5-a]pyrrolo[3,4-d]pyrimidin-4-yl}acetamide, tert-butyl 3-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]azetidine-1-carboxylate, N-(5-fluoropyridin-2-yl)-2-[2-(morpholin-4-yl)-5,8-dioxo-6-(propan-2-yl)-5,6,7,8-tetrahydro-4H-pyrazolo [1,5-a]pyrrolo[3,4-d]pyrimidin-4-yl]acetamide, N-(5-fluoropyridin-2-yl)-2-[2-(4-methylpiperazin-1-yl)-5,8-dioxo-6-(propan-2-yl)-5,6,7,8-tetrahydro-4H-pyrazolo[1,5-a]pyrrolo[3,4-d]pyrimidin-4-yl]acetamide, 4-{2-[(5-fluoropyridin-2-yl)amino]-2-oxoethyl}-N,N-dimethyl-5,8-dioxo-6-(propan-2-yl)-5,6,7,8-tetrahydro-4H-pyrazolo [1,5-a]pyrrolo[3,4-d]pyrimidine-2-carboxamide, 2-[5,8-dioxo-2-(piperidin-1-ylcarbonyl)-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, N-(2,2-difluoroethyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide, N-cyclopentyl-4-{2-[(5-fluoropyridin-2-yl)amino]-2-oxoethyl}-5,8-dioxo-6-(propan-2-yl)-5,6,7,8-tetrahydro-4H-pyrazolo [1,5-a]pyrrolo[3,4-d]pyrimidine-2-carboxamide, N-tert-butyl-4-{2-[(5-fluoropyridin-2-yl)amino]-2-oxoethyl}-5,8-dioxo-6-(propan-2-yl)-5,6,7,8-tetrahydro-4H-pyrazolo [1,5-a]pyrrolo[3,4-d]pyrimidine-2-carboxamide, N-(cyclopropylmethyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide, N-(5-fluoropyridin-2-yl)-2-{2-[(4-methylpiperazin-1-yl)carbonyl]-5,8-dioxo-6-(propan-2-yl)-5,6,7,8-tetrahydro-4H-pyrazolo [1,5-a]pyrrolo[3,4-d]pyrimidin-4-yl}acetamide, 4-{2-[(5-fluoropyridin-2-yl)amino]-2-oxoethyl}-6-[(2S)-1-methoxypropan-2-yl]-N,N-dimethyl-5,8-dioxo-5,6,7,8-tetrahydro-4H-pyrazolo [1,5-a]pyrrolo[3,4-d]pyrimidine-2-carboxamide, N-(cyclopropylmethyl)-4-{2-[(5-fluoropyridin-2-yl)amino]-2-oxoethyl}-6-[(2S)-1-methoxypropan-2-yl]-5,8-dioxo-5,6,7,8-tetrahydro-4H-pyrazolo [1,5-a]pyrrolo[3,4-d]pyrimidine-2-carboxamide, N-(5-fluoropyridin-2-yl)-2-{6-[(2S)-1-methoxypropan-2-yl]-2-(morpholin-4-ylcarbonyl)-5,8-dioxo-5,6,7,8-tetrahydro-4H-pyrazolo[1,5-a]pyrrolo[3,4-d]pyrimidin-4-yl}acetamide, N-cyclopropyl-4-{2-[(5-fluoropyridin-2-yl)amino]-2-oxoethyl}-6-[(2S)-1-methoxypropan-2-yl]-5,8-dioxo-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-6-[(2S)-1-methoxypropan-2-yl]-N-methyl-5,8-dioxo-5,6,7,8-tetrahydro-4H-pyrazolo[1,5-a]pyrrolo[3,4-d]pyrimidine-2-carboxamide, 2-{2-(azetidin-1-ylcarbonyl)-6-[(2S)-1-methoxypropan-2-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide, N-(cyclopropylmethyl)-4-{2-[(5-fluoropyridin-2-yl)amino]-2-oxoethyl}-6-[(2S)-1-methoxypropan-2-yl]-N-methyl-5,8-dioxo-5,6,7,8-tetrahydro-4H-pyrazolo [1,5-a]pyrrolo[3,4-d]pyrimidine-2-carboxamide, N-cyclopropyl-4-{2-[(5-fluoropyridin-2-yl)amino]-2-oxoethyl}-6-[(2S)-1-methoxypropan-2-yl]-N-methyl-5,8-dioxo-5,6,7,8-tetrahydro-4H-pyrazolo[1,5-a]pyrrolo[3,4-d]pyrimidine-2-carboxamide, N-(2,2-difluoroethyl)-4-{2-[(5-fluoropyridin-2-yl)amino]-2-oxoethyl}-6-[(2S)-1-methoxypropan-2-yl]-5,8-dioxo-5,6,7,8-tetrahydro-4H-pyrazolo [1,5-a]pyrrolo[3,4-d]pyrimidine-2-carboxamide, N-(5-fluoropyridin-2-yl)-2-{6-[(2S)-1-methoxypropan-2-yl]-5,8-dioxo-2-(piperidin-1-ylcarbonyl)-5,6,7,8-tetrahydro-4H-pyrazolo[1,5-a]pyrrolo[3,4-d]pyrimidin-4-yl}acetamide, N-(cyclopropylmethyl)-4-{2-[(5-fluoropyridin-2-yl)amino]-2-oxoethyl}-N-methyl-5,8-dioxo-6-(propan-2-yl)-5,6,7,8-tetrahydro-4H-pyrazolo[1,5-a]pyrrolo[3,4-d]pyrimidine-2-carboxamide, N-(2-fluorophenyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-5,8-dioxo-6-(propan-2-yl)-N-(pyridin-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-N-(2-methoxyphenyl)-5,8-dioxo-6-(propan-2-yl)-5,6,7,8-tetrahydro-4H-pyrazolo[1,5-a]pyrrolo[3,4-d]pyrimidine-2-carboxamide, N-(2-chlorophenyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-N-(2-methylphenyl)-5,8-dioxo-6-(propan-2-yl)-5,6,7,8-tetrahydro-4H-pyrazolo[1,5-a]pyrrolo[3,4-d]pyrimidine-2-carboxamide, N-(2,6-difluorophenyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide, N-(3-fluorophenyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-5,8-dioxo-6-(propan-2-yl)-N-(pyridin-3-yl)-5,6,7,8-tetrahydro-4H-pyrazolo [1,5-a]pyrrolo[3,4-d]pyrimidine-2-carboxamide, N-(4-fluorophenyl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-N-(1,3-oxazol-2-yl)-5,8-dioxo-6-(propan-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-5,8-dioxo-6-(propan-2-yl)-N-(pyrimidin-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-N-(1,2-oxazol-3-yl)-5,8-dioxo-6-(propan-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-5,8-dioxo-6-(propan-2-yl)-N-(pyridazin-3-yl)-5,6,7,8-tetrahydro-4H-pyrazolo [1,5-a]pyrrolo[3,4-d]pyrimidine-2-carboxamide, N-(5-chloropyridin-2-yl)-4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-6-[(2S)-1-methoxypropan-2-yl]-N-methyl-5,8-dioxo-N-(pyridin-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-6-[(2S)-1-methoxypropan-2-yl]-N-(1,2-oxazol-3-yl)-5,8-dioxo-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-6-[(2S)-1-methoxypropan-2-yl]-5,8-dioxo-N-(pyridazin-3-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-6-[(2S)-1-methoxypropan-2-yl]-5,8-dioxo-N-(pyrimidin-2-yl)-5,6,7,8-tetrahydro-4H-pyrazolo[1,5-a]pyrrolo[3,4-d]pyrimidine-2-carboxamide, 4-{2-[(5-fluoropyridin-2-yl)amino]-2-oxoethyl}-6-[(2S)-1-methoxypropan-2-yl]-N-methyl-5,8-dioxo-N-[(pyridin-3-yl)methyl]-5,6,7,8-tetrahydro-4H-pyrazolo[1,5-a]pyrrolo[3,4-d]pyrimidine-2-carboxamide, N-(2-fluorophenyl)-4-{2-[(5-fluoropyridin-2-yl)amino]-2-oxoethyl}-6-(oxan-4-yl)-5,8-dioxo-5,6,7,8-tetrahydro-4H-pyrazolo[1,5-a]pyrrolo[3,4-d]pyrimidine-2-carboxamide, N-(2-fluorophenyl)-4-{2-[(5-fluoropyridin-2-yl)amino]-2-oxoethyl}-6-[2-(morpholin-4-yl)ethyl]-5,8-dioxo-5,6,7,8-tetrahydro-4H-pyrazolo[1,5-a]pyrrolo[3,4-d]pyrimidine-2-carboxamide, N-(2-fluorophenyl)-4-{2-[(5-fluoropyridin-2-yl)amino]-2-oxoethyl}-6-[(2S)-1-methoxypropan-2-yl]-5,8-dioxo-5,6,7,8-tetrahydro-4H-pyrazolo [1,5-a]pyrrolo[3,4-d]pyrimidine-2-carboxamide, N-(2-fluorophenyl)-4-{2-[(5-fluoropyridin-2-yl)amino]-2-oxoethyl}-5,8-dioxo-6-[(pyridin-2-yl)methyl]-5,6,7,8-tetrahydro-4H-pyrazolo [1,5-a]pyrrolo[3,4-d]pyrimidine-2-carboxamide, 2-[2-(azetidin-1-ylcarbonyl)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, 4-{2-[(5-fluoropyridin-2-yl)amino]-2-oxoethyl}-N-(3-hydroxypropyl)-5,8-dioxo-6-(propan-2-yl)-5,6,7,8-tetrahydro-4H-pyrazolo[1,5-a]pyrrolo[3,4-d]pyrimidine-2-carboxamide, N-(5-fluoropyridin-2-yl)-2-[2-(morpholin-4-ylcarbonyl)-5,8-dioxo-6-(propan-2-yl)-5,6,7,8-tetrahydro-4H-pyrazolo[1,5-a]pyrrolo[3,4-d]pyrimidin-4-yl]acetamide, tert-butyl(3R)-3-[4-{2-[(5-fluoropyridin-2-yl)amino]-2-oxoethyl}-5,8-dioxo-6-(propan-2-yl)-5,6,7,8-tetrahydro-4H-pyrazolo [1,5-a]pyrrolo[3,4-d]pyrimidin-2-yl]pyrrolidine-1-carboxylate, tert-butyl 4-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]piperidine-1-carboxylate, 2-{5,8-dioxo-6-(propan-2-yl)-2-[(3S)-tetrahydrofuran-3-yl]-5,6,7,8-tetrahydro-4H-pyrazolo [1,5-a]pyrrolo[3,4-d]pyrimidin-4-yl}-N-(5-fluoropyridin-2-yl)acetamide, 2-[2-(1,1-dioxidotetrahydro-2H-thiopyran-4-yl)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, tert-butyl 3-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]azetidine-1-carboxylate, N-(5-fluoropyridin-2-yl)-2-{2-[(2R)-1-methyl-5-oxopyrrolidin-2-yl]-5,8-dioxo-6-(propan-2-yl)-5,6,7,8-tetrahydro-4H-pyrazolo [1,5-a]pyrrolo[3,4-d]pyrimidin-4-yl}acetamide, 2-{5,8-dioxo-2-[(2-oxopyrrolidin-1-yl)methyl]-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide, 2-{2-ethyl-5,8-dioxo-6-[(2R)-pyrrolidin-2-ylmethyl]-5,6,7,8-tetrahydro-4H-pyrazolo [1,5-a]pyrrolo[3,4-d]pyrimidin-4-yl}-N-(5-fluoropyridin-2-yl)acetamide hydrochloride (1:1), 2-[5,8-dioxo-2-(piperidin-4-yl)-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide hydrochloride (1:1), 2-{5,8-dioxo-6-(propan-2-yl)-2-[(3R)-pyrrolidin-3-yl]-5,6,7,8-tetrahydro-4H-pyrazolo [1,5-a]pyrrolo[3,4-d]pyrimidin-4-yl}-N-(5-fluoropyridin-2-yl)acetamide hydrochloride (1:1), 2-{2-ethyl-5,8-dioxo-6-[(3S)-pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide hydrochloride (1:1), 2-[2-ethyl-5,8-dioxo-6-(piperidin-4-yl)-5,6,7,8-tetrahydro-4H-pyrazolo[1,5-a]pyrrolo[3,4-d]pyrimidin-4-yl]-N-(5-fluoropyridin-2-yl)acetamide hydrochloride (1:1), 2-{2-ethyl-5,8-dioxo-6-[(3S)-pyrrolidin-3-ylmethyl]-5,6,7,8-tetrahydro-4H-pyrazolo [1,5-a]pyrrolo[3,4-d]pyrimidin-4-yl}-N-(5-fluoropyridin-2-yl)acetamide hydrochloride (1:1), 2-{2-ethyl-5,8-dioxo-6-[(2R)-pyrrolidin-2-ylmethyl]-5,6,7,8-tetrahydro-4H-pyrazolo [1,5-a]pyrrolo[3,4-d]pyrimidin-4-yl}-N-(5-fluoropyridin-2-yl)acetamide hydrochloride (1:1), 2-[2-ethyl-5,8-dioxo-6-(piperidin-4-ylmethyl)-5,6,7,8-tetrahydro-4H-pyrazolo[1,5-a]pyrrolo[3,4-d]pyrimidin-4-yl]-N-(5-fluoropyridin-2-yl)acetamide hydrochloride (1:1), 2-[2-amino-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide, 2-{6-[(azetidin-3-yl)methyl]-2-ethyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide hydrogen chloride (1:1), 2-[2-(azetidin-3-yl)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide hydrogen chloride (1:1), 2-[6-(2-aminoethyl)-2-ethyl-5,8-dioxo-5,6,7,8-tetrahydro-4H-pyrazolo[1,5-a]pyrrolo[3,4-d]pyrimidin-4-yl]-N-(5-fluoropyridin-2-yl)acetamide, 2-{2-ethyl-6-[(2S)-morpholin-2-ylmethyl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 2-{2-ethyl-6-[(2R)-morpholin-2-ylmethyl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 2-{2-ethyl-6-[(3R)-morpholin-3-ylmethyl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, N-(5-fluoropyridin-2-yl)-2-{2-[(3R)-1-methylpyrrolidin-3-yl]-5,8-dioxo-6-(propan-2-yl)-5,6,7,8-tetrahydro-4H-pyrazolo[1,5-a]pyrrolo[3,4-d]pyrimidin-4-yl}acetamide, 2-{2-[(3R)-1-cyclobutylpyrrolidin-3-yl]-5,8-dioxo-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide, N-(5-fluoropyridin-2-yl)-2-[2-(1-methylpiperidin-4-yl)-5,8-dioxo-6-(propan-2-yl)-5,6,7,8-tetrahydro-4H-pyrazolo[1,5-a]pyrrolo[3,4-d]pyrimidin-4-yl]acetamide, 2-[2-(1-cyclobutylpiperidin-4-yl)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, 2-{2-ethyl-6-[(3S)-1-methylpyrrolidin-3-yl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 2-{6-[(3S)-1-cyclobutylpyrrolidin-3-yl]-2-ethyl-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 2-(2-ethyl-6-{[(2R)-4-methylmorpholin-2-yl]methyl}-5,8-dioxo-5,6,7,8-tetrahydro-4H-pyrazolo[1,5-a]pyrrolo[3,4-d]pyrimidin-4-yl)-N-(5-fluoropyridin-2-yl)acetamide, 2-(2-ethyl-5,8-dioxo-6-{[(2R)-4-(propan-2-yl)morpholin-2-yl]methyl}-5,6,7,8-tetrahydro-4H-pyrazolo[1,5-a]pyrrolo[3,4-d]pyrimidin-4-yl)-N-(5-fluoropyridin-2-yl)acetamide, 2-(6-{[(2R)-4-cyclobutylmorpholin-2-yl]methyl}-2-ethyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide, 2-(6-{[(2R)-4-cyclopropylmorpholin-2-yl]methyl}-2-ethyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide, 2-(2-ethyl-5,8-dioxo-6-{[(2R)-4-(3,3,3-trifluoropropyl)morpholin-2-yl]methyl}-5,6,7,8-tetrahydro-4H-pyrazolo[1,5-a]pyrrolo[3,4-d]pyrimidin-4-yl)-N-(5-fluoropyridin-2-yl)acetamide, 2-(2-ethyl-5,8-dioxo-6-{[(3R)-4-(propan-2-yl)morpholin-3-yl]methyl}-5,6,7,8-tetrahydro-4H-pyrazolo[1,5-a]pyrrolo[3,4-d]pyrimidin-4-yl)-N-(5-fluoropyridin-2-yl)acetamide, 2-(2-ethyl-5,8-dioxo-6-{[(3R)-4-(3,3,3-trifluoropropyl)morpholin-3-yl]methyl}-5,6,7,8-tetrahydro-4H-pyrazolo[1,5-a]pyrrolo[3,4-d]pyrimidin-4-yl)-N-(5-fluoropyridin-2-yl)acetamide, N-(5-fluoropyridin-2-yl)-2-[2-(1-methylazetidin-3-yl)-5,8-dioxo-6-(propan-2-yl)-5,6,7,8-tetrahydro-4H-pyrazolo[1,5-a]pyrrolo[3,4-d]pyrimidin-4-yl]acetamide, 2-[2-(1-acetylpiperidin-4-yl)-5,8-dioxo-6-(propan-2-yl)-5,6,7,8-tetrahydro-4H-pyrazolo [1,5-a]pyrrolo[3,4-d]pyrimidin-4-yl]-N-(5-fluoropyridin-2-yl)acetamide, 2-{2-[1-(difluoroacetyl)piperidin-4-yl]-5,8-dioxo-6-(propan-2-yl)-5,6,7,8-tetrahydro-4H-pyrazolo[1,5-a]pyrrolo[3,4-d]pyrimidin-4-yl}-N-(5-fluoropyridin-2-yl)acetamide, 2-{6-[(3S)-1-acetylpyrrolidin-3-yl]-2-ethyl-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 2-{6-[(3S)-1-(difluoroacetyl)pyrrolidin-3-yl]-2-ethyl-5,8-dioxo-5,6,7,8-tetrahydro-4H-pyrazolo[1,5-a]pyrrolo[3,4-d]pyrimidin-4-yl}-N-(5-fluoropyridin-2-yl)acetamide, 2-(6-{[(2R)-4-acetylmorpholin-2-yl]methyl}-2-ethyl-5,8-dioxo-5,6,7,8-tetrahydro-4H-pyrazolo[1,5-a]pyrrolo[3,4-d]pyrimidin-4-yl)-N-(5-fluoropyridin-2-yl)acetamide, 2-{6-[(1-acetylazetidin-3-yl)methyl]-2-ethyl-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 2-[6-(1-acetylazetidin-3-yl)-2-ethyl-5,8-dioxo-5,6,7,8-tetrahydro-4H-pyrazolo[1,5-a]pyrrolo[3,4-d]pyrimidin-4-yl]-N-(5-fluoropyridin-2-yl)acetamide, N-(5-fluoropyridin-2-yl)-2-{2-[(3R)-1-(methylsulfonyl)pyrrolidin-3-yl]-5,8-dioxo-6-(propan-2-yl)-5,6,7,8-tetrahydro-4H-pyrazolo[1,5-a]pyrrolo[3,4-d]pyrimidin-4-yl}acetamide, 2-[5,8-dioxo-6-(propan-2-yl)-2-{(3R)-1-[(2,2,2-trifluoroethyl)sulfonyl]pyrrolidin-3-yl}-5,6,7,8-tetrahydro-4H-pyrazolo[1,5-a]pyrrolo[3,4-d]pyrimidin-4-yl]-N-(5-fluoropyridin-2-yl)acetamide, 2-{2-ethyl-6-[(3S)-1-(methylsulfonyl)pyrrolidin-3-yl]-5,8-dioxo-5,6,7,8-tetrahydro-4H-pyrazolo[1,5-a]pyrrolo[3,4-d]pyrimidin-4-yl}-N-(5-fluoropyridin-2-yl)acetamide, 2-{2-ethyl-6-[1-(methanesulfonyl)azetidin-3-yl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, (3S)-3-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]-N-(propan-2-yl)pyrrolidine-1-carboxamide, N-(5-fluoropyridin-2-yl)-2-{2-[(1S)-1-hydroxyethyl]-5,8-dioxo-6-(propan-2-yl)-5,6,7,8-tetrahydro-4H-pyrazolo[1,5-a]pyrrolo[3,4-d]pyrimidin-4-yl}acetamide, N-(5-fluoropyridin-2-yl)-2-{2-[(2-hydroxyethyl)amino]-5,8-dioxo-6-(propan-2-yl)-5,6,7,8-tetrahydro-4H-pyrazolo[1,5-a]pyrrolo[3,4-d]pyrimidin-4-yl}acetamide, 2-{2-ethyl-5,8-dioxo-6-[(3S)-pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide, 2-{2-ethyl-5,8-dioxo-6-[(3S)-pyrrolidin-3-yl]-5,6,7,8-tetrahydro-4H-pyrazolo[1,5-a]pyrrolo[3,4-d]pyrimidin-4-yl}-N-(5-fluoropyridin-2-yl)acetamide, 2-{2-ethyl-5,8-dioxo-6-[(2S)-tetrahydrofuran-2-ylmethyl]-5,6,7,8-tetrahydro-4H-pyrazolo [1,5-a]pyrrolo[3,4-d]pyrimidin-4-yl}-N-(5-fluoropyridin-2-yl)acetamide, 2-{5,8-dioxo-6-(propan-2-yl)-2-[(3S)-tetrahydrofuran-3-yl]-5,6,7,8-tetrahydro-4H-pyrazolo [1,5-a]pyrrolo[3,4-d]pyrimidin-4-yl}-N-(5-fluoropyridin-2-yl)acetamide, 2-{5,8-dioxo-6-(propan-2-yl)-2-[(3S)-tetrahydrofuran-3-yl]-5,6,7,8-tetrahydro-4H-pyrazolo [1,5-a]pyrrolo[3,4-d]pyrimidin-4-yl}-N-(5-fluoropyridin-2-yl)acetamide, 2-[2-(acetylamino)-5,8-dioxo-6-(propan-2-yl)-5,6,7,8-tetrahydro-4H-pyrazolo[1,5-a]pyrrolo[3,4-d]pyrimidin-4-yl]-N-(5-fluoropyridin-2-yl)acetamide, 2,2-difluoro-N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]acetamide, N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]tetrahydro-2H-pyran-4-carboxamide, N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-2-methoxyacetamide, N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-1H-1,2,3-triazole-5-carboxamide, 2-(benzyloxy)-N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]acetamide, N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-$N^2,N^2$-dimethylglycinamide, N-[4-{2-[(5-fluoropyridin-2-yl)amino]-2-oxoethyl}-5,8-dioxo-6-(propan-2-yl)-5,6,7,8-tetrahydro-4H-pyrazolo[1,5-a]pyrrolo[3,4-d]pyrimidin-2-yl]-2-hydroxyacetamide, 2-{5,8-dioxo-6-(propan-2-yl)-2-[(propan-2-ylcarbamoyl)amino]-5,6,7,8-tetrahydro-4H-pyrazolo[1,5-a]pyrrolo[3,4-d]pyrimidin-4-yl}-N-(5-fluoropyridin-2-yl)acetamide, 2-{2-ethyl-6-[2-(morpholin-4-yl)-2-oxoethyl]-5,8-dioxo-5,6,7,8-tetrahydro-4H-pyrazolo [1,5-a]pyrrolo[3,4-d]pyrimidin-4-yl}-N-(5-fluoropyridin-2-yl)acetamide, 2-(2-ethyl-5,8-dioxo-6-{2-oxo-2-[(propan-2-yl)amino]ethyl}-5,6,7,8-tetrahydro-4H-pyrazolo [1,5-a]pyrrolo[3,4-d]pyrimidin-4-yl)-N-(5-fluoropyridin-2-yl)acetamide, N-(cyclopropylmethyl)-2-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]-N-methylacetamide, and N-cyclopropyl-2-[2-ethyl-4-{2-[(5-fluoropyridin-2-yl)amino]-2-oxoethyl}-5,8-dioxo-5,8-dihydro-4H-pyrazolo[1,5-a]pyrrolo[3,4-d]pyrimidin-6(7H)-yl]-N-methylacetamide;

or a stereoisomer, an N-oxide, a hydrate, a solvate, a salt thereof, or a mixture of any of the foregoing.

6. A pharmaceutical composition comprising a compound of formula (I) according to claim 1, or a stereoisomer, an N-oxide, a salt thereof, or a mixture of any of the foregoing, and one or more pharmaceutically acceptable excipients.

7. A method for treatment of a neurogenic disorder, comprising administering an effective amount of the compound of claim 1, or a stereoisomer, an N-oxide, a salt thereof, or a mixture of any of the foregoing, to a subject in need thereof.

8. A method for treatment of a disease, wherein the disease is endometriosis, overactive bladder or chronic cough, comprising administering an effective amount of the compound of claim 1, or a stereoisomer, an N-oxide, a salt thereof, or a mixture of any of the foregoing, to a subject in need thereof.

9. A method for treatment of a disease, wherein the disease is neuropathic pain or uterine fibroids-associated pain and discomfort, comprising administering an effective amount of the compound of claim 1, or a stereoisomer, an N-oxide, a salt thereof, or a mixture of any of the foregoing, to a subject in need thereof.

10. The method according to claim 7, wherein the neurogenic disorder is a gynecological disorder, urinary tract disease state, respiratory disorder or a pain-associated disease or disorder.

11. The method according to claim 10, wherein the pain-associated disease or disorder is neuropathic pain or uterine fibroids-associated pain and discomfort.

* * * * *